United States Patent
Hisakawa et al.

(10) Patent No.: US 9,145,425 B2
(45) Date of Patent: *Sep. 29, 2015

(54) CEPHEM COMPOUND HAVING CATECHOL GROUP

(75) Inventors: Shinya Hisakawa, Toyonaka (JP); Yasushi Hasegawa, Toyonaka (JP); Toshiaki Aoki, Toyonaka (JP); Hiroki Kusano, Toyonaka (JP); Masayuki Sano, Toyonaka (JP); Jun Sato, Toyonaka (JP); Kenji Yamawaki, Toyonaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/639,412

(22) PCT Filed: Apr. 4, 2011

(86) PCT No.: PCT/JP2011/058498
§ 371 (c)(1),
(2), (4) Date: Dec. 5, 2012

(87) PCT Pub. No.: WO2011/125967
PCT Pub. Date: Oct. 13, 2011

(65) Prior Publication Data
US 2013/0102583 A1  Apr. 25, 2013

(30) Foreign Application Priority Data

Apr. 5, 2010  (JP) .................. 2010-087131
Dec. 9, 2010  (JP) .................. 2010-274180

(51) Int. Cl.

| C07D 471/08 | (2006.01) |
|---|---|
| C07D 501/56 | (2006.01) |
| C07D 505/24 | (2006.01) |
| C07D 501/46 | (2006.01) |
| C07D 519/06 | (2006.01) |

(52) U.S. Cl.
CPC ............ *C07D 505/24* (2013.01); *C07D 471/08* (2013.01); *C07D 501/46* (2013.01); *C07D 501/56* (2013.01); *C07D 519/06* (2013.01)

(58) Field of Classification Search
None
See application file for complete search history.

(56) References Cited

U.S. PATENT DOCUMENTS

| 4,647,556 A | 3/1987 | Lattrell et al. |
|---|---|---|
| 4,906,623 A | 3/1990 | Matsumura et al. |
| 5,055,462 A | 10/1991 | Davies et al. |
| 5,095,012 A | 3/1992 | Okita et al. |
| 5,104,866 A | 4/1992 | Sakane et al. |
| 5,126,336 A | 6/1992 | Imae et al. |
| 5,143,910 A | 9/1992 | Onoue et al. |
| 5,149,803 A | 9/1992 | Davies et al. |
| 5,234,920 A | 8/1993 | Okita et al. |
| 5,244,890 A * | 9/1993 | Yamanaka et al. ............ 514/202 |
| 2005/0153950 A1 | 7/2005 | Nishitani et al. |
| 2011/0190254 A1 | 8/2011 | Nishitani et al. |
| 2013/0079319 A1 | 3/2013 | Yamawaki et al. |
| 2013/0096299 A1 | 4/2013 | Kusano et al. |

FOREIGN PATENT DOCUMENTS

| AU | 676218 | 3/1997 |
|---|---|---|
| DE | 25 19 400 | 3/1976 |
| EP | 0 114 752 | 8/1984 |
| EP | 0 168 177 | 1/1986 |
| EP | 0 211 656 | 2/1987 |

(Continued)

OTHER PUBLICATIONS

Bryskier. Clinical Microbiology and Infection, V. 3, Supplement 1, Apr. 1997. p. S1-S6.*

(Continued)

*Primary Examiner* — James D Anderson
(74) *Attorney, Agent, or Firm* — Hamre, Schumann, Mueller & Larson, P.C.

(57) ABSTRACT

This invention provides Cephem compounds having the formula:

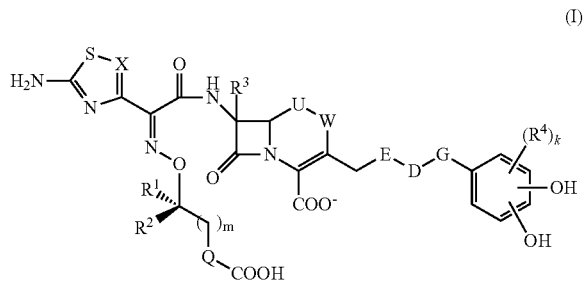

(I)

or an ester, a protected compound at the amino on the ring in the 7-side chain, a pharmaceutically acceptable salt, or a solvate thereof, a pharmaceutical composition thereof, and a method for treating a bacterial infectious disease with the compound, the ester, the protected compound, the salt, or the solvate thereof, wherein the symbols in the formula are defined in the specification. The compounds exhibit potent antimicrobial spectrum against a variety of bacteria including Gram negative bacteria and/or Gram positive bacteria, preferably beta-lactamase producing Gram negative bacteria, more preferably, multi-drug resistant microbials, in particular, Class B type metallo-beta-lactamase producing Gram negative bacteria, and still preferably extended-spectrum beta-lactamase (ESBL) producing bacteria. The compounds most preferably do not exhibit cross-resistance against known Cephem drugs or Carbapenem drugs.

23 Claims, No Drawings

(56) References Cited

FOREIGN PATENT DOCUMENTS

| | | |
|---|---|---|
| EP | 0 241 901 | 10/1987 |
| EP | 0 305 111 | 3/1989 |
| EP | 0 345 671 | 12/1989 |
| EP | 0 346 465 | 12/1989 |
| EP | 0 376 724 | 7/1990 |
| EP | 0 474 049 | 3/1992 |
| EP | 0 485 808 | 5/1992 |
| EP | 1 489 084 | 12/2004 |
| EP | 2 341 053 | 7/2011 |
| JP | 57-118588 | 7/1982 |
| JP | 58-162592 | 9/1983 |
| JP | 62-30788 | 2/1987 |
| JP | 62-158291 | 7/1987 |
| JP | 2-15090 | 1/1990 |
| JP | 2-28185 | 1/1990 |
| JP | 2-28187 | 1/1990 |
| JP | 2-117678 | 5/1990 |
| JP | 2-275886 | 11/1990 |
| JP | 4-364189 | 12/1992 |
| JP | 5-213971 | 8/1993 |
| JP | 6-345776 | 12/1994 |
| JP | 5498393 | 3/2014 |
| WO | WO 86/05183 | 9/1986 |
| WO | WO 92/21683 | 12/1992 |
| WO | WO 99/33839 | 7/1999 |
| WO | WO 03/099826 | 12/2003 |
| WO | WO 2006/104141 | 10/2006 |
| WO | WO 2007/096740 | 8/2007 |
| WO | WO 2007/119511 | 10/2007 |

OTHER PUBLICATIONS

Silley. Antimicrobial Agents and Chemotherapy, 1990, 34(9), 1806-1808.*
Takeda et al. "In Vitro Antibacterial Activity of a New Cephalosporin, FR295389, against IMP-type Metallo-β-lactamase-producers". *J. Antibiot.*, vol. 61, No. 1, pp. 36-39 (2008).
Hashizume et al. "Comparison of Transport Pathways of Catechol-Substituted Cephalosporins, BO-1236, and BO-1341, through the Outer Membrane of *Escherichia coli*". *The Journal of Antibiotics*, vol. 43, No. 12, pp. 1617-1620 (1990).
Weissberger et al. "L-658,310, A New Injectable Cephalosporin". *The Journal of Antibiotics*, vol. 42, No. 5, pp. 795-806 (1989).
Okita et al. "Synthesis and Antibacterial Activity of Cephalosporins having a Catechol in the C3 Side Chain". *The Journal of Antibiotics*, vol. 46, No. 5, pp. 833-839 (1993).
Imae et al. "Cephalosporins having a Heterocyclic Catechol in the C3 Side Chain". *The Journal of Antibiotics*, vol. 46, pp. 840-849 (1993).
Imura et al. "Cephalosporins having a Heterocyclic Catechol in the C3 Side Chain". *The Journal of Antibiotics*, vol. 46, pp. 850-857 (1993).
Baudart et al. "Synthesis and Biological Activity of C-3' *Ortho* Dihydroxyphthalimido Cephalosporin". *The Journal of Antibiotics*, vol. 46, pp. 1458-1470 (1993).
Choi et al. "Studies on New Catechol containing Cephalosporin". *The Journal of Antibiotics*, vol. 48, No. 11, pp. 1371-1374 (1995).
Arnould et al. "Synthesis and Structure-Activity Relationship of Cephalosporins with C-3' Catechol-Containing Residues". *J. Med. Chem.*, vol. 35, pp. 2631-2642 (1992).
Bird et al. "Pharmacokinetics of Catechol Cephalosporins. The Effect of Incorporating Substituents into the Catechol Moiety on Pharmacokinetics in a Marmoset Model". *J. Med. Chem.*, vol. 35, pp. 2643-2651 (1992).
Tsuji et al. "Synthesis and Antibacterial Activity of Cephalosporins having C-3 Catechol-Containing (Pyridinium-4'-Thio) Methyl Groups". *Bioorganic and Medicinal Chemistry Letters*, vol. 5, No. 9, pp. 963-966 (1995).
Adams et al. "Structure-activity Relationships within a Series of C(7)-Substitutedoxyiminocephalosporins containing the C(3)-Methylaminopyridiniumthiomethyl Substituent Synthesis and Biological Properties of BRL 57342 and Some Close Analogues". *The Journal of Antibiotics*, vol. 48, No. 5, pp. 417-424 (1995).
Mochizuki et al. "Antibacterial and Pharmacokinetic Properties of M14659, A new Injectable Semisynthetic Cephalosporin". The Journal of Antibiotics, vol. 41, No. 3, pp. 377-391 (1988).
Kim et al. "Synthesis of Antibacterial Activities of Novel C(7)-Catechol-substituted Cephalosporins". *The Journal of Antibiotics*, vol. 49, pp. 496-498 (1996).
Guest et al. "Synthesis and Biological Activity of 3-(N-Substituted Pyridiuium-4-Thiomethyl)-7α-Formamido Cephalosporins". *The Journal of Antibiotics*, vol. 46, No. 8, pp. 1279-1288 (1993).
Yamano et al. "Ferric iron transport system of *Pseudomonas aeruginosa* PA01 that functions as the uptake pathway of a novel catechol-substituted cephalosporin, S-9096". Appl. Microbiol. Biotechnol., vol. 40, pp. 892-897 (1994).
Tashiro, Tatsuo. Macromol. Mater. Eng. 2001, 286, pp. 63-87.
Wermuth, Camille G., "Molecular Variations Based on Isosteric Replacements." The Practice of Medicinal Chemistry, Academic Press, 1996, pp. 203-237.
Branch et al. "Studies on Semi-Synthetic 7 α-Formamidocephalosporins". *The Journal of Antibiotics*, vol. 40, pp. 646-651 (1987).
Yamawaki et al. "A novel series of parenteral cephalosporins exhibiting potent activities against *Pseudomonas aeruginosa* and other Gram-negative pathogens: Synthesis and structure-activity relationships". *Bioorganic of Medicinal Chemistry*, vol. 15, pp. 6716-6732 (2007).
Almeida et al. "Synthesis of N-(2-chloro-3,4-dimethoxybenzylideneamino)guanidinium acetate [α-$^{14}$C]". *Journal of Labelled Compounds and Radiopharmaceuticals*, vol. 45, pp. 371-377 (2002).
Obi et al. "Novel Cephalosporins having a Benzothiopyran Group-Synthesis and Biological Activity of Catecholic Benzothiopyrain Group at the C-3 Side Chain". *The Journal of Antibiotics*, vol. 48, pp. 278-281 (1995).
Office Action issued on Mar. 5, 2015 in Egyptian Application No. PCT408/2011, which is a corresponding application to co-pending U.S. Appl. No. 13/063,878.

* cited by examiner

CEPHEM COMPOUND HAVING CATECHOL GROUP

TECHNICAL FIELD

The invention is related to cephem compounds, which have a wide antimicrobial spectrum, and in particular exhibit potent antimicrobial activity against beta-lactamase producing Gram negative bacteria, and pharmaceutical composition comprising the same.

BACKGROUND ART

To date, a variety of beta-lactam drugs have been developed and beta-lactam drugs have become clinically extremely important antimicrobial drugs. However, there are increasing number of bacterial types which have obtained resistancy against beta-lactam drugs by producing beta-lactamase, which degrade beta-lactam drugs. According to the Ambler molecular classification, beta-lactamase are largely classified into four classes. Specifically, those are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-beta-lactamase, and on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to beta-lactam drugs including Cephems and Carbapenems by production of Class A (ESBL) or D types serine-beta-lactamase and Class B type metallo-beta-lactamase which have extended their substrate spectrum. Particularly, metallo-beta-lactamase is known to be one of the causes of obtaining multi-resistancy in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular effectivity against a variety of beta-lactamase producing Gram negative bacteria.

One of the known antimicrobials having high anti-Gram negative bactericidal activity is Cephem compounds having a catechol group intramolecularly (e.g., Non-Patent Documents 2-4). The action thereof is that the catechol group forms a chelate with $Fe^{3+}$, thereby the compound is efficiently incorporated into the bacterial body by means of $Fe^{3+}$ transportation system on the cellular membrane (tonB-dependent iron transport system). Therefore, research has been conducted on compounds having catechol or similar structure thereto, on the 3-side chain or 7-side chain on the Cephem backbone.

Patent Documents 8 and Non-patent Documents 2-11 and 16 disclose compounds having a catechol or a structure similar thereto on the 3-side chain of the Cephem backbone.

Patent Document 9 and Non-patent Documents 12-15 disclose compounds having a catechol or a structure similar thereto on the 7-side chain of the Cephem backbone.

Non-patent Documents 7, 9, 10 and 12-15 describe Cephem compounds which have been stabilized against beta-lactamase.

However, these references do not disclose the compounds of the subject invention. Furthermore, these references, which describe Cephem compounds having catechol group intramolecularly, have no specific description regarding met- allo-beta-lactamase of Class B type, or antibacterial activity against wide spectrum of Gram negative bacteria including Class B type.

Patent Documents 10 and 11 do not specifically disclose Cephem compounds having catechol type substituents. However, the present applicant filed a patent application for Cephem compounds having catechol type substituents (Patent Document 12).

PRIOR ART DOCUMENTS

Patent Documents

Patent Document 1: WO2007/119511 A1
Patent Document 2: JP 3-173893 A
Patent Document 3: JP 2-15090 A
Patent Document 4: JP 2-28187 A
Patent Document 5: JP 2-117678 A
Patent Document 6: JP 6-510523 A
Patent Document 7: JP 5-21397: A
Patent Document 8: JP 2-28185 A
Patent Document 9: JP 6-345776 A
Patent Document 10: WO 2007/096740 A1
Patent Document 11: WO 2003/078440 A1
Patent Document 12: international Patent Application No. PCT/JP2009/068400
Patent Document 13: Japanese patent application No. 2010-087130
Patent Document 14: Japanese patent application No. 2010-104035

Non-Patent Document

Non-patent document 1: The Journal of Antibiotics, vol. 61, pp. 36-39 (2008)
Non-patent document 2: The Journal of Antibiotics, vol. 43, pp. 1617-1620 (1990)
Non-patent document 3: The Journal of Antibiotics, vol. 42, pp. 795-806 (1989)
Non-patent document 4: The Journal of Antibiotics, vol. 46, pp. 833-839 (1993)
Non-patent document 5: The Journal of Antibiotics, vol. 46, pp. 840-849 (1993)
Non-patent document 6 The Journal of Antibiotics, vol. 46, pp. 850-857 (1993)
Non-patent document 7: The Journal of Antibiotics, vol. 46, pp. 1458-1470 (1993)
Non-patent document 8: The Journal of Antibiotics, vol. 48, pp. 1371-1374 (1995)
Non-patent document 9: The Journal of Medicinal Chemistry, vol. 35, pp. 2631-2642 (1992)
Non-patent document 10: The Journal of Medicinal Chemistry, vol. 35, pp. 2643-2651 (1992)
Non-patent document 11: Bioorganic & Medicinal Chemistry Letters, pp. 963-966 (1995)
Non-patent document 12: The Journal of Antibiotics, vol. 48, pp. 417-424 (1995)
Non-patent document 13: The Journal of Antibiotics, vol. 41, pp. 377-391 (1988)
Non-patent document 14: The Journal of Antibiotics, vol. 49, pp. 496-498 (1996)
Non-patent document 15: The Journal of Antibiotics, vol. 46, pp. 1279-1298 (1993)
Non-patent document 16: Applied Microbiology and Biotechnology, vol. 40, pp. 892-897 (1994)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria.

Preferably, the subject invention provides Cephem compounds which exhibit potent antimicrobial activity against beta-lactamase producing Gram negative bacteria.

More preferably, the subject invention provides Cephem compounds which exhibit potent antimicrobial activity against multi-drug resistant microbials, in particular, Class B type metallo-beta-lactamase producing Gram negative bacteria.

Still preferably, the subject invention provides Cephem compounds which exhibit effective antimicrobial activity against extended-spectrum beta-lactamase (ESBL) producing bacteria.

Most preferably, the subject invention provides Cephem compounds which do not exhibit cross-resistance against known Cephem drug or Carbapenem drugs.

Means for Solving the Problems

The subject invention provides Cephem compounds which have solved the above-mentioned problems, at least based on the following structural features:

1) The compounds of the subject invention have cyclic quaternary ammonium group (-E-) on the 3-side chain, and a catechol type substituent on the terminus thereof, preferably having one or two chlorine or fluorine atoms on the benzene ring of the catechol group, and more preferably having one chlorine or fluorine atom thereon, and especial preferably having one chlorine atom thereon;

2) The compounds of the subject invention have a spacer moiety (-D-G-) between the quaternary ammonium group (-E-) and the catechol type substituent;

3) In the spacer moiety, D is a single bond or a linear chain group, and it is particularly preferable that G is —C(=O)—, provided D is not a single bond, D is especial preferably —NH—;

4) The compounds of the subject invention have an aminothiadiazole ring or aminothiazole ring on the 7-side chain, and a carboxylic group on the terminus of the oxime moiety; and 5) The feature of another embodiment of the compounds of the subject invention is to have a non-cyclic quaternary ammonium group on the 3-side chain, and a catechol type substituent on the terminus thereof, preferably having one or two chlorine atoms on the benzene ring of the catechol group. In this case, with regard to the spacer moiety (-D-G-), D is a cyclic group, and G is —C(=O)—.

Specifically, the subject invention provides the following inventions:

(Item 1)
A compound of the formula:

[Formula 1]

(I)

wherein,
X is —N=, —CH=, —C(-$R^5$)=, or —C(—Br)= or —C(—Cl)=;
$R^5$ is lower alkyl or halo(lower)alkyl;
W is —$CH_2$—, —S— or —O—;
U is —$CH_2$—, —S— or —O— when W is —$CH_2$—, and U is —$CH_2$— when W is —S— or —O—;
$R^1$ and $R^2$ are independently hydrogen, halogen, hydroxyl, carboxy, optionally substituted lower alkyl, optionally substituted carbocyclic group or optionally substituted heterocyclic group; or
$R^1$ and $R^2$ are taken together with a neighboring atom to form optionally substituted carbocyclic group or optionally substituted heterocyclic group;
$R^3$ is hydrogen, —$OCH_3$ or —NH—CH(=O);
each $R^4$ is independently hydrogen, halogen, hydroxyl, —CN, —C(=O)—$R^6$, —C(=O)—OH, lower alkyl, halo(lower)alkyl or —$OR^6$;
k is an integer from 0 to 2;
$R^6$ is lower alkyl or halo(Lower)alkyl;
m is an integer from 0 to 2;
Q is a single bond, optionally substituted carbocyclic group or optionally substituted heterocyclic group;
G is i) —C(=O)— or ii) 5-membered heterocyclic group;
wherein
i) when G is —C(=O)—, then
a) D is a single bond, —NH— or —$R^7$—NH— wherein $R^7$ is lower alkylene;
and E is optionally substituted cyclic group selected from the following formulae (1) to (45); or
b) D is a group of the formula:

[Formula 2]

wherein q is 0 or 1, and E is a group of the following formula (46); and
ii) when G is 5-membered heterocyclic group,
D is —$CH_2$— or —$CH_2$—$CH_2$—, and E is a group of the formula (10) in the following cyclic groups of the moiety E:

[Formula 3]
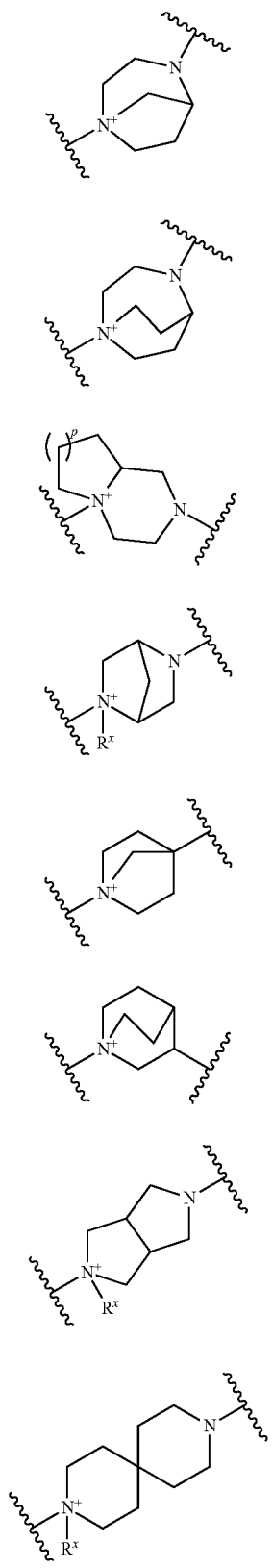
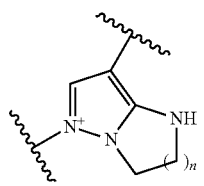
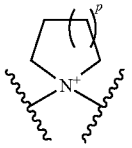
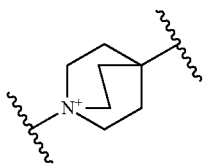
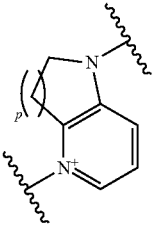
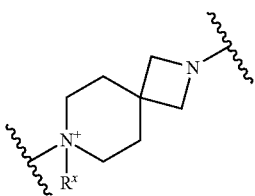
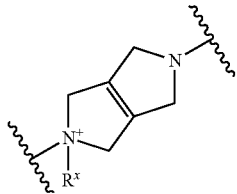
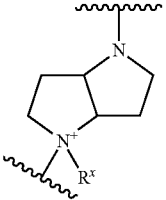
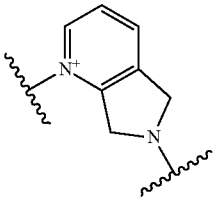

-continued
(17) 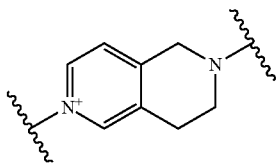
(18) 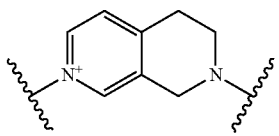
(19) 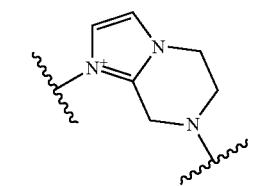
(20) 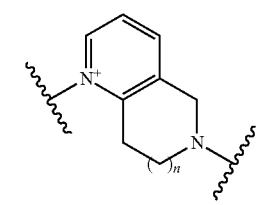
[Formula 4]
(21) 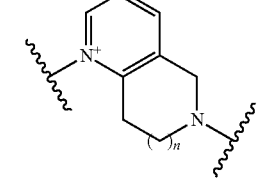
(22) 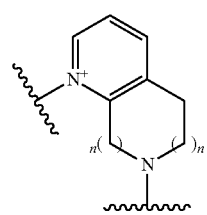
(23) 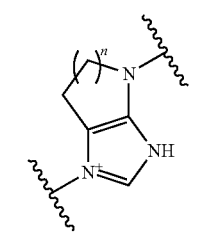
(24) 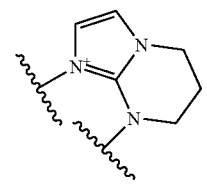
-continued
(25) 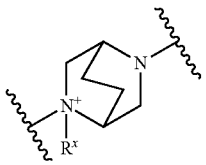
(26) 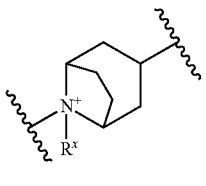
(27) 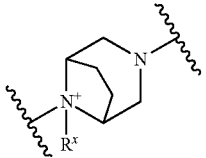
(28) 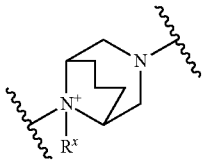
(29) 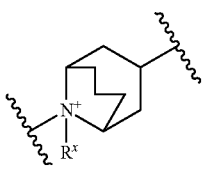
(30) 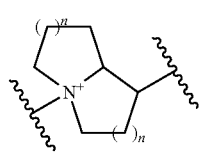
(31) 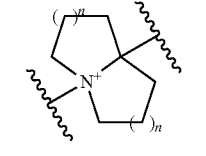
(32) 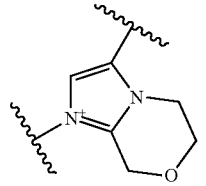
(33) 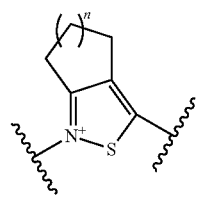

(34) 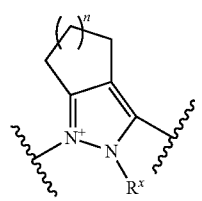
(35) 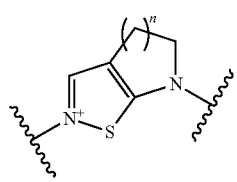
(36) 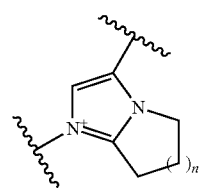
(37) 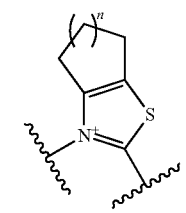
(38) 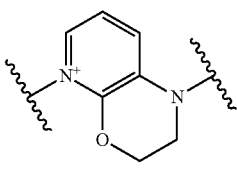
(39) 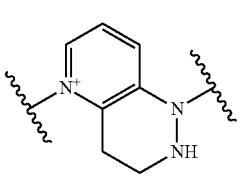
(40) 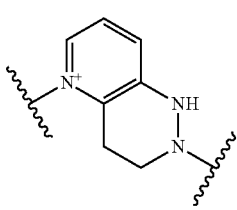
(41) 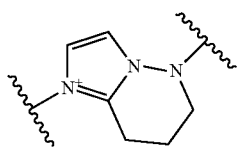
(42) 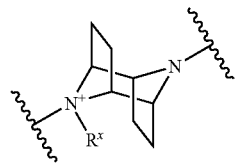
(43) 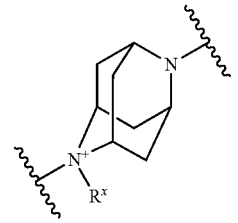
(44) 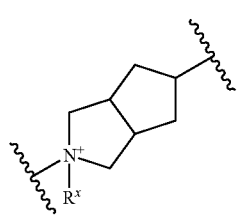
(45) 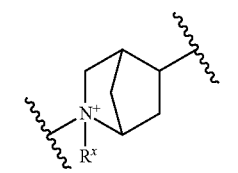
(46) 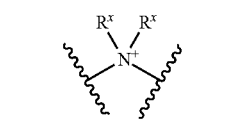
wherein p is an integer from 1 to 3, n is 1 or 2, and $R^x$ is optionally substituted lower alkyl; provided that the following compounds (A-1) to (A-35) are excluded,

[Formula 5]
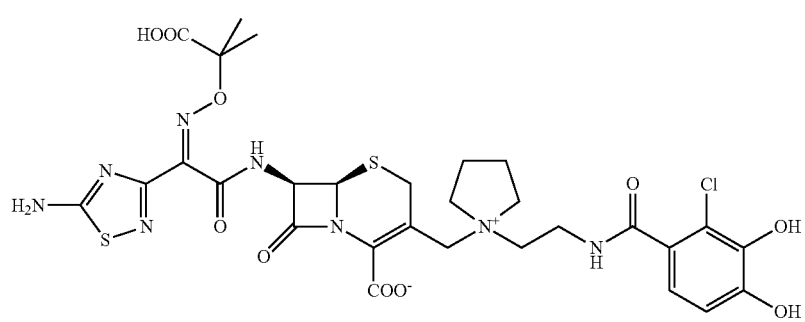
(A-1)
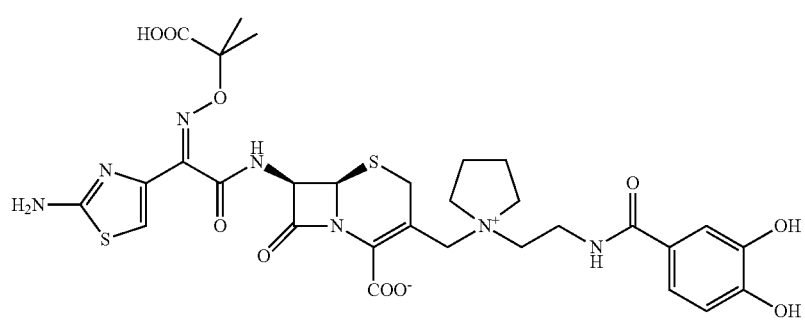
(A-2)
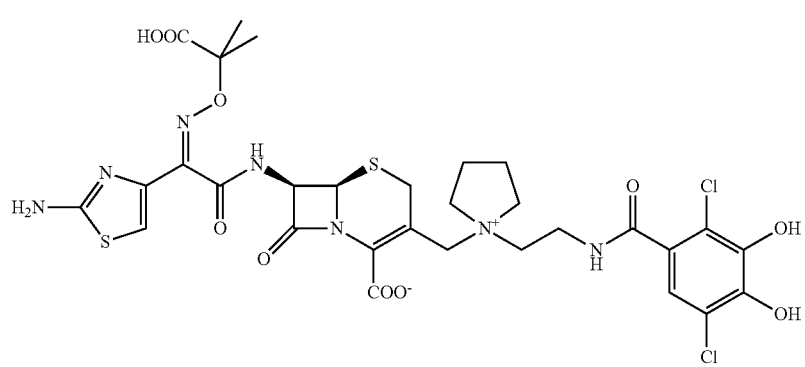
(A-3)
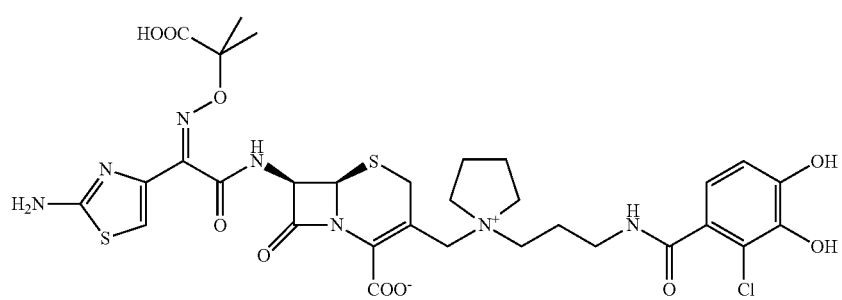
(A-4)
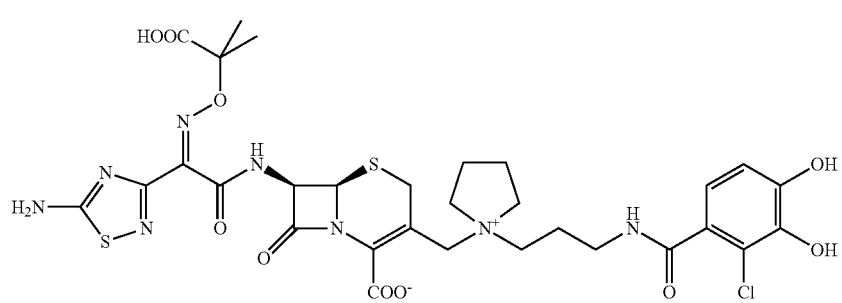
(A-5)

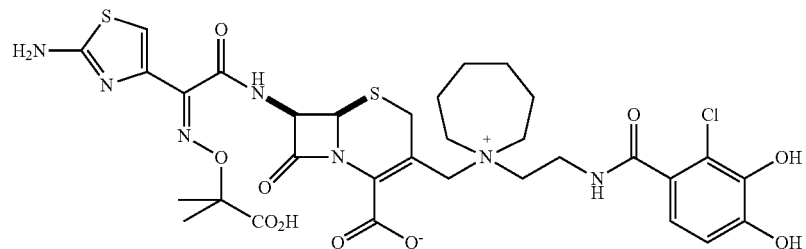
(A-6)
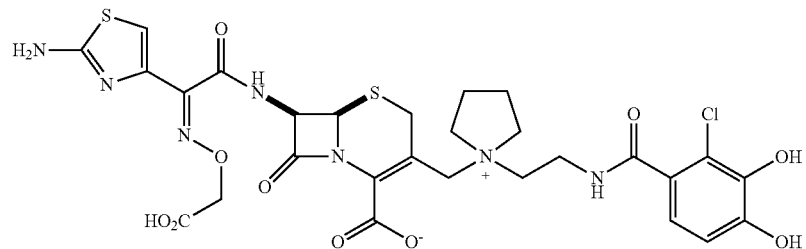
(A-7)
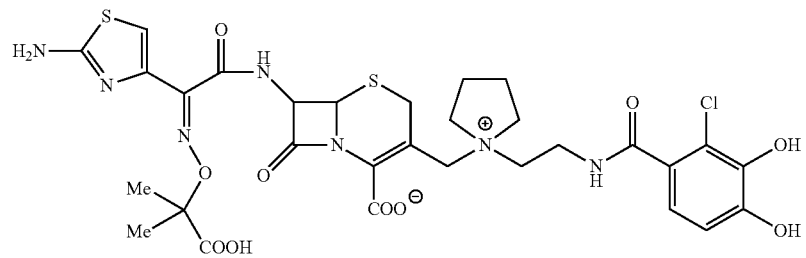
(A-8)
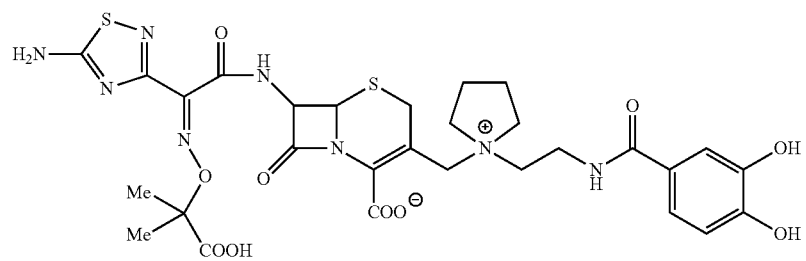
(A-9)
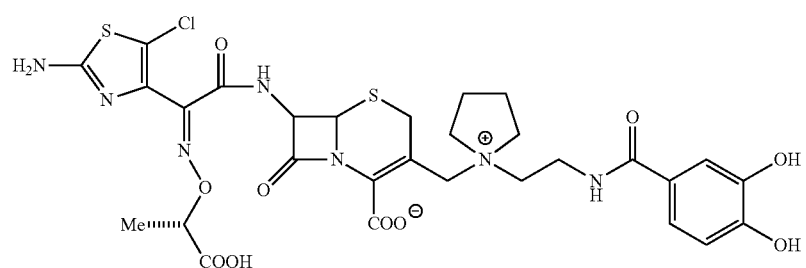
(A-10)
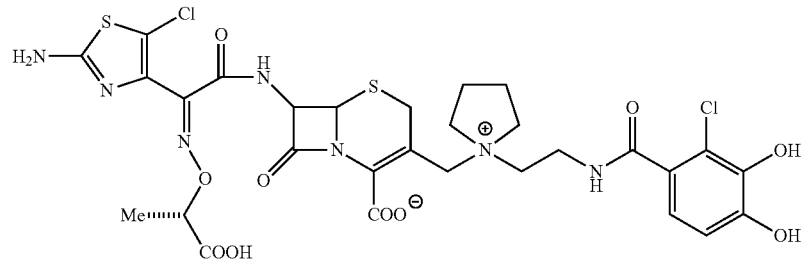
(A-11)

-continued
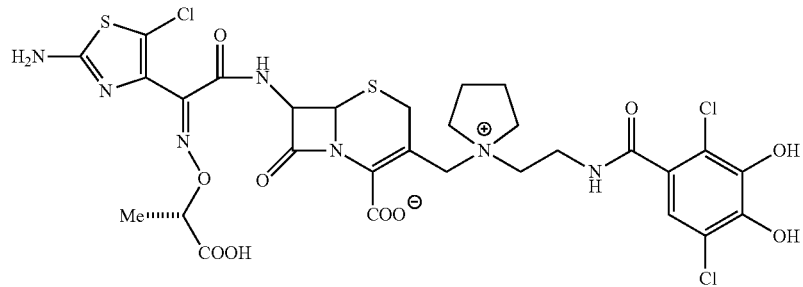
(A-12)
[Formula 6]
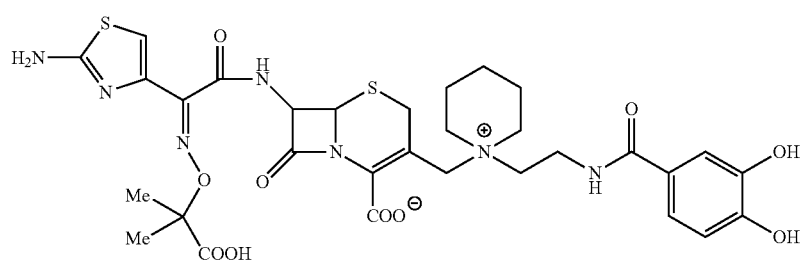
(A-13)
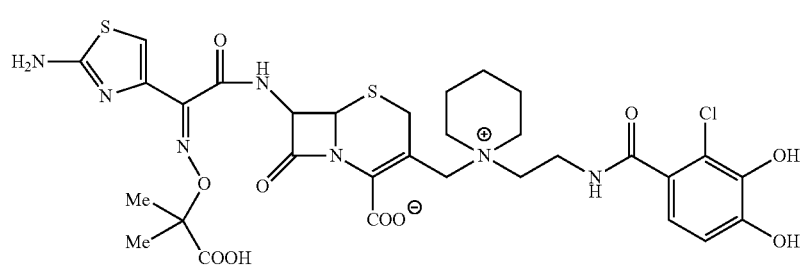
(A-14)
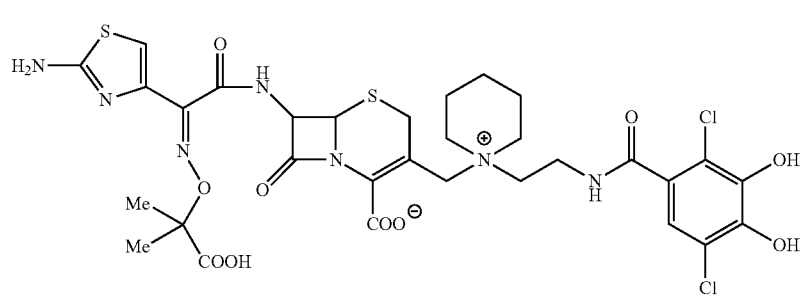
(A-15)

(A-16)

-continued
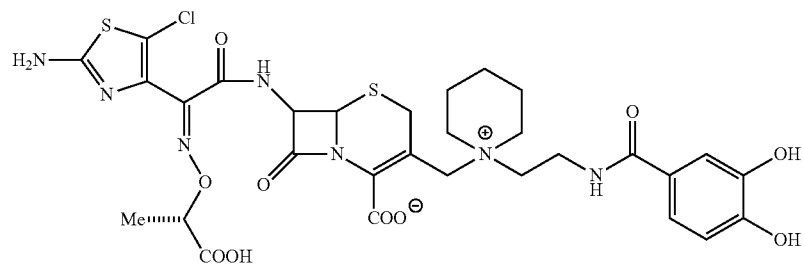
(A-17)
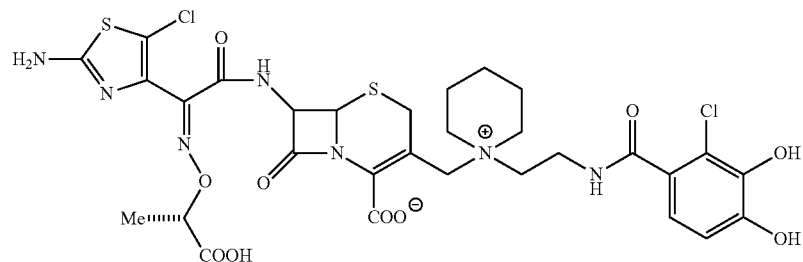
(A-18)
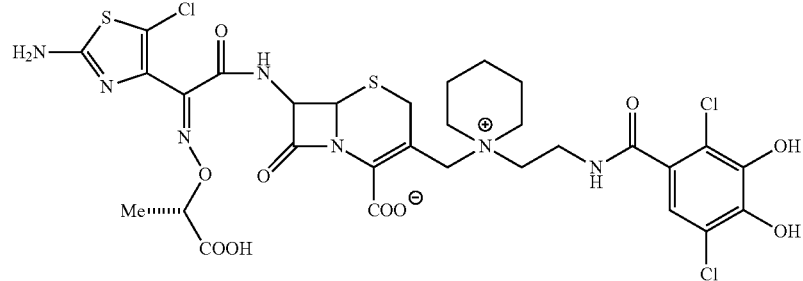
(A-19)
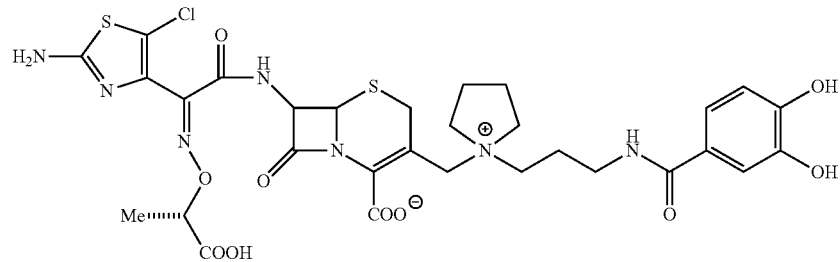
(A-20)
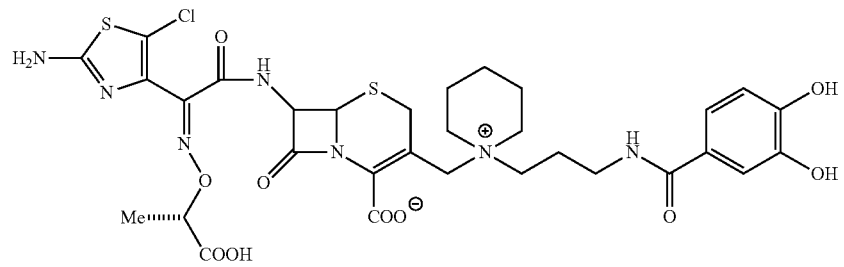
(A-21)

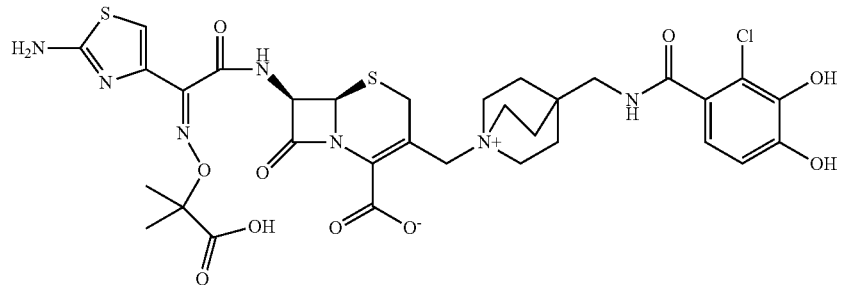
(A-22)
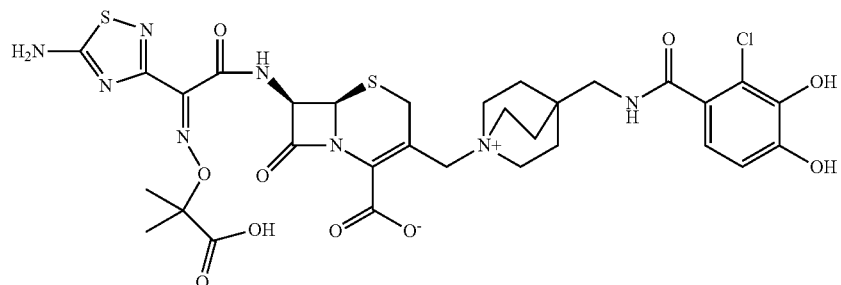
(A-23)
[Formula 7]
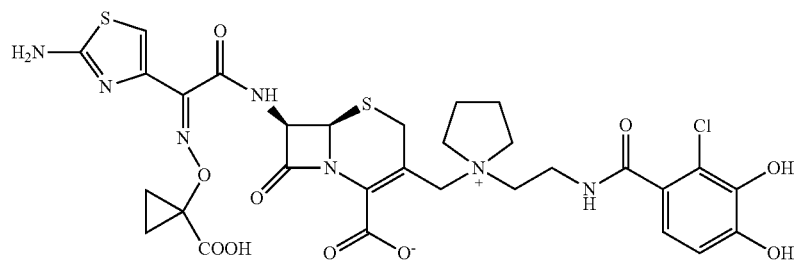
(A-24)
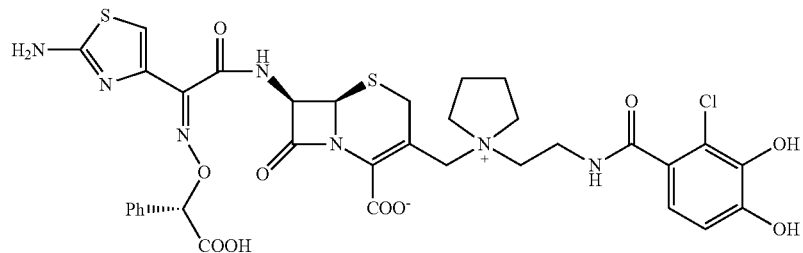
(A-25)
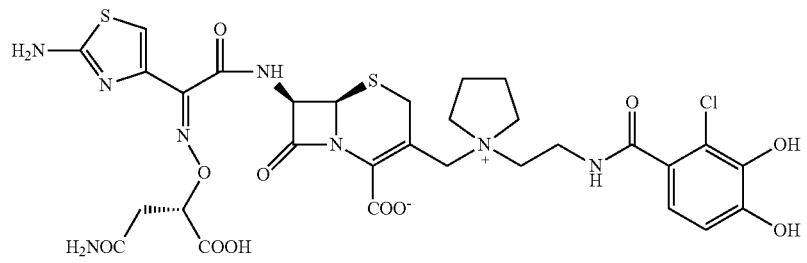
(A-26)

-continued
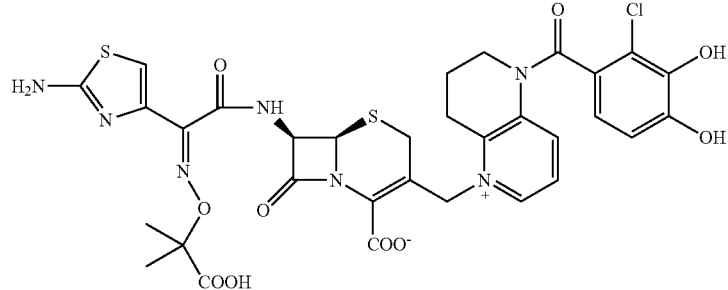
(A-27)
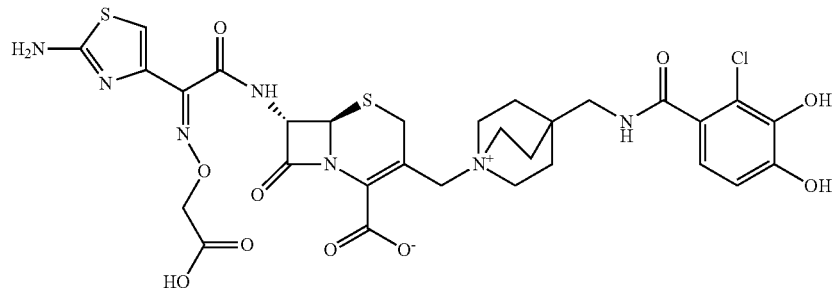
(A-28)
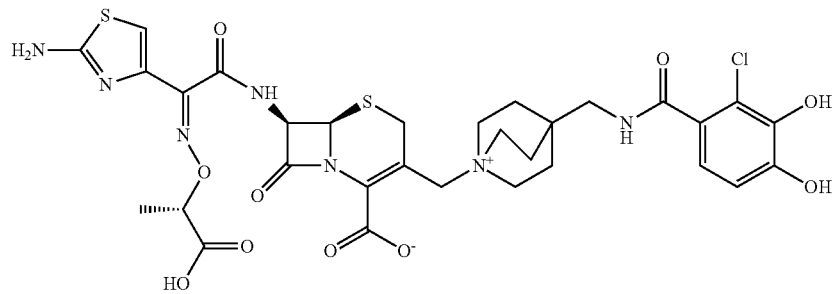
(A-29)
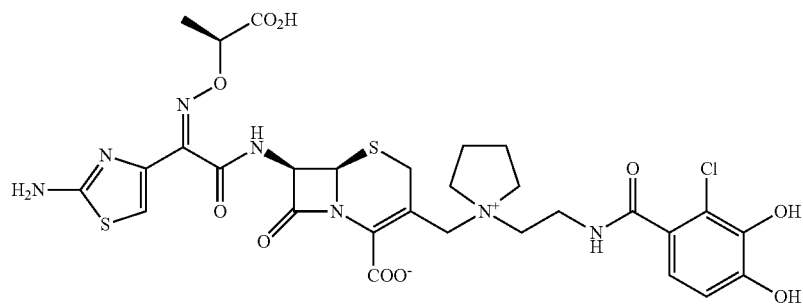
(A-30)
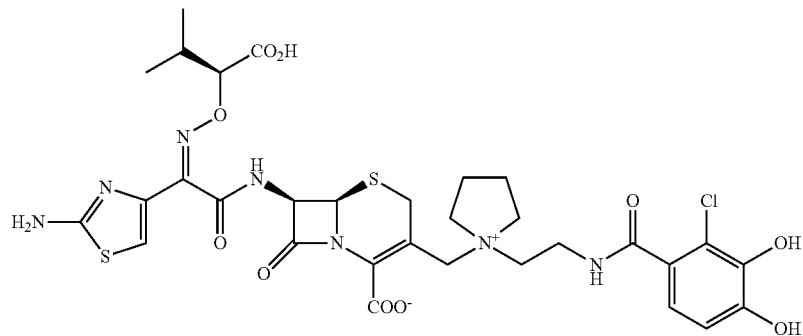
(A-31)

-continued

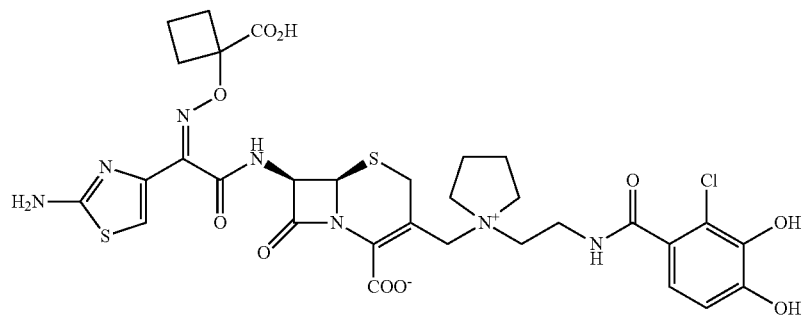
(A-32)

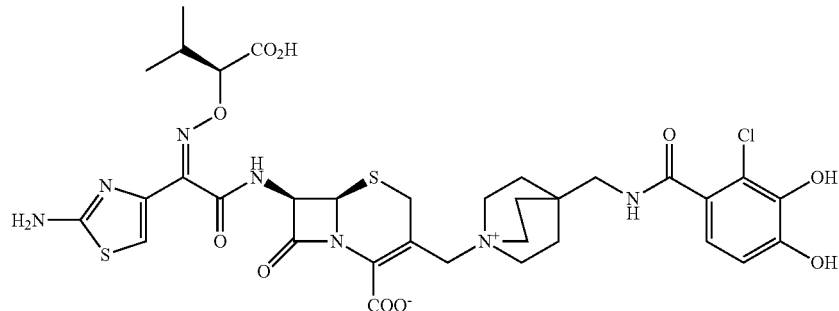
(A-33)

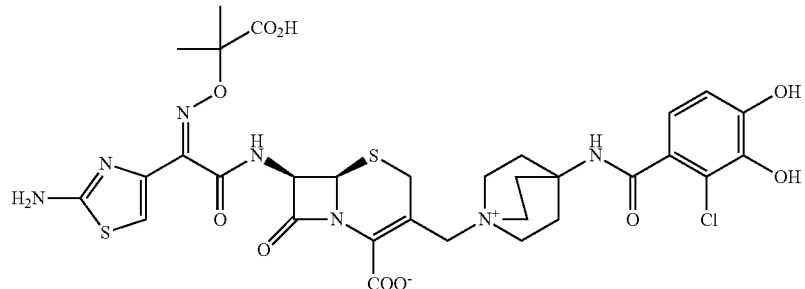
(A-34)

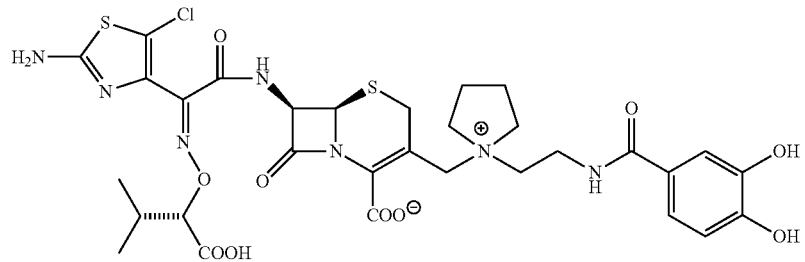
(A-35)

or an ester, a protected compound at the amino on the ring in the 7-side chain, a pharmaceutically acceptable salt, or a solvate thereof.

(Item 2)

The compound, or an ester, a protected compound at the amino on the ring in the 7-side chain, a pharmaceutically acceptable salt, or a solvate thereof according to item 1, wherein G is —C(=O)—; D is a single bond, —NH— or —$R^7$—NH— wherein $R^7$ is lower alkylene; and E is selected from the formulae (1) to (45).

(Item 3)

The compound, or an ester, a protected compound at the amino on the ring in the 7-side chain, a pharmaceutically acceptable salt, or a solvate thereof according to item 2, wherein D is —NH—, —$CH_2$—NH— or —$CH_2$—$CH_2$—NH—.

(Item 4)

The compound, or an ester, a protected compound at the amino on the ring in the 7-side chain, a pharmaceutically acceptable salt, or a solvate thereof according to item 3, wherein E is a group selected from the formulae (5), (6), (13), (11), (26), (29) to (34), (36), (37), (44) and (45).

(Item 5)

The compound, or an ester, a protected compound at the amino on the ring in the 7-side chain, a pharmaceutically acceptable salt, or a solvate thereof according to item 3, wherein E is the formula (26) or (31).

(Item 6)
The compound, or an ester, a protected compound at the amino on the ring in the 7-side chain, a pharmaceutically acceptable salt, or a solvate thereof according to item 2, wherein D is a single bond.

(Item 7)
The compound, or an ester, a protected compound at the amino on the ring in the 7-side chain, a pharmaceutically acceptable salt, or a solvate thereof according to item 6, wherein E is a group selected from the formulae (1) to (4), (7), (8), (12) to (25), (27), (28), (35), and (38) to (43).

(Item 8)
The compound, or an ester, a protected compound at the amino on the ring in the 7-side chain, a pharmaceutically acceptable salt, or a solvate thereof according to item 6, wherein E is a group selected from the formulae (1) to (3), and (7).

(Item 9)
The compound, or an ester, a protected compound at the amino on the ring in the 7-side chain, a pharmaceutically acceptable salt, or a solvate thereof according to item 1, wherein G is —C(=O)—; and D is a group of the formula:

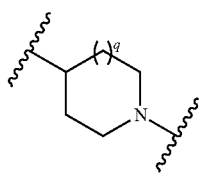

[Formula 8]

wherein, q is as defined in item 1.

(Item 10)
The compound, or an ester, a protected compound at the amino on the ring in the 7-side chain, a pharmaceutically acceptable salt, or a solvate thereof according to item 1, wherein G is a 5-membered heterocyclic group; and D is —CH$_2$— or —CH$_2$—CH$_2$—.

(Item 11)
The compound, or an ester, a protected compound at the amino on the ring in the 7-side chain, a pharmaceutically acceptable salt, or a solvate thereof according to any one of items 1 to 10, wherein U is —S—.

(Item 12)
The compound, or an ester, a protected compound at the amino on the ring in the 7-side chain, a pharmaceutically acceptable salt, or a solvate thereof according to any one of items 1 to 11, wherein W is —CH$_2$—.

(Item 13)
The compound, or an ester, a protected compound at the amino on the ring in the 7-side chain, a pharmaceutically acceptable salt, or a solvate thereof according to any one of items 1 to 12, wherein R$^3$ is hydrogen or —OCH$_3$.

(Item 14)
The compound, or an ester, a protected compound at the amino on the ring in the 7-side chain, a pharmaceutically acceptable salt, or a solvate thereof according to any one of items 1 to 13, wherein X is —N=, —CH= or —C(—Cl)=.

(Item 15)
The compound, or an ester, a protected compound at the amino on the ring in the 7-side chain, a pharmaceutically acceptable salt, or a solvate thereof according to any one of items 1 to 14, wherein a group of the formula:

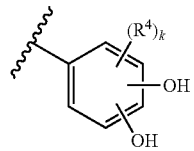

[Formula 9]

is a group of the formula:

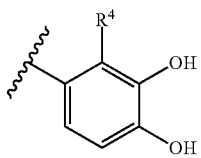

[Formula 10]

wherein, R$^4$ is as defined in item 1.

(Item 16)
The compound, or an ester, a protected compound at the amino on the ring in the 7-side chain, a pharmaceutically acceptable salt, or a solvate thereof according to any one of items 1 to 15, wherein each R$^4$ is independently hydrogen or halogen.

(Item 17)
The compound, or an ester, a protected compound at the amino on the ring in the 7-side chain, a pharmaceutically acceptable salt, or a solvate thereof according to any one of items 1 to 16, wherein R$^1$ is optionally substituted lower alkyl; and R$^2$ is hydrogen.

(Item 18)
The compound, or an ester, a protected compound at the amino on the ring in the 7-side chain, a pharmaceutically acceptable salt, or a solvate thereof according to any one of items 1 to 16, wherein R$^1$ is hydrogen; and R$^2$ is optionally substituted lower alkyl.

(Item 19)
The compound, or an ester, a protected compound at the amino on the ring in the 7-side chain, a pharmaceutically acceptable salt, or a solvate thereof according to any one of items 1 to 16, wherein R$^1$ and R$^2$ are lower alkyl.

(Item 20)
The compound, or an ester, a protected compound at the amino on the ring in the 7-side chain, a pharmaceutically acceptable salt, or a solvate thereof according to any one of items 1 to 19, wherein m is 0.

(Item 21)
A pharmaceutical composition comprising a compound, or an ester, a protected compound at the amino on the ring in the 7-side chain, a pharmaceutically acceptable salt, or a solvate thereof according to any one of items 1 to 20.

(Item 22)
The pharmaceutical composition according to item 21, which possesses an antimicrobial activity.

As another aspect, specifically, the subject invention provides the following inventions:

(Item 1')

A compound of the formula:

[Formula 11]

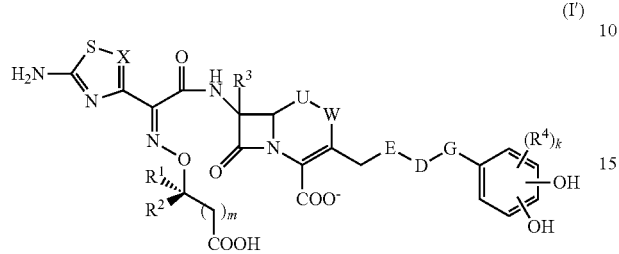

(I')

wherein,

X is —N=, —CH=, —C(—R$^5$)=, —C(—Br)=, or —C(—Cl)=;

R$^5$ is lower alkyl or halo(lower)alkyl;

W is —CH$_2$—, —S—, or —O—;

U is —CH$_2$—, —S— or —O— when W is —CH$_2$—, and U is —CH$_2$— when W is —S— or —O—;

R$^1$ and R$^2$ are independently hydrogen, halogen, hydroxyl, carboxy, optionally substituted lower alkyl, optionally substituted carbocyclic group or optionally substituted heterocyclic group; or R$^1$ and R$^2$ taken together with a neighboring atom may form optionally substituted carbocyclic group or optionally substituted heterocyclic group;

R$^3$ is hydrogen, —OCH$_3$ or —NH—CH(=O);

each R$^4$ is independently hydrogen, halogen, hydroxyl, —CN, —C(=O)—R$^6$, —C(=O)—OH or —OR$^6$;

k is an integer from 0 to 2;

R$^6$ is lower alkyl or halo(lower)alkyl;

m is an integer from 0 to 2;

G is i) —C(=O)— or ii) 5-membered heterocyclic group; wherein i) when G is —C(=O)—, then D is a single bond, —NH—, or —R$^7$—NH— wherein R$^7$ is lower alkylene;

and E is optionally substituted cyclic group selected from the following formulae (1) to (40); or b) D is a group of the formula:

[Formula 12]

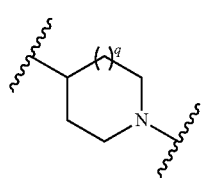

wherein q is 0 or 1, E is a group of the following formula (41); and ii) when G is a 5-membered heterocyclic group, D is —CH$_2$— or —CH$_2$—CH$_2$—, and E is a group of the formula (10) in the following cyclic groups of the moiety E:

[Formula 13]

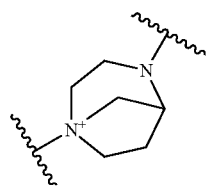 (1)

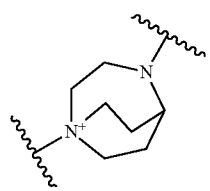 (2)

(3)

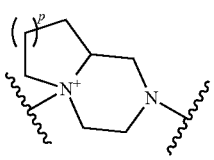 (4)

(5)

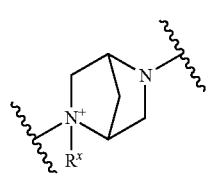 (6)

(7)

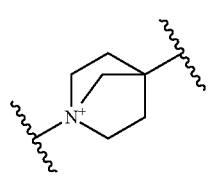

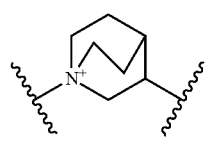 (8)

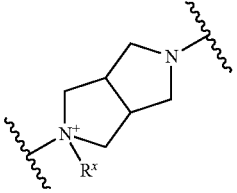

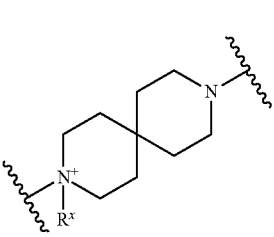 [SMILES: *N1CCC2(CC1)CC[N+](*)(C)CC2]

-continued
(9) 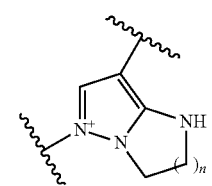
(10) 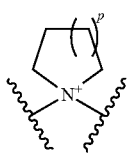
(11) 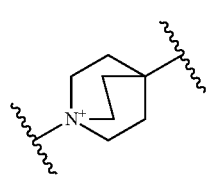
(12) 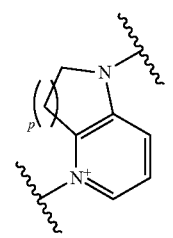
(13) 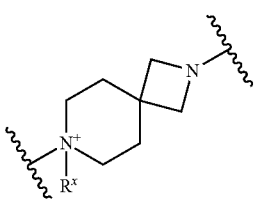
(14) 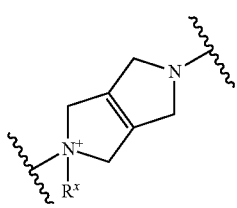
(15) 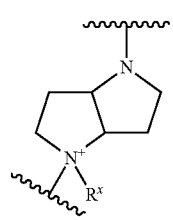
(16) 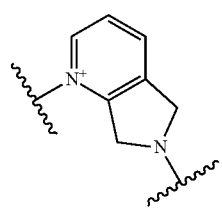
-continued
(17) 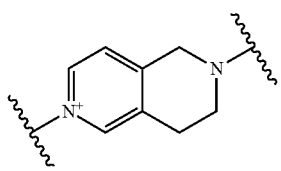 [SMILES: *N1CCc2c[n+](*)ccc2C1]
(18) 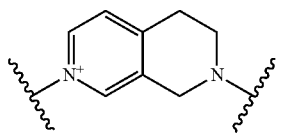 [SMILES: *N1CCc2cc[n+](*)cc2C1]
(19) 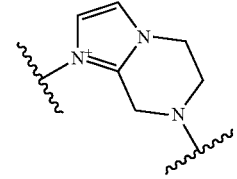
(20) 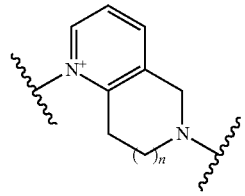 [SMILES: *N1CCc2c(ccc[n+]2*)C1]
[Formula 14]
(21) 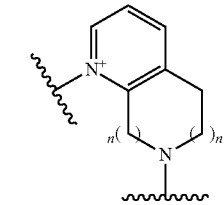
(22) 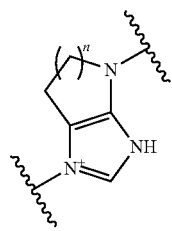
(23) 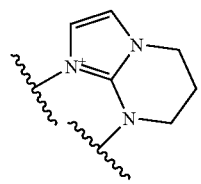
(24) 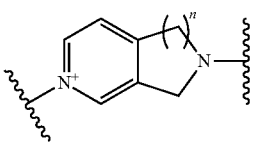

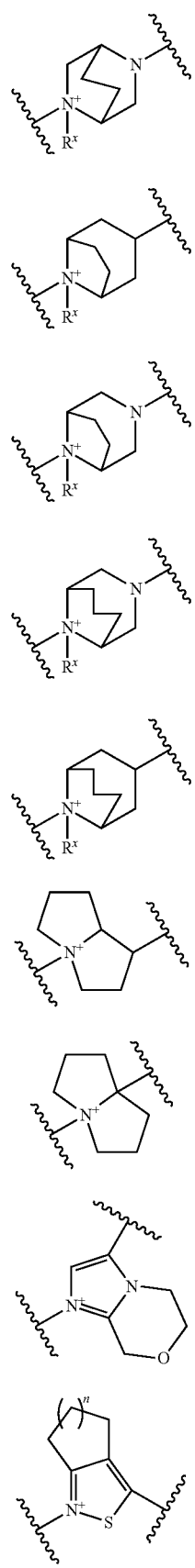
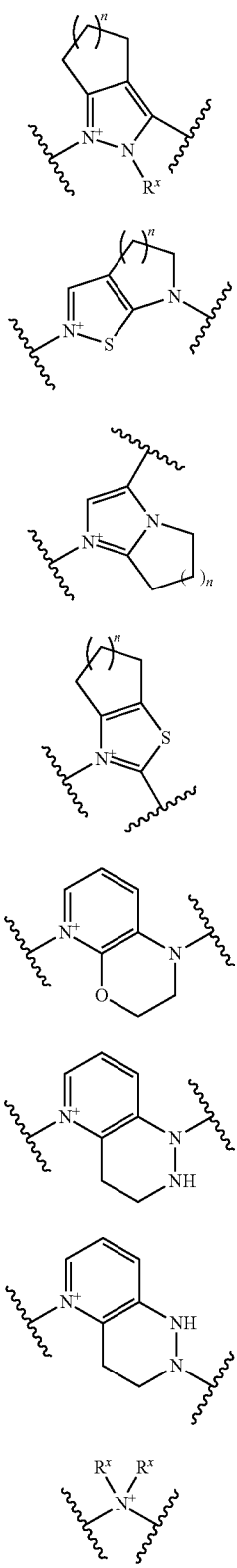
wherein p is an integer from 1 to 3, n is 1 or 2, and $R^x$ is optionally substituted lower alkyl;
provided that the following compounds (A-1) to (A-35) are excluded,

[Formula 15]
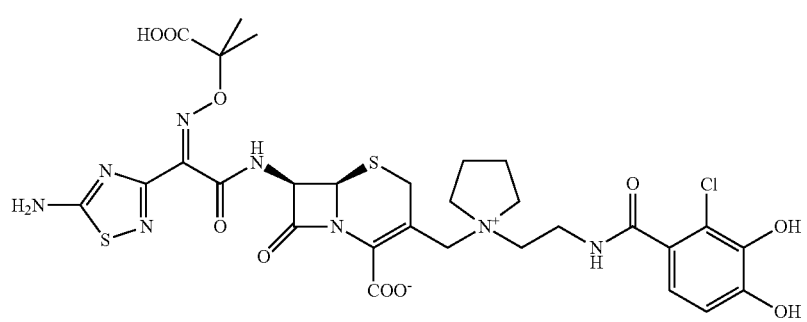 (A-1)
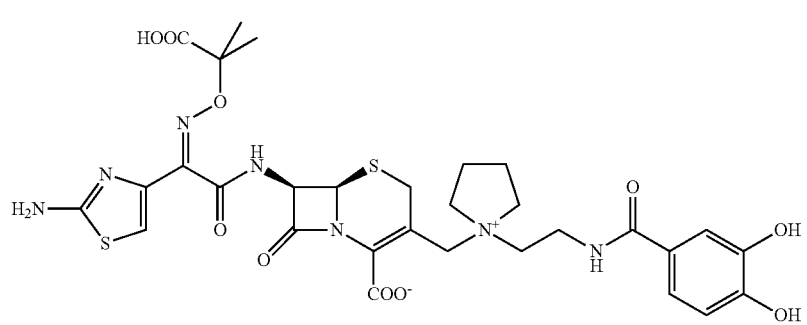 (A-2)
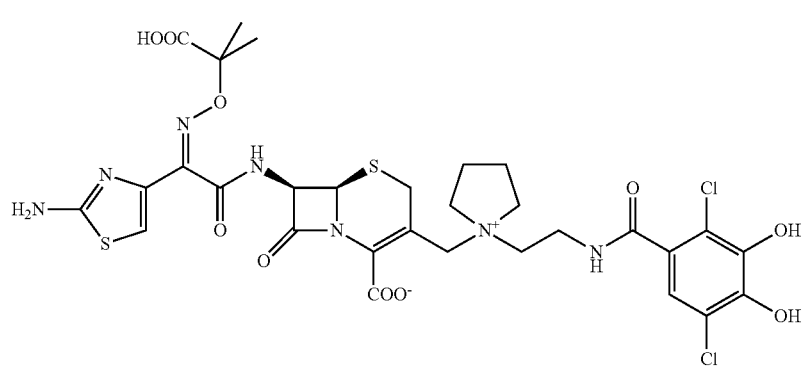 (A-3)
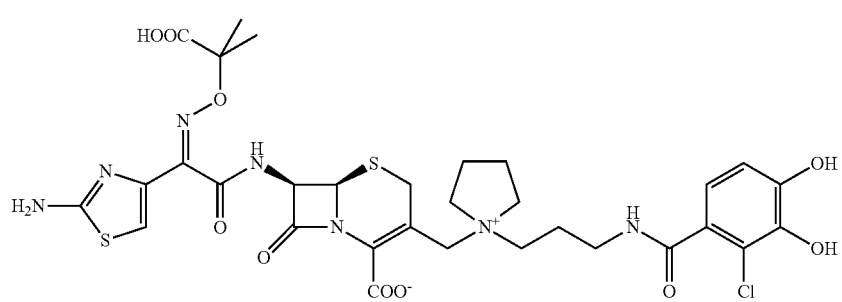 (A-4)
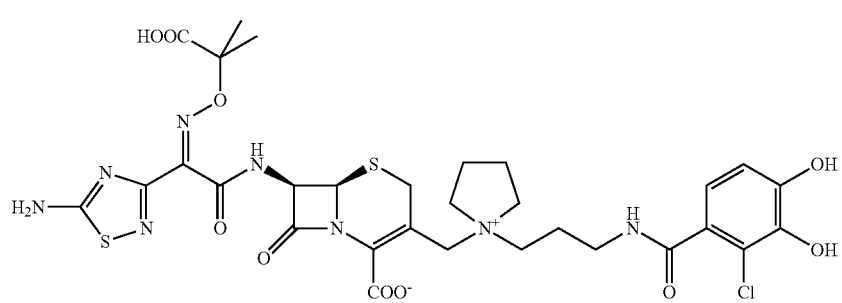 (A-5)

-continued
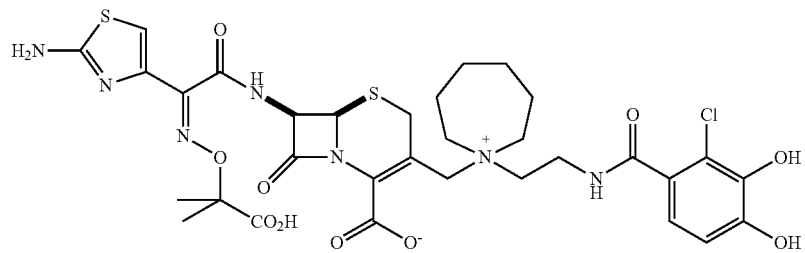
(A-6)
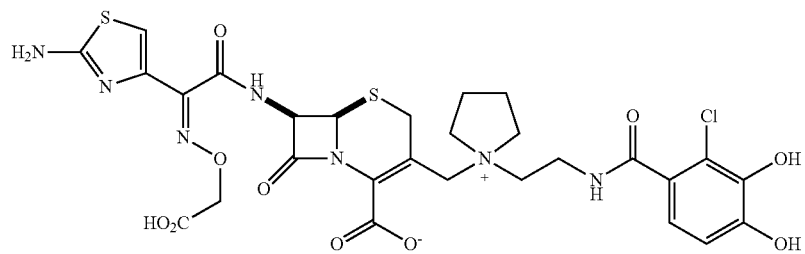
(A-7)
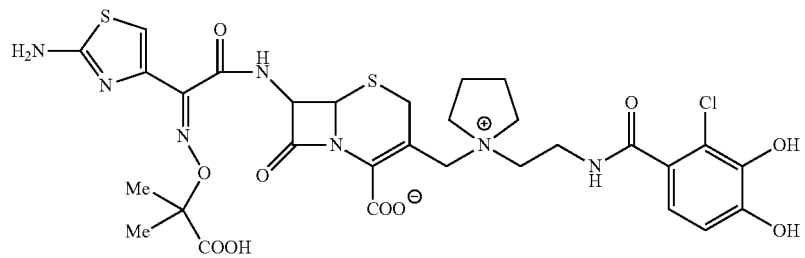
(A-8)
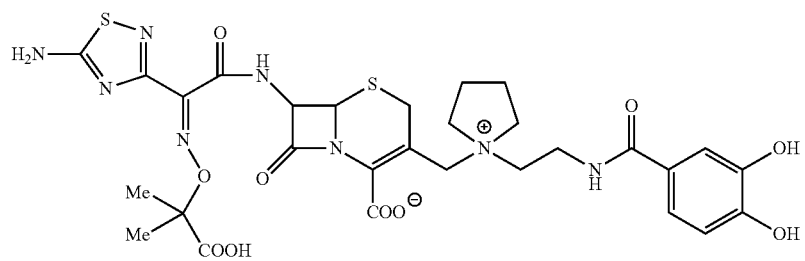
(A-9)
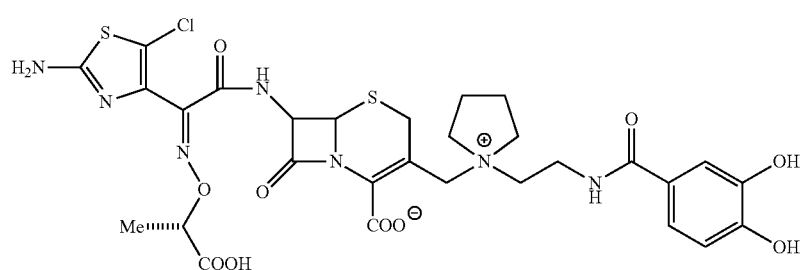
(A-10)
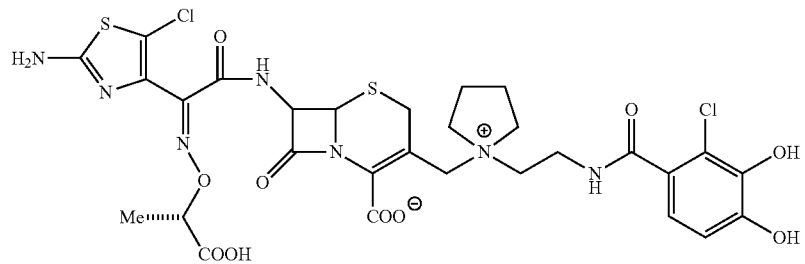
(A-11)

-continued
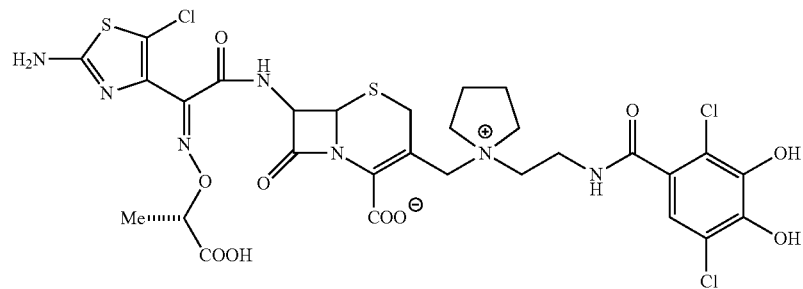
(A-12)
[Formula 16]
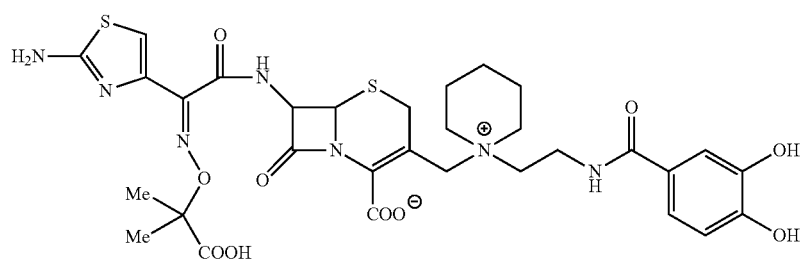
(A-13)
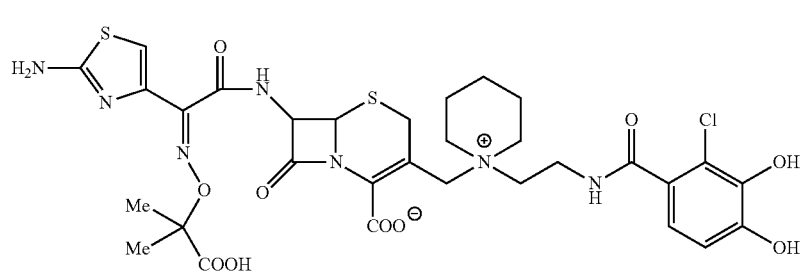
(A-14)
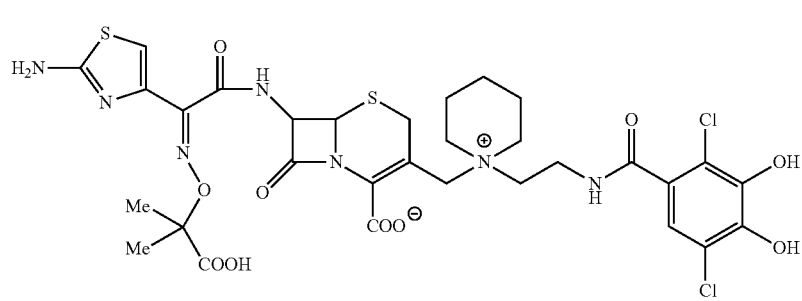
(A-15)
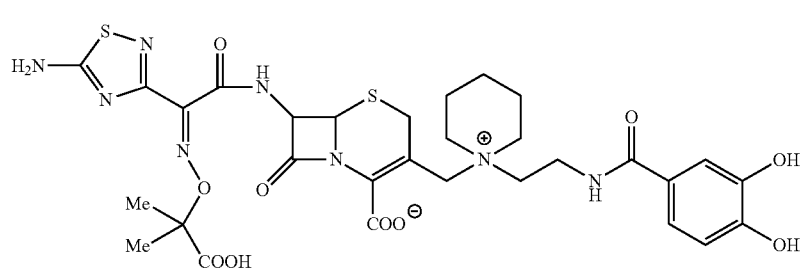
(A-16)

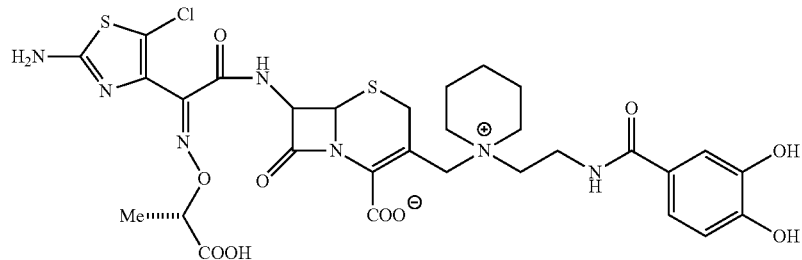
(A-17)
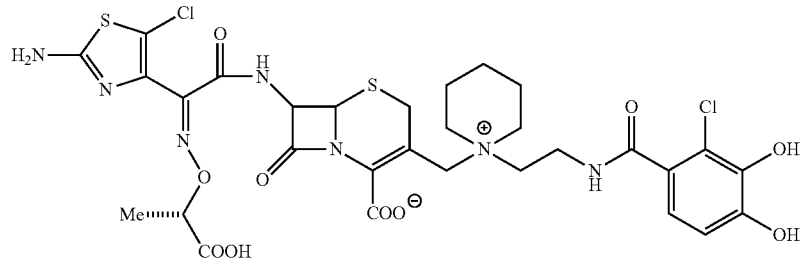
(A-18)
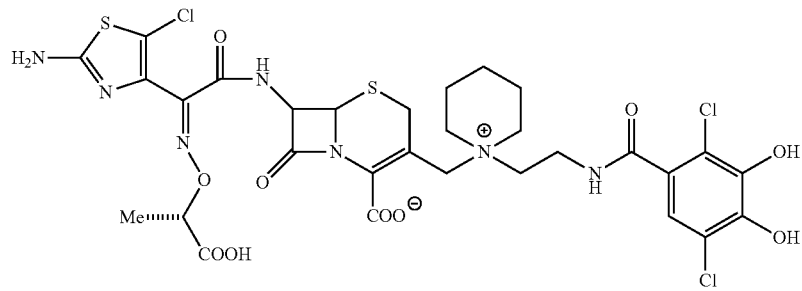
(A-19)
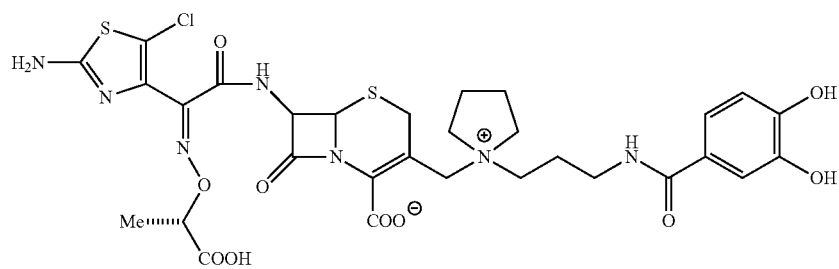
(A-20)
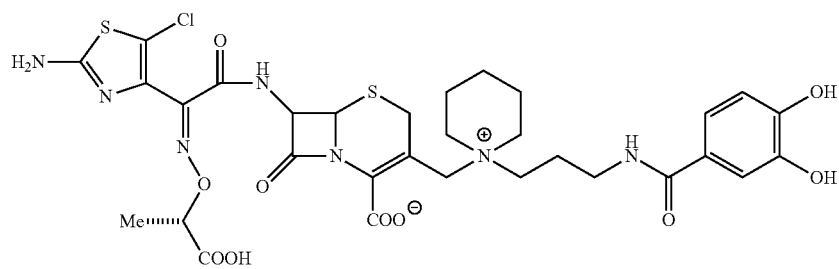
(A-21)

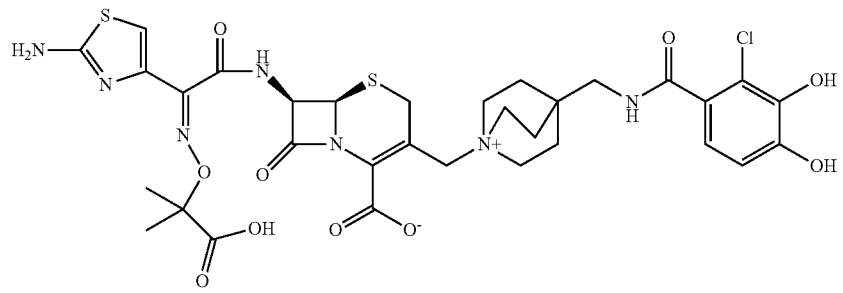
(A-22)
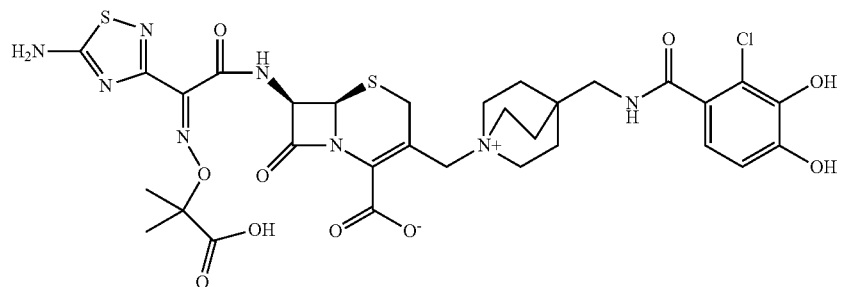
(A-23)
[Formula 17]
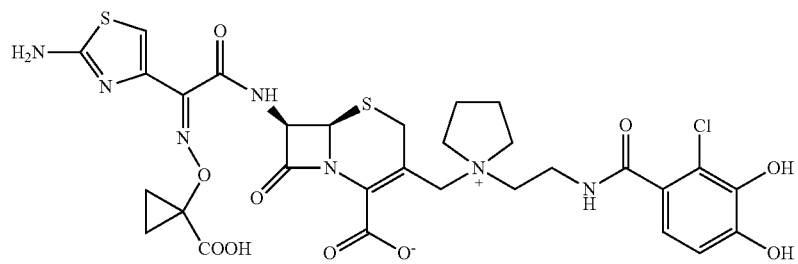
(A-24)
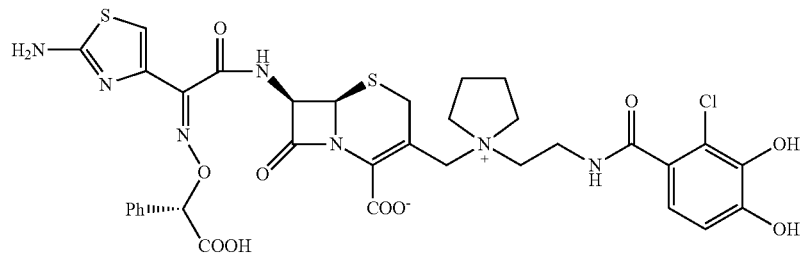
(A-25)
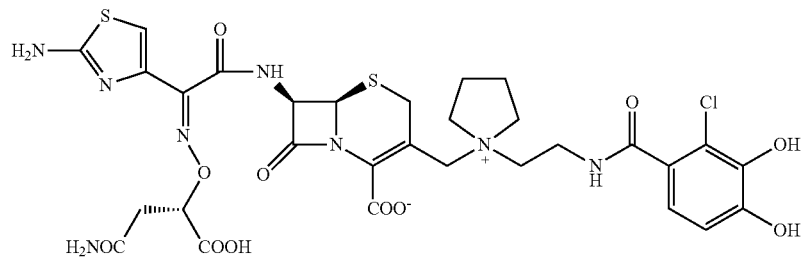
(A-26)

-continued
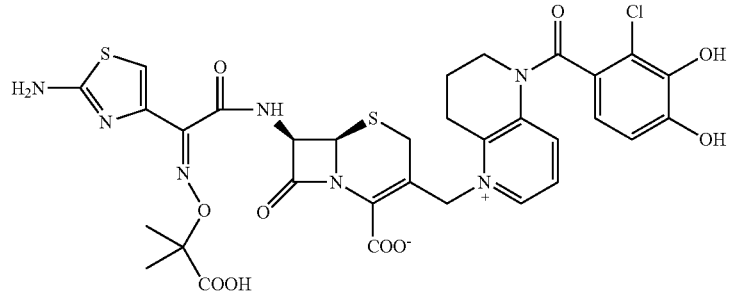
(A-27)
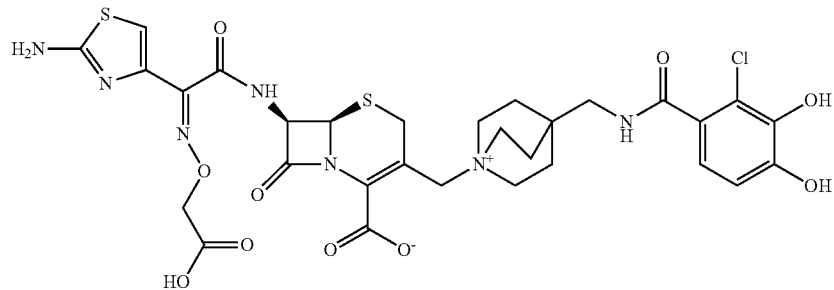
(A-28)
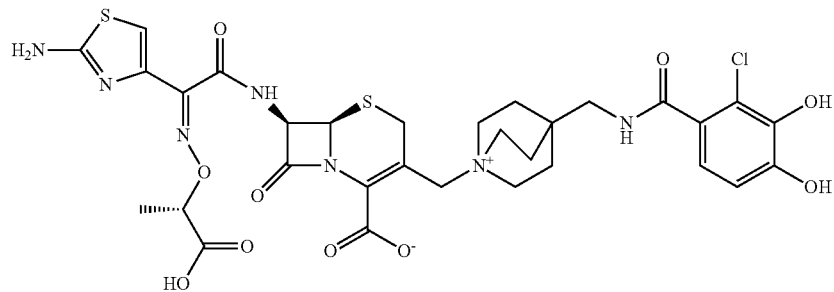
(A-29)
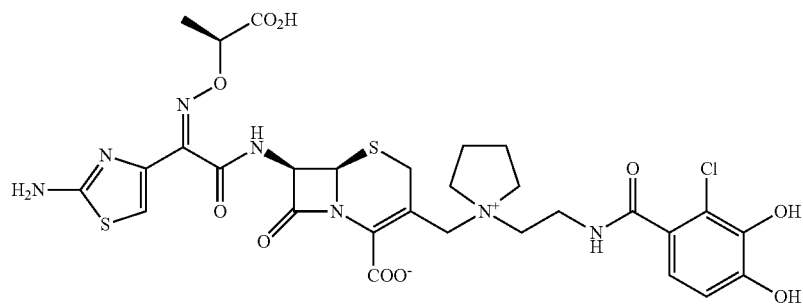
(A-30)
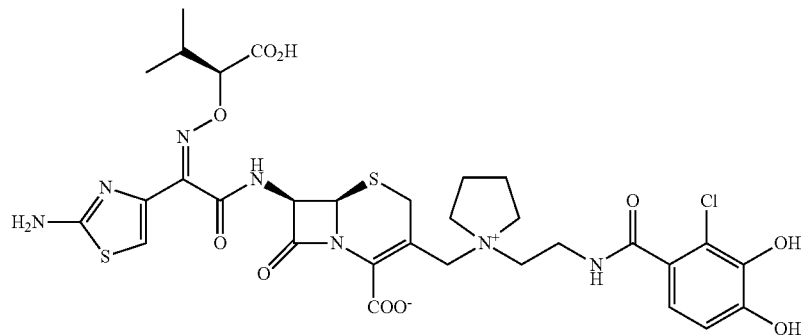
(A-31)

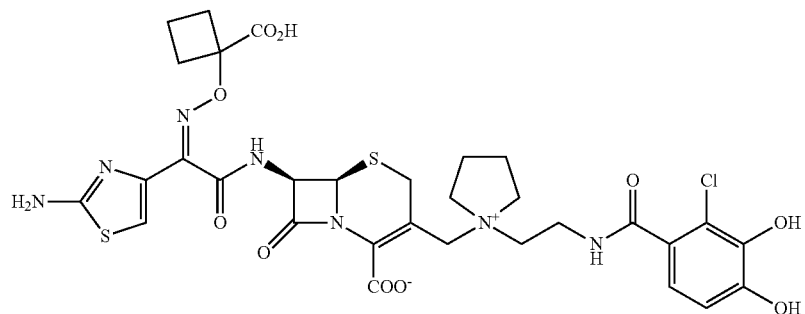

(A-32)

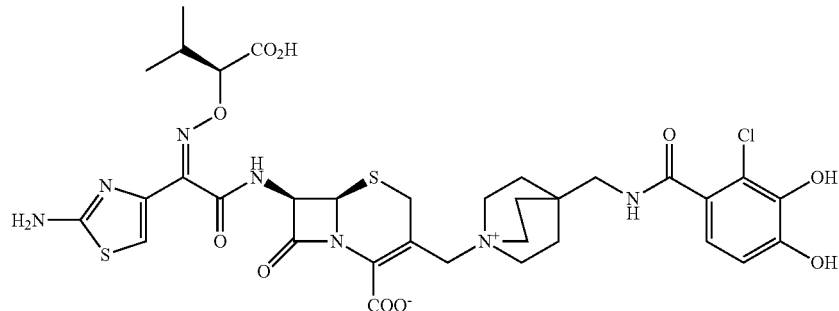

(A-33)

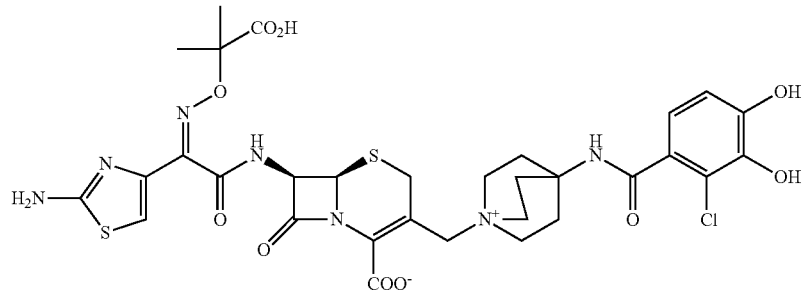

(A-34)

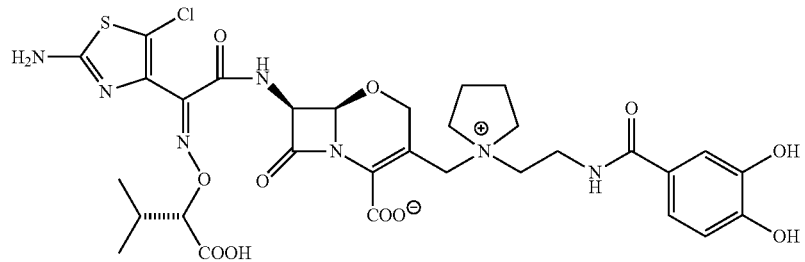

(A-35)

or an ester, a protected compound at the amino on the ring in the 7-side chain, a pharmaceutically acceptable salt, or a solvate thereof.

(Item 2')

The compound, or an ester, a protected compound at the amino on the ring in the 7-side chain, a pharmaceutically acceptable salt, or a solvate thereof according to item 1', wherein G is —C(=O)—; D is a single bond, —NH—, or —W—NH— wherein $R^7$ is lower alkylene; and E is selected from the formulae (1) to (40).

(Item 3')

The compound, or an ester, a protected compound at the amino on the ring in the 7-side chain, a pharmaceutically acceptable salt, or a solvate thereof according to item 2', wherein D is —NH—, —$CH_2$—NH— or —$CH_2$—$CH_2$—NH—.

(Item 4')

The compound, or an ester, a protected compound at the amino on the ring in the 7-side chain, a pharmaceutically acceptable salt, or a solvate thereof according to item 2', wherein D is a single bond.

(Item 5')

The compound, or an ester, a protected compound at the amino on the ring in the 7-side chain, a pharmaceutically acceptable salt, or a solvate thereof according to item 4', wherein E is a group selected from the formulae (1) to (4), (7), (12) to (25), (27) and (28).

(Item 6')

The compound, or an ester, a protected compound at the amino on the ring in the 7-side chain, a pharmaceutically acceptable salt, or a solvate thereof according to item 4', wherein E is a group selected from the formulae (1) to (3), (7) and (12).

(Item 7')

The compound, or an ester, a protected compound at the amino on the ring in the 7-side chain, a pharmaceutically acceptable salt, or a solvate thereof according to item 1', wherein G is —C(=O)—; and D is a group of the formula:

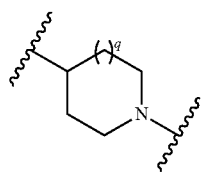

[Formula 18]

wherein q is as defined in item 1'.

(Item 8')

The compound, or an ester, a protected compound at the amino on the ring in the 7-side chain, a pharmaceutically acceptable salt, or a solvate thereof according to item 1', wherein G is a 5-membered heterocyclic group; and D is —CH$_2$— or —CH$_2$—CH$_2$—.

(Item 9')

The compound, or an ester, a protected compound at the amino on the ring in the 7-side chain, a pharmaceutically acceptable salt, or a solvate thereof according to any one of items 1' to 8', wherein U is —S—.

(Item 10')

The compound, or an ester, a protected compound at the amino on the ring in the 7-side chain, a pharmaceutically acceptable salt, or a solvate thereof according to any one of items 1' to 9', wherein W is —CH$_2$—.

(Item 11')

The compound, or an ester, a protected compound at the amino on the ring in the 7-side chain, a pharmaceutically acceptable salt, or a solvate thereof according to any one of items 1' to 10', wherein R$^3$ is hydrogen or —OCH$_3$.

(Item 12')

The compound, or an ester, a protected compound at the amino on the ring in the 7-side chain, a pharmaceutically acceptable salt, or a solvate thereof according to any one of items 1' to 11', wherein X is —N=, —CH= or —C(—Cl)=.

(Item 13')

The compound, or an ester, a protected compound at the amino on the ring in the 7-side chain, a pharmaceutically acceptable salt, or a solvate thereof according to any one of items 1' to 12', wherein a group of the formula:

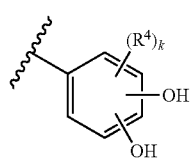

[Formula 19]

is a group of the formula:

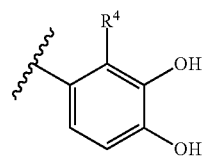

[Formula 20]

wherein R$^4$ is as defined in item 1'.

(Item 14')

The compound, or an ester, a protected compound at the amino on the ring in the 7-side chain, a pharmaceutically acceptable salt, or a solvate thereof according to any one of items 1' to 13', wherein each R$^4$ is independently hydrogen or halogen.

(Item 15')

The compound, or an ester, a protected compound at the amino on the ring in the 7-side chain, a pharmaceutically acceptable salt, or a solvate thereof according to any one of items 1' to 14', wherein R$^1$ is optionally substituted lower alkyl; and R$^2$ is hydrogen.

(Item 16')

The compound, or an ester, a protected compound at the amino on the ring in the 7-side chain, a pharmaceutically acceptable salt, or a solvate thereof according to any one of items 1' to 14', wherein R$^1$ is hydrogen; and R$^2$ is optionally substituted lower alkyl.

(Item 17')

The compound, or an ester, a protected compound at the amino on the ring in the 7-side chain, a pharmaceutically acceptable salt, or a solvate thereof according to any one of items 1' to 14', wherein R$^1$ and R$^2$ are independently lower alkyl.

(Item 18')

The compound, or an ester, a protected compound at the amino on the ring in the 7-side chain, a pharmaceutically acceptable salt, or a solvate thereof according to any one of items 1' to 17', wherein m is 0.

(Item 19')

A pharmaceutical composition, which comprises a compound, or an ester, a protected compound at the amino on the ring in the 7-side chain, a pharmaceutically acceptable salt, or a solvate thereof according to any one of items 1' to 18'.

(Item 20')

The pharmaceutical composition according to item 19', which possesses an antimicrobial activity.

(Item 21')

A method for treating an infectious disease, characterized in the step of administering the compound, or, an ester, a protected compound at the amino on the ring in the 7-side chain, a pharmaceutically acceptable salt, or a solvate thereof according to any one of items 1' to 18'.

(Item 22')

The compound, or an ester, a protected compound at the amino on the ring in the 7-side chain, a pharmaceutically acceptable salt, or a solvate thereof according to anyone of items 1' to 18', for treating an infectious disease.

(Item 23')

Use of the compound, or an ester, a protected compound at the amino on the ring in the 7-side chain, a pharmaceutically acceptable salt, or a solvate thereof according to any one of items 1' to 18', for manufacturing an infectious disease therapeutic agent.

Effects of the Invention

The compounds of the subject invention are useful as a pharmaceutical product in that the compounds have at least one of the following features:

1) The compound exhibits broad antimicrobial spectrum against a variety of bacteria including Gram negative bacteria;
2) the compounds exhibit potent antimicrobial activity against beta-lactamase producing Gram negative bacteria;
3) the compounds exhibit potent antimicrobial activity against multi drug resistant bacteria, in particular, Class B type, metallo-beta-lactamase producing Gram negative bacteria;
4) the compounds exhibit potent antimicrobial activity against extended-spectrum beta-lactamase (ESBL) producing bacteria;
5) the compounds do not exhibit cross resistance with known Cephem drugs and/or Carbapenem drugs; and
6) the compounds do not exhibit side effects such as fever after administration into the body.
7) the compounds are highly soluble in water and suitable for parenteral injection.

EMBODIMENTS FOR CARRYING OUT THE INVENTION

The respective terms used herein are as defined alone or in combination with other terms as follows:

"Halogen" includes fluorine, chlorine, bromine and iodine. Preferably, halogen is fluorine, chlorine and bromine, more preferably halogen is fluorine and chlorine, and especially preferably halogen is chlorine'

"Lower alkyl" includes linear or branched alkyl having 1-8 carbons, preferably 1-6 carbons, and more preferably 1-4 carbons, and includes, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl and the like.

"Lower alkylene" includes linear alkylene having 1-8 carbons, preferably 1-6 carbons, more preferably 1-4 carbons, and most preferably one or two carbons, and includes, for example, methylene, ethylene, n-propylene, n-butylene, n-pentylene, n-hexylene and the like.

"Halo(lower)alkyl" refers to a group in which at least one position of said "lower alkyl" is substituted with the above "halogen", and includes, for example, monofluoromethyl, difluoromethyl, trifluoromethyl, monochloromethyl, dichloromethyl, trichloromethyl, monobromomethyl, monofluoroethyl, monochloroethyl, chlorodifluoromethyl, and the like. Preferably, halo(lower)alkyl is trifluoromethyl, or trichloromethyl.

Substituent groups for "optionally substituted lower alkyl" include at least one group selected from Substituent Group Alpha. When substitution is carried out with a plurality of the group of Substituent Group Alpha, such groups may be the same or different. Substituent groups for "optionally substituted lower alkylene" include optionally substituted lower alkyl, and at least one group selected from Substituent Group Alpha. When substitution is carried out with a plurality of substituent groups, such substituent groups may be the same or different.

Here, "Substituent Group Alpha" is a group consisting of halogen, hydroxy, lower alkoxy, hydroxy, (lower) alkoxy, lower alkoxy(lower)alkoxy, carboxy, amino, acylamino, lower alkylamino, imino, hydroxyimino, lower alkoxyimino, lower alkylthio, carbamoyl, lower alkylcarbomoyl, hydroxy (lower)alkylcarbamoyl, sulfamoyl, lower alkylsulfamoyl, lower alkylsulfinyl, cyano, nitro, carbocyclic group, and heterocyclic group.

The lower alkyl moiety in "lower alkoxy", "hydroxy(lower)alkoxy", "lower alkoxy(lower)alkoxy", "lower alkylamino", "lower alkoxyimino", "lower alkylthio", "lower alkylcarbamoyl", "hydroxy (lower) alkylcarbamoyl" "lower alkylsulfamoyl", and "lower alkylsulfinyl" is as defined above for "lower alkyl".

Preferred embodiments of substituent groups for "optionally substituted lower alkyl" include fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "optionally substituted lower alkyl" include, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, and the like.

"Carbocyclic group" includes cycloalkyl, cycloalkenyl, aryl and non-aromatic fused carbocyclic groups, and the like. The term includes divalent radical (cycloalkylene, cycloalkenylene, arylene), as well as aforementioned monovalent group.

"Cycloalkyl" is a carbocyclic group having 3-10 carbons, preferably 3-8 carbons, more preferably 4-8 carbons, and includes, for example, cyclopropyl, cyclobutyl, cyclopethyl, cyclohexyl, cycloheptyl, cyclooctyl, cyclononyl, cyclodecyl, and the like.

"Cycloalkenyl" includes those having at least one double bond at any position in a cycloalkyl ring, and specifically includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like and in particular, phenyl is preferable.

"Non-aromatic fused carbocyclic group" includes a group in which two or more cyclic groups selected from the "cycloalkyl", "cycloalkenyl," and "aryl" are fused, and specifically includes, for example, indanyl, indenyl, tetrahydronaphthyl, and fluorenyl, and the like.

"Heterocyclic group" includes heterocyclic groups having at least one hetero atom selected from O, S and N, in the ring thereof, and specifically includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl and thienyl and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic group such as carbazolyl, acridinyl, xanthenyl, phenothiadinyl, phenoxathiinyl, phenoxazinyl, dibenzofuryl, imidazoquinolyl and the like; non-aromatic heterocyclic group such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihydrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, heterocyclic group is a 5- or 6-membered heteroaryl or non-aromatic heterocyclic group, and more preferably, a 5- or 6-membered heteroaryl.

These include divalent heterocyclic group, as well as aforementioned monovalent heterocyclic group.

Substituent groups for "optionally substituted carbocyclic group" and "optionally substituted heterocyclic group" include optionally substituted lower alkyl and at least one group selected from Substituent Group Alpha.

Preferred embodiments of substituent groups for "optionally substituted carbocyclic group" and "optionally substituted heterocyclic group" include methyl, ethyl, isopropyl, text-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"5-membered heterocyclic group" includes pyrrolidine, pyrazolidine, imidazolidine, tetrahydrofuran, tetrahydrothiophene, furan, pyrrole, oxazole, oxadiazole, isoxazole, and the like.

Examples of the case that "R$^1$ and R$^2$ taken together with a neighboring atom may form optionally substituted carbocyclic group or optionally substituted heterocyclic group" include the cases where the following formula:

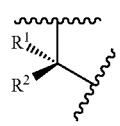

[Formula 21]

wherein each symbol is as defined in item 1, is cycloalkyl, cycloalkenyl, or a non-aromatic heterocyclic group for example, groups of the following formulae:

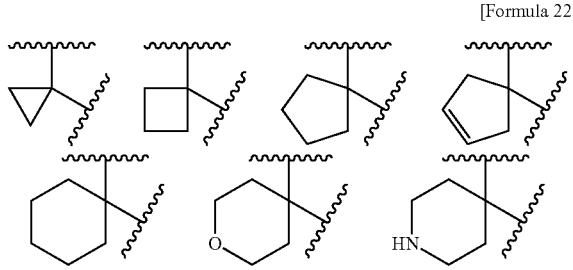

[Formula 22]

optionally having a substituent group selected from Substituent Group Alpha on the ring.

In the moiety "E", "optionally substituted cyclic group selected from the formulae (1) to (45)" includes groups in which a hydrogen atom on a carbon atom of each cyclic group is substituted with one or more groups which are the same or different and selected from optionally substituted lower alkyl or Substituent Group Alpha. Preferred embodiments of the substituent groups include methyl, ethyl, isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like. More preferred embodiment is non-substitution.

The carboxyl group and/oz hydroxyl group in the compound of the invention may exist as anion wherein proton has been eliminated (—COO$^-$ group and/or —O$^-$ group).

The amino group in the compound of the invention may exist as ammonium ion with proton (—NH$_3^+$ group).

Examples or embodiments for each moiety in Formula (I) are shown below. However, the scope of the subject invention is not limited to those described below.

Examples of "X" include —N═, —CH═, —C(—CH$_3$)═, —C(—CF$_3$)═, —C(—Br)═, —C(—Cl)═, and the like. Preferably, "X" is —N═, —CH═, and —C(—Cl)═.

In a preferred embodiment, "W" is —CH$_2$—, and "U" is —CH$_2$—, —S— or —O—. More preferably, "W" is —CH$_2$—, and "U" is —S— or —O—. Still more preferably, "W" is —CH$_2$—, and "U" is —S—.

Examples of "R$^1$ and R$^2$" include a hydrogen atom, a fluorine atom, a chlorine atom, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, phenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, furyl, thienyl, and the like.

Preferred combinations of R$^1$ and R$^2$ include, as (R$^1$, R$^2$), (hydrogen atom, hydrogen atom), (methyl, hydrogen atom), (hydrogen atom, methyl), (methyl, methyl), (ethyl, hydrogen atom), (hydrogen atom, ethyl), (ethyl, ethyl), (phenyl, hydrogen atom), (hydrogen atom, phenyl), (carboxymethyl, hydrogen atom), (hydrogen atom, carboxymethyl), (carboxyethyl, hydrogen atom), (hydrogen atom, carboxyethyl), (hydroxyethyl, hydrogen atom), (hydrogen atom, hydroxylethyl) (carbamoylmethyl, hydrogen atom), (hydrogen atom, carbamoylmethyl) (trifluoromethyl, hydrogen atom), (carboxy, hydrogen atom), (carbamoylethyl, hydrogen atom), (benzyl, hydrogen atom), (4-hydroxybenzyl, hydrogen atom), (cyanomethyl, a hydrogen atom) and the like. More preferred combinations are (hydrogen atom, hydrogen atom), (methyl, methyl), (carboxymethyl, hydrogen atom).

Preferred embodiments of the case where "R$^1$ and R$^2$ taken together with a neighboring atom may form optionally substituted carbocyclic group, or optionally substituted heterocyclic group" include optionally substituted 3- to 8-membered cycloalkyl, optionally substituted 3- to 8-membered cycloalkenyl, or 3- to 8-membered non-aromatic heterocyclic groups. More preferred embodiments include the case where the following formula:

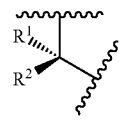
[Formula 23]

wherein each symbol is as defined in item 1, is any one of the following formulae:

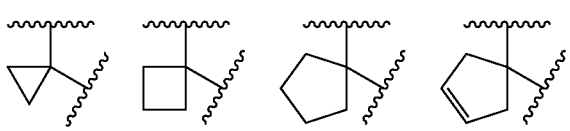
[Formula 24]

Examples of "Q" include a single bond, phenyl, pyridil. Especially preferable is a single bond.

"m" is preferable be integer number of 0 or 1, and especially preferable is 0.

"$R^3$" is preferable to be a hydrogen atom, or —$OCH_3$. Especially preferable is a hydrogen atom.

The preferable of the formula:

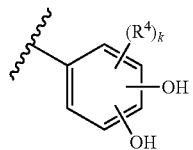
[Formula 9]

are the formula:

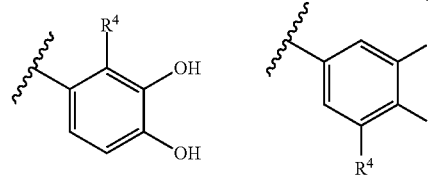
[Formula 26]

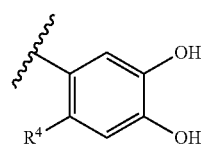

wherein $R^4$ is as defined in item 1.

More preferable is

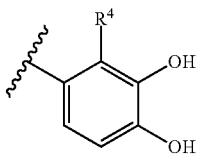
[Formula 27]

Examples of "$R^4$" include a hydrogen atom, a chlorine atom, a fluorine atom, a bromine atom, cyano, hydroxy, acetyl, methoxy, ethoxy, trifluoromethyl, methyl, and the like. Preferably, $R^4$ is a hydrogen atom, a chlorine atom, a fluorine atom, hydroxyl, methoxy, or methyl. More preferably, $R^4$ is a hydrogen atom, a chlorine atom, or a fluorine atom. Especially preferable is a hydrogen atom, or a chlorine atom "K" is preferable to be 1 or 2, and especially preferable is 1.

Examples of "-E-D-G-" include the following formulae (1A)-(46A):

[Formula 28]

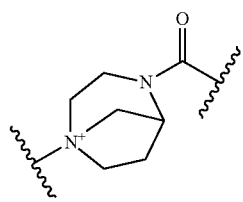
(1A)

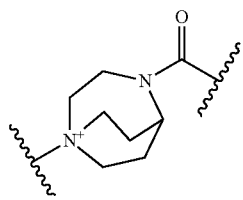
(2A)

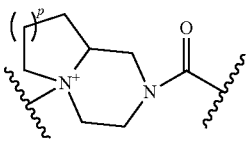
(3A)

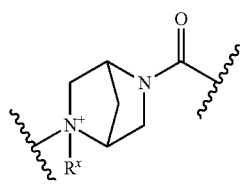
(4A)

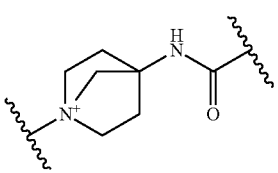
(5A)

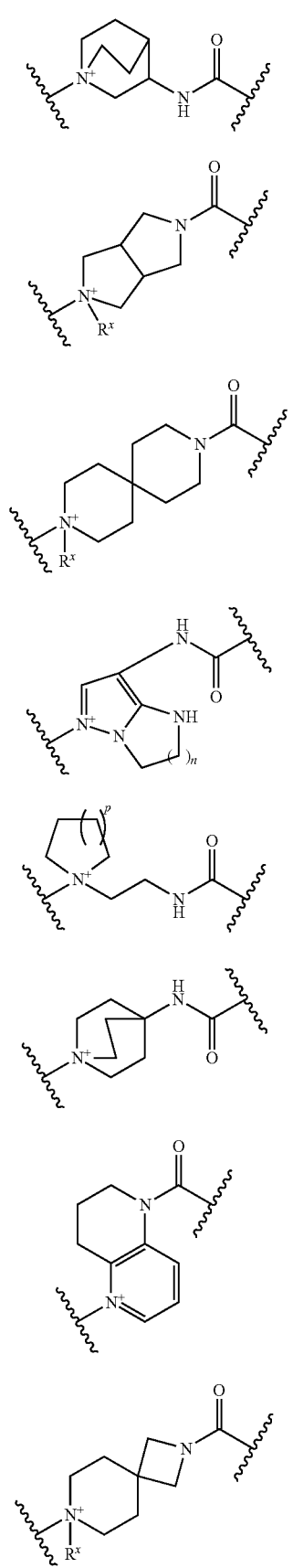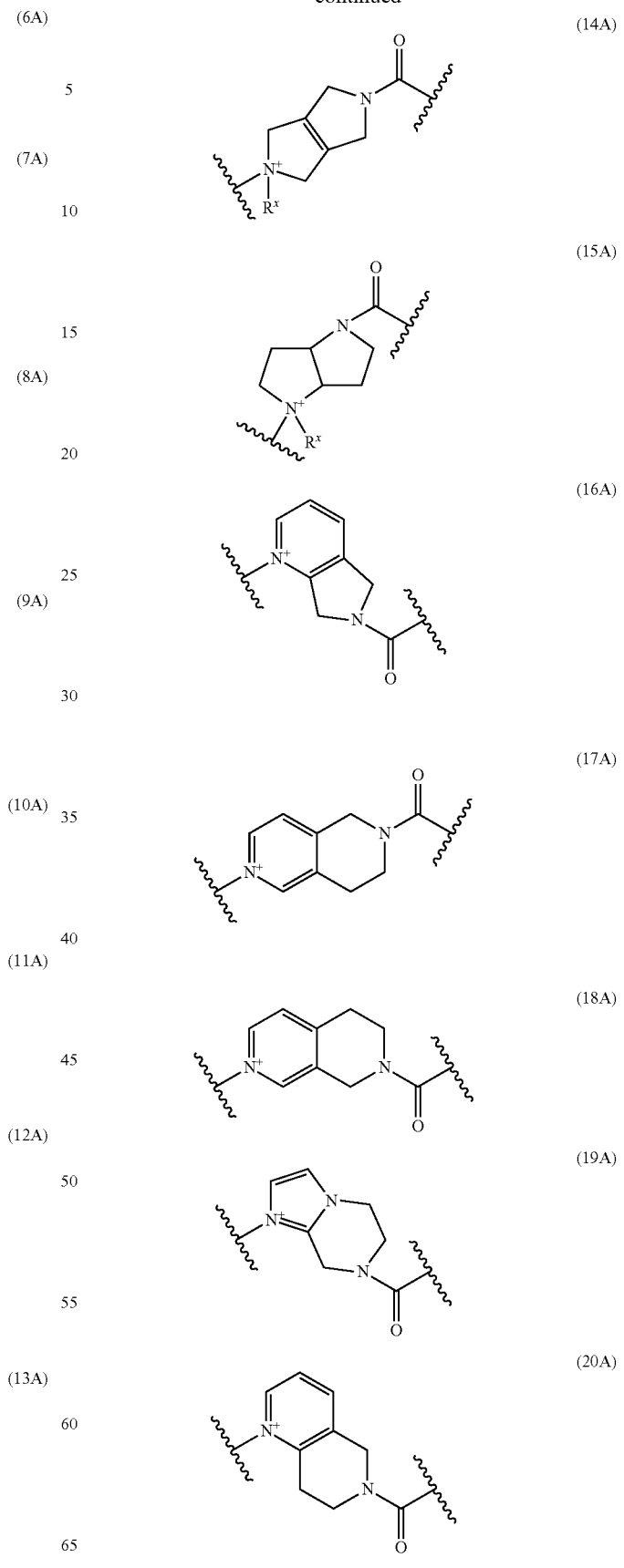

[Formula 29]
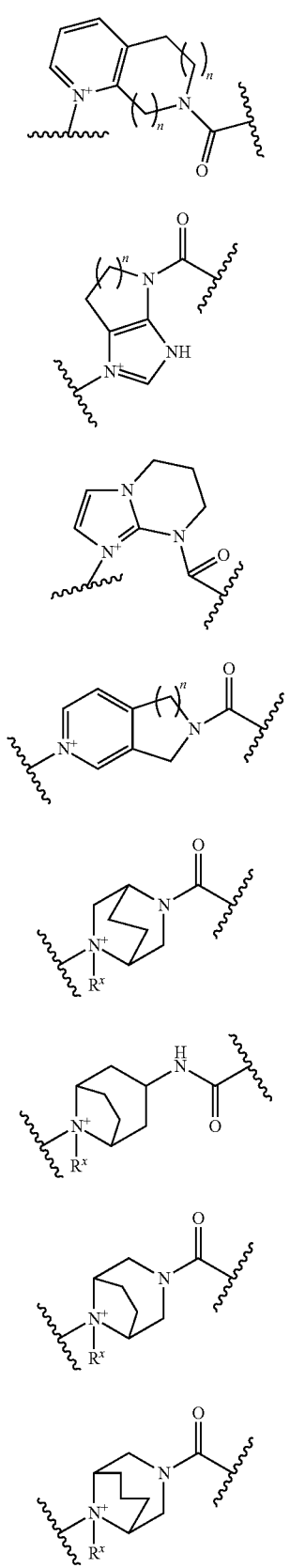
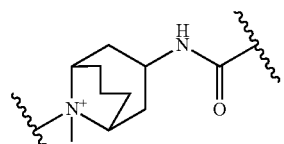
(29A)
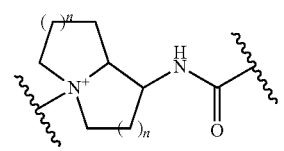
(30A)
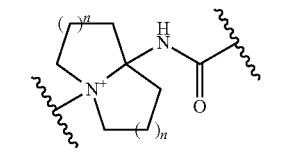
(31A)
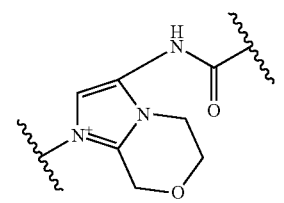
(32A)
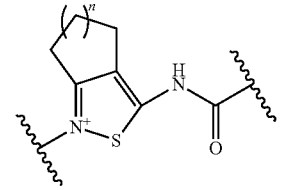
(33A)
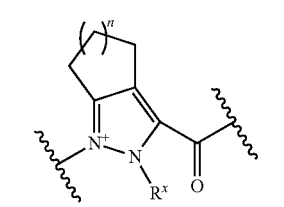
(34A)
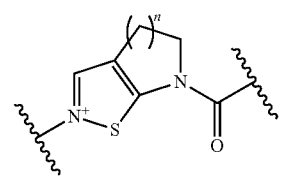
(35A)
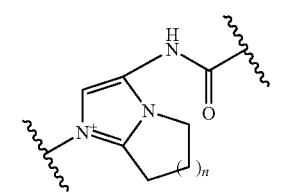
(36A)

-continued
(37A) 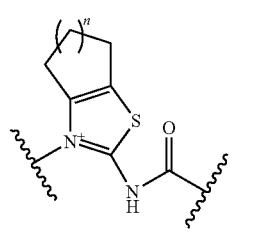
(38A) 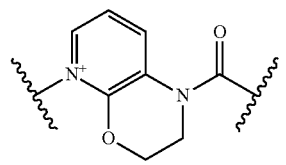
(39A) 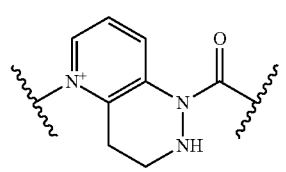
(40A) 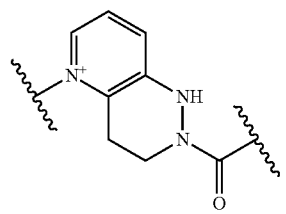
[Formula 30]
(41A) 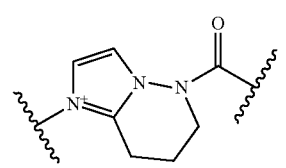
(42A) 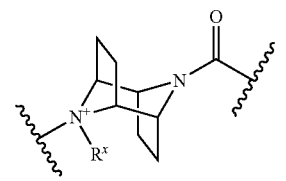
(43A) 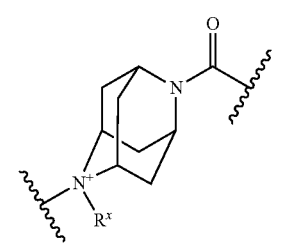
(44A) 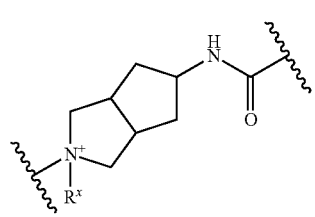
-continued
(45A) 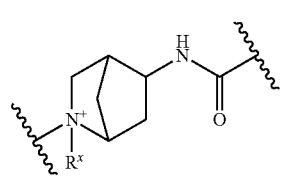
(46A) 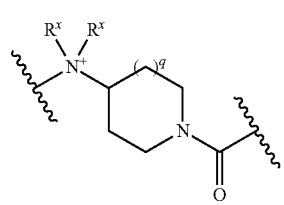
wherein p is an integer from 1 to 3; n is an integer of 1 or and $R^x$ is optionally substituted lower alkyl.
Here, examples of Rx include methyl, ethyl, trifluoromethyl, carboxymethyl, carbamoylmethyl, hydroxyethyl, and the like.
Preferred embodiments of "E-D-G" include the following formulae (1B)-(48E):
[Formula 31]
(1B) 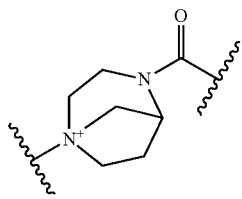
(2B) 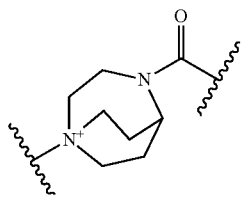
(3B) 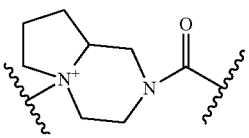
(4B) 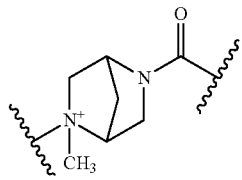
(5B) 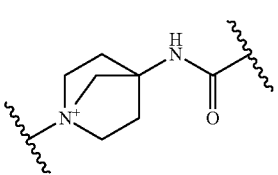

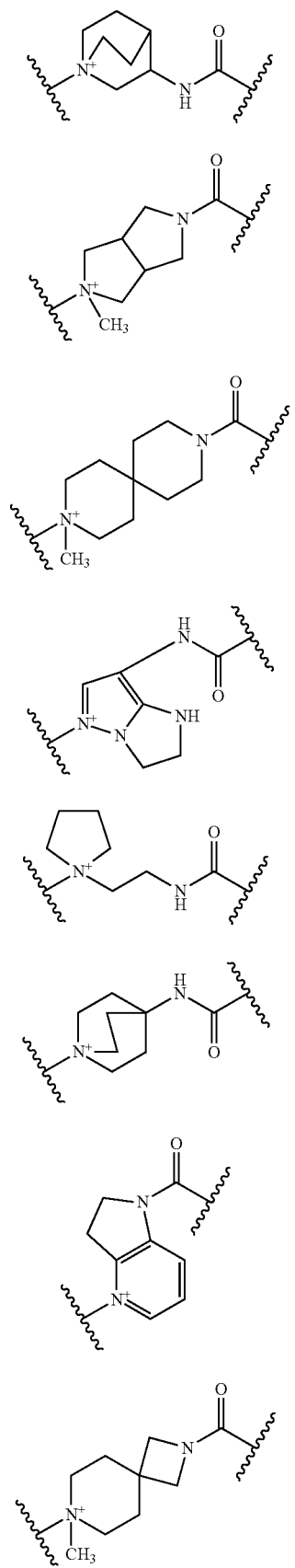
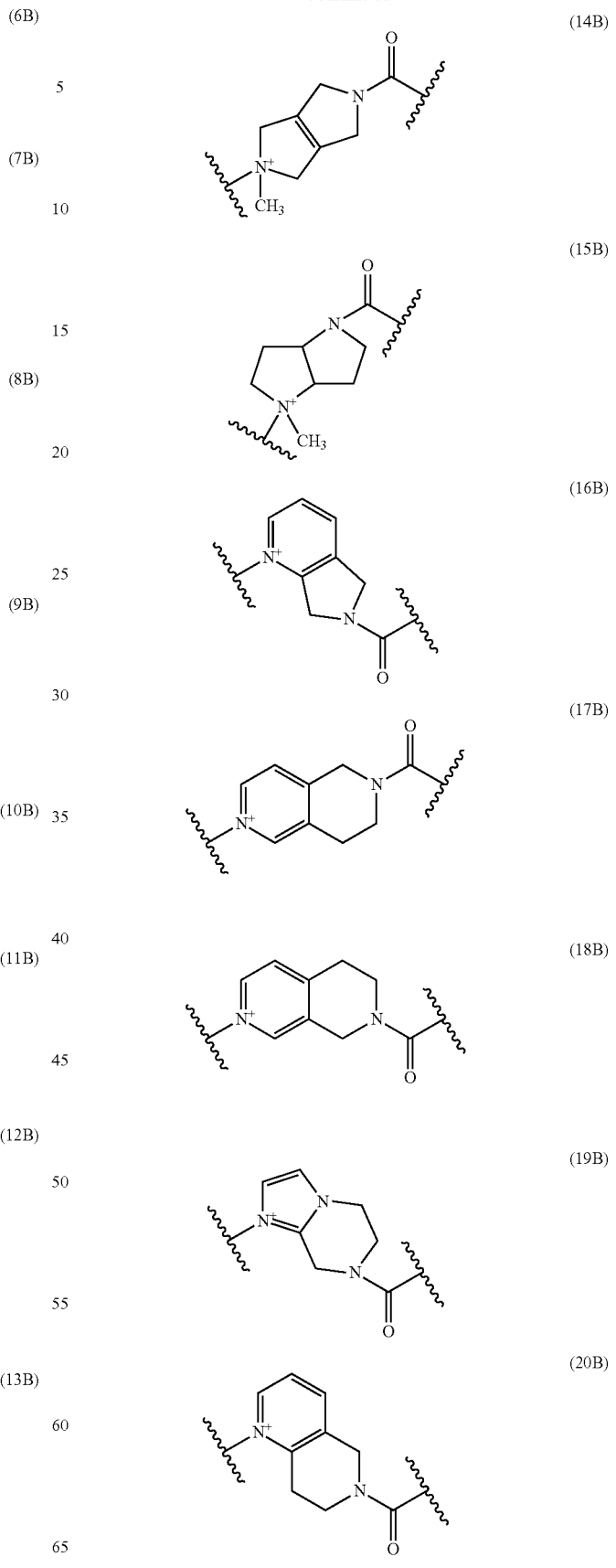

[Formula 32]
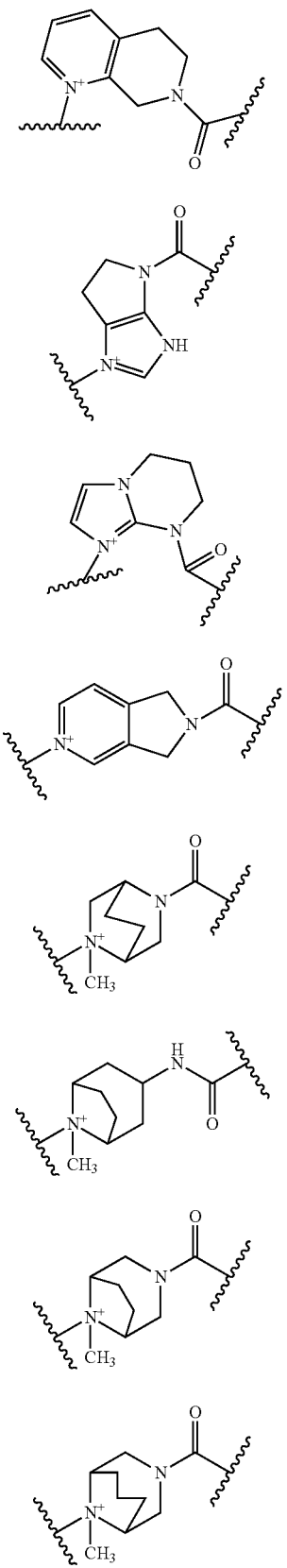
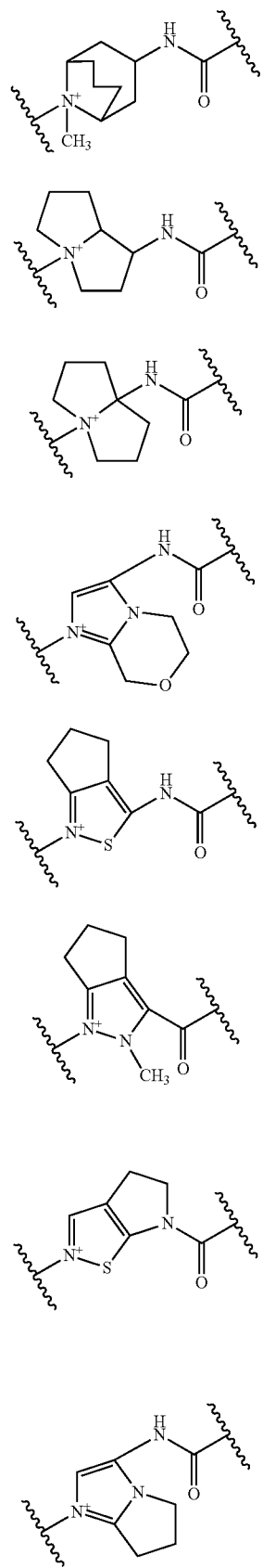

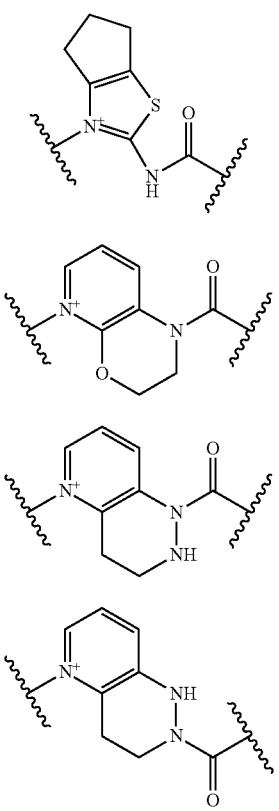
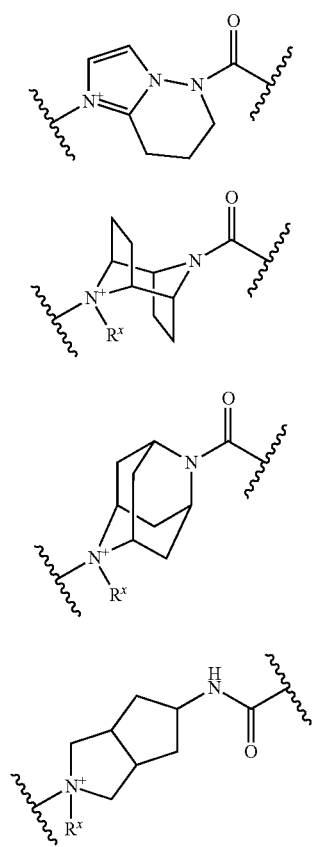
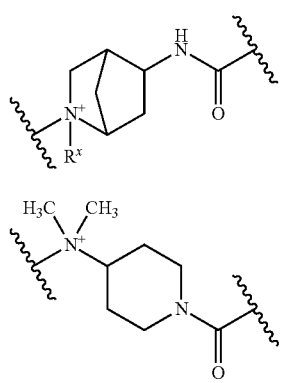
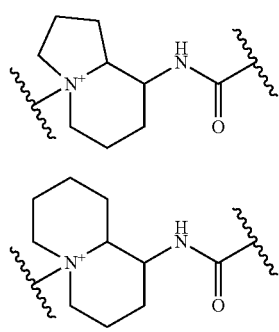
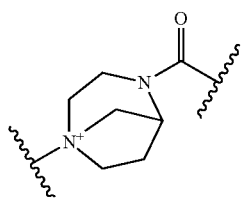
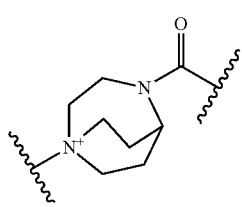
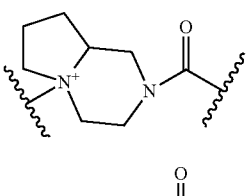
Still more preferred embodiments of "-E-D-G-" include the following formulae:
[Formula 34]

-continued
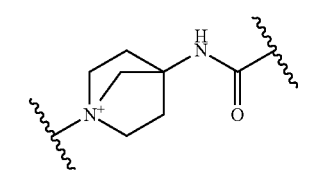
(5B)
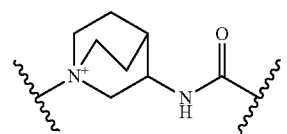
(6B)
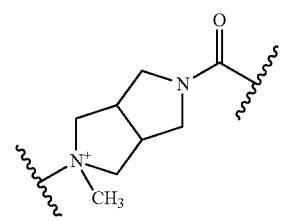
(7B)
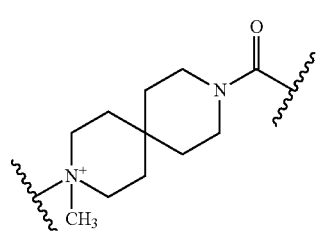
(8B)
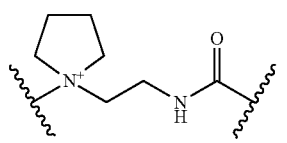
(10B)
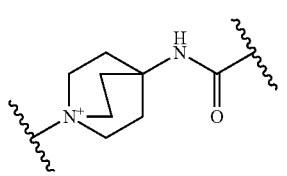
(11B)
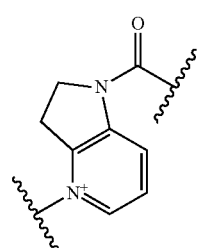
(12B)
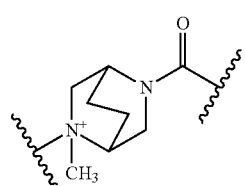
(25B)
-continued
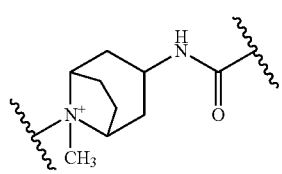
(26B)
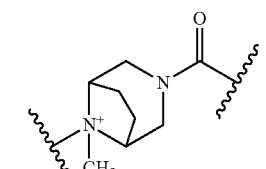
(27B)
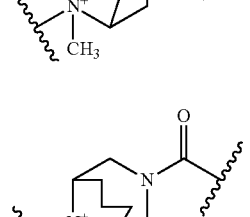
(28B)
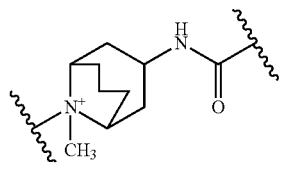
(29B)
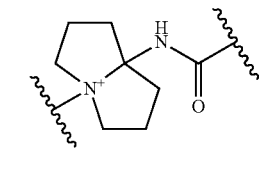
(31B)
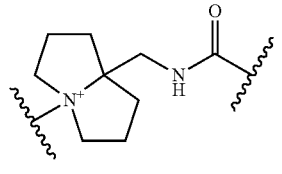
(31B')
Still especially preferred embodiments of "E-D-G" include the following formulae:
[Formula 35]
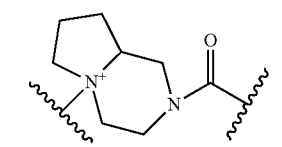
(3B)
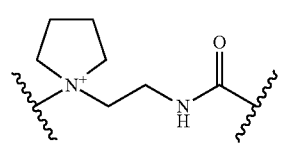
(10B)

-continued

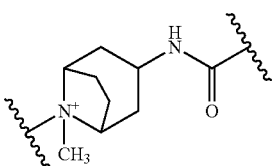
(26B)

The nomenclature of the substitution position on the Cephem skeleton of Formula (I) is as follows. As used herein, 7-side chain and 3-side chain refer to groups binding to the 7-position and the 3-position of the Cephem skeleton as shown below, respectively.

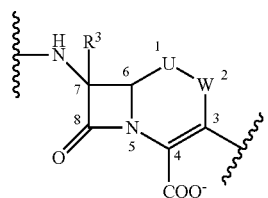
[Formula 36]

Esters of Formula (I) preferably include those esters at the carboxyl on the 7-side chain and/or at the 4-position. Esters at the carboxyl group on the 7-side chain refer to compounds having a structure in which the carboxyl group at the terminal of the oxime group is esterified as shown in the formula:

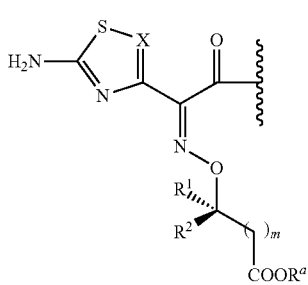
[Formula 37]

wherein each symbol is as defined in Item 1 and $R^a$ represents an ester residue such as a carboxyl-protecting group. Such esters include those esters that are readily metabolized in the body to form a carboxylic state.

Esters at the carboxyl group at the 4-position of Formula (I) refer to compounds having a structure in which the carboxyl group at the 4-position of the cephem skeleton is esterified as shown in the formula:

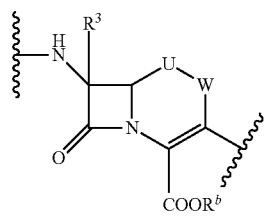
[Formula 38]

wherein each symbol is as defined in Item 1 and $R^b$ is an ester residue such as a carboxyl-protecting group. Such esters include those esters that are easily metabolized in the body to form a carboxylic state.

The aforementioned carboxyl-protecting group may be of any group as long as it can be used for protection and/or deprotection by a method such as described in Protective Groups in Organic Synthesis, Theodora W Green (John Wiley & Sons) and for examples include lower alkyl (e.g., methyl, ethyl, t-butyl), lower alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

A compound protected at the amino on the 7-side chain of Formula (I) refers to a structure in which the amino on the ring has been protected, as shown in the formula:

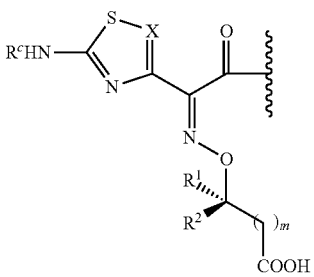
[Formula 39]

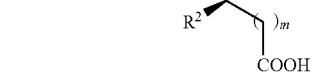

wherein each symbol is as defined in Item 1, and $R^c$ represents an amino-protecting group. Such amino-protecting groups include those groups that are readily metabolized in the body to form amino. The aforementioned amino-protecting group may be of any group as long as it can be used for protection and/or deprotection by a method such as described in Protective Groups in Organic Synthesis, Theodora W Green (John Wiley & Sons) and for examples include lower alkoxycarbonyl (e.g. t-butoxycarbonyl, benzyloxycarbonyl, p-nitrobenzyloxycarbonyl), optionally substituted aralkanoyl (e.g., benzoyl, p-nitrobenzoyl), acyl (e.g., formyl, chloroacetyl), and the like.

Salts of Formula (I) include those formed with a counter cation (s) after the hydrogen atom (s) of the carboxyl group at the 4-position, the carboxyl group at the 7-position side chain, and/or the hydroxyl group on the catechol group is dissociated; those formed by the amino group in the 7-position side chain with an inorganic or organic acid; and those formed by the quaternary amine moiety in the 3-side chain with a counter anion.

Pharmaceutically acceptable salts of Formula (I) include, for example, salts or intramolecular salts formed with inorganic base, ammonia, organic base, inorganic acid, organic acid, basic amino acid, halogen ions, and the like. Such inorganic bases include, for example, alkali metal (Na, K, etc.) and alkali earth metal (Mg, etc.). Organic bases include, for example, procaine, 2-phenylethylbenzyl amine, dibenzylethylenediamine, ethanolamine, diethanolamine, trishydroxymethylaminomethane, polyhydroxyalkylamine, O-methyl glucosamine, and the like. Inorganic acids include, for example, hydrochloric acid, hydrobromic acid, sulfuric acid, nitric acid, phosphoric acid, and the like. Organic acids include, for example, p-toluene sulfonic acid, methane sulfonic acid, formic acid, acetic acid, trifluoroacetic acid, maleic acid and the like. Basic amino acids include, for example, lysine, arginine, ornithine, histidine, and the like.

As used herein, "solvate" refers to a solvate with water or organic solvent (for example, methanol, ethanol, isopropyl alcohol, acetone), and preferably a hydrate.

The Compound (I) of the subject invention is not limited to particular isomers, but includes any possible isomers and racemates as exemplified below:

For example, the formula in Formula (I)

[Formula 40]

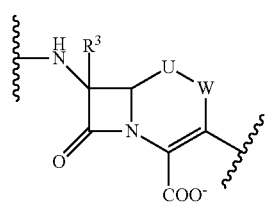

(wherein each symbol is as defined in Item 1) includes

[Formula 41]

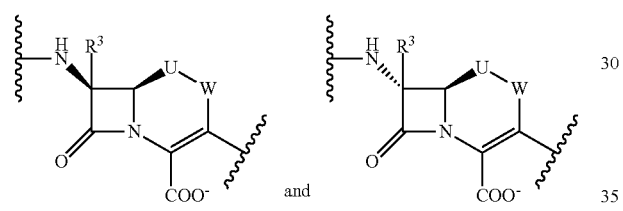

(wherein each symbol is as defined in item 1).

For example, the formula in Formula (I) includes:

[Formula 42]

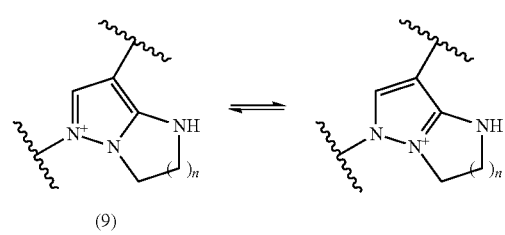

(9)

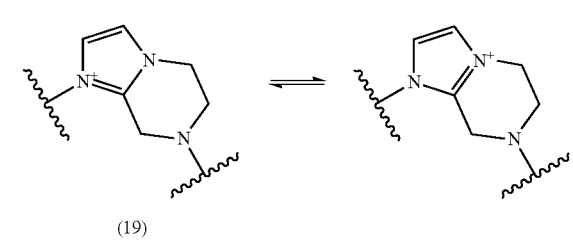

(19)

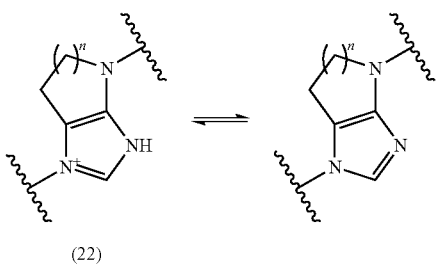

(22)

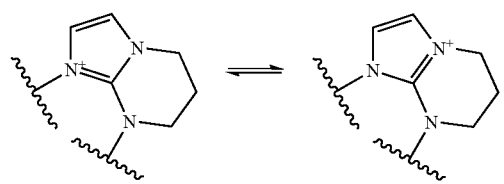

(23)

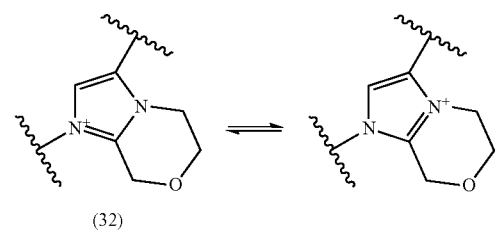

(32)

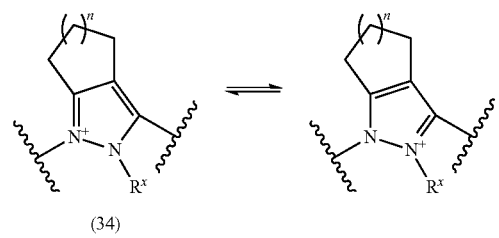

(34)

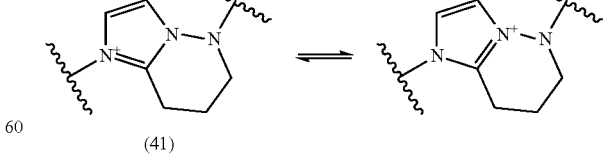

(41)

(wherein each symbol is as defined in item 1).

The compounds represented by Formula (I) of the subject invention can be manufactured, for example, by a general synthesis method described below.

[Formula 43]
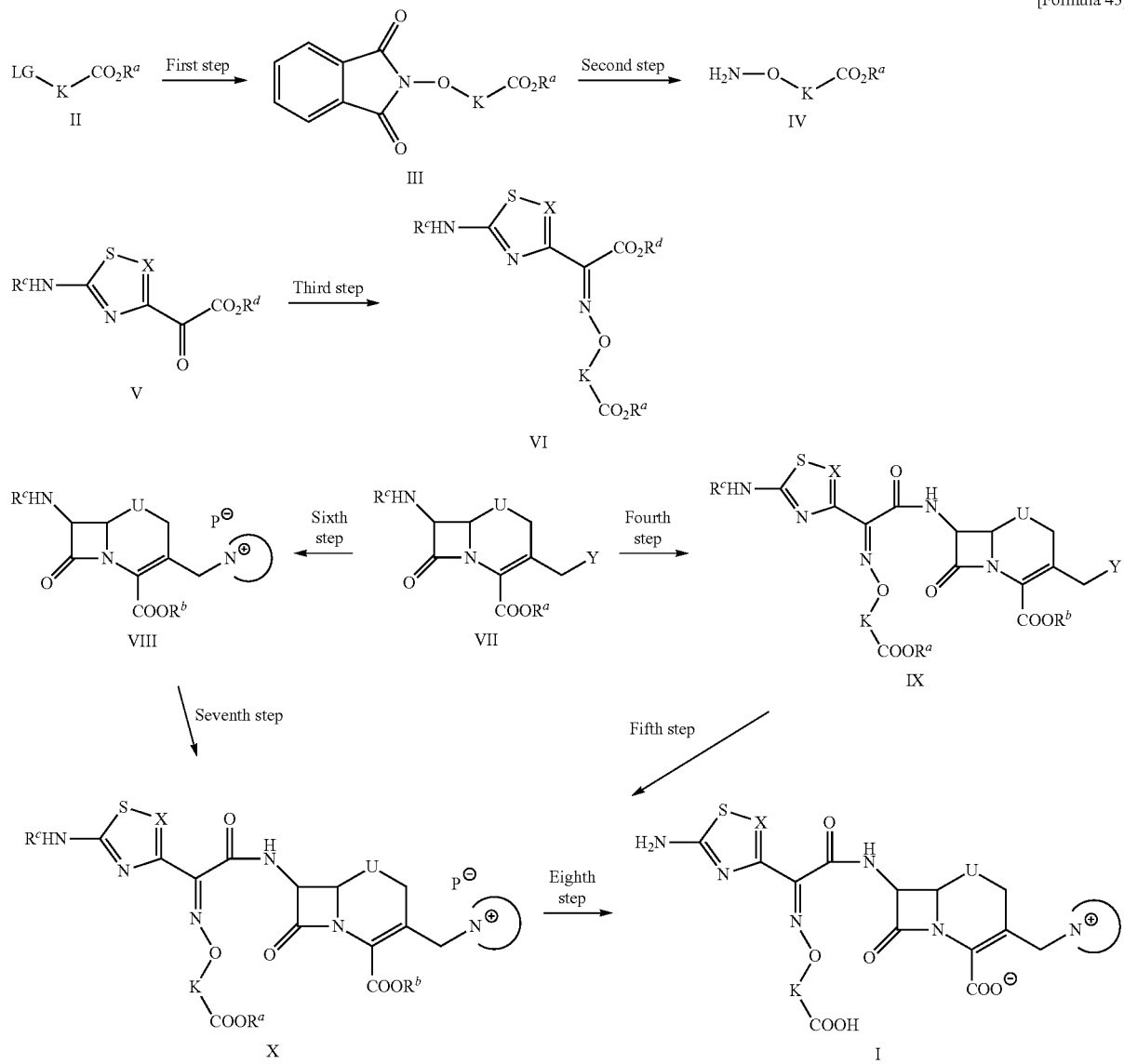
(wherein X, U, $R^a$, $R^b$, $R^c$ are as defined above, $P^-$ is a counter anion of a quaternary amine,
K represents the formula:
[Formula 44]
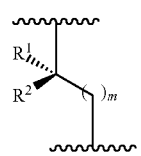
(wherein each symbol is as defined above);
the formula:
[Formula 45]
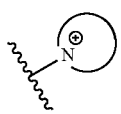
is the following moiety in Formula (I) including a quaternary ammonium group moiety of 3-side chain:
[Formula 46]
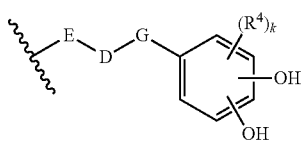
(wherein each symbol is defined as above);

LG and Y are leaving groups (for example, hydroxy, halogen (Cl, Br, I), carbamoyloxy, acyloxy, methanesulfonyloxy, toluenesulfonyloxy that may be substituted, etc.);

$R^d$ is hydrogen or a carboxy protecting group; and $R^e$ is hydrogen or an amino protecting group.)

1) Starting Materials for the 7-Side Chain: Synthesis of Compound (VI)

The First Step:

Compound (III) is obtained by a reaction with N-hydroxyphthalimide in the presence of Compound (II) (LG is hydroxy) and a Mitsunobu reagent, or in the presence of Compound (II) (LG is another leaving group) and a base (such as sodium hydroxide, sodium methoxide). The amount of N-hydroxyphthalimide used is generally 1-5 molar equivalents, preferably, 1-2 molar equivalents, relative to Compound (II)

Examples of reaction solvents include ethers (e.g., dioxane, tetrahydrofuran, diethyl ether, tert-butyl methyl ether, diisopropyl ether), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), and the like, and mixed solvents and the like thereof.

The reaction temperature is in a range of, genera y, about −50 to 100° C., preferably about −40 to 50° C., and more preferably about −30 to 0° C.

The Second Step:

N-Methylhydrazine or hydrazine was added and reacted to Compound (III) to provide Compound (IV).

The amount of N-methylhydrazine or hydrazine used is in a range of about 1-10 molar equivalents, preferably 1-5 molar equivalents, more preferably 1-2 molar equivalents, relative to Compound (III). Examples of reaction solvents include ethers (e.g., dioxane, tetrahydrofuran, diethyl ether, tert-butyl methyl ether, diisopropyl ether), esters (e.g., ethyl formate, ethyl acetate, isopropylacetate), halogenated hydrocarbons (e.g., dichloromethane, chloroform, carbon tetrachloride), hydrocarbons (e.g., n-hexane, benzene, toluene), alcohols (e.g., methanol, ethanol, isopropanol), amides (e.g., formamide, N,N-d*methylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents thereof. The reaction temperature is in a range of, generally, about 0 to 100° C., preferably about 0 to 50° C., more preferably about 10 to 30° C.

The Third Step:

Compound (V), which is commercially available or obtained by a known method, is added and reacted with Compound (IV) to provide Compound (VI). (e.g., as described in Bioorganic & Medicinal Chemistry, vol. 15, p. 6716-6732 (2007)).

Compound (III) is added and reacted with N-Methylhydrazine or hydrazine to provide Compound (IV).

Examples of reaction solvents include ethers (e.g., dioxane, tetrahydrofuran, diethyl ether, tert-butyl methyl ether, diisopropyl ether), esters (e.g., ethyl formate, ethyl acetate, isopropylacetate), halogenated hydrocarbons (e.g., dichloromethane, chloroform, carbon tetrachloride), hydrocarbons (e.g. n-hexane, benzene, toluene), alcohols (e.g., methanol, ethanol, isopropanol), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water and the like, and mixed solvents thereof. The reaction temperature is in a range of, generally, about 0 to 100° C., preferably about 0 to 50° C., more preferably about 10 to 30° C.

2) 7-Amidation and Formation of the 3-Side Chain; Synthesis of Compound (X)

The Fourth Step (7-Amidation Reaction):

Compound (IX) is obtained by reacting Compound (VI) with Compound (VII), which are commercially available or synthesized according to methods described in a document (e.g., JP 60-231689 A, JP 62-149682 A, etc.). In this case, preferably, $R^a$ and $R^b$ are carboxy protecting groups, $R^c$ is an amino protecting group, and $R^d$ and $R^e$ are hydrogen. The amount of Compound (VI) used is in a range of, generally, about 1-5 moles, preferably 1-2 moles, relative to 1 mole of Compound (VII). Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles MeCN, propionitrile), dimethylsulfoxide, water, and the like, and mixed solvents and the like thereof.

The reaction temperature is in a range of, generally, about −40 to 80° C., preferably about −20 to 50° C., more preferably about −10 to 30° C.

The above-described amidation reaction may be carried out after a carboxy moiety is converted to a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, etc.), alkali earth metal (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonates, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound 2-pyridylthiol esters), and the like. Furthermore, in the above-described reaction, a suitable condensing agent may be used as desired. For example, hydrochloric acid salt of 1-dimethylaminopropyl-3-ethylcarbodiimide (WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethyipyridinium iodide, 2-fluoromethylpyridinium iodide, trifluoioaceticanhydride, and the like can be used as a condensing agent.

The Fifth Step (3-Side Chain Forming Reaction):

Compound (X) is obtained by reacting Compound (IX) and a corresponding tertiary amine. In this case, preferably, $R^a$ and $R^b$ are carboxy protecting groups, and $R^c$ is an amino protecting group.

The amount of a corresponding tertiary amine used is in a range of, generally, 1-5 moles, preferably 1-2 moles, relative to 1 mole of Compound (IX).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methylethyl ketone), nitriles (e.g., MeCN, propionitrile), dimethylsulfoxide, water, and the like, and mixed solvents thereof. The reaction temperature is in a range of, generally, −20 to 60° C., preferably −10 to 4.0° C., more preferably 0 to 20° C. Furthermore, Compound (x) wherein U is SO can be obtained by reducing Compound (X) wherein U is SO. Examples of reducing agents include potassium iodide—acetyl chloride, and the like.

3) 3-Side Chain Formation and 7-Amidation; Synthesis of Compound (X)

The Sixth Step (3-Side Chain Forming Reaction):

Compound (VIII) is obtained by reacting Compound (VII) with a corresponding tertiary amine. In this case, preferably, $R^b$ is a carboxy protecting group, and $R^e$ is an amino protecting group. The amount of a corresponding tertiary amine used is in a range of, generally, 1-5 moles, preferably 1-2 moles, relative to 1 mole of Compound (VII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents thereof. The reaction temperature is in a range of, generally, −20 to 60° C., preferably −10 to 4° C., more preferably 0 to 20° C.

Both tertiary amine moieties used in the 3-side chain forming reactions of the fifth and the sixth steps (corresponding to the moiety E in item 1) can be obtained as a commercially available reagent, by a known method, and/or by a method described herein.

The Seventh Step (7-Amidation Reaction):

Compound (X) is obtained by reacting Compound (VIII) and Compound (VI). In this case, preferably, $R^a$ and $R^b$ are carboxy protecting groups, $R^c$ is an amino protecting group, $R^d$ and $R^e$ are hydrogen. The amount of Compound (VI) used is in a range of, generally, about 1-5 moles, preferably 1-2 moles, relative to 1 mole of Compound (VIII). Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents thereof. The reaction temperature is in a range of, generally, about −40 to 80° C., preferably about −20 to 50° C., more preferably about −10 to 30° C.

The above-described amidation reaction may be carried out after a carboxyl moiety is converted to a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, etc.), alkali earth metal (e.g., Ca, Mg), and the like. Examples of organic bases include trimethylamine, triethylamine, tert-butvidimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Examples of active thioesters include esters with aromatic heterocyclic thiol compound (e.g., 2-pyridythiol esters), and the like. Furthermore, in the above-described reaction, a suitable condensing agent may be used as desired. For example, hydrochloric acid salt of 1-dimethylaminopropyl-3-ethylcarbodlimide (WSCD.HCl), N,N'-dicyclohexylcarbodiimide, N,N'-carbonyldiimidazole, N,N'-thiocarbonyldiimiciazole, N-ethoxycarbonyl-2-ethoxy-1,2-dihydroquinoline, phosphorus oxychloride, alkoxyacetylene, 2-chloromethylpyridinium iodide, 2-fluoromethylpyridiniumiodide, t-difluoroacetic anhydride, and the like can be used as a condensing agent.

Furthermore, Compound (X) wherein U is 0 can be obtained using Compound (VII) wherein U is O.

4) Deprotection Reaction

The Eighth Step:

Compound (I) is obtained by subjecting Compound (X) to a deprotection reaction according to a method well known to those skilled in the art.

Examples of reaction solvents include ethers (e.g., anisole, dioxane, tetrahydrofuran, diethyl ether, tert-butyl methyl ether, diisopropyl ether), esters (e.g., ethyl formate, ethyl acetate, n-butyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles MeCN, propionitrile), nitros (e.g., nitromethane, nitroethane, nitrobenzene), dimethylsulfoxide, water, and the like. These solvents may be used alone or in a combination using two or more of such solvents. The reaction temperature is in a range of, generally, about −30 to 100° C., preferably about 0 to 50° C., more preferably about 0 to 10° C. As a catalyst, Lewis acid (e.g., $AlCl_3$, $SnCl_4$, $TiCl_4$), protonic acid (e.g., HCl, HBr, $H_2SO_4$, HCOOH), and the like can be used. The obtained Compound (I) is further chemically modified to obtain an ester, or a compound wherein the amino on the thiazole ring at the 7-position is protected, or a pharmaceutically acceptable salt, or a solvate thereof.

The compounds of the subject invention have a wide antimicrobial activity spectrum, and may be used for the prevention or treatment of a variety of diseases caused by pathogenic bacteria in mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

The compounds of the subject invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus* and the like), Gram negative bacteria colonized in respiratory system (*Haemophilus, Moraxella* and the like), and Gram negative bacteria of glucose non-fermentable (*Pseudomonas aeruginosa, Pseudomonas* other than *P. aeruginosa, Stenotrophomonas, Burkholderia, Acinetobacter* and the like). The compounds are stable against beta-lactamase Class A, B, C and D which are produced by these Gram negative bacteria, and have high antimicrobial activity against a variety of beta-lactam drug resistant Gram negative bacteria, such as ESBL producing bacteria and the like. These are extremely stable against metallo-beta-lactamase belonging to Class B including in particular IMP type, VIM type, L-1 type and the like, and thus, these are effective against Gram negative bacteria resistant to a variety of beta-lactam drug including Cephem and Carbapenem. Still more preferable compounds have features regarding kinetics in the body, such as high blood concentration, long duration of effects, and/or significant tissue migration. More preferable compounds are safe in terms of side effects. Also, more preferable compounds have high water solubility, and thus particularly suitable for injectable formulations.

Compounds (I) may be administered parenterally or orally as injectable formulations, capsules, tablets, and granules, and preferably, administered as an injectable formulation. The dosage may usually be about 0.1 to 100 mg/day, preferably, about 0.5 to 50 mg/day, per 1 kg of body weight of a patient or animal, and optionally be divided into 2 to 4 times per day. The carriers for use in injectable formulation may be, for example, distilled water, saline and the like, and further bases may be used for pH adjustment. The carriers for used in capsules, granules or tablets, carriers include known excipients (for example, starch, lactose, sucrose, calcium carbonate, calcium phosphate and the like), binders (for example, starch, acacia gum, carboxymethyl cellulose, hydroxypropyl cellulose, crystalline cellulose, and the like), lubricants (for example, magnesium stearate, talc and the like), and the like.

EXAMPLES

Hereinafter, the subject invention is described in more detail with working examples and experimental examples. However, the subject invention is not limited to them.

In the Examples, the meaning of each abbreviation is as described below.
ODS: Octadodecylsilyl
MeCN: Acetonitrile
WSCD.HCl: Hydrochloric acid salt of
N-ethyl-N'-(3-dimethylaminopropyl)carbodiimide
Me; Methyl
Et: Ethyl
Pr: Propyl
Ph: Phenyl
PMB: para-Methoxybenzyl
t-Bu: tert-Butyl
i-Pr: Isopropyl
Boc: tert-Butoxycarbonyl
BH: Benzhydryl
Ms: Methanesulfonyl
Trityl
TES: tert-Butyldimethylsilyl
Bn: Benzyl Example 1

Synthesis of Compound (I-1)

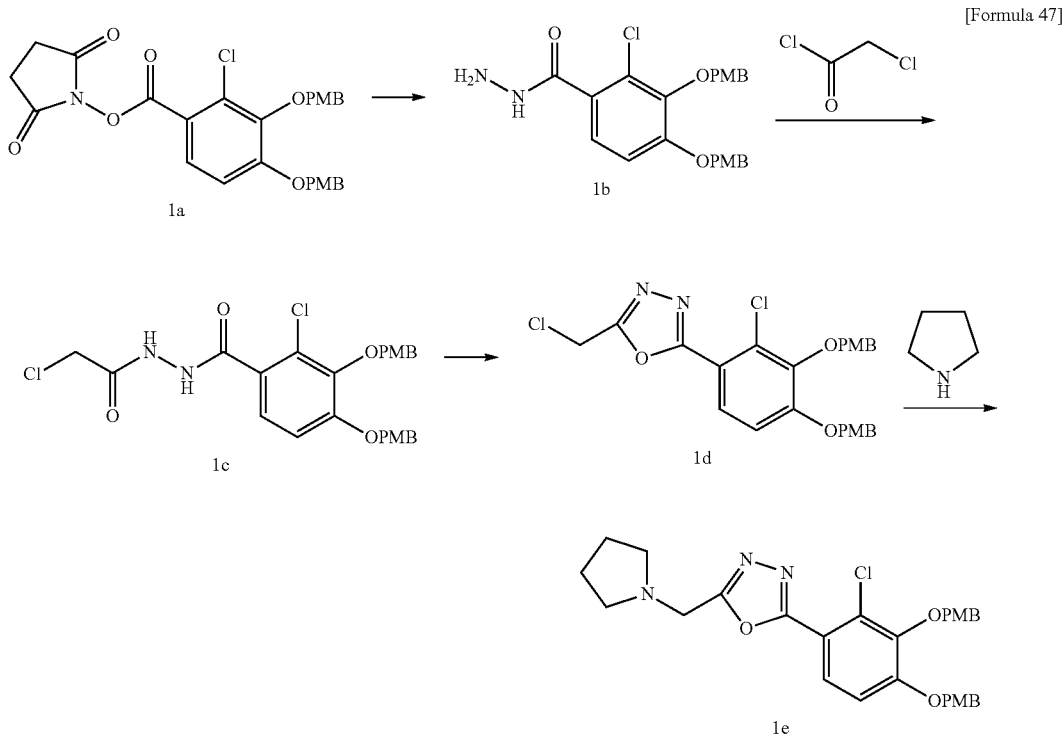

[Formula 47]

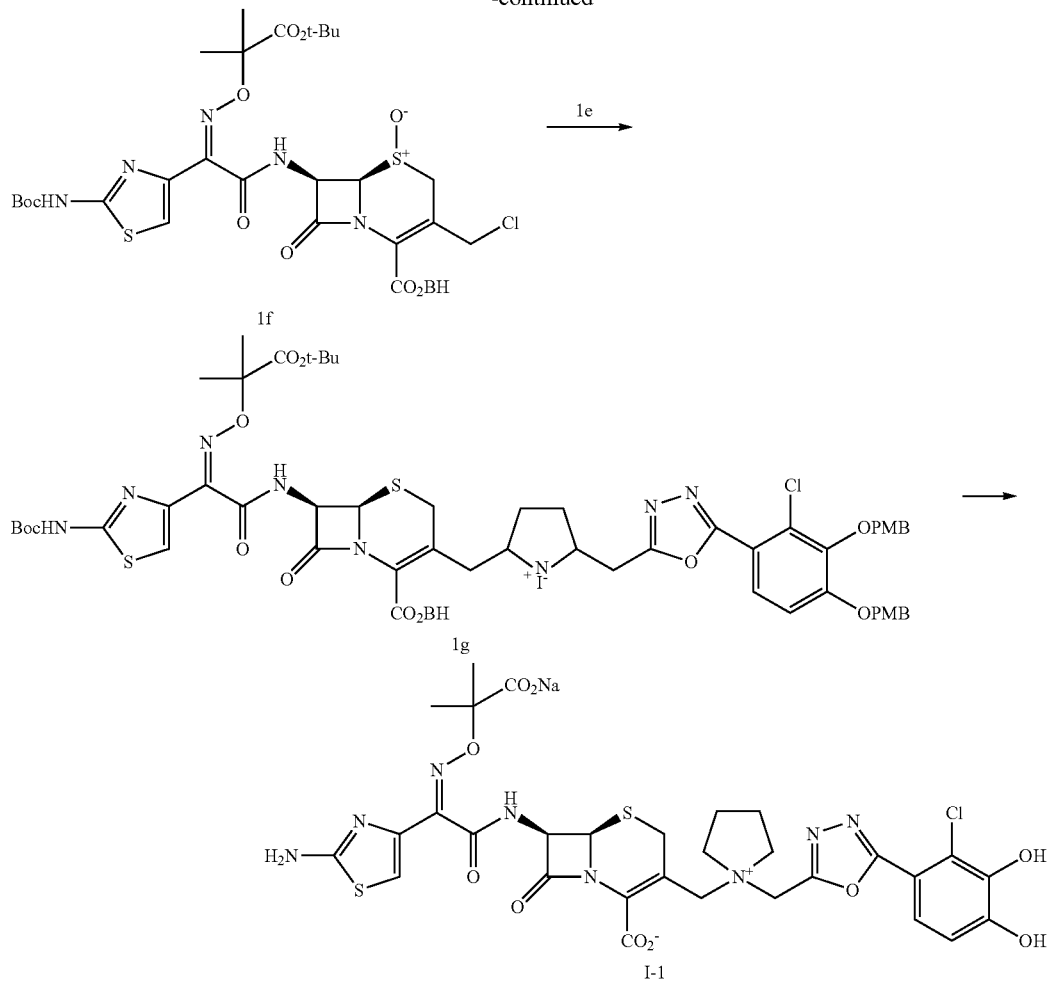

Step (1): Compound 1a→Compound 1b

Compound 1a (5.26 g, 10 mmol) was suspended N,N-dimethylformamide (50 mL). Hydrazine monohydrate (0.73 mL, 15 mmol) was added thereto with stirring, and then stirred at room temperature for 14 hours. Water was added to the reaction solution, the resulting solid was filtrated, washed with isopropanol, then diisopropyl ether, and then dried in vacuo to yield Compound 1b (4.03 g, 91%>.

$^1$H-NMR (DMSO-$d_6$) δ: 9.42 (1H, br s), 7.43 (2H, d, J=8.5 Hz), 7.31 (2H, d, J=8.5 Hz), 7.17 (1H, d, J=8.5 Hz), 7.09 (1H, d, 8.2 Hz), 6.97 (2H, d, J=8.4 Hz), 6.87 (2H, J=8.4 Hz), 5.14 (2H, s), 4.88 (2H, s), 4.43 (2H, br s), 3.77 (3H, s), 3.75 (3H, s).

MS: 443.24 (M+H).

Step (2): Compound 1b→Compound 1c

Compound 1b (5 g, 11.3 mmol) was dissolved in N,N-dimethylformamide (50 mL). Sodium hydrogen carbonate (1.14 g, 13.6 mmol) followed by chloroacetyl chloride (1.09 mL, 13.6 mmol) were added thereto, and then stirred at room temperature for 45 minutes. Ethyl acetate and water were added to the reaction solution, and then the organic layer was separated. The organic layer was washed with water, and then concentrated in vacuo. After water was added to the resulting residue, the resulting solid was filtered, washed with water, then isopropanol, and then dried in vacuo to yield Compound 1c (5.61 g, 96%).

$^1$H-NMR (DMSO-$d_6$) δ: 10.43 (1H, br s), 10.34 (1H, br s), 7.44 (2H, d, J=8.5 Hz), 7.30 (2H, d, J=8.5 Hz), 7.26-7.19 (2H, m), 6.98 (2H, d, J=8.5 Hz), 6.86 (2H, d, J=8.5 Hz), 5.16 (2H, s), 4.89 (2H, s), 4.17 (2H, s), 3.77 (3H, s), 3.75 (3H, s).

Step (3): Compound 1c→Compound 1d

Compound 1c (4.8 g, 9.24 mmol) was suspended in dioxane (75 mL). While stirring at 120° C., Burgess reagent (6.61 g, 27.7 mmol) was added and then stirred at the same temperature for 40 minutes. After the temperature in the reaction solution was cooled to room temperature, the solvent was evaporated in vacuo. Ethyl acetate and water were added thereto, and then the organic layer was separated. The organic layer was washed with water, then saturated brine, and then dried with anhydrous magnesium sulfate. Magnesium sulfate was removed by filtration, followed by concentration in vacuo. The resulting solid was filtered. The filtered residue was washed with water, isopropanol, then diisopropyl ether, and then dried in vacuo to yield Compound 1d (3.86 g, 78%) as a solid.

MS: 501.18 (M+H)

$^1$H-NMR (CDCl$_3$) δ: 7.66 (1H, d, J=8.7 Hz), 7.35 (4H, dd, J=8.4, 5.2 Hz), 6.99 (1H, d, J=8.8 Hz), 6.93 (2H, d, J=8.5 Hz), 6.83 (2H, d, J=8.5 Hz), 5.12 (1H, s), 4.99 (2H, s), 4.01 (2H, s), 3.84 (3H, s), 3.80 (3H, s), 2.74-2.70 (4H, m), 1.87-1.82 (4H, m).

Step (4): Compound 1d→Compound 1e

Compound 1d (3.8 g, 7.58 mmol) was dissolved in N,N-dimethylformamide (40 mL), and than potassium carbonate (1.57 g, 11.4 mmol) and pyrrolidine (0.69 mL, 8.34 mmol) were added in turn thereto, subsequently stirring at room temperature for one hour. Pyrrolidine (0.19 mL, 2.27 mmol) was further added, and then stirred at room temperature for 30 minutes. Ethyl acetate and water were added, and then the organic layer was separated. The organic layer was washed with water, then saturated brine, and then concentrated in vacuo. Isopropanol was then added to the resulting residue. The resulting solid was filtered, and then washed with isopropanol and diisopropyl ether. This solid was recrystallized by methylene chloride isopropanol, and then dried in vacuo to yield Compound 1e (2.77 g, 68%) as a crystalline solid.

MS: 536.20 (M+H).

$^1$H-NMR (CDCl$_3$) δ: 7.66 (1H, d, J=8.7 Hz), 7.35 (4H, dd, J=8.5, 5.3 Hz), 6.99 (1H, d, J=8.8 Hz), 6.93 (2H, d, J=8.5 Hz), 6.33 (2H, d, 8.4 Hz), 5.12 (2H, s), 4.99 (2H, s), 4.01 (2H, s), 3.84 (3H, s), 3.80 (3H, s), 2.76-2.70 (4H, m), 1.82-1.87 (4H, m).

Step (5): Compound 1f+Compound 1e→Compound 1g

In a water bath, Compound 1f (842 mg, 1.0 mmol) was dissolved in N,N-dimethylacetamide (5 mL). After degasification, Compound 1e (536 mg, 1.0 mmol) followed by sodium iodide (540 mg, 3.6 mmol) were added thereto, and then stirred at room temperature for 2 hours and 30 minutes. N,N-dimethylformamide (8 mL) was added to the reaction solution, and then while stirring under ice-cooling, potassium iodide (1.33 g, 8 mmol) followed by acetyl chloride (0.43 mL, 6 mmol) were added thereto, and then stirred at the same temperature for one hour. Ethyl acetate was added to the reaction solution to dilute it, washed with aqueous 10% sodium hydrogen sulfite solution, then water, and then dried with anhydrous magnesium sulfate. Magnesium sulfate was then removed by filtration. Concentrating in vacuo yielded Compound 1g (1.42 g).

MS: 1327.08 (M+H).

Step (6): Compound 1g→Compound (I-1)

The above-described crude Compound 1g (1.42 g) was dissolved in methylene chloride (12 mL) and anisole (1.09 mL, 10 mmol), and then cooled to −40° C. 2 mmol/L-aluminum chloride/nitromethane solution (5.0 mL, 10 mmol) was added, and then stirred under ice-cooling for one hour. The reaction solution was dissolved in 1 N of aqueous hydrochloric acid solution, and acetonitrile, and then washed with diisopropyl ether. HP-20SS resin was added to the aqueous layer, concentrated, and then subjected to ODS column chromatography, eluting with aqueous hydrochloric acid solution (pH=2)-acetonitrile. HP-20SS resin was added again to fractions containing the desired compound, concentrated, and then subjected to HP-20SS column followed by eluting with water-acetonitrile. Aqueous 0.2 N solution of sodium hydroxide was added to fractions containing the desired compound to adjust them to pH=6, and thereby a sodium salt thereof was formed. Concentrating in vacuo and subsequent lyophilization yielded Compound (164.5 mg, 21%) as a powder.

MS: 763.41 (M+H).

$^1$H-NMR (D$_2$O) δ: 7.31 (1H, d, J=8.2 Hz), 6.92 (1H, s), 6.84 (1H, d, J=8.2 Hz), 5.86 (1H, d, J=5.1 Hz), 5.35 (1H, d, J=5.1 Hz), 5.10 (2H, q, J=14.8 Hz), 4.83 (1H, d, J=14.3 Hz), 4.39 (1H, d, J=14.3 Hz), 3.96-3.88 (5H, m), 3.59 (1H, d, J=17.0 Hz), 2.34-2.30 (4H, m), 1.51 (6H, s).

Elemental analysis for $C_{30}H_{30}ClN_8O_{10}S_2Na.4.8(H_2O).0.1$ (NaHCO$_3$)

Calcd.: C, 41.08; H, 4.55; N, 12.73; S, 7.29; Cl, 4.03; Na, 2.87(%).

Found.: C, 41.16; H, 4.59; N, 12.56; S, 7.27; Cl, 3.84; Na, 2.87(%).

Example 2

Synthesis of Compound (I-2)

[Formula 48]

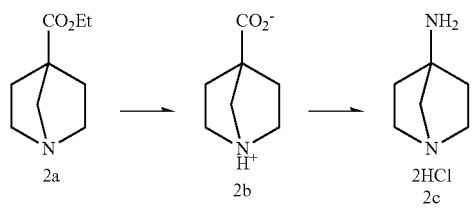

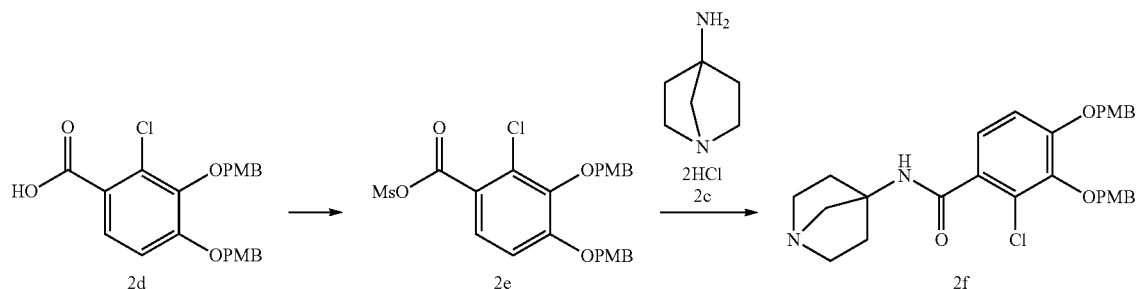

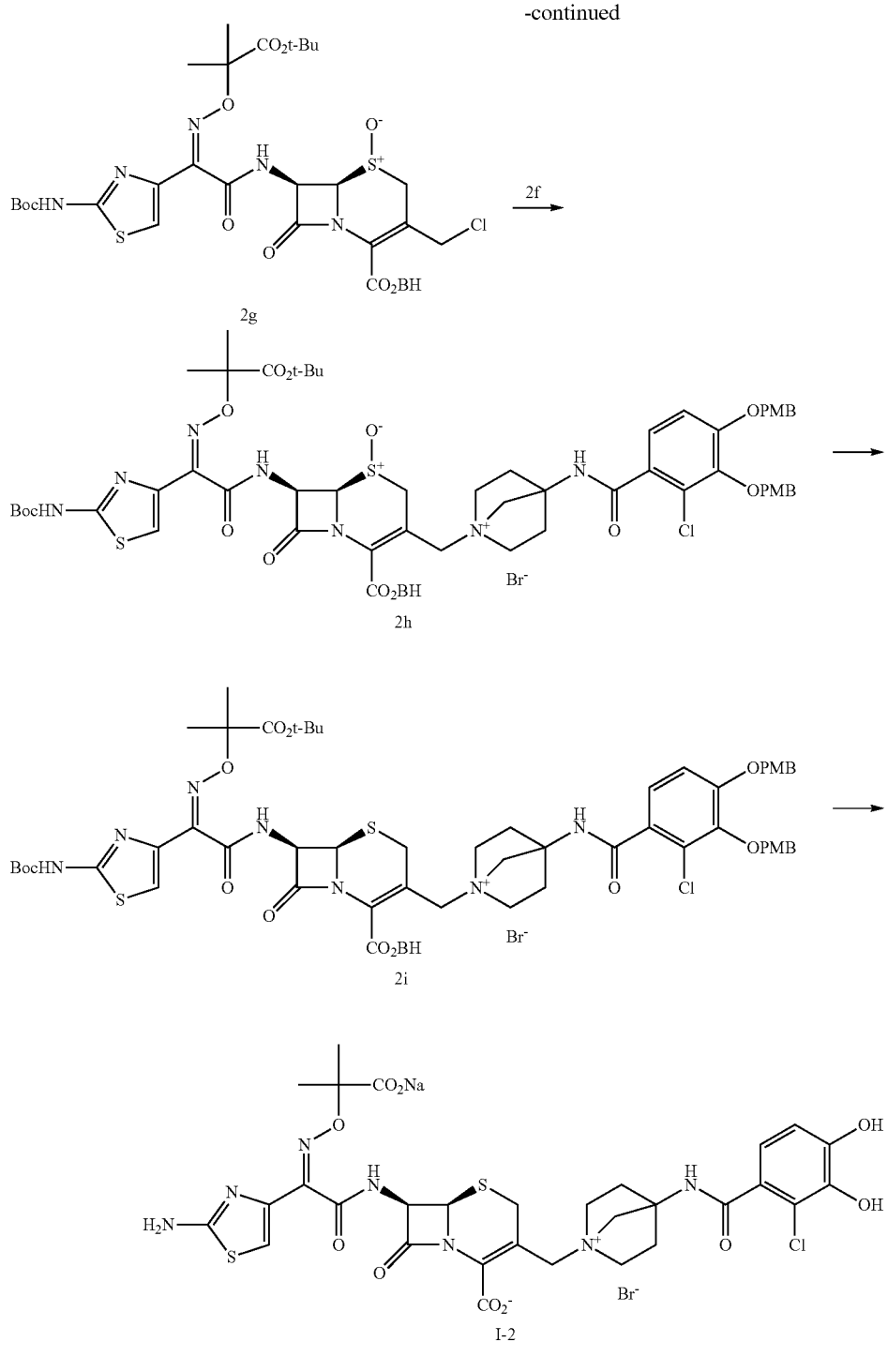

step (1): Compound 2a→Compound 2b

To Compound 2a (5.25 g, 31 mmol), which was synthesized as described in Tet. Lett. 1991, 32, 1245, water was added (35 mL), and the heated at reflux for 8 hours. The reaction solution was cooled to room temperature followed by concentration in vacuo, and then a mixed solution of isopropanol/diisopropyl ether was added to the resulting residue. The resulting solid was filtrated, and then dried in vacuo to yield Compound 2b (3.91 g, 99%).

MS: 142.16 (M+H).

$^1$H-NMR (CD$_3$OD) δ: 3.56-3.46 (2H, m), 3.35-3.25 (4H, m), 2.35-2.23 (2H, m), 1.94-2.02 (2H, m).

step (2): Compound 2b→Compound 2c

To Compound 2b (1.41 g, 10 mmol), thionyl chloride (15 mL) was added, and then heated at reflux for two hours. After evaporating thionyl chloride under reduced pressure, xylene was added thereto, and then concentrated in vacuo again. While stirring under ice-cooling, aqueous sodium azide (2.60 g, 40 mmol) solution (25 mL) was added to the resulting solid, and then stirred at the same temperature for 10 minutes. Potassium carbonate was then added to the reaction solution until effervescence ceased. After extraction with toluene, drying with magnesium sulfate was carried out. After magnesium sulfate was removed by filtration, the resulting solution was heated at reflux for 30 minutes, extracted with aqueous 6 N solution of hydrochloric acid, and then further heated at reflux for 90 minutes. The reaction solution was cooled to room temperature, and then concentrated in vacuo to yield Compound 2c (0.55 g, 30%).

MS: 113.10 (M+H).

$^1$H-NMR (D$_2$O) δ: 3.80-3.71 (2H, m), 3.61-3.46 (4H, m), 2.24-2.40 (4H, m).

step (3): Compound 2d→Compound 2e→Compound 2f

To Compound 2d (1.29 g, 3 mmol), N,N-dimethylacetamide (10 mL) was added, suspended, and then cooled to −15° C. Triethylamine (0.50 mL, 3.6 mmol) was added to the reaction solution, and then methanesulfonyl chloride (0.28 ml, 3.6 mmol) was added thereto, followed by stirring for 30 minutes at a temperature between −10° C. and −5° C., to yield activated ester 2e. Triethylamine (1.5 mL) was added to the prepared reaction mixture 2e (3.0 mmol) and then cooled to −15° C. Compound 2c (0.67 g, 3.6 mmol) was added to the reaction solution, and then stirred under ice-cooling for 90 minutes. Aqueous 0.2 N sodium hydroxide solution was added to the reaction solution, and then extracted with ethyl acetate. The organic layer was washed with water, then saturated brine, and then dried with magnesium sulfate. After magnesium sulfate was filtrated, the filtrate was concentrated in vacuo, and then subjected to silica gel column chromatography, eluting with chloroform-methanol, to yield Compound 2f (0.45 g, 29%).

MS: 523.28 (M+H).

$^1$H-NMR (CDCl$_3$) δ: 7.46 (1H, d, J=8.2 Hz), 7.34 (4H, dd, J=8.5, 4.3 Hz), 6.93 (3H, t, J=8.2 Hz), 6.83 (2H, d, J=8.5 Hz), 6.66 (1H, s), 5.08 (2H, s), 4.95 (2H, s), 3.33 (3H, s), 3.31 (3H, s), 3.22-3.13 (2H, m), 2.88 (2H, s), 2.80-2.72 (2H, m), 2.15-2.05 (2H, m), 1.68-1.78 (2H, m).

step (4): Compound 2g+Compound 2f→Compound 2h

In a water bath, Compound 2g (663 mg, 0.79 mmol) was dissolved in N,N-dimethylacetamide (2 mL), and then degassed. Sodium bromide (162 mg, 1.57 mmol) was added, and then stirred at the same temperature for 20 minutes. A solution of Compound 2f (440 mg, 0.79 mmol) in N,N-dimethylacetamide (1 mL) was added thereto, and then stirred at room temperature for 40 minutes. Ethyl acetate and water were added to the reaction solution, and then the organic layer was separated. The organic layer was washed with water, then saturated brine, and then dried with magnesium sulfate. Magnesium sulfate was then removed. Concentrating in vacuo yielded Compound 2h (1.05 g).

MS: 1329.18 (M+H).

step (5): Compound 2h→Compound 2i

To the above-described crude Compound 2h (1.05 g), N,N-dimethylformamide (10 mL) was added, and then cooled to −30° C. Phosphorus tribromide (0.13 mL, 1.42 mmol) was added, and then stirred at the same temperature for 80 minutes. Ethyl acetate and water were added to the reaction solution, and then the organic layer was separated. The organic layer was washed with water, then saturated brine, and then dried with magnesium sulfate. Magnesium sulfate was then removed by filtration. Concentrating in vacuo yielded Compound 2l (1.05 g).

MS: 1313.08 (M+H).

step (6): Compound 2i→Compound (I-2)

The above-described crude Compound 2l (1.05 g) was dissolved in methylene chloride (10 mL) and anisole (0.78 mL, 7.1 mmol), and then cooled to −40° C. 2 mol/L-aluminum chloride/nitromethane solution (3.55 mL, 7.1 mmol) was added, and then stirred under ice-cooling for 45 minutes. The reaction solution was dissolved in aqueous 1 N hydrochloric acid solution, and acetonitrile, and then washed with diisopropyl ether. HP-20SS resin was added to the aqueous layer, concentrated, and then subjected to ODS column chromatography, eluting with water-acetonitrile. To fractions containing the desired compound, 0.2 N solution of sodium hydroxide was added to adjust them to pH=6, and thereby a sodium salt thereof was formed. Concentrating in vacuo and subsequent lyophilization yielded Compound I-2 (240.5 mg, 49%) as a powder.

MS: 750.32 (M+H)

$^1$H-NMR (D$_2$O) δ: 6.99-6.96 (2H, m), 6.89 (1H, d, J=8.8 Hz), 5.87 (1H, d, J=4.9 Hz), 5.37 (1H, d, J=4.9 Hz), 4.84 (1H, ddd, J=14.0 Hz), 4.20 (1H, d, J=14.0 Hz), 3.62-3.95 (6H, m), 3.47 (1H, d, J=17.1 Hz), 3.07-2.86 (1H, m), 2.62-2.52 (2H, m), 2.42-2.33 (2H, m), 1.52 (8H, td, J=20.4, 4.9 Hz).

Elemental analysis for $C_{30}H_{31}ClN_7O_{10}S_2Na\cdot 4.6(H_2O)$

Calcd.: C, 42.14; H, 4.79; N, 11.47; S, 7.50; Cl, 9.15; Na, 2.69(%).

Found.: C, 42.22; H, 4.84; N, 11.43; S, 7.26; Cl, 4.05; Na, 2.40(%).

Example 3

Synthesis of Compound (I-3)

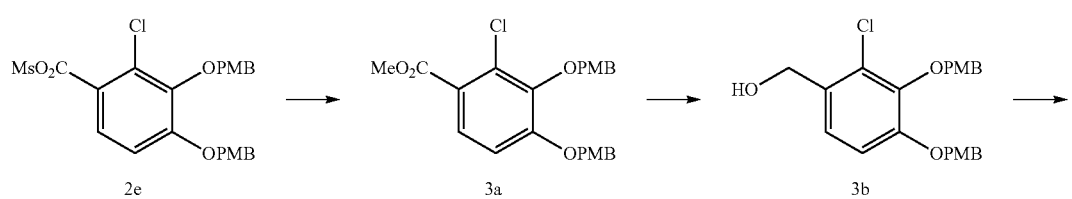

[Formula 49]

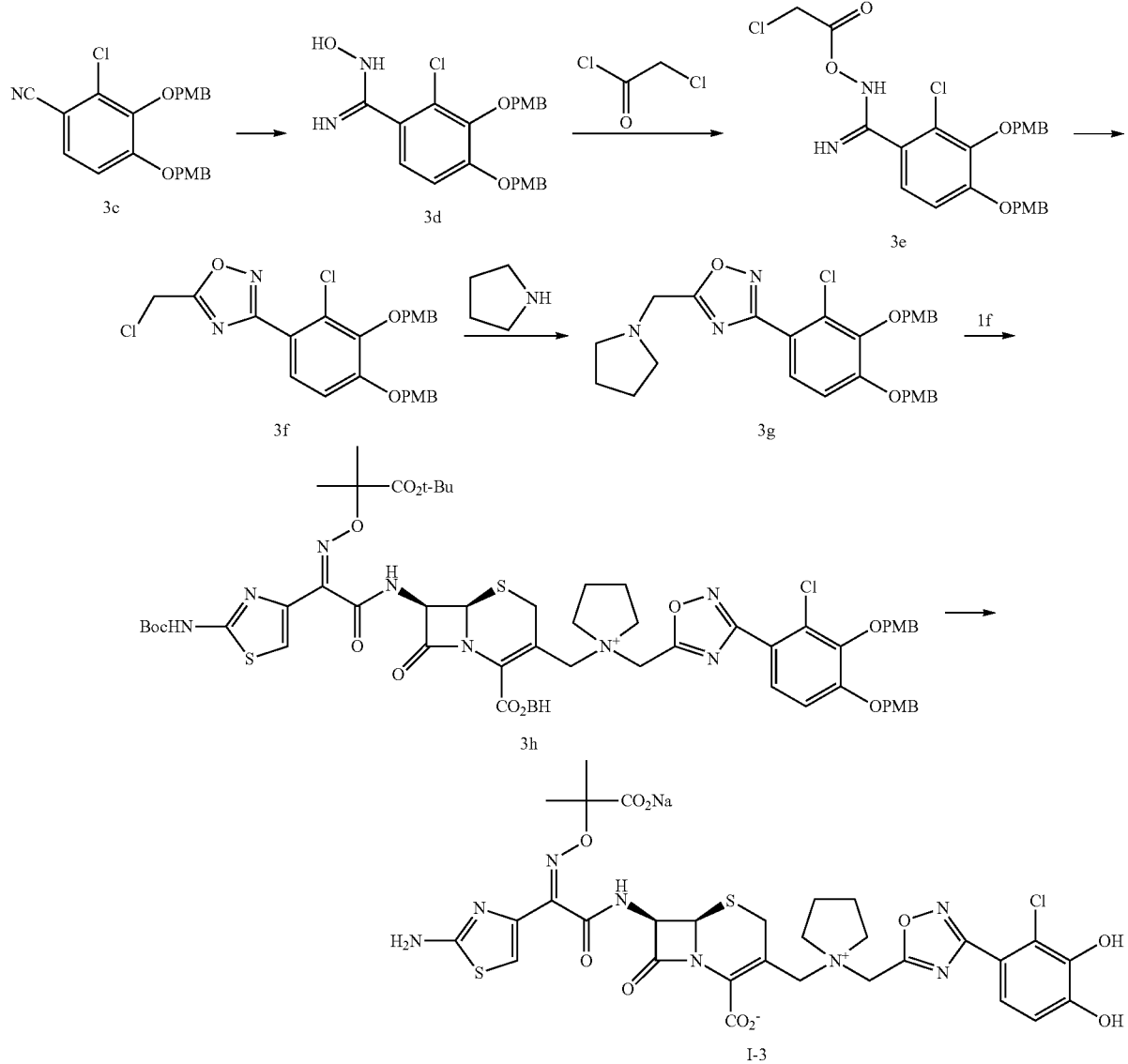

step (1): Compound 2e→Compound 3a

Compound 2e (40 mmol), which was prepared by the same method as Example 2, was cooled to −15° C. Methanol (80 mL) was added thereto, and then stirred at room temperature for 30 minutes. Ethyl acetate and water were added to the reaction solution, and then the organic layer was separated. The organic layer was washed with water, then saturated brine, and then dried with magnesium sulfate. Magnesium sulfate was then filtrated. After concentrating in vacuo, isopropanol was added to the resulting residue. The resulting solid was filtrated, and then washed with isopropanol, then diisopropyl ether. Concentrating and drying yielded Compound 3a (12.8 g, 73%) as a solid.

$^1$H-NMR (DMSO-d$_6$) δ: 7.61 (1H, d, 8.7 Hz), 7.44 (2H, d, J=8.4 Hz), 7.29-7.25 (3H, m), 6.98 (2H, d, J=8.4 Hz), 6.85 (2H, d, J=8.2 Hz), 5.18 (2H, s), 4.89 (2H, s), 3.81 (3H, s), 3.78 (3H, s), 3.74 (3H, s).

step (2): Compound 3a→Compound 3b

Compound 3a (12.0 g, 27.1 mmol) was dissolved in tetrahydrofuran (100 mL), and then under ice-cooling, a suspension of lithium aluminum hydride (1.03 g, 27.1 mmol) in tetrahydrofuran (20 mL) was added drop-wise thereto. After stirring at room temperature (for 5 hours, sodium sulfate decahydrate (10.3 g) was added, and then stirred at room temperature overnight. The resulting solid was then removed by Celite filtration. The filtrate was concentrated under reduce pressure, and then isopropanol was added to the resulting residue. The resulting solid was filtered, washed with isopropanol, then diisopropyl ether, and then dried in vacuo to yield Compound 3b (10.5 g, 94%) as a solid.

$^1$H-NMR (DMSO-d$_6$) δ: 7.42 (2H, d, J=7.5 Hz), 7.31 (2H, d, J=7.3 Hz), 7.20 (2H d, J=8.6 Hz), 7.15 (2H, d, J=8.6 Hz), 6.97 (2H, d, J=8.4 Hz), 6.87 (2H, d, J=8.4 Hz), 5.25 (1H, br s), 5.10 (2H, s), 4.87 (2H, s), 4.47 (2H, s), 3.77 (3H, s), 3.75 (3H, s).

step (3): Compound 3b→Compound 3c

To Compound 3b (10.5 g, 25.3 mmol) tetrahydrofuran (80 mL) was added. Aqueous 28% ammonia solution (80 mL) followed by iodine (19.3 g, 76 mmol) were further added thereto, and then stirred at 60° C. for three hours. The reaction solution was then cooled to room temperature. Ethyl acetate was added, and then separated. The organic layer was washed with aqueous sodium hydrogen sulfite solution, water, then saturated brine, and then dried with magnesium sulfate. After magnesium sulfate was filtered, the filtrate was concentrated in vacuo, and dissolved in a small amount of chloroform, and then isopropanol was added thereto. The resulting solid was filtered, washed with isopropanol, and then dried in vacuo to yield Compound 3c (6.52 g, 63%) as a solid.

MS (FAB): 410 (M+H).

$^1$H-NMR (CDCl$_3$) δ: 7.42-7.30 (6H, m), 6.99-6.94 (4H, m), 6.89-6.85 (2H, m), 5.14 (2H, s), 5.02 (2H, s), 3.88 (3H, s), 3.84 (3H, s).

step (4): Compound 3c→Compound 3d

To Compound 3c (5.0 g, 12.2 mmol), methanol (50 mL) was added. Hydroxylamine hydrochloride (8.5 g, 122 mmol) followed by triethylamine (16.9 mL, 122 mmol) were further added, and then heated at reflux for five hours. The reaction solution was cooled to room temperature, the solvent was evaporated under reduced pressure, and then ethyl acetate and water were added. The organic layer separated was concentrated under reduced pressure, and then diisopropyl ether was added to the resulting residue. The resulting solid was filtered, washed with diisopropyl ether, and then dried in vacuo to yield Compound 3d (5.19 g, 96%>).

MS: 443.24 (M+H).

$^1$H-NMR (CDCl$_3$) δ: 7.35 (4H, d, J=8.7 Hz), 7.19 (1H, d, J=8.7 Hz), 6.98-6.89 (3H, m), 6.83 (2H, d, J=8.7 Hz), 5.07 (2H, s), 4.95 (2H, s), 4.89 (2H, br s), 3.83 (3H, s), 3.80 (3H, s).

step (5): Compound 3d→Compound 3e

To Compound 3d (5.4 g, 12.2 mmol), methylene chloride (75 mL) and triethylamine (1.86 mL, 13.4 mmol) were added, and then ice-cooled. While stirring, chloroacetyl chloride (1.03 mL, 12.8 mmol) was added thereto, and then stirred at room temperature for 30 minutes. After evaporating the solvent, ethyl acetate was added and washed with water. The organic layer separated was concentrated in vacuo. Isopropanol-water (1:1) was then added to the resulting residue. The resulting solid was filtered, washed with isopropanol, then diisopropyl ether, and then dried in vacuo to yield Compound 3e (3.83 g, 61%) as a solid.

$^1$H-NMR (CDCl$_3$) δ: 7.36-7.31 (4H, m), 7.25-7.22 (2H, m), 6.94-6.90 (3H, m), 6.83 (2H, d, J=8.7 Hz), 5.17 (2H, br s), 5.08 (2H, s), 4.94 (2H, s), 4.29 (2H, s), 3.83 (3H, s), 3.80 (3H, s).

MS: 519.20 (M+H).

step (6): Compound 3e→Compound 3f

To Compound 3e (3.8 g, 7.32 mmol) was added dioxane (50 mL), and then stirred at 100° C. for three hours. The reaction solution was cooled to room temperature, and concentrated in vacuo, and then diisopropyl ether was added to the resulting residue. The resulting solid was filtered, and then dried in vacuo to yield Compound 3f (3.42 g, 93%).

MS: 501.19 (M+H).

$^1$H-NMR (CDCl$_3$) δ: 7.65 (1H, d, J=8.7 Hz), 7.36 (4H, dd, J=8.5, 2.1 Hz), 6.99 (1H, d, J=8.7 Hz), 6.94-6.90 (2H, m), 6.80-6.85 (2H, m), 5.11 (2H, s), 9.99 (2H, s), 4.75 (2H, a), 3.84 (3H, s), 3.80 (3H, s).

step (7): Compound 3f→Compound 3g

Compound 3f (3.4 g, 6.78 mmol) was dissolved in N,N-dimethyl formamide (35 mL). Under ice-cooling, potassium carbonate (1.41 g, 10.2 mmol) followed by pyrrolidine (0.62 mL, 7.46 mmol) were added thereto, and then stirred at room temperature for two hours. Ethyl acetate and water were then added to the reaction solution. The organic layer separated was washed with water, and saturated brine, and then dried with magnesium sulfate. After magnesium sulfate was filtered, the filtrate was concentrated in vacuo, and then subjected to silica gel column chromatography, eluting with chloroform-methanol. Fractions containing the desired compound were concentrated in vacuo to yield Compound 3g (1.97 g, 54%) as a solid.

MS: 536.30 (M+H)

$^1$H-NMR (CDCl$_3$) δ: 7.67 (1H, d, J=8.7 Hz), 7.36 (4H, d, J=8.5 Hz), 6.98 (1H, d, J=8.7 Hz), 6.92 (2H, d, J=8.4 Hz), 6.83 (2H, d, J=8.5 Hz), 5.11 (2H, s), 4.99 (2H, s), 4.03 (2H, s), 3.84 (3H, s), 3.80 (3H, s), 2.77-2.72 (4H, m), 1.88-1.84 (4H, m).

step (8): Compound 3g+Compound 1f→Compound 3h→Compound (I-3)

Using Compound 3a (536 mg, 1 mmoll) and Compound 1f (842 mg, 1 mmol), Compound I-3 (91.5 mg, 12%) was obtained according to the same procedure as Example 1.

MS: 763.34 (M+H).

$^1$H-NMR (D$_2$O) δ: 7.38 (1H, d, J=8.3 Hz), 6.90 (1H, d, J=8.3 Hz), 6.85 (1H, s), 5.85 (1H, d, J=5.0 Hz), 5.43 (1H, d, J=14.0 Hz), 5.26 (1H, d, J=4.9 Hz), 4.97 (1H, d, J=14.3 Hz), 4.58 (1H, d, J=14.8 Hz), 4.22-4.17 (1H, m), 3.91-3.82 (5H, m), 3.47 (1H, d, J=16.9 Hz), 2.37-2.29 (4H, m), 1.45 (6H, d, J=5.3 Hz).

Elemental analysis for C$_{30}$H$_{30}$ClN$_8$O$_{10}$S$_2$Na.5.5(H$_2$O).0.2 (NaHCO$_3$)

Calcd.: C, 40.25; H, 4.61; N, 12.44; S, 7.12; Cl, 3.93; Na, 3.06(%).

Found.: C, 40.14; H, 4.69 N, 12.54; S, 7.26; Cl, 3.77; Na, 2.98(%).

Example 4

Synthesis of Compound (I-4)

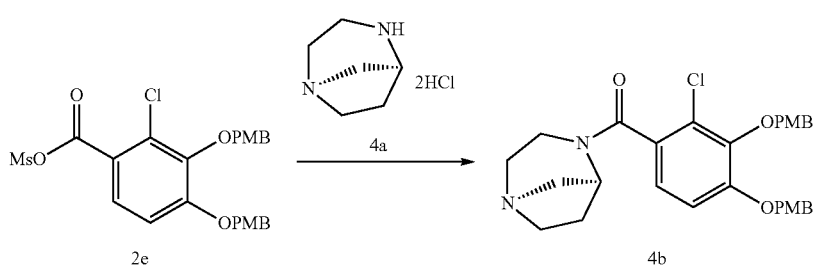

[Formula 50]

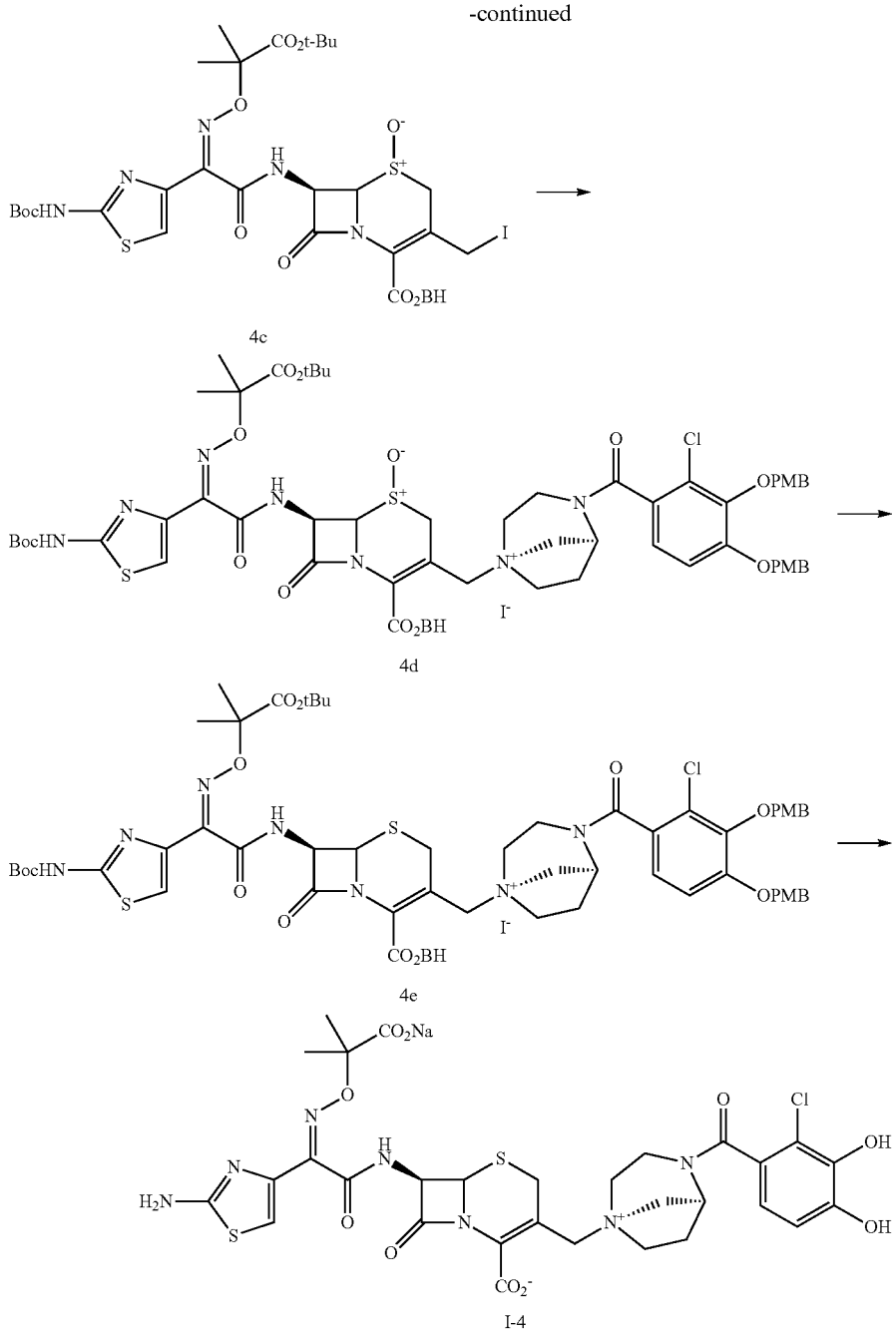

step (1): Compound 2e+Compound 4a→Compound 4b

Using Compound 4a (550 mg, 2.37 mmol), which was synthesized as described in WO200402472, Compound 4b (640 mg, 1.22 mmol) was obtained according to same procedure as Example 2.

MS: 523.18 (M+H).

$^1$H-NMR (CDCl$_3$) δ: 7.38-7.30 (4H, m), 7.01-6.80 (6H, m), 5.25 (0.6H, s), 5.07 (2H, d, J=4.1 Hz), 5.03-4.91 (2H, m), 4.28 (0.6H, d, J=9.2 Hz), 3.85 (3M, s), 3.79-3.73 (3.4H, m), 3.37-3.27 (0.4M, m), 3.17-2.80 (5H, m), 2.66-2.34 (2H, m), 2.07-1.77 (2H, m).

step (2): Compound 4c+Compound 4b→Compound 4d.

Compound 4b (640 mg, 1.22 mmol) was dissolved in N,N-dimethylformamide (4 mL), and then degassed. Compound 4c (1.14 g, 1.22 mmol) was added, and then stirred at room temperature for 40 minutes. Water and ethyl acetate were then added to the reaction solution. The organic layer separated was washed with aqueous 10% sodium hydrogen sulfite solution, and then dried with magnesium sulfate. Magnesium sulfate was filtered. Concentrating in vacuo yielded Compound 4d (1.59 g).

MS: 1329.67 (M+H)

step (3): Compound 4d→Compound 4e→Compound (I-4)

The above-described crude Compound 4d was dissolved in methylene chloride (12 mL), and then cooled to −40° C. Phosphorus tribromide (0.23 mL, 2.44 mmol) was added, and then stirred at −40° C. for 80 minutes. Anisole (1.33 mL, 12.2 mmol) was added to the reaction solution, and then at −40° C., 2 mol/L-aluminum chloride/nitromethane solution (6.1 mL, 12.2 mmol) was added, and then stirred for one hour at a temperature between −10° C. and −5° C. The reaction solution was dissolved in aqueous 1 N hydrochloric acid solution and acetonitrile, and then washed with diisopropyl ether. HP-20SS resin was added to the aqueous layer, concentrated, and then subjected to ODS column chromatography, eluting with water-acetonitrile. Aqueous 0.2 N sodium hydroxide solution was added to the fractions containing the desired compound to adjust them to pH=6, and thereby a sodium salt thereof was formed. Concentrating under reduced pressure and subsequent lyophilization yielded Compound I-4 as a powder (568.6 mg, 60%).

MS: 750.19 (M+H)

$^1$H-NMR (D$_2$O) δ: 7.00-6.95 (2H, m), 6.86-6.79 (1H, m), 5.92-5.87 (1H, m), 5.57 (0.6H, s), 5.41-5.37 (1H, m), 4.94-4.51 (1.4H, m), 4.31-4.17 (1H, m), 3.96-3.35 (10H, m), 2.83-2.32 (2H, m), 1.54 (6H, d, J=4.7 Hz).

Elemental analysis for C$_{30}$H$_{31}$ClN$_7$O$_{10}$S$_2$Na.4.8(H$_2$O).0.3(NaHCO$_3$)

Calcd.: C, 41.17; H, 4.66; N, 11.09; S, 7.26; Cl, 4.01; Na, 3.38(%).

Found.: C, 41.13; H, 4.69; N, 11.19; S, 7.50; Cl, 3.74; Na, 3.34(%).

Example 5

Synthesis of Compound (I-5)

[Formula 51]

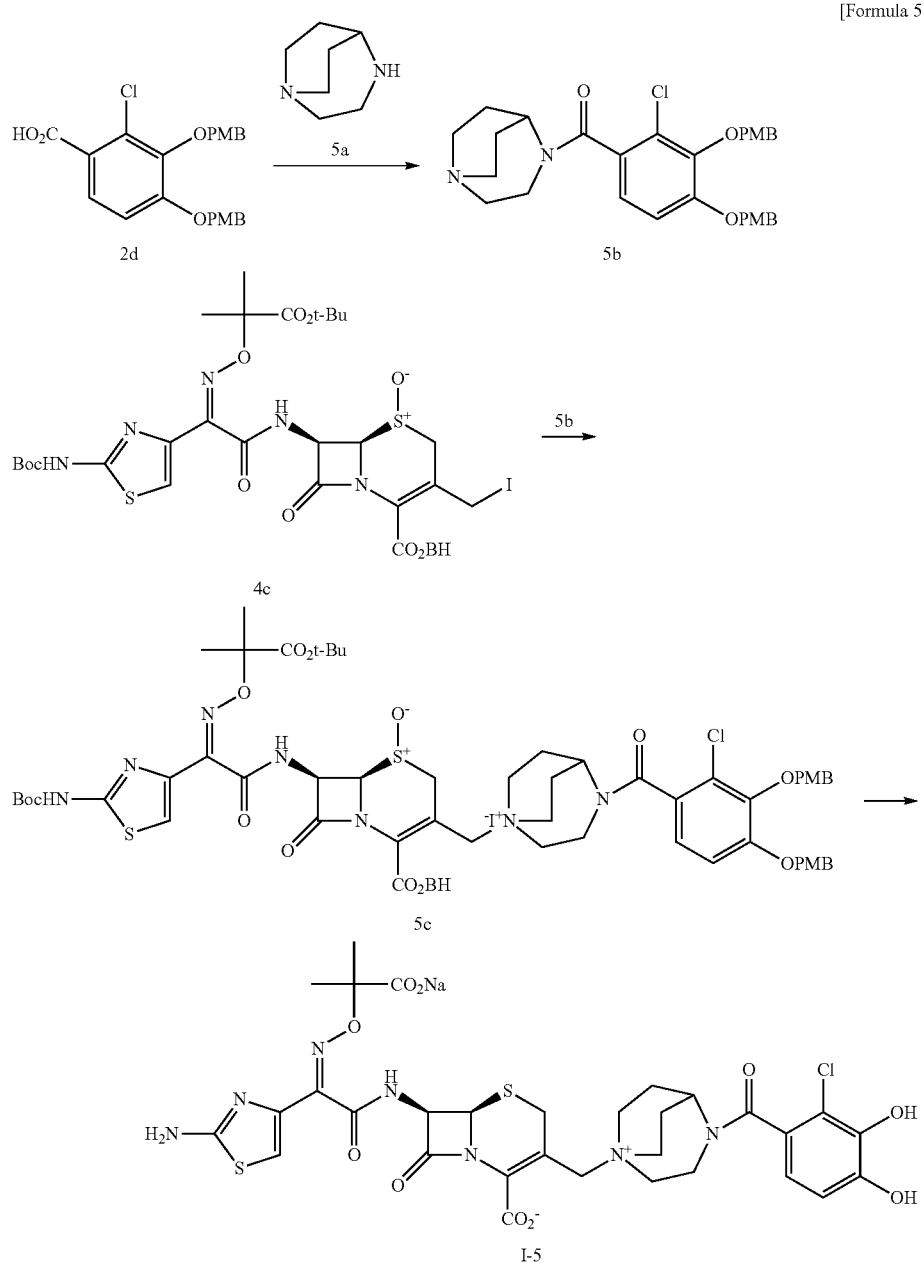

I-5 step (1): Compound 2d+Compound 5a→Compound 5b

Compound 2d (2.55 g, 5.9 mmol) was dissolved in N,N-dimethylformamide (25 mL), and then hydrochloric acid salt of N-ethyl-N'-(3-dimethylaminopropyl)carbodiimide (1.25 g, 6.54 mmol) followed by 1-hydroxybenzotriazole (883 mg, 6.54 mmol) were added, followed by stirring at room temperature for 40 minutes. After the reaction temperature was ice-cooled, a solution of Compound 5a (900 mg, 7.13 mmol), which was synthesized as described in Synth. Common. 2006, 36, 321, in N,N-dimethylformamide (3 mL) was added thereto, and then stirred at room temperature for 90 minutes. The reaction solution was diluted with ethyl acetate, washed with aqueous sodium hydrogen carbonate solution, water, and then saturated brine. The organic layer was dried with magnesium sulfate, and then magnesium sulfate was removed by filtration, followed by concentration in vacuo. The resulting residue was subjected to silica gel column chromatography, eluting with methanol-chloroform. Fractions containing the desired compound were concentrated in vacuo to yield. Compound 5b (1.64 g, 51%).

MS: 537.19 (M+H).

$^1$H-NMR (CDCl$_3$) δ: 7.34 (4H, t, J=9.3 Hz), 6.98-6.87 (4H, m), 6.81 (2H, d, J=8.4 Hz), 5.07 (2H, s), 4.99 (2H, dd, J=26.2, 10.3 Hz), 4.79 (0.8H, m), 4.34-4.26 (0.2H, m), 3.84 (3H, s), 3.79 (3H, s), 3.67-2.80 (8H, m), 2.23-2.00 (2H, m), 1.70-1.86 (2H, m).

step (2): Compound 4c+Compound 5b→Compound 5c→Compound (I-5)

Using Compound 5b (806 mg, 1.5 mmol) and Compound 4c (1.40 g, 1.5 mmol), Compound I-5 (319.7 mg, 46%) was obtained according to the same procedure as Example 4.

MS: 764.16 (M+H)

$^1$H-NMR (D$_2$O) δ: 6.95-6.91 (2H, m), 6.80-6.76 (1H, m), 5.85 (1H, dd, J=9.3, 4.9 Hz), 5.35 (1H, t, J=5.1 Hz), 4.95-4.35 (2H, m), 4.19-4.10 (2H, m), 3.94-3.40 (9H, m), 2.40-2.17 (4H, m), 1.49 (6H, s).

Elemental analysis for C$_{31}$H$_{33}$ClN$_7$O$_{10}$S$_2$Na.4.5(H$_2$O).0.1(NaHCO$_3$)

Calcd.: C, 42.66; H, 4.85; N, 11.20; S, 7.32; Cl, 4.05; Na, 2.89(%).

Found.: C, 42.60; H, 4.78; N, 11.26; S, 7.33; Cl, 4.15; Na, 2.72(%).

Example 6

Synthesis of Compound (I-6)

[Formula 52]

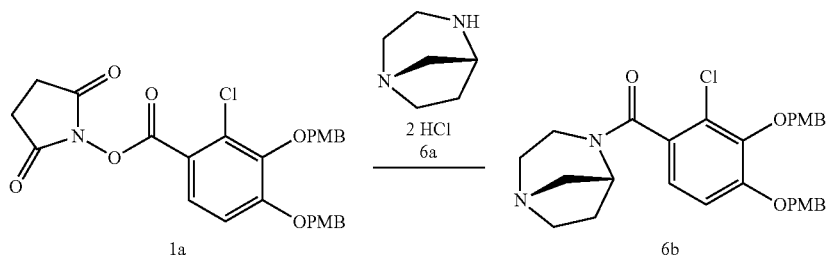

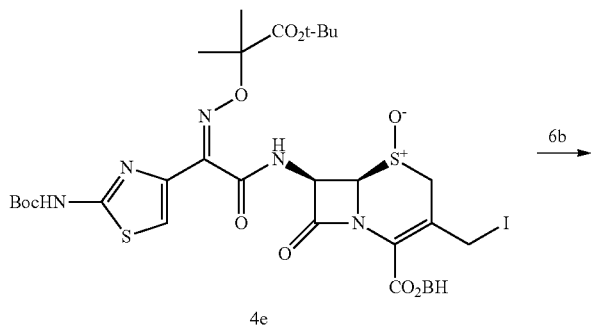

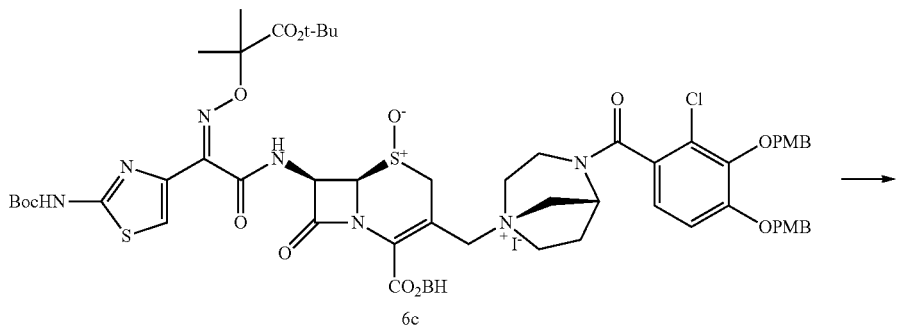

-continued

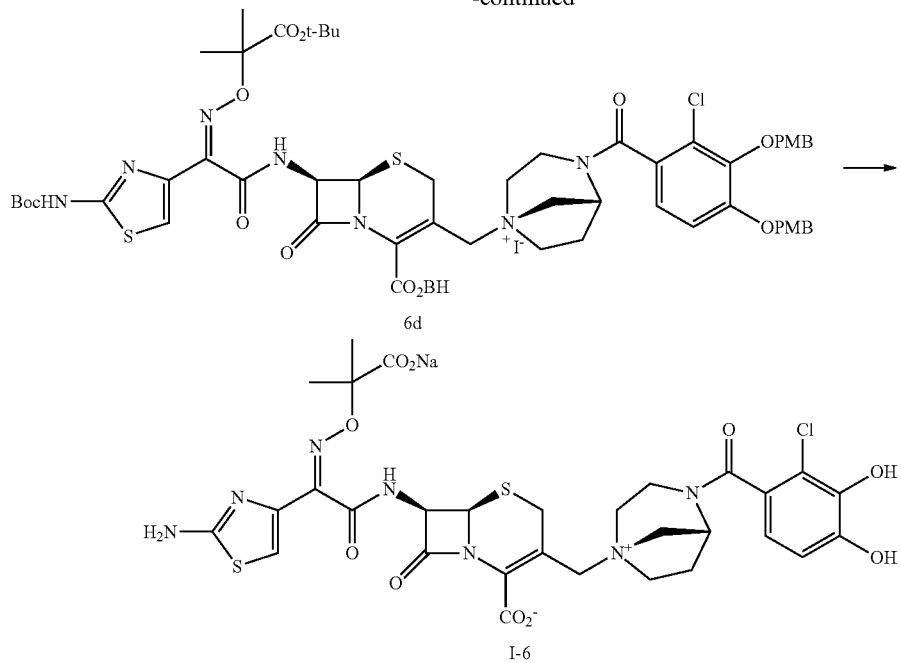

step (1): Compound 1a+Compound 6a→Compound 6b

Compound 1a (1.58 g, 3 mmol) and Compound 6a (555 mg, 3 mmol), which was obtained by the same method as Compound 4a, were suspended in N,N-dimethylformamide (5 mL). Triethylamine (0.92 mL, 6.6 mmol) was added thereto, and then stirred at room temperature for two hours. Triethylamine (0.31 mL, 2.2 mmol) and Compound 6a (55 mg, 0.3 mmol) were added, and then stirred further for five hours. Ethyl acetate and water were then added to the reaction solution. The organic layer separated was then washed with water, then saturated brine, and dried with magnesium sulfate. Magnesium sulfate was then removed by filtration. Concentrating in vacuo yielded Compound 6b (1.54 g, 98%).

MS: 523.18 (M+H).

$^1$H-NMR (CDCl$_3$) δ: 7.38-7.29 (4H, m), 7.00-6.87 (4H, m), 6.81 (2H, dd, J=8.5, 2.1 Hz), 5.26-5.25 (0.6H, m), 5.07 (2H, d, J=4.1 Hz), 5.03-4.93 (2H, m), 4.29 (0.6H, d, J=9.2 Hz), 3.84 (3H, s), 3.79-3.76 (3.4H, m), 3.37-3.27 (0.4H, m), 3.17-2.81 (5H, m), 2.67-2.38 (2H, m), 2.08-1.78 (2H, m).

step (2): Compound 4c+Compound 6b→Compound 6c→Compound 6d→Compound (I-6)

Using Compound 4c (1.12 g, 1.2 mmol) and Compound 6b (628 mg, 1.2 mmol), Compound I-6 (633.8 mg, 68%) was obtained according to the same procedure as Example 4.

MS: 750.23 (M+H).

$^1$H-NMR (D$_2$O) δ: 7.02-6.97 (2H, m), 6.91-6.84 (1H, m), 5.93-5.89 (1H, m), 5.59 (0.6H, s), 5.42-5.38 (1H, m), 4.96-4.56 (1.4H, m), 4.33-4.19 (1H, m), 4.04-3.30 (10H, m), 2.80-2.40 (2H, m), 1.55 (6H, d, J=4.7 Hz).

Elemental analysis for C$_{30}$H$_{31}$ClN$_7$O$_{10}$S$_2$Na.7.3(H$_2$O).0.1(NaHCO$_3$).0.5(NaCl)

Calcd.: C, 38.41; H, 4.89; N, 10.42; S, 6.81; Cl, 5.65; Na, 3.91(%).

Found.: C, 38.37; H, 4.72; N, 10.19; S, 6.94; Cl, 5.71; Na, 4.01(%).

Example 7

Synthesis of Compound (I-7)

[Formula 53]

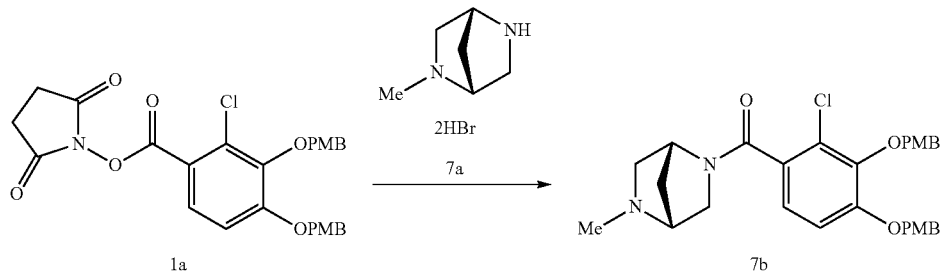

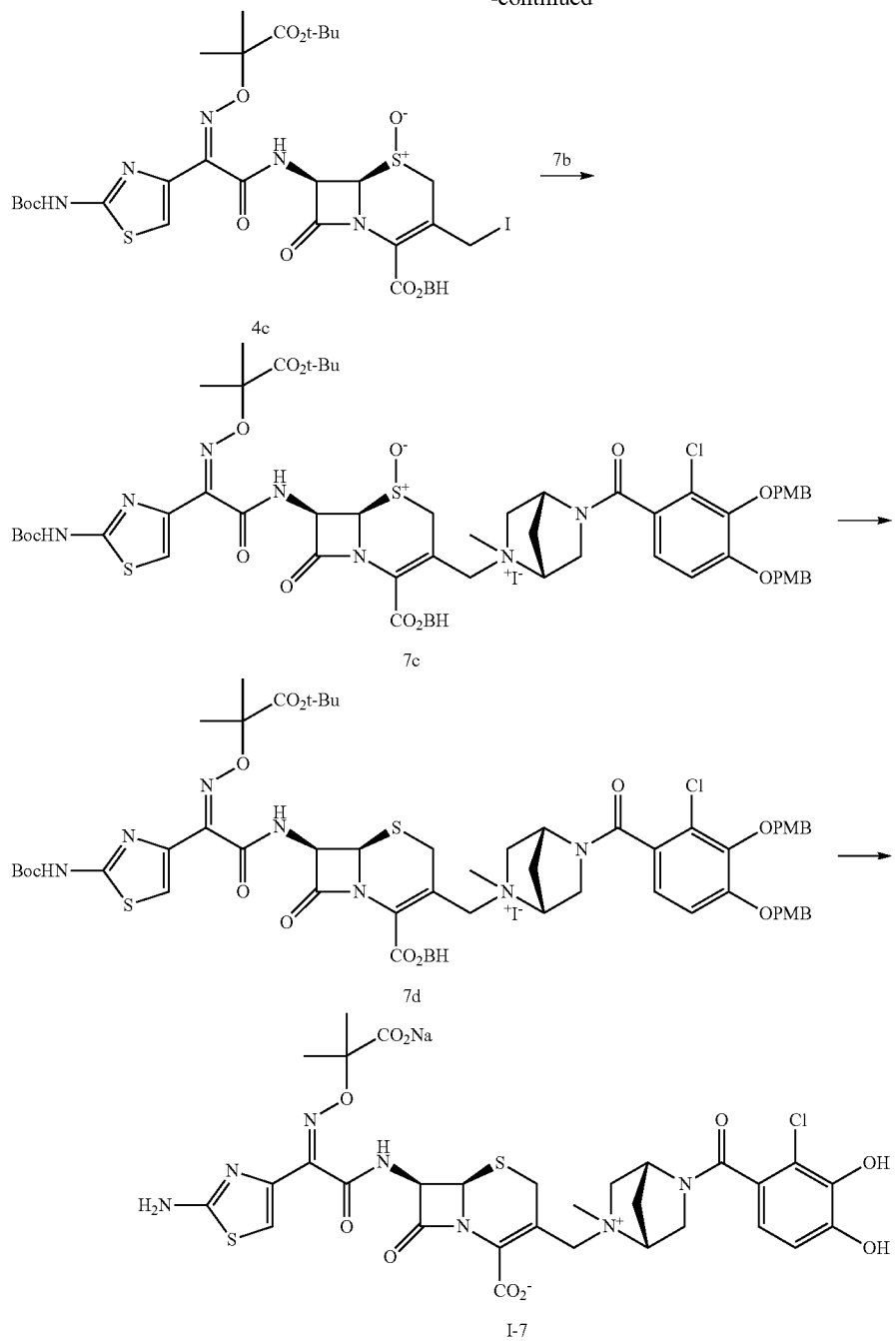

step (1): Compound 1a+Compound 7a→Compound 7b

To Compound 1a (1.58 g, 3 mmol), N,N-dimethylformamide (5 mL) was added. Diisopropylethylamine (1.36 mmol, 7.8 mmol) followed by Compound 7a (0.99 g, 3.6 mmol), synthesized as described in J. Org. Chem. 1990, 55, 1687, were added thereto, and then stirred at room temperature for 4 hours. Ethyl acetate and water were added, and the organic layer separated was washed with water, then saturated brine, and then dried with magnesium sulfate. After magnesium sulfate was removed by filtration, the filtrate was concentrated in vacuo, and then subjected to silica gel column chromatography, eluting with chloroform.methanol. Fractions containing the desired compound were concentrated under reduced pressure to yield Compound 7b (1.14 g, 73%).

$^1$H-NMR (CDCl$_3$) δ: 7.38-7.31 (4H, m), 7.00-6.90 (4H, m), 6.82 (2H, d, J=8.7 Hz), 5.07 (2H, d, J=2.0 Hz), 4.99 (2H, d, J=3.8 Hz), 4.87 (0.6H, s), 3.84 (3H, s), 3.79 (3H, s), 3.77-3.25 (3.4H, m), 3.02-2.93 (1H, m), 2.81-2.76 (1H, m), 2.44, 2.41 (3H, m), 1.94-1.78 (2H, m).

MS: 523.19 (M+H).

step (2): Compound 4c→Compound 7b→Compound 7c→Compound 7d→Compound (I-7)

Using Compound 7b (628 mg, 1.2 mmol) and Compound 4c (1.12 g, 1.2 mmol), Compound I-7 (270.6 mg, 29%) was obtained according to the same procedure as Example 4.

$^1$H-NMR (D$_2$O) δ: 7.03-6.99 (2H, m), 6.95-6.90 (1H, m), 5.91 (1H, d, J=5.0 Hz), 5.42-5.40 (1H, m), 5.18 (0.4H, s), 4.76-4.48 (1.6H, m), 4.38-4.24 (2H, m), 4.04-3.53 (6H, m), 3.27, 3.17 (3H, s×2), 2.70-2.57 (2H, m), 1.55 (6H, d, J=5.5 Hz).

MS: 750.25 (M+H).

Elemental analysis for C$_{30}$H$_{31}$ClN$_7$O$_{10}$S$_2$Na.5.2(H$_2$O).0.1 (NaHCO$_3$)

C, 41.35; H, 4.78; N, 11.21; S, 7.34; Cl, 4.06; Na, 2.89(%).
Found.: C, 41.37; H, 4.70; N, 11.21; S, 7.43; Cl, 3.82; Na, 3.00(%).

Example 8

Synthesis of Compound (I-8)

step (1): Compound 8a+Compound 7b→Compound 8b

In a water bath, Compound 8a (892 mg, 1.0 mmol) was dissolved in N,N-dimethylacetamide (3 mL), and then degassed. Compound 7b (523 mg, 1 mmol) followed by sodium iodide (450 mg, 3.0 mmol) were added, and then stirred at room temperature for 45 minutes. N,N-dimethyl formamide (7 ml) was then added to the reaction solution. While stirring under ice-cooling, potassium iodide (1.33 g, 8 mmol) followed by acetyl chloride (0.43 mL, 6 mmol) were added thereto, and then stirred at the same temperature for 90 minutes. Ethyl acetate was added to the reaction solution to dilute it, and then washed with aqueous 10% sodium hydrogen sulfite solution, then water. The organic layer was then dried with magnesium sulfate. After magnesium sulfate was removed by filtration, the filtrate was concentrated in vacuo to yield Compound 8b (1.52 g).

MS: 1364.04 (M+H)

step (2): Compound 8b→Compound (I-8)

The above-describe crude Compound 8b (1.42 g) was dissolved in methylene chloride (12 mL) and anisole (1.09 mL, 10 mmol), subsequently cooling to −40° C. 2 mol/L-aluminum chloride/nitromethane solution (5.0 mL, 10 mmol) was added thereto, and then stirred under ice-cooling for one hour. The reaction mixture was dissolved in aqueous 1 N hydrochloric acid solution and acetonitrile, and then washed with diisopropyl ether. HP-20SS resin was added to the aqueous

[Formula 54]

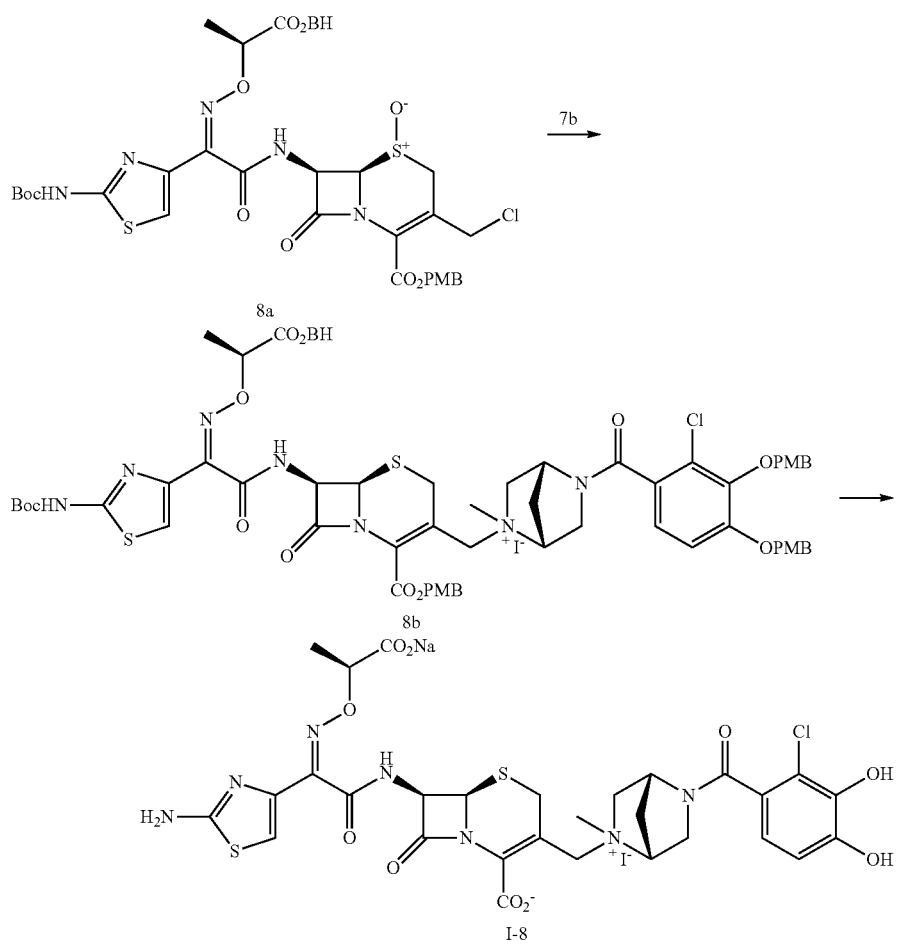

layer, concentrated, subjected to ODS column chromatography, eluting with water-acetonitrile. To fractions containing the desired compound, 0.2 N sodium hydroxide solution was added to adjust them to pH=6, and thereby a sodium salt thereof was formed. Concentrating under reduced pressure and subsequent lyophilization yielded Compound I-8 (173.6 mg, 23%) as a powder.

MS: 736.30 (M+H).

$^1$H-NMR (D$_2$O) δ: 7.01 (1H, s), 6.96 (1H, d, J=7.8 Hz), 6.88 (1H, d, J=7.8 Hz), 5.88 (1H, d, J=4.9 Hz), 5.37 (1H, d,

J=4.9 Hz), 5.13-4.48 (3H, m), 4.34-4.19 (2H, m), 3.99-3.48 (6H, m), 3.30-3.12 (3H, m), 2.67-2.53 (2H, m), 1.48 (3H, d, J=6.7 Hz).

Elemental analysis for $C_{29}H_{29}ClN_{10}O_{10}S_2Na \cdot 5.5(H_2O)$

Calcd.: C, 40.63; H, 4.70; N, 11.44; S, 7.48; Cl, 4.14; Na, 2.68(%).

Found.: C, 40.64; H, 4.70; N, 11.42; S, 7.46; Cl, 3.99; Na, 2.50(%).

Example 9

Synthesis of Compound (I-9)

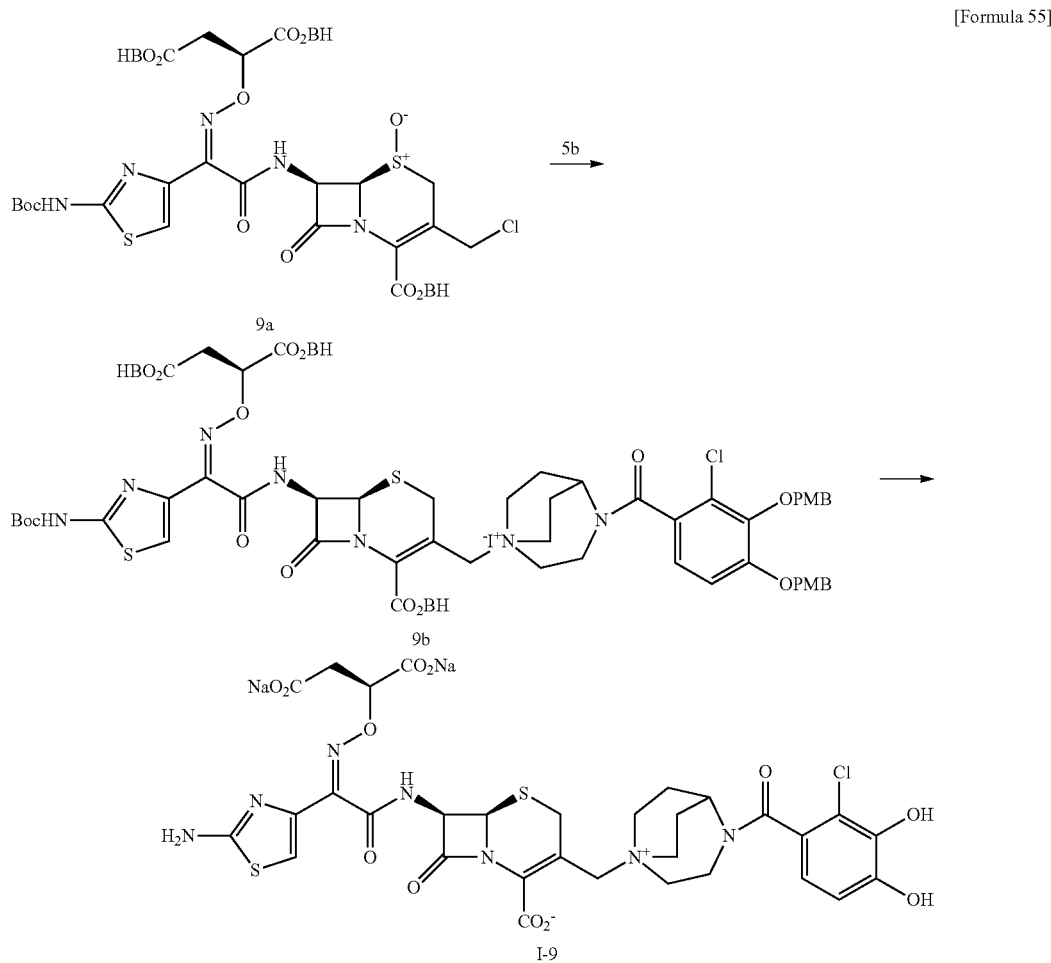

[Formula 55]

step (1): Compound 9a+Compound 5b→Compound 9b→Compound (I-9)

Using Compound 9a (1.38 g, 1.2 mmol) and Compound 5b (0.64 g, 1.2 mmol), Compound I-9 (359.7 mg, 36%) was obtained according to the same procedure as Example 8.

MS: 793.37 (M+H).

$^1$H-NMR ($D_2O$) δ: 7.01-6.94 (2H, m), 6.86-6.81 (1H, m), 5.83 (1H, t, J=4.7 Hz), 5.34 (1H, t, J=4.3 Hz), 5.00-4.95 (2H, m), 4.85-4.52 (1H, m), 4.24-4.12 (2H, m), 3.87-3.41 (9H, m), 2.75-2.71 (2H, m), 2.41-2.19 (4H, m).

Elemental analysis for $C_{31}H_{30}ClN_7O_{12}S_2Na_2 \cdot 7.7(H_2O)$

Calcd.: C, 38.11; H, 4.68; N, 10.04; S, 6.56; Cl, 3.63; Na, 4.71(%).

Found.: C, 38.12; H, 4.69; N, 10.08; S, 6.51; Cl, 3.93; Na, 4.60(%).

Example 10
Synthesis of Compound (I-10)
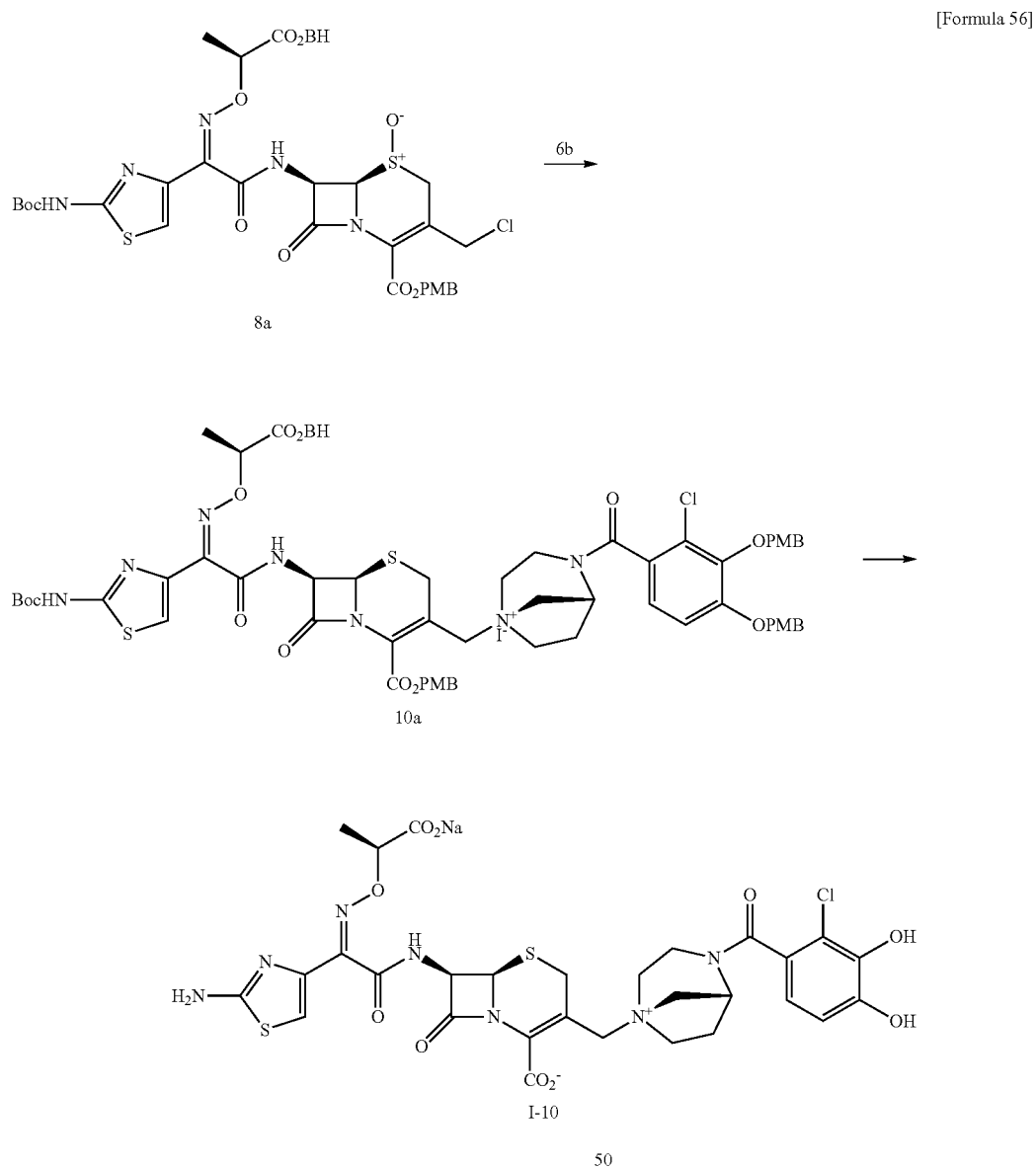
[Formula 56]
step (1): Compound 8a+Compound 6b→Compound 10a→Compound (I-10)
Using Compound 8a (839 mg, 0.94 mmol) and Compound 6b (492 mg, 0.94 mmol), Compound I-10 (219.4 mg, 31%) was obtained according to the same procedure as Example 8.
MS: 736.31 (M+8).
$^1$H-NMR (D$_2$O) δ: 7.01 (1H, s), 6.96-6.94 (1H, m), 6.85-6.78 (1H, m), 5.90-5.87 (1H, m), 5.55 (0.5H, s), 5.38-5.34 (1H, m), 4.90-4.55 (2.5H, m), 4.29-4.14 (1H, m), 3.97-3.32 (10H, m), 2.76-2.38 (2H, m), 1.43 (3H, d, J=6.9 Hz).
Elemental analysis for $C_{29}H_{29}ClN_7O_{10}S_2Na \cdot 6.1(H_2O)$
Calcd.: C, 40.13; H, 4.78; N, 11.30; S, 7.39; Cl, 4.08; Na, 2.65(%).
Found.: C, 40.08; H, 4.75; N, 11.32; S, 7.56; Cl, 4.13; Na, 2.30(%).

Example 11
Synthesis of Compound (I-11)
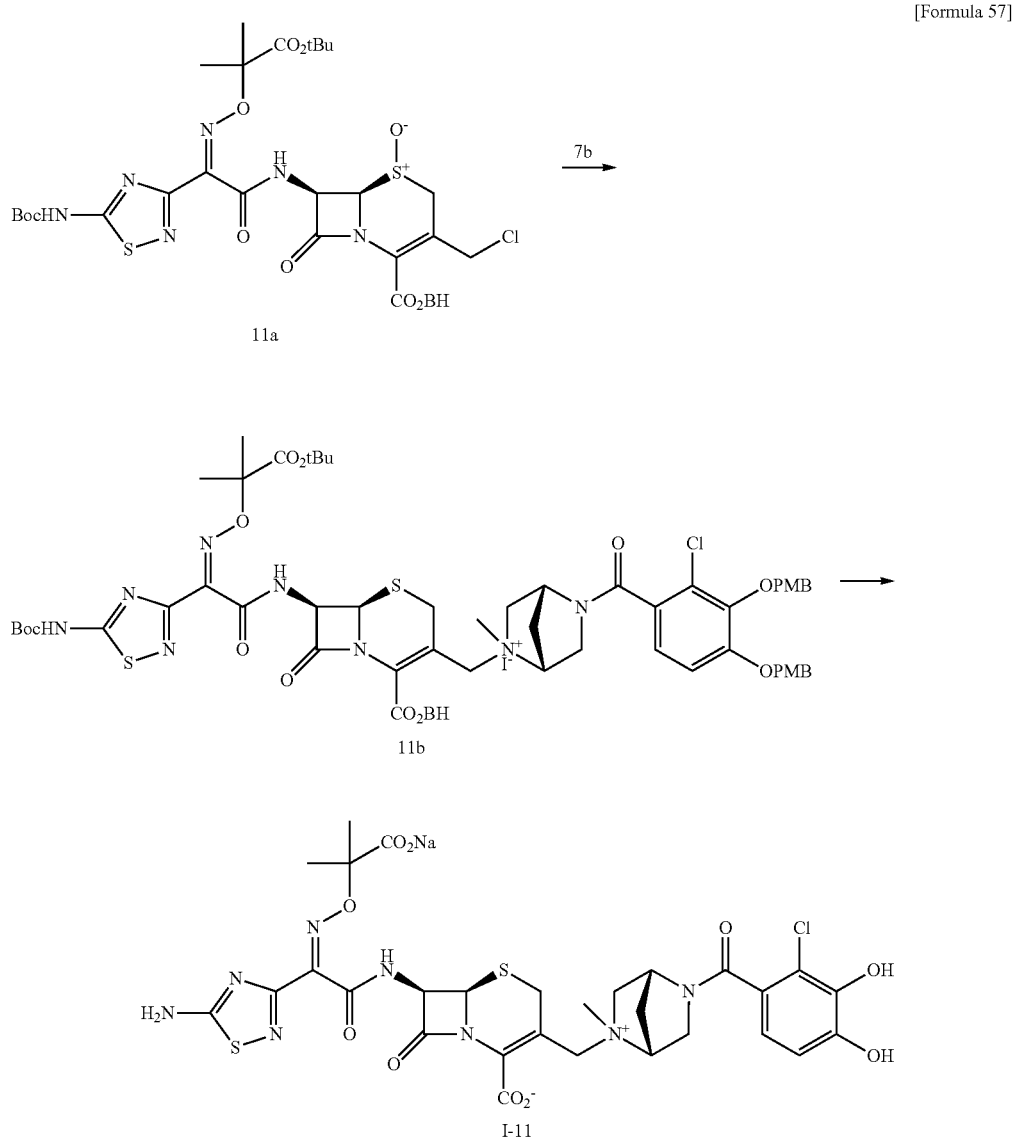
[Formula 57]
step (1): Compound 11a+Compound 7b→Compound 11b→Compound (I-11)
Using Compound 11a (843 mg, 1.0 mmol) and Compound 7b (523 mg, 1.0 mmol), Compound I-11 (260.5 mg, 34%) was obtained according to the same procedure as Example 8.
MS: 751.32 (M+H).
$^1$H-NMR (D$_2$O) δ: 6.95-6.82 (2H, m), 5.89 (1H, d, J=4.8 Hz), 5.37 (1H, dd, J=5.1, 1.8 Hz), 5.13 (0.5H, m), 4.76-4.49 (1.5H, s), 4.34-4.19 (2H, m), 4.00-3.47 (6H, m), 3.26, 3.17 (3H, m), 2.62-2.53 (2H, m), 1.54 (6H, d, J=4.2 Hz).
Elemental analysis for $C_{29}H_{30}ClN_8O_{10}S_2Na·6.7(H_2O)·0.2(NaHCO_3)$
Calcd.: C, 38.51; H, 4.83; N, 12.30; S, 7.04; Cl, 3.89; Na, 3.03(%).
Found.: C, 38.47; H, 4.72; N, 12.35; S, 7.06; Cl, 3.69; Na, 2.97(%).

Example 12
Synthesis of Compound (I-12)
[Formula 58]
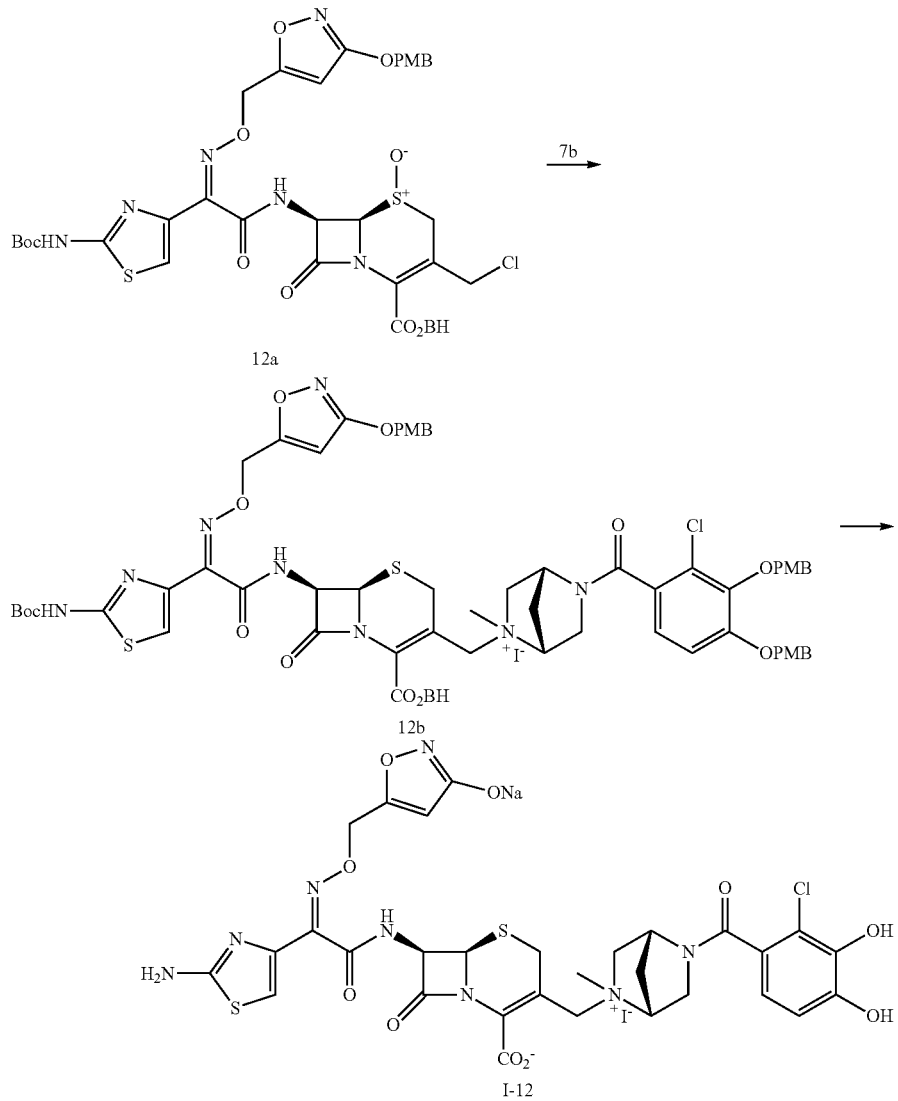
step (1): Compound 12a+Compound 7b→Compound 12b→Compound (I-12)
Using Compound 12a (917 mg, 1.0 mmol) and Compound 7b (523 mg, 1.0 mmol), Compound I-12 (172.5 mg, 22%) was obtained according to the same procedure as Example 8.
MS: 761.34 (M+H).
$^1$H-NMR (DMSO-$d_6$) δ: 6.76 (1H, s), 6.68 (1H, d, J=8.1 Hz), 6.56 (1H, d, J=7.9 Hz), 5.90 (1H, s), 5.65 (1H, d, J=4.7 Hz), 5.08-3.33 (16H, m), 3.09-3.03 (4H, m), 2.29-2.19 (2H, m).
Elemental analysis for $C_{30}H_{28.3}ClN_8O_{10}S_2Na_{0.7}$·5.7($H_2O$)
Calcd.: C, 40.98; H, 4.55; N, 12.74; S, 7.29; Cl, 4.03; Na, 1.83(%).
Found.: C, 41.02; H, 4.38; N, 12.68; S, 7.17; Cl, 4.26; Na, 1.83(%).

Example 13

Synthesis of Compound (I-13)

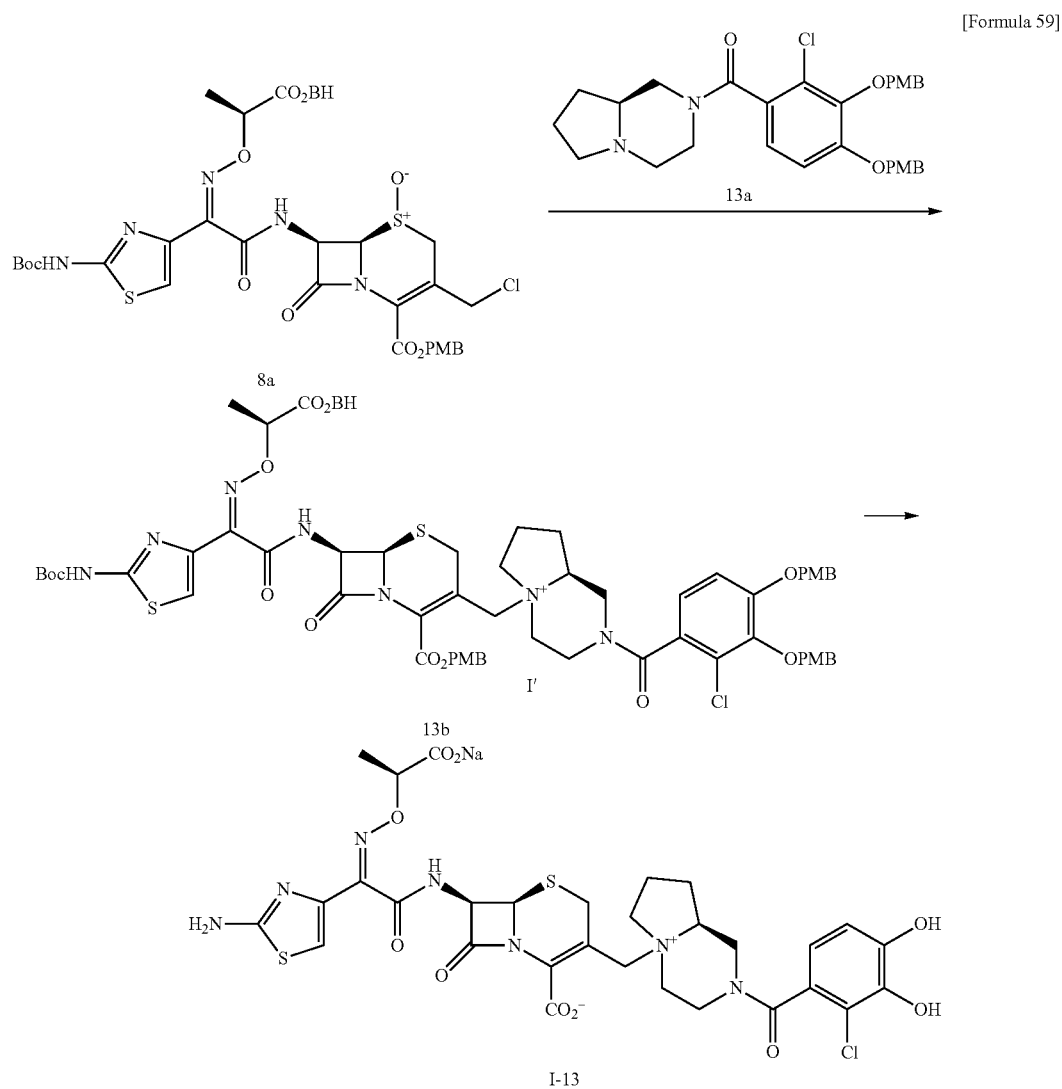

step (1): Compound 8a+Compound 13a→Compound 13b→Compound (I-13)

Using Compound 8a (695 mg, 0.78 mmol) and Compound 13a (418 mg, 0.78 mmol), Compound I-13 (155.7 mg, 27%) was obtained according to the same procedure as Example 8.

MS; 750.42 (M+H).

$^1$H-NMR (D$_2$O) δ: 7.06 (1H, d, J=3.2 Hz), 6.99 (1H, d, J=8.2 Hz), 6.87-6.83 (1H, m), 5.94 (1H, t, J=4.4 Hz), 5.40 (1H, dd, J=8.4, 5.0 Hz), 4.73-4.64 (1H, m), 4.51-4.28 (2H, m), 4.01-3.46 (10H, m), 2.00-2.53 (4H, m), 1.52 (3H, dd, J=7.1, 3.4 Hz).

Elemental analysis for C$_{30}$H$_{31}$ClN$_7$O$_{10}$S$_2$Na.5.5(H$_2$O).0.1 (NaHCO$_3$)

Calcd.: 41.10; H, 4.82; N, 11.15; S, 7.29; Cl, 4.03; Na, 2.87(%).

Found.: C, 41.24; H, 4.86; N, 11.01; S, 6.84; Cl, 3.70; Na, 2.96(%).

Example 14
Synthesis of Compound (I-14)
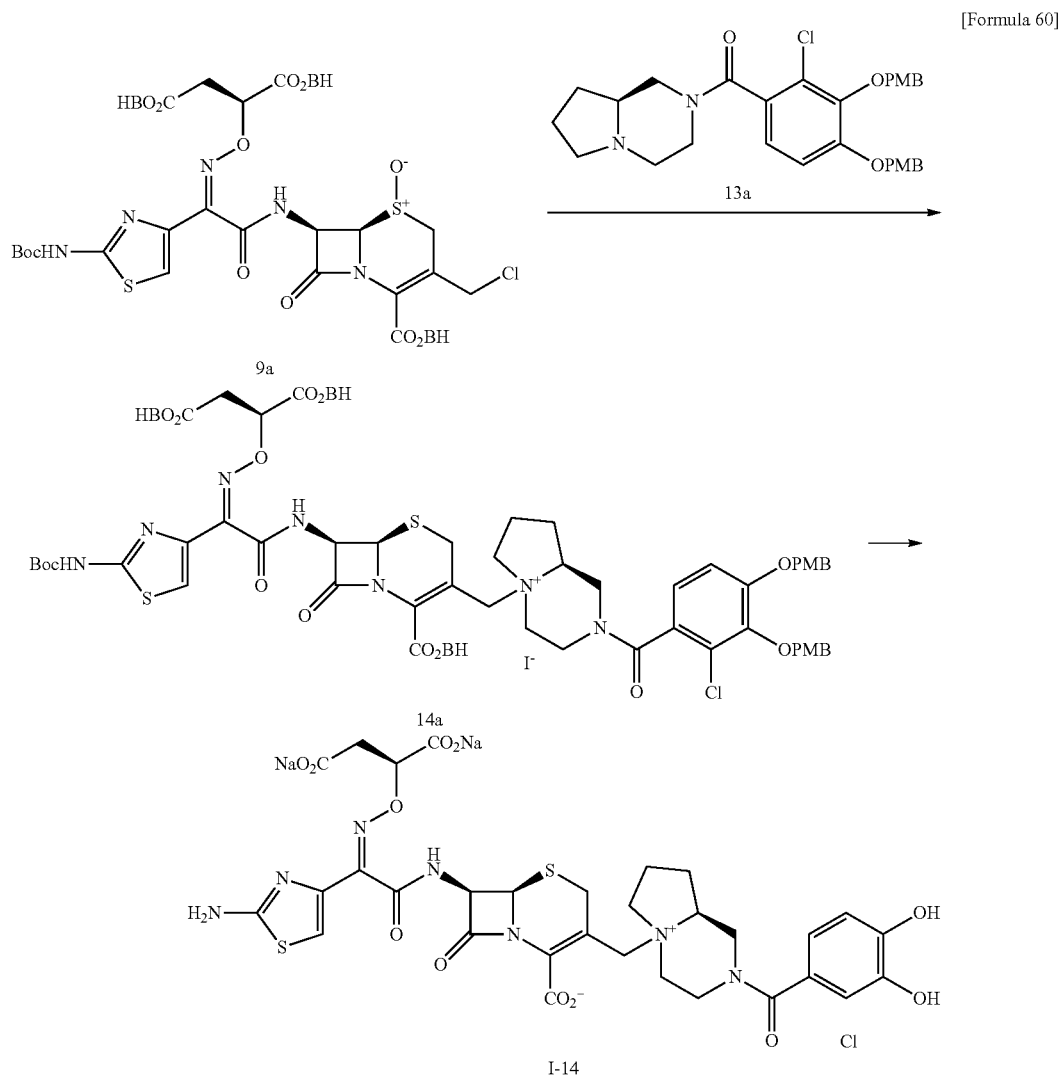
step (1): Compound 9a+Compound 13a→Compound 14a→Compound (I-14)
Using Compound 9a (804 mg, 0.70 mmol) and Compound 13a (376 mg, 0.70 mmol), Compound I-14 (186.3 mg, 32%) was obtained according to the same procedure as Example 8.
MS: 794.43 (M+H).
$^1$H-NMR (D$_2$O) δ: 7.06 (1H, d, J=2.7 Hz), 7.00 (1H, dd, J=8.2, 3.5 Hz), 6.93-6.86 (1H, m), 5.88 (1H, t, J=4.2 Hz), 5.37 (1H, dd, J=8.6, 5.0 Hz), 5.04-4.95 (2H, m), 4.52-4.29 (2H, m), 4.04-3.46 (10H, m), 2.81-2.69 (2H, m), 2.44-2.15 (4H, m).
Elemental analysis for $C_{31}H_{30}ClN_7O_{12}S_2Na_2 \cdot 6.9(H_2O) \cdot 0.1(NaHCO_3)$
Calcd.: C, 38.47; H, 4.56; N, 10.10; S, 6.61; Cl, 3.65; Na, 4.97(%).
Found.: C, 38.49; H, 4.48; N, 10.12; S, 6.41; Cl, 3.85; Na, 4.94(%).

Example 15
Synthesis of Compound (I-15)
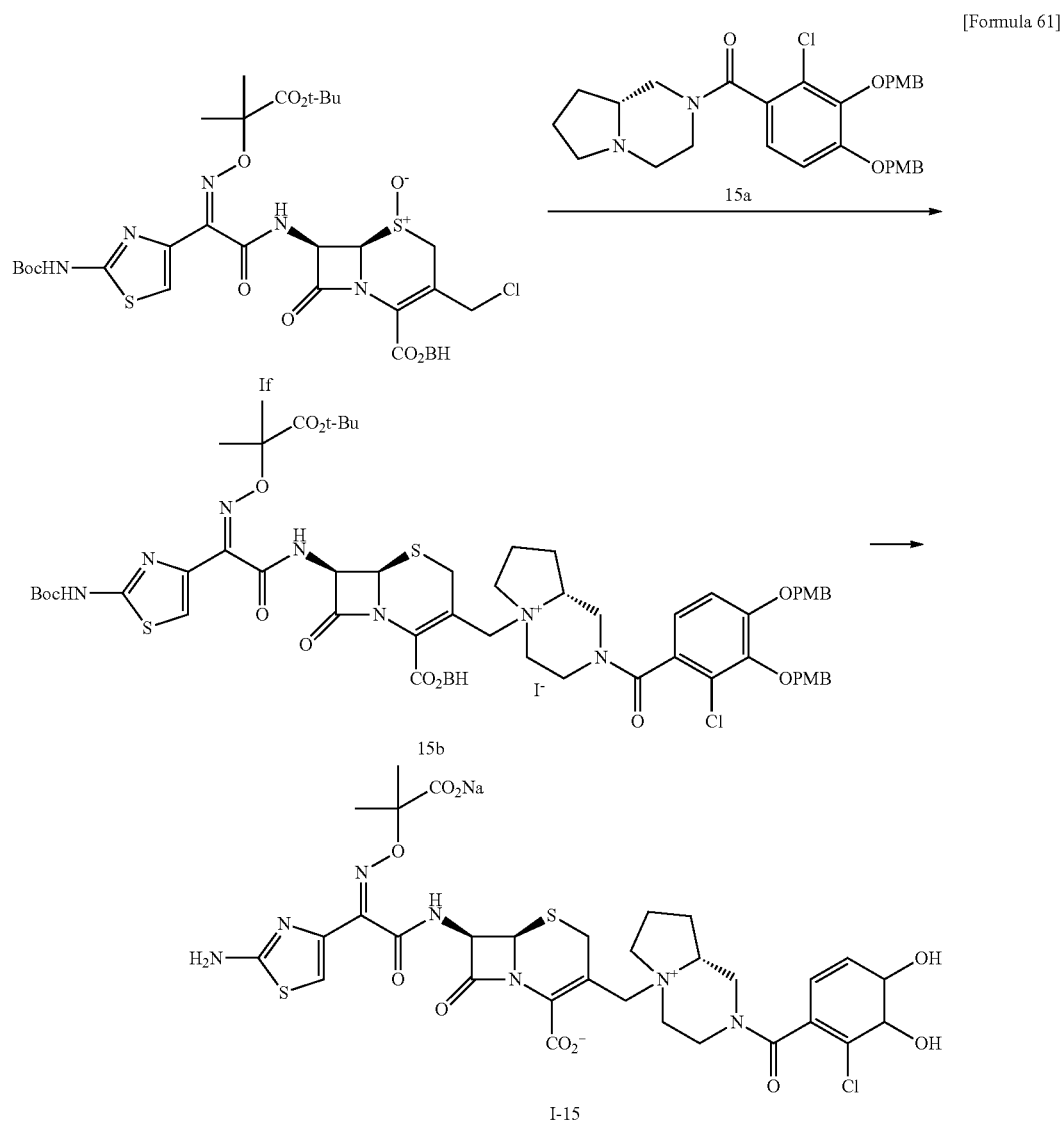
step (1): Compound 1f+Compound 15a→Compound 15b→Compound (I-15)
Using Compound 1f (842 mg, 1.0 mmol) and Compound 15a (537 mg, 1.0 mmol), Compound I-15 (330 mg, 42%) was obtained according to the same procedure as Example 8.
MS: 764.38 (M+H).
$^1$H-NMR (D$_2$O) δ: 7.03-6.98 (2H, m), 6.93-6.84 (1H, m), 5.92 (1H, dd, J=10.2, 4.9 Hz), 5.40 (1H, J=10.6, 5.0 Hz), 5.31-5.21 (1H, m), 4.73-4.56 (1H, m), 4.09-3.30 (11H, m), 2.57-2.02 (4H, m), 1.59-1.48 (6H, m).
Elemental analysis for C$_{31}$H$_{33}$ClN$_2$O$_{10}$S$_2$Na.5.3(H$_2$O).0.1 (NaHCO$_3$)
Calcd.: C, 41.97; H, 4.95; N, 11.02; S, 7.20; Cl, 3.98; Na, 2.84(%).
Found.: C, 41.85; H, 4.86; N, 11.25; S, 7.14; Cl, 4.02; Na, 2.89(%).

Example 16

Synthesis of Compound (I-16)

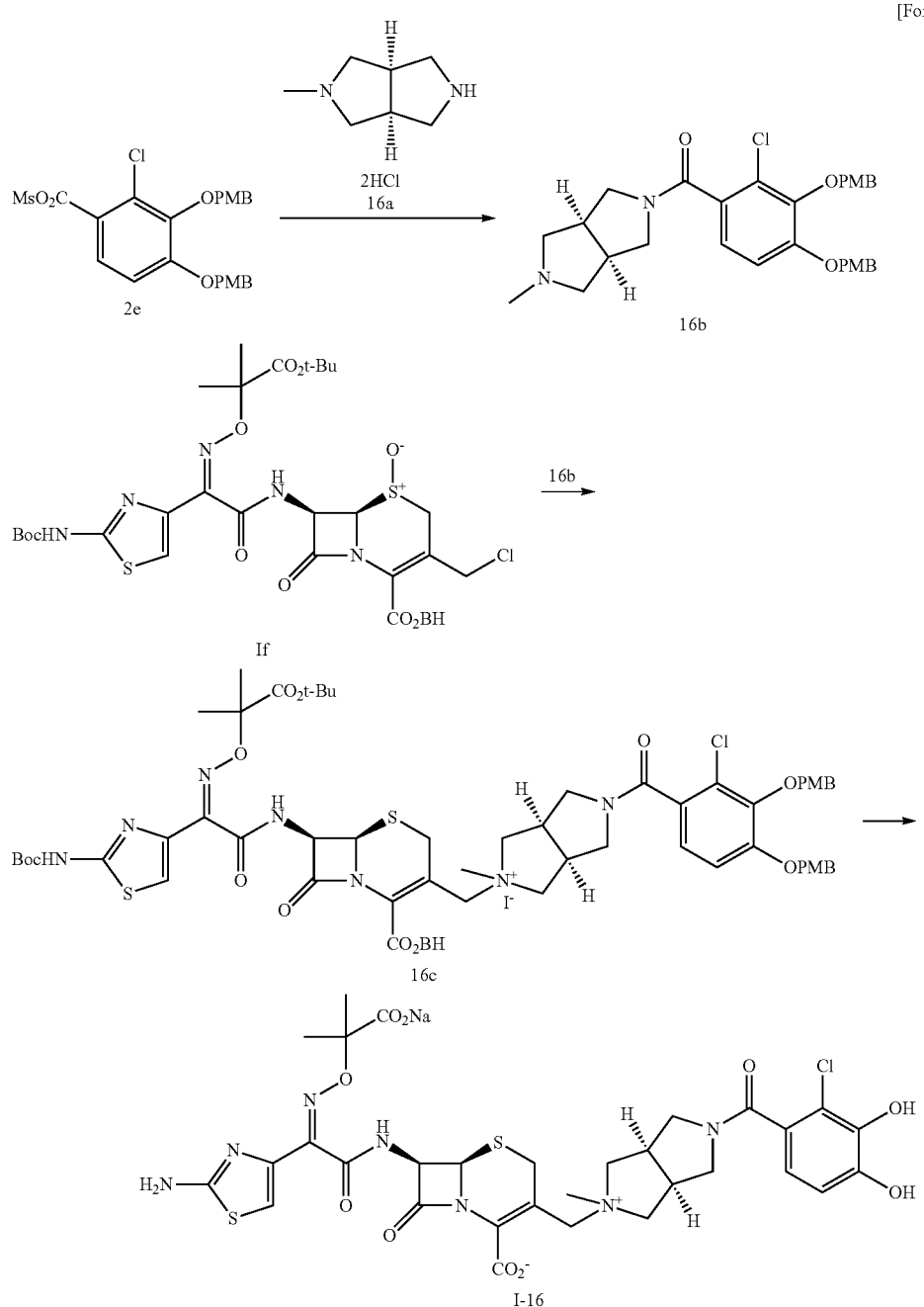

[Formula 62]

step (1): Compound 2e+Compound 16a→Compound 16b

Using Compound 2e (6 mmol) and Compound 16a (1.43 g, 7.2 mmol), which was synthesized as described in J. Heterocycl. Chem. 1983, 20, 321, Compound 16b (1.69 g, 52%) was obtained according to the same procedure as Example 2.

MS: 537.35 (M+H).

$^1$H-NMR (CDCl$_3$) δ: 7.38-7.30 (4H, m), 6.98-6.89 (4H, m), 6.83-6.79 (2H, m), 5.06 (2H, s), 4.98 (2H, s), 3.91-3.87 (1H, m), 3.83 (3H, s), 3.79 (3H, s), 3.58 (1H, dd, J=4.3, 12.8 Hz), 3.30-3.37 (1H, m), 3.00 (1H, dd, J=4.4, 11.6 Hz), 2.94-2.85 (1H, m), 2.82-2.74 (1H, m), 2.68 (1H, t, J=7.2 Hz), 2.57 (1H, t, J=7.2 Hz), 2.42 (1H, dd, J=4.6, 9.5 Hz), 2.31 (3H, s), 2.25 (1H, dd, J=4.6, 9.5 Hz).

Step (2): Compound 1f+Compound 1.6b→Compound 16c→Compound (I-1)

Using Compound 1f (842 mg, 1.0 mmol) and Compound 16b (537 mg, 1.0 mmol), Compound I-16 (330 mg, 42%) was provided according Co the same procedure as Example 9.

MS: 764.38 (M+H).

¹H-NMR (D₂O) δ: 6.97-6.92 (2H, m), 6.85-6.81 (1H, m), 5.88 (1H, dd, J=4.9, 2.9 Hz), 5.38 (1H, dd, J=5.0, 2.9 Hz), 4.77-4.68 (1H, m), 4.20-3.84 (5H, m), 3.68-2.95 (11H, m), 1.51 (6H, d, J=5.0 Hz).

Elemental analysis for C₃₁H₃₃ClN₇O₁₀S₂Na.5.9(H₂O).0.2 (NaHCO₃)

Calcd.: C, 41.21; H, 4.99; N, 10.78; S, 7.03; Cl, 3.90; Na, 3.03(%).

Found.: C, 41.13; H, 4.97; N, 10.86; S, 7.27; Cl, 3.91; Na, 2.99(%).

Example 17

Synthesis of Compound (I-17)

chloric acid solution (2 mL) was added to the reaction solution, and then methylene chloride was evaporated under reduced pressure. Ethyl acetate and water were then added to the resulting residue. The organic layer separated was washed with saturated brine, dried with magnesium sulfate, filtered, and concentrated in vacuo to yield Compound 17c (2.33 g).

MS: 1412.14 (M+H)

step (2): Compound 17c→Compound (I-17)

The above-describe crude Compound 17c (2.33 g) was dissolved in methylene chloride (25 ml) and anisole (1.64 mL, 15 mmol), and then cooled to −40° C. 2 mol/L-aluminum chloride/nitromethane solution (7.5 mL, 15 mmol) was added thereto, and then stirred under ice-cooling or 75 minutes. The reaction solution was dissolved in Aqueous 1 N hydrochloric acid solution and acetonitrile, and then the aqueous layer

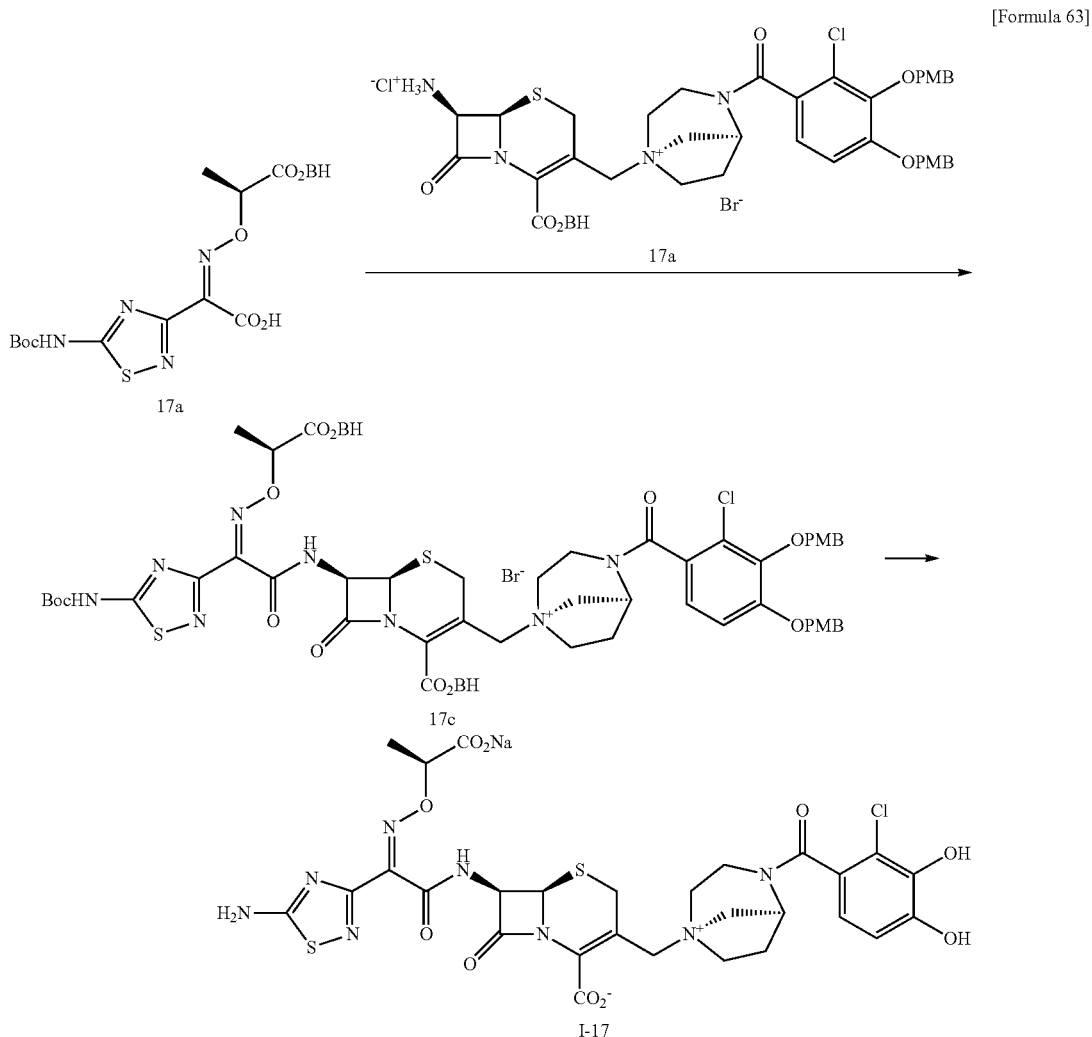

[Formula 63]

step (1): Compound 17a+Compound 17b→Compound 17c

Compound 17a (750 mg, 1.43 mmol) and Compound 17b (1.60 g, 1.5 mmol), which were obtained using the some method as described in Bioorg. Med. Chem. 2007, 15, 6716, were dissolved in methylene chloride (20 mL), and then cooled to −15° C. pyridine (0.145 mL, 1.8 mmol) followed by hydrochloric acid salt of N-ethyl-N'-(3-dimethylaminopropyl)carbodiimide (345 mg, 1.8 mmol) were added, and then stirred under ice-cooling for two hours. Aqueous 2 N hydroseparated was washed with diisopropyl ether. HP-2055 resin was added to the aqueous layer, concentrated, and then subjected to ODS column chromatography, eluting with water-acetonitrile. Aqueous 0.2 N sodium hydroxide solution was added to fractions containing the desired compound to adjust them to pH=6, and thereby a sodium salt thereof was formed. Lyophilization yielded Compound I-17 (308.5 mg, 27%) as a powder.

MS: 737.36 (M+H).

¹H-NMR (D₂O) δ: 6.96-6.92 (1H, m), 6.85-6.79 (1H, m), 5.91 (1H, t, J=5.3 Hz), 5.54 (0.4H, s), 5.35 (1H, t, J=5.6 Hz), 4.77-4.67 (2H, m), 4.55 (0.6H, s), 4.16 (1H, d, J=13.7 Hz), 3.90-3.33 (10H, m), 2.76-2.36 (2H, m), 1.51 (3H, d, J=7.0 Hz).
Elemental analysis for $C_{28}H_{28}ClN_8O_{10}S_2Na \cdot 4.9(H_2O)$
Calcd.: C, 39.69; H, 4.50; N, 13.22; S, 7.57; Cl, 4.18(%).
Found.: C, 39.77; H, 4.51; N, 12.80; S, 7.56; Cl, 4.54(%).
Example 18
Synthesis of Compound (I-18)
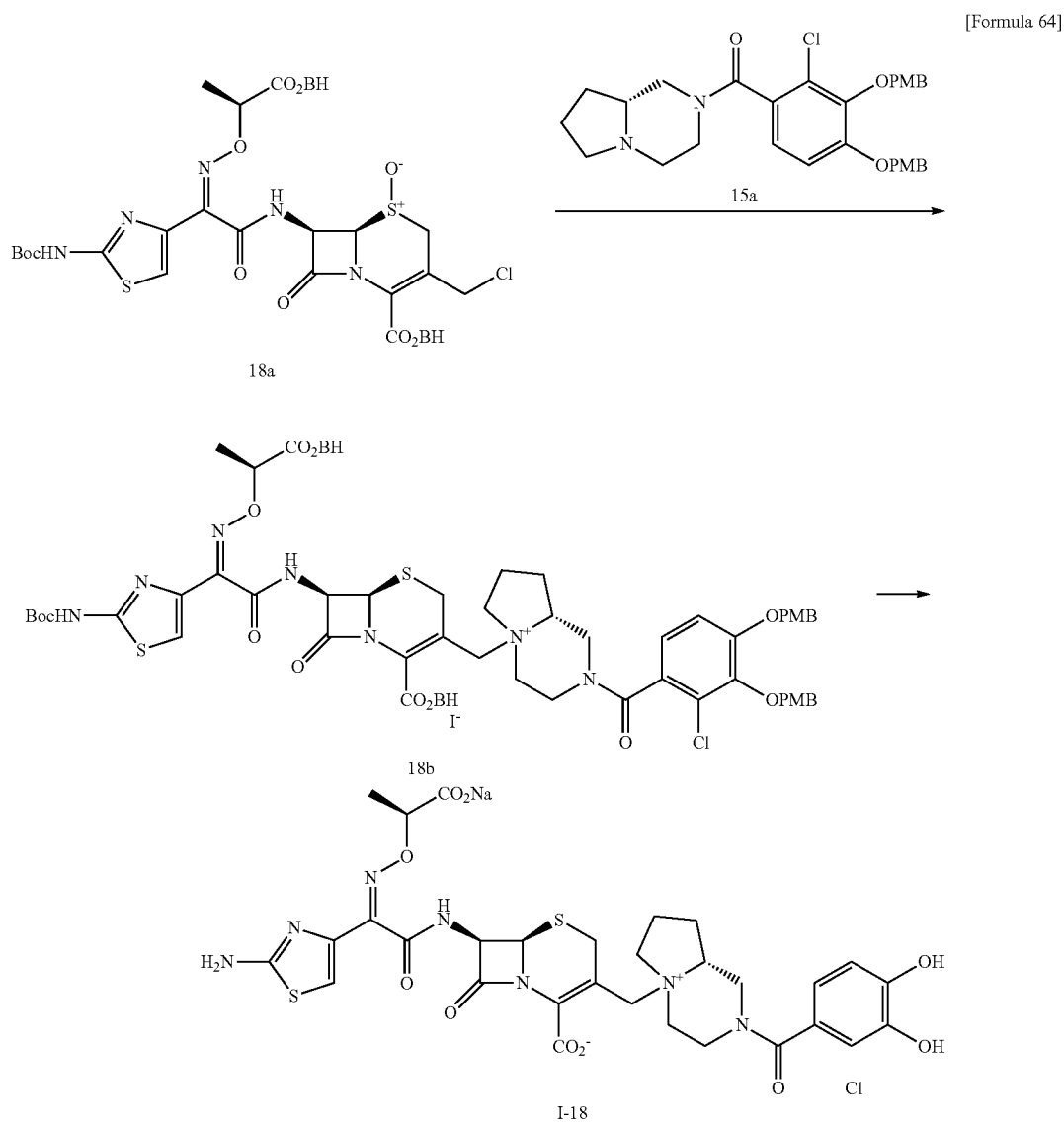
[Formula 64]
step (1): Compound 18a+Compound 15a→Compound 18b→Compound (I-18)
Using Compound 18a (751 mg, 0.80 mmol) and Compound 15a (430 mg, 0.80 mmol), Compound I-18 (224.2 mg, 36%) was obtained according to the same procedure as Example 8.
MS: 750.39 (M+H).

¹H-NMR (D₂O) δ: 7.01 (1H, d, J=3.2 Hz), 6.97-6.93 (1H, m), 6.89-6.80 (1H, m), 5.89 (1H, dd, J=10.0, 4.8 Hz), 5.36 (1H, dd, J=10.1, 5.1 Hz), 5.26-5.16 (1H, m), 4.70-4.56 (2H, m), 4.05-3.25 (12H, m), 2.19-2.50 (4H, m), 1.48 (3H, d, J=7.0 Hz).

Elemental analysis for $C_{30}H_{31}ClN_7O_{10}S_2Na.5.3(H_2O).0.1$ $(NaHCO_3)$

Calcd.: C, 41.27; H, 4.80; N, 11.19; S, 7.32; Cl, 4.05; Na, 2.89(%).

Found.: C, 41.22; H, 4.72; N, 11.21; S, 7.44; Cl, 4.17; Na, 2.78(%).

Example 19

Synthesis of Compound (I-19)

step (1): Compound 2d+Compound 19a→Compound 19b

A solution of Compound 2d (1.28 g, 3 mmol) in N,N-dimethylformamide (4 mL) was cooled to 0° C. Hydrochloric acid salt of N-ethyl-N'-(3-dimethylaminopropyl)carbodiimide (663 mg, 3.30 mmol) and 1-hydroxybenzotriazole (446 mg, 3.30 mmol) were added thereto, and then stirred at room temperature for 30 minutes. After cooling it to 0° C. again, Compound 19a (747 mg, 3.75 mmol) and triethylamine (1.25 mL, 9 mmol) were added, and then stirred for 1 hour. Ethyl acetate (50 mL) and aqueous 5% sodium hydrogen carbonate solution were added to the reaction solution, and then the organic layer separated was washed with water, then saturated brine. Drying with magnesium sulfate and then evaporation in vacuo yielded Compound 19b.

Yield: 1.46 g (91%)

[Formula 65]

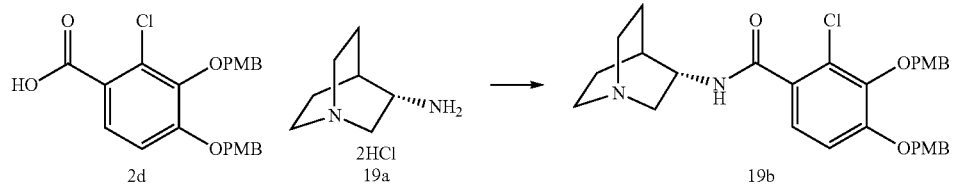

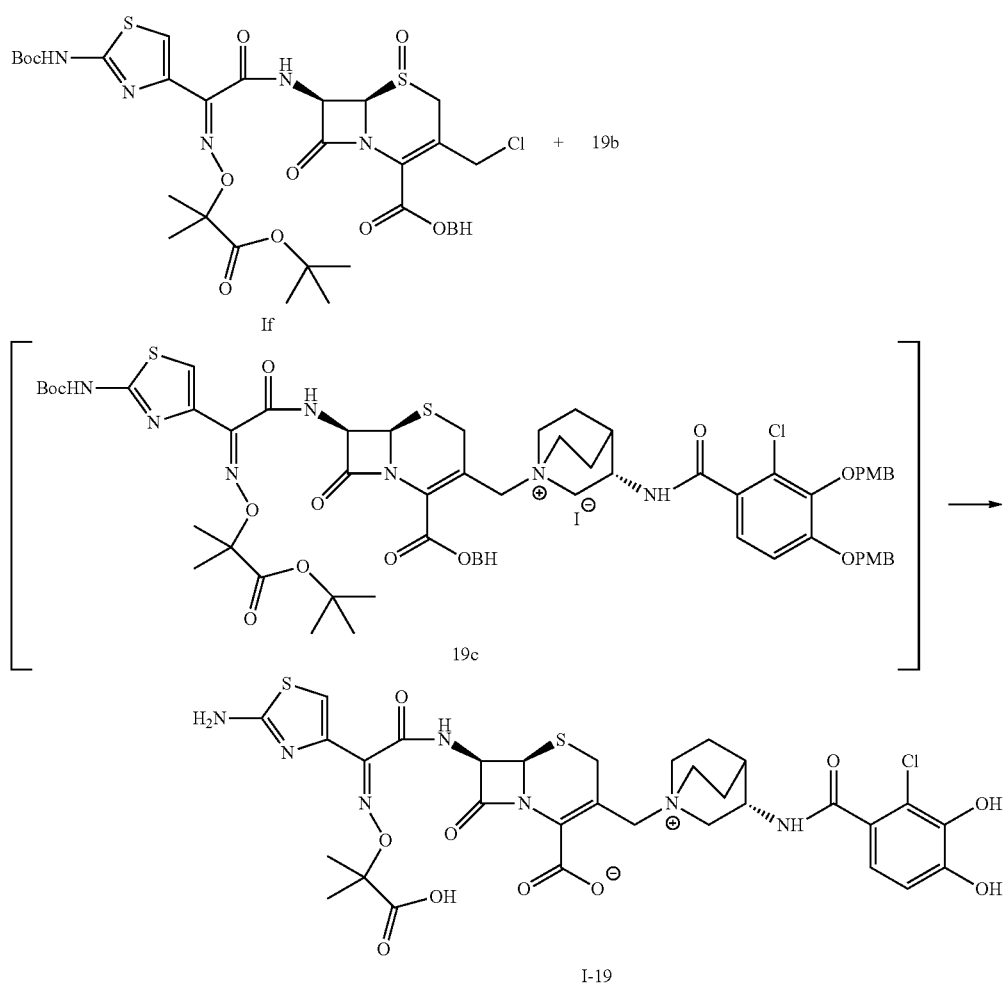

$^1$H-NMR (CDCl$_3$) δ: 1.80-3.45 (11H, m), 3.79 (3H, s), 3.83 (3H, s), 4.94 (2H, s), 5.08 (2H, s), 6.80-7.52 (10H, m)

step (2): Compound 2g+Compound 19b→Compound 19c→Compound (I-19)

A solution of Compound 2g (877 mg, 1 mmol), Compound 19b (537 mg, 1 mmol), and sodium bromide (206 mg, 2 mmol) in N,N-dimethylformamide (3 mL) was stirred at room temperature for 1 hour. The reaction solution was diluted with 14, N-dimethylformamide (6 mL), then cooled to −40° C. Phosphorus tribromide (0.189 mL, 2 mmol) was added thereto, and then stirred for 1 hour. Ice and ethyl acetate were added there to, and then the organic layer separated was washed with water, then saturated brine. Drying over magnesium sulfate, and then concentrating under reduced pressure yielded Compound 19c. The resulting Compound 19c was dissolved in methylene chloride (10 ml) and anisole (0.6 ml), and then cooled to −40° C. 2 mol/L-aluminum chloride/nitromethane solution (2.7 ml) was added, and then stirred at 0° C. for 50 minutes. Aqueous 2 N hydrochloric acid (60 mL), acetonitrile (50 mL), and diethyl ether (100 ml) were added to the reaction solution. The aqueous layer separated was washed with diethyl ether, concentrated in vacuo, and then subjected to HP-20SS column chromatography, eluting the desired compound with acetonitrile-water. To the eluant, 0.02 N sodium hydroxide was added to adjust it to pH=6, and then concentrated in vacuo. The condensate solution was lyophilized to yield Compound I-19 as a white non-crystalline powder.

Yield: 451 mg (57%)

$^1$H-NMR (D$_2$O) δ: 1.34 (6H, s), 1.80-2.20 (4H, m), 2.21-2.50 (1H, m) 3.15-3.90 (8H, m), 5.12 (1H, d, J=5.1 Hz), 5.71 (1H, d, J=5.1 Hz), 6.80-6.95 (3H, m)

Example 20

Synthesis of Compound (I-20)

[Formula 66]

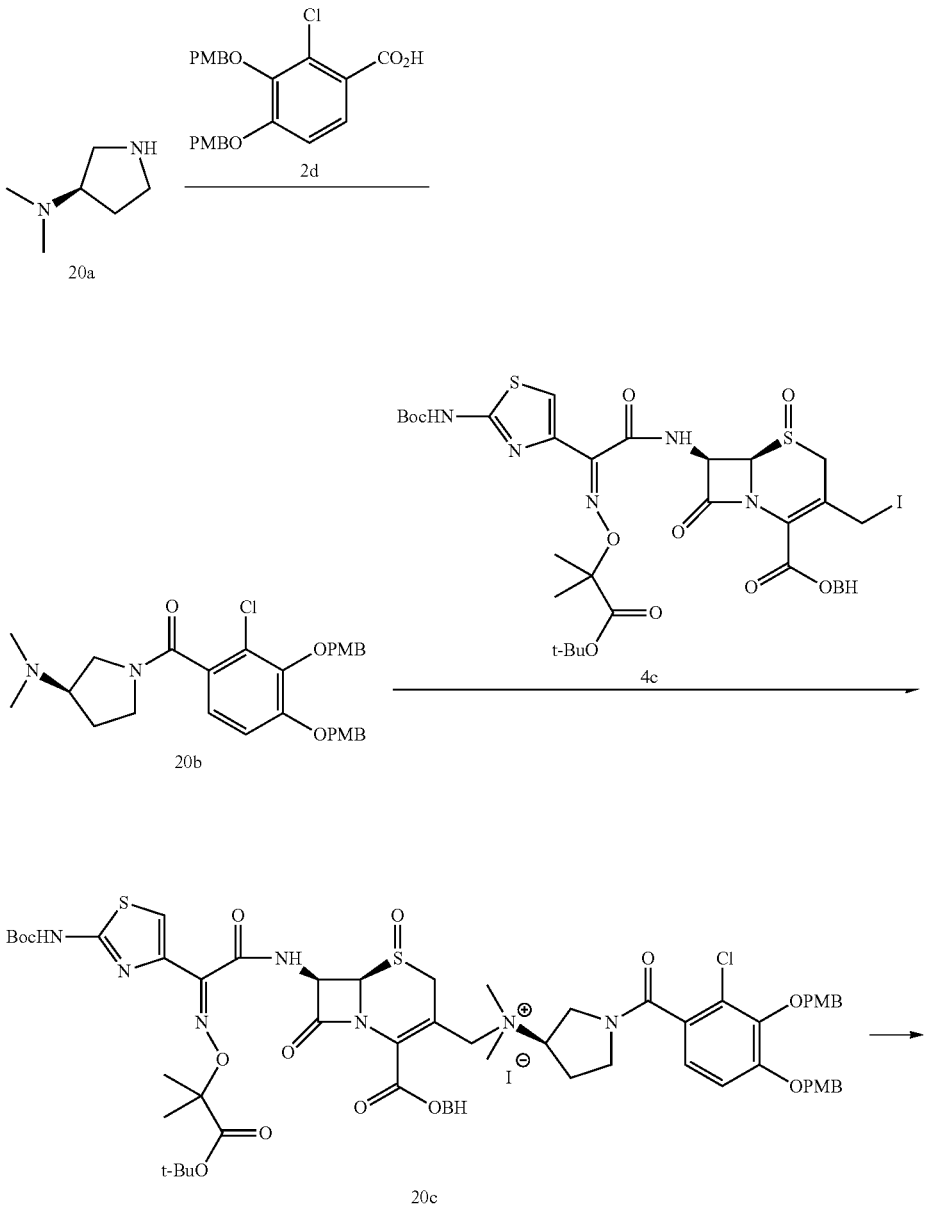

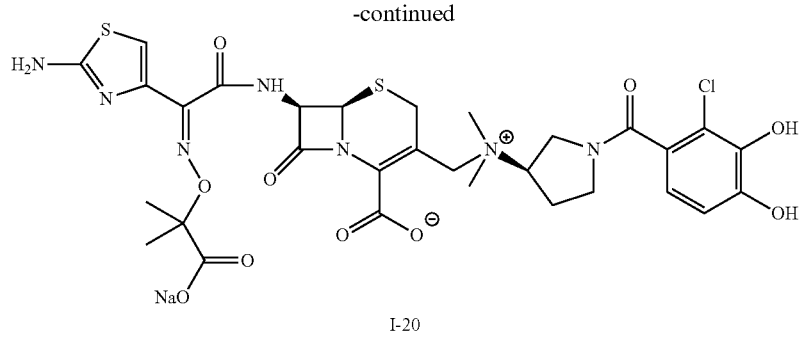

I-20 step (1): Compound 20a+Compound 2d→Compound 20b

To a solution of Compound 2d (2.14 g, 5 mmol) in N,N-dimethylacetamide (20 mL) triethylamine (0.83 ml, 6 mmol) was added, and then stirred at −10° C. for 5 minutes. Methanesulfonyl chloride (0.51 ml, 6.5 mmol) was added in one portion, and then stirred at −10° C. for 30 minutes. Subsequently, Compound 20a (0.57 g, 5 mmol) was added thereto, and then stirred at the same temperature for 30 minutes. The reaction solution was diluted with ethyl acetate, and then washed with aqueous saturated sodium hydrogen carbonate solution, water, then saturated brine. The organic layer was then dried with magnesium sulfate. After magnesium sulfate was filtered, the filtrate was concentrated vacuo, and then subjected to silica gel column chromatography, eluting with chloroform-methanol. Fractions containing the desired compound were concentrated under reduced pressure to yield Compound 20b (2.3 g, 88%).

MS: 525.83 (M+H)

$^1$H-NMR (CDCl$_3$) δ: 1.69-1.86 (2H, m), 2.71-2.78 (1H, m), 2.94 (3H, s), 3.01 (3H, s), 3.16-3.38 (2H, m), 3.51-3.61 (1H, m), 3.79 (3H, s), 3.83 (3H, s), 3.87-4.16 (1H, m), 4.97 (2H, s), 5.06 (2H, s), 6.81 (2H, d, J=6.8), 6.89-6.99 (4H, m), 7.31-7.36 (4H, m).

step (2): Compound 20b→Compound 20c

To a solution of Compound 4c (4.09 g, 4.38 mmol) in N,N-dimethylformamide (30 mL): Compound 20b (2.38 g, 4.38 mmol) was added, and then stirred at room temperature for 30 minutes. The reaction solution was diluted with aqueous 0.2 N hydrochloric acid solution, and then separated with ethyl acetate. The organic layer was washed with water, then saturated brine, dried with magnesium sulfate, and then concentrated under reduced pressure to yield Compound 20c.

MS: 1331.53 (M+H)

step (3): Compound 20c→Compound (I-20)

The above-described crude Compound 20c was dissolved in methylene chloride (40 mL). Under the condition of −40° C., 1 mol/L-phosphorus tribromide/methylene chloride solution (13.14 mL, 13.14 mmol) was added thereto, and then stirred at −30° C. for 30 minutes. After the reaction solution was cooled to −40° C. again, anisole (4.78 mL, 43.8 mmol) and 2 mol/L-aluminum chloride/nitromethane solution (21.9 mL, 43.8 mmol) was added, followed by stirring at 0° C. for one hour. The reaction solution was dissolved in aqueous 1 N hydrochloric acid solution and acetonitrile, and then the aqueous layer separated was washed with diisopropyl ether. HP-20SS resin was added to the aqueous layer, concentrated, and then subjected to ODS column chromatography, eluting with water-acetonitrile. Fractions containing the desired compound were collected, and then adjusted to pH=5.5 with aqueous 0.02 N sodium hydroxide solution. Concentrating under reduced pressure and subsequent lyophilization yielded Compound I-20 (1.7 g, 50%) as a powder.

MS: 752.39 (M+H)

$^1$H-NMR (DMSO-d$_6$) δ: 1.39 (3H, s), 1.47 (3H, s), 2.20-2.41 (1H, br m), 2.92 (1H, br s), 2.96 (3H, s), 3.03 (3H, s), 3.51-3.96 (9H, m), 4.19-4.28 (1H, m), 5.02-5.06 (1H, br m), 5.15 (1H, d, J=5.0 Hz), 5.77 (1H, dd, J=8.5, 5.0 Hz), 6.56-6.64 (1H, m), 6.74 (1H, s), 6.84 (1H, d, J=8.1 Hz), 7.21 (2H, s), 11.37 (1H, s).

Elemental analysis for $C_{10}H_{33}ClN_7NaO_{10}S_2 \cdot (H_2O)_{4.9}$ $(NaHCO_3)_{0.1}$ Calcd.: C, 41.51; H, 4.97; Cl, 4.07; N, 11.26; Na, 2.90; O, 27.92; S, 7.36(%).

Found.: C, 41.39; 4.69; Cl, 4.60; N, 11.24; Na, 2.78; S, 7.56; (%).

Example 21

Synthesis of Compound (I-21)

[Formula 67]

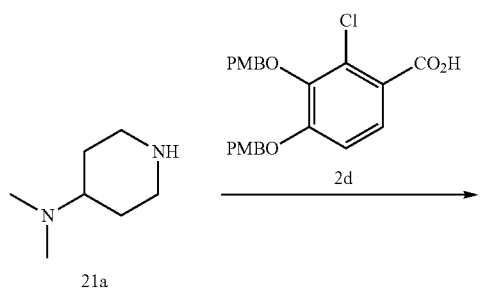

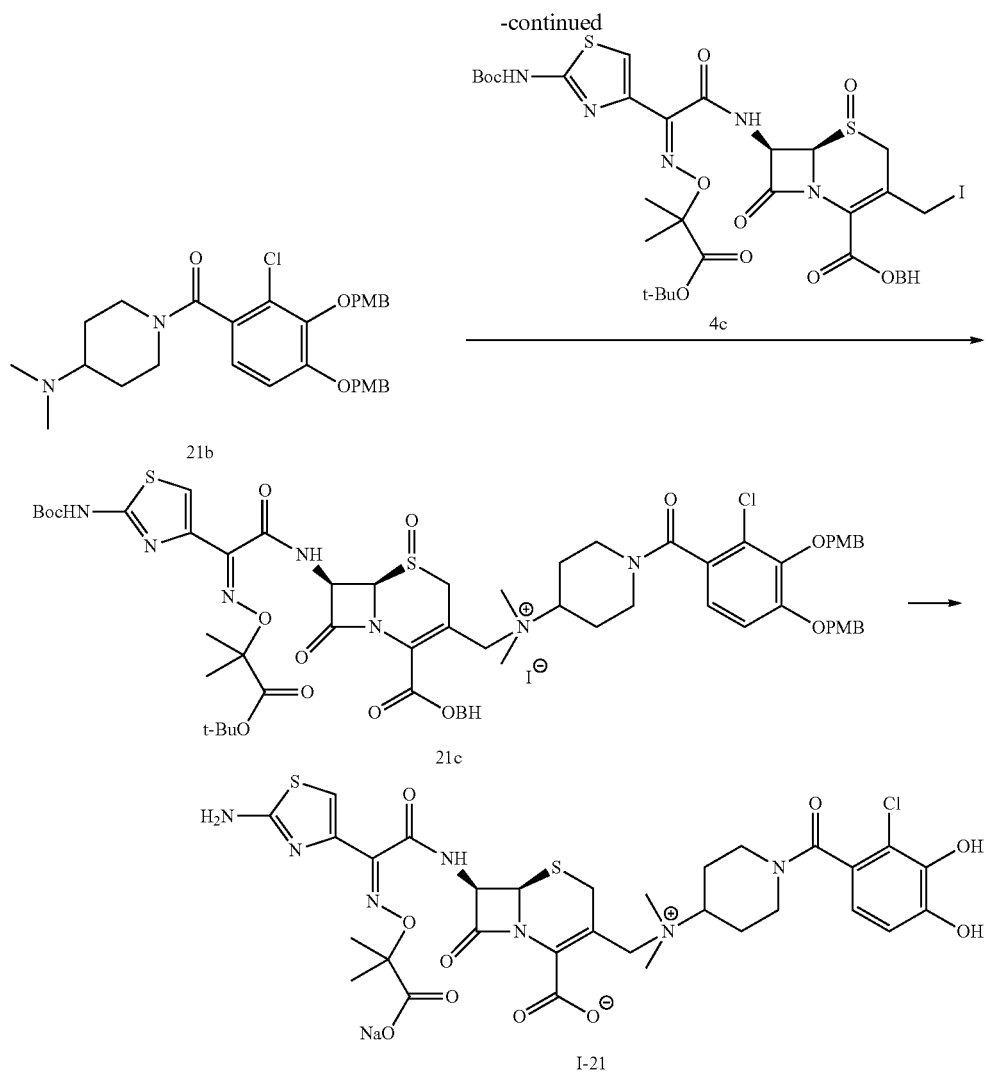

step (1): Compound 21a+Compound 2d→Compound 21b

To a solution of Compound 21a (0.33 g, 2.57 mmol) and Compound 2d (1.16 g, 2.70 mmol) in methylene chloride (10 mL), under the condition of 0° C., hydrochloric acid salt of N-ethyl-N'-(3-dimethylaminopropyl)carbodiimide (0.59 g, 3.09 mmol) was added, and then stirred at 0° C. for 30 minutes. The reaction solution was diluted with ethyl acetate, and then washed with water, then saturated brine. The organic layer separated was then dried with magnesium sulfate. After magnesium sulfate was filtered, the filtrate was concentrated in vacuo, and then subjected to silica gel column chromatography, eluting with chloroform-methanol. Fractions containing the desired compound were concentrated under reduced pressure to yield Compound 21b (0.4 g, 29%).

MS: 539.4 (M+H)

$^1$H-NMR (CDCl$_3$) δ: 1.46-1.74 (3H, m), 1.93 (1H, brt, J=7.8), 2.23-2.34 (1H, m), 2.27 (6H, s), 2.73-3.03 (2H, m), 3.38 (1H, brt, J=7.8), 3.79 (3H, s), 3.83 (3H, s), 4.73 (1H, brt, J=9.2), 4.92-5.00 (2H, m), 5.06 (2H, s), 6.80 (2H, d, J=7.8), 6.90-6.98 (4H, m), 7.29-7.37 (4H, m).

step (2): Compound 21b→Compound 21c

To a solution of Compound 4c (0.83 g, 0.89 mmol) in N,N-dimethylformamide (10 mL): Compound 21b (0.40 g, 0.74 mmol) was added, and then stirred at room temperature for 1 hour. The reaction solution was diluted with aqueous 0.2 N hydrochloric acid solution, and then separated with ethyl acetate. The organic layer was washed with water, then saturated brine, dried with magnesium sulfate, and then concentrated under reduced pressure to yield Compound 21c.

MS: 1345.23 (M+H)

step (3): Compound 21c→Compound (I-21)

The above-described crude Compound 21c was dissolved in methylene chloride (10 mL). Under the condition of −40° C., phosphorus tribromide (0.22 mL, 2.23 mmol) was added thereto, and then stirred at −30° C. for 30 minutes. After the reaction solution was cooled to −40° C. again, anisole (0.81 mL, 7.42 mmol) and 2 mol/L-aluminum chloride/nitromethane solution (3.71 mL, 7.42 mmol) were added, and then stirred at 0° C. for 1 hour. The reaction solution was dissolved in aqueous 1 N hydrochloric acid solution and acetonitrile, and then washed with diisopropyl ether. HP-20SS resin was added to the aqueous layer separated, concentrated, subjected to ODS column chromatography, eluting with water-acetonitrile. Fractions containing the desired compound were collected, and then adjusted to pH=5.5 with aqueous 0.0 N sodium hydroxide solution. Concentrating under reduced pressure, and subsequent lyophilization yielded Compound I-21 (301 mg, 52%) as a powder.

MS: 766.41 (M+H)

¹H-NMR (D₂O) δ: 1.49 (6H, d, J=5.2 Hz), 1.68-1.98 (2H, m), 2.17 (1H, t, J=9.1 Hz), 2.40 (1H, d, J=9.1 Hz), 2.86-3.01 (5H, m), 3.06 (3H, s), 3.13-3.32 (1H, m), 3.46 (1H, d, 17.4 Hz), 3.64-3.78 (2H, m), 3.89-4.02 (2H, m), 4.94 (1H, d, J=17.4 Hz), 5.37 (1H, d, J=5.0 Hz), 5.87 (1H, d, J=5.0 Hz), 6.80 (1H, dd, J=22.4, 8.3 Hz), 6.93 (1H, dd, J=8.3, 4.0 Hz), 6.97 (1H, s)

Elemental analysis for $C_{31}H_{35}ClN_7NaO_{10}S_2 \cdot (H_2O)_{6.7} \cdot (NaHCO_3)_{0.1}$ Calcd.: C, 40.72; H, 5.33; Cl, 3.86; N, 10.69; Na, 2.76; O, 29.65; S, 6.99(%).

Found.: C, 40.65; H, 5.33; Cl, 3.86; N, 10.68; Na, 2.91; S, 7.17; (%).

Example 22

Synthesis of Compound (I-22)

N hydrochloric acid were added to the reaction solution. The organic layer was extracted by separation, washed with 0.2 N hydrochloric acid, then saturated brine, and then dried with magnesium sulfate. Filtrating, concentrating, and then drying under reduced pressure yielded Compound 22a as a foamed solid. The obtained compound 22a was used in the next reaction without purification.

step (2): Compound 22a→Compound (I-22)

The whole amount of 22a obtained was dissolved in methylene chloride (11 ml). After cooling to −40° C., phosphorus tribromide (0.15 ml, 1.55 mmol) was added thereto. After stirring at −90° C. for 1 hour, anisole (0.85 ml, 7.74 mmol) followed by 2 mol/L-aluminum chloride/nitromethane solution (3.9 ml, 7.79 mmol) were added, and then stirred at 0° C. for 50 minutes. Distilled water, acetonitrile, diisopropyl ether, and aqueous 2 N hydrochloric acid were added to the reaction solution, then stirred for a while, and consequently the insoluble appeared. The supernatant and the insoluble were then separated by decantation. The aqueous layer was sepa-

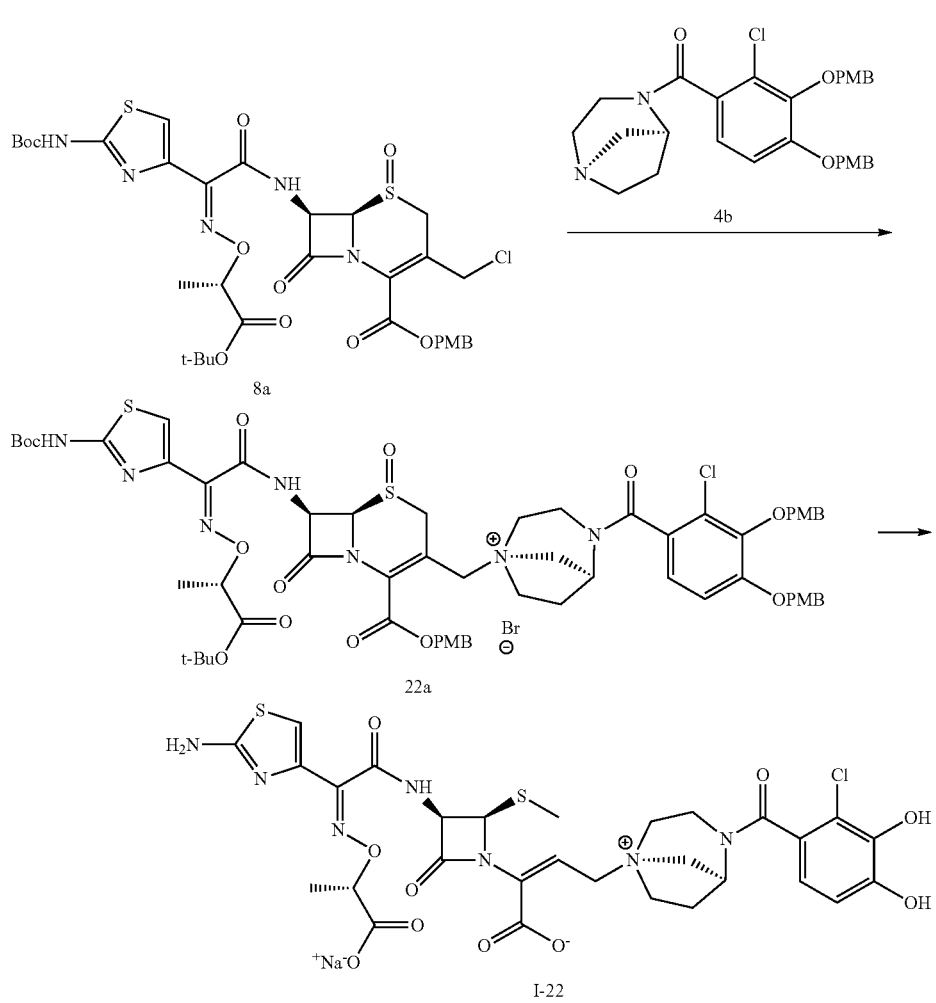

[Formula 68]

step (1): Compound 8a+Compound 4b→Compound 22a

Compound 8a (0.892 g, 1.00 mmol) and sodium bromide (0.206 g, 2.00 mmol) were added to N,N-dimethylformamide (3.0 ml), cooled to 0° C., and then stirred for 10 minutes. Compound 4b (0.551 g, 1.00 mmol) was added, and then stirred at room temperature for 3 hours. Ethyl acetate and 0.2 rated from the supernatant, and then combined with the insoluble. To the insoluble, 2 N hydrochloric acid and acetonitrile was added to dissolve the insoluble, and then HP-20SS resin was added thereto, followed by concentration. The resulting mixed solution was then purified by HP and ODS chromatography. Fractions containing the desired compound were collected, adjusted to pH=6.7 with aqueous 0.2 N sodium hydroxide solution, and then adjusted to a pH of 6 or less by adding dry ice. The solution was concentrated in vacuo, and then lyophilized to yield I-22 as a white powder.

Yield: 248 mg (42%)

$^1$H-NMR (D$_2$O) δ: 7.00 (1H, s), 6.93 (1H, d, J=8.5 Hz), 6.84-6.77 (1H, m), 5.89-5.85 (1H, m), 5.36-5.32 (1H, m), 4.94-2.31 (16H, m), 1.46 (3H, d, J=7.0 Hz).

MS (m+1)=736

Elemental analysis for $C_{29}H_{29}ClN_7NaO_{10}S_2(NaHCO_3)_{0.3}(H_2O)_6$

Calcd.: C, 39.48; H, 4.67; Cl, 3.98; N, 11.00; 3, 7.19; Na, 3.35(%).

Found.: C, 39.43; H, 4.69; Cl, 4.45; N, 11.11; S, 6.85; Na, 3.09(%).

Example 23

Synthesis of Compound (I-23)

step (1): Compound 8a+Compound 5b→Compound 23a→Compound (I-23)

Treating Compound 8a (0.778 g, 0.872 mmol) and Compound 5b (0.421 g, 0.785 mmol) using the same method as Example 22 gives Compound I-23 as a white powder.

Yield: 317 mg (47%)

$^1$H-NMR (D$_2$O) δ: 7.01-6.99 (1H, m), 6.96-6.92 (1H, m), 6.84-6.80 (1H, m), 5.89-5.85 (1H, m), 5.38-5.34 (1H, m), 4.90-2.22 (18H, m), 1.46 (3H, d, J=7.1 Hz).

MS (m+1)=773

Elemental analysis for $C_{30}H_{31}ClN_7NaO_{10}S_2(NaHCO_3)_{0.1}(H_2O)_{8.9}$ Calcd.: C, 38.42; H, 5.24; Cl, 3.77; N, 10.42; S, 6.82; Na, 2.69(%).

Found.: C, 38.35; H, 5.02; Cl, 3.79; N, 10.54; S, 7.10; Na, 2.76(%).

[Formula 69]

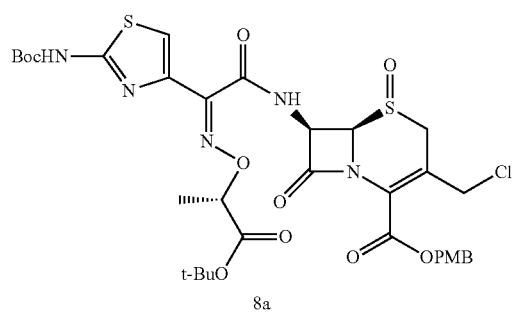
8a

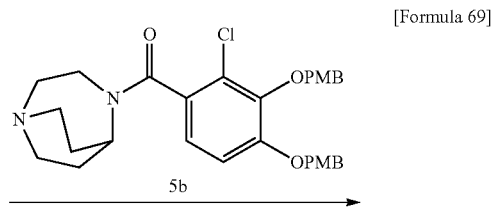
5b

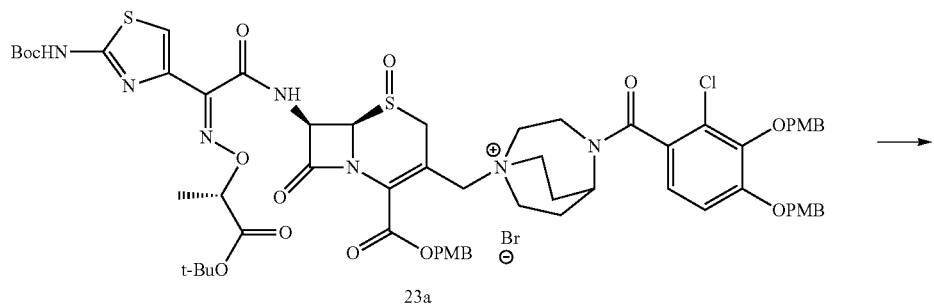
23a

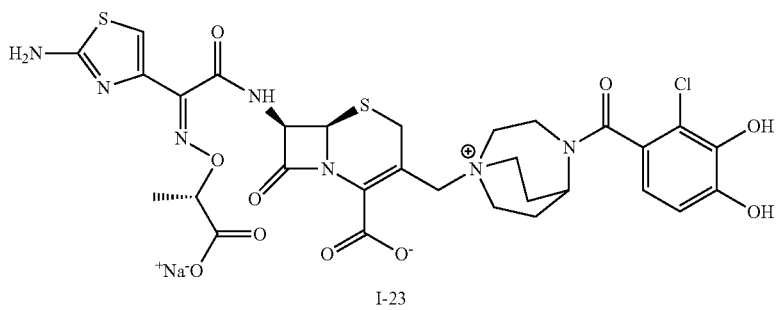
I-23

Example 24
Synthesis of Compound (I-24)
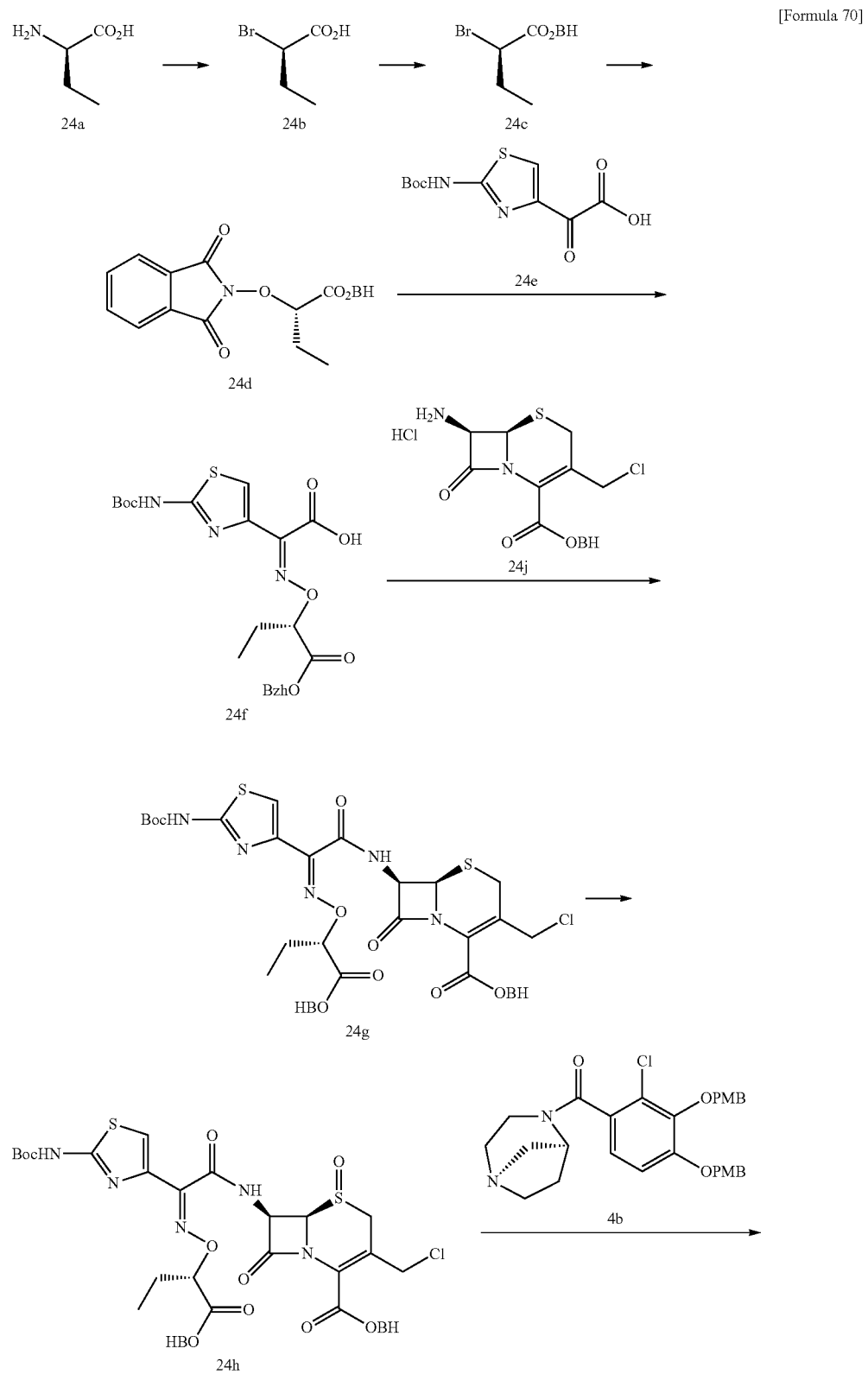
[Formula 70]

-continued

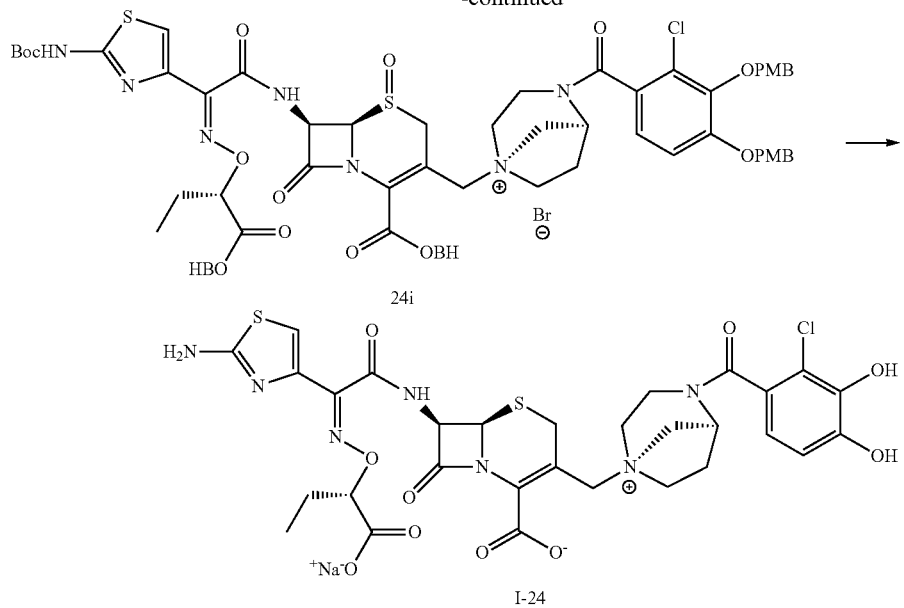

step (1): Compound 24a→Compound 24b

Compound 24a (5.14 g, 49.8 mmol) and potassium bromide (20.76 g, 174 mmol) were dissolved in 2 N sulfuric acid (150 ml). Sodium nitrite (5.16 g, 74.8 mmol) was added thereto, and then stirred at 0° C. for 2 hours. Sodium nitrite (1.03 g, 14.9 mmol) was further added, and then stirred at 0 for 1 hour. Ethyl acetate was then added thereto, followed by extraction. The organic layer was washed with aqueous 10% sodium hydrogen sulfite solution, distilled water, then saturated brine, dried with anhydrous sodium sulfate, filtered, concentrated, and then dried under reduced pressure to yield Compound 24b as a colorless oil.

Yield: 7.15 g (86%)

$^1$H-NMR (CDCl$_3$) δ: 4.20 (1H, dd, J=7.8, 6.7 Hz), 2.19-1.98 (2H, m), 1.07 (3H, t, J=7.3 Hz).

step (2): Compound 24b→Compound 24c

Compound 24b (7.15 g, 42.8 mmol) was dissolved in tetrahydrofuran (35 ml), and then diphenyldiazomethane (9.15 g, 47.1 mmol) was added thereto. After stirring at room temperature for 2 hours, distilled water and ethyl acetate were added, and then extracted. The organic layer was washed with saturated brine, dried with anhydrous magnesium sulfate, filtered, concentrated, dried under reduced pressure, and then purified by silica gel column chromatography to yield Compound 24c as a colorless oil.

Yield: 9.06 g (64%)

$^1$H-NMR (CDCl$_3$) δ: 7.38-7.27 (10H, m), 6.88 (1H, s), 4.26 (1H, dd, J=7.7, 6.6 Hz), 2.18-1.96 (2H, m), 0.98 (3H, q, J=6.8 Hz).

step (3): Compound 24c→Compound 24d.

To N-hydroxyphthalimide (4.44 g, 27.2 mmol) and potassium carbonate (3.76 g, 27.2 mmol), N,N-dimethylformamide (120 ml) was added, and then stirred at room temperature for 30 minutes. Compound 24c (9.06 g, 27.2 mmol) was added to the reaction solution, and then stirred at room temperature for 2 hours. Ethyl acetate and distilled water were added to the reaction solution, and then extracted. The organic layer was washed with aqueous saturated brine, and consequently crystallized. After filtration, the residue filtrated was dried under reduced pressure to yield Compound 24d as a white solid.

Yield: 6.19 g (55%)

$^1$H-NMR (CDCl$_3$) δ: 7.78-7.70 (4H, m), 7.35-7.20 (10H, m), 6.94 (1H, s), 4.87 (1H, t, J=6.4 Hz), 2.08-2.02 (2H, m), 1.07 (3H, t, J=7.5 Hz).

step (4): Compound 24d+Compound 24e→Compound 24f

Compound 24d (6.19 g, 14.9 mmol) was dissolved in methylene chloride (60 ml), then cooled to −30° C., and then methylhydrazine (0.793 ml, 14.9 mmol) was added thereto. After stirring at −30° C. for 2 hours, the insoluble was filtered. The reaction solution was diluted with methanol (30 ml), and then Compound 24e (4.06 g, 14.9 mmol) was added thereto. After stirring at room temperature for 2 hours followed by concentration in vacuo, ethyl acetate and distilled water were added, and then extracted. The organic layer was washed with saturated brine, dried with anhydrous magnesium sulfate, filtered, concentrated, and then dried under reduced pressure to yield Compound 24f as a brown solid. The obtained compound 24f was used in the next reaction without purification.

step (5): Compound 24f→Compound 24g

Compound 24f (8.00 g, 14.8 mmol) and Compound 24j (6.69 g, 14.8 mmol) were suspended in ethyl acetate (70 mL), and then cooled to −40° C. Phenylphosphoryl dichloride (2.26 ml, 14.8 mmol) and N-methylmorpholine (4.89 ml, 44.5 mmol) were added thereto, and then stirred at −40° C. for 2.5 hours. After warming to 0° C., aqueous 10% citric acid solution was added thereto, and then extracted. The organic layer was washed with aqueous 10% sodium hydrogen carbonate, then saturated brine, dried with anhydrous magnesium sulfate, filtered, concentrated, dried under reduced pressure, and then purified by silica gel column chromatography to yield Compound 24g as a brown solid (10.6 g, 76% yield).

Yield: 10.6 g (76%)

$^1$H-NMR (CDCl$_3$) δ: 8.22 (1H, d, J=8.2 Hz), 7.46-7.18 (21H, m), 6.97 (1H, s), 6.92 (1H, s), 5.95 (1H, dd, J=8.2, 5.0 Hz), 5.05 (1H, d, J=5.0 Hz), 4.97 (1H, dd, J=7.1, 5.3 Hz), 4.50 (1H, d, J=11.6 Hz), 4.38 (1H, d, J=11.6 Hz), 3.57 (1H, d, J=18.0 Hz), 3.42 d, J=18.0 Hz), 2.06-1.96 (2H, m), 1.82 (9H, s), 1.00 (3H, t, J=7.4 Hz).

step (6): Compound 24g→Compound 24h

Compound 24g (10.5 g, 11.2 mmol) was dissolved in methylene chloride (105 ml), then cooled to −50° C., and then m-chloroperbenzoic acid (2.98 g, 11.2 mmol) was added. After stirring at −50° C. for 2.5 hours, ethyl acetate was added, and then methylene chloride was evaporated in vacuo. Aqueous 10% sodium hydrogen sulfite solution was added, and then extracted. The organic layer was washed with aqueous 5% sodium hydrogen carbonate, then saturated brine, dried with anhydrous magnesium sulfate, filtered, concentrated, and then dried under reduced pressure to yield Compound 24 h as a brown solid (yield: 9.10 g (85%)). The obtained Compound 24 h was used for next reaction without purification.

step (7): Compound 24h→Compound (I-24)

Compound 24h (0.952 g, 1.00 mmol) was treated using the same method as Example 22 to obtain Compound I-24.

Yield: 356 mg (46%)

$^1$H-NMR (D$_2$O) δ: 6.99-6.91 (2H, m), 6.86-6.80 (1H, m), 5.88-5.84 (1H, m), 5.36-5.32 (1H, m), 4.92-2.36 (16H, m), 1.91-1.82 (2H, m), 0.96 (3H, t, J=7.4 Hz).

MS (m+1)=750

Elemental analysis $C_{30}H_{31}ClN_7NaO_{10}S_2(NaHCO_3)_{0.2}$ $(H_2O)_{5.4}$

Calcd.: C, 40.93; H, 4.78; Cl, 4.00; N, 11.06; S, 7.24; Na, 3.11(%).

Found.: C, 40.85; H, 4.84; Cl, 4.15; N, 11.11; S, 7.29; Na, 2.95(%).

Example 25

Synthesis of Compound (I-25)

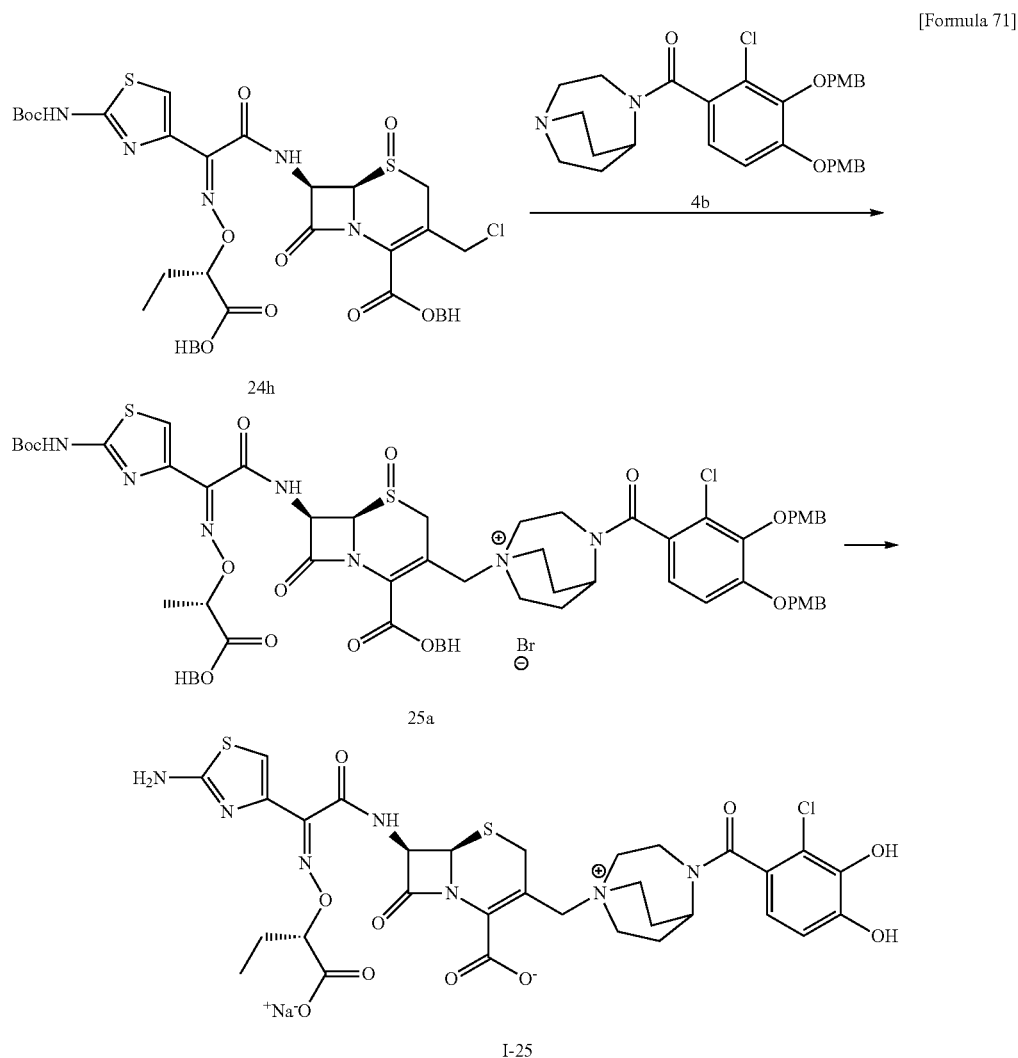

step (8): Compound 24h→Compound (I-25)

Compound 24h (0.952 g, 1.00 mmol) was treated with the same method as Example 22 to obtain Compound I-25.

Yield: 478 mg (61%)

$^1$H-NMR (D$_2$O) δ: 6.97-6.92 (2H, m), 6.83-6.79 (1H, m), 5.87-5.83 (1H, m), 5.37-5.33 (1H, m), 4.92-2.34 (18H, m), 1.90-1.81 (2H, m), 0.96 (3H, t, J=7.4 Hz).

MS (m+1)=764

Elemental analysis for $C_{31}H_{33}ClN_7NaO_{10}S_2(NaHCO_3)_{0.2}$ $(H_2O)_{5.7}$ Calcd.: C, 41.38; H, 4.96; Cl, 3.91; N, 10.83; S, 7.08; Na, 3.05(%).

Found.: C, 41.38; H, 5.01; Cl, 3.87; N, 10.91; S, 7.32; Na, 2.80(%).

Example 26
Synthesis of Compound (I-26)
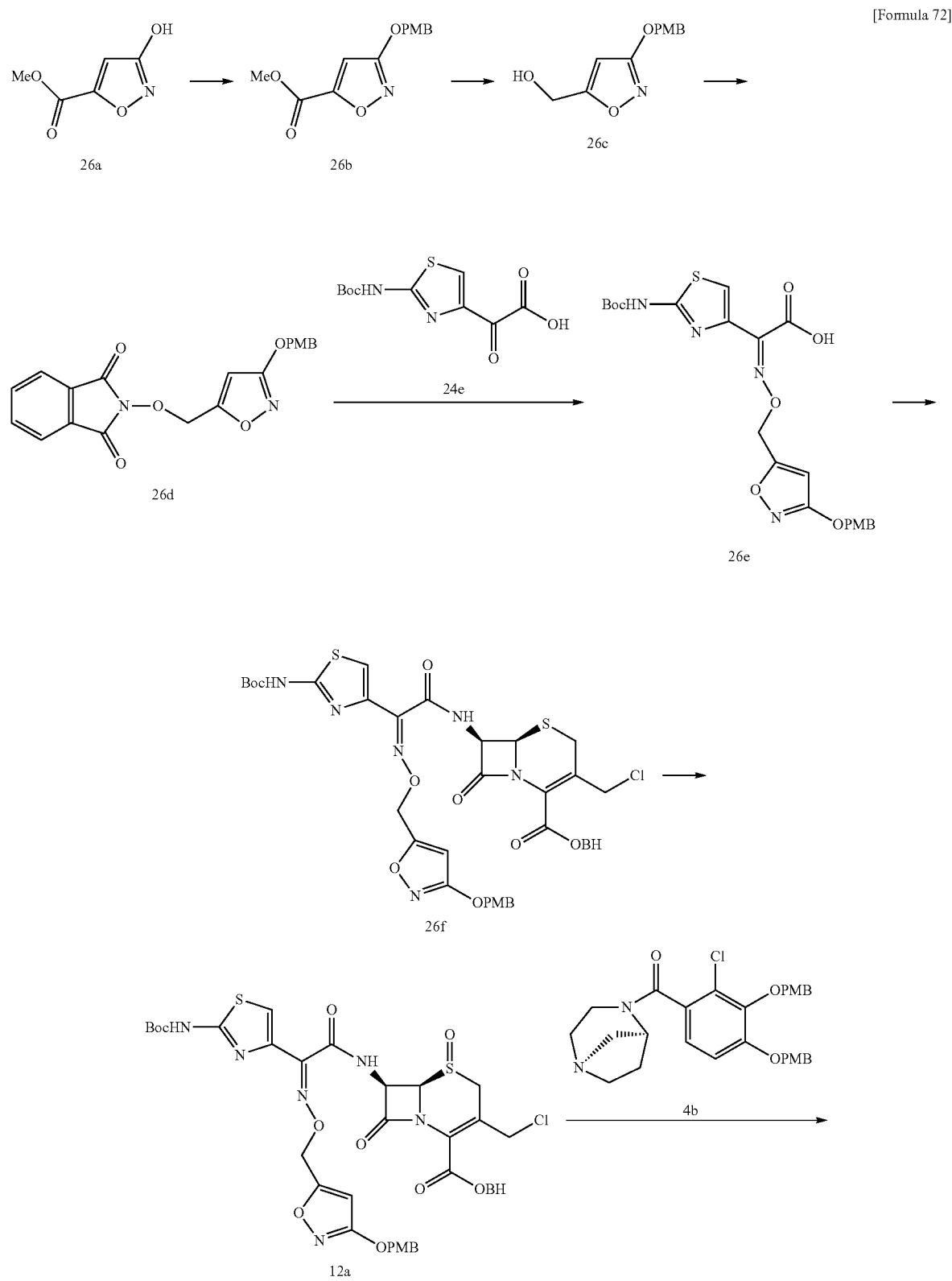

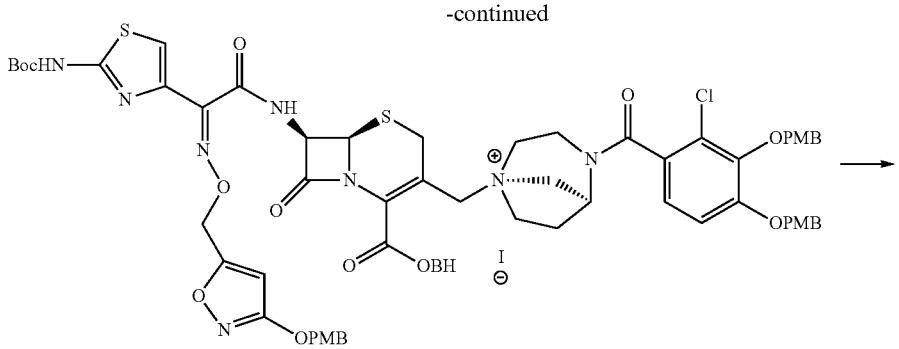

26g

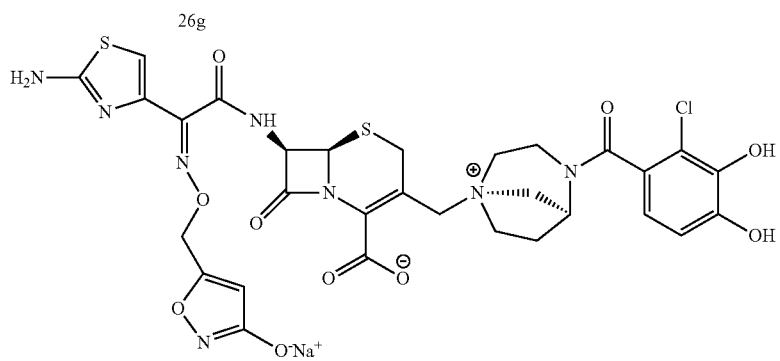

I-26 step (1): Compound 26a→Compound 26b

Compound 26a (10.0 g, 69.9 mmol) was dissolved in N,N-dimethylformamide (70 ml), then cooled to 0° C., and then 60% sodium hydride/mineral oil (3.07 g, 77.0 mmol) was added thereto. After stirring at 0° C. for 30 minutes, p-methoxybenzyl chloride (11.4 ml, 77.0 mmol) was added. The reaction solution was then stirred at 50° C. overnight. Sodium hydride (3.07 g, 77.0 mmol), p-methoxybenzyl chloride (11.4 ml, 77.0 mmol) and sodium iodide (12.6 g, 84.0 mmol) were added, and then stirred for another 1 hour, and then ethyl acetate and distilled water were added, followed by extraction. The organic layer separated was washed with saturated brine and dried with anhydrous sodium sulfate. After the inorganic, substance was Entered, the filtrate was concentrated, dried under reduced pressure, and then purified by column chromatography, Compound 26b was obtained as a brown oil.

Yield: 11.7 g (64%)

$^1$H-NMR (CDCl$_3$) δ: 7.38 (2H, d, J=8.6 Hz), 6.92 (2H, d, J=8.6 Hz), 6.53 (1H, s), 5.24 (2H, s), 3.94 (3H, s), 3.82 (3H, s).

step (2): Compound 26b→Compound 26c

Compound 26b (11.7 g, 44.4 mmol) was dissolved in ethanol (120 ml), then cooled to 0° C., and then sodium borohydride (3.36 g, 89.0 mmol) was added. After stirring at 0° C. for 2.5 hours, aqueous saturated ammonium chloride solution and ethyl acetate were added, followed by extract ion. The organic layer separated was washed with saturated brine and dried with anhydrous magnesium sulfate. After the inorganic substance was filtered, the filtrate was concentrated and subsequently dried under reduced pressure, Compound 26c was obtained as a brown oil.

Yield: 9.47 g (91%)

$^1$H-NMR (CDCl$_3$) δ: 7.37 (2H, d, J=8.8 Hz), 6.91 (2H, d, J=8.8 Hz), 5.88 (1H, s), 5.18 (2H, s), 4.65 (2H, d, J=5.8 Hz), 3.81 (3H, s).

step (3): Compound 26c→Compound 26d

Compound 26c (9.47 g, 40.3 mmol) was dissolved in tetrahydrofuran (110 ml), and then N-hydroxyphthalimide (7.88 g, 48.3 mmol) and triphenylphosphine (12.7 g, 48.3 mmol) were added thereto. After cooling to 0° C., diisopropyl azodicarboxylate (9.39 ml, 48.3 mmol) was added thereto. The reaction solution was stirred at room temperature for 3 hours, and then concentrated. Methanol and tetrahydrofuran were added to the concentrated residue for solidification, and then filtered to yield Compound 26d as a white solid.

Yield: 8.10 g (53%)

$^1$H-NMR (CDCl$_3$) δ: 7.86-7.83 (2H, m), 7.78-7.75 (2H, m), 7.37 (2H, d, J=8.7 Hz), 6.91 (2H, d, J=8.7 Hz), 6.18 (1H, s), 5.20 (2H, s), 5.19 (2H, s), 3.82 (3H, s).

step (4): Compound 26d→Compound 26e

Compound 26d (8.10 g, 21.3 mmol) was treated using the same method as example 24 to obtain Compound 26e.

Yield: 10.8 g (quant.)

$^1$H-NMR (CDCl$_3$) δ: 7.34 (2H, d, J=8.9 Hz), 6.88 (2H, d, J=8.9 Hz), 5.98 (1H, s), 5.14 (4H, s), 3.80 (3H, s), 1.53 (9H, s).

Step (5): Compound 26e→Compound 26f

Compound 26e (10.7 g, 21.3 mmol) was treated using the same method as Example 24 to obtain Compound 26f.

Yield: 13.7 g (72%)

$^1$H-NMR (CDCl$_3$) δ: 8.71 (1H, br s), 7.46-7.22 (13H, m), 6.94 (1H, s), 6.90 (1H, s), 6.87 (1H, s), 6.04 (1H, dd, J=9.1, 5.0 Hz), 5.99 (1H, s), 5.30 (1H, d, J=14.4 Hz), 5.21 (1H, d, J=14.4 Hz), 5.15 (2H, s), 5.09 (1H, d, J=5.0 Hz), 4.49 (1H, d, J=11.8 Hz), 4.34 (1H, d, J=11.8 Hz), 3.79 (3H, s), 3.63 (1H, d, J=18.4 Hz), 3.46 (1H, d, J=18.4 Hz), 1.50 (9H, s).

Step (6): Compound 26f→Compound 12a

Compound 26f (13.6 g, 15.1 mmol) was treated using the same method as Example 24 to obtain Compound 12a.

Yield: 7.45 g (54%)

¹H-NMR (CDCl₃) δ: 7.62 (1H, d, J=10.0 Hz), 7.45 (2H, d, J=7.8 Hz), 7.37-7.28 (10H, m), 6.95 (1H, s), 6.92-6.86 (2H, m), 6.20 (1H, dd, J=10.0, 4.9 Hz), 6.04 (1H, s), 5.23 (2H, s), 5.19-5.15 (3H, m), 4.93 (1H, d, J=12.4 Hz), 4.59 (1H, dd, J=4.8, 1.4 Hz), 4.18 (1H, d, J=12.4 Hz), 3.81-3.72 (4H, m), 3.36 H, d, J=18.3 Hz), 1.54 (9H, s).

Step (7): Compound 12a+Compound 4b→Compound 26g

Compound 12a (0.917 g, 1.00 mmol) and sodium iodide (0.300 g, 2.00 mmol) were dissolved in N,N-dimethylformamide (3.0 ml), and then stirred at room temperature for 5 minutes. After the reaction solution was cooled to 0° C., Compound 4b (0.366 g, 0.700 mmol) was added, and then stirred at room temperature for 30 minutes. After the reaction solution was cooled to 0° C., potassium iodide (0.300 g, 2.00 mmol) and acetyl chloride (0.285 ml, 4.00 mmol) were added, and then stirred at 0° C. for 1 hour. Distilled water containing 10% of sodium hydrogen sulfite and 5% of sodium chloride was poured into the reaction solution. The precipitated deposits were filtered, and then the residue was suspended in distilled water, and then lyophilized to yield Compound 26g as a yellow solid. The obtained Compound 26g was used in the next reaction without purification.

Step (8): Compound 26g→Compound (I-26)

The whole amount of Compound 26g obtained was dissolved in methylene chloride (13 ml), then cooled to −20° C., and then anisole (0.944 ml, 8.65 mmol) followed by 2 mol/L-aluminum chloride/nitromethane solution (4.32 ml, 8.65 mmol) were added thereto, subsequently stirring at 0° C. for 1 hour. Distilled water, acetonitrile, diisopropyl ether, and aqueous 2 N hydrochloric acid were added to the reaction solution, and then stirred for a while, and consequently the insoluble appeared. The supernatant and the insoluble were separated by decantation, and then the aqueous layer was separated from the supernatant, subsequently combined with the insoluble. To the insoluble, 2 N hydrochloric acid and acetonitrile was added to dissolve the insoluble, and then HP-20SS resin was added thereto, followed by concentration. The resulting mixed solution was then purified by HP and ODS chromatography. Fractions containing the desired compound were collected, adjusted to pH=6.7 with aqueous 0.2 N sodium hydroxide solution, and then adjusted to a pH of 6 or less by adding dry ice. The solution was concentrated in vacuo, and then lyophilized to yield I-26 as a white powder.

Yield: 203 mg (30%)

¹H-NMR (DMSO-d₆) δ: 6.83-6.69 (3H, m), 6.60-6.43 (1H, m), 5.93 (1H, s), 5.66-5.62 (1H, m), 5.12-4.90 (4H, m), 4.54-4.35 (1H, m), 4.25-4.00 (2H, m), 3.83-3.23 (7H, m), 2.20-1.96 (1H, m).

MS (m+1)=761

Elemental analysis for $C_{30}H_{28}ClN_8NaO_{10}S_2(NaHCO_3)_{0.1}(H_2O)_{6.7}$ Calcd.: C, 39.63; H, 4.59; Cl, 3.89; N, 12.28; S, 7.03; Na, 2.77 (%).

Found.: C, 39.62; H, 4.59; Cl, 3.99; N, 12.37; S, 6.98; Na, 2.15 (%).

Example 27

Synthesis of Compound (I-27)

[Formula 73]

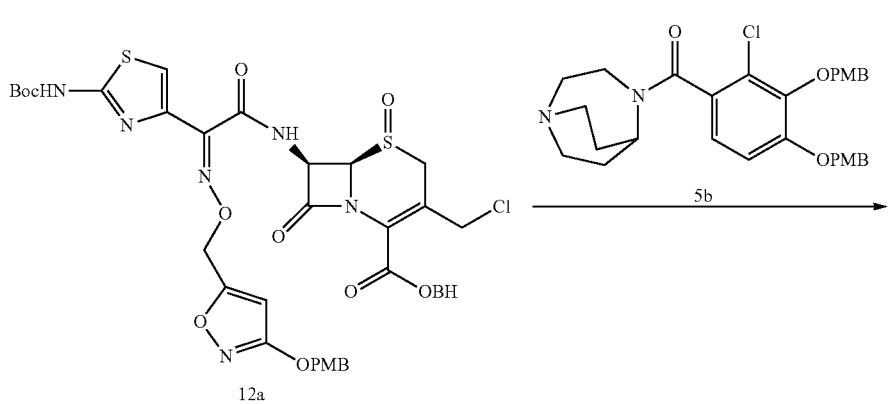

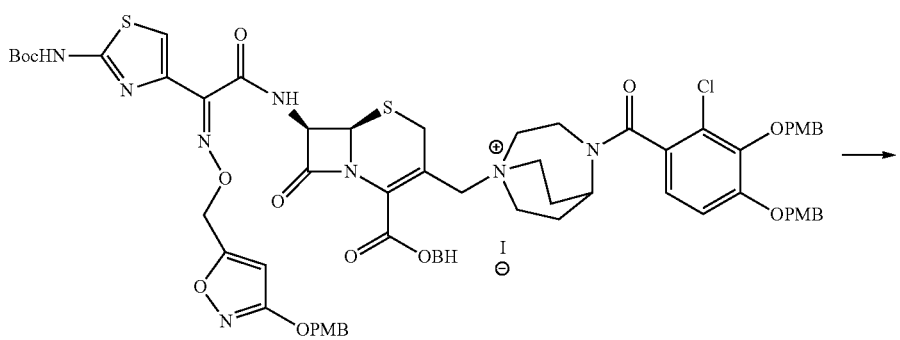

-continued

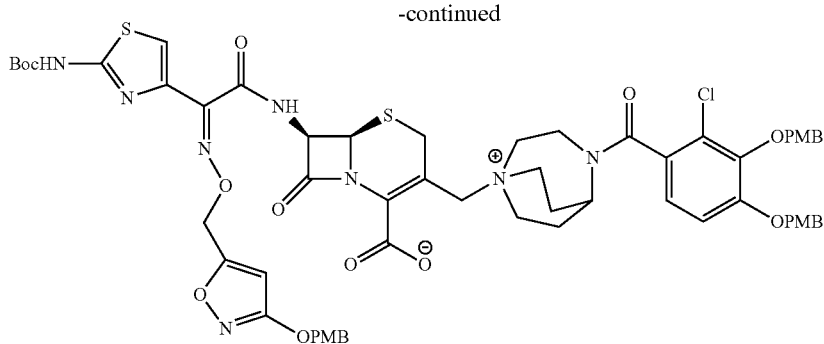

I-27

Step (1): Compound 12a+Compound 5b→Compound 27a

Compound 12a (0.917 g, 1.00 mmol) and Compound 5b (0.376 g, 0.700 mmol) were used and treated using the same way as Example 26 to obtain Compound 27a as a yellow solid. The Compound 27a obtained was used in the next reaction without purification.

Step (2): Compound 27a→Compound (I-27)

Compound 27a was treated using the same method as Example 26 to obtain Compound I-27.

Yield: 330 mg (51%)

$^1$H-NMR (DMSO-$d_6$) δ: 6.79-6.70 (3H, m), 6.58-6.48 (1H, m), 5.98-5.90 (1H, m), 5.70-5.61 (1H, m), 5.16-4.88 (6H, m), 4.78-2.83 (11H, m), 2.30-1.94 (6H, m).

MS (m+1)=775

Elemental analysis for $C_{31}H_{30}ClN_8NaO_{10}S_2(NaHCO_3)_{0.1}(H_2O)_{6.8}$ Calcd.: C, 40.25; H, 4.75; Cl, 3.82; N, 12.07; S, 6.91; Na, 2.72 (%).

Found.: C, 40.28; H, 4.81; Cl, 3.87; N, 12.25; S, 7.07; Na, 2.07 (%).

Example 28

Synthesis of Compound (I-28)

[Formula 74]

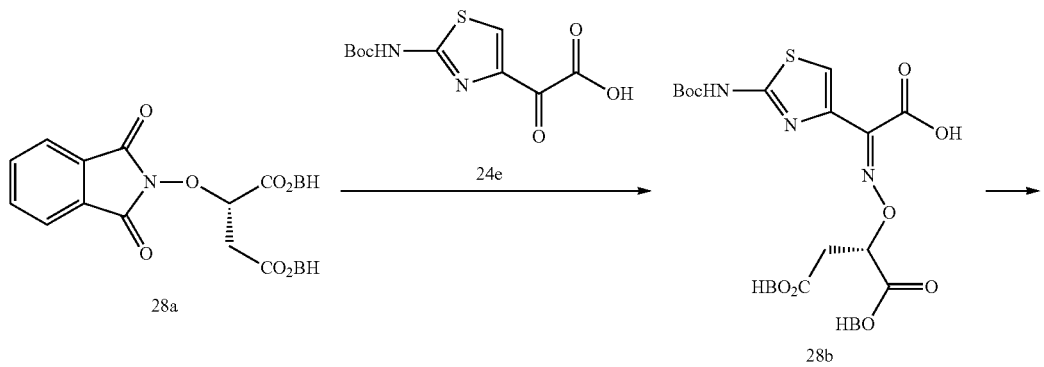

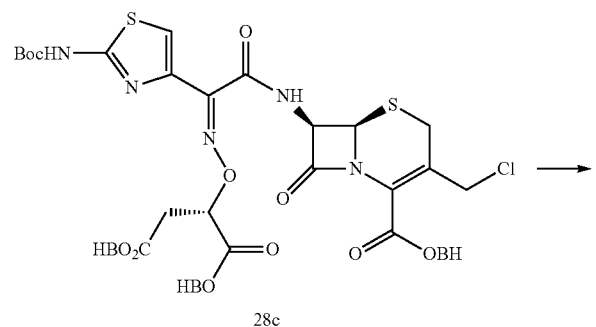

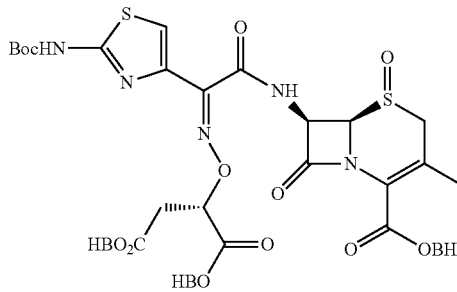
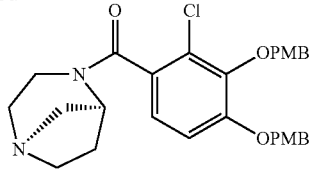

9a

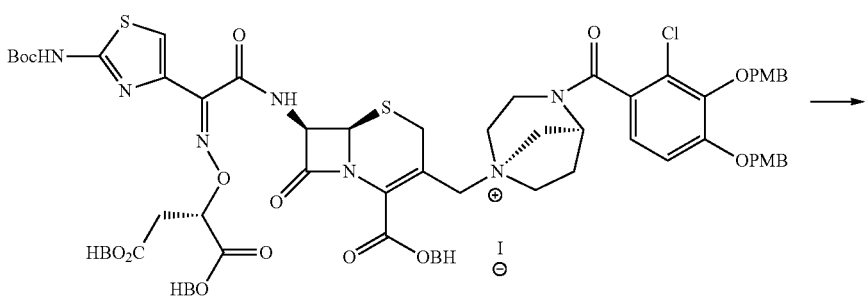

28d

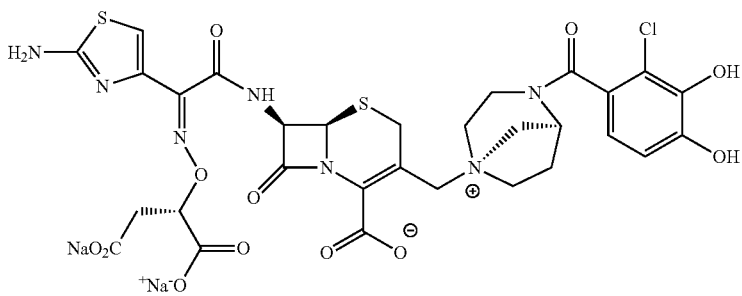

I-28

Step (1): Compound 28a→Compound 28b

Compound 28a (5.57 g, 9.11 mmol) was treated using the same method as Example 24 to obtain Compound 28b. The Compound 28b obtained was used in the next reaction without purification.

Yield: 6.8 g (quant.)

Step (2): Compound 28b→Compound 28c

Compound 28b (6.7 g, 9.11 mmol) was treated using the same method as Example 24 to obtain Compound 28c.

Yield: 13.7 g (76%)

$^1$H-NMR (CDCl$_3$), δ: 8.07 (1H, br s), 7.63 (1H, d, J=8.8 Hz), 7.46-7.18 (31H, m), 6.95 (1H, s), 6.88 (2H, s), 5.81 (1H, dd, J=8.5, 5.0 Hz), 5.49 (1H, dd, J=8.5, 4.9 Hz), 4.97 (1H, d, J=4.9 Hz), 4.51 (1H, d, J=11.7 Hz), 4.28 (1H, d, J=11.7 Hz), 3.44 (1H, d, J=17.8 Hz), 3.29 (1H, d, J=17.8 Hz), 3.19-3.13 (2H, m), 1.51 (9H, s).

Step (3): Compound 28c→Compound 9a

Compound 28c (7.8 g, 6.89 mmol) was treated using the same method as Example 24 to obtain Compound 9a.

Yield: 6.08 g (77%)

$^1$H-NMR (CDCl$_3$) δ: 7.74 (1H, d, J=9.5 Hz), 7.47-7.16 (31H, m), 6.94 (1H, s), 6.87 (1H, s), 6.86 (1H, s), 6.06 (1H, dd, J=9.5, 4.9 Hz), 5.47-5.43 (1H, m), 4.98-4.60 (2H, m), 4.28-4.26 (1H, m), 4.06 (1H, d, J=11.4 Hz), 3.42 (1H, d, J=18.3 Hz), 3.22-3.20 (2H, m), 3.06 (1H, d, J=18.3 Hz), 1.51 (9H, s).

Step (4): Compound 9a→Compound (I-28)

Compound 9a (0.917 g, 1 mmol) was treated using the same method as Example 26 to obtain Compound I-28.

Yield: 40 mg (7%)

$^1$H-NMR (D$_2$O) δ: 7.00-6.80 (3H, m), 5.84-5.28 (3H, m), 5.10-2.35 (15H, m).

Elemental analysis for C$_{30}$H$_{28.3}$ClN$_7$Na$_{1.7}$O$_{12}$S$_2$(H$_2$O)$_{11}$ Calcd.: C, 35.48; H, 4.99; Cl, 3.49; N, 9.65; S, 6.31; Na, 3.85 (%).

Found.: C, 35.30; H, 4.78; Cl, 3.89; N, 9.58; S, 6.00; Na, 4.52 (%).

Example 29
Synthesis of Compound (I-29)
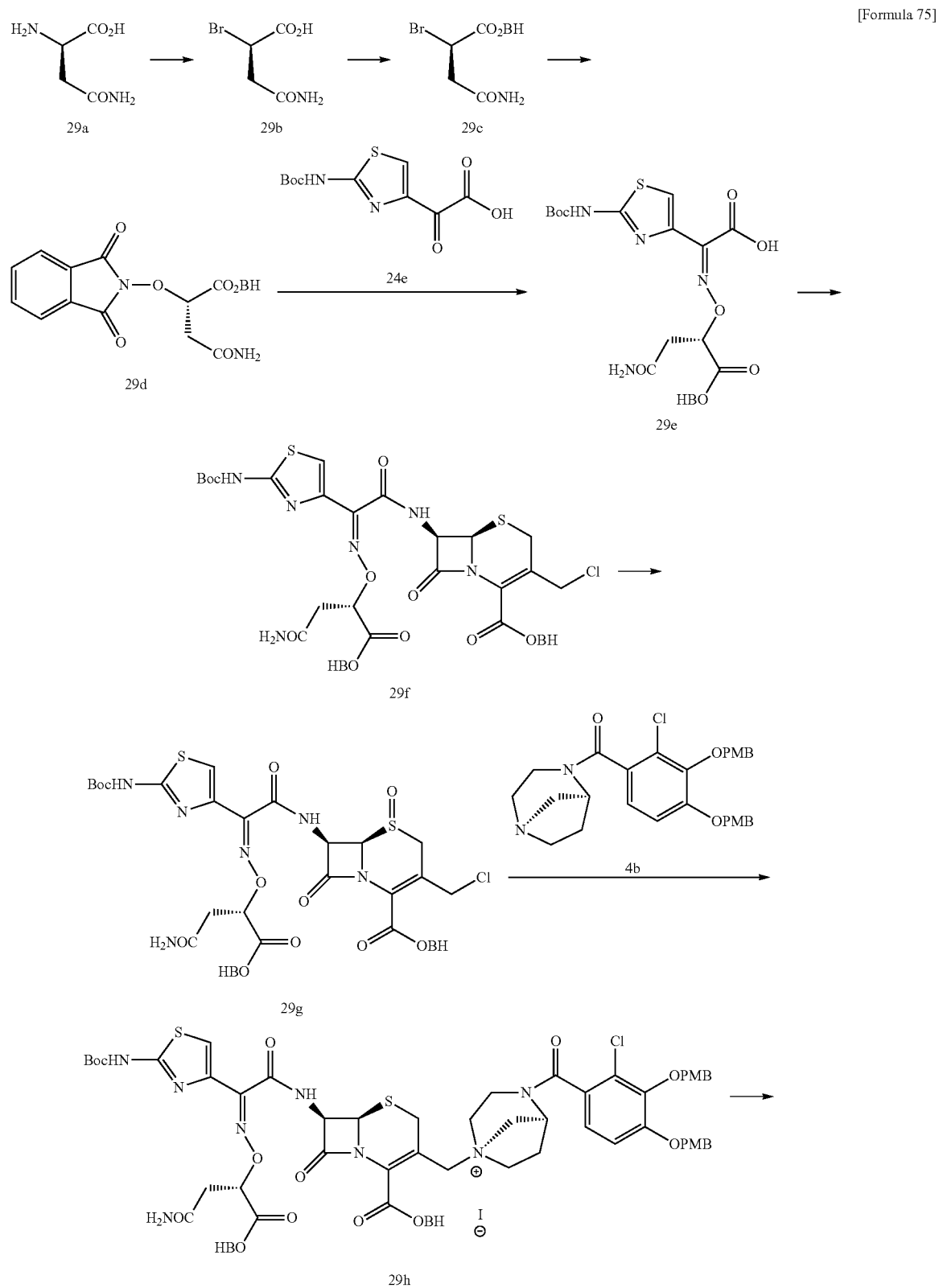
[Formula 75]

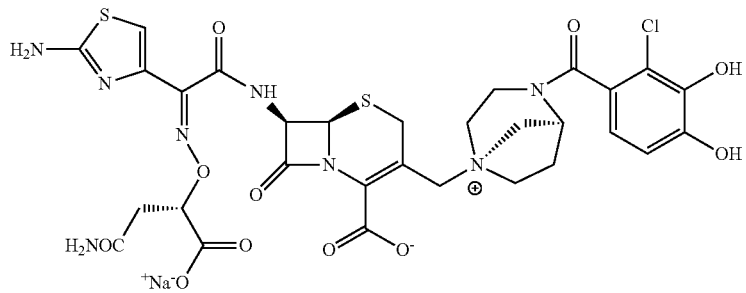

I-29

Step (1): Compound 29a→Compound 29b

Compound 29a (6.7 g, 9.11 mmol) was treated using the same method as Example 24 to obtain Compound 29b. The Compound 29b obtained was used in the next reaction without purification.

Yield: 5.64 g (76%)

Step (2): Compound 29b→Compound 29c

Compound 29b (6.7 g, 9.11 mmol) was treated using the same method as Example 24 to obtain Compound 29c. The Compound 29c obtained was used in the next reaction without purification.

Yield: 12.1 g (90%)

Step (3): Compound 29c→Compound 29d

N-hydroxyphthalimide (5.49 g, 33.7 mmol), Potassium carbonate (3.94 g, 28.5 mmol), and tetrabutylammonium bromide (0.835 g, 25.9 mmol) were dissolved in water (60 ml) and ethyl acetate (100 ml). Compound 29c (12.1 g, 25.9 mmol) was added to the reaction solution, then stirred at room temperature for 5 hours, and then the reaction solution was filtered. The organic layer was separated, washed with aqueous saturated sodium hydrogen carbonate, then saturated brine, and then dried with anhydrous magnesium sulfate. After the inorganic substance was filtered, the filtrate was concentrated, and then dried under reduced pressure. Diisoprobyl ether and methanol were added to the concentrated residue to crystallize it. The precipitation was filtered, and then washed with isopropanol to yield. Compound 29d as a white solid.

Yield: 5.11 g (40%)

$^1$H-NMR (CDCl$_3$) δ: 7.78-7.71 (4H, m), 7.38-7.21 (10H, m), 6.92 (1H, s), 6.49 (1H, br s), 5.46 (1H, br s), 5.25 (1H, dd, J=7.5, 5.0 Hz), 3.04-2.95 (2H, m).

Step (4): Compound 29d→Compound 29e

Compound 29d (3.63 g, 8.17 mmol) was treated using the same method as Example 24 to obtain Compound 29e.

Yield: 4.06 g (quant.)

$^1$H-NMR (CDCl$_3$) δ: 7.33-7.07 (11H, m), 6.84 (1H, s), 5.24-5.15 (1H, m), 2.89-2.74 (2H, m).

Step (5): Compound 29e→Compound 29f

Compound 29e (4.06 g, 8.18 mmol) was treated using the same method as Example 24 to obtain Compound 29f.

Yield: 4.64 g (59%)

$^1$H-NMR (CDCl$_3$) δ: 8.21 (1H, br s), 8.09 (1H, d, 9.9 Hz), 7.42-7.25 (21H, m), 6.99 (1H, s), 6.90 (1H, s), 6.23 (1H, br s), 6.08 (1H, dd, J=9.9, 5.2 Hz), 5.43-5.36 (2H, m), 5.07 (1H, d, J=5.2 Hz), 4.54 (1H, d, J=11.9 Hz), 4.38 (1H, d, J=11.9 Hz), 3.56 (1H, d, J=18.0 Hz), 3.40 (1H, d, J=18.0 Hz), 2.75-2.72 (2H, m), 1.54 (9H, s).

Step (6): Compound 29f→Compound 29g

Compound 29f (4.64 g, 4.81 mmol) was treated using the same method as Example 24 to obtain Compound 29g.

Yield: 4.33 g (92%)

$^1$H-NMR (CDCl$_3$) δ: 8.18 (1H, d, J=9.7 Hz), 7.45-7.25 (21H, m), 6.95 (1H, s), 6.92 (1H, s), 6.59 (1H, br s), 6.18 (1H, dd, J=9.7, 4.8 Hz), 5.41-5.38 (1H, m), 4.93 (1H, d, J=12.3 Hz), 4.52 (1H, d, J=4.8 Hz), 4.19 (1H, d, J=12.3 Hz), 3.71 (1H, d, J=18.9 Hz), 3.28 (1H, d, J=18.9 Hz), 2.81-2.79 (2H, m), 1.54 (9H, s).

Step (7): Compound 29g→Compound (I-29)

Compound 29g was treated using the same method as Example 26 to obtain Compound I-29.

Yield: 146 mg (18%)

$^1$H-NMR (D$_2$O) δ: 7.01 (1H, s), 6.95-6.91 (1H, m), 6.84-6.77 (1H, m), 5.86-5.82 (1H, m), 5.35-5.31 (1H, m), 4.94-2.35 (16H, m).

MS (m+1)=779

Elemental analysis for $C_{30}H_{30}ClN_8NaO_{11}S_2(NaHCO_3)_{0.16}(H_2O)_{6.0}$ Calcd.: C, 39.26; H, 4.61; Cl, 3.84; N, 12.14; S, 6.95; Na, 2.89 (%).

Found.: C, 39.35; H, 4.67; Cl, 3.84; N, 12.01; S, 6.89; Na, 2.77 (%).

Example 30

Synthesis of Compound (I-30)

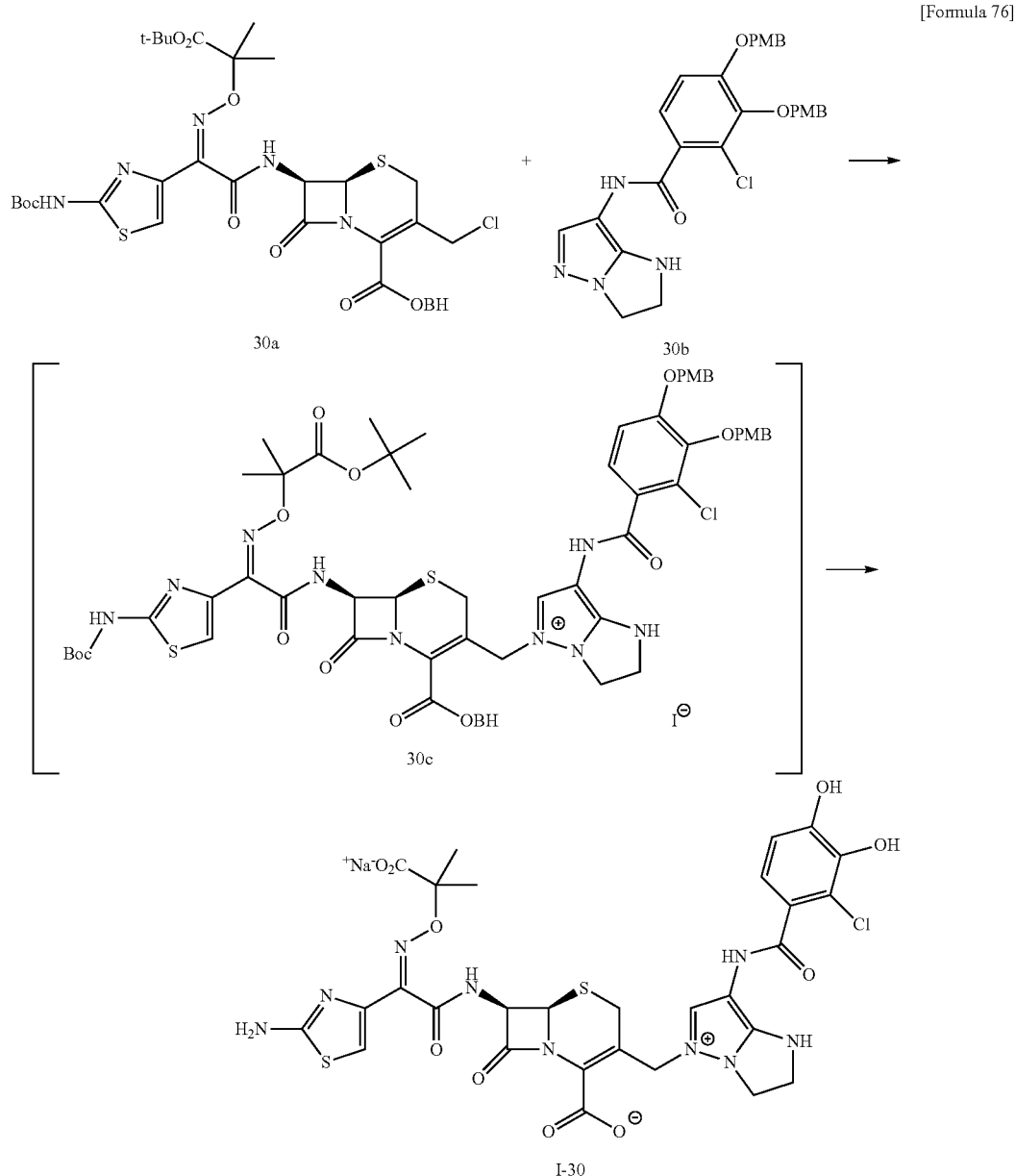

[Formula 76]

Step (1): Compound 30a+Compound 30b→Compound 30c→Compound (I-30)

To a solution of Compound 30a (826 mg, 1.0 mmol) in N,N-dimethylformamide (3 mL), potassium iodide (332 mg, 2.0 mmol) was added and then stirred at room temperature for 10 minutes. Compound 30b (535 mg, 1.0 mmol) was added to the reaction solution, and then stirred at 40° C.: for 3 hours. N,N-dimethylformamide (2 mL) was added thereto, and then the reaction solution was slowly added to pre-ice-cooled aqueous 5% sodium chloride containing 1g of sodium thiosulfate. The precipitated solid was then filtered. The residue was washed with water, suspended in water, and then lyophilized to yield Compound 30c as a light orange solid.

The whole amount of Compound 30c obtained was dissolved in methylene chloride (12 ml), then cooled to −40° C., and then anisole (1.12 ml, 10.24 mmol) followed by 2 mol/L-titanium tetrachloride/methylene chloride solution (5.12 ml, 10.24 mmol) were added thereto, subsequently stirring at CC for 1 hour. 2 N hydrochloric acid, acetonitrile, and diisopropyl ether were added to the reaction solution, then stirred, and then the organic layer was removed. Water, acetonitrile, and diisopropyl ether were added thereto again, and then stirred to completely dissolve the insoluble. After the organic layer was extracted with water, HP20-SS resin was added to the aqueous layer, and then acetonitrile was evaporated under reduced pressure. The resulting mixed solution was purified by HP20SS column chromatography. To the obtained fractions containing the intended compound, aqueous 0.2 N sodium hydroxide solution was added until pH became equal to 6.0. One piece of dry ice was then added to neutralize the excess sodium hydroxide. The resulting solution was concentrated in vacuo, and then lyophilized to yield Compound I-30 as an orange powder.

Yield: 239 mg, (27%)

$^1$H-NMR (D$_2$O) δ: 7.41 (1H, s), 7.06 (1H, d, J=8.39 Hz), 7.00 (1H, s), 6.91 (1H, d, J=8.39 Hz), 5.76 (1H, d, J=4.70 Hz), 5.22 (1H, t, J=7.47 Hz), 4.92 (1H, t, J=2.27 Hz), 4.65 (1H, t, J=2.27 Hz), 4.16 (2H, t, J=8.23 Hz), 4.07 (2H, s), 3.74-3.46 (2H, m), 1.48 (6H, d, J=4.53 Hz).

Elemental analysis for: C$_{29}$H$_{27}$ClN$_9$O$_{10}$S$_2$Na.0.15NaHCO$_3$.5.8H$_2$O Calcd.: C, 38.85; H, 4.33; Cl, 3.93; N, 13.99; S, 7.12; Na, 2.93 (%).

Found.: C, 38.81; H, 3.98; Cl, 3.92; N, 13.82; S, 7.21; Na, 2.93 (%).

Example 31

Synthesis of Compound (I-31)

[Formula 77]

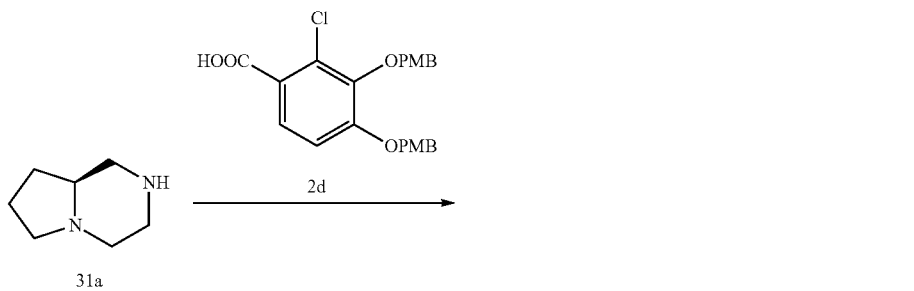

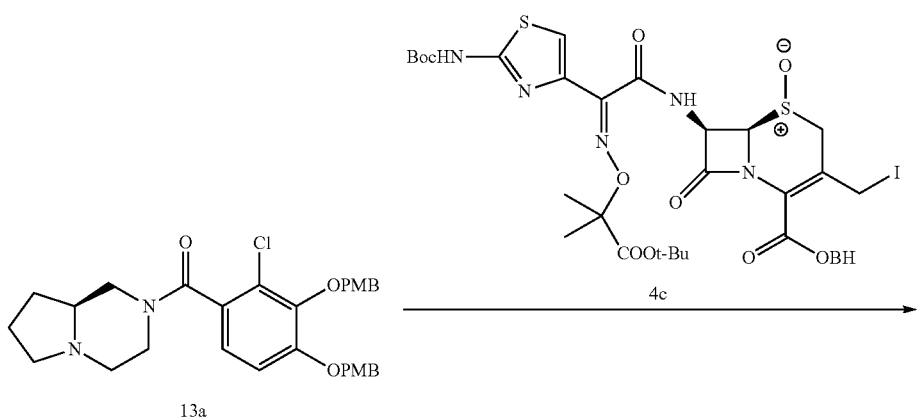

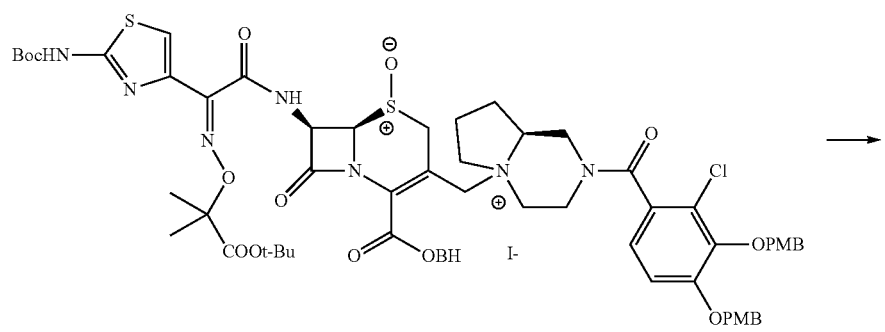

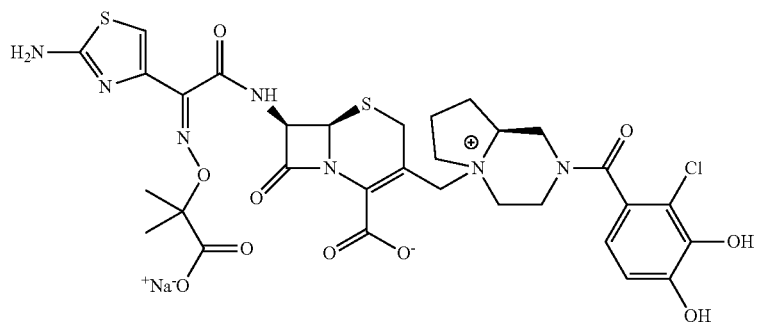

I-31

Step (1): Compound 31a→Compound 13a

Compound 2d was dissolved in N,N-dimethylacetamide (20 mL), and then triethylamine (0.97 mL, 7.00 mmol) was added thereto, subsequently cooled to −15° C. Methanesulfonyl chloride (0.55 mL, 7.00 mmol) was added to the reaction solution, and then stirred for 30 minutes. Compound 31a (ref. J. Med. Chem., 1986, 29 (10), pp. 1814-1820) (2.144 g, 5 mmol) was added to the reaction solution, and then stirred at −10° C. Purified water, acetonitrile, and HP20SS resin were added to the reaction solution, concentrated under reduced pressure, and then subjected to ODS chromatography, eluting with aqueous 0.02 N hydrochloric acid-acetonitrile. Fractions containing the intended compound were concentrated to evaporate acetonitrile. Aqueous 2 N sodium hydroxide solution was added to the resulting solution to adjust it to pH 11.5, and then the aqueous layer was extracted with ethyl acetate. The organic layer was washed with saturated brine, then dried with magnesium sulfate, and then magnesium sulfate was filtered. Concentrating in vacuo yielded Compound 13a. (Yield: 1.55 g, Yield: 58%)

$^1$H-NMR (CDCl$_3$) δ: 7.39-7.28 (4H, m), 7.01-6.89 (4H, m), 6.85-6.76 (2H, m), 5.06-4.61 (4H, m), 3.83 (3H, s), 3.79 (3H, s), 3.44-2.51 (5H, m), 2.31-1.41 (8H, m).

Step (2): Compound 13a→Compound 31b→Compound (I-31)

Compound 4c (1.14 g, 1.11 mmol) was dissolved in N,N-dimethylacetamide (3.3 mL). Compound 13a (659 mg, 1 mmol) was added thereto, and then stirred at room temperature for 1 hour. Purified water was added to the reaction solution, and then extracted with ethyl acetate. The organic layer was washed with purified water, then saturated brine, and then dried with magnesium sulfate. After filtering the magnesium sulfate, the solvent, was evaporated under reduced pressure to yield Compound 31b.

Compound 31b was dissolved in methylene chloride (15 mL), and then cooled to −50° C. Phosphorus tribromide (0.189 mL, 2 mmol) was added thereto, and then stirred at −50° C. for 1 hour. Subsequently, anisole (1.09 mL, 10 mmol) and 2 mmol/L aluminum chloride nitromethane solution (5 mL, 10 mmol) were added, and then stirred at 0° C. Purified water (30 mL) and diisopropyl ether (50 mL) were then added to the reaction solution. Acetonitrile and 2 N hydrochloric acid were added to the reaction solution to dissolve the precipitation, and then the aqueous layer was separated. The organic layer was then extracted with water/acetonitrile/diluted hydrochloric acid-mixed solution. HP20SS was added to the combined aqueous layer, and then concentrated. The concentrated suspension was subjected to HP20SS/ODS column chromatography, eluting with water-acetonitrile. For the eluted fractions containing the intended compound, aqueous 0.2 N sodium hydroxide was used to adjust them to pH=6.0, and thereby a sodium salt thereof was formed. After concentrating in vacuo, the condensate solution was lyophilized to yield Compound I-31 as a powder. (Yield: 623 mg, Yield: 72%)

MS (m+1)=764.25

Elemental analysis for $C_{31}H_{33}ClN_7O_{10}S_2Na(NaHCO_3)_{0.2}(H_2O)_{5.8}$ Calcd.: C, 41.29; H, 4.98; Cl, 3.91; N, 10.80; S, 7.07; Na, 3.04.

Found.: C, 41.33; H, 4.95; Cl, 4.03; N, 10.53; S, 7.24; Na, 2.89.

$^1$H-NMR (D$_2$O) δ: 6.95 (2H, dd, J=9.5, 3.1 Hz), 6.89-6.79 (1H, m), 5.87 (1H, t, J=4.3 Hz), 5.34 dd, 8.6, 5.0 Hz), 4.45-3.41 (14H, m), 2.45-2.01 (4H, m), 1.49 (6H, ddd, J=19.9, 14.6, 3.4 Hz).

Example 32

Synthesis of Compound (I-32)

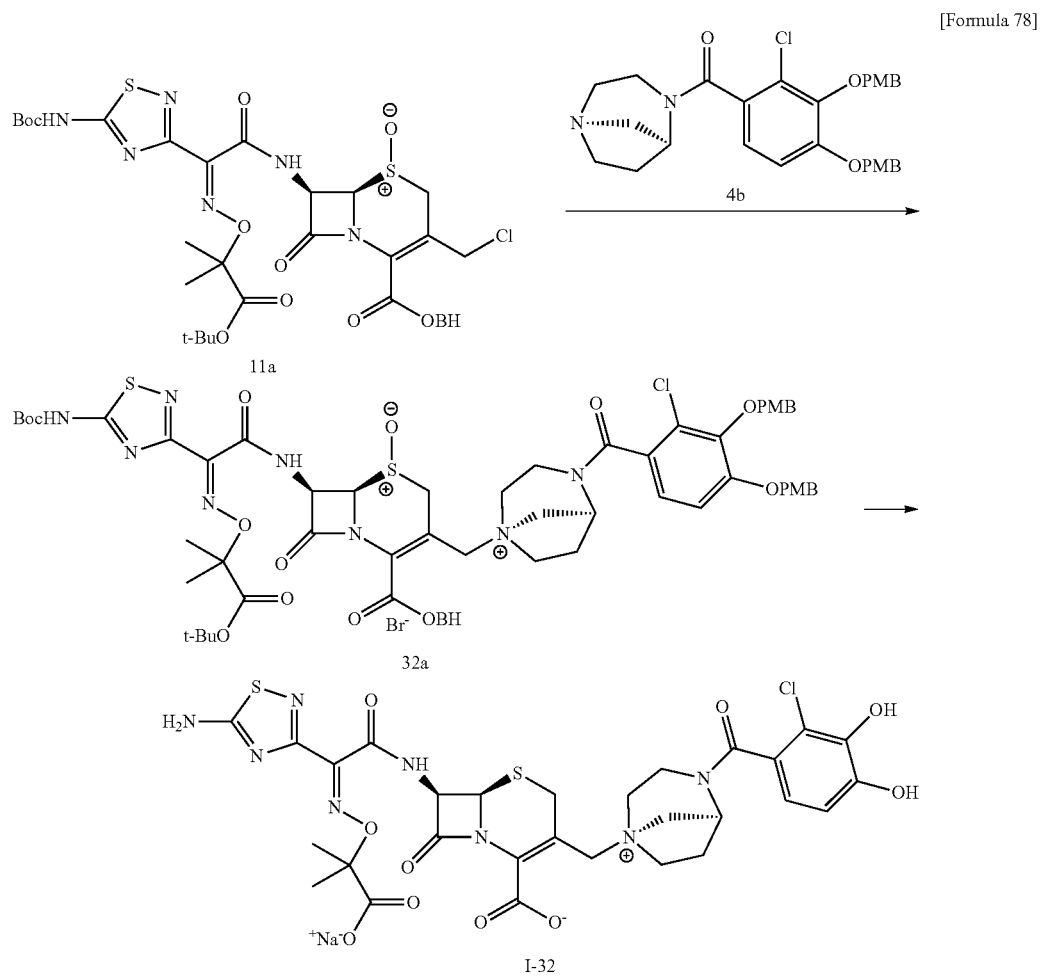

Step (1): Compound 11a→Compound 32a→Compound (I-32)

N,N-dimethylformamide (4.5 mL) was added to Compound 11a (1.5 mmol) to dissolve it. Compound 4b (785 mg, 1.5 mmol.) and sodium bromide (309 mg, 3 mmol) were added, and then stirred. Purified water was added to the reaction solution, and then extracted with ethyl acetate. The organic layer was washed with purified water, then saturated brine. The organic layer was dried with magnesium sulfate, and then magnesium sulfate was removed by filtration to yield Compound 32a. Compound 32a was treated using the same method as Compound 31b of Example 31 to obtain Compound I-32. (Yield: 553 mg, Yield: 48%)

MS (m+1)=751.26

Elemental analysis for $C_{25}H_{30}ClN_8O_{10}S_2Na(NaHCO_3)_{0.1}(H_2O)_{5.8}$ Calcd.: C, 39.45; H, 4.74; Cl, 4.00; N, 12.65; S, 7.24; Na, 2.85.

Found.: C, 39.38; H, 4.74; Cl, 4.24; N, 12.65; S, 7.27; Na, 2.87.

$^1$H-NMR (D$_2$O) δ: 6.93 (1H, d, J=8.2 Hz), 6.80 (1H, dd, J=13.0, 7.3 Hz), 5.88 (1H, t, J=5.3 Hz), 5.59-5.29 (1H, m), 4.59-4.45 (1H, m), 4.21-3.29 (12H, m), 2.83-2.25 (2H, m), 1.57-1.47 (6H, m).

Example 33
Synthesis of Compound (I-33)
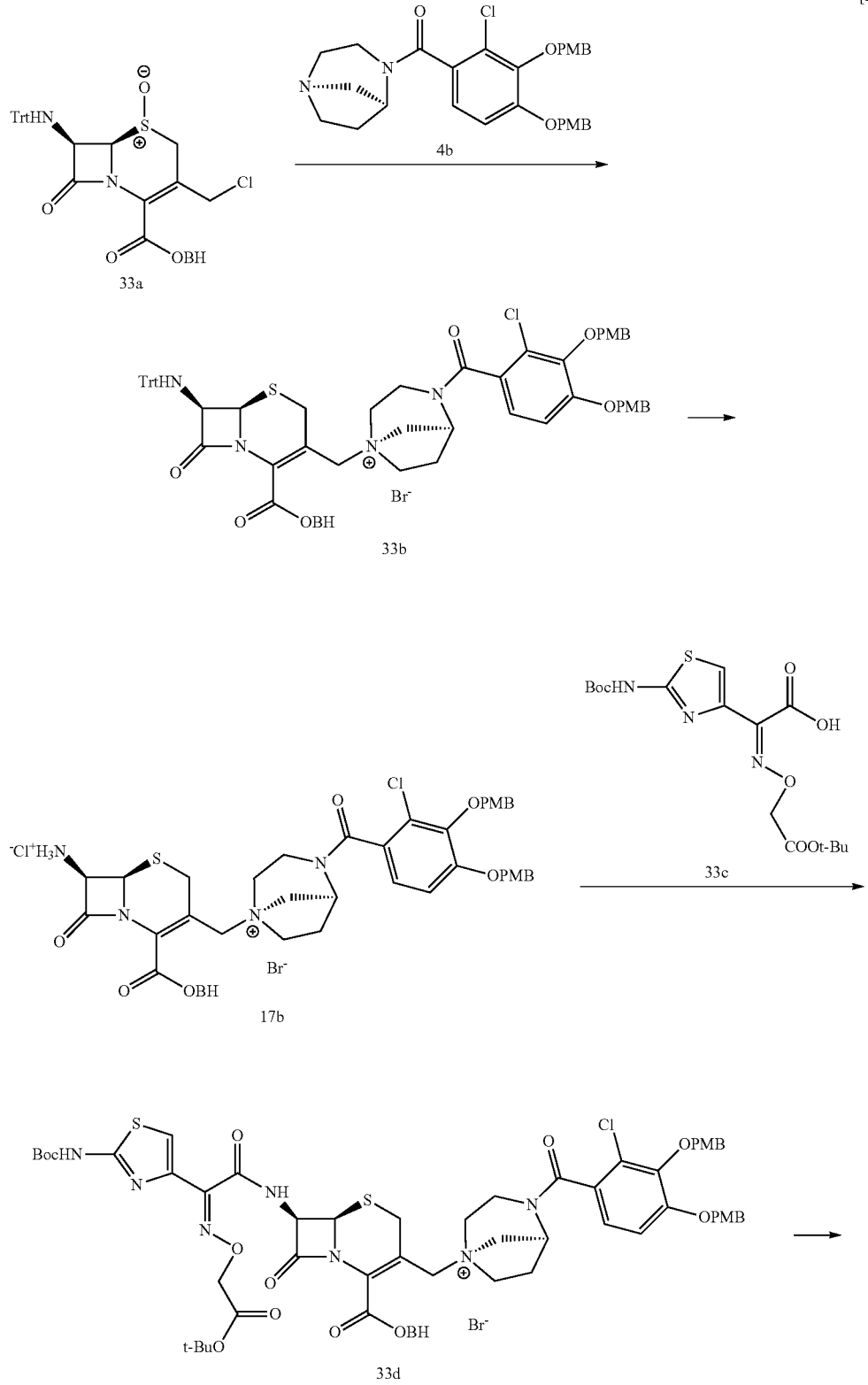

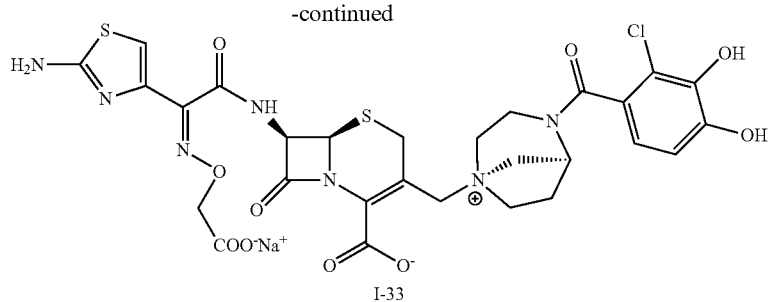

I-33

Step (1): Compound 33a→Compound 33b→Compound 17b→Compound 33d→Compound (I-33)

Compound 33a (4.09 g, 6 mmol) was dissolved in N,N-dimethylacetamide (18 mL). Compound 4b (3.14 g, 6 mmol) and sodium bromide (1.24 g, 12 mmol) were added, and then stirred at room temperature for 4 hours. N,N-dimethylformamide (36 mL) was added thereto, and then cooled to −20° C. Potassium iodide (7.97 g, 48 mmol) and acetyl chloride (2.83 g, 36 mmol) were added, and then stirred at 0° C. The mixture was poured into aqueous sodium hydrogen sulfite solution. The resulting solid precipitation was filtered, and then dried under reduced pressure to yield Compound 33b. (Yield: 7.70 g, Yield: 107%) Compound 33b (7.35 g, 6 mmol) was dissolved in acetone (36 mL) Aqueous 6 N hydrochloric acid (2.5 mL) was added thereto, and then stirred at room temperature for 3 hours. The reaction solution was diluted with methylene chloride, and then dried with anhydrous magnesium sulfate. After magnesium sulfate was removed by filtration, evaporation in vacuo yielded Compound 17b. (Yield: 8.18 g, 134%)

Compound 17b (2.05 g, equivalent to 1.5 mmol) was dissolved in methylene chloride (20 mL). After cooling to −10° C., Compound 33c (0.60 mg, 1.5 mmol), pyridine (0.154 g, 1.3 mmol), and hydrochloric acid salt of 1-(dimethylaminopropyl)-3-ethylcarbodiimide (345 mg, 1.8 mmol) were added, and then stirred at the same temperature. Purified water was added to the reaction solution, and then the aqueous layer was extracted with ethyl acetate. The organic layer was washed with purified water, then saturated brine. The organic layer was dried with magnesium sulfate, and then magnesium sulfate was removed by filtration to yield Compound 33d. Compound 33d was treated using the same method as 31b of Example 31 to obtain Compound I-33. (Yield: 325 mg, Yield: 29%)

MS (m+1)=722.26

Elemental analysis for $C_{28}H_{27}ClN_7O_{10}S_2Na(NaHCO_3)_{0.1}$ $(H_2O)_{6.7}$ Calcd.: C, 38.65; H, 4.67; Cl, 4.06; N, 11.23; S, 7.34; Na, 2.90.

Found.: C, 38.61; H, 4.52; Cl, 4.06; N, 11.25; S, 7.19; Na, 2.88.

$^1$H-NMR (D$_2$O) δ: 7.04 (1H, br s), 6.99-6.91 (1H, m), 6.86-6.80 (1H, m), 5.93-5.85 (1H, m), 5.59-5.29 (1H, m), 4.62-4.54 (1H, m), 4.30-4.08 (1H, m), 3.91-3.32 (12H, m), 2.86-2.24 (2H, m).

Example 34

Synthesis of Compound (I-34)

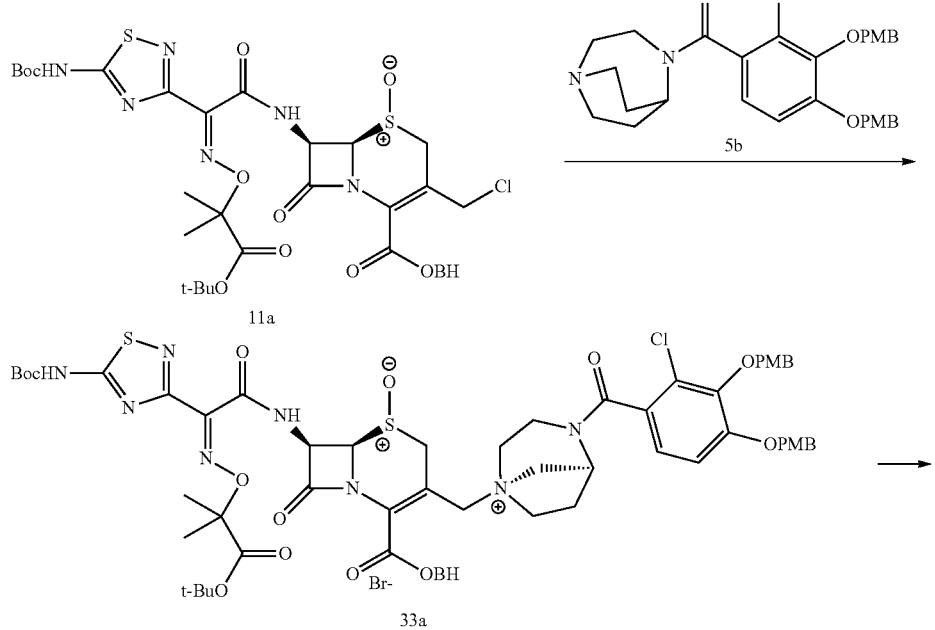

[Formula 80]

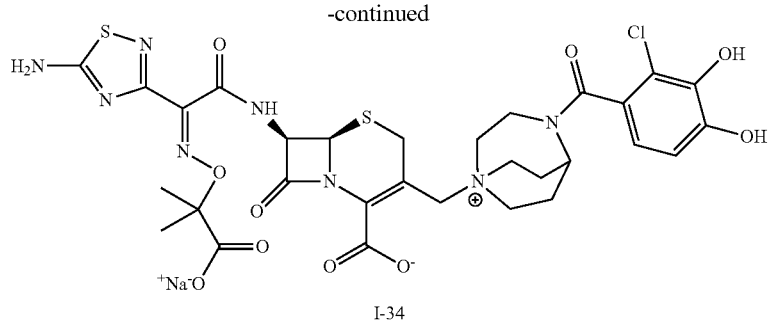
I-34
Step (1): Compound 11a→Compound 34a→Compound (I-34)
Compound 11a (843 mg, 1 mmol) and Compound 5b (537 mg, 1 mmol) were treated using the same method as Example 32 to obtain Compound I-34. (Yield: 554 mg, Yield: 70%)
MS (m+1)=765.32
Elemental analysis for $C_{28}H_{27}ClN_7O_{10}S_2Na(NaHCO_3)_{0.1}(H_2O)_{6.7}$
Calcd.: C, 39.45; H, 5.01; Cl, 3.87; N, 12.23; S, 7.00; Na, 2.76.
Found.: C, 39.46; H, 5.00; Cl, 4.03; N, 12.24; S, 6.87; Na, 2.79.
$^1$H-NMR (D$_2$O) δ: 6.94 (1H, d, J=8.4 Hz), 6.82 (1H, dd, J=8.4, 4.2 Hz), 5.89 (1H, dd, J=7.2, 5.1 Hz), 5.37 (1H, t, J=5.1 Hz), 5.00-4.90 (1H, m), 4.25-4.06 (1H, m), 3.90-3.41 (11H, m), 2.28 (5H, t, J=23.3 Hz), 1.57-1.51 (6H, m).
Example 35
Synthesis of Compound (I-35)
[Formula 81]
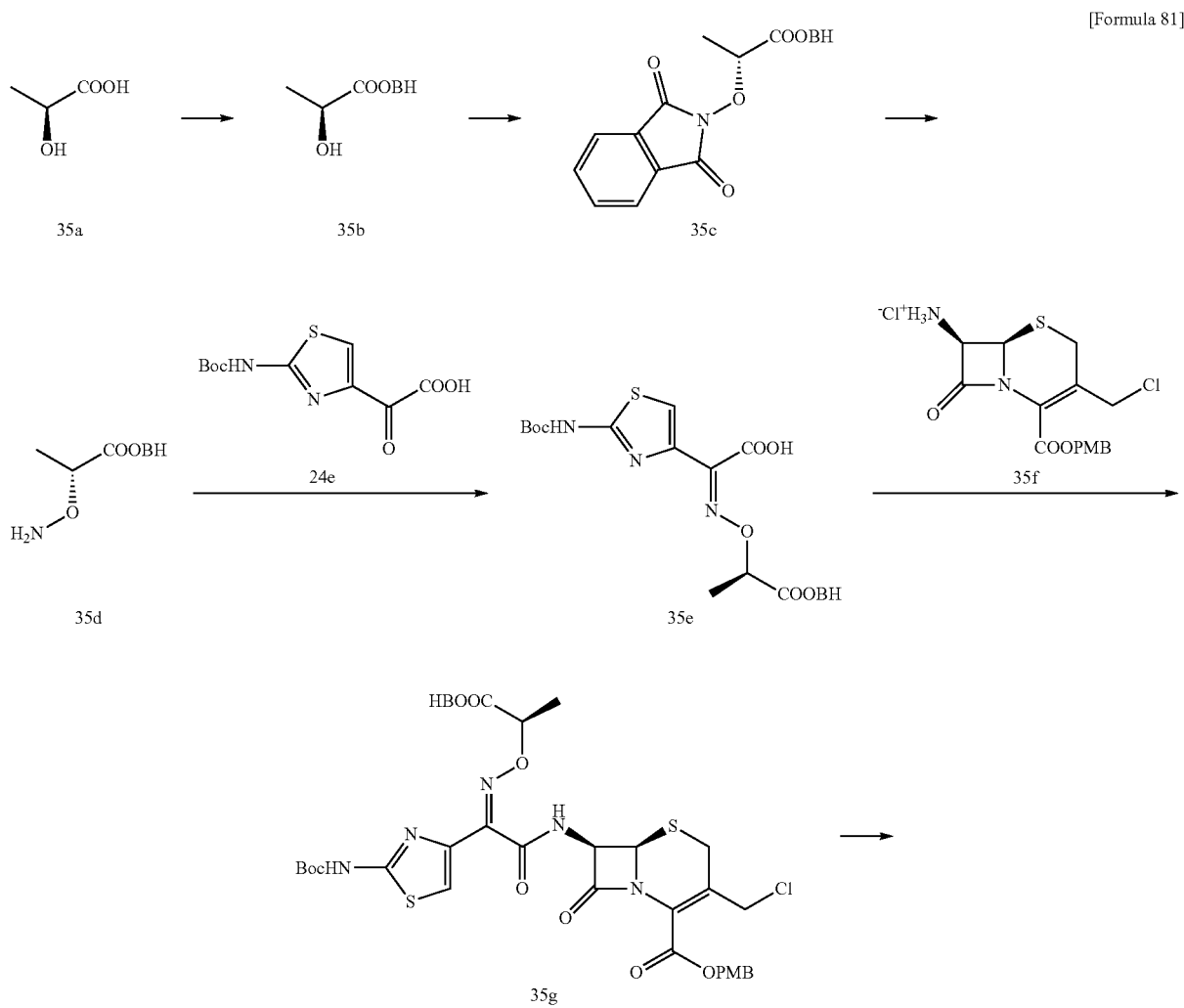

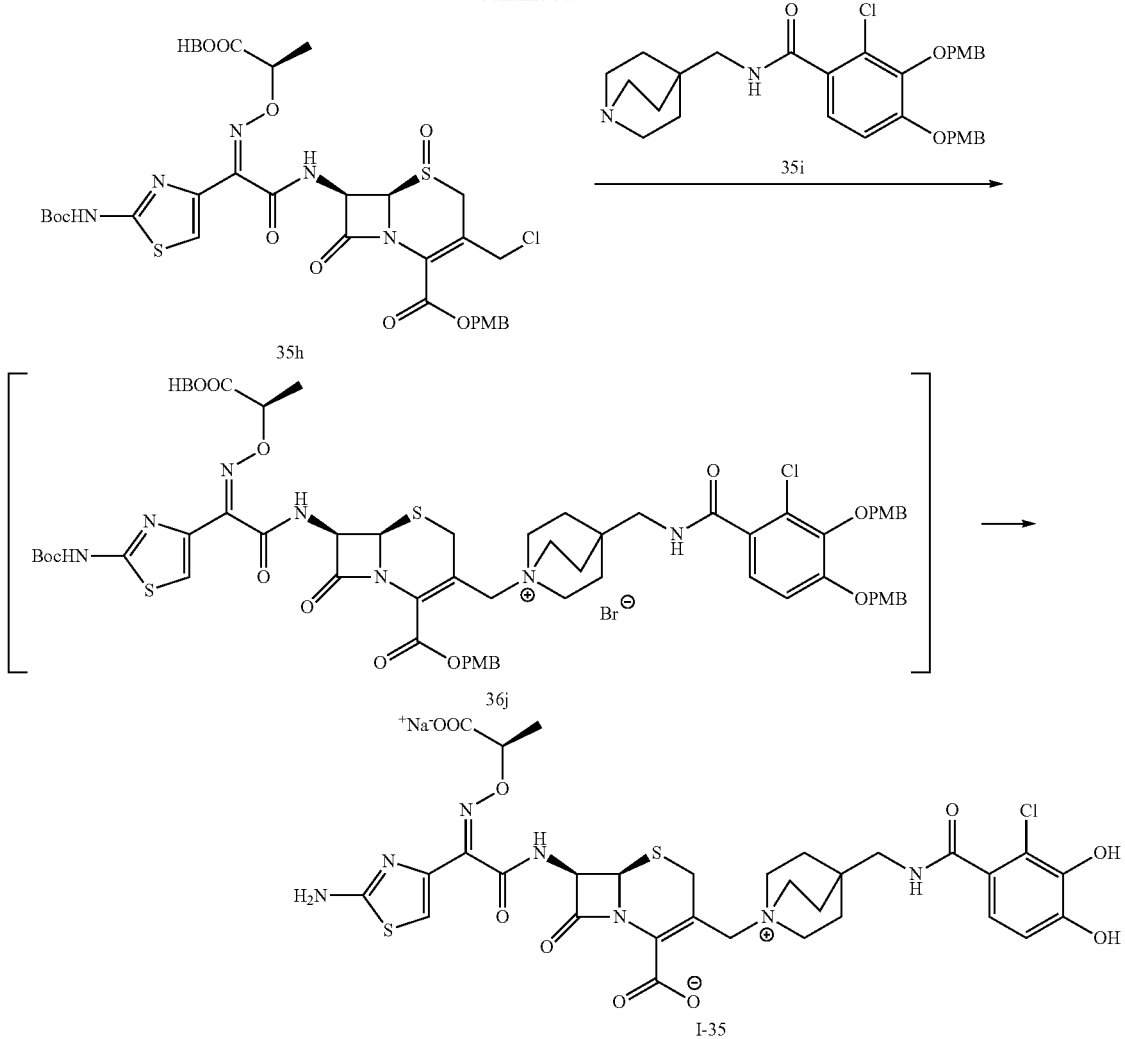

Step (1): Compound 35a→Compound 35b

A solution of Compound 35a (10.60 g, 100 mmol) in acetonitrile (72 mL) was cooled to 0° C. A solution of diphenyldiazomethane (6.99 g, 36 mmol) in acetonitrile (18 mL) was then added drop-wise thereto over 2 hours. The reaction solution stood at 4° C. overnight. After the insoluble was filtered, the reaction mixture was concentrated, and then diisopropyl ether was added to the residue. The resulting solid was filtered, and then dried under reduced pressure to yield Compound 35b as a white solid.

Yield: 10.91 g, (43%)

$^1$H-NMR (CDCl$_3$) δ: 1.48 (3H, d, J=6.9 Hz), 2.81 (1H, d, J=5.1 Hz), 4.34-4.42 (1H, m), 6.92 (1H, s), 7.24-7.38 (11H, m)

Step (2): Compound 35b→Compound 35c

To a solution of Compound 35b (5.13 g, 20.0 mmol) in tetrahydrofuran (50 mL), N-hydroxyphthalimide (3.92 g, 24.0 mmol) and triphenylphosphine (6.29 g, 24.0 mmol) were added and then cooled to 0° C. Diisopropylazodicarboxylate (4.67 ml, 24.0 mmol) was added drop-wise thereto over 1 hour. After stirring at room temperature for 40 minutes, the insoluble was filtered, followed by concentration in vacuo. The resulting crude product was purified by silica gel column chromatography to yield Compound 35c as a white solid.

Yield: 7.30 g, (91%)

$^1$H-NMR (CDCl$_2$) δ: 1.67 (3H, d, J=6.9 Hz), 5.04 (2H, q, J=6.9 Hz), 6.92 (1H, s), 7.20-7.34 (11H, m), 7.69-7.78 (4H, m)

Step (3): Compound 35c→Compound 35d→Compound 35e

A solution of Compound 35c (7.30 g, 18.2 mmol) in methylene chloride (70 mL) was cooled to 0° C. Methylhydrazine (1.16 ml, 21.8 mmol) was added in one portion thereto, and then stirred at 0° C. for 2 hours. After the resulting crystals were removed by filtration, concentrated and subsequently dried under reduced pressure, Compound 35d was obtained as a yellow white oil. The obtained Compound 35d was used in the next reaction without purification.

To the solution of the whole amount of Compound 35d obtained in methanol (50 ml), Compound 24e (4.94 g, 18.2 mmol) was added and then stirred at room temperature for 2 hours, and then stood overnight. The resulting crystals were filtered, washed with diisopropyl ether and dried under reduced pressure to yield Compound 35e as a white solid.

Yield: 5.64 g, (57%)

$^1$H-NMR (CDCl$_3$) δ: 1.38 (3H, d, J=7.2 Hz), 4.38 (2H, q, J=7.2 Hz), 5.67 (2H, br), 6.95 (1H, s), 7.25-7.34 (11H, m)

Step (4): Compound 35e+Compound 35f→Compound 35g→Compound 35h

To a solution of Compound 35e (2.63 g, 5.0 mmol) in ethyl acetate (32 mL), Compound 35f (2.23 g, 5.5 mmol) was added and then cooled to −40° C. Phenyl dichlorophosphate (1.12 ml, 7.5 mmol) was slowly added, and then N-methylmorpholine (2.20 mL, 20 mmol) was added drop-wise over 25 minutes. After stirring at −40° C. for 1.5 hours, aqueous 0.2 N hydrochloric acid was added to the reaction mixture, followed by extraction with ethyl acetate. The organic layer was washed with water, aqueous 5% sodium hydrogen carbonate, then saturated brine, and then dried with anhydrous magnesium sulfate. The inorganic substance was removed by filtration, and then concentrated and subsequently drying under reduced pressure to yield Compound 35g as a yellow foam. The obtained Compound 35g was used in the next reaction without purification.

A solution of the whole amount of Compound 35g obtained in methylene chloride (22 ml) was cooled to −40° C. A solution of m-chloroperbenzoic acid (1.46 g, 5.5 mmol) in methylene chloride (22 ml) was added drop-wise thereto over 30 minutes. After stirring at −40° C. for 30 minutes, aqueous 15% sodium thiosulfate solution was added thereto, methylene chloride was evaporated under reduced pressure, followed by extraction with ethyl acetate. The organic layer was washed with aqueous 5% sodium hydrogen carbonate, then saturated brine, and then dried with anhydrous sodium sulfate. The inorganic substance was removed by filtration, followed by concentration in vacuo. The resulting crude product was purified by silica gel column chromatography to yield Compound 35h as a white foam.

Yield: 4.00 g, (90%)

$^1$H-NMR (CDCl$_3$) δ: 1.53 (9H, s), 1.63 (3H, d, J=6.9 Hz), 3.29 (1H, d, J=18.6 Hz), 3.69 (1H, d, J=18.6 Hz), 3.81 (3H, s), 4.22 (1H, d, J=12.3 Hz), 4.50 (1H, d, J=3.6 Hz), 4.98 (1H, d, J=12.3 Hz), 5.04 (1H, q, J=7.5 Hz), 5.26 (1H, d, J=2.4 Hz), 6.11 (1H, q, J=4.8 Hz), 6.89 (1H, s), 6.92 (2H, s), 7.16 (1H, s), 7.22-7.37 (10H, m), 8.01 (1H, d, J=9.6 Hz), 8.34 (1H, br)

Step (5): Compound 35h+Compound 35i→Compound 35j→Compound (I-35)

To a solution of Compound 35h (392 mg, 1.0 mmol) in N,N-dimethylacetamide (3 mL), sodium bromide (206 mg, 2.0 mmol) was added and then stirred at room temperature for 30 minutes. After cooling to 15° C., a solution of Compound 35i (551 mg, 1.0 mmol) in N,N-dimethylacetamide (1.5 ml) was added drop-wise over 10 minutes, and then stirred at 15° C. for 3 hours. N,N-Dimethylformamide (2.5 mL) was added thereto, and then cooled to −40° C. Phosphorus tribromide (169 µl, 2.0 mmol) was added, and then stirred at −40° C. or 1 hour. The reaction mixture was slowly added to pre-ice-cooled aqueous 5% sodium chloride. The precipitated solid was filtered, washed with water, suspended in water, and then lyophilized to yield Compound 35j as a brown solid. The obtained Compound 35j was used in the next reaction without purification.

The whole amount of Compound 35j obtained was dissolved in methylene chloride (10 ml). After cooling to −40° C., anisole (1.09 ml, 10 mmol) followed by 2 mol/L-aluminum chloride/nitromethane solution (5.0 ml, 10 mmol) were added thereto, and then stirred at −40° C. for 1 hour. Aqueous 2 N hydrochloric acid, acetonitrile, and diisopropyl ether were added to the reaction solution. After stirring, the insoluble and the supernatant were separated by decantation. The aqueous layer was separated from the supernatant. Meanwhile, water and acetonitrile were added to the insoluble attached to the container, and then stirred. After the insoluble was completely dissolved, diisopropyl ether was added thereto, and then the aqueous layer was separated. The organic layer was then extracted with water. All the aqueous layers were combined, HP20-SS resin was added thereto, and then acetonitrile was evaporated in vacuo. The resulting mixture was purified by ODS column chromatography. To the resulting solution of the intended compound, aqueous 0.2 N sodium hydroxide solution was added until pH=5.3. The resulting solution was concentrated in vacuo, and then lyophilized to yield Compound I-35 as a yellow powder.

Yield: 556 mg, (71%)

$^1$H-NMR (DMSO-d$_6$) δ: 1.41 (3H, d, J=7.2 Hz), 1.74 (4H, br) 3.12-3.78 (13H, m), 4.42 (1H, q, J=6.9 Hz), 4.90 (1H, d, J=13.5 Hz), 5.14 (1H, d, J=5.1 Hz), 5.71 (1H, dd, J=4.8, 8.7 Hz), 6.73 (1H, d, J=8.4 Hz), 6.80 (1H, d, J=8.4 Hz), 6.82 (1H, s), 7.18 (2H, br), 8.31 (1H, br)

MS (m+1)=764.25

Elemental analysis for: $C_{31}H_{33}ClN_7O_{10}S_2Na \cdot 0.3H_2O$

Calcd.: C, 42.23; H, 4.98; Cl, 4.02; N, 11.12; S, 7.23; Na, 2.61 (%).

Found.: C, 42.05; H, 4.94; Cl, 4.32; N, 11.06; S, 7.50; Na, 2.64 (%).

Example 36

Synthesis of Compound (I-36)

[Formula 82]

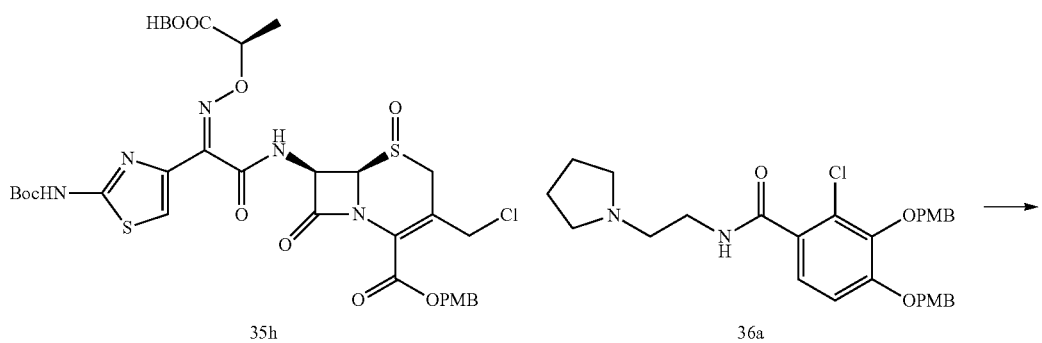

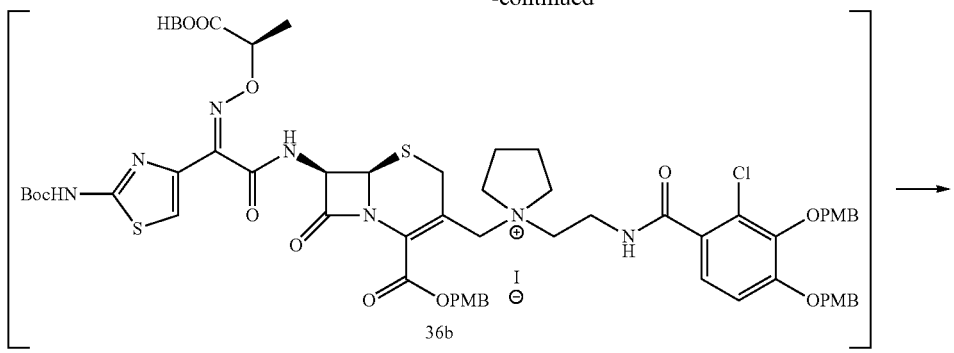

36b

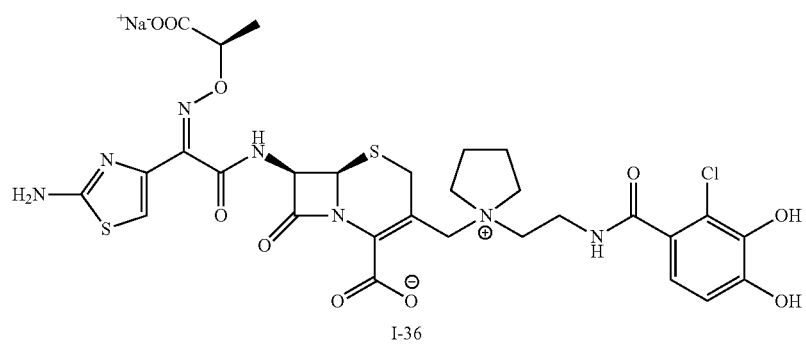

I-36

Step (1): Compound 35h+Compound 36a→Compound 36b→Compound (I-36)

To a solution of Compound 35h (892 mg, 1.0 mmol) in N,N-dimethylacetamide (3 mL), sodium iodide (300 mg, 2.0 mmol) was added and then stirred at room temperature for 30 minutes. After cooling to 15° C., a solution of Compound 36a (534 mg, 1.0 mmol) in N,N-dimethylacetamide (1.5 mL) was added drop-wise thereto over 10 minutes, and then stirred at 15° C. for 7 hours. N,N-dimethylformamide (2.5 mL) was added thereto, and then cooled to −40° C. Phosphorus tribromide (199 μl, 2.0 mmol) was added thereto, and then stirred at −40° C. for 30 minutes. The reaction mixture was slowly added to ice-cooled aqueous 5% sodium chloride. The precipitated solid was filtered, washed with water, suspended in water, and then lyophilized to yield Compound 36b as a brown solid. The obtained Compound 36b was used in the next reaction without purification.

The whole amount of Compound 36b obtained was dissolved in methylene chloride (10 ml). After cooling to −40° C., anisole (1.09 ml, 10 mmol) followed by 2 mol/L-aluminum chloride/nitromethane solution (5.0 ml, 10 mmol) were added, and then stirred at −40° C. for 1 hour. Aqueous 2 N hydrochloric acid, acetonitrile, and diisopropyl ether were then added to the reaction mixture. After stirring, the insoluble and the supernatant were separated by decantation. The aqueous layer was then separated from the supernatant. Meanwhile, water and acetonitrile were added to the insoluble attached to the container, and then stirred. After the insoluble was completely dissolved, diisopropyl ether was added thereto, and then the aqueous layer was separated. The organic layer was then extracted with water. All the aqueous layers were combined, HP20-SS resin was added thereto, and then acetonitrile was evaporated in vacuo. The resulting mixed solution was then purified by ODS column chromatography. To the resulting solution of the intended compound, aqueous 0.2 N sodium hydroxide solution was added until pH=5.2. The resulting solution was concentrated in vacuo, and then lyophilized to yield Compound I-36 as a light yellow powder.

Yield: 276 mg, (36%)

$^1$H-NMR (D$_2$O) δ: 1.38 (3H, d, J=6.9 Hz), 2.14 (4H, br) 3.42-3.71 (10H, m), 3.85 (1H, d, J=16.5 Hz), 4.04 (1H, d, J=13.8 Hz), 4.54 (1H, q, J=6.9 Hz), 5.27 (1H, d, J=3.1 Hz), 3.77 (1H, d, J=4.9 Hz), 6.79 (1H, d, J=8.4 Hz), 6.87 (1H, d, J=8.4 Hz), 6.91 (1H, MS (m+1)=738.24

Elemental analysis for: C$_{29}$H$_{31}$ClN$_7$O$_{10}$S$_2$Na.0.1NaHCO$_3$.4.3H$_2$O Calcd. C, 41.31; H, 4.73; Cl, 4.19; N, 11.59; S, 7.58; Na, 2.99 (%).

Found.: C, 41.31; H, 4.72; Cl, 4.16; N, 11.54; S, 7.71; Na, 2.99 (%).

Example 37

Synthesis of Compound (I-37)

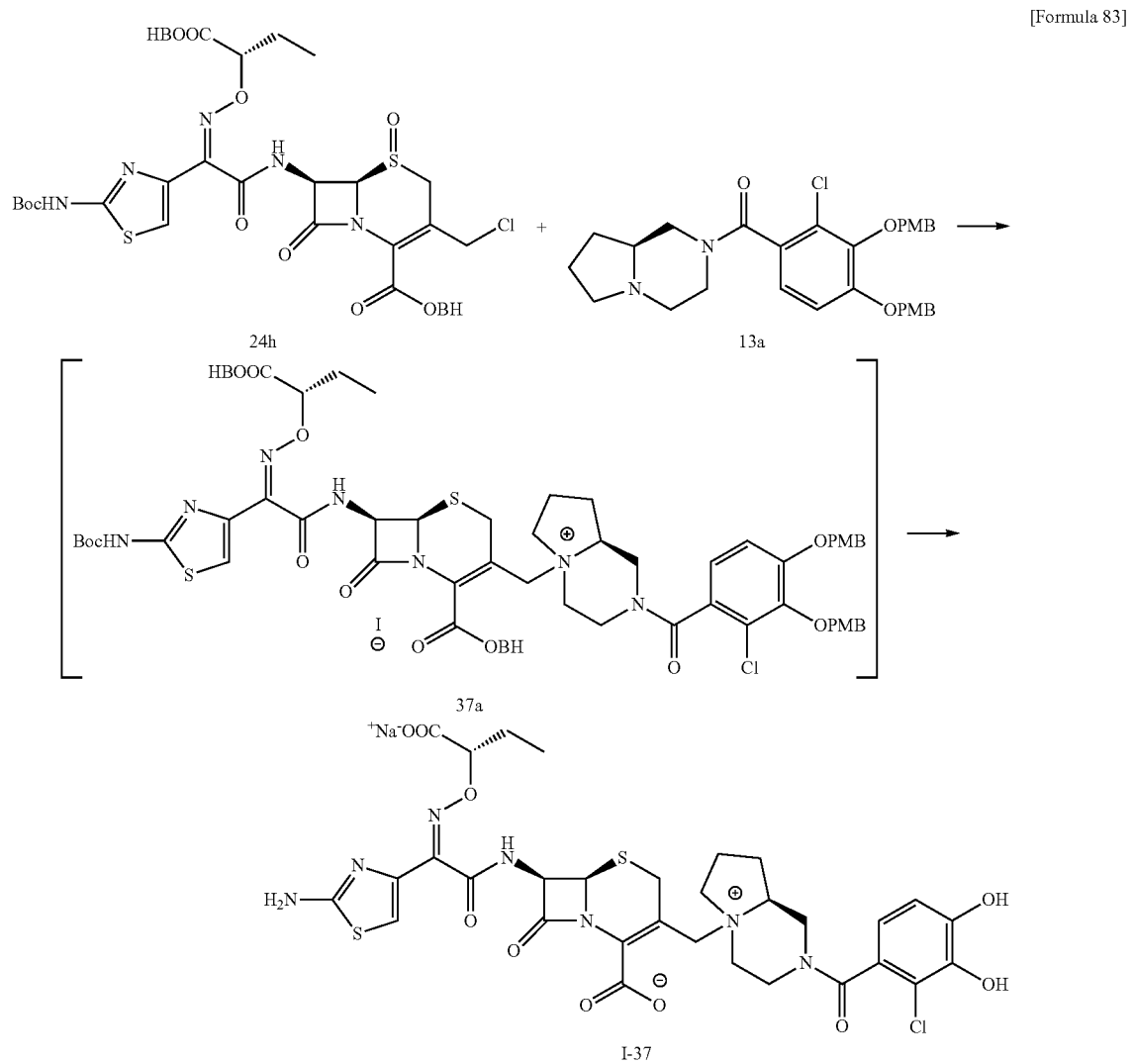

Step (1): Compound 24h+Compound 13a→Compound 37a→Compound (I-37)

From Compound 24h (952 mg, 1.0 mmol) and Compound 13a (537 mg, 1.0 mmol), Compound I-37 was obtained as a light yellow powder using the same method as Example 36.

Yield: 467 mg, (59%)

$^1$H-NMR (D$_2$O) δ: 0.75-0.82 (3H, m), 1.63-1.71 (2H, m), 2.00 (4H, br), 3.24-3.77 (11H, m), 4.05-4.27 (2H, m), 4.33-4.37 (1H, m), 5.16 (1H, dd, J=5.1, 8.7 Hz), 5.69 (1H, t, J=5.4 Hz), 6.65 (1H, d, J=8.4 Hz), 6.77 (1H, dd, J=3.3, 8.4 Hz), 6.80 (1H, d, J=3.9 Hz)

MS (m+1)=764.28

Elemental analysis for: $C_{31}H_{33}ClN_7O_{10}S_2Na\cdot4.8H_2O$

Calcd.: C, 42.67; H, 4.92; Cl, 4.06; N, 11.24; 3, 7.35; Na, 2.63 (%).

Found.: C, 42.58; H, 4.81; Cl, 4.21; N, 11.18; 3, 7.55; Na, 2.64 (%).

Example 38

Synthesis of Compound (I-38)

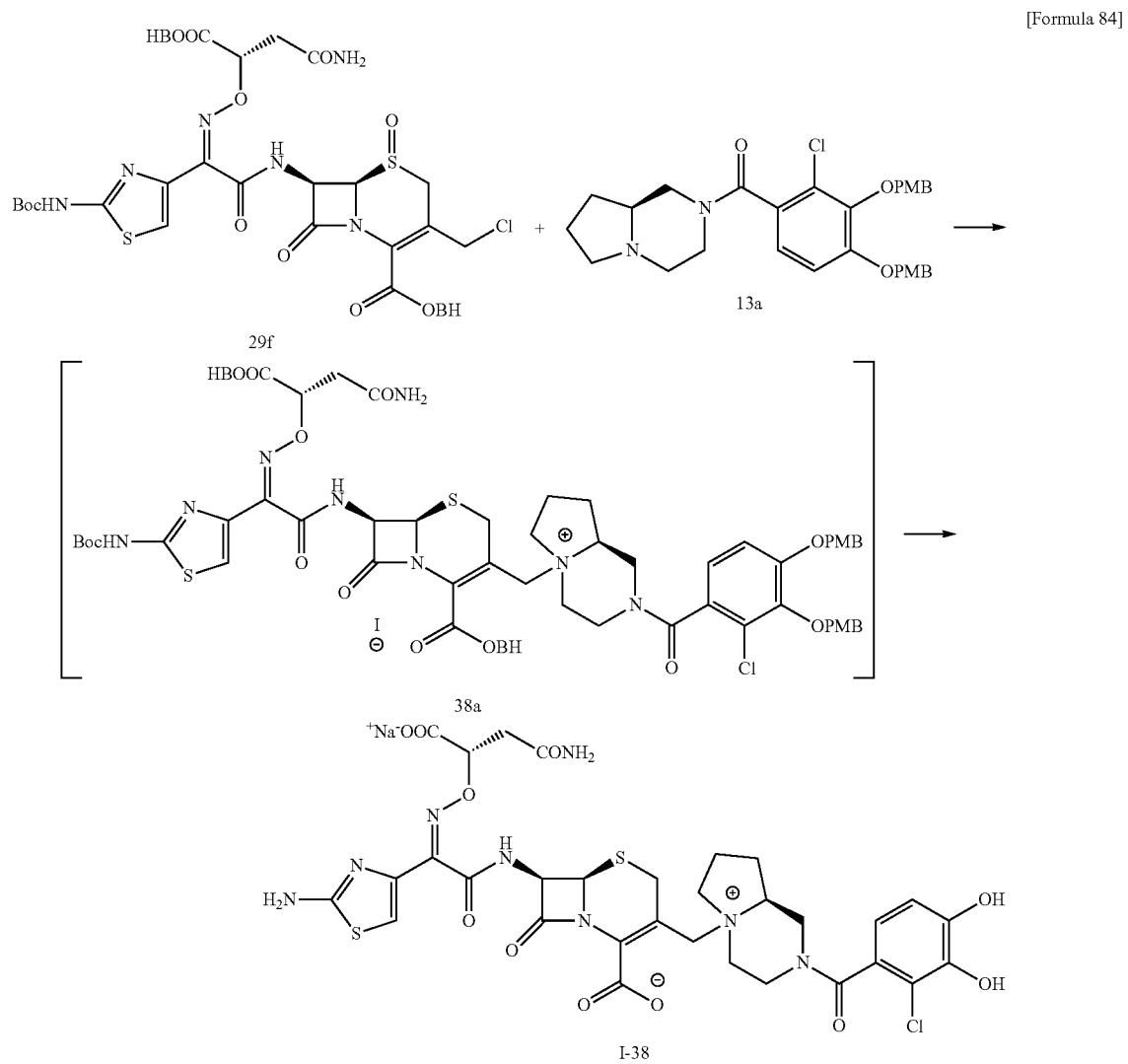

[Formula 84]

Step (1): Compound 29f+Compound 13a→Compound 38a→Compound (I-38)

From Compound 29f (981 mg, 1.0 mmol) and Compound 13a (537 mg, 1.0 mmol), Compound I-38 was obtained as a light yellow powder using the same method as Example 36.

Yield: 176 mg, (22%)

$^1$H-NMR (D$_2$O) δ: 2.14 (4H, br), 2.75-2.77 (2H, m), 3.37-3.91 (11H, m), 4.18-4.40 (2H, m), 4.82-4.87 (1H, m), 5.28 (1H, dd, J=5.1, 8.7 Hz), 5.68 (1H, t, J=4.5 Hz), 6.78 (1H, d, J=7.8 Hz), 6.90 (1H, dd, J=3.3, 8.4 Hz), 6.96 (1H, d, J=3.6 Hz)

MS (m+1)=793.27

Elemental analysis for: $C_{31}H_{32}ClN_8O_{11}S_2Na \cdot 0.1NaHCO_3 \cdot 5.6H_2O$ Calcd.: C, 40.40; H, 4.72; Cl, 3.83; N, 12.12; S, 6.94; Na, 2.74 (%).

Found.: C, 40.12; H, 4.50; Cl, 3.93; N, 12.15; S, 7.24; Na, 2.90 (%).

Example 39

Synthesis of Compound (I-39)

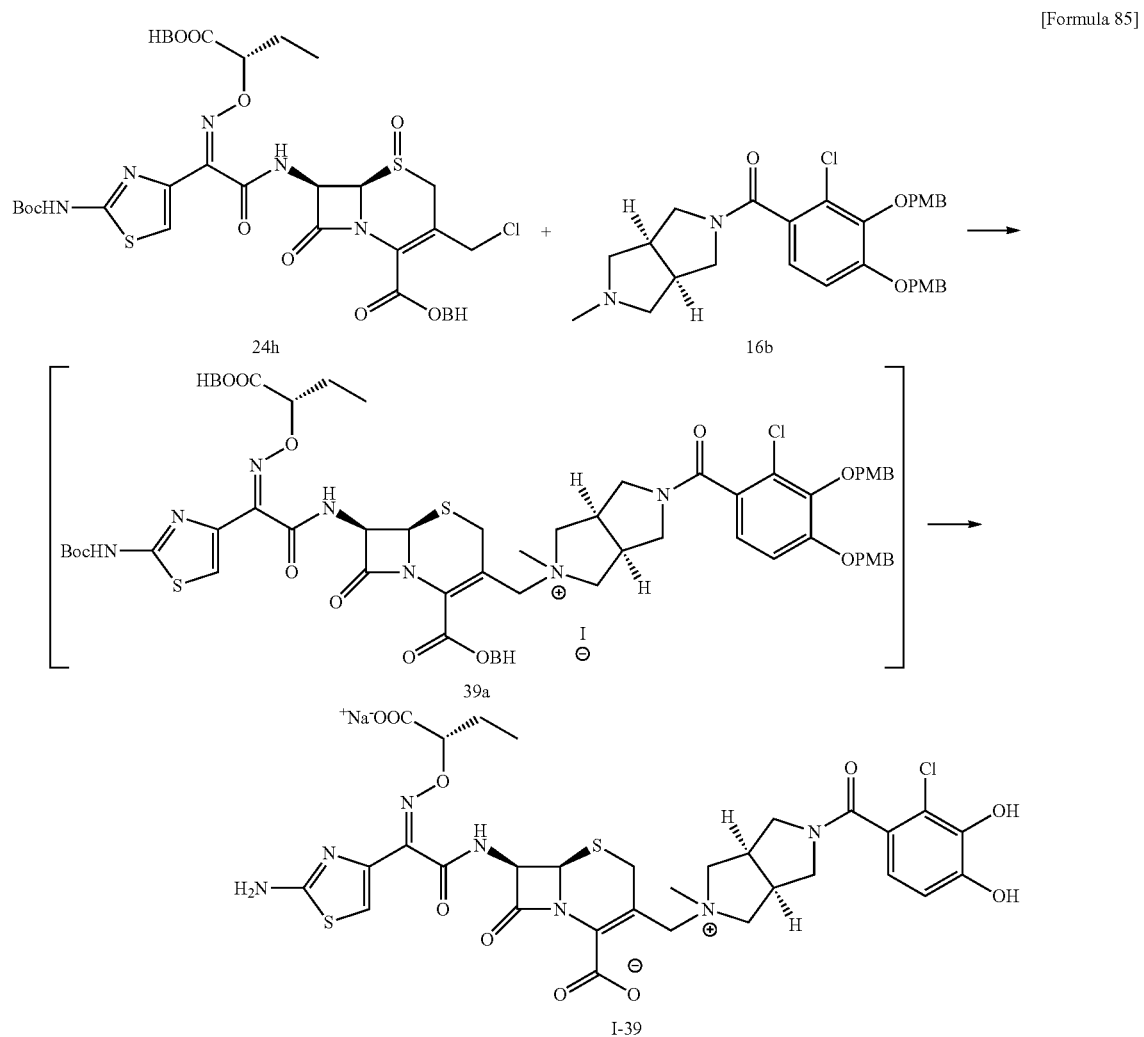

[Formula 85]

Step (1): Compound 24h+Compound 16b→Compound 39a→Compound (I-39)

From Compound 24h (952 mg, 1.0 mmol) and Compound 16b (537 mg, 1.0 mmol), Compound I-39 was obtained as a light yellow powder using the same method as Example 36.

Yield: 545 mg, (69%)

$^1$H-NMR (D$_2$O) δ: 0.91 (3H, t, J=7.2 Hz), 1.81 (2H, quint, J=8.1 Hz) 2.88-3.56 (11H, m), 3.76-4.13 (8H, m), 4.47 (1H, t, J=6.0 Hz), 5.30 (1H, q, J=2.4 Hz), 5.81 (1H, dd, J=2.4, 4.8 Hz), 6.78 (1H, d, J=8.4 Hz), 6.88 (1H, d, J=8.4 Hz), 6.92 (1H, s)

MS (m+1)=764.24

Elemental analysis for: C$_{31}$H$_{33}$ClN$_7$O$_{10}$S$_2$Na.4.6H$_2$O

Calcd.: C, 42.84; H, 4.89; Cl, 4.08; N, 11.28; S, 7.38; Na, 2.65 (%).

Found.: C, 42.84; H, 4.93; Cl, 4.31; N, 11.25; 7.44; Na, 2.59 (%).

Example 40
Synthesis of Compound (I-40)
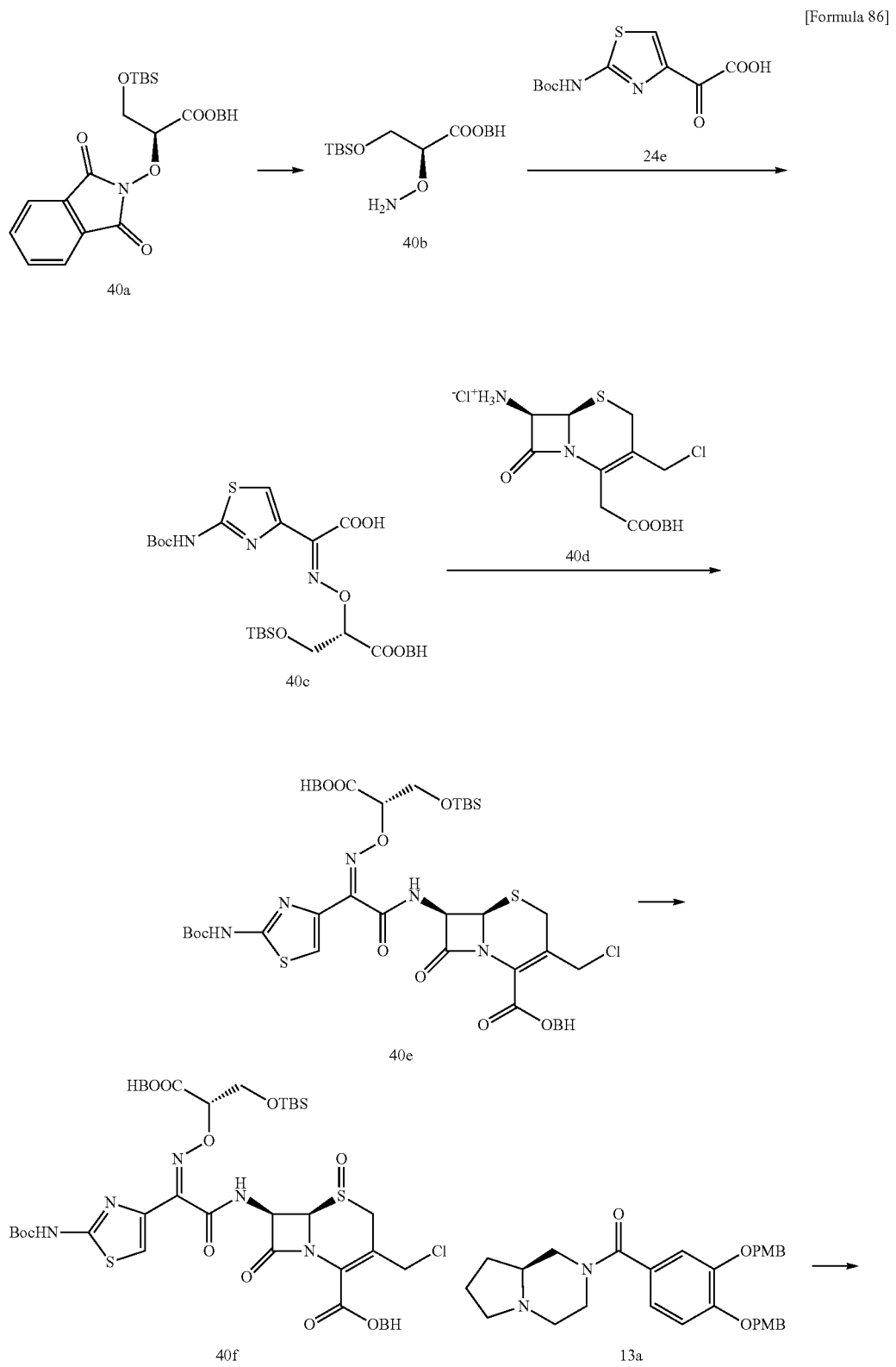

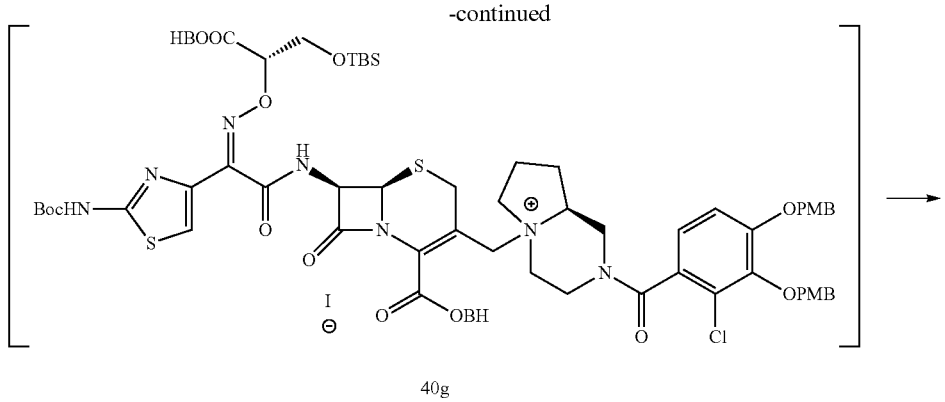

40g

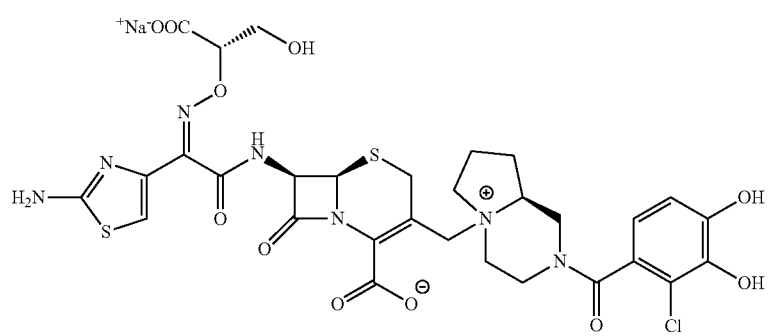

I-40

40

Step (1): Compound 40a→Compound 40b→Compound 40c

A solution of Compound 40a (7.09 g, 13.3 mmol) in methylene chloride (70 mL) was cooled to 0° C. Methylhydrazine (851 μl, 16 mmol) was added in one portion, and then stirred at 0° C. for 2 hours. The resulting crystals were then removed by filtration. Concentrating and subsequent drying under reduced pressure yielded Compound 40b as a yellowish white oil. The obtained Compound 40b was used in the next reaction without purification.

To a solution of the whole amount of Compound 40b obtained in methanol (50 ml), Compound 24e (4.00 g, 14.7 mmol) was added and then stirred at room temperature for 1.5 hours. After the solvent was evaporated in vacuo, water and tetrahydrofuran were added to the resulting concentrated residue, and then extracted with ethyl acetate. The organic layer was washed with water, then saturated brine, and then dried with anhydrous magnesium sulfate. Magnesium sulfate was then removed by filtration, followed by concentration in vacuo. Diisopropyl ether was added to the residue. The resulting crystals were filtered, and then dried under reduced pressure to yield Compound 40c as a white solid.

Yield: 8.27 g, (95%)

$^1$H-NMR (DMSO-d$_6$) δ: 0.01 (6H, s), 0.79 (9H, s), 1.49 (9H, s), 4.00-4.13 (2H, m), 4.95 (1H, t, J=4.2 Hz), 6.88 (91H, s), 7.23-7.35 (11H, m), 7.39-7.47 (10H, m)

Step (2): Compound 40c→Compound 40d→Compound 40e→Compound 40f

From Compound 40c (6.56 g, 10 mmol) and Compound 40d (4.97 g, 11 mmol), Compound 40f was provided as a peach-colored foam in the same way as Example 35.

Yield: 6.80 g, (64%)

$^1$H-NMR (CDCl$_3$) δ: 0.02 (6H, s), 0.83 (9H, s), 1.53 (9H, s), 3.30 (1H, d, J=19.2 Hz), 3.69 (1H, d, J=18.3 Hz), 4.08-4.19 (2H, m), 4.49-4.51 (1H, m), 4.91-5.11 (2H, m), 6.15 (1H, q, J=4.8 Hz), 6.95 (2H, d, J=12.3 Hz), 7.16-7.48 (21H, m), 7.97 (1H, d, J=9.3 Hz), 8.16 (1H, br)

Step (3): Compound 40f+Compound 13a→Compound 40g→Compound (I-40)

From Compound 40f (1.07 g, 1.0 mmol) and Compound 13a (537 mg, 1.0 mmol), Compound I-40 was obtained as a yellow powder using the same method as Example 36.

Yield: 550 mg, (70%)

$^1$H-NMR (D$_2$O) δ: 2.06 (4H, br), 3.30-4.10 (13H, m), 4.18-1.33 (2H, m), 4.57-4.61 (1H, m), 5.22 (1H, dd, J=5.1, 8.7 Hz), 5.78 (1H, t, J=4.5 Hz), 6.71 (1H, d, J=7.8 Hz), 6.82 (1H, dd, J=3.3, 8.4 Hz), 6.89 (1H, d, J=3.3 Hz)

MS (m+1)=766.32

Elemental analysis for: $C_{30}H_{31}ClN_7O_{10}S_2Na \cdot 4.5H_2O$

Calcd.: C, 41.45; H, 4.64; Cl, 4.08; N, 11.28; S, 7.38; Na, 2.64 (%).

Found.: C, 41.54; H, 4.72; Cl, 4.44; N, 10.94; S, 7.28; Na, 2.40 (%).

Example 41

Synthesis of Compound (I-41)

[Formula 87]

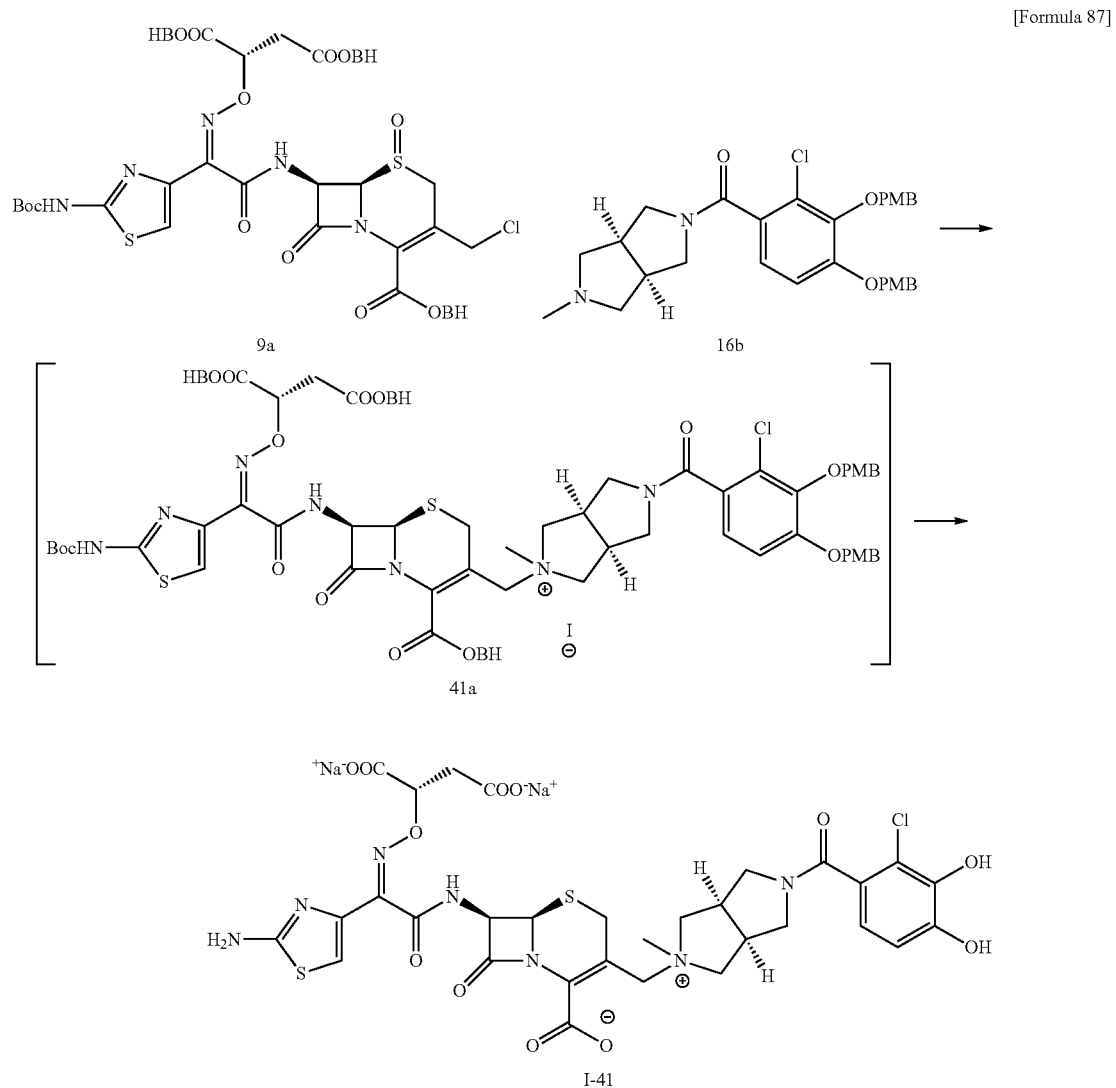

Step (1): Compound 9a+Compound 16b→Compound 41a→Compound (I-41)

From Compound 9a (1.28 g, 1.0 mmol) and Compound 16b (537 mg, 1.0 mmol), Compound I-41 was obtained as a light yellow powder using the same method as Example 36.

Yield: 443 mg, (53%)

$^1$H-NMR (D2O) δ: 2.69-2.72 (2H, m), 2.88-3.59 (12H, m), 3.81-4.14 (5H, m), 4.90 (1H, dd, J=5.1, 8.4 Hz), 5.27 (1H, q, J=2.4 Hz), 5.76 (1H, dd, J=3.0, 4.2 Hz), 6.78 (1H, d, J=8.1 Hz), 6.88 (1H, d, J=8.4 Hz), 6.95 (1H, s)

MS (m+1)=794.15

Elemental analysis for: $C_{31}H_{30}ClN_7O_{12}S_2 \cdot 1.6Na \cdot 5.3H_2O$

Calcd.: C, 40.28; H, 4.43; Cl, 3.84; N, 10.61; S, 6.94; Na, 3.98 (%).

Found.: C, 40.25; H, 4.42; Cl, 4.12; N, 10.67; S, 6.92; Na, 3.94 (%).

Example 42
Synthesis of Compound (I-42)
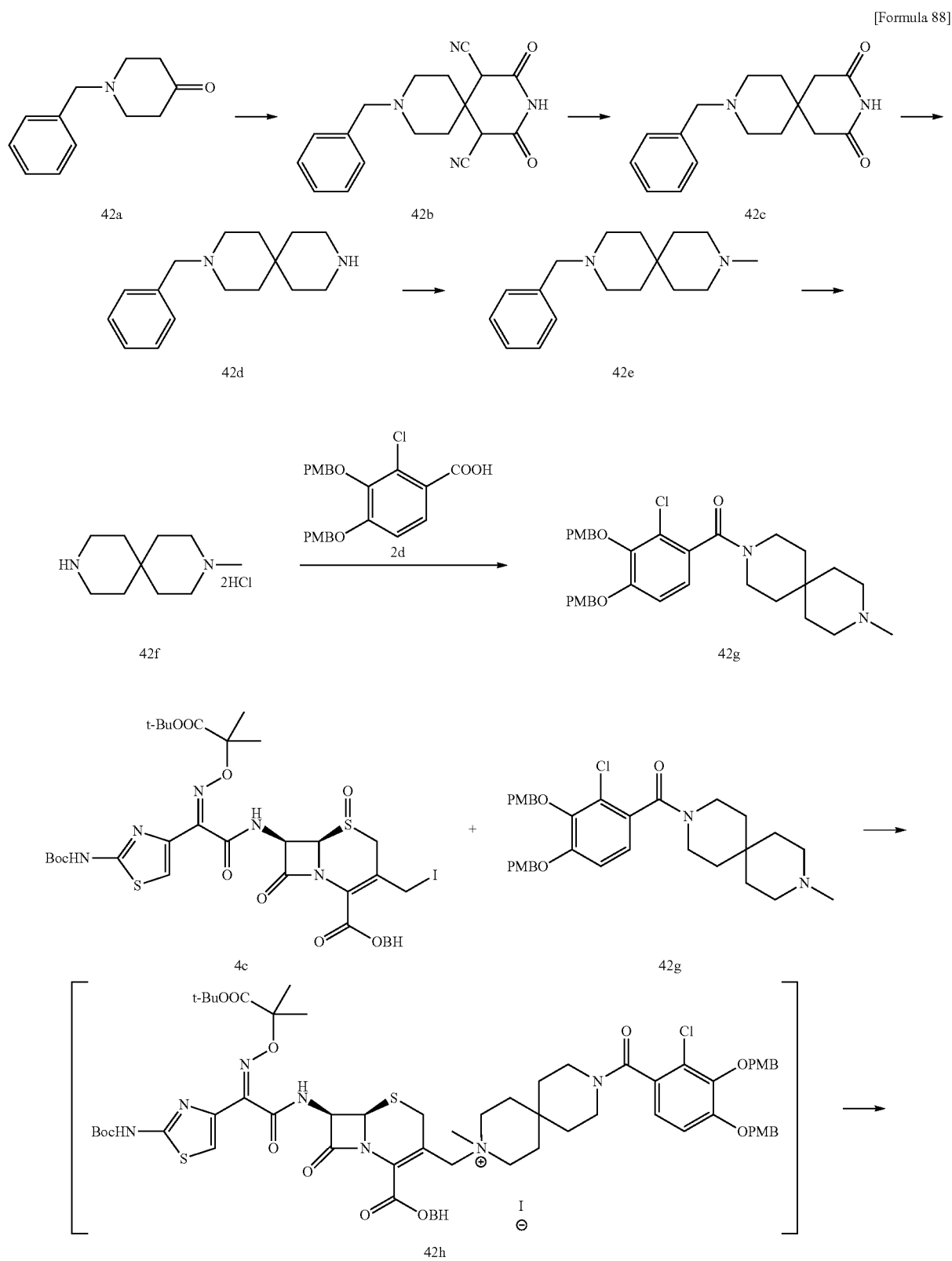

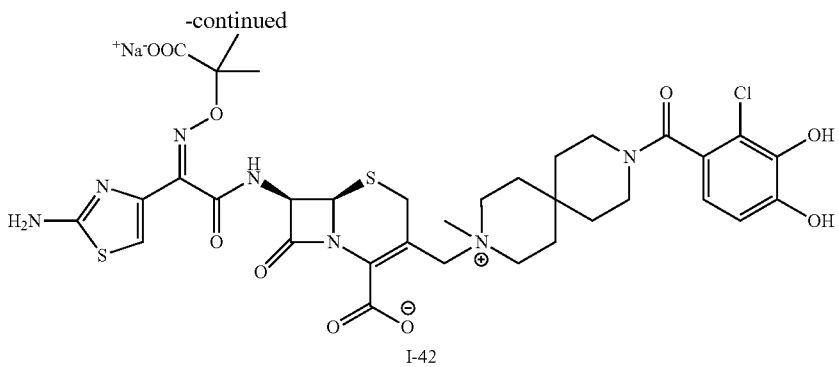

I-42

Step (1): Compound 42a→Compound 42b 7 mol/L-ammonia/methanol solution (160 mL, 1.12 mol) was cooled to 0° C. Compound 42a (37.9 g, 200 mmol) and cyanoethyl acetate (92.4 mL, 400 mmol) were added thereto, and then stirred at 0° C. for 15 minutes. After standing at 4° C. for 2 days, the resulting crystals were filtered, and then dried under reduced pressure to yield Compound 42b as a white solid.

Yield: 34.4 g, (53%)

$^1$H-NMR (DMSO-d$_6$) δ: 1.57 (2H, br), 1.64 (2H, br), 2.42-2.57 (4H, m), 3.91 (2H, a), 7.20-7.34 (5H, m)

Step (2): Compound 42b→Compound 42c

To Compound 42b (34.4 g, 107 mmol), 65% sulfuric acid (65 mL, 793 mmol) was added and subsequently heating at reflux for 16 hours. After cooling to room temperature, aqueous 10 N sodium hydroxide solution was added thereto until pH=8. After methylene chloride was added, the insoluble was filtered, and then the organic layer was separated. The organic layer was dried with anhydrous magnesium sulfate, and then the inorganic substance was removed by filtration. After concentrating in vacuo, diisopropyl ether was added to the residue. The resulting crystals were filtered, and then dried under reduced pressure to yield Compound 42c as a white solid.

Yield: 9.95 g, (34%)

$^1$H-NMR (CDCl$_2$) δ: 1.60 (4H, t, J=5.7 Hz), 2.45 (4H, t, J=5.7 Hz), 2.53 (4H, s), 3.52 (2H, s), 7.25-7.32 (5H, m), 7.95 (1H, br)

Step (3): Compound 42c→Compound 42d

To a solution of Compound 92c (9.95 g, 36.5 mmol) in diethyl ether (150 mL), lithium aluminum hydride (4.16 g, 110 mmol) was added and subsequently heated at reflux for 16 hours. While cooling in an ice bath, sodium sulfate decahydrate (40g) was slowly added thereto, and then potassium fluoride (4g) was added thereto, subsequently stirring at room temperature for 2 hours. After standing at room temperature overnight, the insoluble was filtered, and then the filtrate was concentrated in vacuo. The residue, as it is, was dried under reduced pressure to yield Compound 42d as a yellow oil.

Yield: 3.84 g, (43%)

$^1$H-NMR (CDCl$_3$) δ: 1.41 (4H, J=5.7 Hz), 1.52 (4H, t, J=3.7 Hz), 2.38 (4H, t, J=5.7 Hz), 2.77 (4H, t, J=5.7 Hz), 3.49 (2H, s), 7.25-7.31 (5H, m)

Step (4): Compound 42d→Compound 42e

To a solution of Compound 42d (3.67 g, 15 mmol) in tetrahydrofuran (36 mL), water (18 mL) formalin (11 mL, 150 mmol), then formic acid (5.8 mL, 150 mmol) were added and subsequently heating and stirring at 100° C. for 3 hours. After cooling to room temperature, ethyl acetate was added thereto, and then aqueous 2 N sodium hydroxide solution was added thereto until pH=10. The organic layer separated was washed with saturated brine, and then dried with anhydrous sodium sulfate. The inorganic substance was removed by filtration. After concentrating in vacuo, the resulting crude product was purified by silica gel column chromatography to yield Compound 42e as a yellow oil.

Yield: 3.12 g, (80%)

$^1$H-NMR (CDCl$_3$) δ: 1.48 (4H, t, J=5.1 Hz), 1.51 (4H, t, J=5.1 Hz), 2.26 (3H, s), 2.36 (4H, t, J=5.7 Hz), 2.38 (4H, t, J=5.7 Hz), 3.49 (2H, s), 7.25-7.31 (5H, m)

Step (5): Compound 42e→Compound 42f

To a solution of Compound 42e (1.29 g, 5.0 mmol) in acetic acid (13 mL), 5% palladium carbon (532 mg, 250 mmol) was added and then stirred under a hydrogen atmosphere of 5 atm at room temperature for 2 days. The insoluble was removed by filtration through a Celite, and then washed with methanol. The mother liquor was then concentrated in vacuo. The residue was dissolved in a mixed solvent of ethyl acetate and diisopropyl ether, and then 4 N hydrochloric, acid/ethyl acetate solution was added thereto. The resulting crystals were filtered, and then dried under reduced pressure to yield Compound 42f as a white crystal.

Yield: 865 mg, (72%)

$^1$H-NMR (DMSO-d$_6$) δ: 1.53 (2H, d, J=5.7 Hz), 1.65 (2H, dt, J=3.6, 13.8 Hz), 1.80 (4H, br), 2.70 (3H, d, J=4.5 Hz), 3.02 (6H, br), 3.20 (2H, d, J=11.7 Hz), 8.96 (2H, br)

Step (6): Compound 42f→Compound 42g

To a solution of Compound 2d (2.57 g, 6.0 mmol) in N,N-dimethylacetamide (20 triethylamine (1.25 mL, 9.0 mmol) was added and then cooled to −15° C. Methanesulfonyl chloride (655 μl, 8.4 mmol) was added thereto, and then stirred at −15° C. for 1 hour. Triethylamine (1.66 mL, 12 mmol) and Compound 42f (724 mg, 3.0 mmol) were further added, and then stirred at −15° C. for 2 hours. Aqueous 1 N sodium hydroxide solution was added to the reaction mixture, and then extracted with ethyl acetate. The organic layer was washed with water, then saturated brine and dried with anhydrous sodium sulfate. The inorganic substance was then removed by filtration. After concentrating in vacuo, the resulting crude product was purified by silica gel column chromatography to yield Compound 42g as a light yellow foam.

Yield: 1.66 g, (95%)

$^1$H-NMR (CDCl$_3$) δ: 1.25-1.51 (4H, m), 1.57 (6H, br), 2.34 (3H, br), 2.78 (2H, q, J=7.2 Hz), 3.05-3.13 (2H, m), 3.72 (2H, q, J=5.7 Hz), 3.79 (3H, s), 3.83 (3H, s), 5.06 (2H, s), 6.81 (2H, q, J=8.7 Hz), 6.91-6.94 (4H, m), 7.34 (4H, L, J=9.0 Hz)

Step (7): Compound 9c+Compound 42g→Compound 42h→Compound (I-42)

To a solution of Compound 4c (1.04 g, 1.0 mmol) in N,N-dimethylacetamide (3 mL), Compound 42g (579 mg, 1.0 mmol) was added and then stirred at 15° C. for 2 hours.

N,N-dimethylformamide (4.0 mL) was added thereto, and then cooled to −40° C. Phosphorus tribromide (189 μl, 2.0 mmol) was added, and then stirred at −40° C. for 30 minutes. The reaction mixture was slowly added to pre-ice-cooled aqueous 5% sodium chloride. The precipitated solid was filtered, washed with water, suspended in water, and then lyophilized to yield Compound 42h as a brown solid. The obtained Compound 42h was used in the next reaction without purification. The whole amount of Compound 42h obtained was dissolved in methylene chloride (10 ml). After cooling to −90° C., anisole (1.09 ml, 10 mmol) followed by 2 mol/L-aluminum chloride/nitromethane solution (5.0 ml, 10 mmol) were added, and then stirred at −40° C. for 1 hour. Aqueous 2 N hydrochloric acid, acetonitrile, and diisopropyl ether were added to the reaction solution, and then the insoluble and the supernatant were separated by decantation. The aqueous layer was separated from the supernatant. Meanwhile, water and acetonitrile were added to the insoluble attached to the contain, and then stirred. After it was completely dissolved, diisopropyl ether was added thereto, and then the aqueous layer was separated. The organic layer was then extracted with water. All the aqueous layers were combined, HP20-SS resin was added thereto, and then acetonitrile was evaporated in vacuo. The resulting mixed solution was purified by ODS column chromatography. Aqueous 0.2 N sodium hydroxide solution was added to the resulting solution of the intended compound until pH=5.2. The resulting solution was concentrated in vacuo, and then lyophilized to yield Compound I-42 as a light yellow powder.

Yield: 406 mg, (49%)

$^1$H-NMR (D$_2$O) δ: 1.34 (6H, s), 1.53 (1H, br), 1.59 (1H, br), 1.75 (4H, br), 2.86 (3H, d, J=7.5 Hz), 3.20 (4H, br), 3.29 (1H, dd, J=9.3, 16.8 Hz), 3.56 (2H, d, J=5.1 Hz), 3.75 (1H, dd, J=6.9, 16.8 Hz), 3.89 (1H, dd, J=11.1, 12.9 Hz), 5.20 (1H, t, J=5.1 Hz), 5.71 (1H, t, J=5.4 Hz), 6.61 (1H, d, J=8.4 Hz), 6.77 (1H, d, J=8.4 Hz), 6.81 (1H, d, J=3.6 Hz)

MS (m+1)=806.33

Elemental analysis for: C$_{34}$H$_{39}$ClN$_7$O$_{10}$S$_2$Na.6.0H$_2$O

Calcd.: C, 43.61; H, 5.49; Cl, 3.79; N, 10.47; S, 6.85; Na, 2.46 (%).

Found.: C, 43.55; H, 5.36; Cl, 4.18; N, 10.30; S, 7.10; Na, 2.32 (%).

Example 43

Synthesis of Compound (I-43)

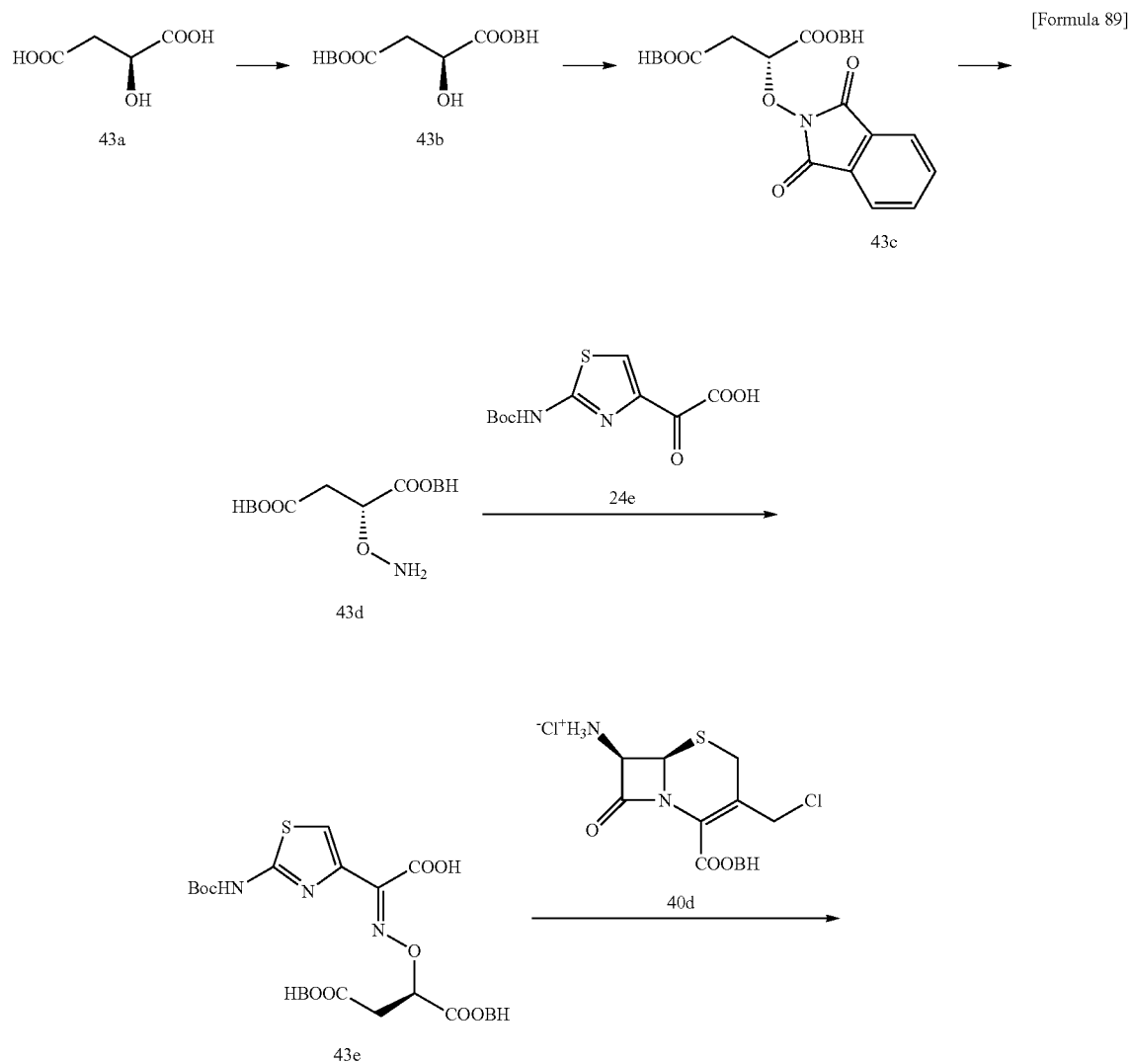

[Formula 89]

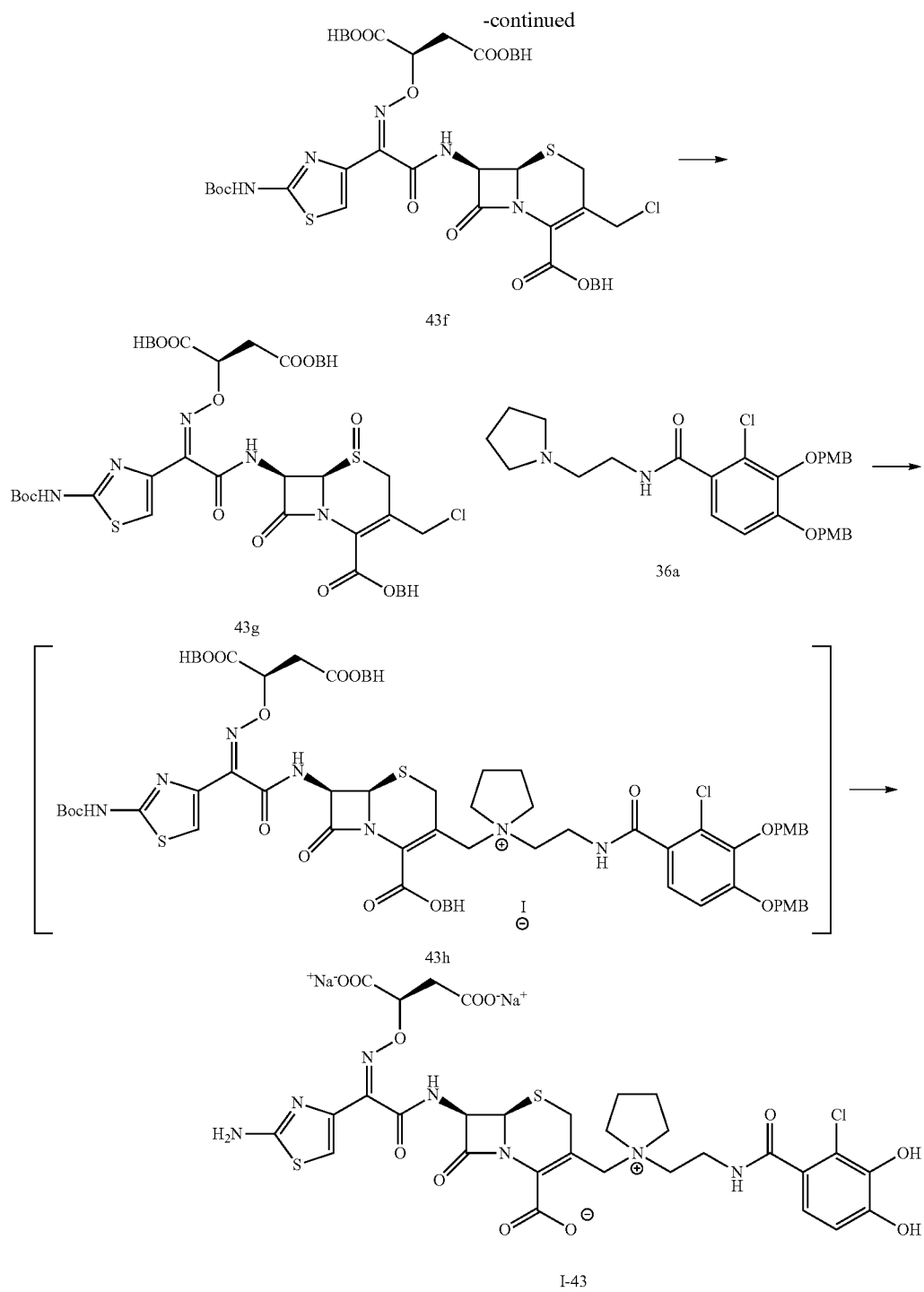

I-43

Step (1): Compound 43a→Compound 43b

A solution of Compound 43a (21.45 g, 160 mmol) in tetrahydrofuran (150 mL) was cooled to 0° C. A solution of diphenyldiazomethane (68.4 g, 352 mmol) in tetrahydrofuran (70 mL) was added drop-wise thereto over 1 hour, and then stood at room temperature overnight. After the insoluble was filtered, the reaction mixture was concentrated, and then diisopropyl ether was added to the residue. The resulting solid was filtered, and then dried under reduced pressure to yield Compound 43b as a white solid.

Yield: 67.49 g, (90%)

$^1$H-NMR (CDCl$_3$) δ: 2.94 (1H, dd, J=6.6, 16.5 Hz), 3.03 (1H, dd, J=4.5, 16.5 Hz), 3.16 (1H, br), 4.63 (1H, t, J=4.5 Hz), 6.88 (1H, s), 6.90 (1H, s), 7.26-7.36 (20H, m)

Step (2): Compound 43b→Compound 43c

To a solution of Compound 43b (68 g, 146 mmol) in tetrahydrofuran (340 mL), N-hydroxyphthalimide (54.7 g, 335 mmol) and triphenylphosphine (103 g, 394 mmol) were added. After ice-cooling, dimethyl azodicarboxylate (57.5 g, 394 mmol) was added drop-wise over 1 hour. After stirring under ice-cooling for 40 minutes, the insoluble was filtered, followed by concentration in vacuo. Toluene was added to the resulting residue, the precipitated insoluble was filtered, followed by concentration in vacuo. This step was performed three times. The crude product was purified by silica gel column chromatography to yield Compound 43c as a white foam.

Yield: 27.5 g, (31%)

$^1$H-NMR (CDCl$_3$) δ: 3.25 (2H, d, J=6.6 Hz), 5.32 (1H, t, J=6.6 Hz), 6.84 (1H, s), 6.87 (1H, s), 7.18-7.31 (20H, m), 7.69-7.71 (4H, m)

Step (3): Compound 43c→Compound 43d→Compound 43e+Compound 40d→Compound 43f→Compound 43g The solution of Compound 43c (13.75 g, 22.5 mmol) in methylene chloride (140 mL) was cooled to −30° C. and methylhydrazine (1.32 ml, 24.7 mmol) was added in one portion, and then stirred at room temperature for 1 hour. The resulting crystals were then removed by filtration. Concentrating and subsequent drying under reduced pressure yielded Compound 43d as a yellowish white oil. The Compound 62 obtained was used in the next reaction without purification.

To a solution of the whole amount of Compound 43d obtained in methanol (65 ml), Compound 2.4e (6.43 g, 23.6 mmol) was added and then stirred at room temperature for 1.5 hours. The solvent was then evaporated in vacuo. Water was added to the resulting concentrated residue, and then extracted with ethyl acetate. The organic layer was washed with water, then saturated brine, and then dried with anhydrous magnesium sulfate. The inorganic substance was then removed by filtration. Concentrating in vacuo and subsequent drying under reduced pressure yielded Compound 43e as a yellow foam. The obtained Compound 43e was used in the next reaction without purification. To a solution of the whole amount of Compound 43e obtained in ethyl acetate (200 mL), Compound 40d (11.16 g, 24.7 mmol) was added and then cooled to −40° C. Phenyldichlorophosphate (5.04 ml, 33.7 mmol) was slowly added, and then N-methylmorpholine (9.89 mL, 90 mmol) was added drop-wise thereto over 30 minutes. After stirring at −40° C. for 40 minutes, 0.2 hydrochloric acid was added to the reaction mixture, followed by extraction with ethyl acetate. The organic layer was washed with water, aqueous 5% sodium hydrogen carbonate, then saturated brine, and then dried with anhydrous magnesium sulfate. The inorganic substance was removed by filtration, and then concentrated and subsequently dried under reduced pressure to yield Compound 43f as a yellow foam. The obtained Compound 43f was used in the next reaction without purification.

The solution of the whole amount of Compound 43f obtained in methylene chloride (125 ml) was cooled to −40° C. A solution of m-chloroperbenzoic acid (6.56 g, 24.7 mmol) in methylene chloride (125 ml) was added drop-wise thereto over 1 hour. After stirring at −40° C. for 1 hour, aqueous 15% sodium thiosulfate solution was added thereto. Methylene chloride was evaporated under reduced pressure, and then extracted with ethyl acetate. The organic layer was washed with aqueous 5% sodium hydrogen carbonate, then saturated brine, and then dried with anhydrous sodium sulfate. The inorganic substance was removed by filtration, and then concentrated in vacuo. The resulting crude product was purified by silica gel column chromatography to yield Compound 43g as a white foam.

Yield: 21.92 g, (85%)

$^1$H-NMR (CDCl$_3$) δ: 1.53 (9H, s), 3.02 (1H, d, J=18.6 Hz), 3.12 (1H, dd, J=4.8, 16.8 Hz), 3.32 (1H, d, J=9.3 Hz), 3.42 (1H, d, J=19.2 Hz), 4.29 (1H, d, J=4.8 Hz), 4.91 (1H, d, J=12.3 Hz), 5.49 (1H, dd, J=4.5, 9.3 Hz), 5.97 (1H, dd, J=4.5, 9.3 Hz), 6.87 (1H, s), 6.92 (1H, s), 6.95 (1H, s), 7.16-7.38 (31H, m), 7.47 (2H, d, J=8.1 Hz), 7.95 (1H, d, J=9.3 Hz), 8.26 (1H, br)

Step (4): Compound 43g+Compound 36a→Compound 43h→Compound (I-43)

From Compound 43g (1.26 g, 1.0 mmol) and Compound 36a (525 mg, 1.0 mmol), Compound I-43 was obtained as a light yellow powder using the same method as Example 36.

Yield: 268 mg, (32%)

$^1$H-NMR (D$_2$O) δ: 2.05 (4H, br), 2.60 (1H, d, J=3.0 Hz), 2.62 (1H, s), 3.32-3.76 (11H, m), 3.96 (1H, d, J=14.4 Hz), 4.76 (1H, dd, J=5.4, 8.4 Hz), 5.16 (1H, d, J=4.8 Hz), 5.63 (1H, d, J=5.1 Hz), 6.71 (1H, d, J=8.4 Hz), 6.79 (1H, d, J=8.4 Hz), 6.83 (1H, s)

MS (m+1)=782.32

Elemental analysis for: C$_{30}$H$_{30}$ClN$_7$O$_{12}$S$_2$.1.6Na.4.9H$_2$O

Calcd.: C, 39.80; H, 4.43; Cl, 3.92; N, 10.83; S, 7.08; Na, 4.06 (%).

Found.: C, 39.77; H, 4.38; Cl, 3.95; N, 10.83; S, 7.08; Na, 3.9 8(%).

Example 44

Synthesis of Compound (I-44)

[Formula 90]

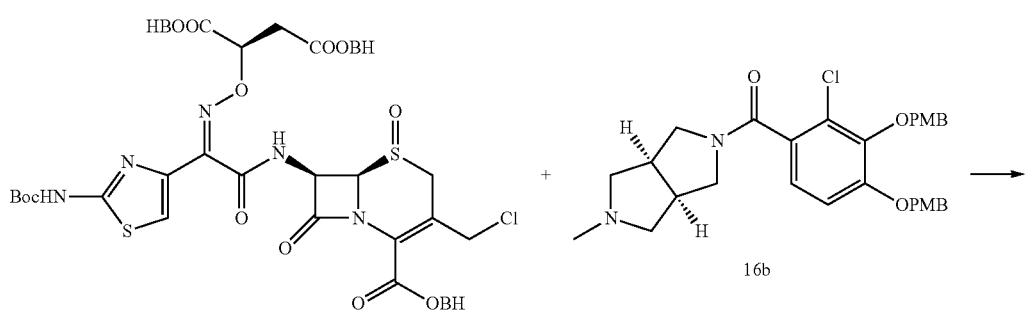

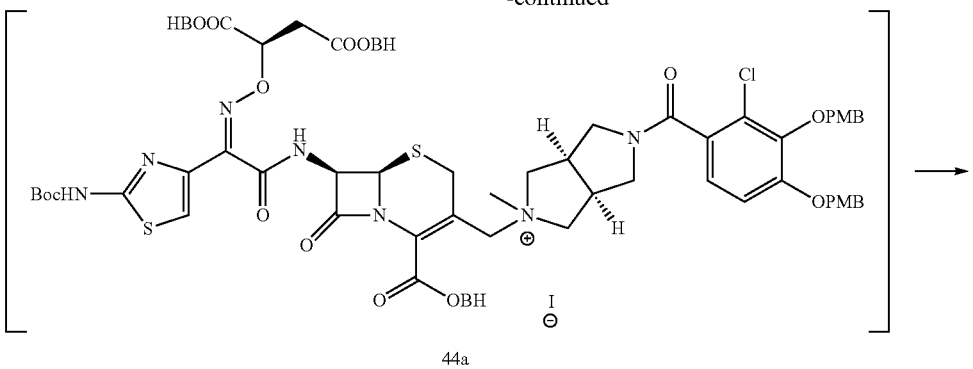

44a

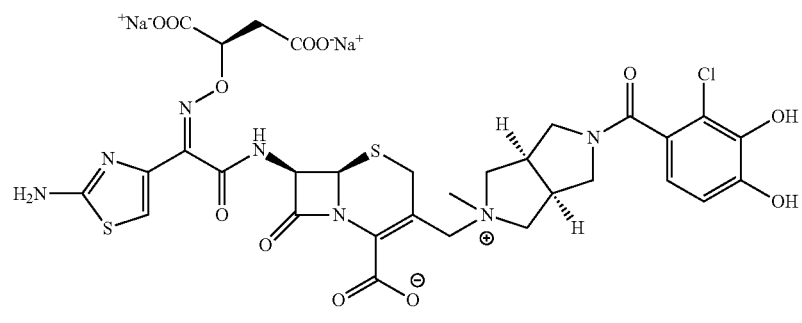

I-44

Step (1): Compound 43g+Compound 16b→Compound 44a→Compound (I-44)

From Compound 43g (1.26 g, 1.0 mmol) and Compound 16b (537 mg, 1.0 mmol), Compound I-44 was obtained as a light yellow powder using the same method as Example 36.

Yield: 568 mg, (68%)

$^1$H-NMR (D$_2$O) δ: 2.53 (1H, s), 2.59 (1H, s), 2.61-3.48 (12H, m), 3.65-3.99 (5H, m), 4.74-4.78 (1H, m), 5.16-5.19 (1H, m), 5.62-5.65 (1H, m), 6.67 (1H, d, J=8.4 Hz), 6.77 (1H, d, J=8.4 Hz), 6.83 (1H, s)

MS (m+1)=794.37

Elemental analysis for: $C_{31}H_{30}ClN_7O_{12}S_2 \cdot 1.6Na \cdot 5.4H_2O$

Calcd.: C, 40.20; H, 4.44; Cl, 3.83; N, 10.59; S, 6.92; Na, 3.97 (%).

Found.: C, 40.11; H, 4.38; Cl, 4.15; N, 10.62; S, 6.94; Na, 4.13 (%).

Example 45

Synthesis of Compound (I-45)

[Formula 91]

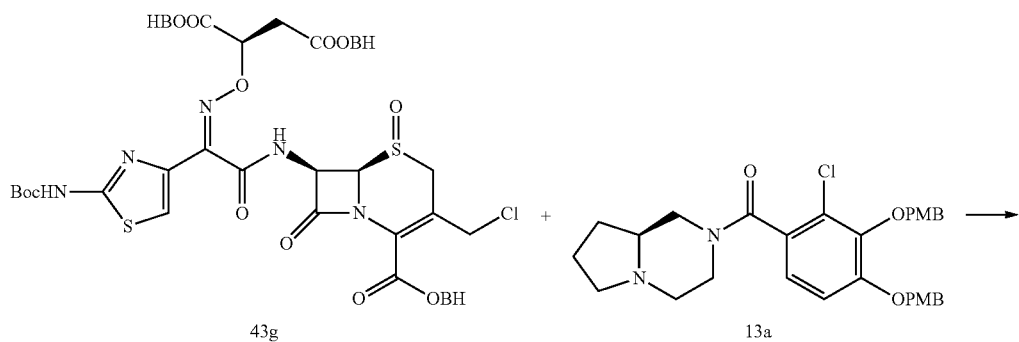

43g                                    13a

-continued

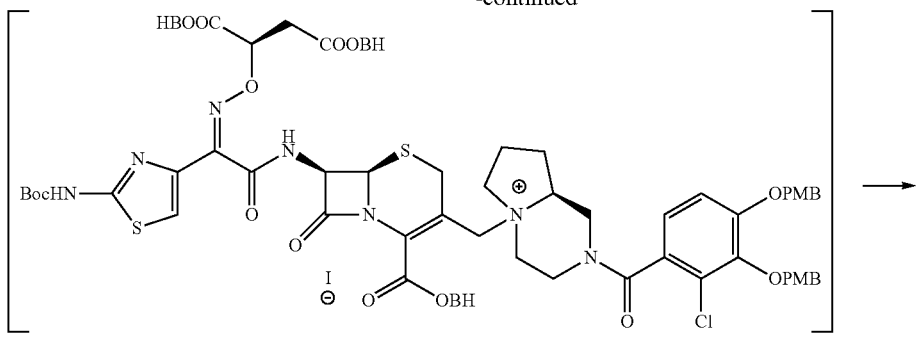

45a

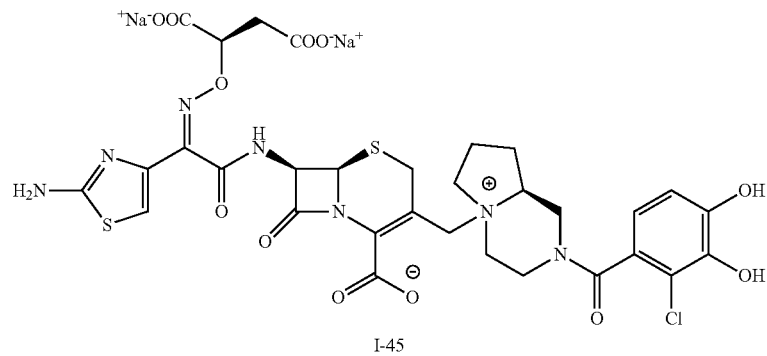

I-45

Step (1): Compound 65+Compound 29→Compound 70→Compound 69

From Compound 43g (1.26 g, 1.0 mmol) and Compound 13a (537 mg, 1.0 mmol), Compound I-45 was obtained as a light yellow powder using the same method as Example 36.

Yield: 566 mg, (68%)

$^1$H-NMR (D$_2$O) δ: 2.06 (4H, br), 2.63-2.70 (2H, m), 3.30-3.86 (11H, m), 4.09-4.33 (2H, m), 4.77-4.83 (1H, m), 5.20 (1H, dd, J=4.8, 8.1 Hz), 5.68 (11H, d, J=4.8 Hz), 6.72 (1H, dd, J=4.2, 8.1 Hz), 6.83 (1H, dd, J=4.2, 8.1 Hz), 6.88 (1H, d, J=3.9 Hz)

MS (m+1)=794.32

Elemental analysis for: $C_{31}H_{30}ClN_7O_{12}S_2 \cdot 1.6Na \cdot 5.2H_2O$

Calcd.: C, 40.35; H, 4.41; Cl, 3.84; N, 10.63; S, 6.95; Na, 3.99 (%).

Found.: C, 40.40; H, 4.38; Cl, 3.94; N, 10.56; S, 6.50; Na, 3.95 (%).

Example 46

Synthesis of Compound (I-46)

[Formula 92]

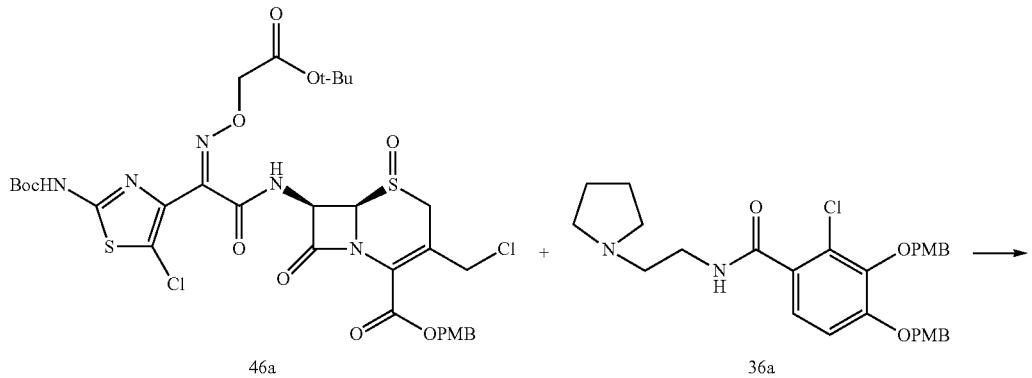

46a                36a

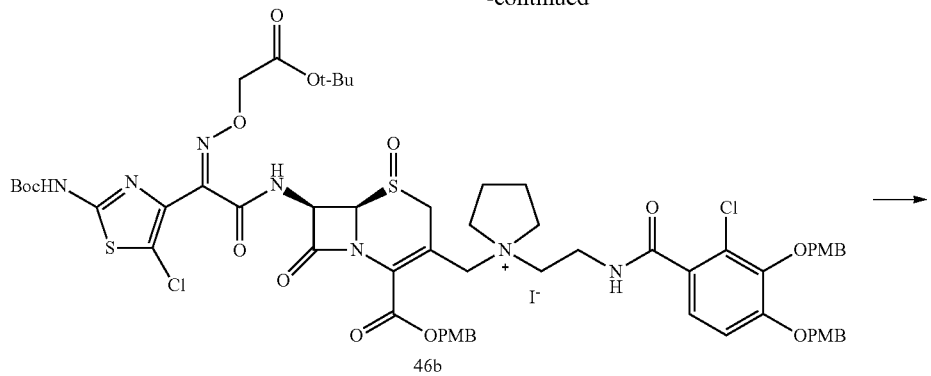

46b

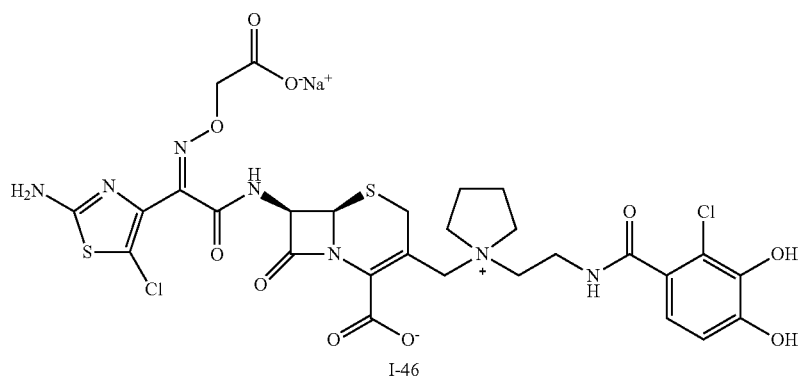

I-46

Step (1): Compound 46a+Compound 36a→Compound 46b

Compound 46a (623 mg, 0.777 mmol) was dissolved in N,N-dimethylacetamide (3 mL). After degasification, under ice-cooling, sodium iodide (233 mg, 1.55 mmol) was added thereto, and then stirred at room temperature for 20 minutes. Compound 36a (408 mg, 0.777 mmol) was added to the reaction solution, and then stirred at room temperature for 3 hours. Ethyl acetate and water were then added to the reaction solution. The organic layer separated was washed with aqueous 0.2 N hydrochloric acid solution, than saturated brine, and then dried with anhydrous magnesium sulfate. After magnesium sulfate was removed by filtration, concentrated under reduced pressure yielded Compound 46b (1.10 g).

MS: 1292.61 (M+H)

Step (2): Compound 46b→Compound (I-46)

The above-described crude Compound 46b was dissolved in methylene chloride (15 mL), and then cooled to −40° C. Phosphorus tribromide (0.22 mL, 2.33 mmol) was added thereto, and then stirred at −40° C. for 1 hour. Anisole (849 mL, 7.77 mmol) was then added to the reaction solution. At −40° C., 2 mol/L-aluminum chloride/nitromethane solution (3.89 mL, 7.77 mmol) was added thereto, and then stirred for 30 minutes while maintaining the temperature from −20° C. to −10° C. The reaction solution was dissolved in aqueous 1 N hydrochloric acid solution and acetonitrile, and then washed with diisopropyl ether. HP-20SS resin was added to the aqueous layer, concentrated, subjected to ODS column chromatography, eluting with water-acetonitrile. Aqueous 0.2 N sodium hydroxide solution was then added to fractions containing the desired compound to form a sodium salt thereof. Concentrating under reduced pressure and subsequently lyophilzation yielded Compound I-46 as a powder. Yield: 157 mg (26%)

MS: 758.27 (M+H)

$^1$H-NMR (D$_2$O) δ: 6.94 (1H, d, J=7.9 Hz), 6.86 (1H, d, J=7.9 Hz), 5.90 (1H, d, J=5.0 Hz), 5.34 (1H, d, J=5.0 Hz), 4.60 (2H, s), 1.13 (1H, d, J=14.0 Hz), 3.95-3.49 (12H, m), 2.23-2.09 (4H, m).

Elemental analysis for $C_{30}H_{32}Cl_2N_7NaO_{10}S_2(H_2O)_{4.3}$ $(NaHCO_3)_{0.1}$ Calcd.: C, 39.29; H, 4.27; N, 11.77; S, 7.71; Cl, 7.95; Na, 2.91 (%).

Found.: C, 39.32; H, 4.24; N, 11.44; S, 7.48; Cl, 8.28; Na, 2.82 (%).

Example 47
Synthesis of Compound (I-47)
[Formula 93]
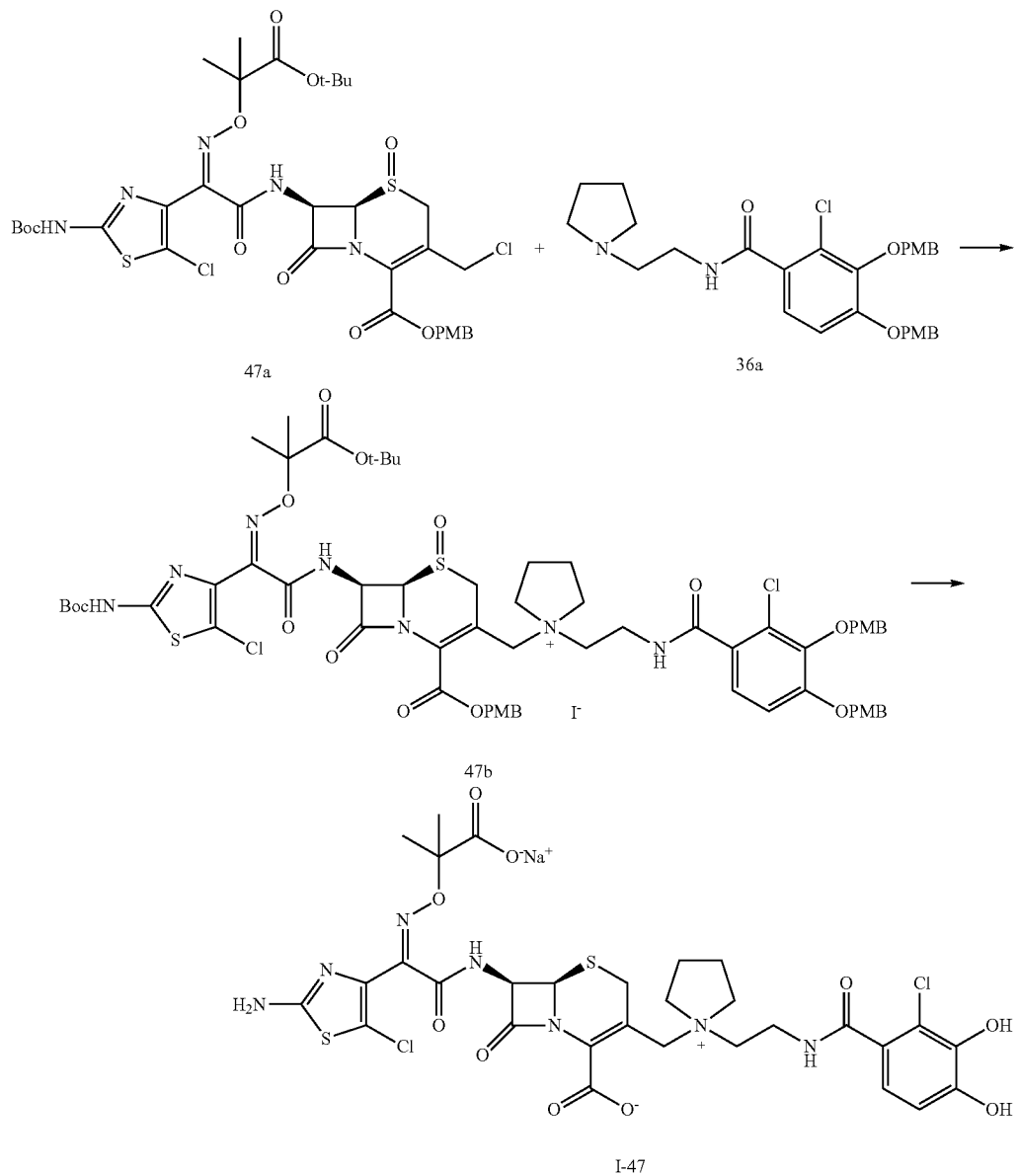
Step (1): Compound 47a→Compound 47b→Compound (I-47)
Compound 47a (830 mg, 1 mmol) was treated using the same method as Example 46 to obtain Compound I-47. (Yield: 303 mg, Yield: 47%)
$^1$H-NMR (D$_2$O) δ: 6.97-6.89 (2H, m), 5.88 (1H, d, J=4.7 Hz), 5.36 (1H, d, J=4.7 Hz), 4.16-4.11 (1H, m), 3.97-3.51 (12H, m), 2.25-2.22 (4H, m), 1.52-1.51 (6H, m).
Elemental analysis for $C_{30}H_{32}Cl_2N_7NaO_{10}S_2(H_2O)_4$ $(NaHCO_3)_{0.1}$
Calcd.: C, 40.53; H, 4.67; Cl, 7.47; N, 10.94; S, 7.01; Na, 2.74.
Found.: C, 40.42; H, 4.59; Cl, 7.93; N, 10.96; S, 7.17; Na, 2.83.

Example 48
Synthesis of Compound (I-48)
[Formula 94]
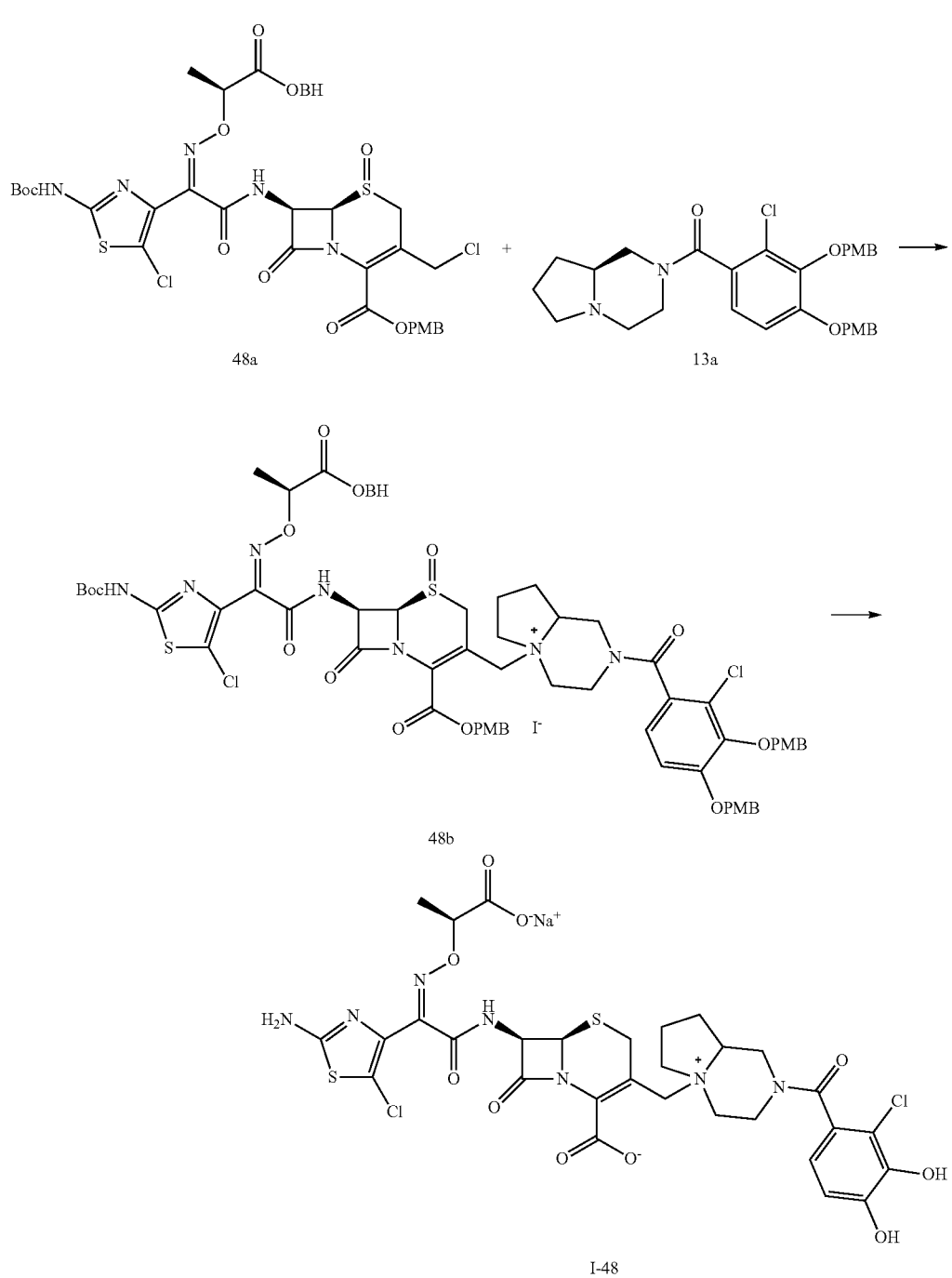
Step (1): Compound 48a→Compound 48b→Compound (I-48)
Compound 48a (697 mg, 0.752 mmol) was treated using the same method as Example 46 to obtain Compound I-48. (Yield: 188 mg, Yield: 31%)
MS: 784.29 (M+H)
$^1$H-NMR (D2O) 6.96 (1H, d, J=8.2 Hz), 6.82 (1H, d, J=8.2 Hz), 5.86 (1H, d, J=5.0 Hz), 5.33 (1H, d, J=5.0 Hz), 4.81 (1H, d, J=14.1 Hz), 4.68 (1H, q, J=7.1 Hz), 3.99-3.46 (12H, m), 2.48-2.04 (4H, m), 1.48 (3H, d, J=7.1 Hz).
Elemental analysis for $C_{30}H_{30}Cl_2N_7NaO_{10}S_2(H_2O)_{5.5}$ $(NaHCO_3)_{0.1}$
Calcd.: C, 39.63; H, 4.64; Cl, 7.52; N, 10.90; S, 6.83; Na, 2.67.
Found.: C, 39.55; H, 4.53; Cl, 7.76; N, 10.73; S, 7.02; Na, 2.77.

Example 49
Synthesis of Compound (I-49)
[Formula 95]
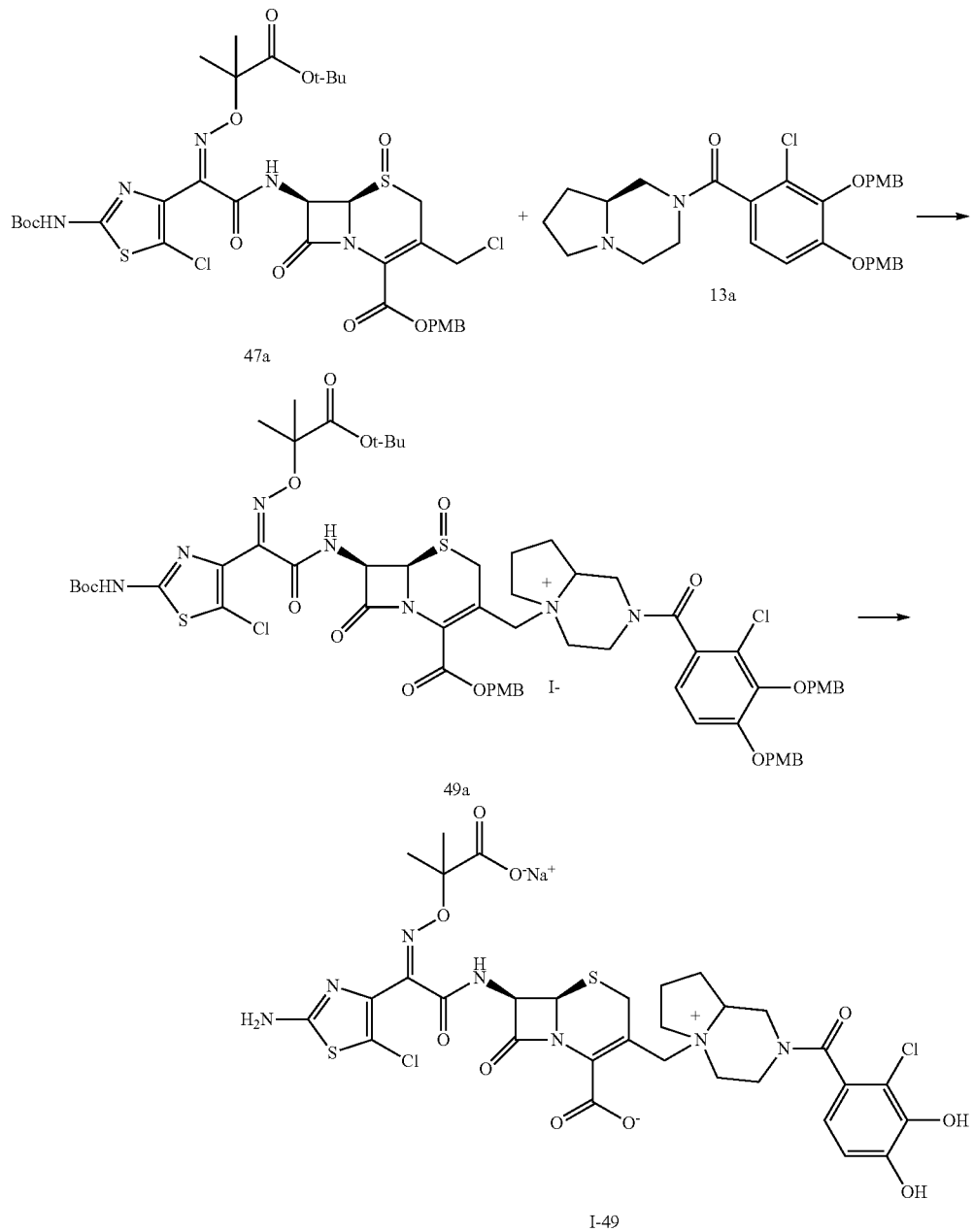
Step (1): Compound 47a→Compound 49a→Compound (I-49)
Compound 47a (645 mg, 0.776 mmol) was treated using the same method as Example 46 to obtain Compound I-49. (Yield: 257 mg, Yield: 40%)
MS: 798.29 (M+H)
$^1$H-NMR (D$_2$O) δ: 6.96 (1H, d, J=7.7 Hz), 6.83 (1H, d, J=7.7 Hz), 5.84 (1H, br s), 5.33 (1H, br s), 4.84 (1H, d, J=13.9 Hz), 4.00-3.45 (12H, m), 2.48-2.04 (4H, m), 1.53-1.50 (6H, m).
Elemental analysis for $C_{31}H_{32}Cl_2N_7NaO_{10}S_2(H_2O)_{5.4}$ $(NaHCO_3)_{0.08}$
Calcd.: C, 40.56; H, 4.87; Cl, 6.90; N, 10.79; S, 6.67; Na, 2.50.
Found.: C, 40.37; H, 4.67; Cl, 7.67; N, 10.60; S, 6.94; Na, 2.69.

Example 50
Synthesis of Compound (I-50)
[Formula 96]
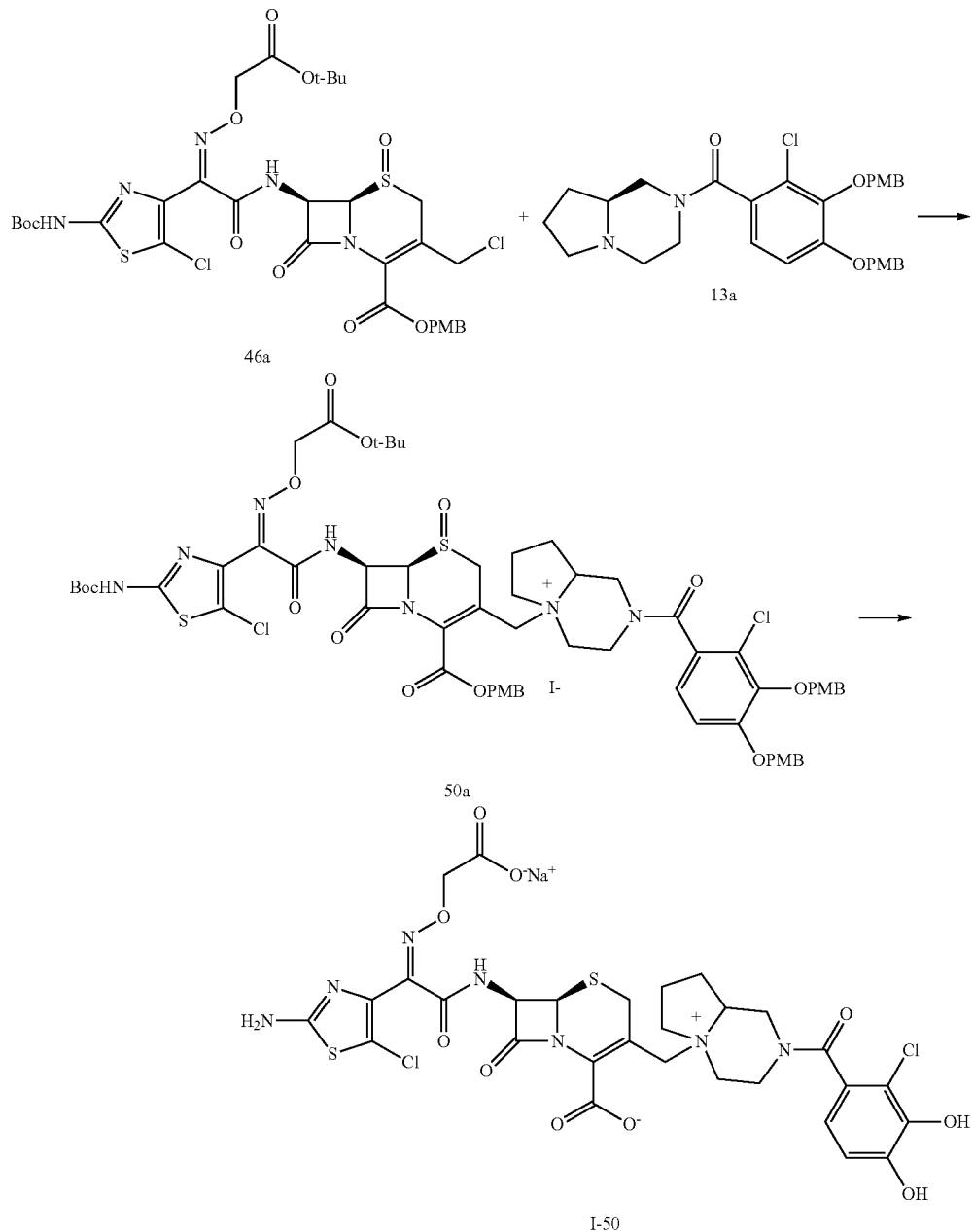
Step (1): Compound 46a→Compound 50a→Compound (I-50)
Compound 46a (625 mg, 0.778 mmol) was treated using the same method as Example 46 to obtain Compound I-50. (Yield: 175 mg, Yield: 28%)
MS: 770.25 (M+H)
$^1$H-NMR (D$_2$O) δ: 6.97 (1H, d, J=8.1 Hz), 6.83 (1H, d, J=8.1 Hz), 5.86 (1H, s), 5.35-5.31 (1H, m), 4.83 (1H, d, J=12.4 Hz), 4.61-4.58 (2H, m), 4.14-3.44 (10H, m), 2.48-2.02 (4H, m).
Elemental analysis for $C_{29}H_{28}Cl_2N_7NaO_{10}S_2(H_2O)_4$ $(NaHCO_3)_{0.1}$
Calcd.: C, 39.93; H, 4.28; Cl, 7.96; N, 11.34; S, 7.24; Na, 2.88.
Found.: C, 40.03; H, 4.17; Cl, 8.12; N, 11.23; S, 7.35; Na, 2.90.

Example 51

Synthesis of Compound (I-51)

[Formula 97]

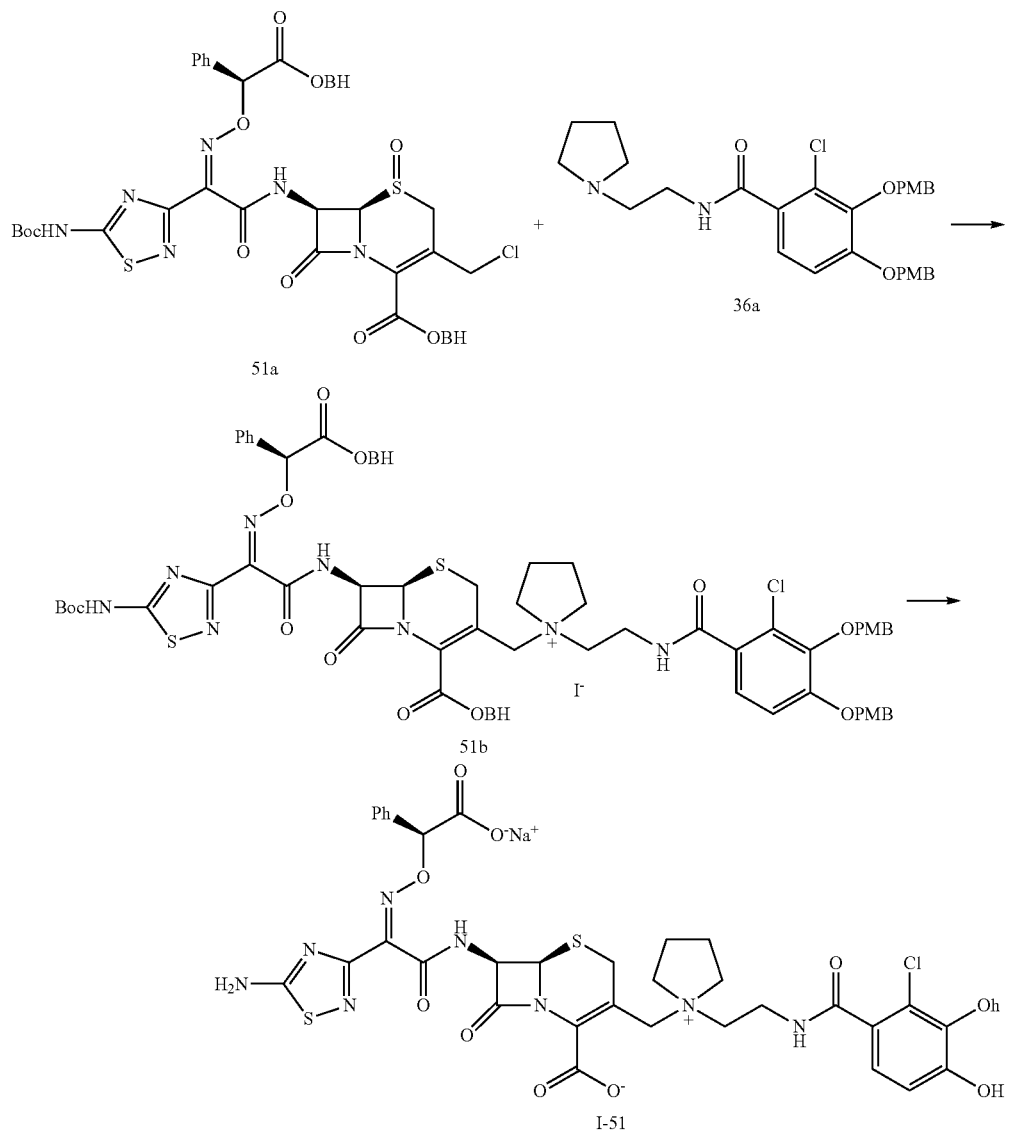

Step (1): Compound 51a+Compound 36a→Compound 51b

Compound 51a (1.002 g, 1.00 mmol) and Compound 36a (0.525 g, 1.00 mmol) were dissolved in N,N-dimethylacetamide (3 ml), and then degassed. Sodium iodide (300 mg, 2.00 mmol) was added to the reaction solution, and then stirred at room temperature for 2 hours. N,N-Dimethylformamide (3 ml) was then added to the reaction solution. After cooling to −40° C., phosphorus tribromide (0.283 mL, 3.00 mmol) was added thereto, and then stirred for 20 minutes while maintaining the temperature at −40° C. The reaction solution was poured into distilled water containing 5% of sodium chloride. The precipitate was then filtered. The residue was suspended in distilled water, and then lyophilized to yield Compound 51b (1.60 g) as a yellow solid.

Step (2): Compound 51b→Compound (I-51)

The above-described crude Compound 51b was dissolved in methylene chloride (15 ml). After cooling to −40'C, anisole (1.09 ml, 10.0 mmol) followed by 2 mol/L-aluminum chloride/nitromethane solution (5.00 ml, 10.0 mmol) were added thereto. The reaction solution was then stirred at 0° C. for 1 hour. The reaction solution was dissolved in aqueous 0.2 N hydrochloric acid solution and acetonitrile, and then washed with diisopropyl ether. HP-20SS resin was added to the aqueous layer separated, concentrated, and then subjected to ODS column chromatography, eluting with water-acetonitrile. Aqueous 0.2 N sodium hydroxide solution was then added to fractions containing the desired compound to form a sodium salt thereof. Concentrating under reduced pressure and subsequent lyophilization yielded Compound I-51 as a powder.

Yield: 105 mg (13%)

$^1$H-NMR (D$_2$O) δ: 7.52 (2H, d, J=5.0 Hz), 7.42 (3H, d, J=5.0 Hz), 6.95 (1H, d, J=8.6 Hz), 6.87 (1H, d, J=8.6 Hz), 5.79 (1H, d, J=4.9 Hz), 5.63 (1H, s), 5.23 (1H, d, J=4.9 Hz), 4.12-4.07 (1H, m), 3.95-3.53 (11H, m), 3.20 (1H, d, J=17.1 Hz), 2.24-2.21 (4H, m).
MS: 801.34 (M+H)
Elemental analysis for C$_{33}$H$_{32}$ClN$_8$NaO$_{10}$S$_2$(H$_2$O)$_{4.8}$(NaHCO$_3$)$_{0.2}$
Calcd.: C, 42.89; H, 4.64; Cl, 3.44; N, 12.42; S, 6.95; Na, 3.15 (%).
Found.: C, 43.04; H, 4.55; Cl, 3.83; N, 12.09; S, 6.92; Na, 2.98 (%).
Example 52
Synthesis of Compound (I-52)
[Formula 98]
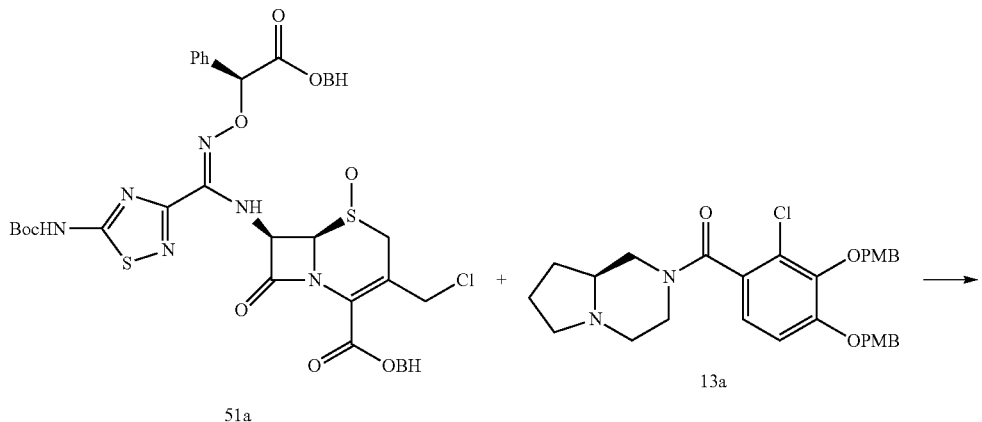
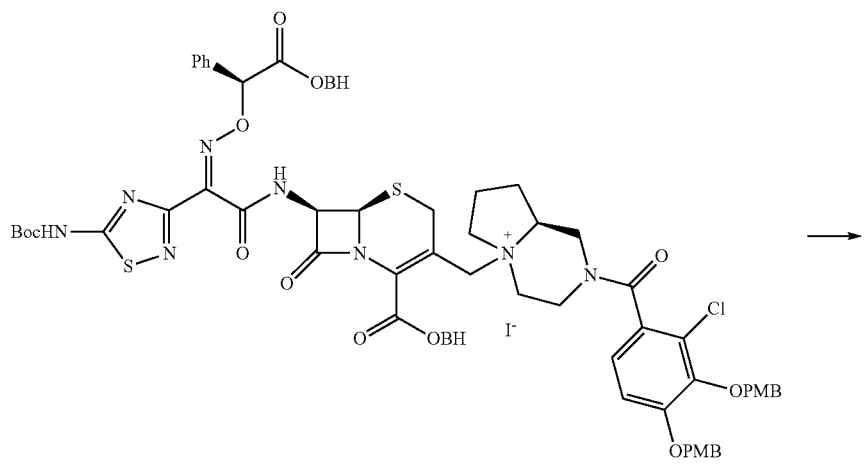
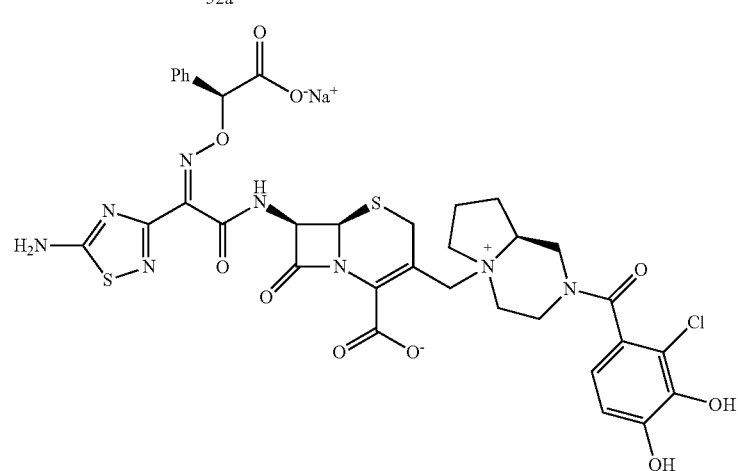

Step (1): Compound 51a→Compound 52a→Compound (I-52)
Compound 51a (1.00 g, 1.00 mmol) was treated using the same method as Example 51 to obtain Compound I-52. (Yield: 161 mg, Yield: 20%)
MS: 813.37 (M+H)
$^1$H-NMR (D$_2$O) δ: 7.54-7.51 (2H, m), 7.46-7.42 (3H, m), 6.98-6.94 (1H, m), 6.87-6.82 (1H, m), 5.83 (1H, t, J=5.6 Hz), 5.65 (1H, d, J=2.9 Hz), 5.25-5.21 (1H, m), 4.32-4.22 (2H, m), 4.04-3.15 (11H, m), 2.48-2.01 (4H, m).
Elemental analysis for C$_{34}$H$_{32}$ClN$_8$NaO$_{10}$S$_2$(H$_2$O)$_{4.6}$(NaHCO$_3$)$_{0.1}$
Calcd.: C, 44.16; H, 4.54; Cl, 3.56; N, 12.22; S, 7.01; Na, 2.97.
Found.: C, 44.21; H, 4.49; Cl, 3.83; N, 12.09; S, 6.92; Na, 2.73.
Example 53
Synthesis of Compound (I-53)
[Formula 99]
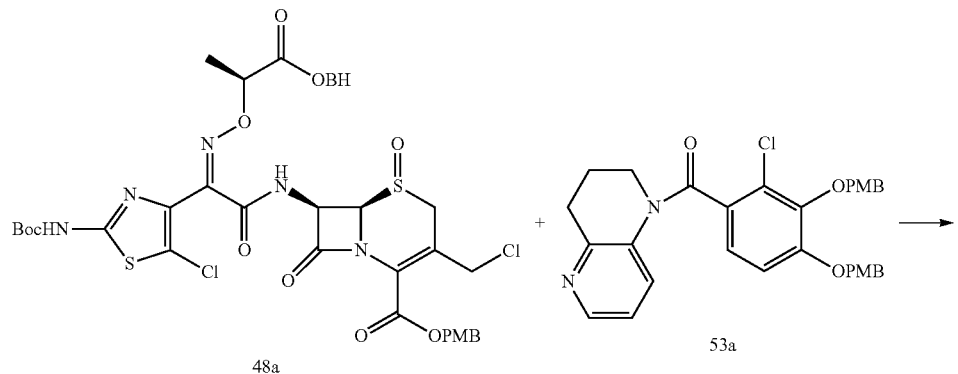
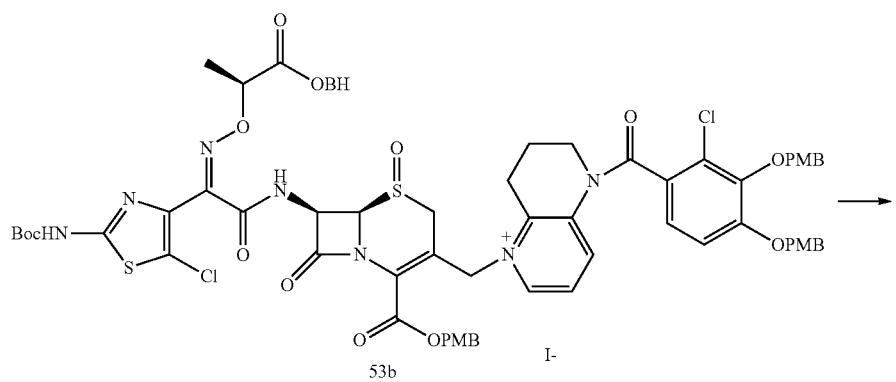
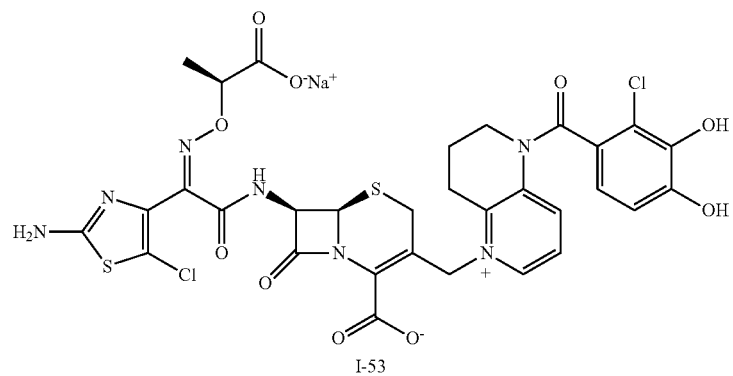

Step (1): Compound 48a→Compound 53b→Compound (I-53)
Compound 48a (927 mg, 1.00 mmol) was treated using the same method as Example 46 to obtain Compound I-53. (Yield: 223 mg, Yield: 27%)
MS: 792.28 (M+H)
$^1$H-NMR (D$_2$O) δ: 8.61 (1H, s), 7.66 (1H, s), 7.04-6.93 (3H, m), 5.92 (1H, d, J=5.0 Hz), 5.64-5.34 (2H, m), 5.27 (1H, d, J=5.0 Hz), 4.67 (1H, q, J=7.1 Hz), 4.10 (1H, s), 3.68-3.02 (5H, m), 2.22-2.09 (2H, m), 1.17 (3H, d, J=7.1 Hz).
Elemental analysis for C$_{31}$H$_{26}$Cl$_2$N$_7$NaO$_{10}$S$_2$(H$_2$O)$_{3.4}$(NaHCO$_3$)$_{0.2}$
Calcd.: C, 11.78; H, 3.55; Cl, 7.69; N, 11.57; S, 7.83; Na, 3.13.
Found.: C, 41.98; H, 3.73; Cl, 7.94; N, 10.98; S, 7.18; Na, 3.09.
Example 54
Synthesis of Compound (I-1)
[Formula 100]
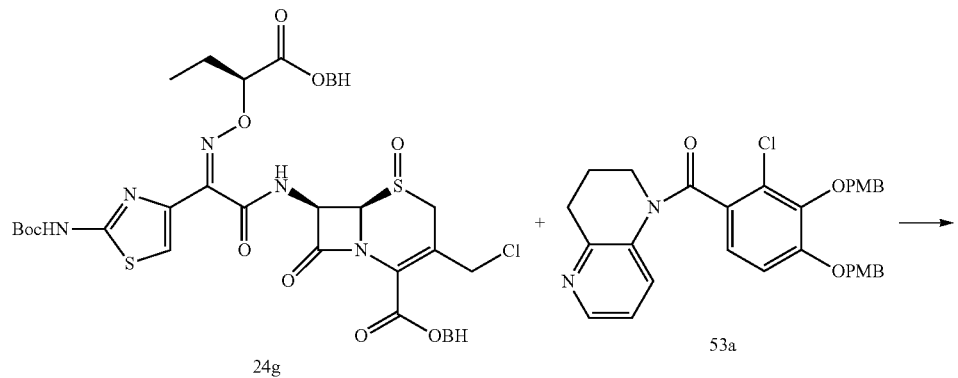
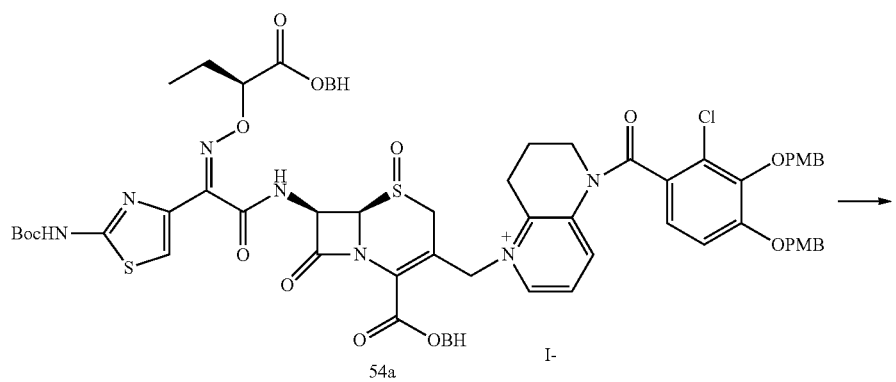
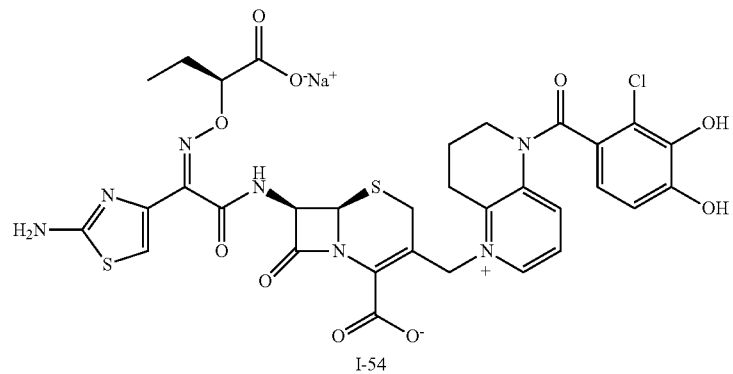

Step (1): Compound 24g→Compound 54a→Compound (I-54)
Compound 24g (906 mg, 1.00 mmol) was treated using the same method as Example 46 to obtain Compound I-54. (Yield: 194 mg, Yield: 24%)
MS: 772.32 (M+H)
$^1$H-NMR (D$_2$O) δ: 8.63-8.57 (1H, m), 7.65 (1H, s), 7.04-6.94 (3H, m), 5.88 (1H, d, J=5.0 Hz), 5.63-5.34 (2H, m), 5.29 (1H, d, J=5.0 Hz), 4.53 (1H, t, J=6.1 Hz), 4.12 (1H, s), 3.68-3.00 (6H, m), 2.25-2.20 (2H, m), 1.91-1.81 (2H, m), 0.97-0.95 (3H, m).
Elemental analysis for $C_{32}H_{20}ClN_7NaO_{10}S_2(H_2O)_{4.4}(NaHCO_3)_{0.1}$
Calcd.: C, 43.67; H, 4.36; Cl, 3.80; N, 11.37; S, 7.39; Na, 3.02.
Found.: C, 43.72; H, 4.33; Cl, 4.02; N, 11.12; S, 7.27; Na, 2.87.
Example 55
Synthesis of Compound (I-55)
[Formula 101]
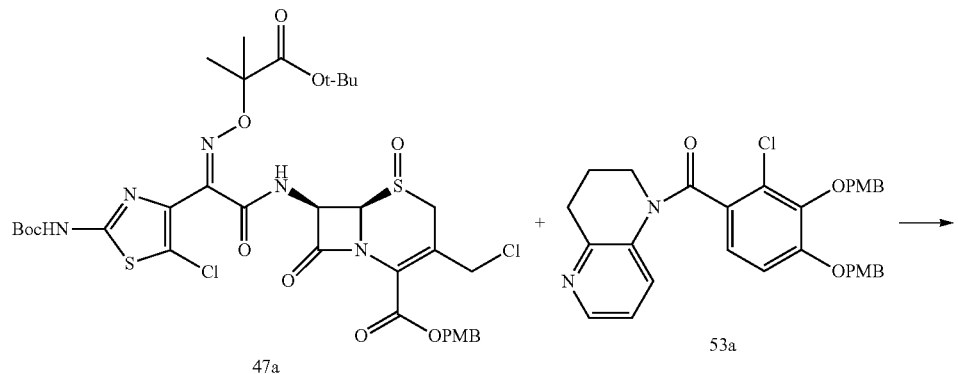
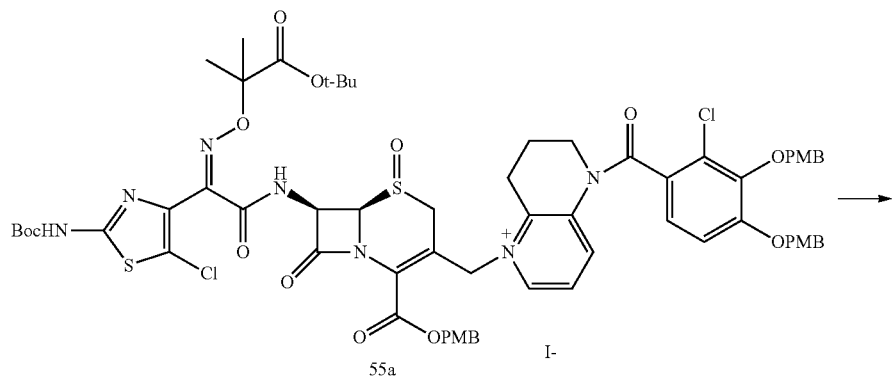
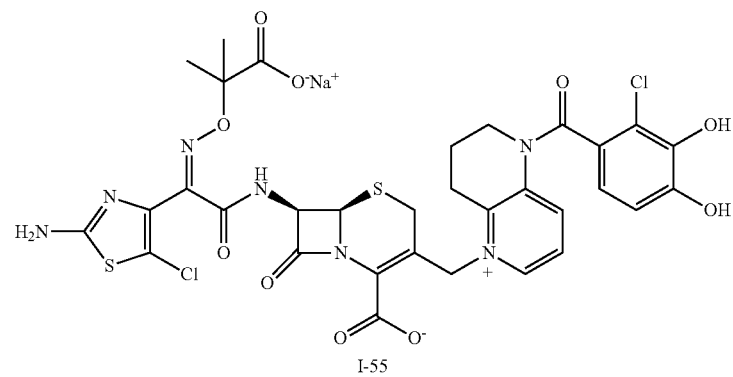

Step (1): Compound 47a→Compound 55a→Compound (I-55)
Compound 47a (665 mg, 0800 mmol) was treated using the same method as Example 46 to obtain Compound I-55. (Yield: 155 mg, Yield: 23%)
MS: 806.39 (M+H)
$^1$H-NMR (D$_2$O) δ: 8.62 (1H, br s), 7.66 (1H, br s), 7.05-6.95 (3H, m), 5.88 (1H, d, J=4.8 Hz), 5.64-5.33 (2H, m), 5.28 (1H, d, 4.8 Hz), 4.12 (1H, s), 3.69-3.19 (5H, m), 2.23 (2H, br s), 1.51-1.50 (6H, m).
Elemental analysis for C$_{32}$H$_{28}$Cl$_2$N$_7$NaO$_{10}$S$_2$(H$_2$O)$_{4.3}$(NaHCO$_3$)$_{0.1}$
Calcd.: C, 42.14; H, 4.13; Cl, 7.55; N, 10.93; S, 6.94; Na, 2.76.
Found.: C, 42.16; H, 4.04; Cl, 7.75; N, 10.72; S, 7.01; Na, 2.77.
Example 56
Synthesis of Compound (I-56)
[Formula 102]
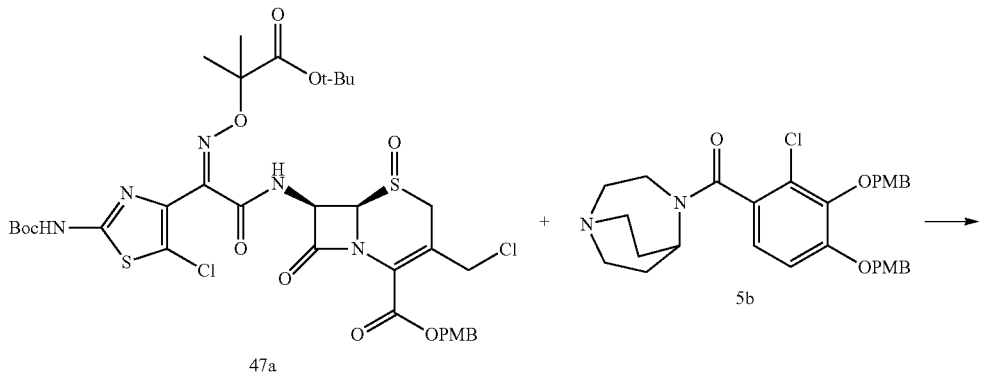
47a + 5b →
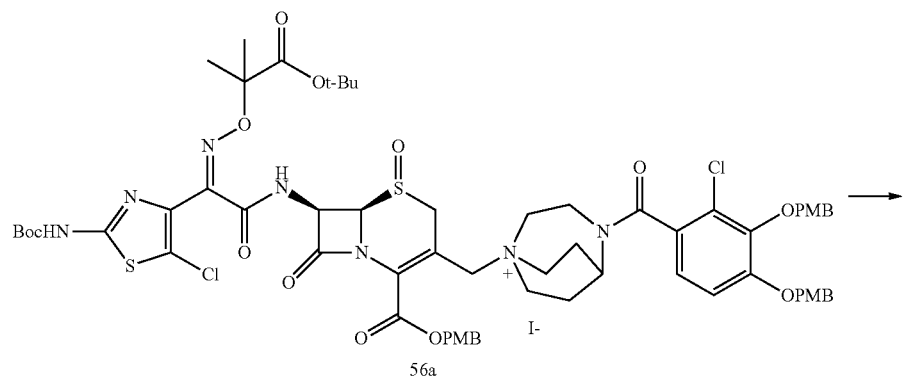
56a →
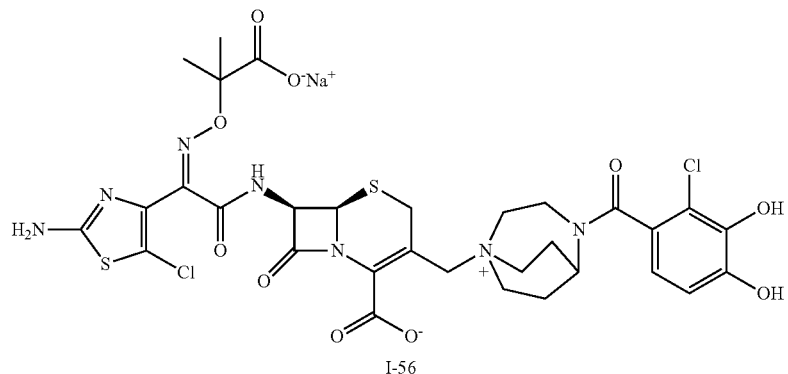
I-56

225
Step (1): Compound 47a→Compound 56a→Compound (I-56)
Compound 47a (778 mg, 0.937 mmol) was treated using the same method as Example 46 to obtain Compound I-56. (Yield: 281 mg, Yield: 37%)
MS: 798.31 (M+H)
$^1$H-NMR (D$_2$O) δ: 6.94 (1H, d, J=8.4 Hz), 6.82-6.78 (1H, m), 5.84 (1H, dd, J=14.5, 4.9 Hz), 5.37-5.33 (1H, m), 4.96-4.91 (1H, m), 4.20-4.10 (1H, m), 3.88-3.41 (10H, m), 2.37-2.18 (5H, m), 1.53-1.51 (6H, m).
226
Elemental analysis for C$_{31}$H$_{32}$Cl$_2$N$_7$NaO$_{10}$S$_2$(H$_2$O)$_{4.3}$(NaHCO$_3$)$_{0.1}$
Calcd.: C, 41.09; H, 4.46; Cl, 7.79; N, 11.12; S, 7.36; Na, 2.66.
Found.: C, 41.21; H, 4.53; Cl, 7.82; N, 10.82; S, 7.07; Na, 2.79.
Example 57
Synthesis of Compound (I-57)
[Formula 103]
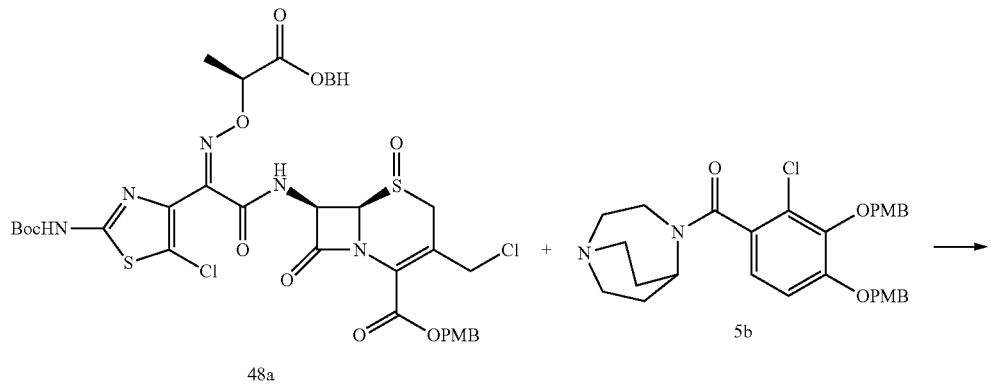
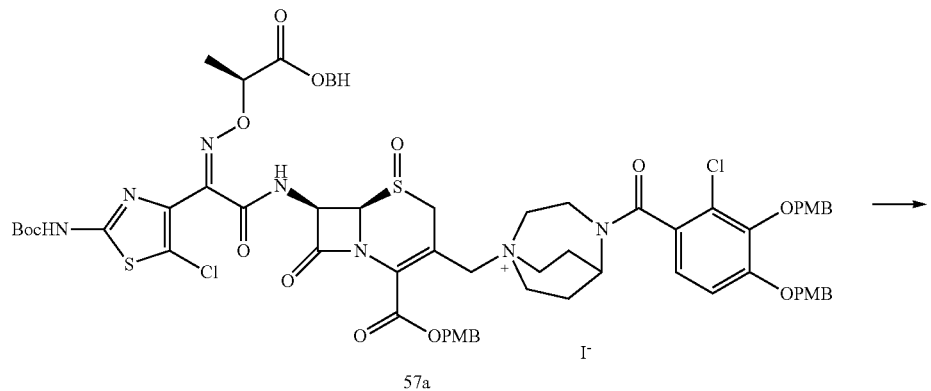
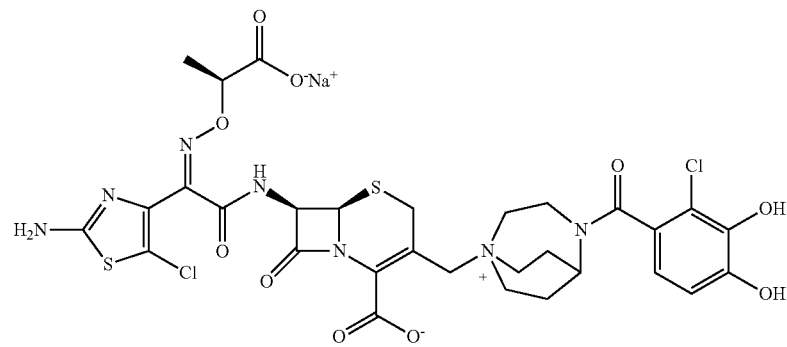

Step (1): Compound 48a→Compound 57a→Compound (I-57)
Compound 48a (868 mg, 0.937 mmol) was treated using the same method as Example 46 to obtain Compound I-57. (Yield: 226 mg, Yield: 30%)
MS: 784.20 (M+H)
$^1$H-NMR (D$_2$O) δ: 6.94 (1H, d, J=8.3 Hz), 6.81 (1H, dd, J=8.3, 3.7 Hz), 5.91-5.87 (1H, m), 5.37-5.33 (1H, m), 4.96-4.92 (1H, m), 4.73-4.63 (1H, m), 4.20-4.10 (1H, m), 3.88-3.41 (10H, m), 2.35-2.20 (5H, m), 1.50-1.47 (3H, m).
Elemental analysis for C$_{30}$H$_{30}$Cl$_2$O$_7$NaO$_{10}$S$_2$(H$_2$O)$_{4.3}$(NaHCO$_3$)$_{0.2}$
Calcd.: C, 39.98; H, 4.17; Cl, 7.44; N, 11.59; S, 7.81; Na, 3.08.
Found.: C, 40.26; H, 4.34; Cl, 7.87; N, 10.88; S, 7.12; Na, 3.06.
Example 58
Synthesis of Compound (I-58)
[Formula 104]
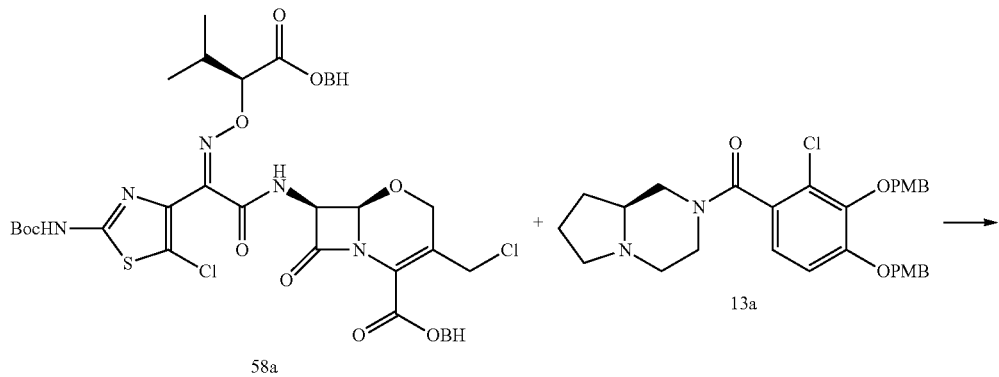
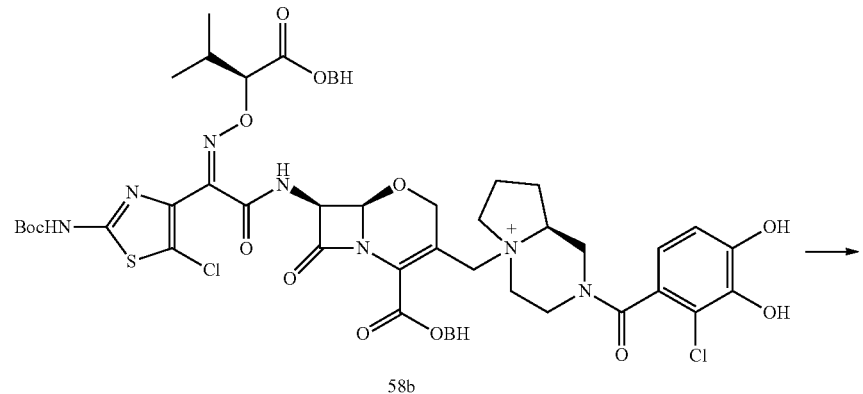
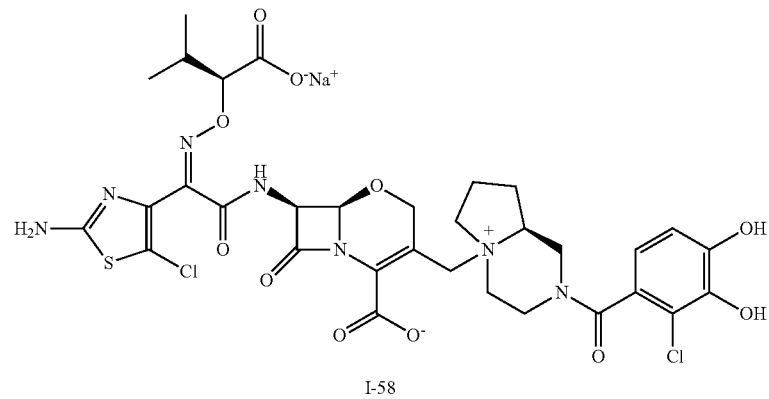

Step (1): Compound 58a→Compound 58b→Compound (I-58)

Compound 58a (873 mg, 0.900 mmol) was treated using the same method as Example 46 (phosphorus tribromide was not added) to obtain Compound I-58. (Yield: 100 mg, Yield: 14%)

MS: 796.31 (M+H)

$^1$H-NMR (D$_2$O) δ: 6.97-6.93 (1H, m), 6.86-6.82 (1H, m), 5.72-5.68 (1H, m), 5.41 (1H, dd, J=7.8, 4.0 Hz), 5.00-4.91 (1H, m), 4.72-4.28 (4H, m), 4.00-3.40 (9H, m), 2.47-2.20 (5H, m), 1.03-0.90 (6H, m).

Elemental analysis for C$_{32}$H$_{34}$Cl$_2$N$_7$NaO$_{11}$S(H$_2$O)$_{4.5}$(NaHCO$_3$)$_{0.1}$ Calcd.: C, 42.52; H, 4.91; Cl, 7.17; N, 10.96; S, 3.47; Na, 2.98.

Found.: C, 42.46; H, 4.78; Cl, 7.81; N, 10.80; S, 3.53; Na, 2.78.

Example 59

Synthesis of Compound (I-59)

[Formula 105]

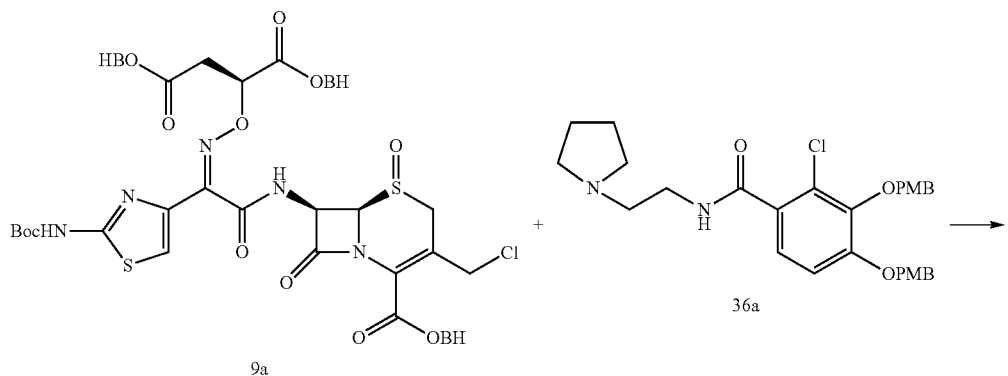

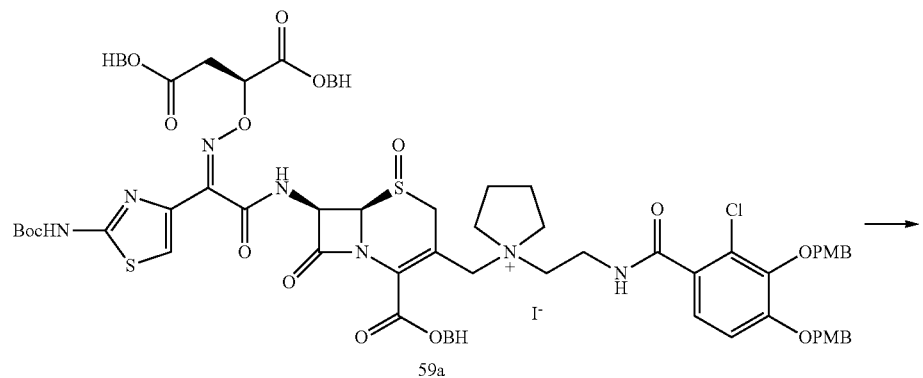

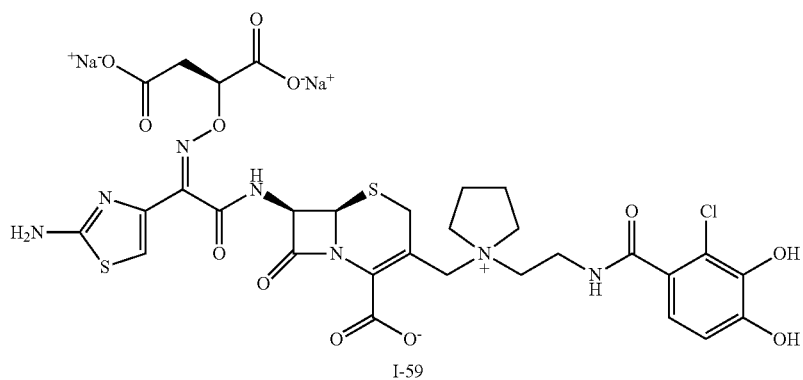

Step (1): Compound 9a→Compound 59a→Compound (I-59)
Compound 9a (1.148 g, 1.00 mmol) was treated using the same method as Example 46 to obtain Compound I-59. (Yield: 253 mg, Yield: 31%)
MS: 792.23 (M+H)
$^1$H-NMR (D$_2$O) δ: 7.00-6.96 (2H, m), 6.90-6.87 (1H, m), 5.82 (1H, d, J=4.9 Hz), 5.33 (1H, d, J=4.9 Hz), 4.96 (1H, dd, J=3.2, 4.9 Hz), 4.15 (1H, d, J=14.3 Hz), 3.94-3.44 (11H, m), 2.73-2.70 (2H, m), 2.25-2.22 (4H, m).
Elemental analysis for $C_{30}H_{31}ClN_7Na_2O_{12}S_2(H_2O)_{4.4}(NaHCO_3)_{0.1}$
Calcd.: C, 39.43; H, 4.45; Cl, 3.65; N, 10.67; S, 7.07; Na, 5.80.
Found.: C, 39.52; H, 4.40; Cl, 3.88; N, 10.72; S, 7.01; Na, 5.28.
Example 60
Synthesis of Compound (I-60)
[Formula 106]
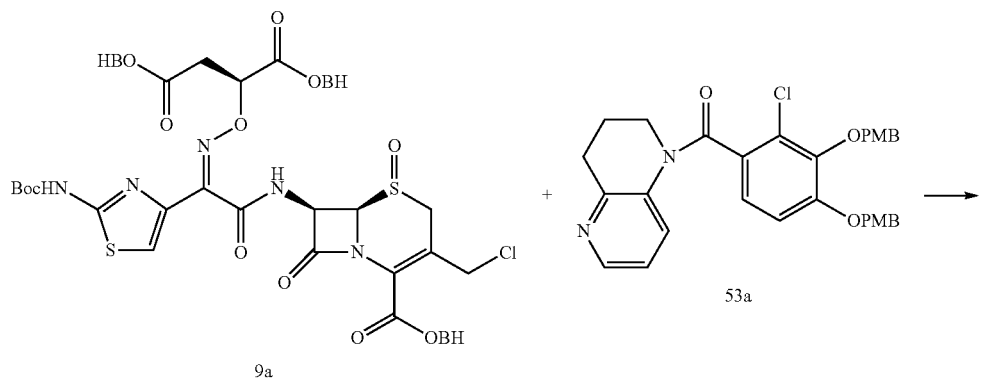
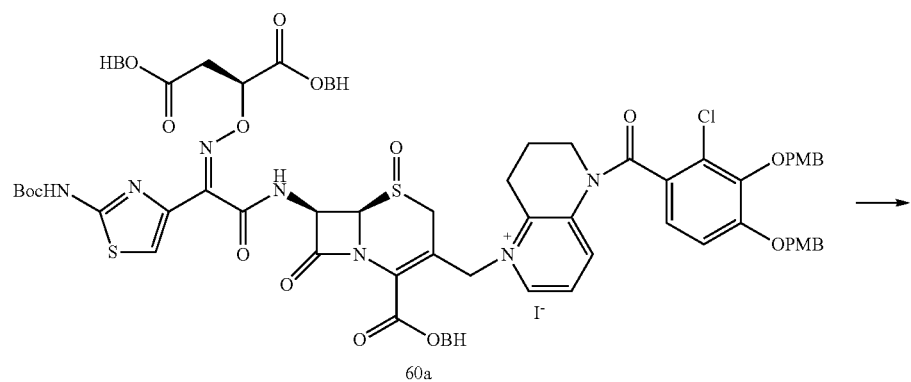
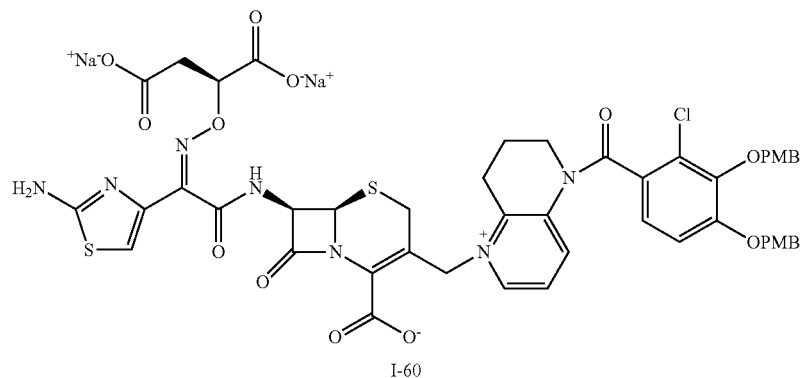

Step (1): Compound 9a→Compound 60a→Compound (I-60)
Compound 9a (1033 mg, 0.900 mmol) was treated using the same method as Example 46 to obtain Compound I-60. (Yield: 156 mg, Yield: 20%)
MS: 802.23 (M+H)
$^1$H-NMR (D$_2$O) δ: 8.63 (1H, br s), 7.68 (1H, br s), 7.06-6.95 (3H, m), 5.84 (1H, d, J=4.9 Hz), 5.66-5.35 (2H, m), 5.25 (1H, d, J=4.9 Hz), 4.97 (1H, dd, J=8.4, 4.9 Hz), 4.89-4.87 (1H, m), 4.77-4.75 (1H, m), 3.72 (1H, d, J=18.1 Hz), 3.52-3.22 (4H, m), 2.73-2.70 (2H, m), 2.24 (2H, br s).
Elemental analysis for C$_{32}$H$_{27}$ClN$_7$Na$_2$O$_{12}$S$_2$(H$_2$O)$_{5.9}$(NaHCO$_3$)$_{0.1}$
Calcd.: C, 39.51; H, 4.58; Cl, 2.57; N, 9.88; S, 6.20; Na, 5.14.
Found.: C, 39.35; H, 4.21; Cl, 3.62; N, 10.01; S, 6.54; Na, 4.93.
Example 61
Synthesis of Compound (I-61)
[Formula 107]
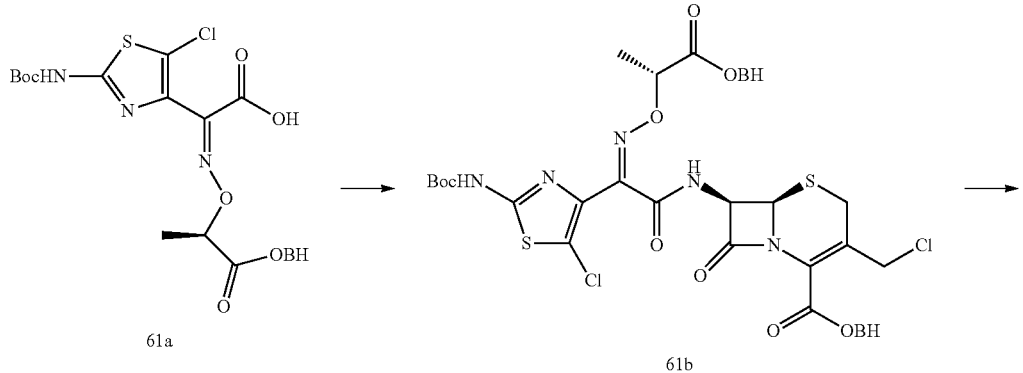
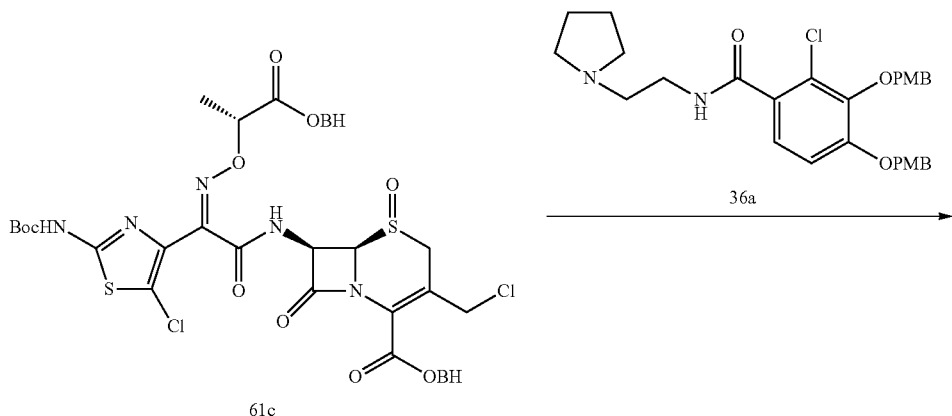
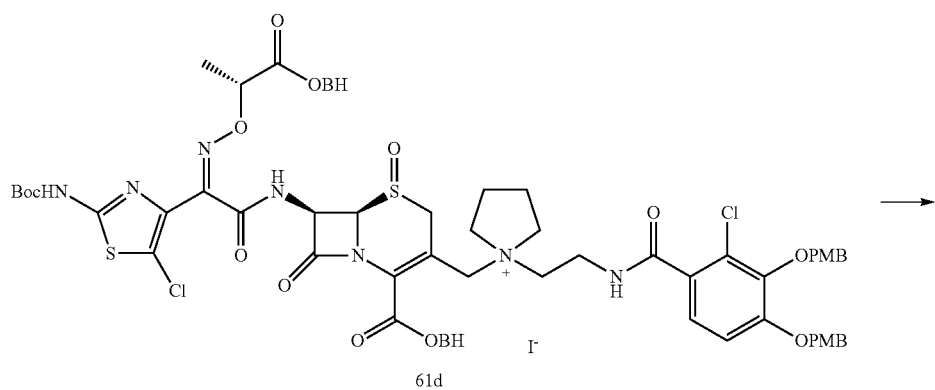

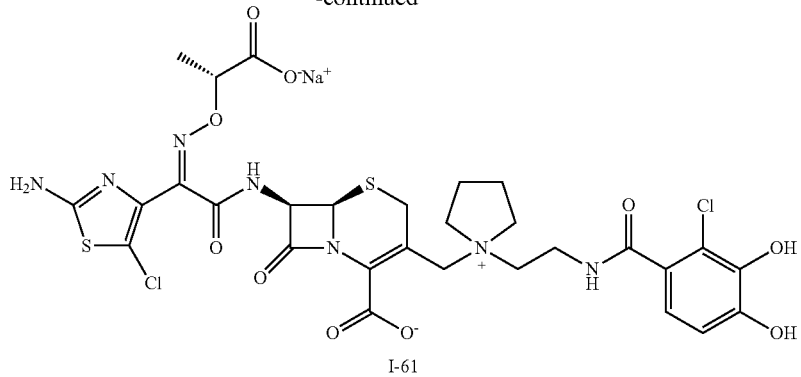

I-61

Step (1): Compound 61a→Compound 61b

Compound 40d (9.03 g, 20.0 mmol) was suspended in ethyl acetate (200 mL). Compound 61a (11.2 g, 20.0 mmol) was added thereto, and then cooled to −40° C. Phenyl dichlorophosphate (3.59 mL, 24.0 mmol) followed by N-methylmorpholine (7.48 mL, 68.0 mmol) were added drop-wise, and then stirred at −30° C. for 1.5 hours. Aqueous 0.1 N hydrochloric acid solution (200 mL) was then added to the reaction solution. The organic layer was separated, and then washed with saturated brine. The organic layer was dried with magnesium sulfate, and then filtered. The solvent was evaporated under reduced pressure. The resulting residue was purified by silica gel chromatography to yield compound 61b as a yellow oil. (Yield: 16.7 g, Yield: 87%)

$^1$H-NMR (CDCl$_3$) δ: 8.02 (1H, s), 7.69 (1H, d, J=9.7 Hz), 7.47-7.23 (20H, m), 6.96 (1H, s), 6.90 (1H, s), 6.02 (1H, dd, J=9.7, 5.0 Hz), 5.10 (1H, q, J=7.4 Hz), 5.02 (1H, d, J=5.0 Hz), 4.45 (1H, d, J=11.7 Hz), 4.33 (1H, d, J=11.7 Hz), 3.44 (1H, d, J=18.2 Hz), 3.24 (1H, d, J=18.2 Hz), 1.65 (3H, d, J=7.4 Hz), 1.53 (9H, s).

Step (2): Compound 61b→Compound 61c

Compound 61b (16.7 g, 17.5 mmol) was dissolved in methylene chloride (200 mL), and then cooled to −40° C. Subsequently, 65% meta-chloroperbenzoic acid (4.64 g, 17.5 mmol) was added thereto, and then stirred for 40 minutes. Aqueous 5% sodium hydrogen sulfite solution (200 mL) was added, and then the organic layer was separated. The organic layer was washed with aqueous saturated sodium hydrogen carbonate, then saturated brine, and then dried with anhydrous magnesium sulfate. Magnesium sulfate was filtered, and then the solvent was evaporated under reduced pressure. The resulting residue was purified by silica gel chromatography to yield Compound 61c as a yellow oil. (Yield: 16.5 g, Yield: 97%)

$^1$H-NMR (CDCl$_3$) δ: 8.24 (1H, s), 7.93 (1H, d, J=9.8 Hz), 7.48-7.21 (20H, m), 6.96 (1H, s), 6.92 (1H, s), 6.12 (1H, dd, J=9.8, 4.9 Hz), 5.02 (1H, q, J=7.0 Hz), 4.90 (1H, d, J=12.2 Hz), 4.55-4.53 (1H, m), 4.19 (1H, d, J=12.2 Hz), 3.70 (1H, d, J=18.7 Hz), 3.34 (1H, d, J=18.7 Hz), 1.64 (3H, d, J=7.0 Hz), 1.52 (9H, s).

Step (3): Compound 61c→Compound 61d→Compound (I-61)

Compound 61c (973 mg, 1.00 mmol) was treated using the same method as Example 46 to obtain Compound I-61. (Yield: 248 mg, Yield: 31%)

$^1$H-NMR (D$_2$O) δ: 6.97 (1H, d, J=8.8 Hz), 6.88 (1H, d, J=8.8 Hz), 5.87 (1H, d, J=4.9 Hz), 5.36 (1H, d, J=4.9 Hz), 4.66 (1H, q, J=7.1 Hz), 4.13 (1H, d, J=13.6 Hz), 3.96-3.50 (11H, m), 2.26-2.20 (4H, m), 1.49 (3H, d, J=7.1 Hz).

Elemental analysis for C$_{29}$H$_{30}$Cl$_2$N$_7$NaO$_{10}$S$_2$(H$_2$O)$_4$ (NaHCO$_3$)$_{0.1}$ Calcd.: C, 40.01; H, 4.42; Cl, 8.04; N, 11.14; S, 7.16; Na, 2.82.

Found.: C, 39.94; H, 4.39; Cl, 8.10; N, 11.20; S, 7.33; Na, 2.89.

Example 62

Synthesis of Compound (I-62)

[Formula 108]

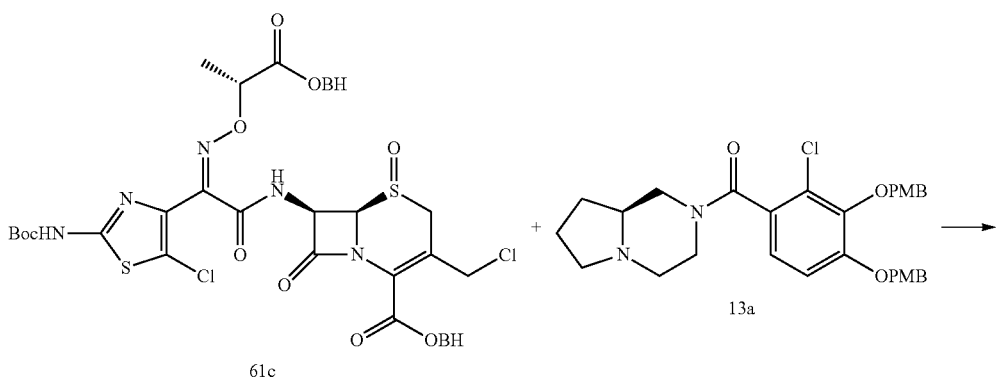

61c     13a

-continued
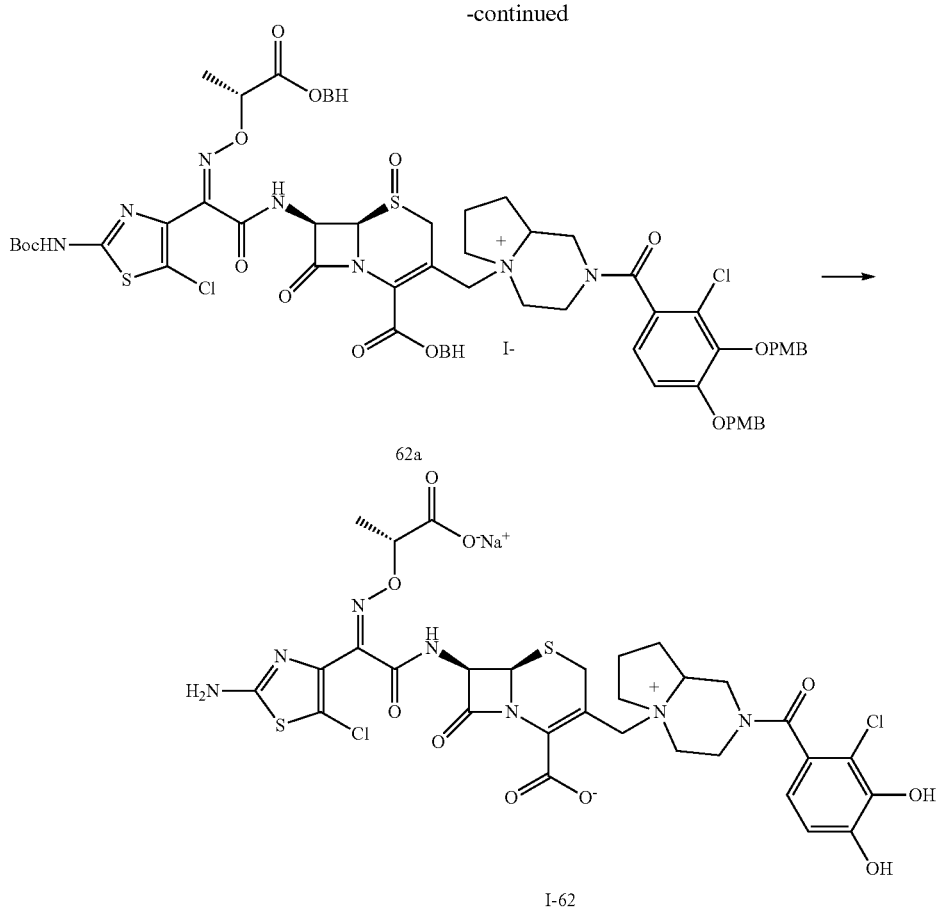
Step (1): Compound 61c→Compound 62a→Compound (I-62)
Compound 61c (973 mg, 1.00 mmol) was treated using the same method as Example 46 to obtain Compound I-62. (Yield: 282 mg, Yield: 35%)
$^1$H-NMR (D$_2$O) δ: 6.96 (1H, dd, J=8.2, 2.1 Hz), 6.83 (1H, d, J=8.2 Hz), 5.87 (1H, d, J=5.0 Hz), 5.35 (1H, dd, J=8.1, 5.0 Hz), 4.92-4.60 (1H, m), 4.46-4.23 (2H, m), 3.99-3.41 (11H, m), 2.39-2.09 (4H, m), 1.49 (3H, q, J=4.4 Hz).
Elemental analysis for C$_{30}$H$_{30}$Cl$_2$N$_7$NaO$_{10}$S$_2$(H$_2$O)$_{4.6}$(NaHCO$_3$)$_{0.1}$
Calcd.: C, 40.33; H, 4.53; Cl, 7.78; N, 10.93; S, 6.99; Na, 2.78.
Found.: C, 40.26; H, 4.41; Cl, 7.90; N, 10.92; S, 7.14; Na, 2.82.
Example 63
Synthesis of Compound (I-63)
[Formula 109]
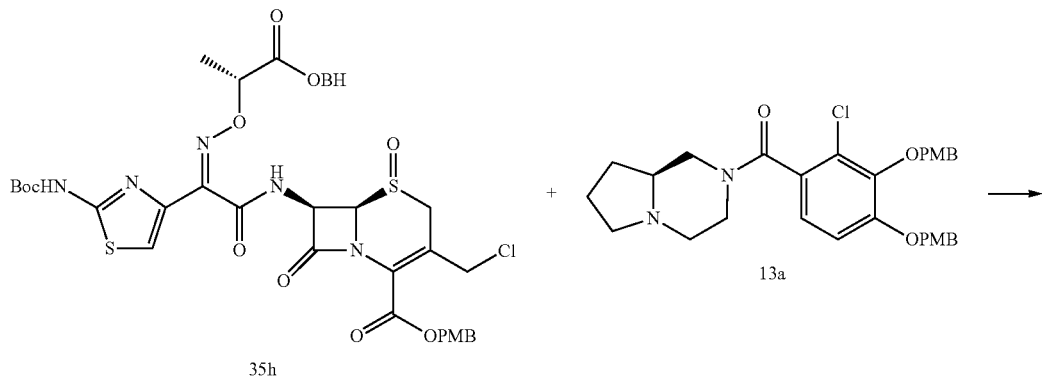

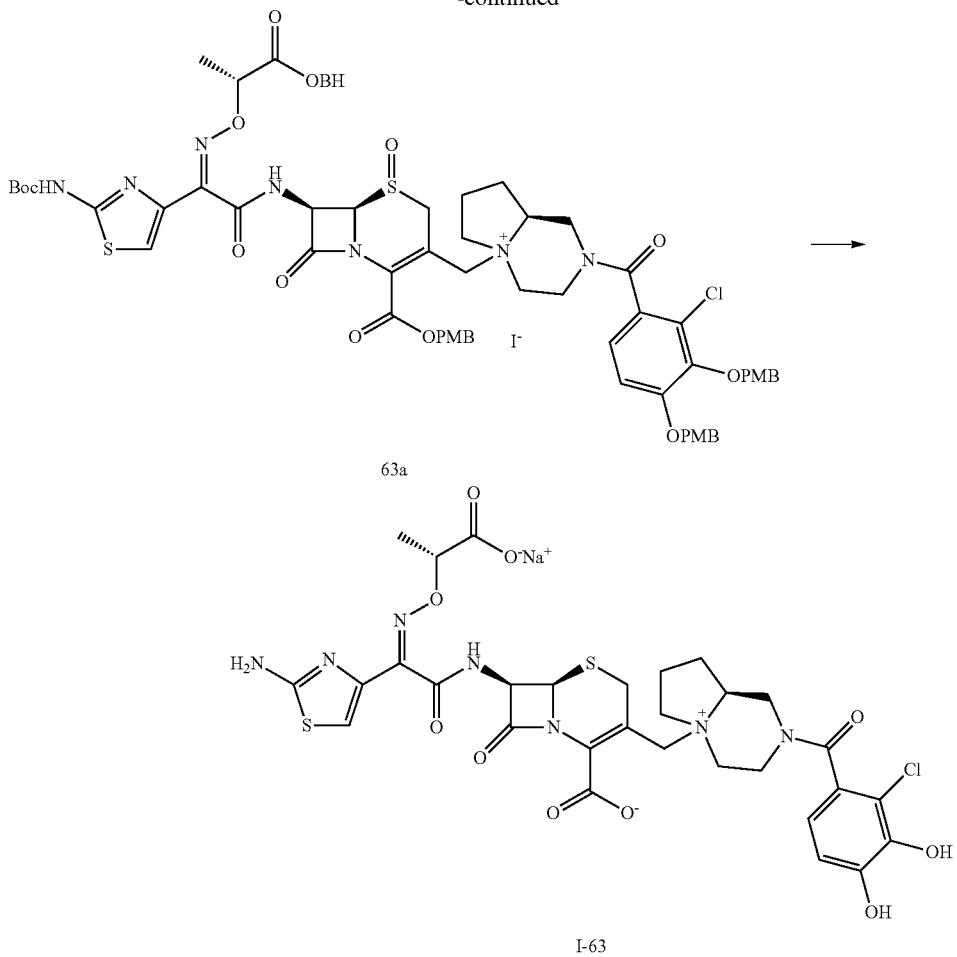
63a
I-63
Step (1): Compound 35h→Compound 63a→Compound (I-63)
Compound 35h (892 mg, 1.00 mmol) was treated using the same method as Example 46 to obtain Compound I-63. (Yield: 443 mg, Yield: 57%)
$^1$H-NMR (D$_2$O) δ: 7.01-6.94 (2H, m), 6.86-6.82 (1H, m), 5.88 (1H, d, J=4.9 Hz), 5.36 (1H, dd, 8.4, 4.9 Hz), 4.89-4.84 (1H, m), 4.69-4.61 (1H, m), 4.46-4.23 (2H, m), 4.00-3.42 (10H, m), 2.49-1.99 (4H, m), 1.48 (3H, q, J=4.9 Hz).
Elemental analysis for C$_{30}$H$_{31}$ClN$_7$NaO$_{10}$S$_2$(H$_2$O)$_{5.2}$(NaHCO$_3$)$_{0.1}$
Calcd.: C, 41.50; H, 4.96; Cl, 4.08; N, 11.02; S, 6.83; Na, 2.70.
Found.: C, 41.35; H, 4.78; Cl, 4.06; N, 11.21; S, 7.34; Na, 2.89.
Example 64
Synthesis of Compound (I-64)
[Formula 110]
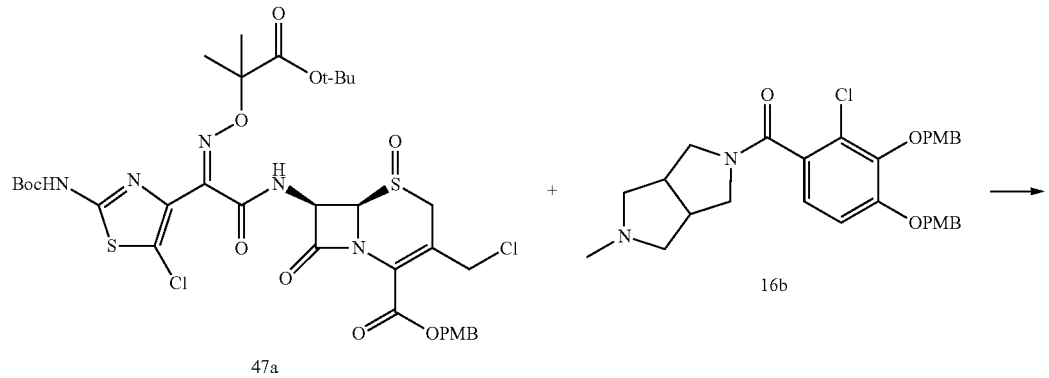

-continued
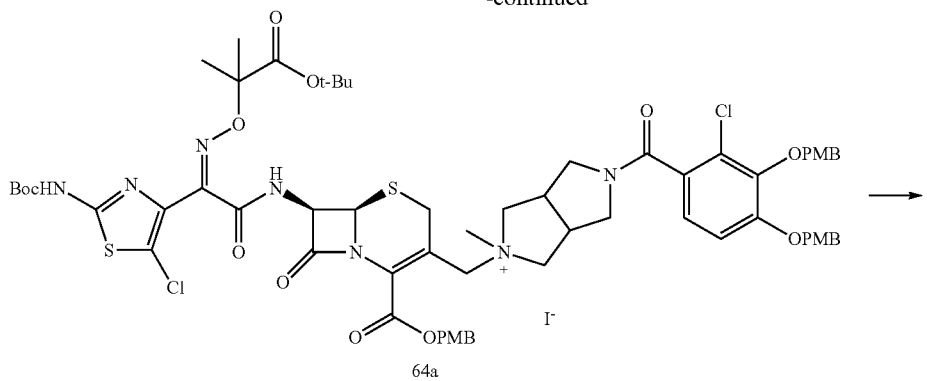
64a
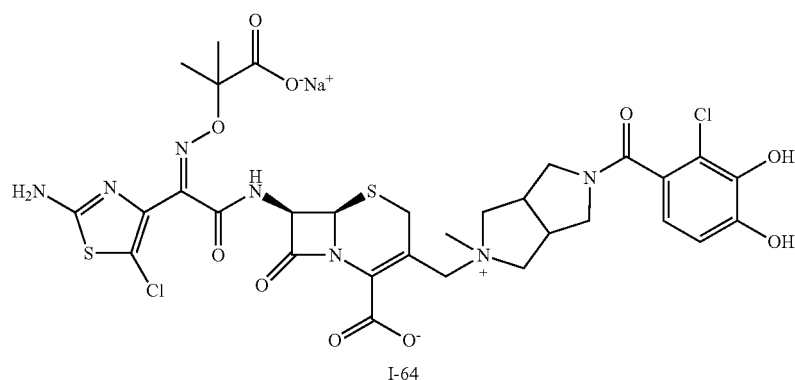
I-64
Step (1): Compound 47a→Compound 64a→Compound (I-64)
Compound 47a (831 mg, 1 mmol) was treated using the same method as Example 46 to obtain Compound I-64. (Yield: 488 mg, Yield: 60%)
$^1$H-NMR (D$_2$O) δ: 6.97-6.93 (1H, m), 6.87-6.83 (1H, m), 5.90-5.86 (1H, m), 5.38-5.33 (1H, m), 4.20-3.82 (5H, m), 3.65-2.95 (12H, m), 1.53-1.51 (6H, m).
Elemental analysis for C$_{31}$H$_{32}$Cl$_2$N$_7$NaO$_{10}$S$_2$(H$_2$O)$_{4.6}$ (NaHCO$_3$)$_{0.1}$
Calcd.: C, 41.00; H, 4.58; Cl, 8.04; N, 10.76; S, 7.79; Na, 2.82.
Found.: C, 40.96; H, 4.56; Cl, 7.78; N, 10.75; S, 7.03; Na, 2.77.
Example 65
Synthesis of Compound (I-65)
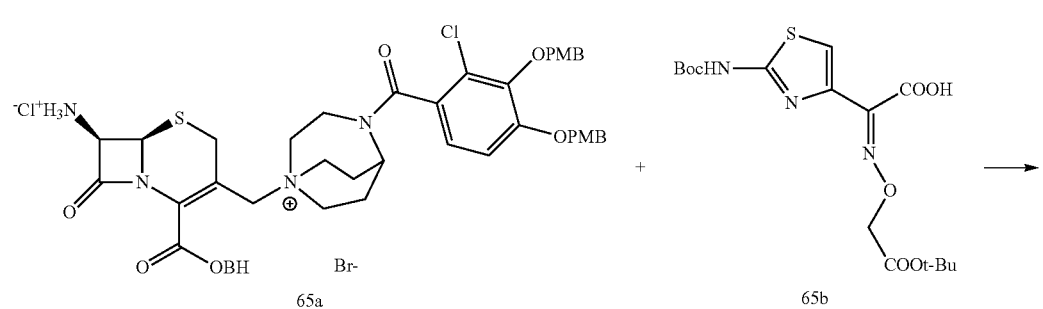

-continued

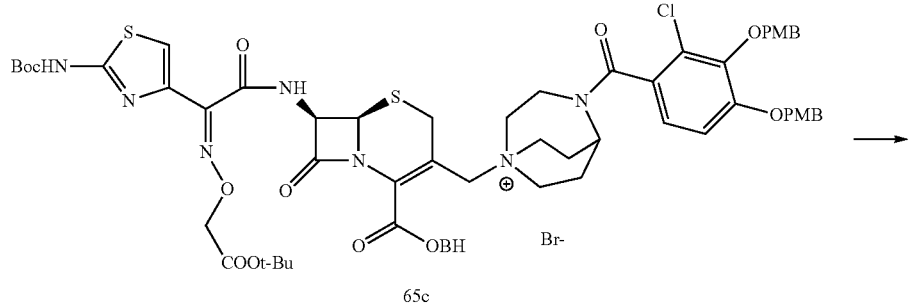

65c

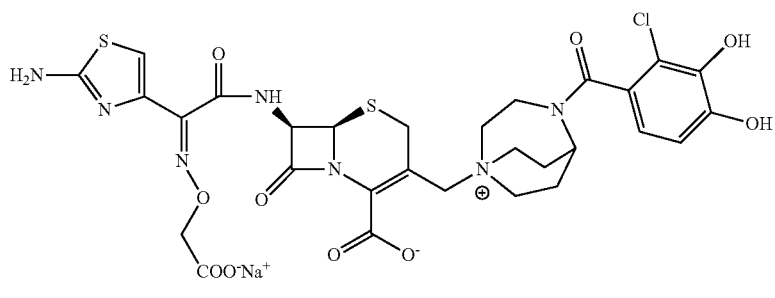

I-65

Step (1): Compound 65a→Compound 65c→Compound 91

Compound 65a (1.03 g, 1.0 mmol) was dissolved in methylene chloride (10 mL). Compound 65b (0.40 g, 1.0 mmol), pyridine (0.103 g, 1.3 mmol), and hydrochloric acid salt of 1-(dimethylaminopropyl)-3-ethylcarbodiimide (230 mg, 1.2 mmol) were added, and then stirred at −10° C. Purified water was added to the reaction solution, and then the aqueous layer was extracted with ethyl acetate. The organic layer was washed with purified water, then saturated brine. The organic layer was then dried with anhydrous magnesium sulfate. Magnesium sulfate was removed by filtration to yield Compound 65c. Compound 65c was treated using the same method as Compound 31b of Example 31 to yield Compound I-65. (Yield: 170 mg, Yield: 23%).

MS (m+1)=736.32

Elemental analysis for $C_{29}H_{29}ClN_7O_{10}S_2Na(NaHCO_3)_{0.3}$ $(H_2O)_{7.9}$ Calcd.: C, 37.97; H, 4.89; Cl, 3.62; N, 10.77; S, 6.96; Na, 3.12.

Found.: C, 38.02; H, 4.91; Cl, 3.83; N, 10.59; S, 6.93; Na, 3.23.

$^1$H-NMR (D$_2$O) δ: 7.04-7.03 (1H, m), 6.94-6.91 (1H, m), 6.80-6.77 (1H, m), 5.89-5.88 (1H, m), 5.37-5.35 (1H, m), 4.91 (1H, t, J=4.0 Hz), 4.24-4.06 (1H, m), 3.91-3.42 (12H, m), 2.50-2.11 (5H, m).

Example 66

Synthesis of Compound (II-1)

[Formula 112]

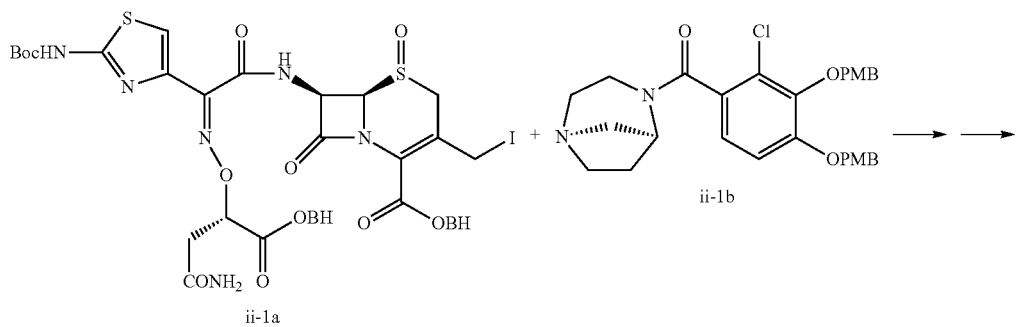

ii-1a     ii-1b

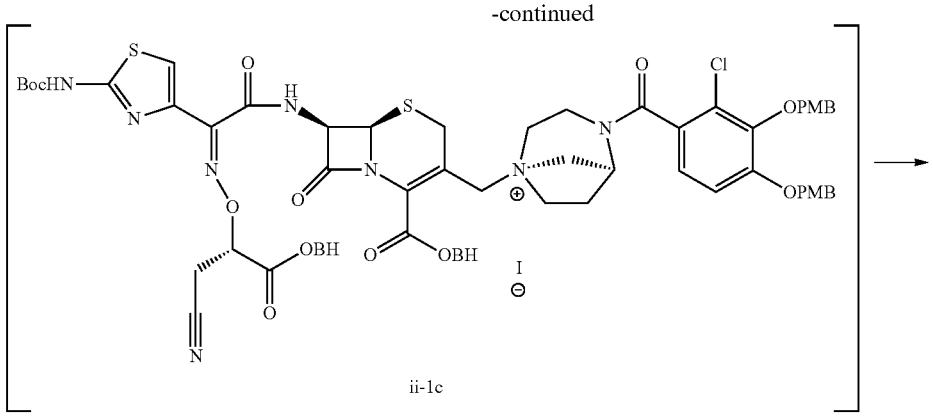

ii-1c

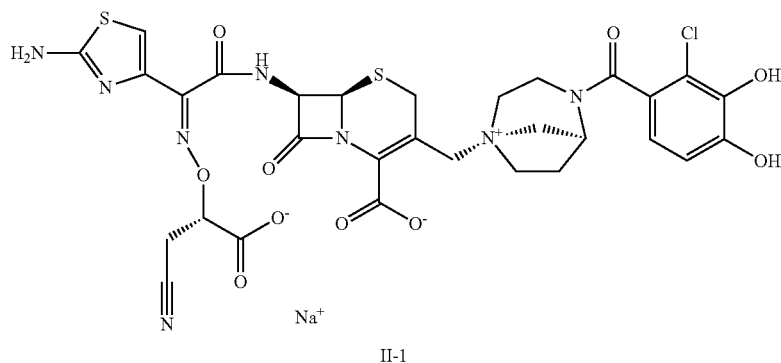

II-1

Step (1): Compound ii-1a+compound ii-1b→compound ii-1c→compound II-1

Sodium iodide (9.07 g, 60.5 mmol) was added to a solution of compound (32.99 g, 30.3 mmol) dimethylacetoamide (99 mL), and the resultant solution was stirred at room temperature for 5 minutes. The reaction solution was cooled to 0° C., and thereto was dropwise added compound ii-1b (15.8 g, 30.3 mmol) over 1 hour. Thereto was added sodium hydrogencarbonate (10.2 g, 121 mmol), and the solution was stirred at 15° C. for 1 hour. Next, thereto was added N,N-dimethylformamide (200 mL), and the solution was cooled to −40° C. Thereto was added phosphorus tribromide (5.71 mL, 60.5 mmol), and the solution was stirred for 1 hour. The reaction solution was added to a cooled 5% aqueous sodium hydrogensulfite solution (3 L). The resultant was filtrated, and the target phase was washed with water, and air-dried to yield compound ii-1c. Next, anisole (1.0 mL, 10 mmol) was added to a solution of yielded compound ii-1c (1.95 g, 1 mmol) in methylene chloride (10 mL), and the resultant solution was cooled to −40° C. Thereto was added a 2M/L, solution (5 ml) of aluminum chloride in nitromethane, and then the resultant solution was stirred at 0° C. for 50 minutes. The reaction liquid was poured to 2 N hydrochloric acid (60 mL), acetonitrile (50 mL) and diethyl ether (100 mL). The water phase was washed with diethyl ether, concentrated under reduced pressure, and then subjected to BP-20SS column chromatography to elute out a desired compound with acetonitrile/a 0.02 N aqueous hydrochloric acid solution. The eluent was concentrated under reduced pressure, and again subjected to HP-20SS column chromatography to elute out the compound again with acetonitrile/water. The resultant desired fraction was collected, and then a 0.2 N aqueous sodium hydroxide solution was added to the fraction to adjust the pH thereof to 6. In this way, the compound was converted to a sodium salt thereof, and then the salt was concentrated under reduced pressure. The liquid condensate was freeze-dried to yield compound II-1 as a white non-crystalline powder.

Yield: 57.8 mg (7.4%)

$^1$H-NMR (D$_2$O) δ: 2.20-4.80 (15.5H, m), 5.33-37 (1H, m), 5.45-5.60 (0.5H, m), 5.85-5.88 (1H, m), 6.75-6.76 (1H, m), 6.90-6.93 (1H, m), 7.07 (1H, s)

Elem. Anal C$_{30}$H$_{29}$N$_8$ClN$_8$O$_{10}$S$_2$Na.5.8H$_2$O.(NaHCO3) 0.2

Calcd.: C, 40.06; H, 4.54; Cl, 3.92; N, 12.38; S, 7.08; Na, 3.05 (%).

Found: C, 39.95; H, 4.27; Cl, 4.20; N, 12.41; S, 7.00; Na, 3.28 (%).

Example 67

Synthesis of Compound (II-2)

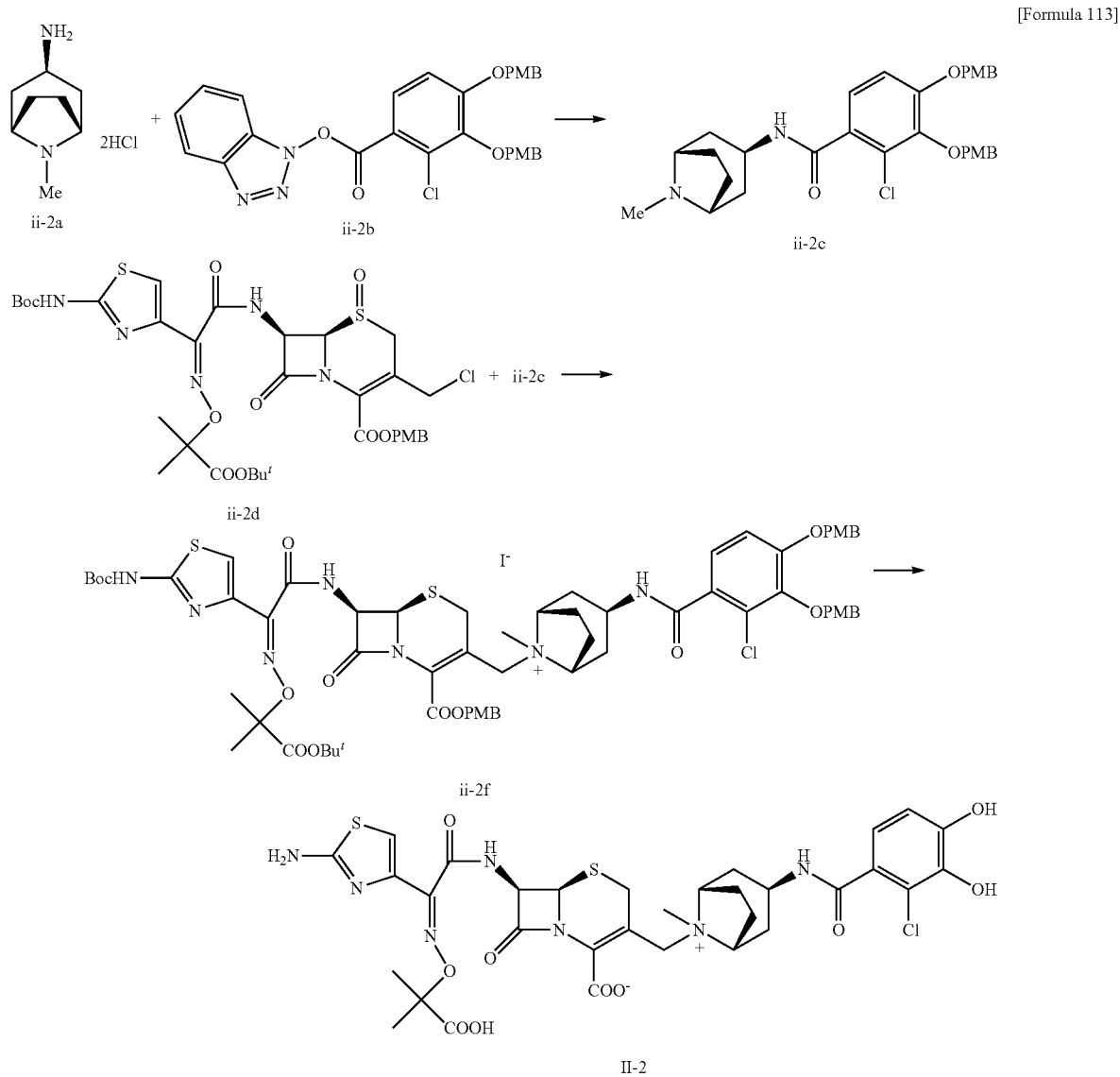

[Formula 113]

Step (1): compound ii-2→compound ii-2c

Compound ii-2b (12.81 g, 23.5 mmol) and diisopropylamine (14.3 mL, 82 mmol) were added to a suspension of compound ii-2a (5.0 g, 23.5 mmol) in methylene chloride (80 mL) while cooled with ice. At room temperature, the liquid was stirred at room temperature for 2 hours, and then allowed to stand still overnight. To the reaction liquid was added 0.2 N sodium hydroxide, and then the resultant liquid was subjected to extraction 3 times with chloroform. The collected organic phase was dried over anhydrous magnesium sulfate, filtrated, and then concentrated. The resultant crude product was purified by silica gel column chromatography (methanol/ethyl acetate containing 2% triethylamine) to yield compound ii-2c (11.6 g, 90%)

$^1$H-NMR (CDCl$_3$) δ: 1.68 (2H, d, J=15.0 Hz), 1.91-2.04 (5H, m), 2.14 (3H, s), 2.97 (2H, brs), 3.75 (3H, s), 3.76 (3H, s), 3.83 (1H, m), 4.87 (2H, s), 5.15 (2H, s), 6.87 (2H, d, J=8.10 Hz), 6.97 (2H, d, J=8.40 Hz), 7.07 (1H, d, J=9.00 Hz), 7.32 (2H, d, J=8.40), 7.42 (2H, d, J=8.10 Hz), 8.00 (1H, d, J=4.80 Hz).

Step (2) compound ii-2d→compound II-2

Compound ii-2c (463 mg, 0.84 mmol) and sodium iodide (240 mg, 160 mmol) were added to a solution of compound ii-2d (637 mg, 0.80 mmol) in dimethylacetoamide (2 mL) while cooled with ice. The resultant solution was stirred at 10° C. for 8 hours. The solution was allowed to stand still in a refrigerator overnight, and then diluted with N,N-dimethylformamide (4 mL) and cooled to −40° C. Thereto was added phosphorus tribromide (0.156 mL, 1.6 mmol), and the solution was stirred at the same temperature for 1 hour. The reaction liquid was poured into a 5% salt solution in an ice bath. The precipitated solid was collected by filtration, and dried under reduced pressure to yield a crude product (1.18 g) containing compound ii-2f. This crude product was dissolved in methylene chloride (12 mL), and then thereto were added anisole (0.87 mL, 8.0 mmol), and an aluminum chloride solution (2.0 M, 4 mL, 8.0 mmol) in nitromethane at −40° C. The reaction liquid was stirred inside an ice bath for 1 hour, and then poured into a mixed liquid of 1 N hydrochloric acid and acetonitrile (1:1). This solution was washed with diisopropyl ether. HP-20SS was added to the water phase, and then acetonitrile was distilled off under reduced pressure. The resultant suspension was purified by ODS column chromatography. The resultant target-substance-containing fraction was concentrated, and then freeze-dried to yield compound II-2 (25 mg).

$^1$H-NMR (D$_2$O+NaHCO3) δ: 1.50 (3H, s), 1.52 (3H, s), 2.16 (2H, d, J=16.8 Hz), 2.40-2.58 (4H, m), 2.66-2.80 (2H, m), 3.09 (3H, s), 3.48 (1H, d, J=17.1 Hz), 3.92-4.08 (4H, m), 4.21 (1H, t, J=7.5 Hz), 4.62 (1H, d, J=14.1 Hz), 5.36 (1H, d, J=4.8 Hz), 5.88 (1H, d, J=4.8 Hz), 6.88 (1H, d, J=8.4 Hz), 6.93 (1H, d, J=8.4 Hz), 6.96 (1H, s).

Elem. Anal.: C32H36ClN7O10S2(H2O)4.0
Calcd.: C, 45.20; H, 5.22; Cl, 4.17; N, 11.53; S, 7.54 (%).
Found: C, 45.17; H, 5.20; Cl, 4.33; N, 11.11; S, 7.62 (%).

Example 68

Synthesis of Compound (II-3)

[Formula 114]

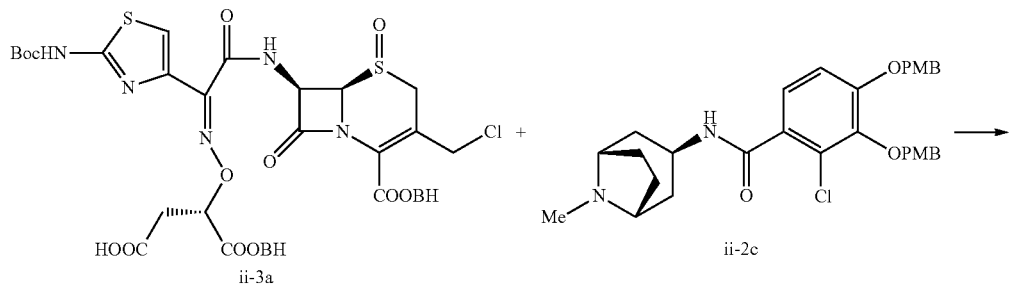

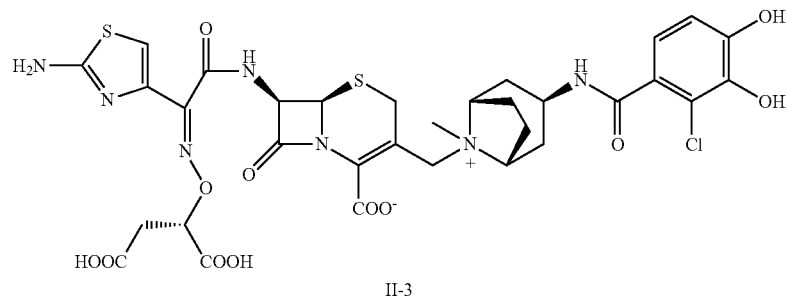

Step (1): compound ii-3a→compound II-3
Compound ii-3a (919 mg) was used to conduct the same may in step 2 in Example 67 to yield compound II-3 (191 mg).
$^1$H-NMR (D$_2$O+NaHCO3) δ: 2.16 (2H, d, J=16.8 Hz), 2.39-2.59 (4H, m), 2.70-2.82 (4H, m), 3.09 (3H, s), 3.48 (1H, d, J=16.8 Hz), 3.89-4.11 (4H, m), 4.22 (1H, t, J=7.2 Hz), 4.60 (1H, d, J=13.8 Hz), 4.97 (1H, m), 5.34 (1H, d, J=4.8 Hz), 5.83 (1H, d, J=4.8 Hz), 6.90 (1H, d, J=8.4 Hz), 6.94 (1H, d, J=8.4 Hz), 7.10 (1H, s).
Elem. Anal.: C32H34ClN7O12S2(H2O)2.9
Calcd.: C, 44.67; H, 4.66; Cl, 4.12; N, 11.39; S, 7.45 (%).
Found: C, 44.67; H, 4.80; Cl 4.12; N, 11.36; S, 7.37 (%).

Example 69

Synthesis of Compound (II-4)

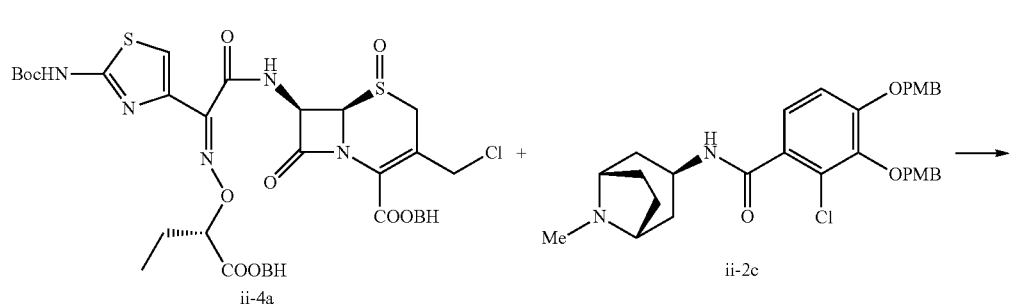

[Formula 115]

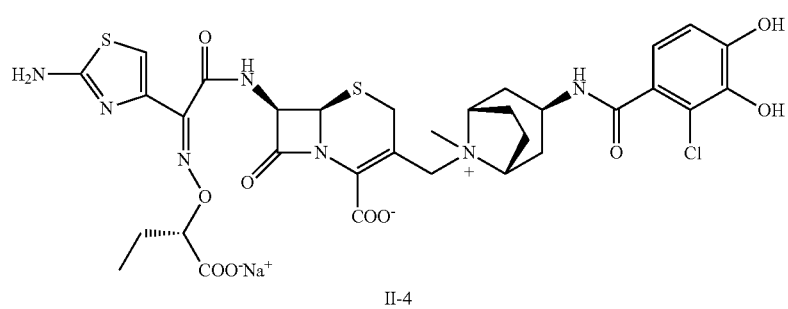

II-4

Step (1): compound ii-4a→compound II-4

Compound ii-4a (819 mg) was used to conduct the same way in step 2 in Example 67 to synthesize and purify a compound. Thereafter, to the fraction containing compound II-4 was added 0.2 N sodium hydroxide to adjust the pH thereof to 7. A piece of dry ice was added to this solution, and then the resultant was concentrated and freeze-dried to yield compound II-4.

$^1$H-NMR (D$_2$O) δ: 0.98 (3H, t, J=7.5 Hz), 1.88 (2H, m), 2.17 (2H, d, J=16.8 Hz), 2.42-2.55 (4H, m), 2.70-2.82 (2H, m), 3.09 (3H, s), 3.48 (1H, d, J=16.8 Hz), 3.93-4.09 (4H, m), 4.23 (1H, t, J=7.20 Hz), 4.51-4.64 (2H, m), 5.37 (1H, d, J=5.0 Hz), 5.86 (1H, d, J=5.0 Hz), 6.86 (1H, d, J=8.4 Hz), 6.90 (1H, d, J=8.4 Hz), 7.00 (1H, s).

Elem. Anal.: C32H35ClN7O10S2(H2O)4.1(NaHCO3)0.4

Calcd.: C, 42.87; H, 4.84; Cl, 3.91; N, 10.80; S, 7.07; Na, 3.55 (%).

Found: C, 42.81; H, 5.03; Cl, 4.19; N, 11.08; S, 7.08; Na, 3.58 (%).

Example 70

Synthesis of Compound (II-5)

[Formula 116]

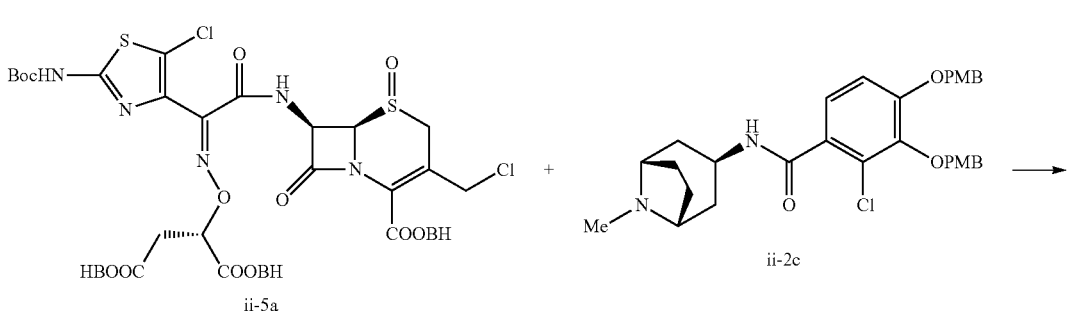

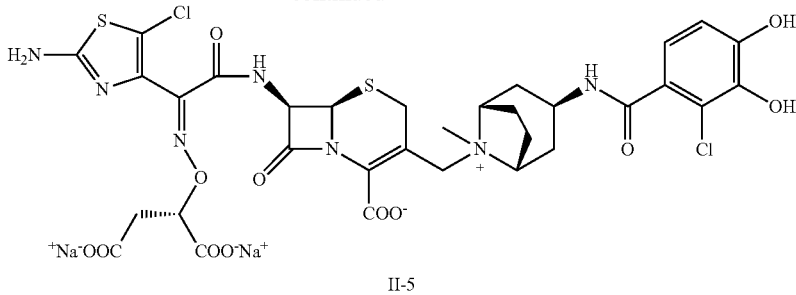

II-5

Step (1): compound ii-5a→compound II-5

The same synthesis method as in step (2) in Example 67 was used to yield, from compound ii-5a (996 mg), compound II-5 (325 mg).

$^1$H-NMR (D$_2$O) δ: 2.17 (2H, d, J=16.2 Hz), 2.36-2.60 (4H, m), 2.71-2.82 (4H, m), 3.09 (3H, s), 3.49 (1H, d, J=16.8 Hz), 3.88-4.02 (3H, m), 4.11 (1H, d, J=13.8 Hz), 4.23 (1H, t, J=7.2 Hz), 4.60 (1H, d, J=13.8 Hz), 4.98 (1H, m), 5.33 (1H, d, J=4.8 Hz), 5.84 (1H, d, J=4.8 Hz), 6.85 (1H, d, J=8.4 Hz), 6.89 (1H, d, J=8.4 Hz).

Elem. Anal.: C32H31Cl2N7NaO12S2(H2O)5.7 (NaHCO3)0.2

Calcd.: C, 38.44; H, 4.27; Cl, 7.05; N, 9.74; S, 6.37; Na, 5.03 (%).

Found: C, 38.43; H, 4.20; Cl, 6.94; N, 9.82; S, 6.18; Na, 5.26 (%).

Example 71

Synthesis of Compound (II-6)

[Formula 117]

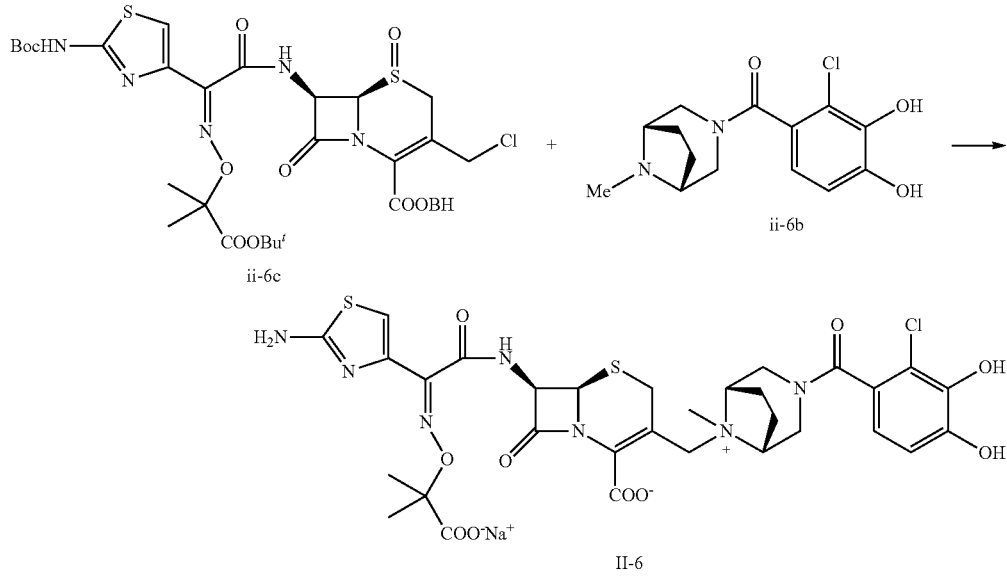

II-6

Step (1): compound ii-6a→compound ii-6b

The same synthesis method as in step (1) in Example 67 was used to yield compound ii-6b (2.30 g) from compound ii-6a (734 mg).

$^1$H-NMR (CDCl$_3$) δ: 1.65-2.04 (4H, m), 2.29 (3H, s), 2.88-3.39 (5H, m), 3.79 (3H, s), 3.83 (3H, s), 4.34 (1H, m), 4.91-5.06 (4H, m), 6.79 (2H, m), 6.82-7.01 (4H, n), 7.29-7.37 (4H, m).

Step (2): compound ii-6b+compound ii-6c→compound II-6

The same method as in step (2) in Example 67 was used to yield compound II-6 (241 mg) from compound ii-6c (678 mg) and compound ii-6b (473 mg).

$^1$H-NMR (D$_2$O) δ: 1.50 (3H, s), 1.51 (3H, s), 2.00-2.38 (2H, m), 2.40-2.61 (2H, m), 3.27 (3H, s), 3.40-3.62 (3H, m), 3.72-4.30 (5H, m), 4.45 (1H, m), 4.65 (1H, m), 5.36 (1H, m), 5.88 (1H, d, J=4.8 Hz) 6.71-7.00 (3H, m).

Elem. Anal.: C31H33ClN7NaO10S2(H2O)7.9(NaHCO3)0.2

Calcd.: C, 39.64; H, 5.22; Cl, 3.75; N, 10.37; S, 6.78; Na, 2.92 (%).

Found: C, 39.58; H, 5.10; Cl, 3.79; N, 10.47; S, 6.91; Na, 2.97 (%).

Example 72
Synthesis of Compound (II-7)
[Formula 118]
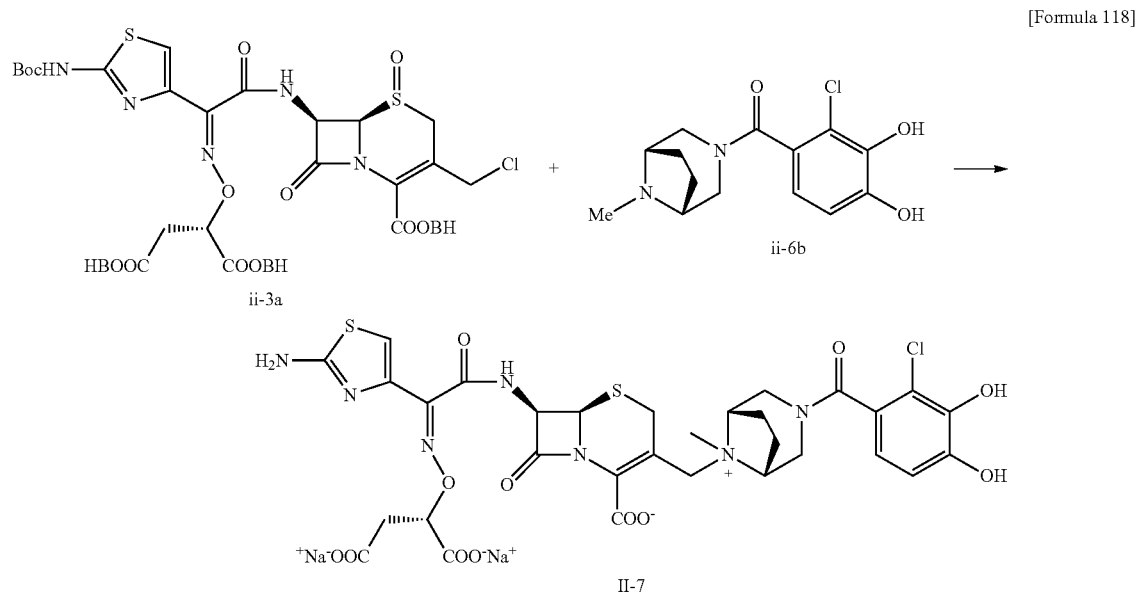
Step (1): compound ii-3a→compound II-7
By the same method as in step (2) in Example 67, compound ii-3a (1.12 g) and compound ii-6b (532 mg) were used to yield compound. II-7 (403 mg).
$^1$H-NMR (D$_2$O) δ: 2.00-2.30 (2H, m), 2.40-2.61 (2H, m), 2.70 (2H, m), 3.28 (3H, s), 3.42-3.62 (3H, m), 3.75-4.32 (5H, m), 4.45 (1H, d, J=15.9 Hz), 4.70 (1H, m), 4.96 (1H, m), 5.33 (1H, m), 5.83 (1H, d, J=2.4 Hz), 6.77-7.00 (3H, m).
Elem. Anal.: C31H30ClN7NaO2O12S2(H2O)7.6
Calcd.: C, 38.18; H, 4.67; Cl, 3.64; N, 10.06; S, 6.58; Na, 4.72 (%).
Found: C, 37.98; H, 4.58; Cl, 3.91; N, 10.04; S, 7.05; Na, 4.86 (%).
Example 73
Synthesis of Compound (II-8)
[Formula 119]
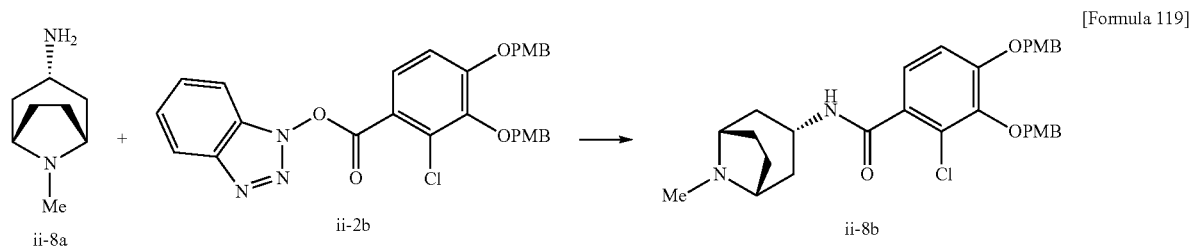
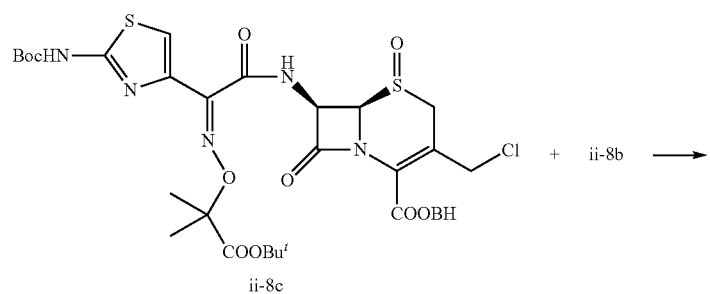

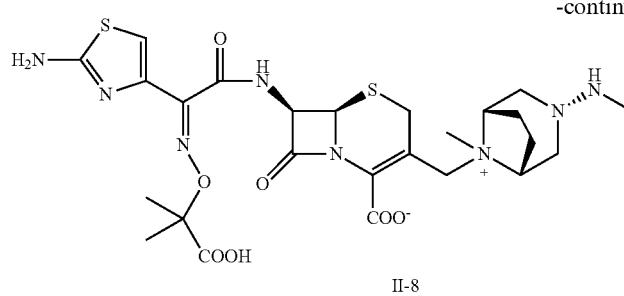

II-8

Step (1): compound ii-8a+compound ii-2b→compound ii-8b

Compound ii-2b (5.46 g, 10 mmol) was added to a solution of compound 11-8a (1.40 g, 10 mmol) in methylene chloride (20 mL), and then the resultant solution was stirred at room temperature for 3 hours. To the reaction liquid was added a 0.2 N aqueous sodium hydroxide solution, and then the resultant liquid was subjected to extraction 3 times with chloroform. The target phase was dried over anhydrous magnesium sulfate and filtrated, and then concentrated under reduced pressure. The precipitated solid was washed with diisopropyl ether containing 5% methylene chloride, and then collected by filtration. This compound was dried under reduced pressure to yield compound ii-8b (5.20 g).

$^1$H-NMR (CDCl$_3$) δ: 1.57-1.78 (4H, m), 1.92-2.01 (4H, s), (3H, s), 3.19 (2H, brs), 3.80 (3H, s), 3.82 (3H, s), 4.30 (1H, m), 4.93 (2H, s), 5.07 (2H, s), 6.03 (1H, d, J=8.4 Hz), 6.82 (2H, m), 6.91 (3H, m), 7.31-7.40 (5H, m).

Step (2): compound ii-8c→compound II-8

By the same method as in step (2) in Example 67, compound ii-8c (749 mg, purity: 99%) and compound ii-8b (485 mol were used to yield compound ii-8 (258 mg).

$^1$H-NMR (D$_2$O) δ: 1.50 (3H, s), 1.52 (3H, s), 2.10-2.60 (8H, m), 3.17 (3H, s), 3.49 (1H, d, J=16.5 Hz), 3.91-4.10 (4H, m), 4.48 (1H, m), 4.62 (1H, d, J=13.8 Hz), 5.36 (1H, d, J=5.1 Hz), 5.88 (1H, d, J=5.1 Hz), 6.85-6.97 (3H, m).

Elem. Anal.: C32H35ClN7NaO$_{10}$S2(H2O)5.9(NaHCO3) 0.1

Calcd.: C, 12.29; H, 5.18; Cl, 3.89; N, 10.75; S, 7.03; Na, 2.77 (%).

Found: C, 42.36; H, 5.23; Cl, 3.96; N, 10.64; S, 6.99; Na, 2.85 (%).

Example 74

Synthesis of Compound (II-9)

[Formula 120]

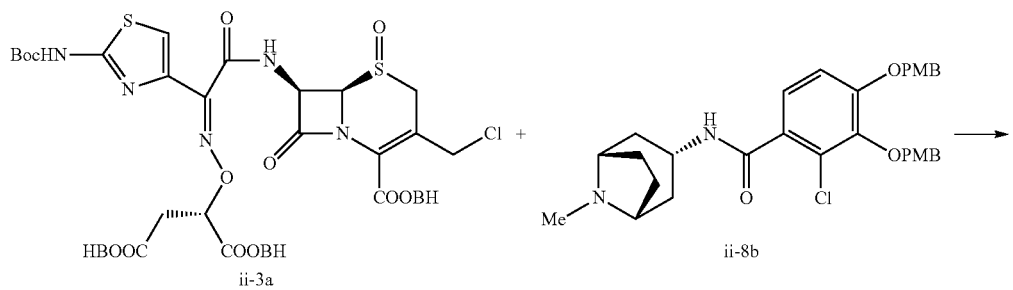

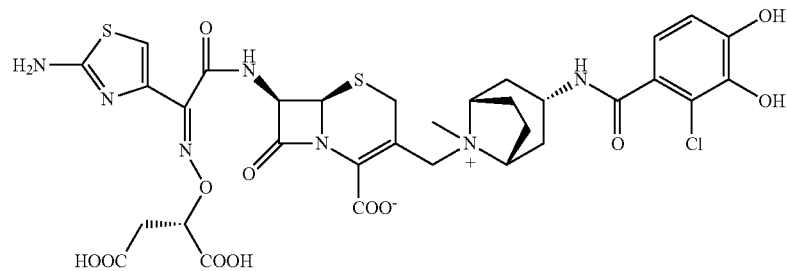

II-9

Step (1): compound ii-3a→compound II-9
By the same method as in step (2) in Example 67, compound ii-3a (1.14 g, purity: 91%) and compound ii-8b (546 ma) were used to yield compound II-9 (186 mg).
¹H-NMR (D₂O) δ: 2.14-2.40 (6H, m), 2.55 (2H, m), 2.71 (2H, m), 3.17 (3H, s), 3.48 (1H, d, J=17.1 Hz), 3.90 (1H, d, J=17.1 Hz), 3.99-4.13 (2H, m), 4.52 (1H, m), 4.60 (1H, d, J=14.4 Hz), 4.97 (1H, m), 5.33 (1H, d, J=5.1 Hz), 5.83 (1H, d, J=5.1 Hz), 6.88 (1H, d, J=8.4 Hz), 6.94 (1H, d, J=8.4 Hz), 7.00 (1H, s).
Elem. Anal.: C32H22ClN7Na2O12S2(H2O)6.0
Calcd.: C, 40.02; H, 4.62; Cl, 3.69; N, 10.21; S, 6.68; Na, 4.79 (%).
Found: C, 40.12; H, 4.71; Cl, 3.81; N, 9.97; S, 6.60; Na, 4.72 (%).
Example 75
Synthesis of Compound (II-10)
[Formula 121]
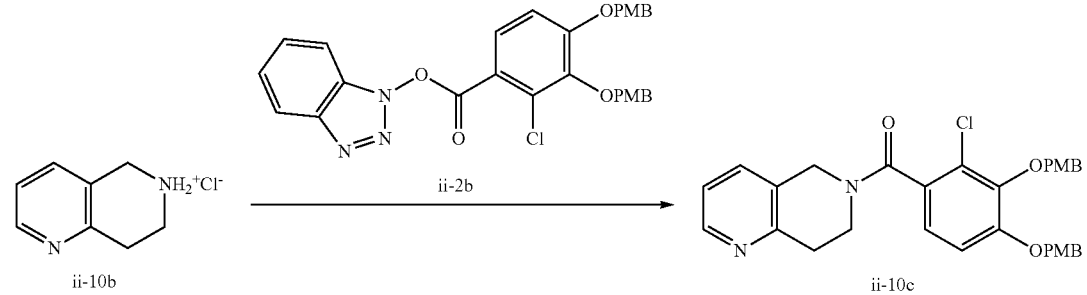
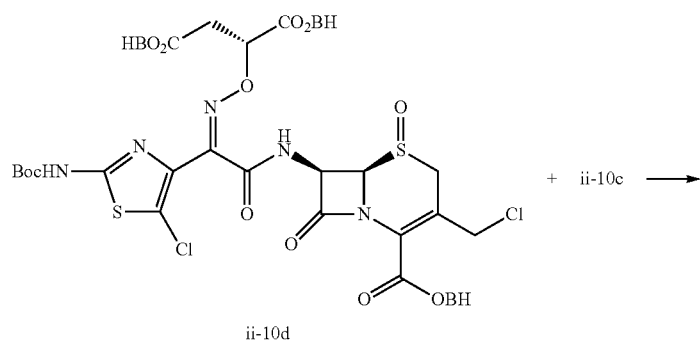
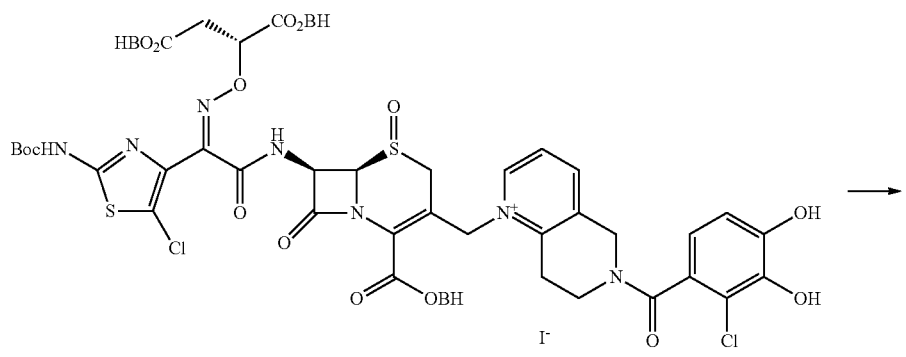

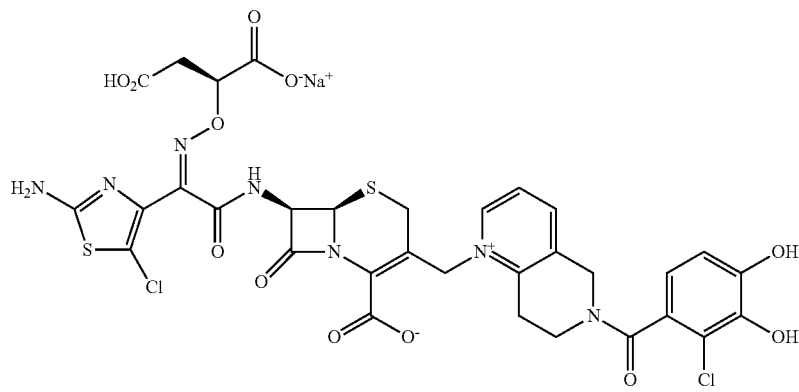

II-10

Step (1): compound ii-10b+compound ii-2b+compound ii-10c

Triethylamine (1.56 mL, 11.25 mmol) was added to a solution of compound ii-10b (1.92 g, 11.25 mmol) in N,N-dimethylformamide (15 mL) while cooled with ice and stirred. The resultant solution was then stirred at room temperature for 10 minutes, and then thereto was added compound ii-2b (6.14 g, 11.25 mmol). The solution was stirred at 60° C. for 4 hours, and then the solvent was distilled off under reduced pressure. The residue was subjected to extraction with ethyl acetate, tetrahydrofuran, and a saturated aqueous potassium carbonate solution. The organic phase was washed with a saturated salt solution, and then dried over magnesium sulfate. Magnesium sulfate was removed, and the organic phase was concentrated and then subjected to silica gel column chromatography. The resultant desired-compound-containing fraction was concentrated and dried under reduced pressure to yield compound ii-10c (3.15 g, yield: 51%)

$^1$H-NMR (CDCl$_3$) δ: 8.44 (1H, d, J=4.5 Hz), 7.50 (1H, d, J=7.6 Hz), 7.37-7.33 (4H, m), 7.18 (1H, dd, J=4.5, 7.6 Hz), 7.11-6.80 (6H, m), 5.09-4.79 (6H, m), 3.34 (3H, s), 3.80 (3H, s), 3.55-2.65 (4H, m).

Step (2): compound ii-10d→compound ii-10e

Compound ii-10d (1.18 g, 1.00 mmol) was dissolved in dimethylacetoamide (3.5 mL), and then the reaction vessel was degassed. Thereafter, thereto was added sodium iodide (300 mg, 2.00 mmol), and the solution was stirred at room temperature for 10 minutes. To this solution was added compound ii-10c (545 mg, 1.00 mmol), and the resultant solution was stirred at room temperature for 6.5 hours. To the reaction liquid were added ethyl acetate and a 0.2 N aqueous hydrochloric acid solution to conduct extraction. Thereafter, the organic phase was washed with a saturated salt solution, and dried over magnesium sulfate. Magnesium sulfate was removed, and the organic phase was concentrated under reduced pressure to yield compound ii-10e (1.10 g)

Step (3): compound ii-10e→compound II-10

The total amount of compound ii-10e yielded in step (2) was dissolved in dichloromethane (18 mL), and the solution was cooled to −40° C. Thereto was added phosphorus tribromide (0.283 mL, 3.00 mmol), and the solution was stirred at −40° C. for 30 minutes. Anisole (1.092 ml, 10.0 mmol) was added to the reaction liquid, and then thereto was added a 2M aluminum chloride solution (5.00 mL, 10.0 mmol) in nitromethane at −40° C. The solution was then stirred at −20° C. to −10° C. for 40 minutes. The reaction liquid was dissolved in a 0.2 N aqueous hydrochloric acid solution and acetonitrile, and then the resultant solution was washed with diisopropyl ether. RP-20SS resin was added to the water phase, and the resultant was concentrated. Thereafter, the liquid condensate was subjected to ODS column chromatography to elute out a desired compound with water/acetonitrile. To the desired-compound-containing fraction was added a 0.2 N aqueous sodium hydroxide solution to convert the compound to a sodium salt thereof. The salt-containing solution was then concentrated under reduced pressure and freeze-dried to yield compound II-10 (303 mg, yield: 34%) as a powder.

MS: 836.21 (M+H).

$^1$H-NMR (D$_2$O) δ: 8.79-7.86 (3H, m), 6.96 (1H, t, J=8.4 Hz), 6.85 (1H, t, J=8.4 Hz), 5.81-4.93 (6H, m), 3.80 (1H, br s), 4.39-3.17 (6H, m), 2.74 (2H, d, J=6.7 Hz).

Elem. Anal. C32H25Cl2N7Na2O12S2(H2O)8.5 (NaCl) 1.5

Calcd.: C, 34.27; H, 3.78; N, 8.74; S, 5.72; Cl, 11.07; Na, 7.18 (%).

Found: C, 34.10; H, 3.51; N, 8.86; S, 6.11; Cl, 11.35; Na, 7.53 (%).

Example 76
Synthesis of Compound (II-11)
[Formula 122]
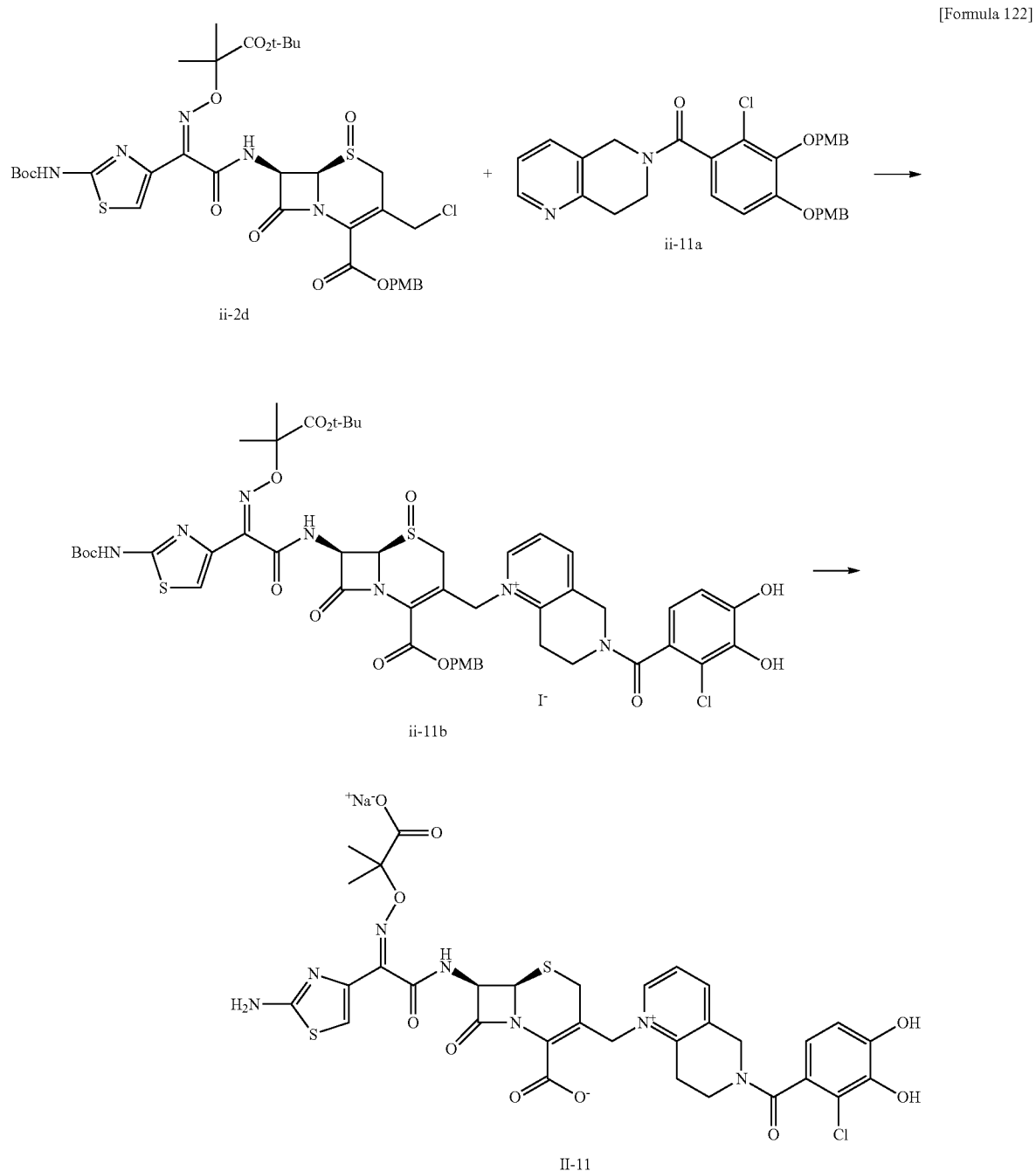
Step (1): compound ii-2d+compound ii-11a→compound ii-11b→compound II-11
Compound ii-2d (796 mg, 1.00 mmol) was treated in the same may as in step (2) followed by step (3) in Example 75 to yield compound II-11 (yielded amount: 341 mg, yield: 36%).
MS: 772.18 (M+H)
$^1$H-NMR (D$_2$O) δ: 8.76 (1H, d, J=5.3 Hz), 8.43-7.82 (2H, m), 6.98-6.82 (3H, m), 5.88 (1H, d, J=4.6 Hz), 5.60-5.10 (4H, m), 4.40-2.91 (7H, m), 1.50 (3H, s), 1.49 (3H, s).
Elem. Anal. C32H29ClN7NaO10S2(H2O)6.0(NaHCO3) 0.01
Calcd.: C, 42.57; H, 4.58; Cl, 3.93; N, 10.86; S, 7.10; Na, 2.57.
Found: C, 43.39; H, 4.34; Cl, 4.21; N, 11.03; S, 7.29; Na, 2.83.

Example 77
Synthesis of Compound (II-12)
[Formula 123]
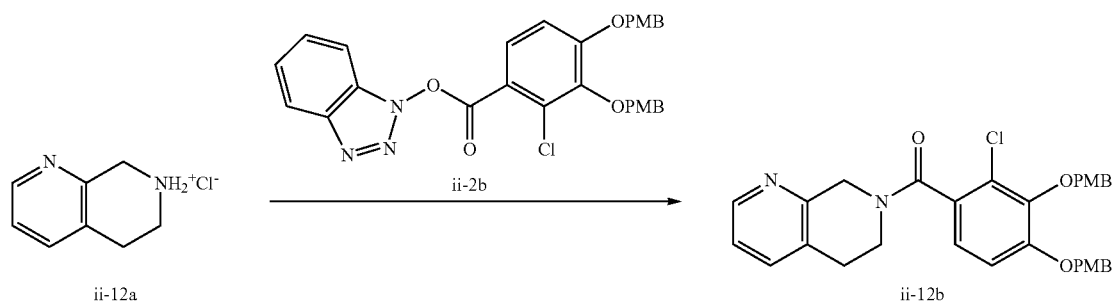
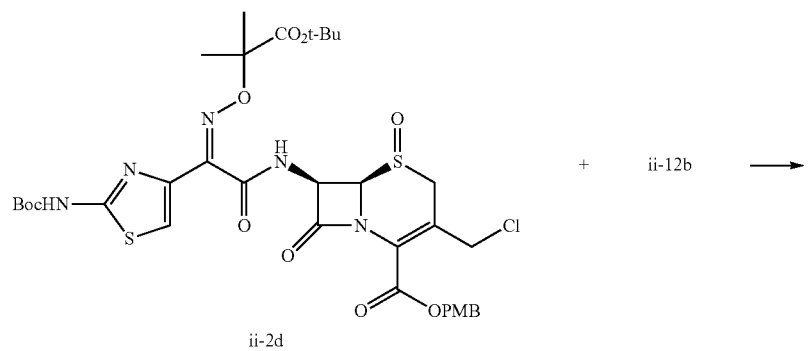
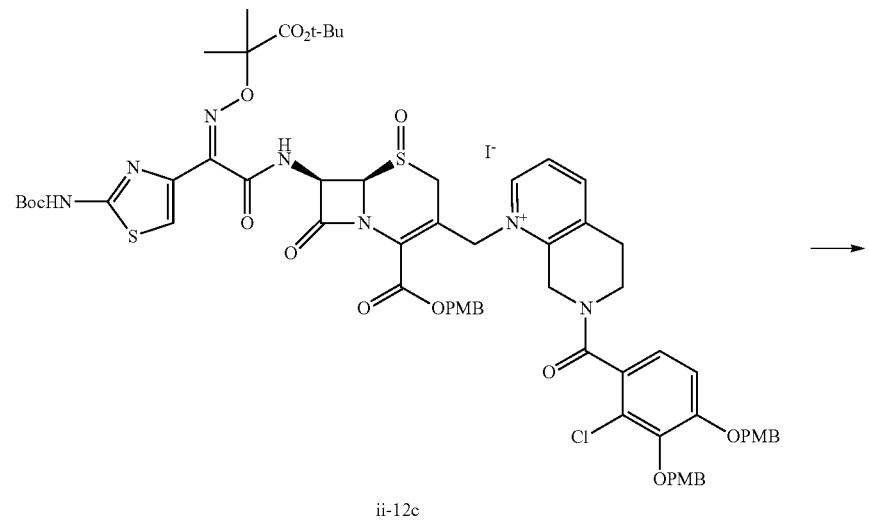

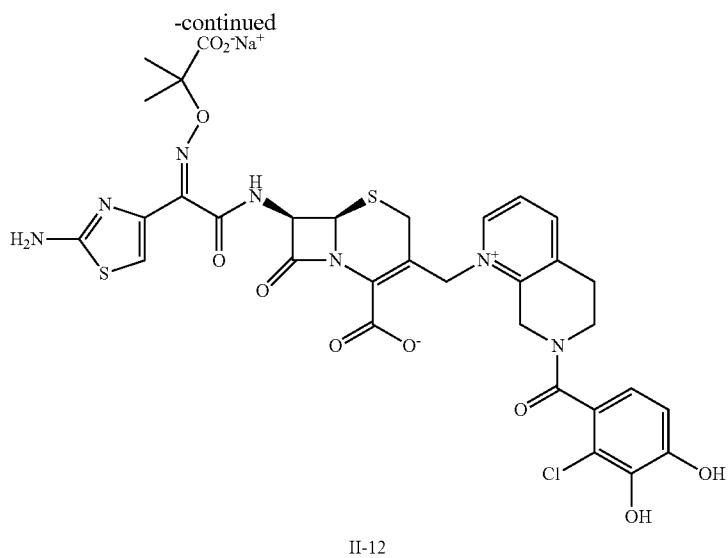

II-12

Step (1): compound ii-12a→compound ii-2b→compound ii-12b

Compound ii-12a (2.00 g, 11.72 mmol) was treated in the same way as in step (1) in Example 75 to yield compound ii-12b (yielded amount: 3.34 g, yield: 52%).

$^1$H-NMR (CDCl$_3$) δ: 8.48-8.34 (1H, m), 7.49-7.31 (5H, m), 7.12 (1H, dd, J=7.5, 4.5 Hz), 7.02-6.89 (4H, m), 6.86-6.83 (2H, m), 5.10-5.07 (8H, m), 4.58-4.40 (1H, m), 4.15-3.96 (1H, m), 3.83 (3H, s), 3.79 (3H, s), 3.52-3.35 (1H, m), 3.00-2.65 (2H, m).

Step (2): compound ii-2d→compound ii-12b→compound II-12

Compound ii-2d (956 mg, 1.20 mmol) was treated in the same way as in step (2) followed by step (3) in Example 75 to yield compound II-12 (yielded amount: 109 mg, yield: 11%).

MS: 773.38 (M+H)

$^1$H-NMR (D$_2$O) δ: 8.82-7.70 (3H, m), 7.03-6.81 (3H, m), 5.92-5.83 (1H, m), 5.46-4.47 (5H, m), 3.78-2.84 (6H, m), 1.51 (3H, s), 1.50 (3H, s).

Elem. Anal. C32H29ClN7NaO10S2(H2O)7.5 (NaCl) 0.5

Calcd.: C, 40.10; H, 4.63; Cl, 5.55; N, 10.23; S, 6.69; Na, 3.60.

Found: C, 40.04; H, 4.41; Cl, 5.32; N, 10.01; S, 7.04; Na, 3.99.

Example 78

Synthesis of Compound (II-13)

[Formula 124]

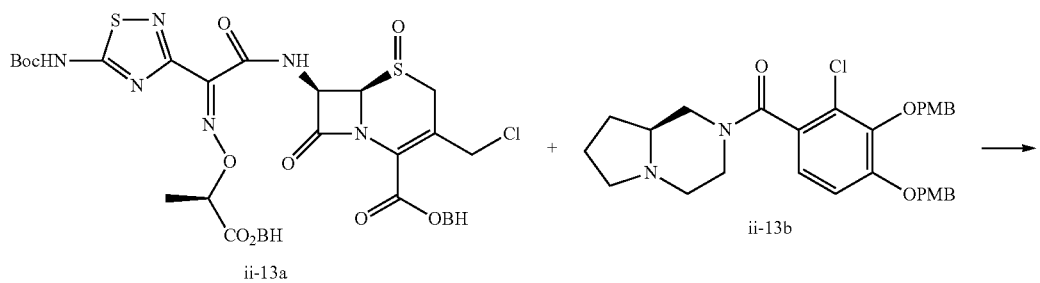

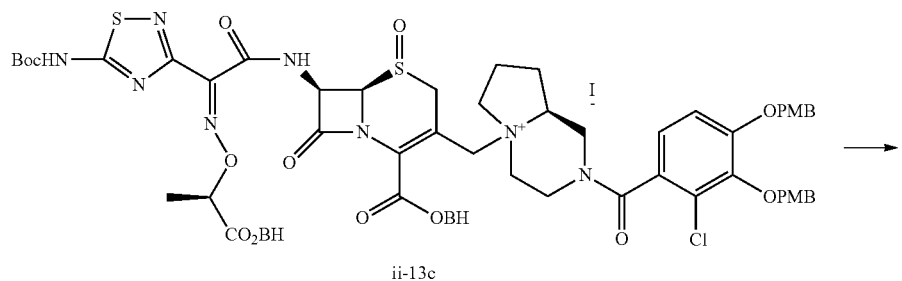

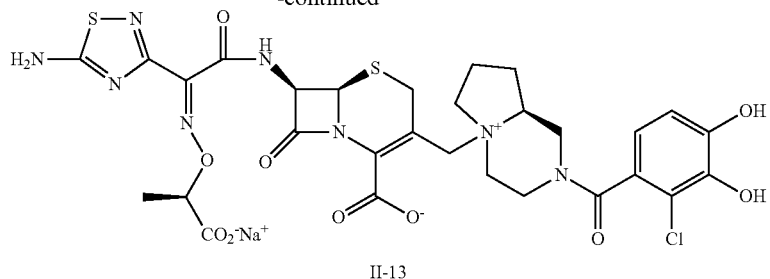
II-13
Step (1): compound ii-13a→compound ii-13b→compound II-13
Compound ii-13a (1.15 g, 1.00 mmol) was treated in the same way as in step (2) followed by step (3) in Example 75 to yield compound 11-13 (yielded amount: 384 mg, yield.: 46%).
MS: 795.39 (M+H)
$^1$H-NMR (D$_2$O) δ: 6.98-6.94 (1H, m), 6.87-6.82 (1H, m), 5.86-5.82 (1H, m), 5.34-5.29 (1H, m), 5.08-5.03 (1H, m), 4.46-3.25 (12H, m), 2.78-2.74 (2H, m), 2.50-1.99 (5H, m).
Elem. Anal. C30H29ClN8Na2O12S2(H3O)9.3 (NaCl) 0.1
Calcd.: C, 35.59; H, 4.74; Cl, 3.85; N, 11.07; S, 6.33; Na, 4.77.
Found: C, 35.64; H, 4.68; Cl, 3.84; N, 11.16; S, 6.32; Na, 4.43.
Example 79
Synthesis of Compound (II-14)
[Formula 125]
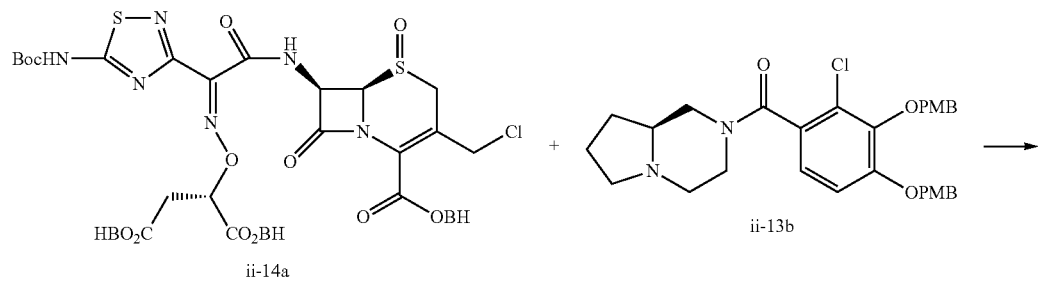
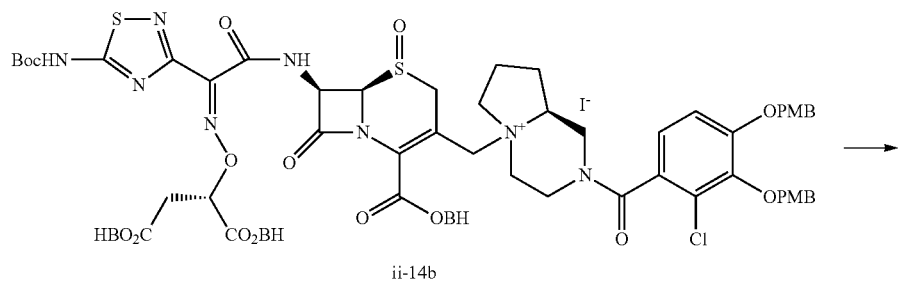
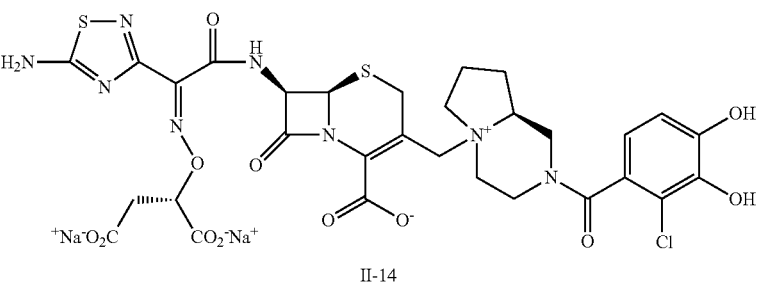
II-14

Step (1): compound ii-14a→compound ii-13b→compound II-14
Compound ii-14a (1.03 g, 1.10 mmol) was treated in the same way as in step (2) followed by step (3) in Example 75 to yield compound II-14 (yielded amount: 256 mg, yield: 33%).
MS: 751.37 (M+H)
$^1$H-NMR (D$_2$O) δ: 6.97-6.93 (1H, m), 6.86-6.81 (1H, m), 5.91-5.87 (1H, m), 5.38-5.33 (1H, m), 4.76-4.72 (1H, m), 4.46-3.24 (13H, m), 2.50-1.98 (4H, m), 1.51 (3H, q, J=3.5 Hz).
Elem. Anal. C29H30ClN8NaO10S2(H2O)5.6(NaHCO3)0.1
Calcd.: C, 39.61; H, 4.72; Cl, 4.02; N, 12.70; S, 7.27; Na, 2.87.
Found: C, 39.68; H, 4.81; Cl, 4.18; N, 12.63; S, 7.20; Na, 2.54.
Example 80
Synthesis of Compound (II-15)
[Formula 126]
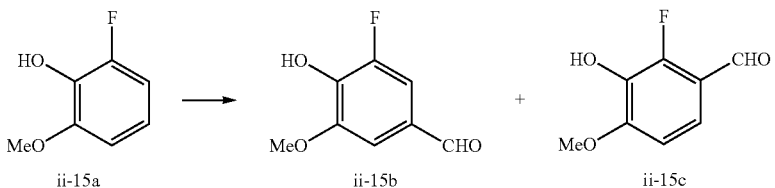
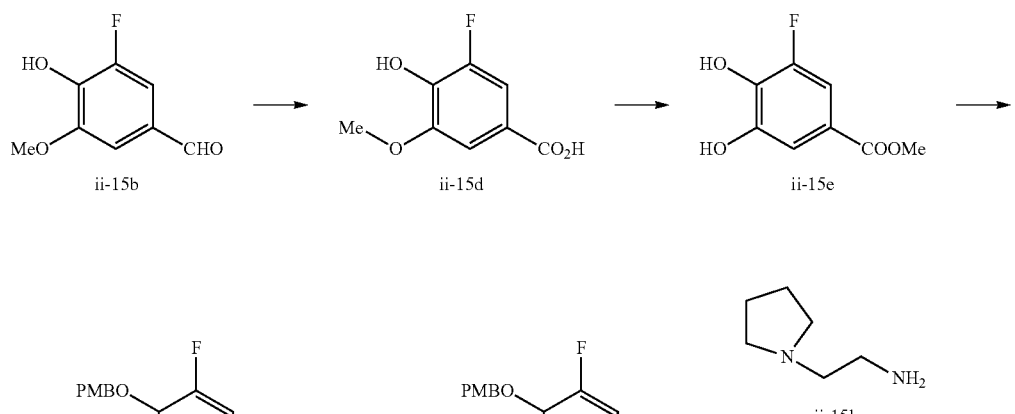
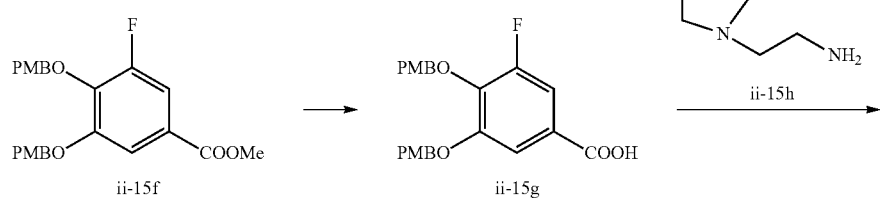
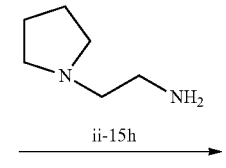
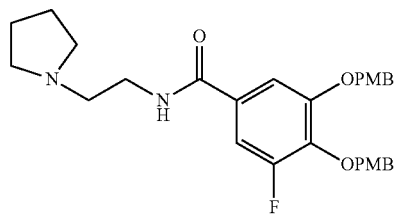
[Formula 127]
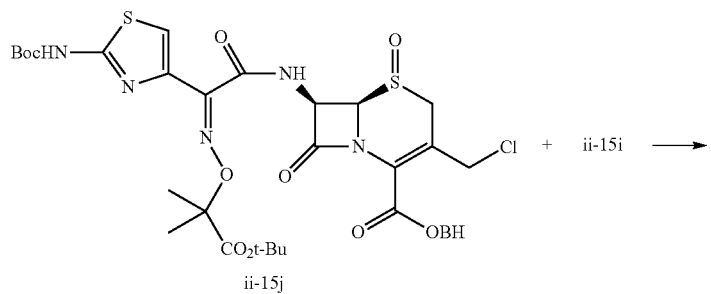

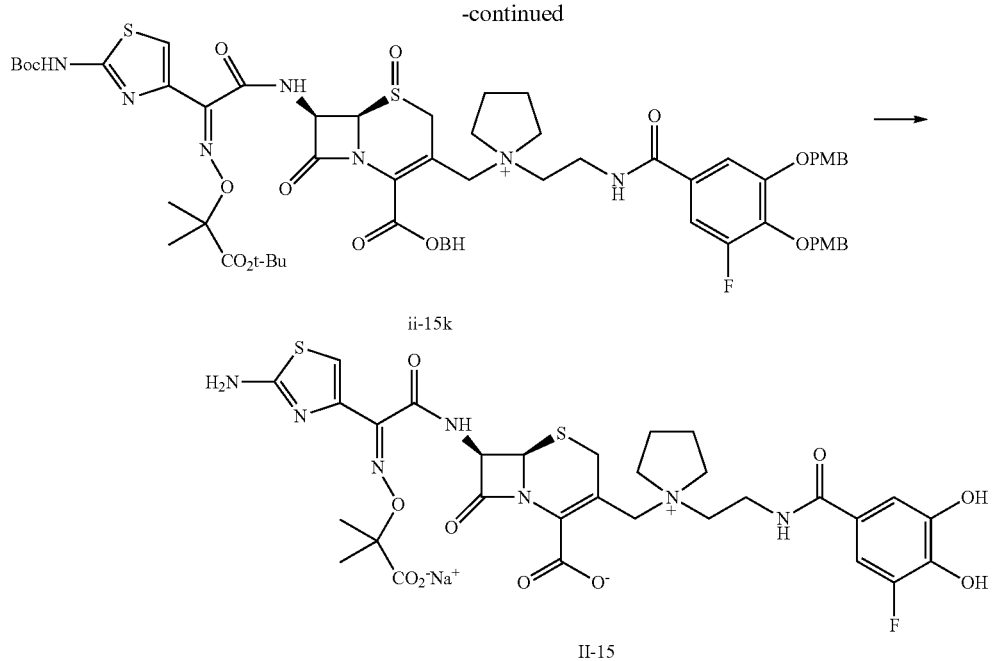

ii-15k

II-15

Step (1): compound ii-15a→compound ii-15b+compound ii-15c

Hexamethylenetetramine (178 g, 1.27 mmol) was dissolved in trifluoroacetic acid (330 ml), and the solution was heated to 80° C. To the solution was dropwise added a solution of compound ii-15a (90 g, 633 mmol) in trifluoroacetic acid (330 mL) over 1.5 hours. Thereafter, the solution was stirred at 80° C. for 1 hour. The reaction liquid was cooled to room temperature, and thereto was added a 20% aqueous sodium carbonate solution to adjust the pH thereof to 8. Thereafter, a 2 N aqueous hydrochloric acid solution was used to adjust the pH to 4. The liquid was subjected to extraction with ethyl acetate, and then activated carbon and magnesium sulfate were added to the target phase. The solution was subjected to filtration. The solution was concentrated while the residue was subjected to silica chromatography. The resultant desired-compound-containing fraction was concentrated and dried under reduced pressure to yield each of compound ii-15b (38.8 g, yield: 36%) and compound ii-15c (28.0 g, yield: 26%).

$^1$H-NMR (DMSO-$d_6$) δ: 10.48 (1H, s), 9.77 (1H, s), 7.39 (1H, d, J=10.2 Hz), 7.34 (1H, s), 3.89 (3H, s) 15b $^1$H-NMR (DMSO-$d_6$) δ: 10.02 (1H, s), 9.65 (1H, s), 7.31 (1H, dd, J=8.1, 8.1 Hz), 6.98 (1H, d, J=8.1 Hz), 3.90 (3H, s). 15c

Step (2): compound ii-15b→compound ii-15d

Amide sulfuric acid (48.7 g, 501 mmol) and water (750 mL) were added to a solution of compound ii-15b (38.8 g, 228 mmol) in dioxane (750 mL). The resultant solution was stirred while cooled with ice. To the solution was added sodium chlorite (45.3 g, 501 mmol). While cooled with ice, the solution was stirred for 30 minutes, and then thereto was dropwise added a 25% aqueous sodium hydrogensulfite solution (100 mL). Next, the resultant was subjected to extraction with ethyl acetate, and the organic phase was washed with a saturated salt solution. The solution was dried over magnesium sulfate. Magnesium sulfate was filtrated off, and then the solution was concentrated. The residue was dried under reduced pressure to yield compound ii-15d (42.6 g, yield: 100%).

$^1$H-NMR (DMSO-$d_6$) δ: 10.08 (1H, s), 7.33-7.29 (2H, m), 3.85 (3H, s).

Step (3): compound ii-15d→compound ii-15e

Boron tribromide (64.9 mL, 687 mmol) was dropwise added to a solution of compound ii-15d (42.5 g, 228 mmol) in methylene chloride (480 mL) while cooled with ice. The resultant solution was then stirred at room temperature for 2 hours. To the solution was added methanol (720 mL). The resultant solution was then stirred at room temperature overnight. Thereto was added ice water, and this liquid system was subjected to extraction with ethyl acetate. Thereafter, the organic phase was washed with a saturated salt solution. The solution was dried over magnesium sulfate, and magnesium sulfate was filtrated off. The solution was then concentrated. The residue was dried under reduced pressure to yield compound ii-15e (80.9 g).

$^1$H-NMR (DMSO-$d_6$) δ: 9.98 (1H, br s), 7.24-7.14 (2H, m), 3.78 (3H, s>.

Step (4): compound ii-15e→compound ii-15f

Potassium carbonate (145 g, 1.05 mg), sodium iodide (10.3 g, 68.7 mmol) and p-methoxybenzyl chloride (108 mL, 790 mmol) were successively added to a solution of compound ii-15e (42.5 g, 228 mmol) in N,N-dimethylformamide (420 mL), and then the resultant solution was stirred at 50° C. for 4 hours. Furthermore, thereto was added p-methoxybenzyl chloride (15 mL, 110 mmol), and the solution was stirred at 50° C. for 2 hours. The solution was cooled to room temperature, and thereto were added ethyl acetate (1 L) and distilled water (1 L) to conduct extraction. The organic phase was washed with a saturated salt solution. The solution was dried over magnesium sulfate, and magnesium sulfate was filtrated off. The solution was then concentrated. The residue was subjected to silica chromatography. The resultant desired-compound-containing fraction was then concentrated, and dried under reduced pressure to yield compound ii-15f (53.0 g, yield: 51%).

$^1$H-NMR (CDCl$_3$) δ: 7.46-7.24 (6H, m), 6.93-6.88 (2H, m), 6.82-6.77 (2H, m), 5.09 (2H, s), 5.06 (2H, s), 3.88 (3H, s), 3.82 (3H, s), 3.78 (3H, s).

Step (5): compound ii-15f→compound ii-15g

A 2 N aqueous sodium hydroxide solution (110 mL, 220 mmol) was added to a solution of compound ii-15f (47.0 g, 110 mmol) in tetrahydrofuran (250 mL) and methanol (250 mL). The solution was then stirred for 1.5 hours while heated and refluxed. The solution was cooled to room temperature, and thereto was added 2 N hydrochloric acid (130 mL). The resultant was concentrated. The resultant residue was filtrated, and the target phase was washed with tetrahydrofuran and then dried under reduced pressure to yield compound ii-15g (41.9 g, yield: 92%).

$^1$H-NMR (CDCl$_3$) δ: 7.50-7.44 (2H, m), 7.35 (2H, d, J=8.5 Hz), 7.28 (2H, d, J=8.5 Hz), 6.92 (2H, d, J=8.5 Hz), 6.81 (2H, d, J=8.5 Hz), 5.12 (2H, s), 5.08 (2H, s), 3.83 (3H, s), 3.79 (3H, s).

Step (6): compound ii-15g→compound ii-15i

Compound ii-15g (0.475 g, 1.15 mmol) was treated in the same way as described in Japanese Patent Application No. 2010-087131 to yield compound ii-15i (0.586 g, yield: 100%).

$^1$H-NMR (DMSO-d$_6$) δ: 8.46 (1H, dr s), 7.48-7.41 (3H, m), 7.31 (1H, d, J=10.1 Hz), 7.24 (2H, d, J=8.0 Hz), 6.98 (2H, d, J=8.0 Hz), 6.85 (2H, d, J=8.0 Hz), 5.13 (2H, s), 5.01 (2H, s), 3.78 (3H, s), 3.73 (3H, s), 3.41-2.50 (8H, n), 1.70-1.65 (4H, m).

Step (7): compound ii-15j→compound II-15

Compound ii-1.5j (970 mg, 1.15 mmol) was treated in the same way as in step (2) followed by step (3) in Example 75 to yield compound II-15 (yielded amount: 350 mg, yield: 40%).

$^1$H-NMR (D$_2$O) δ: 7.12-7.09 (2H, m), 6.94 (1H, s), 5.86 (1H, d, J=4.5 Hz), 5.36 (1H, d, J=4.5 Hz), 4.10 (1H, d, J=12.6" Hz), 3.95-3.84 (2H, m), 3.74-3.43 (9H, m), 2.22 (4H, s), 1.51 (3H, s), 1.50 (3H, s).

MS: 736.49 (M+H)

Elem. Anal. C31H32Cl2N7NaO10S2(H2O)4.6 (NaHCO3)0.1

Calcd.: C, 41.52; H, 5.17; F, 2.18; N, 11.26; S, 7.37; Na, 2.90.

Found: C, 41.48; H, 5.03; F, 2.20; N, 11.32; S, 7.67; Na, 2.92.

Example 81

Synthesis of Compound (II-16)

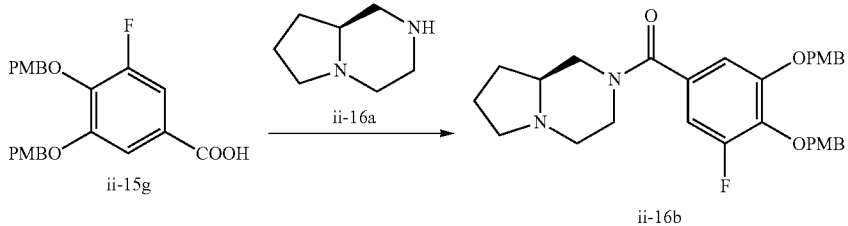

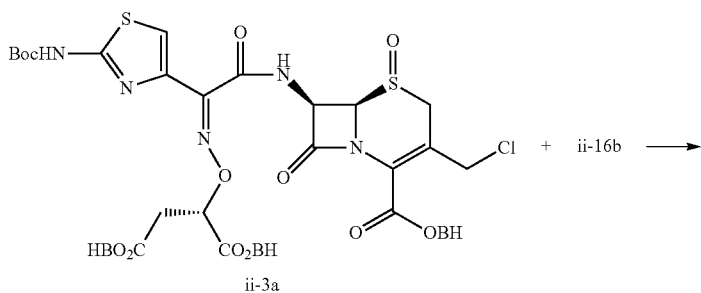

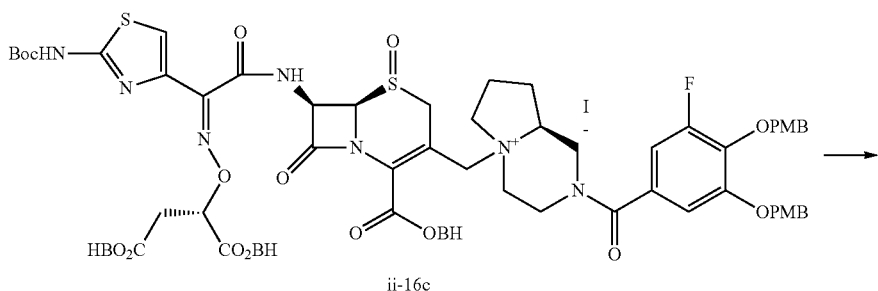

-continued

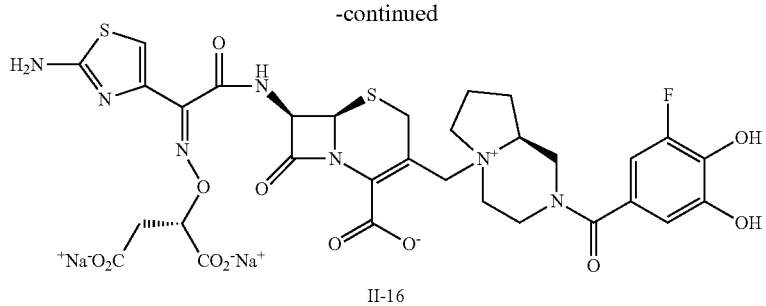

II-16

Step (1): compound ii-15g→compound ii-16b

Compound ii-15g (0.475 g, 1.15 mmol) was treated in the same way as in step (6) in Example 80 to yield compound ii-16b (0.600 g, yield: 100%).

$^1$H-NMR (DMSO-$d_6$) δ: 7.40 (2H, d, J=8.3 Hz), 7.27 (2H, d, J=2.3 Hz), 6.97-6.94 (3H, m), 6.87-6.82 (3H, m), 5.13 (2H, s), 4.99 (2H, s), 3.76 (3H, s), 3.73 (3H, s), 1.97-1.94 (13H, m).

Step (2): compound ii-3a→compound II-16

Compound ii-3a (1.29 g, 1.12 mmol) was treated in the same way as in step (2) followed by step (3) in Example 75 to yield compound II-16 (yielded amount: 295 mg, yield: 32%).

MS: 778.46 (M+H)

$^1$H-NMR (D$_2$O) δ: 7.01 (1H, s), 6.92-6.84 (2H, m), 5.83 (1H, d, J=4.3 Hz), 5.33 (1H, d, J=4.3 Hz), 5.00-4.96 (1H, m), 4.88-3.46 (13H, m), 2.76-1.95 (6H, m).

Elem. Anal. C31H30FN7Na2O12S2(H2O)7.1(NaHCO3) 0.1

Calcd.: C, 38.99; H, 4.66; F, 1.98; N, 10.23; S, 6.69; Na, 5.04.

Found: C, 38.91; H, 4.67; F, 1.85; N, 10.43; S, 6.97; Na, 4.91.

Example 82

Synthesis of Compound (II-17)

[Formula 129]

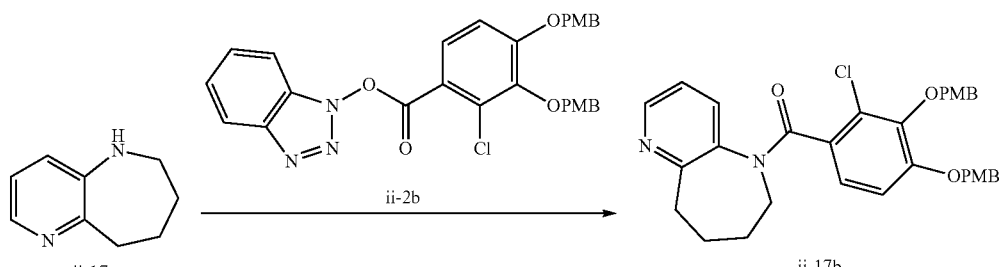

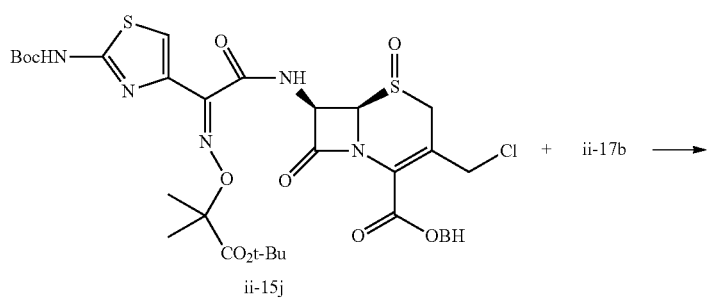

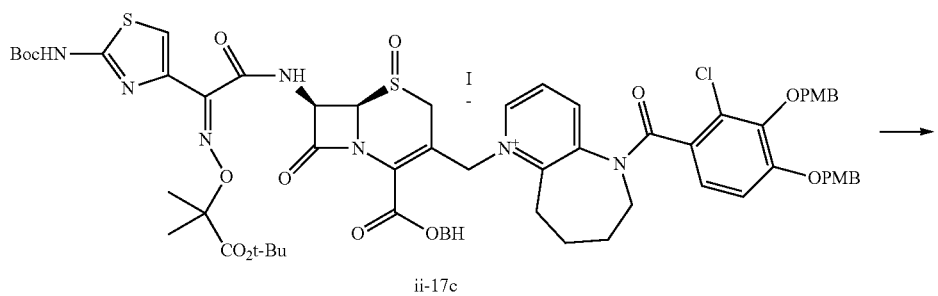

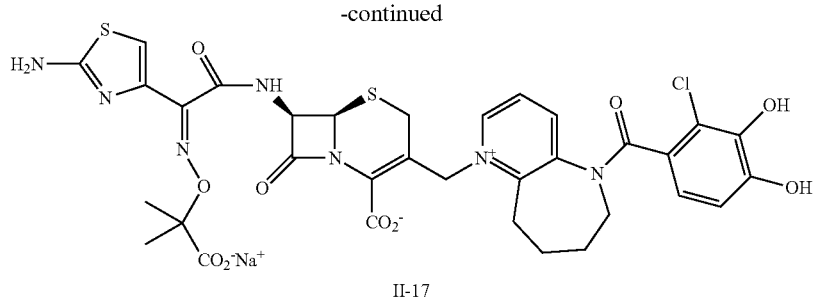

II-17

Step (1): compound ii-17a→compound ii-17b

Compound ii-17b (1.00 g, 6.75 mmol) synthesized in the same way as in U.S. Pat. No. 5,532,235 A1 (1996) was treated in the same way as in step (1) in Example 75 to yield compound ii-17b (yielded amount: 1.65 g, yield: 44%).

$^1$H-NMR (CDCl$_3$) δ: 8.45-6.62 (13H, m), 4.93-4.88 (4H, m), 3.84-3.79 (6H, m), 3.16-1.27 (8H, m).

Step (2): compound ii-15j→compound II-17

Compound ii-15j (0.678 g, 0.805 mmol) was treated in the same way as in step (2) followed by step (3) in Example 75 to yield compound 11-17 (yielded amount: 189 mg, yield: 29%).

MS: 786.57 (M+H)

$^1$H-NMR (D$_2$O) δ: 8.91-6.97 (6H, m), 5.99-5.11 (2H, m), 4.62-1.43 (18H, m).

Elem. Anal. C33H31ClN7NaO10S2(H2O)8.3(NaHCO3)0.1

Calcd.: C, 41.15; H, 4.98; Cl, 3.67; N, 10.15; S, 6.64; Na, 2.62.

Found: C, 40.98; H, 4.79; Cl, 3.51; N, 10.51; S, 7.20; Na, 2.82.

Example 83

Synthesis of Compound (II-18)

[Formula 130]

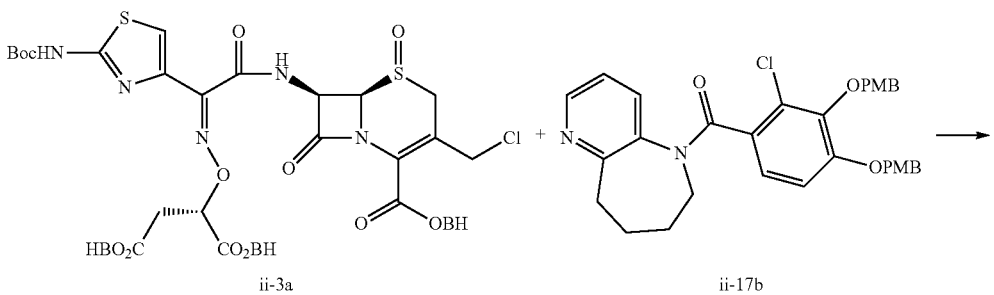

ii-3a      ii-17b

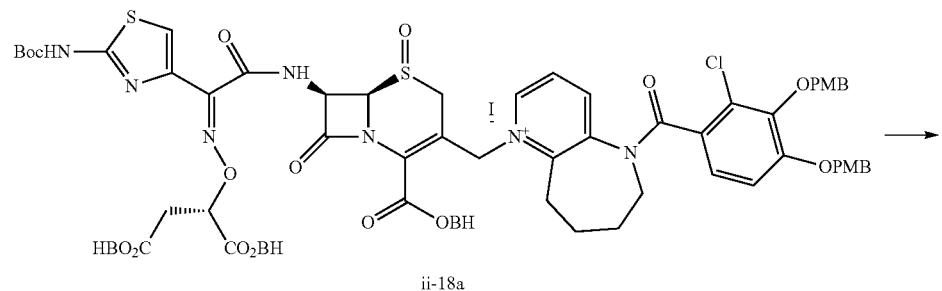

ii-18a

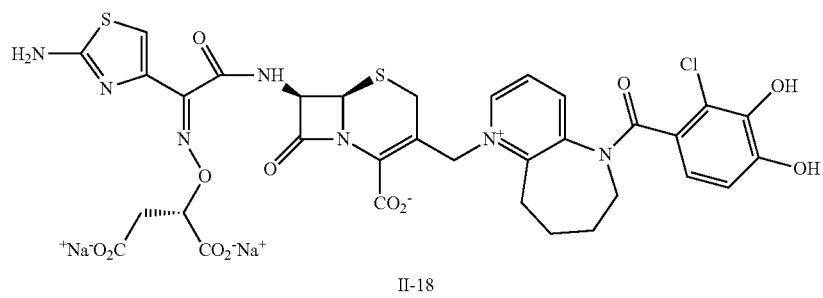

II-18

Step (1): compound ii-3a→compound II-18
Compound ii-3a (0.925 g, 0.805 mmol) was treated in the same way as in step (2) followed by step (3) in Example 75 to yield compound II-18 (yielded amount: 245 mg, yield: 35%).
MS: 816.51 (M+H)
$^1$H-NMR (D$_2$O) δ: 8.93-7.01 (6H, m), 5.84-4.94 (3H, m), 4.66-2.69 (8H, m), 2.23-1.56 (6H, m).
Elem. Anal. C33H28ClN7Na2O12S2(H2O)5.6(NaHCO3)0.1
Calcd.: C, 41.01; H, 4.09; Cl, 3.66; N, 10.11; S, 6.61; Na, 4.98.
Found: C, 41.36; H, 4.35; Cl, 4.30; N, 9.85; S, 6.01; Na, 4.16.
Example 84
Synthesis of Compound (II-19)
[Formula 131]
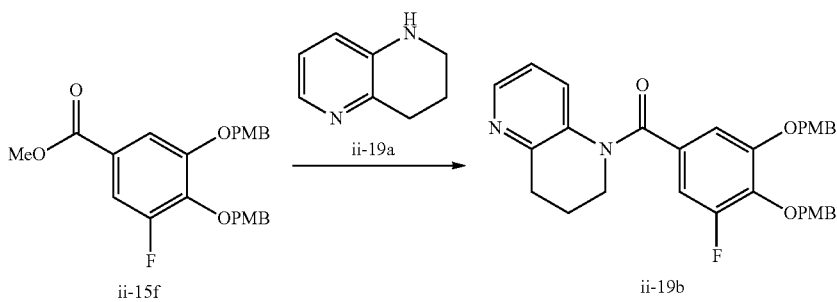
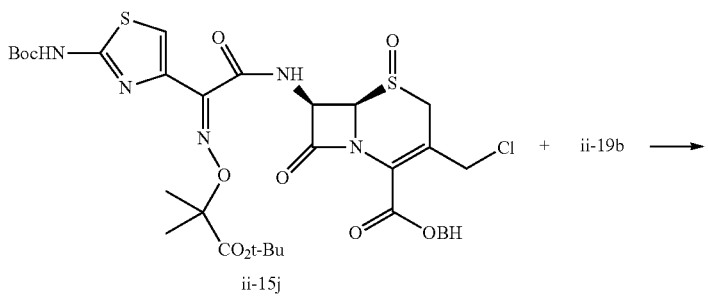
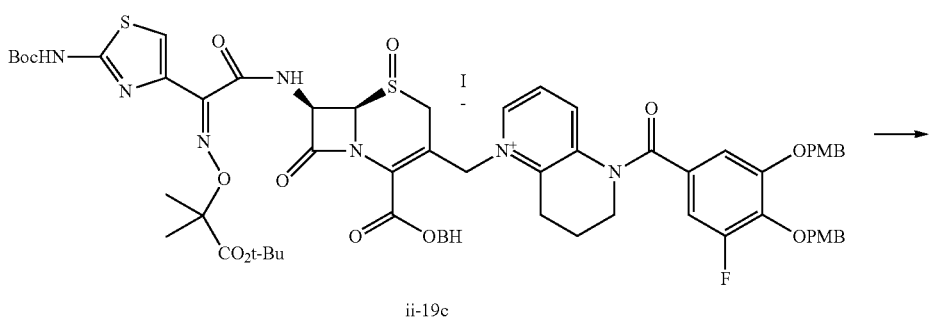
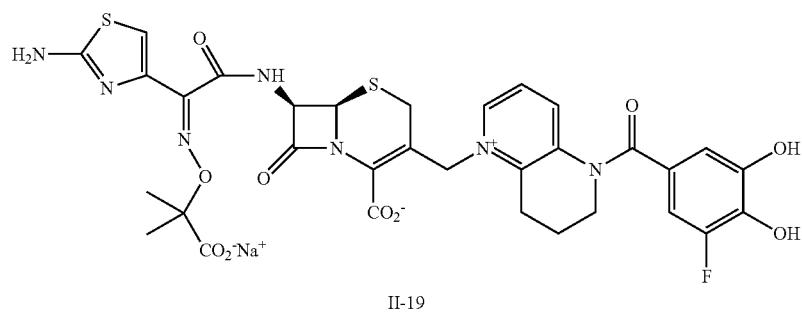

Step (1): compound ii-15f→compound ii-19b

To a solution of compound ii-19a (0.470 g, 3.50 mmol) in tetrahydrofuran (420 mL) was dropwise added a 2.75 M n-butyllithium solution (2.80 mL, 7.70 mmol) in hexane while cooled with ice. The resultant solution was stirred for 10 minutes while cooled with ice. To the solution was added compound ii-15f (1.49 g, 3.50 mmol). The solution was stirred for 30 minutes while cooled with ice. Thereto were added 0.02 N hydrochloric acid and ethyl acetate. This liquid system was made to room temperature, and then subjected to extraction. The organic phase was washed with a saturated salt solution, and dried over magnesium sulfate. Magnesium sulfate was removed, and then the resulting solution was concentrated. The residue was subjected to silica chromatography. The resultant desired-compound-containing fraction was concentrated and dried under reduced pressure to yield compound ii-19b (0.758 g, yield: 41%).

$^1$H-NMR (CDCl$_3$) δ: 8.26 (1H, d, J=4.5 Hz), 7.29-6.73 (12H, m), 5.06 (2H, s), 4.93 (2H, s), 3.82-3.79 (6H, m), 3.04 (2H, t, J=6.8 Hz), 2.11-2.02 (2H, m), 1.60-1.57 (2H, m).

Step (2): compound ii-15j→compound II-19

Compound ii-15j (0.842 g, 1.00 mmol) was treated in the same way as in step (2) followed by step (3) in Example 75 to yield compound II-19 (yielded amount: 265 mg, yield: 34%).

$^1$H-NMR (D$_2$O) δ: 8.59 (1H, d, J=6.2 Hz), 8.26 (1H, d, J=8.5 Hz), 7.70 (1H, dd, J=8.5, 6.2 Hz), 7.03-6.97 (2H, m), 6.89 (1H, s), 5.89 (1H, d, J=4.8 Hz), 5.56 (1H, d, J=15.6 Hz), 5.36 (1H, d, J=15.6 Hz), 5.29 (1H, d, J=4.8 Hz), 4.03-3.85 (2H, m), 3.57 (1H, d, J=16.0 Hz), 3.31-3.26 (3H, m), 2.21-2.17 (2H, m), 1.51 (3H, s), 1.49 (3H, s)

Elem. Anal. C32H29FN7NaO10S2(H2O)5.3(NaHCO3)0.1

Calcd.: C, 43.73; H, 4.54; F, 2.15; N, 11.12; S, 7.27; Na, 2.87.

Found: C, 43.70; H, 4.50; F, 2.26; N, 11.05; S, 7.32; Na, 2.78.

Example 85

Synthesis of Compound (II-20)

[Formula 132]

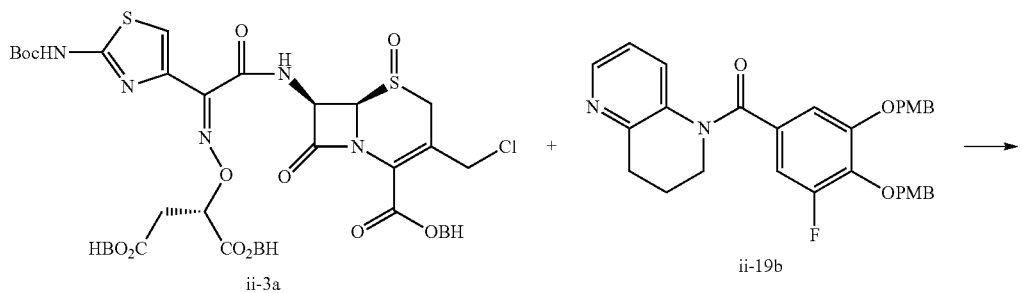

ii-3a    ii-19b

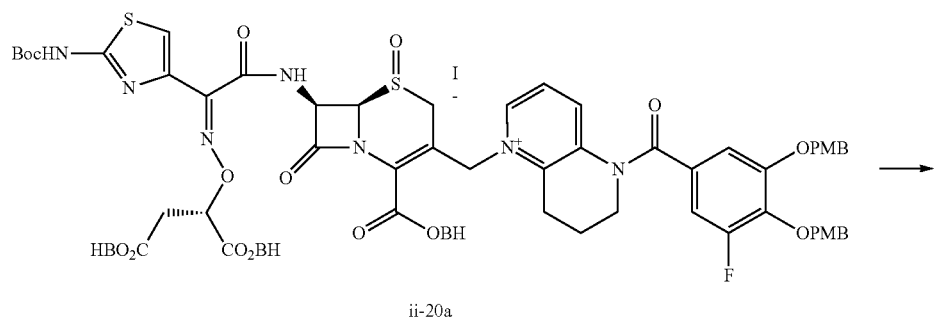

ii-20a

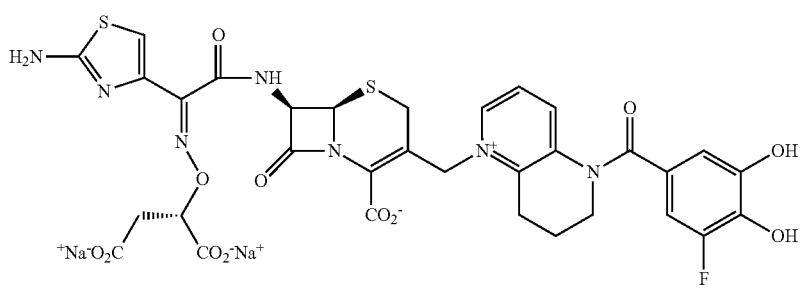

II-20

Step (1): compound ii-3a→compound II-20

Compound ii-3a (1.15 g, 1.00 mmol) was treated in the same way as in step (2) followed by step (3) in Example 75 to yield compound II-20 (yielded amount: 168 mg, yield: 20%).

$^1$H-NMR (D$_2$O) δ: 8.60 (1H, d, J=6.3 Hz), 8.27 (1H, d, J=8.6 Hz), 7.72 (1H, dd, J=8.6, 6.3 Hz), 7.04-7.00 (2H, m), 6.90-6.89 (1H, m), 5.84 (1H, d, J=4.8 Hz), 5.56 (1H, d, J=15.5 Hz), 5.37 (1H, d, J=15.5 Hz), 5.26 (1H, d, J=4.8 Hz), 4.99-4.94 (1H, m), 4.01-3.86 (2H, m), 3.54 (1H, d, J=17.7 Hz), 3.32-3.28 (3H, m), 2.73-2.70 (2H, m), 2.23-2.16 (2H, m).

Elem. Anal. C32H26FN7Na2O12S2(H2O)7.1(NaHCO3)0.1

Calcd.: C, 39.91; H, 4.20; F, 1.97; N, 10.15; S, 6.64; Na, 5.00.

Found: C, 39.91; H, 4.22; F, 1.99; N, 10.19; S, 6.72; Na, 4.60.

Example 86

Synthesis of Compound (II-21)

to extraction with ethyl acetate. The organic phase was washed with 0.1 N hydrochloric acid, purified water and a saturated salt solution in turn, and then dried over anhydrous magnesium sulfate. Magnesium sulfate was filtrated off from the organic phase, and then the solvent was distilled off therefrom under reduced pressure to yield compound ii-21c.

The total amount of compound ii-21c yielded was dissolved in dichloromethane (15 mL), and the solution was cooled to −40° C. Thereto was added phosphorus tribromide (0.189 mL, 2 mmol), and the solution was stirred at −40° C. After the end of the reaction, to the reaction liquid were added anisole (1.09 mL, 10 mmol) and a 2 mol/L aluminum chloride solution (5 mL, 10 mmol) in nitromethane. The resultant solution was stirred at −20° C. for 30 minutes. To the reaction liquid were added purified water (15 mL) and diisopropyl ether (30 mL). To the reaction liquid were added acetonitrile and 2N hydrochloric acid to dissolve the precipitate. Thereafter, the water phase was separated therefrom. The organic phase was subjected to extraction with a mixed liquid of water, acetonitrile and diluted hydrochloric acid. To the com-

[Formula 133]

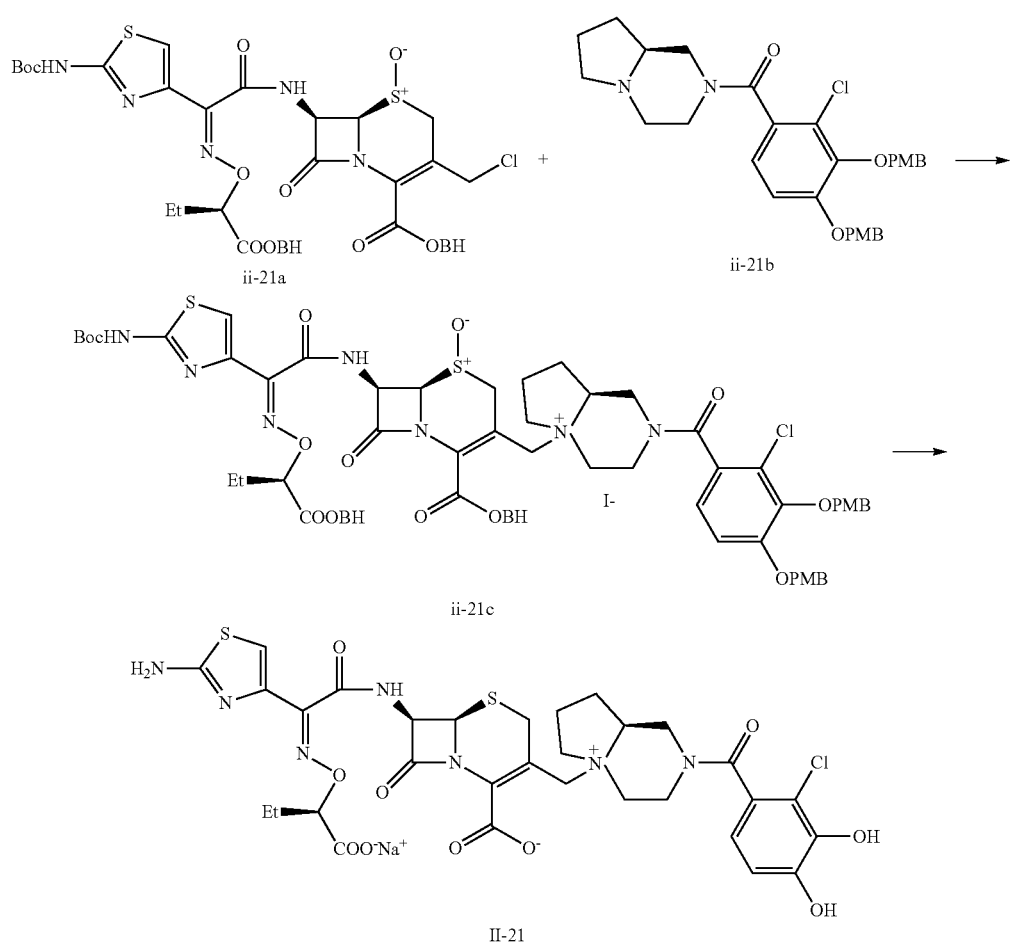

Step (1): compound ii-21a→compound II-21

Compound ii-21a (1.003 g corresponding to 1 mmol) was dissolved in N,N-dimethylacetoamide (4.5 mL), and thereto was added compound ii-21b (537 mg, 1 mmol). The resultant was stirred at room temperature for 6 hours. Purified water was added to the reaction liquid, and this liquid was subjected bined water phases was added HP20SS, and the resultant was concentrated. The concentrated suspension was subjected to HP20SS/ODS column chromatography. The target-material-containing fraction eluted out with water and acetonitrile was converted to a Na salt thereof by use of a 0.2 N aqueous sodium hydroxide solution. The salt-containing liquid was concentrated under reduced pressure, and then the liquid concentrate was freeze-dried to yield compound II-21 as a powder (yielded amount: 429 mg, yield: 55%).

MS (m+1)=764.2

Elem. Anal.: C31H33ClN7O10S2Na (H2O)6.8

Calcd.: C, 41.38; H, 5.11; Cl, 3.94; N, 10.90; S, 7.13.

Found: C, 41.37; H, 5.07; Cl, 3.96; N, 10.64; S, 7.18.

$^1$H-NMR (D$_2$O) δ: 7.02-6.90 (2H, m), 6.88-6.78 (1H, m), 5.89-5.83 (1H, brm), 5.40-5.31 (1H, brm), 4.52-4.19 (3H, m), 4.06-3.37 (10H, m), 2.55-1.78 (7H, m), 1.04-0.93 (3H, br m).

Example 87

Synthesis of Compound (II-22)

Step (1): compound ii-22a→compound II-22

Compound ii-22a (1.615 g, 1 mmol) was treated in the same way as in step (1) in Example 86 to yield compound II-22 (yielded amount: 372 mg, yield.: 45%).

MS (m+1)=798.29

Elem. Anal.: C31H32Cl2N7O10S2Na (H2O)6.2

Calcd.: C, 39.93; H, 4.80; Cl, 7.61; N, 10.52; S, 6.88.

Found: C, 40.10; H, 4.75; Cl, 7.44; N, 10.10; S, 6.75.

1H-NMR (D2O) δ: 6.99-6.92 (1H, m), 6.89-6.79 (1H, m), 5.89-5.86 (1H, br m), 5.35 (1H, dd, J=8.1, 5.0 Hz), 4.54-4.45 (2H, m), 4.42-4.23 (2H, m), 4.01-3.42 (12H, m), 2.55-1.79 (7H, m), 1.02-0.96 (3H, m).

[Formula 134]

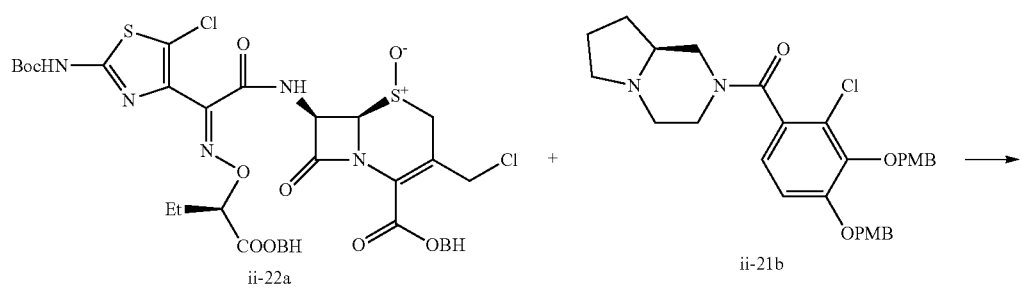

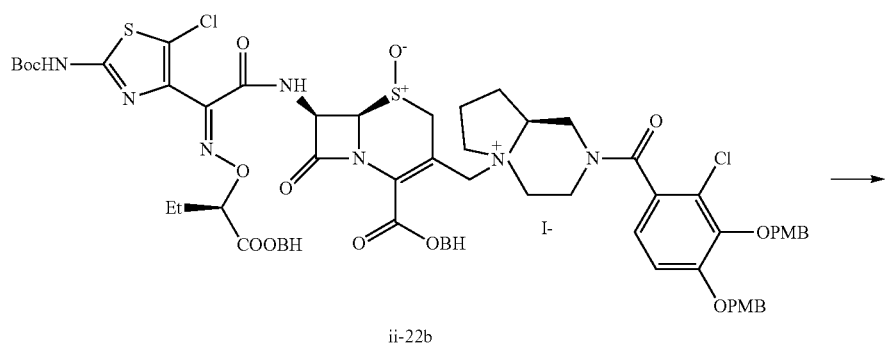

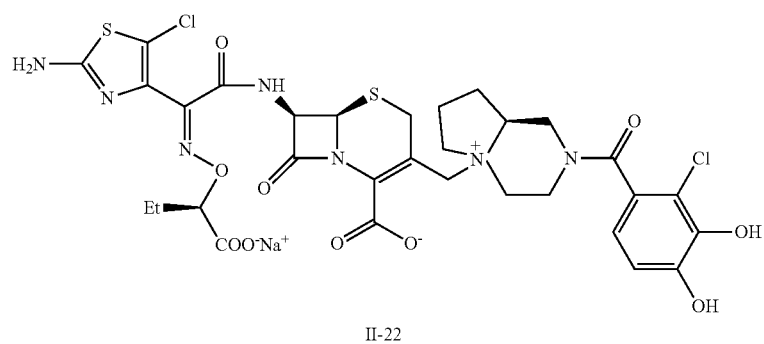

Example 88
Synthesis of Compound (II-23)
[Formula 135]
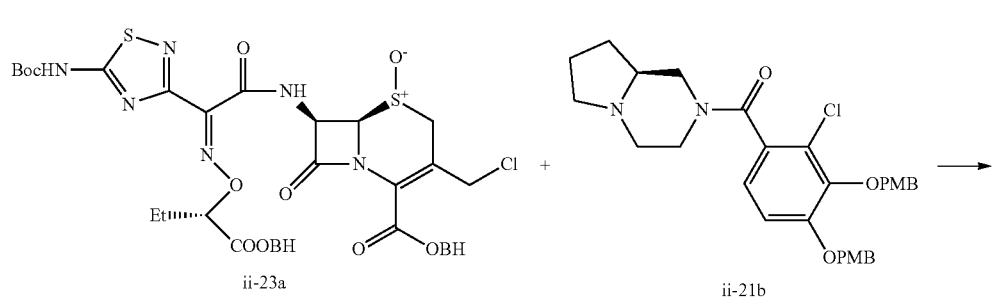
ii-23a
ii-21b
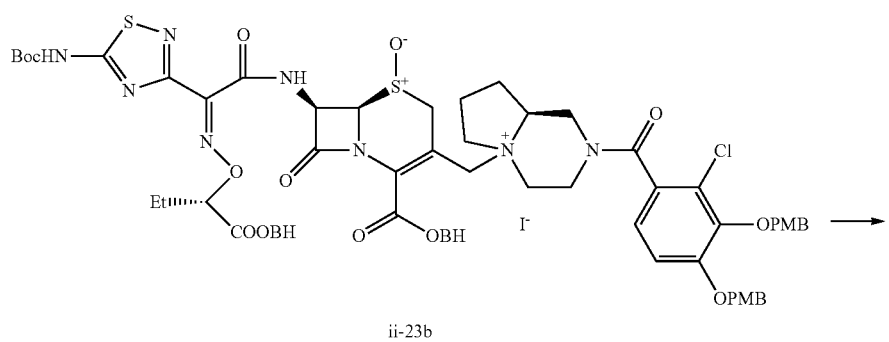
ii-23b
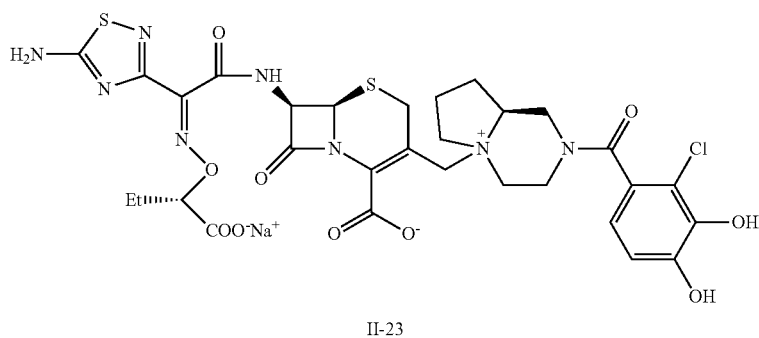
II-23
Step (1): compound ii-23a→compound II-23
Compound ii-23a (0.953 g, 1 mmol) was treated in the same way as in step (1) in Example 86 to yield compound II-23 (yielded amount: 281 mg, yield.: 36%).
MS (m+1)=765.42
Elem. Anal. C30H32ClN8O10S2Na (H2O)5.1
Calcd.: C, 40.99; H, 4.84; Cl, 4.03; N, 12.75; S, 7.30; Na, 2.62.
Found: C, 41.03; H, 4.79; Cl, 4.16; N, 12.47; S, 7.44; Na, 2.76.
1H-NMR (D2O) δ: 7.00-6.91 (1H, m), 6.89-6.78 (1H, m), 5.96-5.89 (1H, m), 5.41-5.32 (1H, m), 4.57-4.49 (1H, m), 4.42-4.24 (1H, m), 4.10-3.22 (11H, m), 2.47-1.89 (6H, m), 1.03-0.94 (3H, m).

Example 89
Synthesis of Compound (II-24)
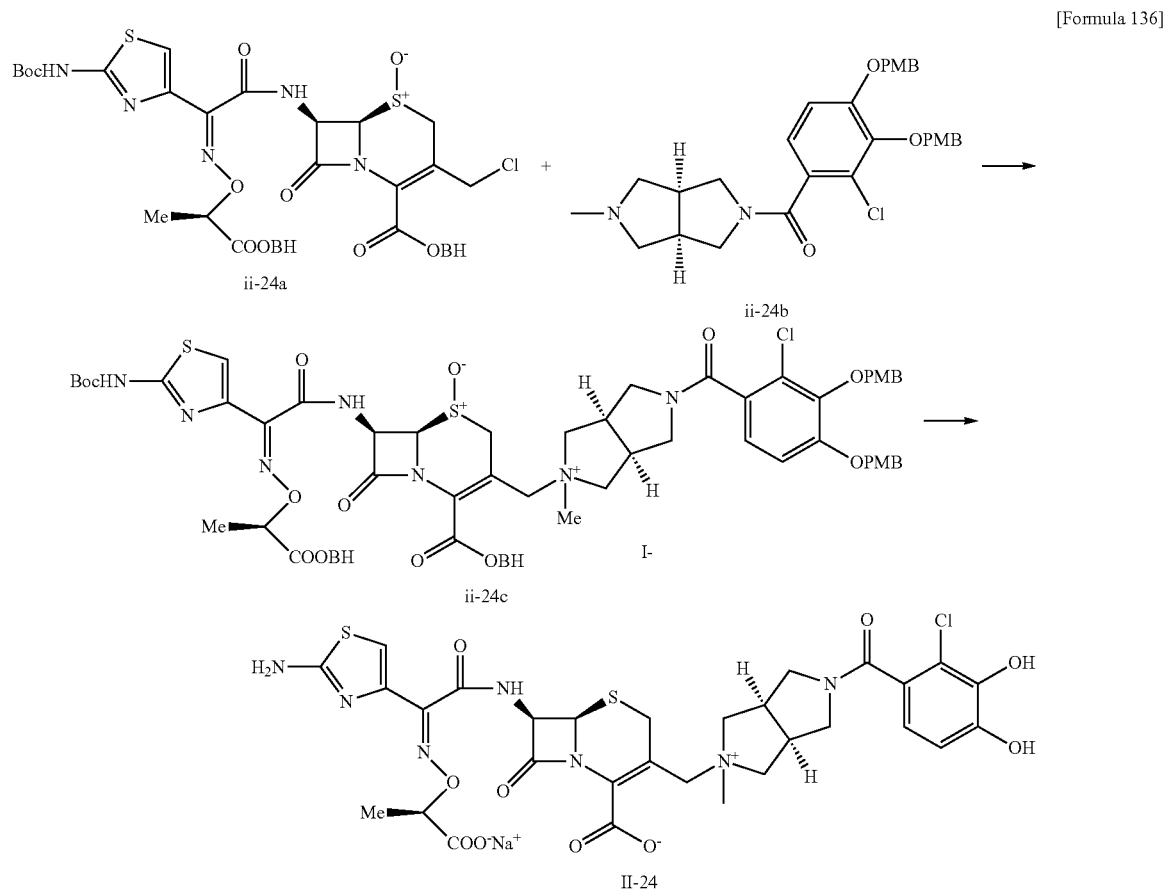
[Formula 136]
Step (1): compound ii-24a→compound II-24
Compound ii-24a (0.938 g, 1 mmol) was treated in the same way as in step (1) in Example 86 to yield compound II-24 (yielded amount: 280 mg, yield.: 36%).
MS (m+1)=750.39
Elem. Anal. C30H31ClN7NaO10S2(H2O)5.0
Calcd.: C, 41.79; H, 4.79; Cl, 4.11; N, 11.37; S, 7.44; Na, 2.67.
Found: C, 41.75; H, 4.61; Cl, 4.22; N, 12.48; S, 7.55; Na, 2.89.
1H-NMR (D2O) δ: 7.02 (1H, s), 6.94 (1H, d, J=8.4 Hz), 6.84 (1H, d, J=8.4 Hz), 5.91-5.84 (1H, m), 5.40-5.35 (1H, m), 4.70-4.62 (1H, m), 4.22-3.82 (6H, m), 3.72-2.94 (13H, m), 1.52-1.45 (3H, m).
Example 90
Synthesis of Compound (II-25)
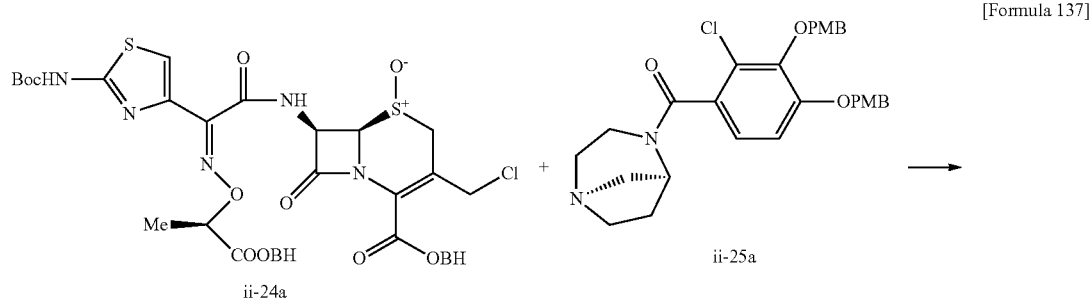
[Formula 137]

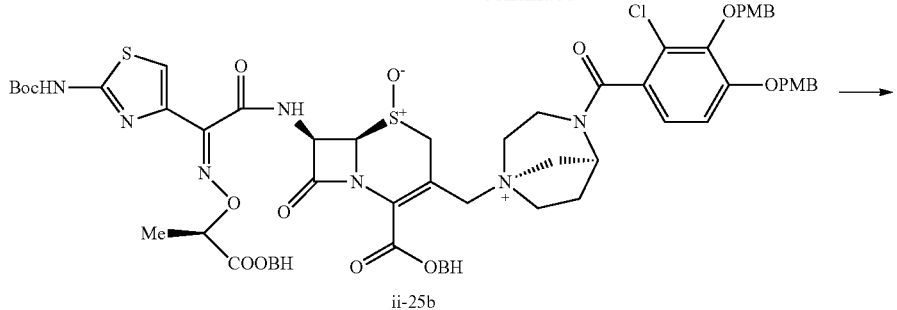
ii-25b
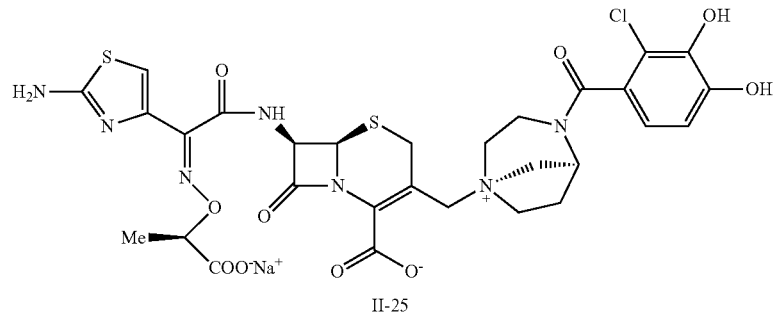
II-25
Step (1): compound ii-24a→compound II-25
Compound ii-24a (938 mg, 1 mmol) and compound ii-25a (523 mg, 1 mmol) were treated in the same way as in step (1) in Example 86 to yield compound ii-25 (yielded amount: 343 mg, yield: 45%).
MS (m+1)=736.36
Elem. Anal.: C29H29ClN7O10S2Na (H2O)7.1
Calcd.: C, 39.31; H, 4.91; Cl, 4.00; N, 11.07; S, 7.24; Na, 2.59.
Found: C, 39.16; H, 4.88; Cl, 4.15; N, 11.10; S, 7.68; Na, 3.00.
1H-NMR (D2O) δ: 7.02 (1H, s), 6.98-6.91 (1H, m), 6.88-6.77 (1H, m), 5.88 (1H, t, J=5.6 Hz), 5.36 (1H, t, J=5.6 Hz), 4.55 (1H, s), 4.24-4.12 (1H, m), 3.99-3.37 (10H, m), 2.37 (1H, s), 1.48 (3H, d, J=7.4 Hz).
Example 91
Synthesis of Compound (II-26)
[Formula 138]
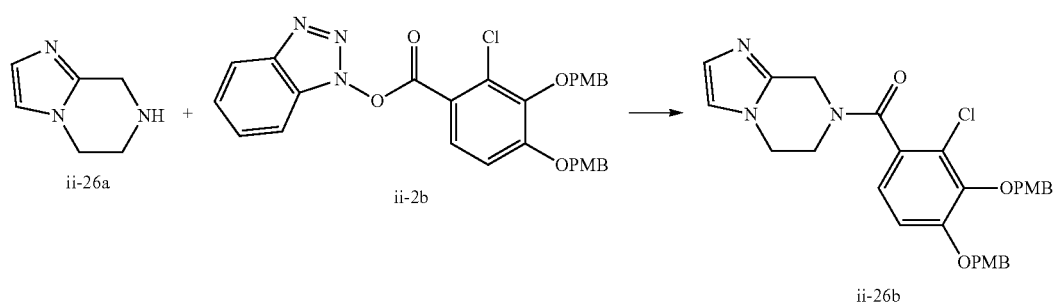
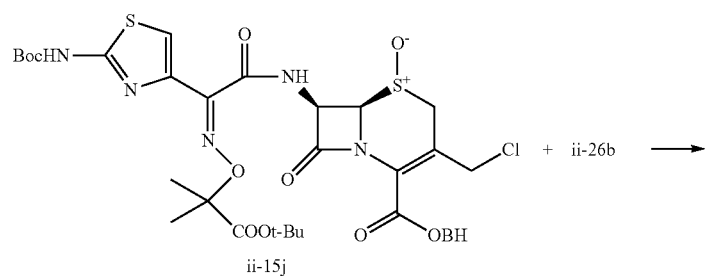

-continued

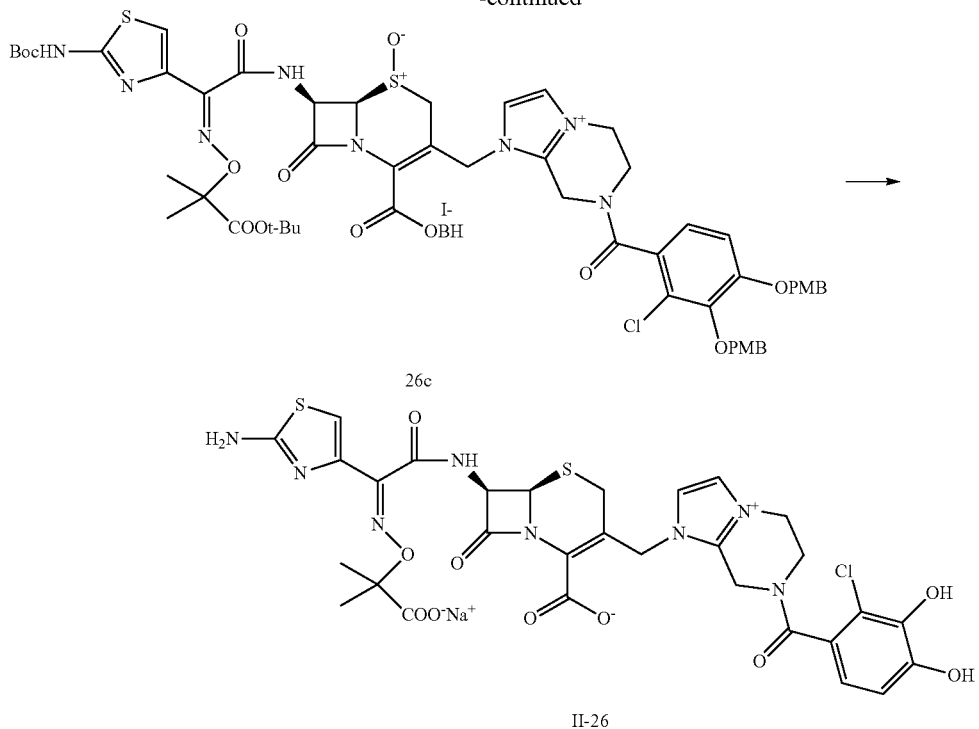

26c

II-26

Step (1): compound ii-26a→compound ii-26b

Compound ii-26a (2.38 g, 19.33 mmol) (see US 2008/153943 A1 and others) was dissolved in tetrahydrofuran (95 ml), and thereto was added compound ii-2b (9.50 g, 17.39 mmol). The resultant solution was stirred at room temperature. After the end of the reaction, purified water was added to the reaction liquid. From the water phase, the resultant reaction product was extracted with ethyl acetate The resultant organic phase was washed with a 5% aqueous sodium hydrogencarbonate solution, purified water, and a saturated salt solution in turn. The organic phase was dried over anhydrous magnesium sulfate, and magnesium sulfate was then removed therefrom by filtration. The solvent was distilled off therefrom under reduced pressure. The resultant residue was subjected to silica gel chromatography to yield compound ii-26b (yielded amount: 8.3 g, yield: 80%).

$^1$H-NMR (CDCl$_3$) δ: 7.40-7.30 (4H, m), 7.08-6.81 (8H, m), 5.09-4.98 (4H, m), 4.54-4.51 (1H, m), 4.48-4.33 (1H, m), 4.17-3.94 (2H, m), 3.84 (3H, s), 3.80 (3H, s), 3.63-3.45 (1H, m), 1.88-1.60 (1H, m).

Step (2): compound ii-24a→compound II-26

Compound ii-26b (534 mg, 1 mmol) and compound ii-15j (952 mg, 1 mmol) were treated in the same way as in step (1) in Example 86 to yield compound II-26 (yielded amount: 429 mg, yield.: 55%).

MS (m+1)=761.33

Elem. Anal.: C30H28ClN8O10S2Na (H2O)4(H2O)1.5

Calcd.: C, 40.84; H, 4.46; Cl, 4.02; N, 12.70; S, 7.27; Na, 2.61.

Found: C, 40.89; H, 4.37; Cl, 4.14; N, 12.70; S, 7.27; Na, 2.61.

$^1$H-NMR (D$_2$O) δ: 7.62-7.48 (2H, m), 7.03-6.82 (3H, m), 5.92-5.80 (1H, m), 5.38-5.21 (2H, m), 5.12-5.04 (2H, m), 4.46-4.36 (2H, m), 4.33-4.22 (1H, m), 3.95-3.86 (1H, m), 3.57-3.23 (2H, m), 1.55-1.47 (6H, m).

Example 92

Synthesis of Compound (II-27)

[Formula 139]

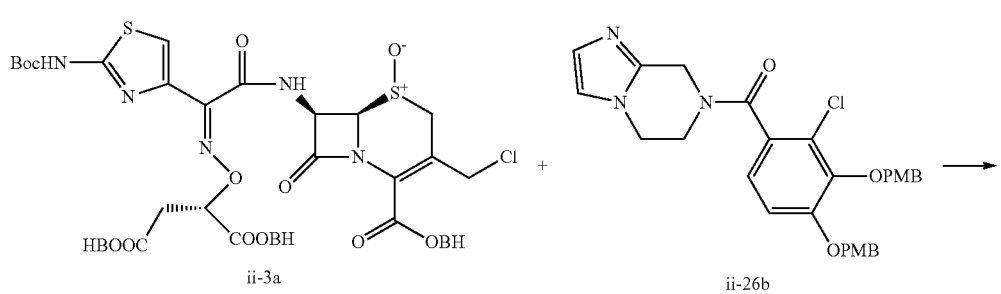

-continued
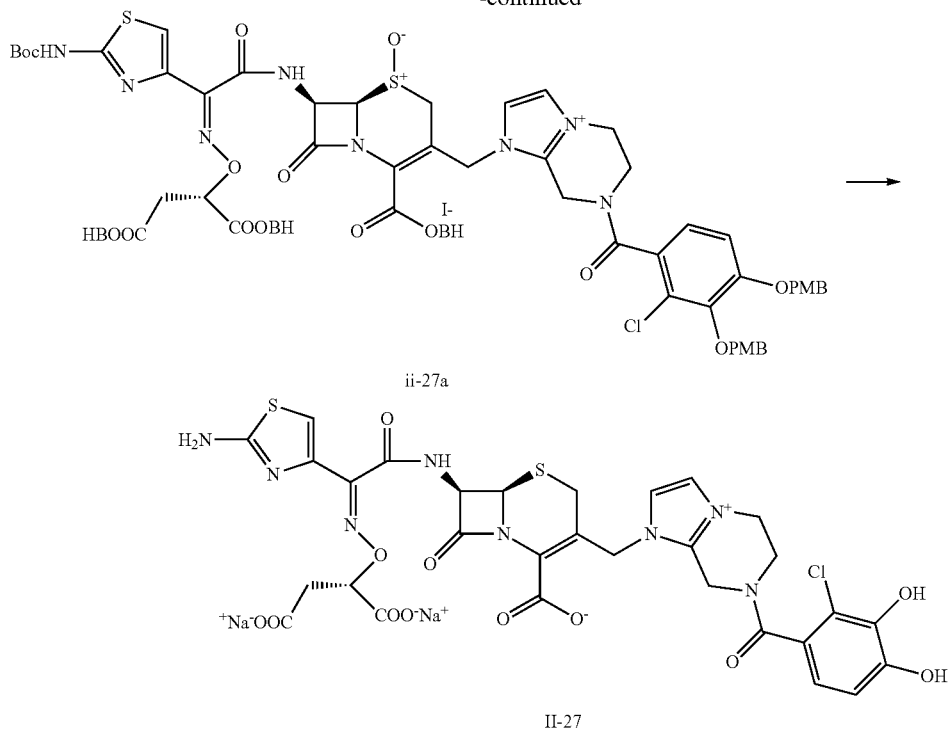
ii-27a
II-27
Step (1): compound ii-3a→compound II-27
Compound ii-3a (1.149 g, 1 mmol) and Compound ii-26b (534 mg, 1 mmol) were treated in the same way as in step (1) in Example 86 to yield compound II-27 (yielded amount: 386 mg, yield: 46%).
MS (m+1)=791.32
Elem. Anal.: C30H25ClN8O12S2Na2(H2O)6.3
Calcd.: C, 37.98; H, 4.00; Cl, 3.74; N, 11.81; S, 6.76; Na, 4.85.
Found: C, 38.00; H, 3.94; Cl, 3.96; N, 11.78; S, 7.01; Na, 4.72.
$^1$H-NMR (D$_2$O) δ: 7.64-7.47 (2H, m), 7.08-6.83 (3H, m), 5.82 (1H, br s), 5.27 (2H, br s), 5.10-4.86 (3H, m), 4.25-3.83 (4H, m), 3.35-3.21 (1H, m), 2.72 (2H, br s).
Example 93
Synthesis of Compound (II-28)
[Formula 140]
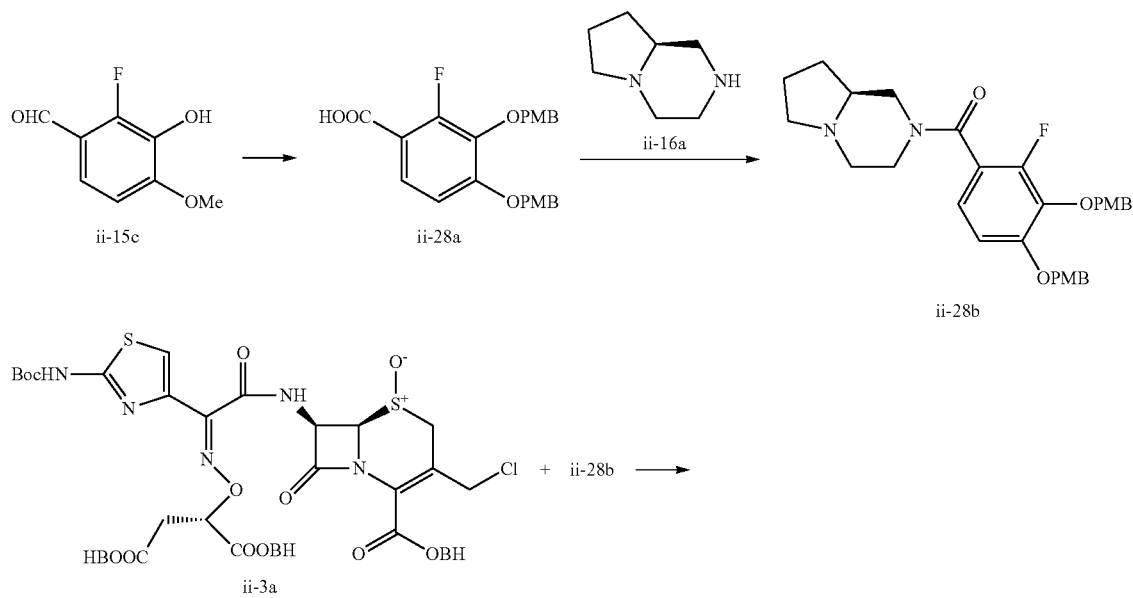

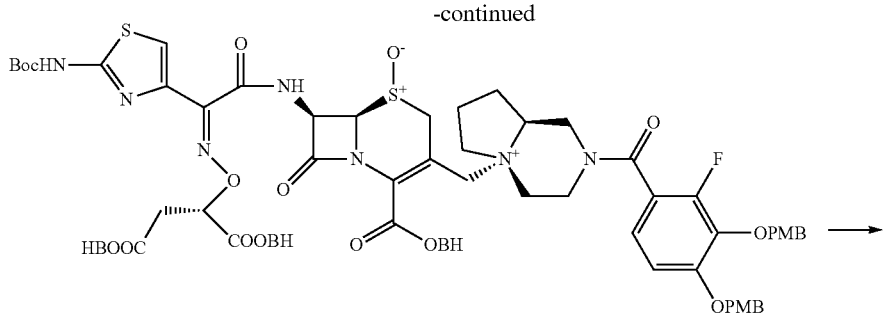

ii-28c

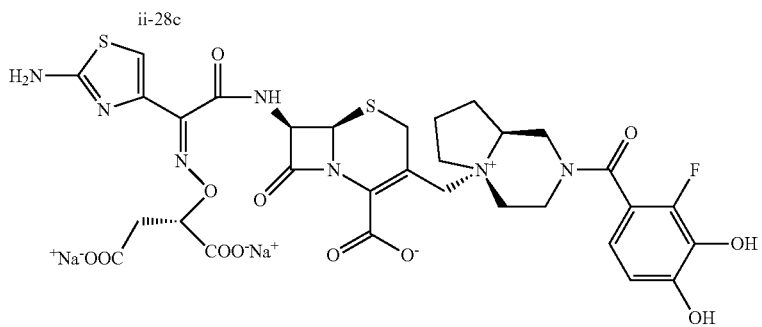

II-28

Step (1): compound ii-15c→compound ii-28a

Compound ii-15c (4.06 g, 23.9 mmol) was treated in the same way as in steps (2), (3), (4) and (5) in Example 80 in accordance with this step order, so as to yield compound ii-28a (yielded amount: 3.43 g, yield: 35%).

$^1$H-NMR (CDCl$_3$) δ: 7.70 (1H, dd, J=7.8, 7.8 Hz), 7.30-7.33 (4H, m), 6.91 (2H, d, J=8.4 Hz), 6.78 (2B, m), 5.09 (2H, s), 5.02 (2H, s), 3.82 (3H, s), 3.79 (3H, s).

Step (2): compound ii-28a→compound ii-28b

Compound ii-28a (1.24 g, 3.00 mmol) was dissolved in tetrahydrofuran (15 mL), and thereto were added compound ii-16a (606 mg, 4.80 mmol), 1-hydroxybenzotriazole (446 mg, 3.30 mmol), and 1-ethyl-3-(3-dimethylaminopropyl)carbodiimide hydrochloride (633 mg, 3.30 mmol). The resultant was stirred at room temperature. After the end of the reaction, purified water was added to the reaction liquid. From the water phase, the reaction product was extracted with ethyl acetate. The resultant organic phase was washed with purified water and a saturated salt solution in turn. The organic phase was dried over anhydrous magnesium sulfate, and magnesium sulfate was removed by filtration. The solvent was distilled off therefrom under reduced pressure. The resultant residue was subjected to silica gel chromatography to yield compound ii-28b (yielded amount: 1.26 g, yield: 81%).

$^1$H-NMR (CDCl$_3$) δ: 7.41-7.27 (3H, m), 7.01 (1H, t, J=7.8 Hz), 6.95-6.88 (2H, m), 6.82-6.76 (3H, m), 5.06 (2H, s), 5.02 (2H, s), 3.83 (3H, s), 3.78 (3H, s), 3.54-3.27 (1H, m), 3.20-3.04 (2H, m), 3.02-2.86 (2H, m), 2.55 (1B, t, J=11.2 Hz), 2.27-1.68 (7H, m), 1.54-1.29 (2H, m).

Step (3): compound ii-28b→compound II-28

Compound ii-28b (700 mg, 1 mmol) and compound ii-3a (1.55 g, 1 mmol) were treated in the same way as in step (1) in Example 86 to yield compound II-28 (yielded amount: 602 mg, yield: 55%).

MS (m+1)=778.61

Elem. Anal.: C31H30FN7O12S2Na1.5(H2O)5.9

Calcd.: C, 40.62; H, 4.60; F, 2.07; N, 10.70; S, 7.00; Na, 3.76.

Found: C, 10.65; H, 4.66; F, 2.13; N, 10.65; S, 7.05; Na, 3.62.

$^1$H-NMR (D$_2$O) δ: 7.02 (1H, s), 6.91-6.82 (2H, m), 5.86-5.80 (1H, m), 5.37-5.30 (1H, m), 5.03-4.92 (1H, m), 4.41-4.21 (2H, m), 4.04-3.40 (11H, m), 2.80-2.74 (2H, m), 2.53-1.89 (4H, m),

Example 94

Synthesis of Compound (II-29)

[Formula 141]

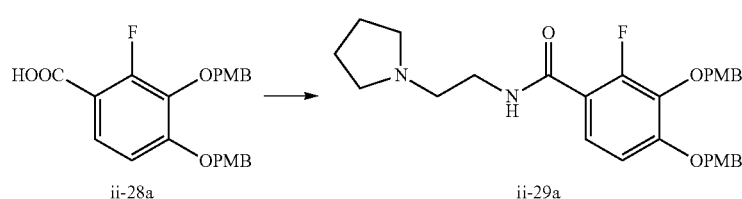

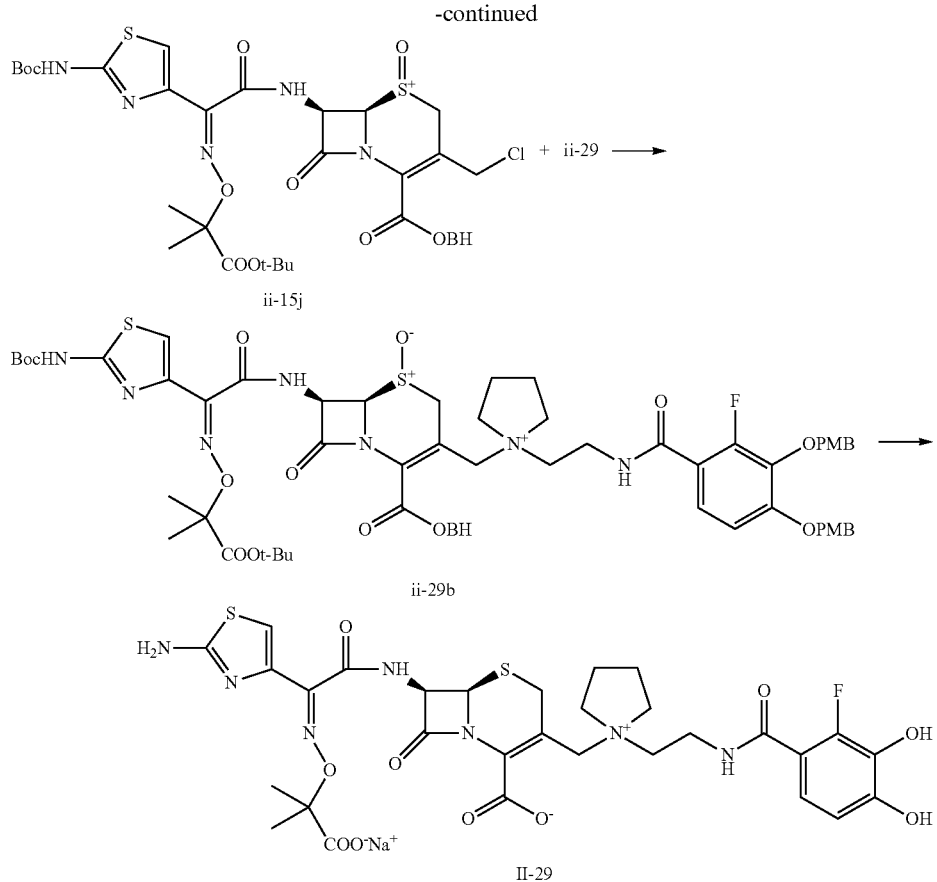

ii-15j ii-29b

II-29

Step (1): compound ii-28a→compound ii-29a

Compound ii-28a (824 mg, 2.00 mmol) was treated in the same way as in step (2) in Example 93 to yield compound ii-29a (yielded amount: 840 mg, yield: 83%).

$^1$H-NMR (CDCl$_3$) δ: 7.74 (1H, t, J=8.7 Hz), 7.33 (2H, d, J=8.4 Hz), 7.29 (21H, d, J=8.6 Hz), 7.19-7.08 (1H, m), 6.91 (2H, d, J=8.4 Hz), 6.85-6.78 (3H, m), 5.08 (2H, s), 4.99 (2H, s), 3.83 (3H, s), 3.79 (3H, s), 3.56 (2H, dd, J=11.3, 5.3 Hz), 2.69 (2H, t, J=6.2 Hz), 2.59-2.52 (4H, m), 1.84-1.74 (4H, m).

Step (2): compound ii-29a→compound II-19

Compound ii-29a (509 mg, 1.00 mmol) and compound ii-15j (952 mg, 1.00 mmol) were treated in the same way as in step (1) in Example 86 to yield compound II-29 (yielded amount: 547 mg, yield: 72%).

MS (m+1)=736.58

Elem. Anal.: C30H33FN7O10S2Na (H2O)5 (NaCl) 0.1

Calcd.: C, 42.21; H, 5.08; F, 2.23; N, 11.49; S, 7.51; Na, 2.96; Cl, 0.42.

Found: C, 42.24; H, 5.18; F, 2.15; N, 11.50; S, 7.51; Na, 2.77; Cl, 0.54.

$^1$H-NMR (D$_2$O) δ: 7.18 (1H, t, J=8.5 Hz), 6.97 (1H, s), 6.79 (1H, dd, J=8.5, 1.5 Hz), 5.87 (1H, d, J=5.0 Hz), 5.36 (1H, d, J=5.0 Hz), 4.12 (1H, d, J=13.9 Hz), 4.03-3.88 (2H, m), 3.85-3.40 (8H, m), 2.31-2.16 (4H, m), 1.52-1.47 (6H, m).

Example 95

Synthesis of Compound (II-30)

[Formula 142]

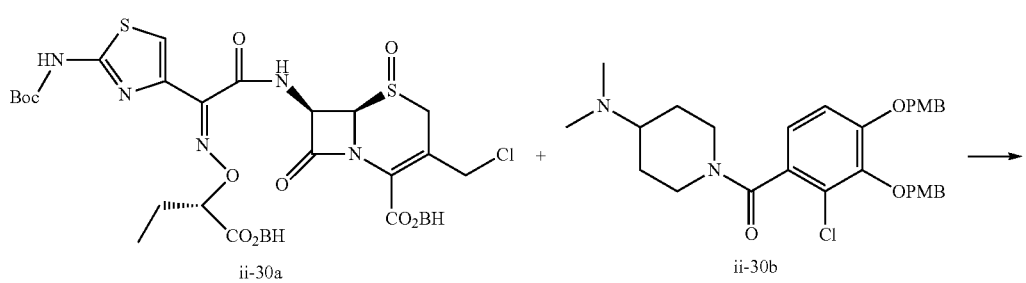

ii-30a    ii-30b

-continued

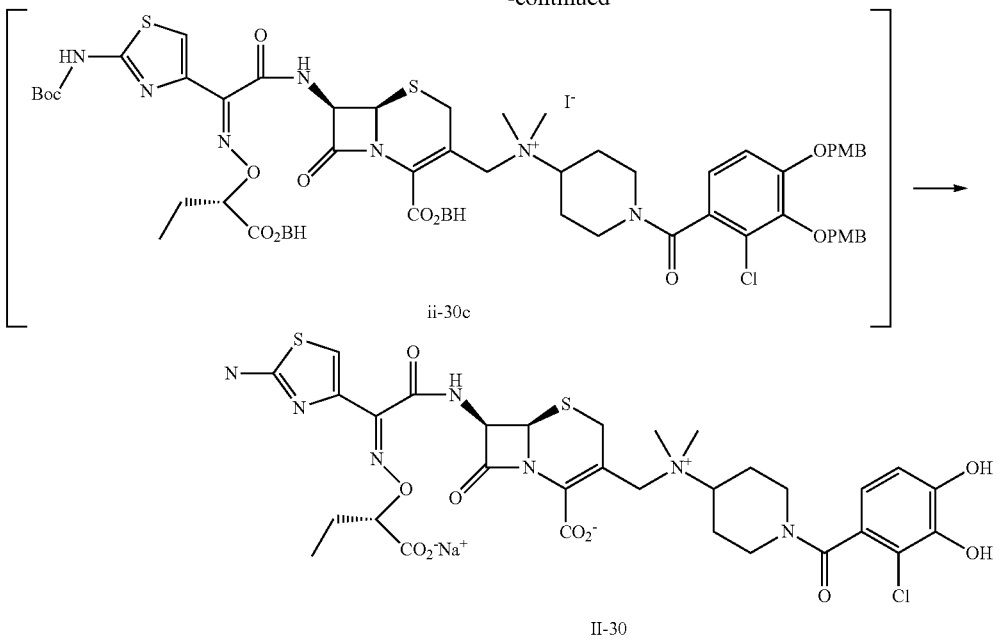

ii-30c

II-30

Step (1): compound ii-30a+compound ii-30b→) compound II-30

Sodium iodide (300 mg, 2.0 mmol) was added to a solution of compound ii-30a (1.024 g, 1.0 mmol) in dimethylacetoamide (2, and the resultant solution was stirred at room temperature for 10 minutes. The solution was cooled to 15° C., and then thereto was added compound II-30b (539 mg, 1.0 mmol). Thereafter, the solution was stirred at 15° C. for 1 hour. Thereto was added N,N-dimethylformamide (2, and then the solution was cooled to −40° C. Thereto was added phosphorus tribromide (189 μL, 2.0 mmol), and the solution was stirred at −40° C. for 30 minutes. The reaction mixture was slowly added to a 5% salt solution cooled with ice. The precipitated solid was collected by filtration, washed with water, and then suspended into water. The suspension was freeze-dried to yield compound ii-30c as a pale yellow solid. Compound ii-30c yielded was used as it was, without being purified, in the next reaction.

The total amount of compound ii-30c yielded was dissolved in methylene chloride (10 mL), and the solution was cooled to −40° C. Thereto were then added anisole (1.092 mL, 10.0 mmol) and a 2 M aluminum chloride solution (5.00 ml, 10.0 mmol) in nitromethane in turn. The resultant was stirred at 0° C. for 1 hour. The reaction liquid was dissolved in water, a 2 N aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added a 0.2N aqueous sodium hydroxide solution until the whole gave a pH of 6.0. Thereafter, a piece of dry ice was added thereto. The resultant solution was concentrated under reduced pressure, and then freeze-dried to yield compound II-30 as a pale yellow powder.

Yielded amount: 373.1 mg (42%).

$^1$H-NMR (D$_2$O) δ: 7.00 (1H, s), 6.94 (1H, dd, J=8.39, 3.97 Hz), 6.80 (1H, dd, J=21.73, 8.31 Hz), 5.89 (1H, d, J=4.88 Hz), 5.38 (1H, d, J=4.88 Hz), 4.53 (1H, t, J=6.10 Hz), 3.97 (2H, t, J=17.84 Hz), 3.82-3.65 (2H, m), 3.47 (1H, d, J=17.84 Hz), 3.32-2.88 (9H, m), 2.42 (1H, d, J=11.44 Hz), 2.19 (1H, t, J=11.44 Hz), 1.92-1.83 (3H, m), 0.97 (3H, t, J=7.40 Hz).

Elem. Anal.: C31H35ClN7O10S2Na (H2O)5.2

Calcd.: C, 42.22; H, 5.19; Cl, 4.02; N, 11.12; S, 7.27; Na, 2.61(%).

Found: C, 42.18; H, 5.19; Cl, 4.18; N, 11.17; S, 7.19; Na, 2.62(%).

Example 96

Synthesis of Compound (II-31)

[Formula 143]

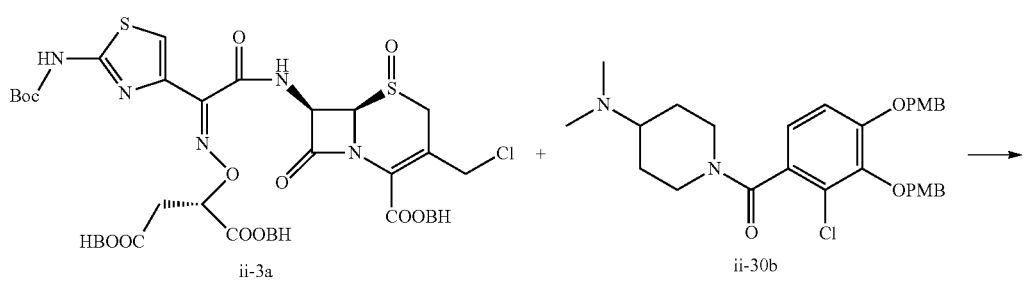

ii-3a  ii-30b

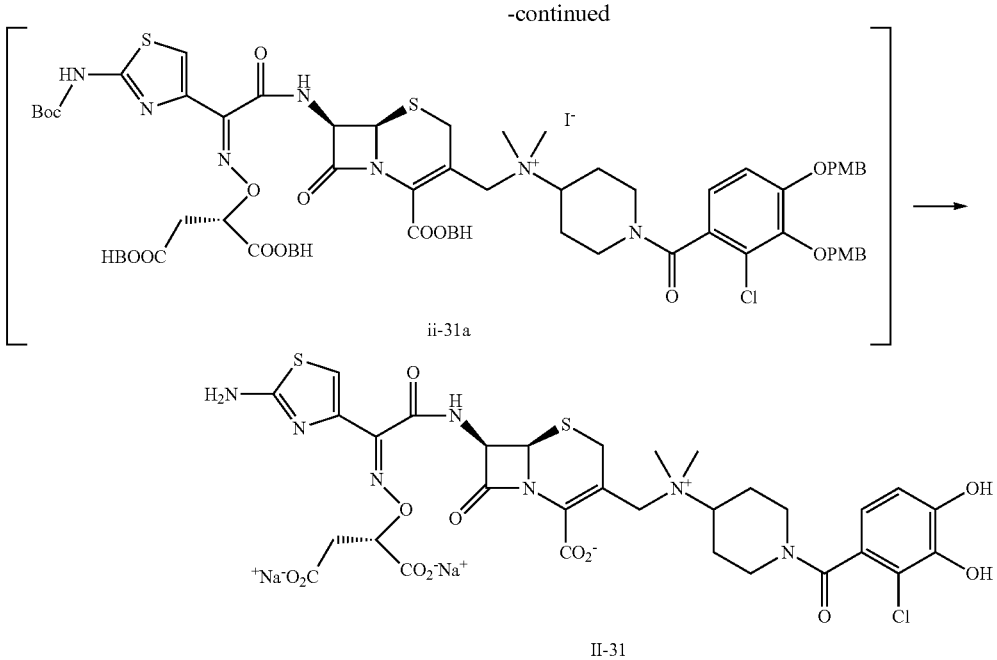

ii-31a

II-31

Step (1): compound ii-3a+compound ii-30b→compound II-31

Compound ii-3a (1.249 g, 1.0 mmol) and compound ii-30b (539 mg, 1.0 mmol) were used to synthesize the target compound in the same way as in step (1) in Example 95.

Yielded amount: 484.1 mg (49%)

$^1$H-NMR (D$_2$O) δ: 7.01 (1H, s), 6.94 (1H, dd, J=8.24, 4.42 Hz), 6.82 (1H, dd, J=22.50, 8.46 Hz), 5.83 (1H, d, J=4.73 Hz), 5.35 (1H, d, J=4.73 Hz), 4.97 (1H, t, 6.02 Hz), 4.04 (1H, d, J=13.15 Hz), 3.91 (1H, d, J=17.01 Hz), 3.74 (2H, dd, J=20.82, 13.15 Hz), 3.47 (1H, d, J=17.01 Hz), 3.32-3.16 (1H, m), 3.09-2.87 (8H, m), 2.71 (2H, d, J=5.64 Hz), 2.43 (1H, d, J=12.96 Hz), 2.20 (1H, t, J=11.06 Hz), 0.99-0.97 (1H, m).

Elem. Anal.: C31H32.2ClN7O12S2Na1.8(H2O)5.4

Calcd.: C, 39.90; H, 4.65; Cl, 3.80; N, 10.51; S, 6.87; Na, 4.43(%).

Found: C, 39.95; H, 4.62; Cl, 4.09; N, 10.42; S, 6.63; Na, 4.41(%).

Example 97

Synthesis of Compound (II-32)

[Formula 144]

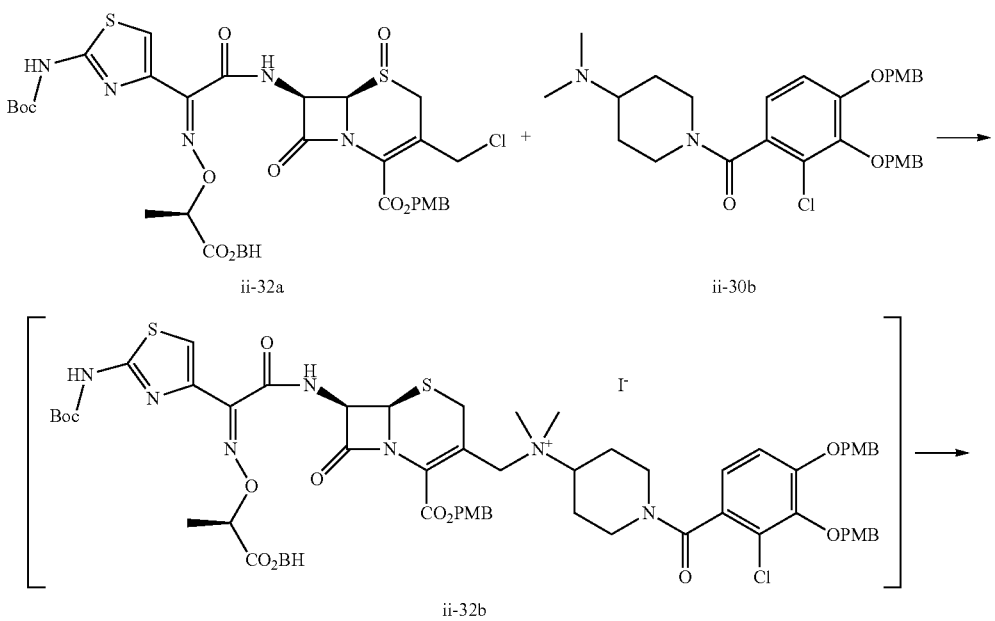

ii-32a + ii-30b ii-32b

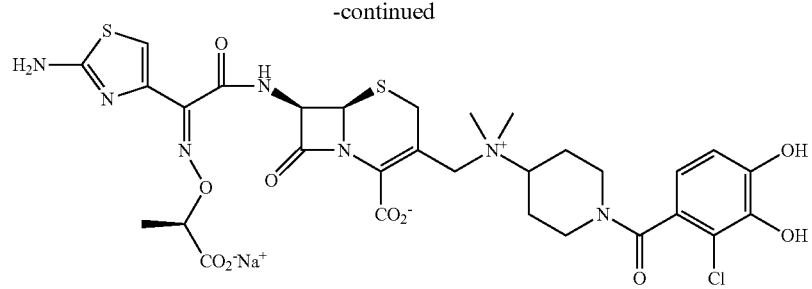

II-32

Step (1): compound ii-32a+compound ii-30b→compound II-32

Compound ii-32a (0.892 g, 1.0 mmol) and compound ii-30b (539 mg, 1.0 mmol) were used to synthesize the target compound in the same way as in step (1) in Example 95.

Yielded amount: 512.1 mg (57%)

$^1$H-NMR (D$_2$O) δ: 7.02 (1H, s), 6.93 (1H, dd, J=8.31, 3.58 Hz), 6.79 (1H, dd, J=21.66, 8.39 Hz), 5.86 (1H, d, J=4.58 Hz), 5.38 (1H, d, J=5.03 Hz), 4.65 (1H, q, J=7.02 Hz), 3.98 (2H, t, J=17.46 Hz), 3.79-3.68 (2H, m), 3.49 (1H, d, J=17.54 Hz), 3.31-3.15 (1H, m), 3.08-2.88 (7H, m), 2.42 (1H, d, J=11.59 Hz), 2.23-2.15 (1H, m), 1.96-1.74 (2H, m), 1.48 (3H, d, J=7.02 Hz).

Elem. Anal.: C30H33ClN7O10S2Na (H2O)5.1(NaHCO3) 0.09

Calcd.: C, 41.37; H, 4.99; Cl, 4.06; N, 11.22; S, 7.34; Na, 2.87(%).

Found: C, 41.37; H, 4.94; Cl, 3.99; N, 11.28; S, 7.16; Na, 2.86(%).

Example 98

Synthesis of Compound (II-33)

[Formula 145]

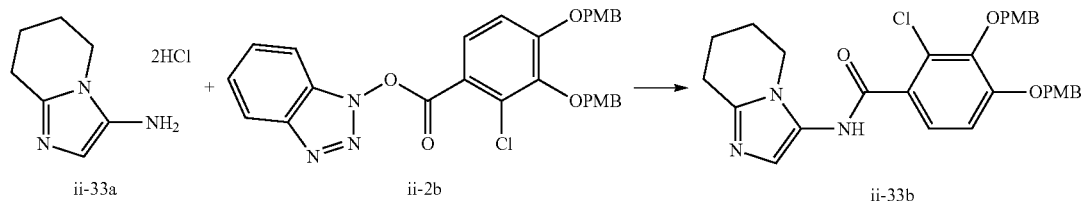

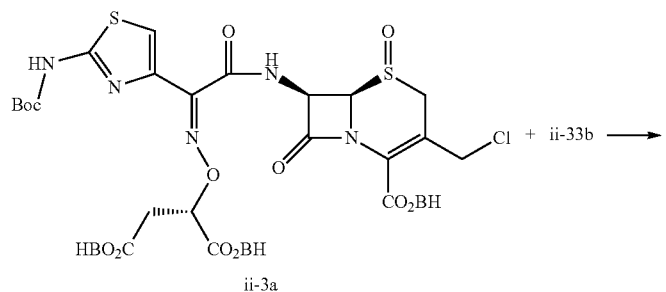

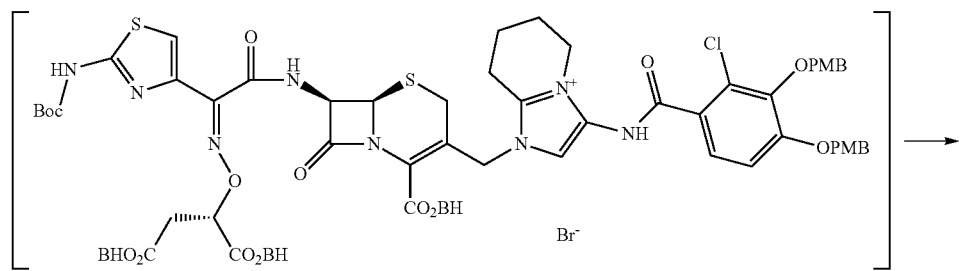

33c

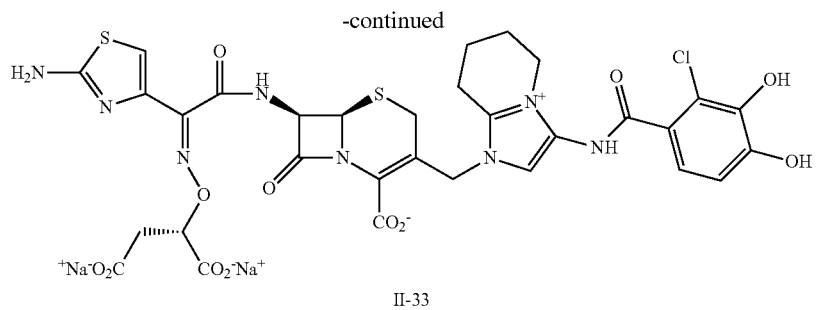

II-33

Step (1): compound ii-33a+compound ii-2b→compound ii-33b

Compound ii-33a (2.00 g, 9.52 mmol) was suspended into, (40 mL), and thereto were then added diisopropylethylamine (4.99 mL, 28.6 mmol) and compound ii-2b (5.20 g, 9.52 mmol) in turn. The liquid was stirred at 50° C. for 1 hour and at 80° C. for 3 hours. The reaction liquid was diluted with ethyl acetate, washed with a saturated aqueous sodium hydrogencarbonate solution, water and a saturated salt solution, and dried over magnesium sulfate. Magnesium sulfate was filtrated off, and then the liquid was concentrated under reduced pressure. Thereto were added hexane and ethyl acetate to precipitate a solid. Thus, compound ii-33b (1.88 g, 36%) was yielded. The solid precipitated while the filtrate was separated to two phases was washed with water to yield compound ii-33b (2.60 g, 50%).

$^1$H-NMR (DMSO-$d_6$) δ: 9.96 (1H, s), 7.44 (2H, d, J=8.54 Hz), 7.32 (3H, d, J=8.54 Hz), 7.24 (1H, d, J=8.69 Hz), 6.98 (2H, d, J=8.54 Hz), 6.87 (2H, d, J=8.54 Hz), 6.72 (1H, s), 5.18 (2H, s), 4.90 (2H, s), 3.79-3.75 (8H, m), 2.70 (2H, t, J=6.25 Hz), 1.78-1.91 (4H, m)

Step (2): compound ii-3a+compound ii-33b→compound II-33

Compound ii-33b (603 mg, 1.1 mmol) and sodium bromide (206 mg, 2.0 mmol) were successively added to a solution of compound ii-3a (1.249 g, 1.0 mmol) in N,N-dimethylformamide (2, and the resultant solution was stirred at room temperature for 6 hours. Thereto was added N,N-dimethylformamide (6 mL), and then cooled to −40° C. Thereto was added phosphorus tribromide (189 μL, 2.0 mmol), and the resultant solution was stirred at −40° C. for 1 hour. To the reaction mixture was slowly added a 5% salt solution cooled with ice. The precipitated solid was collected by filtration, washed with water, and suspended into water. The suspension was freeze-dried to yield compound ii-33c as a pale brown solid. Compound ii-33c yielded was used as it was, without being purified, in the next reaction.

The total amount of compound ii-33c yielded was dissolved in methylene chloride (10 mL), and the solution was cooled to −40° C. Thereto were then added anisole (1.311 mL, 12.0 mmol) and a 2 M aluminum chloride solution (6.00 mL, 12.0 mmol) in nitromethane in turn. The resultant was stirred at 0° C. for 1 hour. The reaction liquid was dissolved in water, a 2 N aqueous hydrochloric acid solution, and acetonitrile. The resultant solution was then washed with diisopropyl ether. To the water phase was added HP20-SS resin, and then acetonitrile was concentrated under reduced pressure. The resultant mixed liquid was purified by ODS column chromatography.

To the resultant target-compound solution was added a 0.2 N aqueous sodium hydroxide solution to not the pH thereof to 6.0. Thereafter, apiece of dry ice was added thereto in order to neutralize an excess of sodium hydroxide. The resultant solution was concentrated under reduced pressure, and then freeze-dried to yield compound II-33 as a pale yellow powder.

Yielded amount: 587.0 mg (55%).

$^1$H-NMR ($D_2O$) δ: 7.59 (1H, s), 7.17 (1H, d, J=8.31 Hz), 7.01 (1H, s), 6.95 (1H, d, J=8.31 Hz), 3.80 (1H, d, J=4.50 Hz), 5.22 (1H, d, 4.50 Hz), 5.11 (1H, d, J=15.40 Hz), 4.97-4.90 (2H, m), 4.05 (2H, br s), 3.54 (1H, d, J=17.31 Hz), 3.27 (1H, d, J=17.31 Hz), 3.04 (2H, br s), 2.71-2.68 (2H, m), 2.06 (4H, br s).

Elem. Anal.: C31H27.5ClN8O12S2Na1.5(H2O)8
Calcd.: C, 37.90; H, 4.46; Cl, 3.61; N, 11.11; S, 6.53; Na, 3.51(%).
Found: C, 38.06; H, 4.39; Cl, 3.35; N, 11.22; S, 6.36; Na, 3.59(%).

Example 99

Synthesis of Compound (II-34)

[Formula 146]

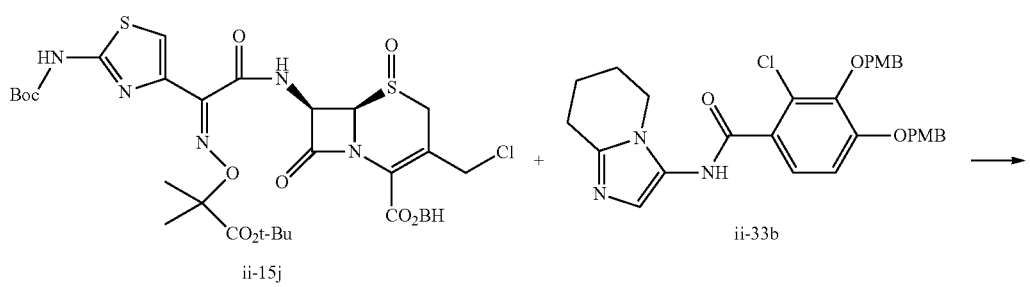

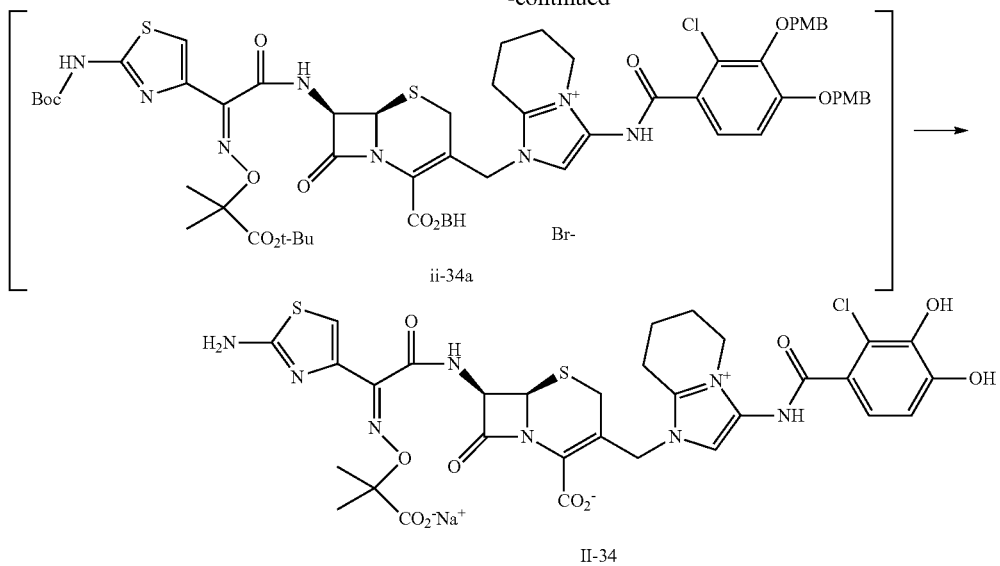

Step (1): compound ii-15j+compound ii-33b→compound II-34

Compound ii-15j (0.936 g, 1.0 mmol) and compound ii-33b (603 mg, 1.1 mmol) were used to synthesize the target compound in the same way as in step (2) in Example 98.

Yielded amount: 586.2 mg (61%)

$^1$H-NMR (D$_2$O) δ: 7.57 (1H, s), 7.15 (1H, d, J=8.54 Hz), 6.98 (1H, s), 6.93 (1H, d, J=8.54 Hz), 5.84 (1H, d, J=4.73 Hz), 5.26 (1H, d, J=4.73 Hz), 5.13-5.07 (1H, m), 4.05 (2H, br s), 3.59 (1H, d, J=17.69 Hz), 3.27 (1H, d, J=17.69 Hz), 3.04 (2H, br s), 2.06 (4H, br s), 1.49 (6H, br s).

Elem. Anal.: C31H30ClN8O10S2Na (H2O)7.3

Calcd.: C, 40.09; H, 4.84; Cl, 3.82; N, 12.07; S, 6.91; Na, 2.48(%).

Found: C, 40.08; H, 4.83; Cl, 4.03; N, 11.99; S, 6.94; Na, 2.41(%).

Example 100

Synthesis of Compound (II-35)

[Formula 147]

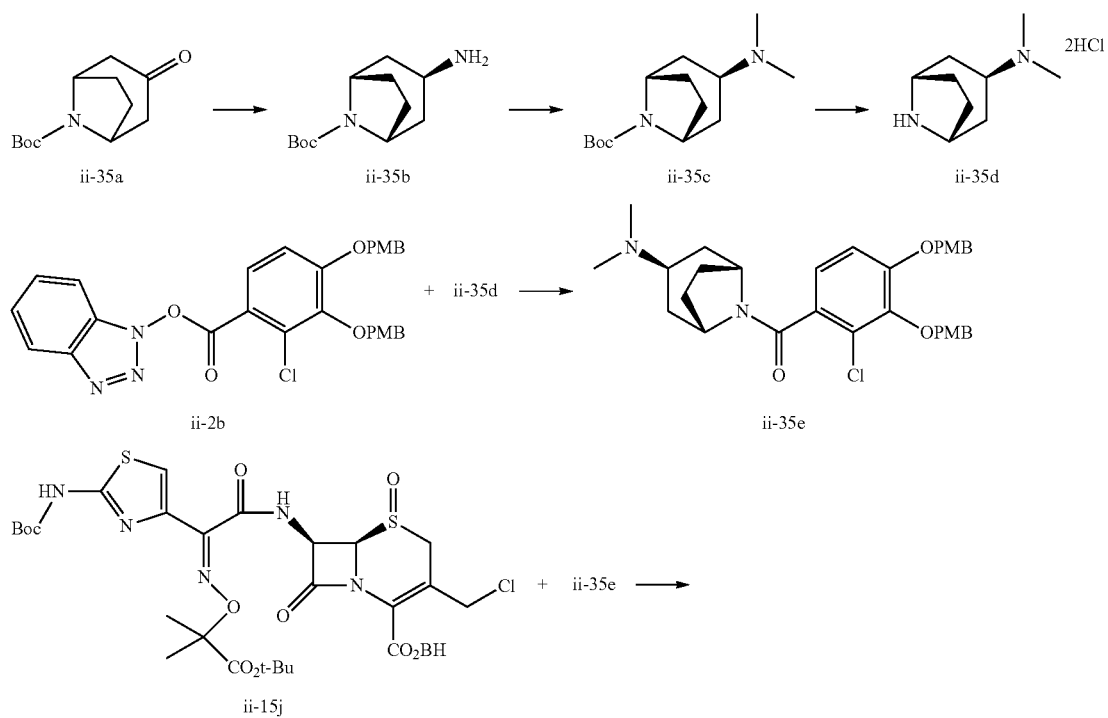

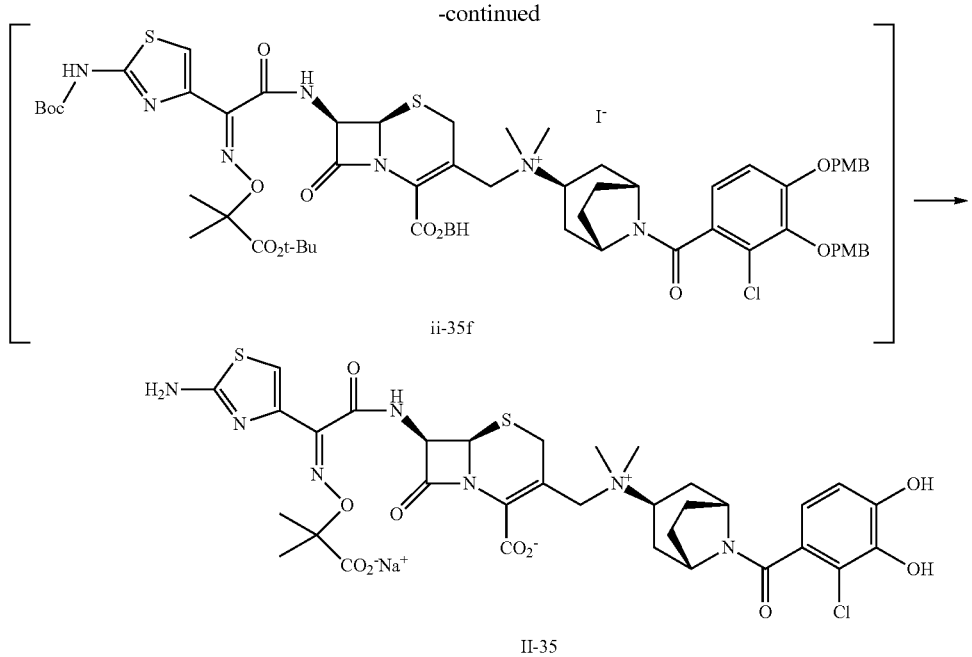

ii-35f

II-35

Step (1) compound ii-35a→compound ii-35c

To a solution of compound ii-35a (5.00 g, 22.19 mmol) in methanol (100 mL) and water (10 mL) were added ammonium formate (13.99 g, 222 mmol) and 10%-palladium/carbon (2.362 g) in turn. The resultant was stirred at room temperature for 2 days. Celite was used to filtrate the reaction liquid, and then the filtrate was diluted with chloroform, washed with an aqueous sodium hydroxide solution and a saturated salt solution, and dried over magnesium sulfate. Magnesium sulfate was filtrated off, and then the liquid was concentrated under reduced pressure to yield compound ii-35b (5.60 g): Compound ii-35b yielded was used as it was, without being purified, in the next reaction.

The total amount of compound ii-35b yielded was dissolved in methanol (50 mL) and acetic acid (3 mL). Thereto were then added a 36% aqueous formalin solution (8.49 mL, 111 mmol) and hydrogenated sodium triacetoxyborate (9.41 g, 44.4 mmol) in turn. The resultant was stirred at room temperature for 1 hour. To the reaction liquid was added an 8 N aqueous sodium hydroxide solution to set the pH thereof to 10. Thereafter, this liquid system was subjected to extraction with chloroform. To the organic phase was added a 0.5 N aqueous hydrochloric acid solution, and then the liquid-system was separated to two phases. Thereafter, the water phase was made into basicity, and then subjected to extraction with chloroform. The organic phase was washed with a saturated salt solution, and dried over magnesium sulfate. Magnesium sulfate was filtrated off, and then the organic phase was concentrated under reduced pressure to yield compound ii-35c (2.43 g, 43%).

$^1$H-NMR (CDCl$_3$) δ: 4.16 (2H, d, J=29.04 Hz), 2.22 (6H, s), 2.12-1.59 (OH, m), 1.46 (9H, s).

Step (2): compound ii-35c→compound ii-35d

Compound ii-35c (2.43 g, 9.55 mmol) was dissolved in ethanol, and thereto was added a 3.9 N hydrochloric acid/ethanol solution (9.80 mL, 38.2 mmol). The solution was stirred at room temperature for one day. Thereto was added a 4 N hydrochloric acid/1,4-dioxane solution (20 mL, 20 mmol), and then the liquid was stirred at 50° C. for 2 hours. The reaction liquid was concentrated to yield compound ii-35d (1.89 g, 87%).

$^1$H-NMR (DMSO-d$_6$) δ: 10.64 (1H, s), 9.17 (2H, s), 3.99 (2H, s), 3.58-3.47 (1H, m), 2.73 (3H, s), 2.71 (3H, s), 2.52-2.61 (2H, m), 2.03-1.90 (6H, m).

Step (3): compound ii-35d→compound ii-35e

Compound ii-35d (1.89 g, 8.32 mmol) was suspended into dichloromethane (20 mL), and thereto were added diisopropylethylamine (4.36 mL, 24.96 mmol) and compound ii-2b (4.54 g, 8.32 mmol) in turn. The liquid was stirred at room temperature for 2 hours. The reaction liquid was diluted with dichloromethane/methanol, washed with an aqueous sodium hydroxide solution, water, and a saturated salt solution, and dried over magnesium sulfate. Magnesium sulfate was filtrated off, and then the liquid was concentrated under reduced pressure. The resultant was subjected to amino silica gel column chromatography to elute out a desired compound with hexane/ethyl acetate. The desired-compound-containing fraction was concentrated under reduced pressure to yield compound ii-35e (4.40 g, 94%).

$^1$H-NMR (CDCl$_3$) δ: 7.36 (2H, d, J=8.39 Hz), 7.32 (2H, d, J=8.54 Hz), 6.94-6.88 (4H, m), 6.81 (2H, d, J=8.54 Hz), 5.06 (2H, s), 4.99 (2H, br s), 4.77 (1H, br s), 3.83 (3H, s), 3.79 (3H, s), 3.50 (1H, s), 2.23 (6H, s), 2.01-1.93 (1H, m), 1.88-1.74 (2H, m), 1.63 (4H, br s), 1.18 (2H, br s).

Step (4): compound ii-15j+compound ii-35e→compound II-35

Compound ii-15j (0.936 g, 1.0 mmol) and compound ii-35e (622 mg, 1.1 mmol) were used to synthesize the target compound in the same way as in step (1) in Example 95.

Yielded amount: 672.7 mg (67%)

$^1$H-NMR (D$_2$O) δ: 6.98 (1H, s), 6.94 (1H, d, J=8.24 Hz), 6.81 (1H, d, J=8.24 Hz), 5.87 (1H, t, J=4.77 Hz), 5.38 (1H, dd, 4.77, 1.37 Hz), 4.08-3.89 (3H, m), 3.59-3.42 (2H, m), 3.08 (3H, br s), 2.93 (4H, br s), 2.87 (1H, s), 2.68 (1H, br s), 2.15 (2H, br s), 1.94-1.66 (4H, m), 1.52 (3H, s), 1.50 (3H, s).

Elem. Anal.: C33H37ClN7O10S2Na (H2O)8.2
Calcd.: C, 41.20; H, 5.60; Cl, 3.69; N, 10.19; S, 6.67; Na, 2.39(%).
Found: C, 41.21; H, 5.62; Cl, 3.86; N, 10.16; S, 6.48; Na, 2.29(%).

Example 101

Synthesis of Compound (II-36)

[Formula 148]

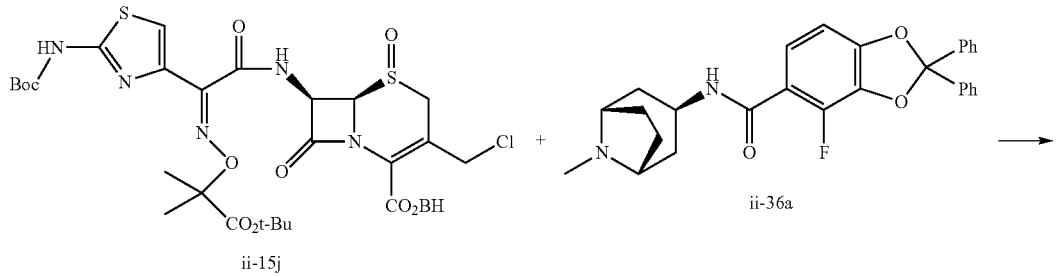

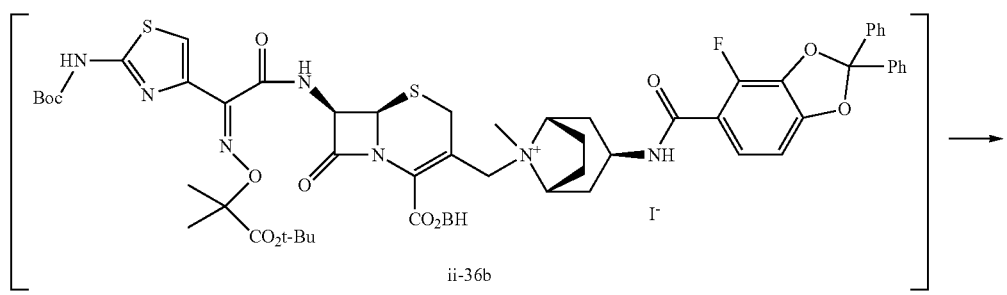

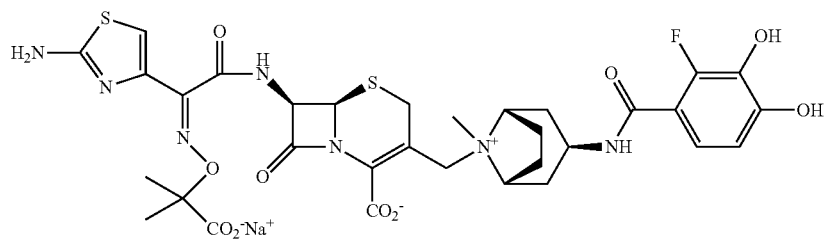

Step (1): compound ii-15j→compound ii-36a→compound II-36

Compound ii-15j (0.936 g, 1.0 mmol) and compound ii-36a (459 mg, 1.0 mmol) synthesized with reference to a method described in J. Med. Chem. 2008, 51, 2115 were used to synthesize the target compound in the same way as in step (1) in Example 95.

Yielded amount: 444.5 mg (45%)

$^1$H-NMR (D$_2$O) δ: 7.11 (1H, t, J=8.44 Hz), 6.99 (1H, s), 6.79 (1H, dd, J=8.44, 1.59 Hz), 5.89 (1H, d, J=4.95 Hz), 5.38 (1H, d, J=4.95 Hz), 4.24 (1H, t, J=6.97 Hz), 4.10-3.94 (4H, m), 3.51 (1H, d, J=16.95 Hz), 3.11 (3H, br 2.81-2.69 (2H, m), 2.59-2.40 (4H, m), 2.21 (1H, br s), 2.16 (1H, br s), 1.52 (3H, s), 1.50 (3H, s).

Elem. Anal.: C32H35FN7O10S2Na1(H2O)8.5
Calcd.: C, 41.02; H, 5.59; F, 2.03; N, 10.46; S, 6.84; Na, 2.45(%).
Found: C, 41.03; H, 5.46; F, 2.20; N, 10.39; S, 6.80; Na, 2.38(%).

Example 102

Synthesis of Compound (II-37)

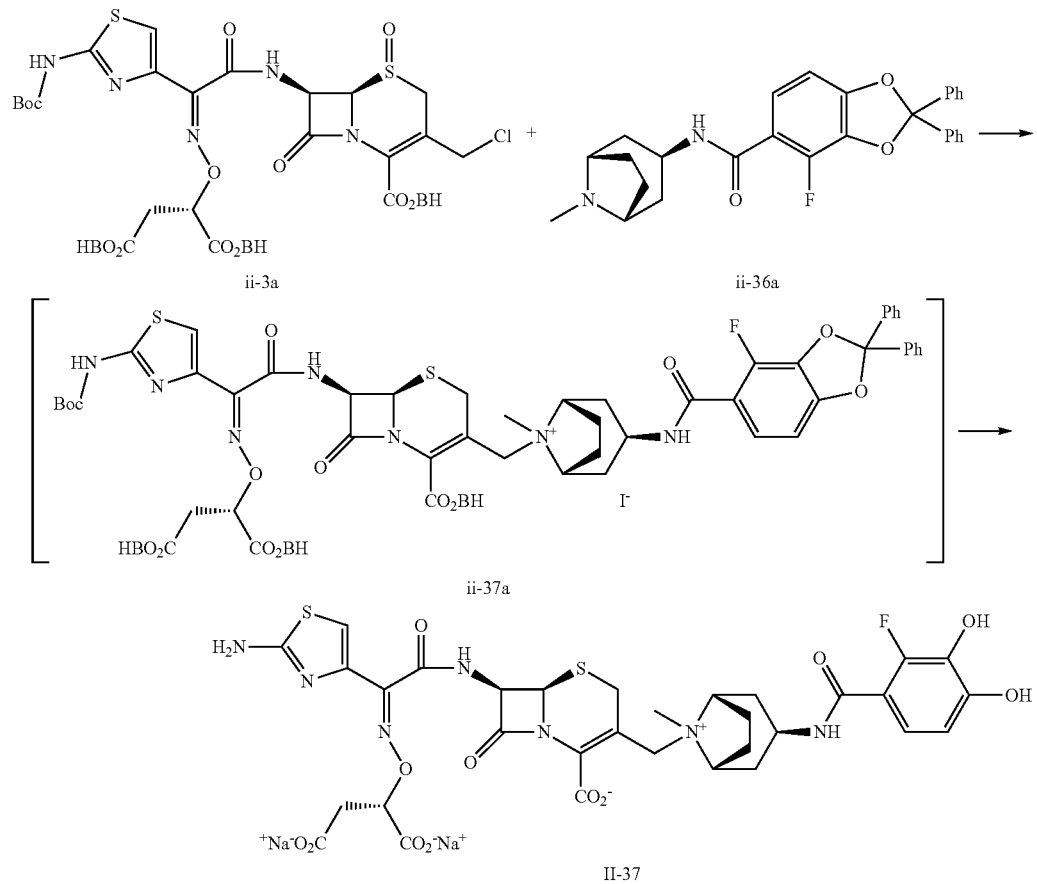

[Formula 149]

Step (1): compound ii-3a+compound ii-36a→compound II-37

Compound ii-3a (1.249 g, 1.0 mmol) and compound ii-36a (459 mg, 1.0 mmol) were used to synthesize the target compound in the same way as in step (1) in Example 95.

Yielded amount: 353.5 mg (32%)

$^1$H-NMR (D$_2$O) δ: 7.11 (1H, t, J=8.44 Hz), 7.02 (1H, s), 6.79 (1H, dd, J=8.44, 1.43 Hz), 5.84 (1H, d, J=4.87 Hz), 5.35 (1H, d, J=4.87 Hz), 5.00-4.94 (1H, m), 4.62 (1H, d, J=15.11 Hz), 4.24 (1H, t, J=7.05 Hz), 4.12 (1H, d, J=14.27 Hz), 4.03 (1H, br s), 3.95-3.90 (2H, m), 3.50 (1H, d, J=16.95 Hz), 3.10 (3H, br s), 2.80-2.70 (4H, m), 2.56-2.39 (4H, m), 2.21 (1H, br s), 2.15 (1H, br s).

Example 103

Synthesis of Compound (II-38)

[Formula 150]

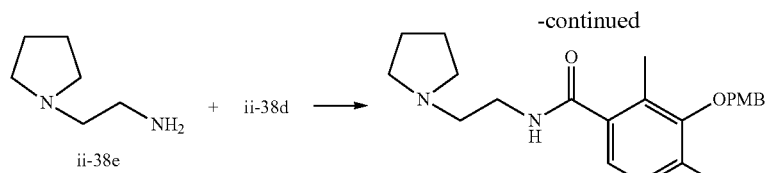

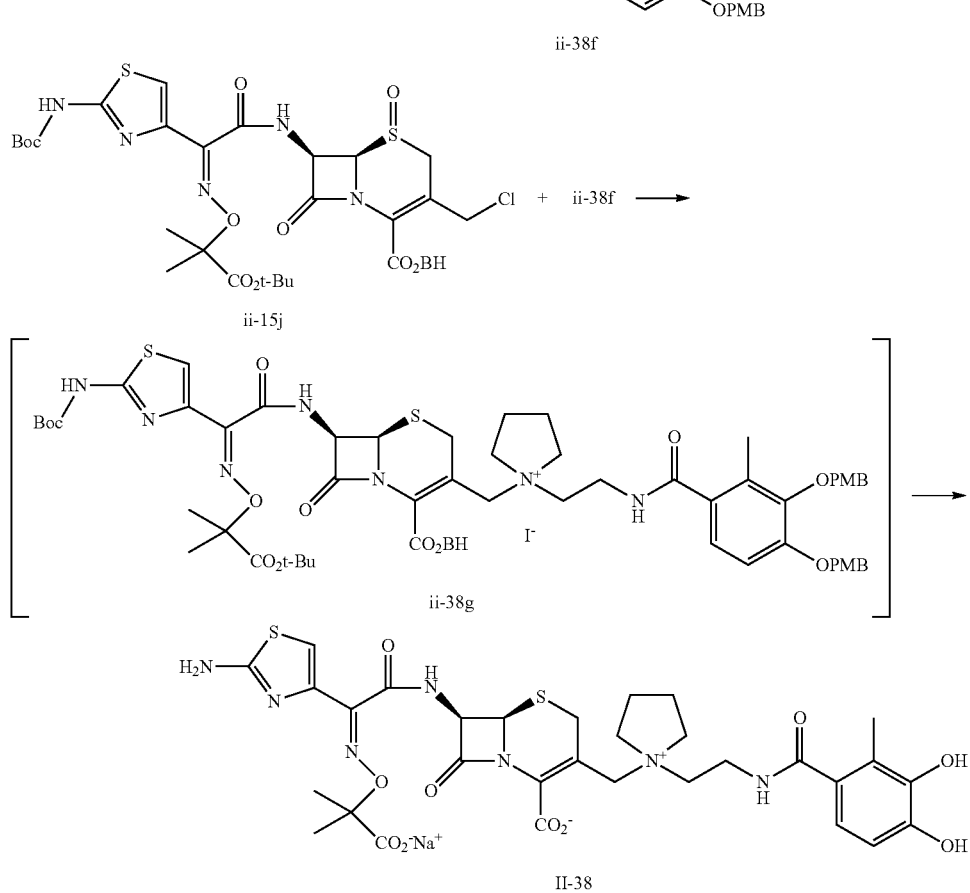

Step (1): compound ii-38a→compound ii-38b

Boron tribromide (12.05 mL, 127 mmol) was added to a solution of compound ii-38a (10.0 g, 51.0 mmol, synthesized with reference to a method described in WO 2009/55077 A1) in dichloromethane (60 mL) while cooled with ice. The resultant solution was stirred at room temperature for 2 hours. The reaction liquid was added to methanol (100 ml) while cooled with ice. The resultant was stirred at room temperature for 2 days. The reaction liquid was diluted with dichloromethane/methanol, washed with a saturated salt solution, and dried over magnesium sulfate. Magnesium sulfate was filtrated off, and then the liquid was concentrated under reduced pressure. Thereto was added diisopropyl ether to precipitate a solid. The solid was collected by filtration, so as to yield compound ii-38b (2.86 g, 31%). The solid precipitated while the filtrate was separated to two phases was filtrated, and washed with water to yield compound ii-38b (3.30 g, 36%).

$^1$H-NMR (DMSO-$d_6$) δ: 10.05 (1H, br s), 8.46 (1H, br s), 7.23 (1H, d, J=8.46 Hz), 6.67 (1H, d, J=8.46 Hz), 3.73 (3H, s), 2.34 (3H, s).

Step (2): compound ii-38b→compound ii-38c

Compound ii-38b (6.16 g, 33.8 mmol) was suspended into N,N-dimethylformamide (60 mL), and thereto were added potassium carbonate (14.02 g, 101 mmol), p-methoxybenzyl chloride (11.05 mL, 81.0 mmol) and sodium iodide (5.07 g, 33.8 mmol) in turn. The liquid was stirred at 70° C. for 7 hours. Furthermore, thereto were added potassium carbonate (7.01 g, 51 mmol), and p-methoxybenzyl chloride (5.53 mL, 41.0 mmol) in turn. The liquid was stirred at 70° C. for 3 hours. The reaction liquid was poured into water, and the precipitated solid was collected by filtration, and washed with water and diisopropyl ether to yield compound ii-38c (12.39 g, 89%).

$^1$H-NMR (CDCl$_3$) δ: 7.68 (1H, d, J=8.69 Hz), 7.37 (2H, d, J=8.62 Hz), 7.28 (2H, d, J=8.62 Hz), 6.91 (2H, d, J=8.62 Hz), 6.85 (1H, d, J=8.69 Hz), 6.82 (2H, d, 8.62 Hz), 5.09 (2H, s), 4.84 (2H, s), 3.85 (3H, s), 3.83 (3H, s), 3.80 (3H, s), 2.49 (3H, s).

Step (3): compound ii-38c→compound ii-38d

An 8 N aqueous sodium hydroxide solution (7.10 mL, 56.8 mmol) was added to a solution of compound ii-38c (12.0 g, 28.4 mmol) in tetrahydrofuran (45 ml) and methanol (35 ml). The resultant solution was stirred at 70° C. for 2 hours. To the reaction liquid was added a 2 N aqueous hydrochloric acid solution (30 mL), and the solution was concentrated under reduced pressure. The precipitated solid was then collected by filtration, and washed with water and diisopropyl ether to yield compound ii-38d (11.45 g, 96%).

¹H-NMR (DMSO-d₆) δ: 12.49 (1H, br s), 7.61 (1H, d, J=8.85 Hz), 7.44 (2H, d, J=8.58 Hz), 7.25 (2H, d, J=8.58 Hz), 7.08 (1H, d, J=8.85 Hz), 6.97 (2H, d, J=8.56 Hz), 6.85 (2H, d, J=8.58 Hz), 5.14 (2H, s), 4.79 (2H, s), 3.77 (3H, s), 3.74 (3H, s), 2.36 (3H, s).

Step (4): compound ii-38e→compound ii-38d→compound ii-38f

Compound ii-38d (2.00 g, 4.90 mmol) was suspended into dichloromethane (20 mL). Thereto were then added 1-ethyl-3-(3-dimethylaminopropyl)carbodiimide hydrochloride (1.033 g, 5.39 mmol) and HOBt (794 mg, 5.88 mmol) in turn while cooled with ice. The liquid was stirred at room temperature for 30 minutes. Thereto was added compound ii-38e (683 µl, 5.39 mmol) while cooled with ice. The resultant was stirred at room temperature overnight. The reaction liquid was diluted with dichloromethane, washed with an aqueous sodium hydroxide solution, water and a saturated salt solution, and dried over magnesium sulfate. Magnesium sulfate was filtrated off, and then the liquid was concentrated under reduced pressure. Thereto was added diisopropyl ether to precipitate a solid. In this way, compound ii-38f was yielded (2.36 g, 96%).

¹H-NMR (DMSO-d₆) δ: 8.02 (1H, t, J=5.57 Hz), 7.42 (2H, d, J=8.54 Hz), 7.27 (2H, d, J=8.54 Hz), 7.01 (2H, s), 6.96 (2H, d, J=8.54 Hz), 6.86 (2H, d, J=8.54 Hz), 5.11 (2H, s), 4.80 (2H, s), 3.76 (3H, s), 3.74 (3H, s), 3.25-3.30 (2H, m), 2.17 (3H, s), 1.69-1.64 (4H, m).

Step (5): compound ii-15j→compound ii-38f→compound II-38

Compound ii-15j (0.936 g, 1.0 mmol) and compound ii-38f (555 mg, 1.1 mmol) were used to synthesize the target compound in the same way as in step (1) in Example 95.

Yielded amount: 483.1 mg (51%)

¹H-NMR (D₂O) δ: 6.97 (1H, s), 6.90 (1H, d, J=8.31 Hz), 6.80 (14, d, J=8.31 Hz), 5.87 (1H, d, J=4.96 Hz), 5.36 (1H, d, J=4.96 Hz), 4.13 (1H, d, J=14.18 Hz), 3.98-3.86 (2H, m), 3.79-3.46 (8H, m), 2.23 (8H, br s), 1.51 (3H, s), 1.49 (3H, s).

Elem. Anal.: C31H36N7O10S2Na (H2O)7.4(NaHCO3) 0.1

Calcd.: C, 41.71; H, 5.73; N, 10.95; S, 7.16; Na, 2.82(%).
Found: C, 41.62; H, 5.59; N, 11.14; S, 7.31; Na, 2.81(%).

Example 104

Synthesis of Compound (II-39)

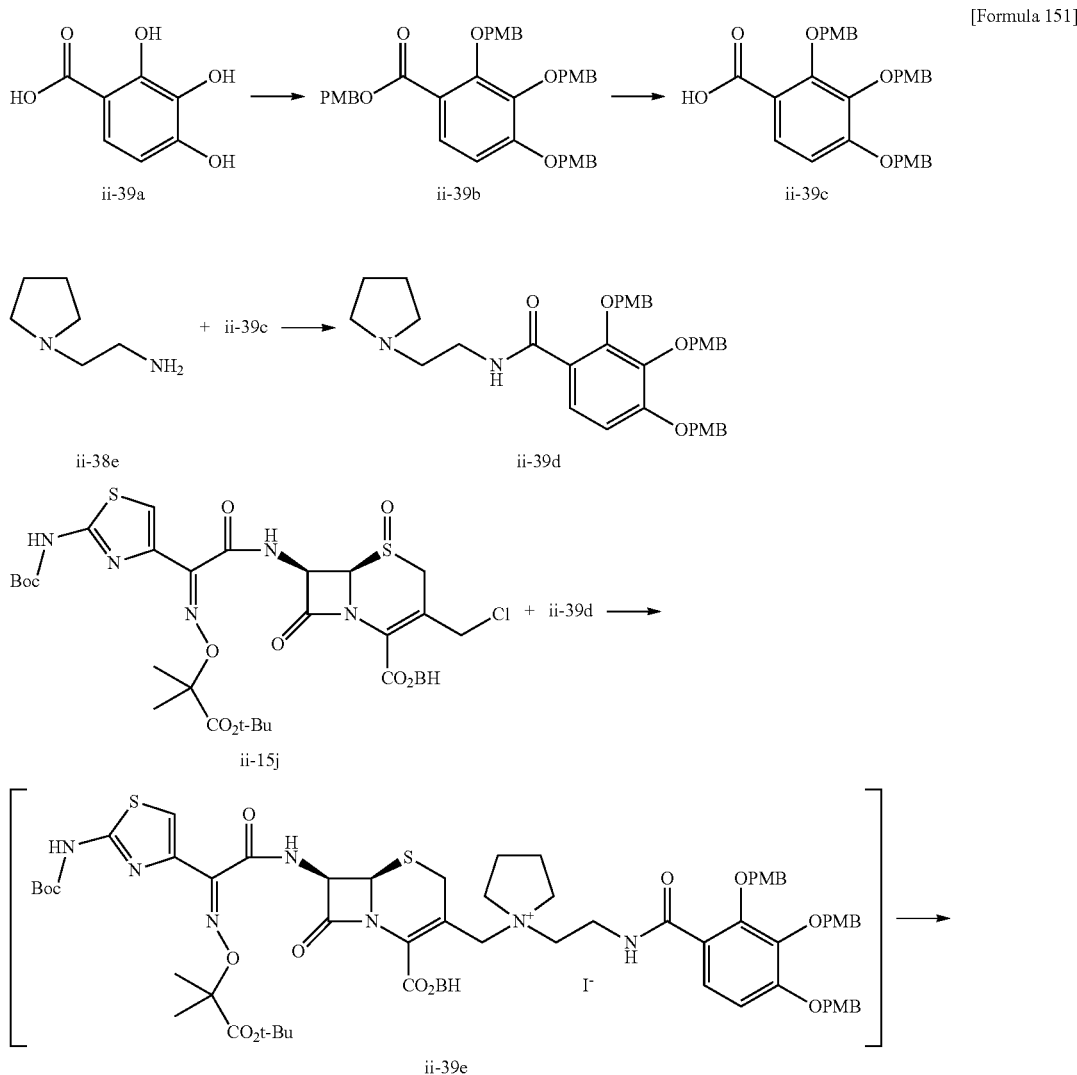

[Formula 151]

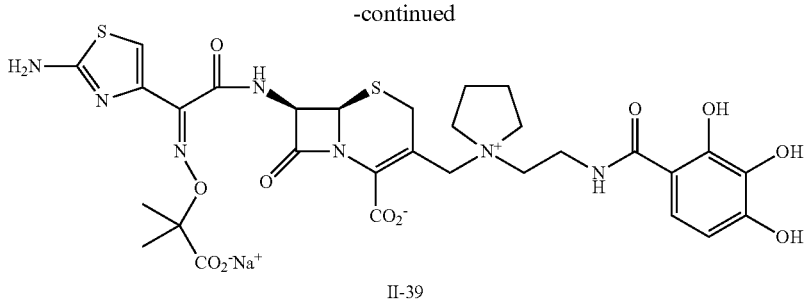

II-39

Step (1): compound ii-39a compound ii-39b

Compound ii-39a (5.00 g, 29.4 mmol) was suspended into N,N-dimethylformamide (60 mL), and thereto were then added potassium carbonate (24.37 g, 176 mmol) p-methoxybenzyl chloride (19.21 mL, 141 mmol) and sodium iodide (4.41 g, 29.4 mmol) in turn. The liquid was stirred at 70° C. for 4 hours. Furthermore, thereto were added potassium carbonate (12.19 g, mmol), and p-methoxybenzyl chloride (9.61 mL, 71 mmol) in turn. The liquid was stirred at 70° C. overnight. The reaction liquid was diluted with ethyl acetate, and the organic phase was washed with water and a saturated salt solution, and dried over magnesium sulfate. Magnesium sulfate was filtrated off. The organic phase was then concentrated under reduced pressure and subjected to silica gel column chromatography to elute out a desired compound with hexane/ethyl acetate. The desired-compound-containing fraction was concentrated under reduced pressure to yield compound ii-39b (17.77 g, 93%).

$^1$H-NMR (CDCl$_3$) δ: 7.59 (1H, d, J=8.85 Hz), 7.23-7.36 (8H, m), 6.92-6.73 (9H, m), 5.24 (2H, s), 5.05 (2H, s), 4.97 (2H, s), 4.91 (2H, s), 3.83-3.79 (12H, m)

Step (2): compound ii-39b→compound ii-39c

An 8 N aqueous sodium hydroxide solution (6.83 mL, 54.6 mmol) was added to a solution of compound ii-39b (17.77 g, 27.3 mmol) in tetrahydrofuran (45 mL) and methanol (35 mL). The solution was stirred at 70° C. for 4 hours. Furthermore, thereto was added an 8 N aqueous sodium hydroxide solution (3.42 mL, 27.3 mmol). The solution was stirred at 70° C. for 3 hours. To the reaction liquid was added a 2 N aqueous hydrochloric acid solution (45 mL), and the resultant was concentrated under reduced pressure. Thereafter, the precipitated solid was collected by filtration, and washed with water and diisopropyl ether to yield compound ii-39c (11.23 g, 78%).

$^1$H-NMR (DMSO-d$_6$) δ: 12.57 (1H, s), 7.49 (1H, d, J=8.85 Hz), 7.41 (2H, d, J=8.46 Hz), 7.34 (2H, d, J=8.46 Hz), 7.23 (2H, d, J=8.46 Hz), 7.01 (1H, d, J=8.85 Hz), 6.97 (2H, d, J=8.46 Hz), 6.90 d, J=8.46 Hz), 6.82 (2H, d, J=8.46 Hz), 5.12 (2H, s), 4.90 (2H, s), 4.86 (2H, s), 3.77 (3H, s), 3.76 (3H, s), 3.74 (3H, s)

Step (3): compound ii-38e+compound ii-39c→compound ii-39d

Compound ii-39c (2.00 g, 3.77 mmol) was used to synthesize a desired compound in the same way as in step (4) in Example 103. The compound-containing liquid was subjected to amino silica gel column chromatography to elute out the desired compound with hexane/ethyl acetate. The desired-compound-containing fraction was concentrated under reduced pressure to yield compound ii-39d (2.44 g, 103%).

$^1$H-NMR (DMSO-d$_6$) δ: 8.10 (1H, t, J=5.26 Hz), 7.51 (1H, d, J=8.77 Hz), 7.41 (2H, d, J=8.31 Hz), 7.30 (2H, d, J=8.31 Hz), 7.25 (2H, d, J=8.31 Hz), 7.02 (1H, d, J=8.77 Hz), 6.97 (2H, d, J=8.31 Hz), 6.90 (2H, d, J=8.31 Hz), 6.84 (2H, d, J=8.31 Hz), 5.11 (2H, s), 5.01 (2H, s), 4.89 (2H, s), 3.77 (3H, s), 3.74 (6H, s), 3.30-3.26 (2H, m), 2.42-2.35 (6H, m), 1.63-1.58 (4H, m).

Step (4): compound ii-15j+compound ii-39d→compound II-39

Compound ii-15j (0.936 g, 1.0 mmol) and compound ii-39d (689 mg, 1.1 mmol) were used to synthesize the target compound in the same way as in step (1) in Example 95.

Yielded amount: 427.2 mg (49%)

$^1$H-NMR (D$_2$O) δ: 7.19 (1H, d, J=8.77 Hz), 6.97 (1H, s), 6.53 (1H, d, J=8.77 Hz), 5.86 (1H, d, J=4.88 Hz), 5.35 (1H, d, J=4.88 Hz), 4.11 (1H, d, J=14.03 Hz), 3.97-3.86 (2H, m), 3.79-3.42 (10H, m), 2.21 (4H, br s), 1.50 (3H, s), 1.49 (3H, s).

Elem. Anal.: C30H34N7O11S2Na (H2O)7.5

Calcd.: C, 40.45; H, 5.54; N, 11.01; S, 7.20; Na, 2.58(%).

Found: C, 40.37; H, 5.43; N, 11.05; S, 7.21; Na, 2.62(%).

Example 105

Synthesis of Compound (II-40)

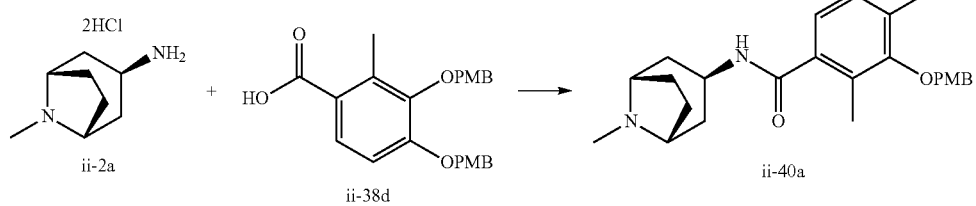

[Formula 152]

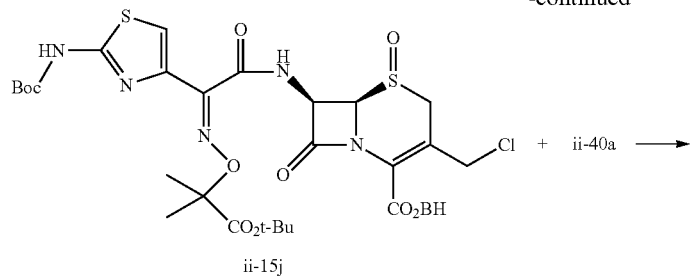

ii-15j

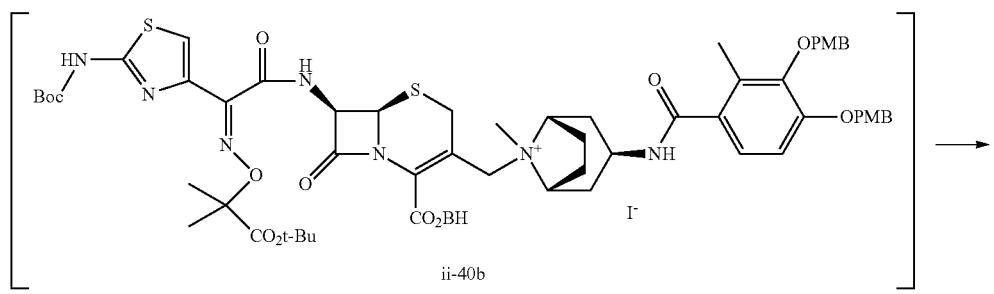

ii-40b

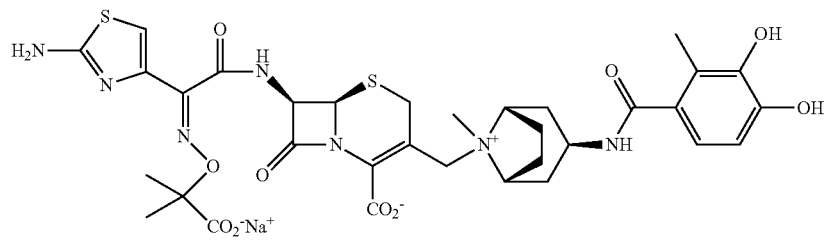

II-40

Step (1): compound ii-2a+compound ii-38d→compound ii-40a

Compound ii-38d (3.00 g, 7.34 mmol) was suspended into dichloromethane (30 mL). Thereto were added 1-ethyl-3-(3-dimethylaminopropyl)carbodiimide hydrochloride (1.549 g, 8.08 mmol) and 1-hydroxybenzotriazole (1.191 g, 8.81 mmol) in turn while cooled with ice. The liquid was stirred at room temperature for 30 minutes. Thereto were added compound ii-2a (1.879 g, 8.81 mmol) and diisopropylethylamine (3.85 mL, 22.03 mmol) while cooled with ice. The resultant was stirred at room temperature overnight. The reaction liquid was diluted with dichloromethane, and the organic phase was washed with an aqueous sodium hydroxide solution, water and a saturated salt solution, and dried over magnesium sulfate. Magnesium sulfate was filtrated off, and then the organic phase was concentrated under reduced pressure. Thereto was added diisopropyl ether to precipitate a solid. In this way, compound ii-40a (3.52 g, 90%) was yielded.

$^1$H-NMR (DMSO-$d_6$) δ: 7.82 (1H, d, J=4.42 Hz), 7.42 (2H, d, J=8.46 Hz), 7.29 (2H, d, J=8.46 Hz), 7.04 (1H, d, J=8.54 Hz), 6.99-6.94 (3B, m), 6.87 (2H, d, J=8.46 Hz), 5.11 (2H, s), 4.80 (2H, s), 3.85-3.79 (1H, m), 3.76 (3H, s), 3.74 (3H, s), 3.00 (2H, br s), 2.17 (3H, s), 2.15 (3H, s), 1.89-2.03 (6H, m), 1.70 (2H, d, J=14.49 Hz).

Step (2): compound ii-15j→compound ii-40a→compound II-40

Compound ii-15j (0.936 g, 1.0 mmol) and compound ii-40a (584 mg, 1.1 mmol) were used to synthesize the target compound in the same way as in Step (1) in Example 95.

Yielded amount: 465.9 mg (46%)

$^1$H-NMR (D$_2$O) δ: 6.98 (1H, s), 6.87 (1H, d, J=7.93 Hz), 6.79 (1H, d, J=7.93 Hz), 5.89 (1H, d, J=4.65 Hz), 5.37 (1H, d, J=4.65 Hz), 4.23 (1H, t, J=6.63 Hz), 4.09-3.92 (4H, m), 3.50 (1H, d, J=17.08 Hz), 3.10 (3H, br s), 2.82-2.70 (2H, m), 2.58-2.33 (4H, m), 2.23 (3H, s), 2.20 (1H, br s), 2.15 (1H, br s), 1.52 (3H, s), 1.50 (3H, s).

Elem. Anal.: C33H38N7O10S2Na (H2O)9.5

Calcd.: C, 41.68; H, 6.04; N, 10.31; S, 6.74; Na, 2.42(%).

Found: C, 41.60; H, 5.97; N, 10.45; S, 6.66; Na, 2.54(%).

Example 106

Synthesis of Compound (II-41)

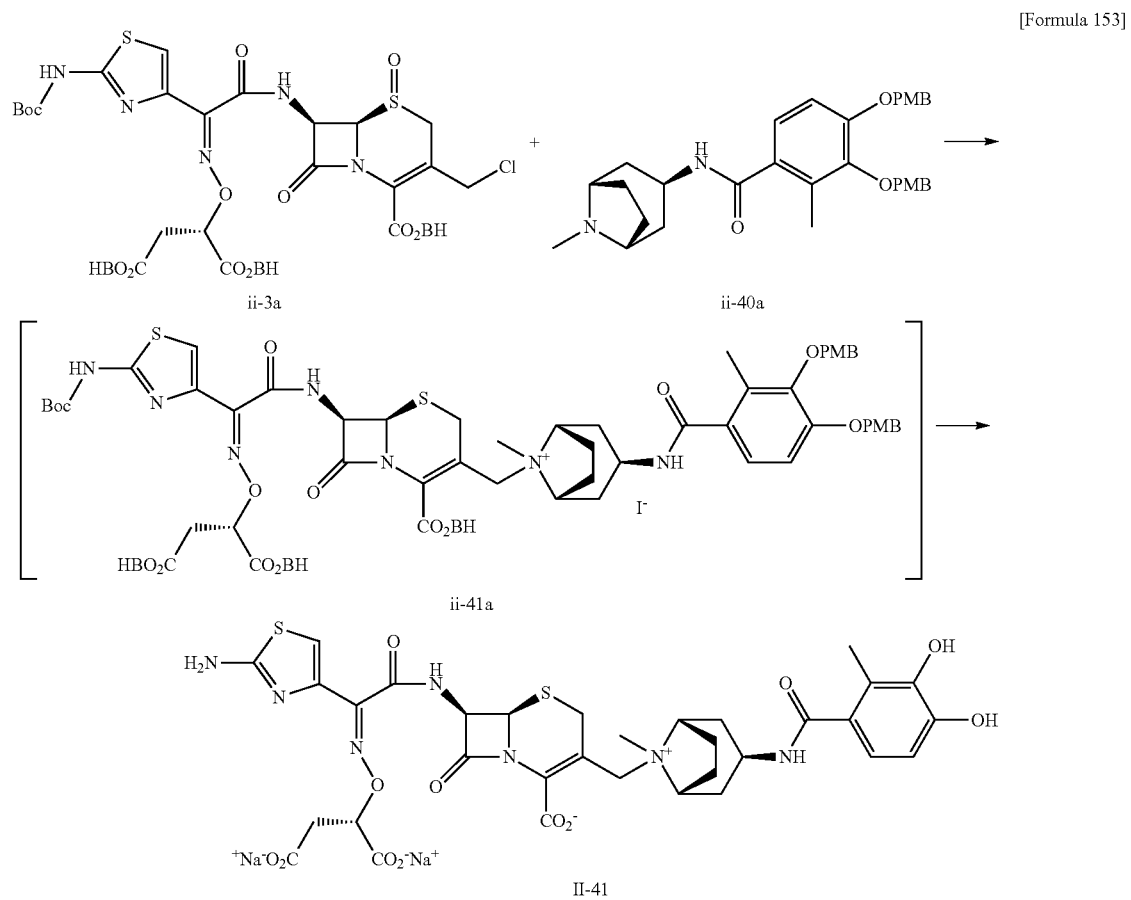

[Formula 153]

Step (1): compound ii-3a+compound ii-41a→compound II-41

Compound ii-3a (1.249 g, 1.0 mmol) and compound ii-41a (584 mg, 1.1 mmol) were used to synthesize the target compound in the same way as in step (1) in Example 95.

Yielded amount: 456.3 mg (43%)

$^1$H-NMR (D$_2$O) δ: 7.01 (1H, d, 1.98 Hz), 6.87 (1H, d, 8.24 Hz), 6.80 (1H, d, J=8.24 Hz), 5.83 (1H, d, J=4.80 Hz), 5.34 (1H, d, J=4.80 Hz), 4.99-4.95 (1H, m), 4.56 (1H, d, J=19.22 Hz), 4.23 (1H, t, J=7.55 Hz), 4.10 (1H, d, J=14.34 Hz), 4.02 (1H, br s), 3.95-3.89 (2H, m), 3.50 (1H, d, J=16.93 Hz), 3.10 (3H, brs), 2.79-2.69 (4H, m), 2.58-2.33 (4H, m), 2.23 (3H, s), 2.20 (1H, br s), 2.14 (1H, br s).

Elem. Anal.: C33H35.2N7O12S2Na1.8(H2O)10.3

Calcd.: C, 39.13; H, 5.55; N, 9.68; S, 6.33; Na, 4.09(%).

Found: C, 39.13; H, 5.60; N, 9.75; S, 6.14; Na, 4.12(%).

Example 107

Synthesis of Compound (II-42)

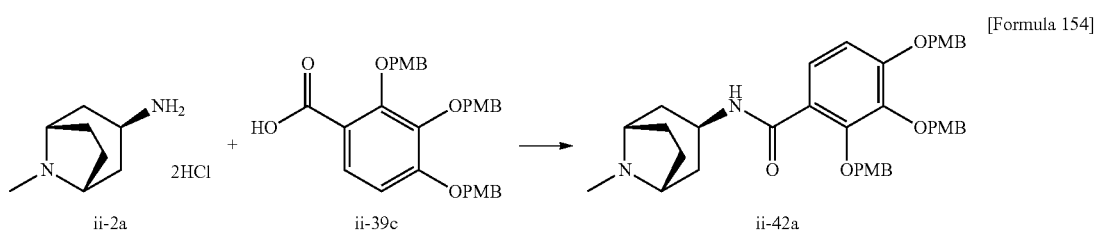

[Formula 154]

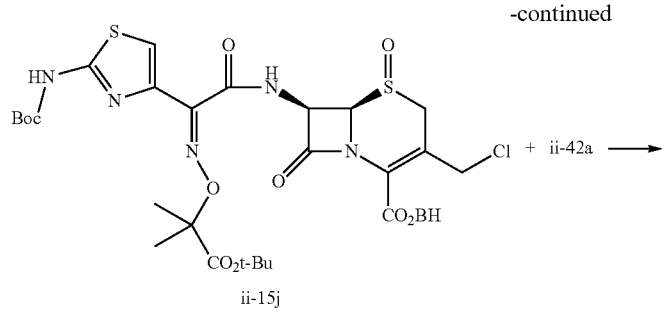

ii-15j

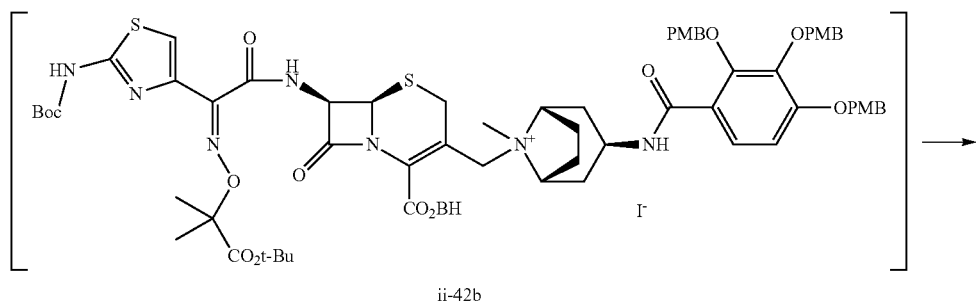

ii-42b

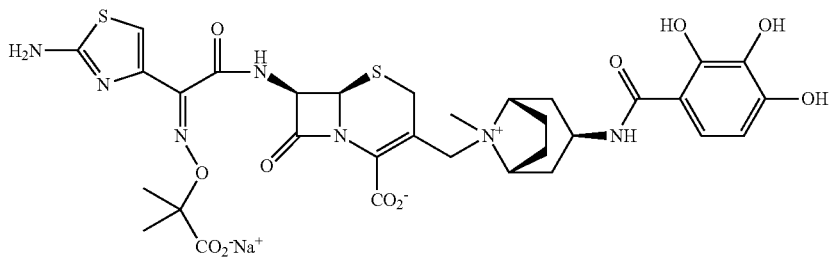

II-42

Step (1): compound ii-2a+compound ii-39c→compound ii-42a Compound ii-39c (3.00 g, 5.65 mmol) was used to synthesize a desired compound in the same way as in step (1) in Example 105. The compound-containing liquid was subjected to amino silica gel column chromatography to elute out the desired compound with hexane/ethyl acetate. The desired-compound-containing fraction was concentrated under reduced pressure to yield compound ii-42a (3.21 g, 87%).

$^1$H-NMR (DMSO-$d_6$) δ: 8.08 (1H, d, J=6.71 Hz), 7.55 (1H, d, J=8.69 Hz), 7.43 (2H, d, J=8.49 Hz), 7.31 (2H, d, J=8.49 Hz), 7.27 (2H, d, J=8.49 Hz), 7.04 (1H, d, J=8.69 Hz), 6.97 (2H, d, J=8.49 Hz), 6.91 (2H, d, J=8.49 Hz), 6.83 (2H, d, J=8.49 Hz), 5.13 (2H, s), 5.04 (2H, s), 4.95 (2H, s), 3.89-3.82 (1H, m), 3.77 (3H, s), 3.75 (3H, s), 3.73 (3H, s), 2.82 (2H, br s), 2.07 (3H, s), 1.95-1.86 (2H, m), 1.78-1.70 (2H, m), 1.34-1.42 (2H, m), 1.28 (2H, d, J=14.34 Hz).

Step (2): compound ii-15j+compound ii-42a→compound II-42

Compound ii-15j (0.936 g, 1.0 mmol) and compound ii-42a (718 mg, 1.1 mmol) were used to synthesize the target compound in the same way as in step (1) in Example 95.

Yielded amount: 477.9 mg (44%)

$^1$H-NMR (D$_2$O) δ: 7.27 (1H, d, J=8.85 Hz), 6.98 (1H, s), 6.52 (1H, d, J=8.85 Hz), 5.89 (1H, d, J=4.96 Hz), 5.37 (1H, d, J=4.96 Hz), 4.28 (1H, t, J=7.09 Hz), 4.10-3.93 (4H, m), 3.50 (1H, d, J=16.78 Hz), 3.11 (3H, br s), 2.70-2.81 (2H, m), 2.39-2.60 (4H, m), 2.14 (2H, d, J=16.93 Hz), 1.52 (3H, s), 1.5.0 (3H, s).

Elem. Anal.: C32H36N7O11S2Na (H2O)8.9(NaHCO3) 0.1

Calcd.: C, 40.56; H, 5.72; N, 10.32; S, 6.75; Na, 2.66(%).

Found: C, 40.56; H, 5.68; N, 10.52; S, 6.83; Na, 2.59(%).

Example 108

Synthesis of Compound (II-43)

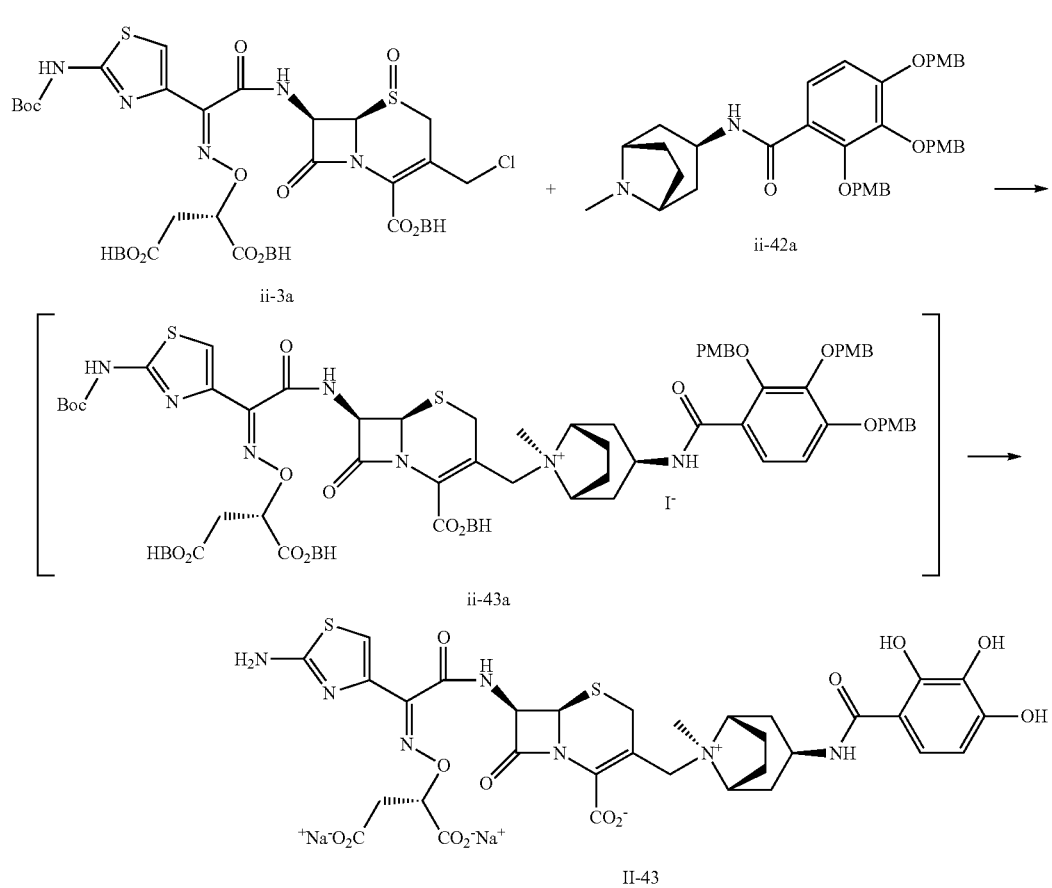

Step (1): compound ii-3a compound ii-42a compound II-43

Compound ii-3a (1.249 g, 1.0 mmol) and compound ii-42a (718 mg, 1.1 mmol) were used to synthesize the target Compound in the same way as in step (1) in Example 95.

Yielded amount: 280.1 mg (25%)

$^1$H-NMR (D$_2$O) δ: 7.27 (1H, d, J=8.85 Hz), 7.01 (1H, s), 6.54 (1H, d, J=8.85 Hz), 5.83 (1H, d, J=4.88 Hz), 5.34 (1H, d, J=4.88 Hz), 4.97 (1H, dd, J=7.70, 5.57 Hz), 4.61 (1H, d, J=13.73 Hz), 4.27 (1H, t, J=7.09 Hz), 4.10 (1H, d, J=14.34 Hz), 4.02 (1H, br s), 3.95-3.89 (2H, m), 3.49 (1H, d, J=16.47 Hz), 3.10 (3H, br s), 2.80-2.71 (4H, m), 2.37-2.60 (4H, m), 2.13 (2H, d, J=18.15 Hz).

Elem. Anal.: C32H33.3N7O13S2Na1.7(H2O)10.5
Calcd.: C, 37.82; H, 5.39; N, 9.65; S, 6.31; Na, 3.85(%).
Found: C, 37.97; H, 5.50; N, 9.54; S, 6.01; Na, 3.83(%).

Example 109

Synthesis of Compound (II-44)

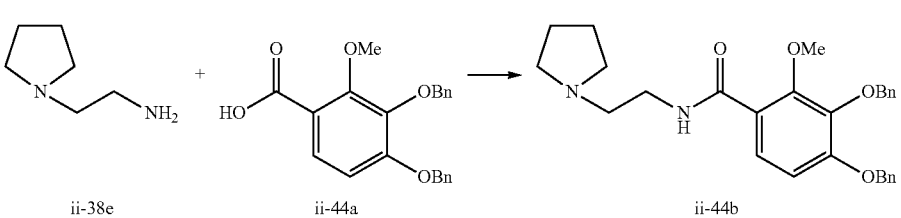

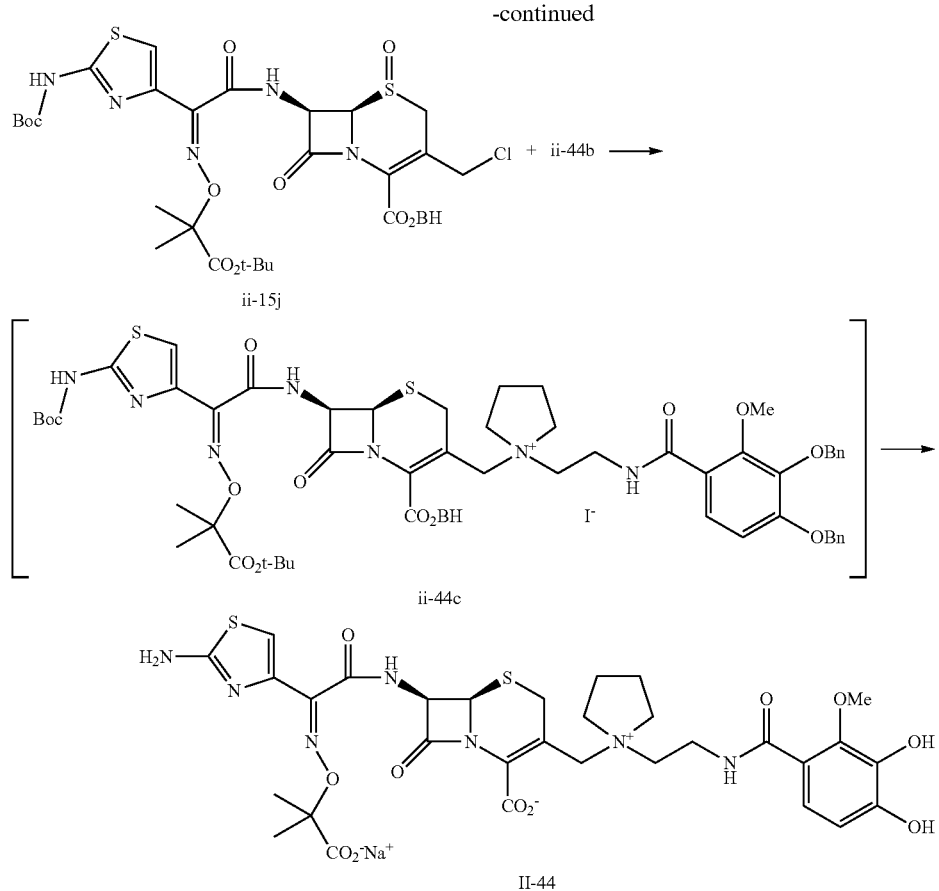

ii-15j ii-44c

II-44

Step (1): compound ii-39e+compound ii-44a→compound ii-44h

Compound ii-44a (0.74 g, 2.031 mmol) synthesized with reference to a method described in Helvetica Chemica Acta. 2006, 89, 1395 was used to synthesize a desired compound in the same way as in step (4) in Example 103. The compound-containing liquid was subjected to amino silica gel column chromatography to elute out the desired compound with chloroform. The desired-compound-containing fraction was concentrated under reduced pressure to yield compound ii-44b (1.00 g, 106%).

$^1$H-NMR (DMSO-$d_6$) δ: 8.31 (1H, t, J=4.88 Hz), 7.57-7.31 (11H, m), 7.03 (1H, d, J=9.00 Hz), 5.19 (2H, s), 4.98 (2H, s), 3.86 (3H, s), 3.38 (2H, q, J=6.00 Hz), 2.58 (2H, t, J=6.41 Hz), 1.68-1.72 (4H, m).

Step (2): compound ii-15j→compound ii-44b→compound II-44

Compound ii-15j (0.936 g, 1.0 mmol) and compound ii-44b (507 mg, 1.1 mmol) were used to synthesize the target compound in the same way as in step (1) in Example 95.

Yielded amount: 450.5 mg (46%)

$^1$H-NMR (D$_2$O) δ: 7.23 (1H, d, J=8.62 Hz), 6.98 (1H, s), 6.79 (1H, d, J=8.62 Hz), 5.87 (1H, d, J=4.96 Hz), 5.37 (1H, d, J=4.96 Hz), 4.13 (1H, d, J=14.64 Hz), 4.01-3.89 (2H, m), 3.84-3.75 (5H, m), 3.67-3.44 (6H, m), 2.23 (4H, br s), 1.51 (3H, s), 1.49 (3H, s).

Elem. Anal.: C31H36N7O11S2Na (H2O)7.1(NaHCO3) 0.1

Calcd.: C, 41.22; H, 5.60; N, 10.82; S, 7.08; Na, 2.79(%).
Found: C, 41.14; H, 5.53; N, 10.91; S, 7.26; Na, 2.79(%).

Example 110

Synthesis of Compound (II-45)

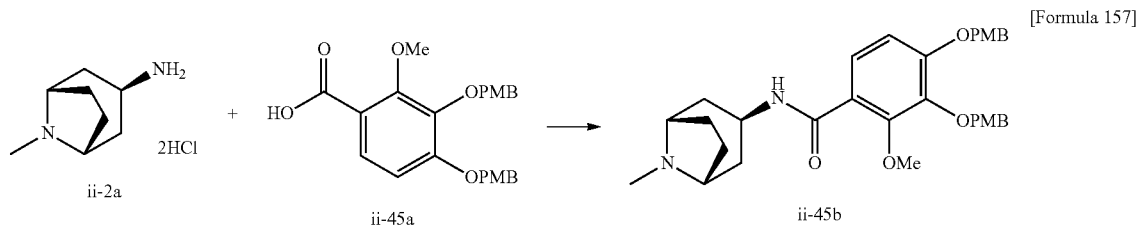

[Formula 157]

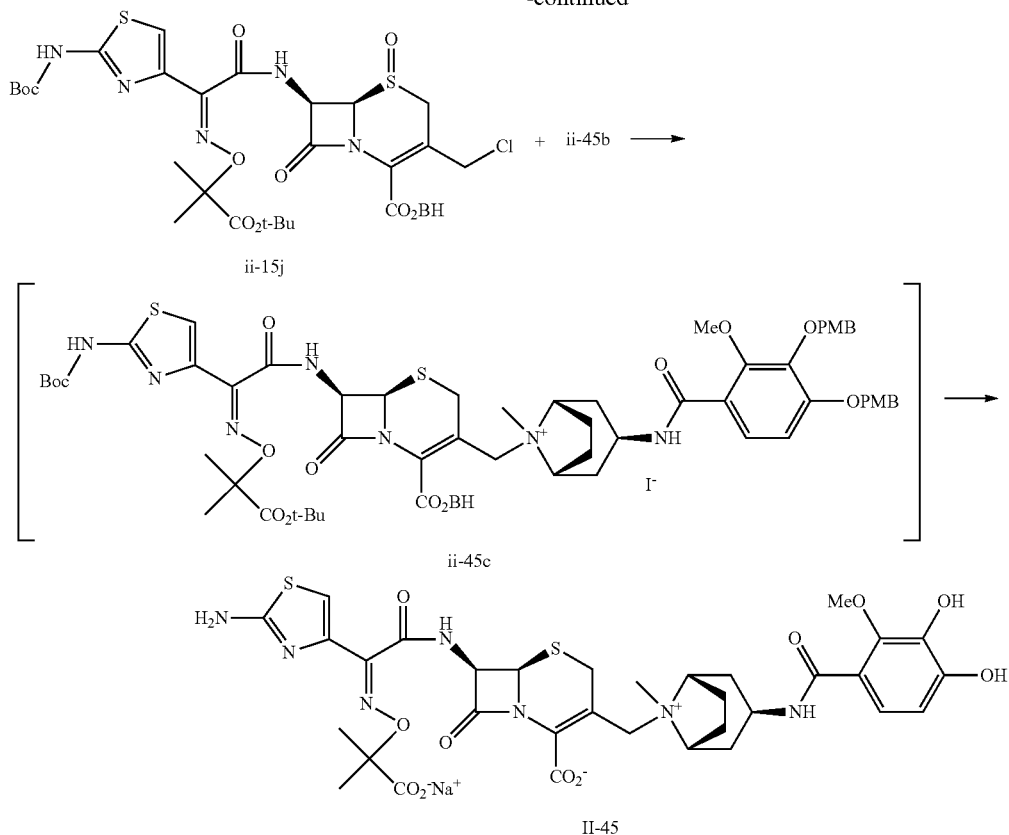

ii-15j ii-45c

II-45

Step (1): compound ii-2a+compound ii-45a→compound ii-45b

Compound ii-45a (1.04 g, 2.45 mmol) synthesized with reference to a method described in Helvetica Chemica Acta. 2006, 89, 1395 was used to synthesize a desired compound in the same may as in step (1) in Example 105. The compound-containing liquid was subjected to amino silica gel column chromatography to elute out the desired compound with chloroform. The desired-compound-containing fraction was concentrated under reduced pressure to yield compound ii-45b (1.17 g, 87%).

$^1$H-NMR (DMSO-$d_6$) δ: 8.24 (1H, d, J=6.71 Hz), 7.55 (1H, d, J=8.92 Hz), 7.41 (2H, d, J=8.51 Hz), 7.27 (2H, d, J=8.54 Hz), 7.02 (1H, d, J=8.92 Hz), 6.96 (2H, d, J=8.54 Hz), 6.84 (2H, d, J=8.54 Hz), 5.10 (2H, s), 4.88 (2H, s), 4.01 (1H, q, J=7.12 Hz), 3.91 (3H, s), 3.77 (3H, s), 3.74 (3H, s), 3.03 (2H, br s), 2.16 (3H, s), 2.11-2.01 (4H, m), 1.71-1.79 (2H, m), 1.58 (2H, d, J=14.18 Hz).

Step (2): compound ii-15j+compound ii-45b→compound II-45

Compound ii-15j (0.936 g, 1.0 mmol) and compound ii-45b (574 mg, 1.05 mmol) were used to synthesize the target compound in the same way as in step (1) in Example 95.

Yielded amount: 450.5 mg (46%)

$^1$H-NMR (D$_2$O) δ: 7.19 (1H, d, J=8.16 Hz), 6.99 (1H, s), 6.79 (1H, d, J=8.16 Hz), 5.89 (1H, d, J=4.80 Hz), 5.38 (1H, d, J=4.80 Hz), 4.31 (1H, t, J=7.78 Hz), 4.12-3.91 (4H, m), 3.88 (3H, s), 3.51 (1H, d, 15.86 Hz), 3.11 (3H, br s), 2.85-2.73 (2H, m), 2.56-2.65 (2H, m), 2.41 (2H, d, J=13.88 Hz), 2.15 (2H, d, J=17.39 Hz), 1.52 (3H, s), 1.50 (3H, s).

Elem. Anal.: C33H38N7O11S2Na (H2O)8.4
Calcd.: C, 41.85; H, 5.83; N, 10.35; S, 6.77; Na, 2.43(%).
Found: C, 41.81; H, 5.70; N, 10.39; S, 6.77; Na, 2.39(%).

Example 111

Synthesis of Compound (II-46)

[Formula 158]

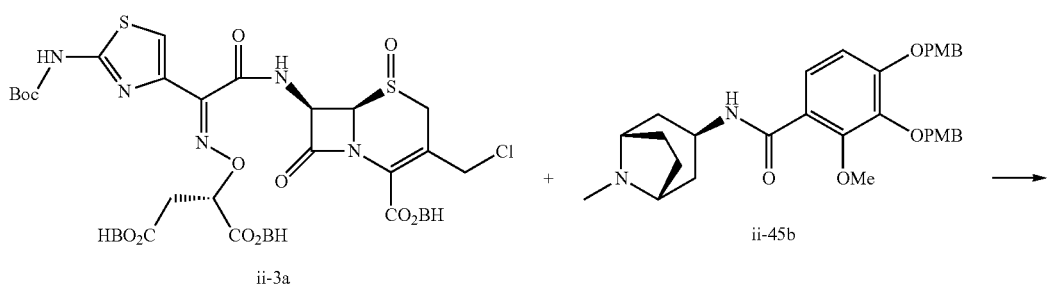

ii-3a ii-45b

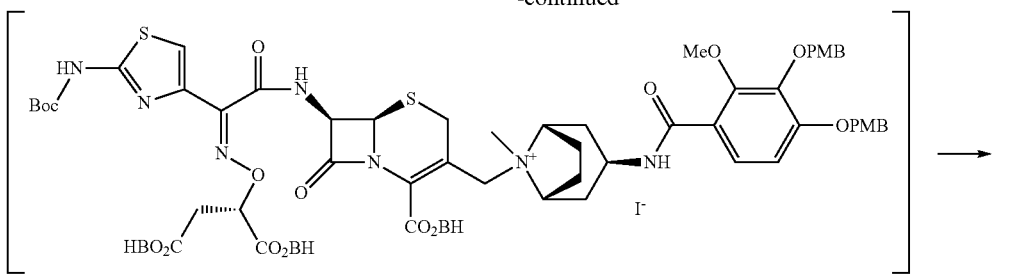

ii-46a

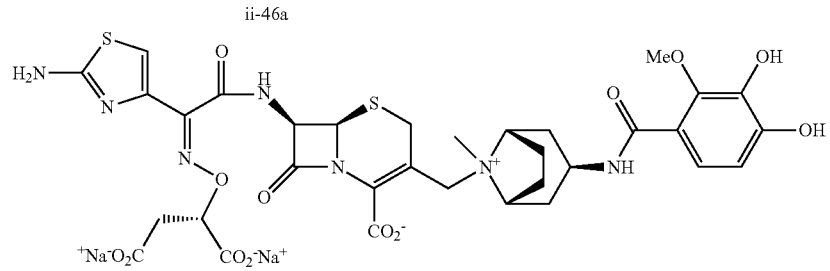

II-46

Step (1): compound ii-3a+compound ii-45b→compound II-46

Compound ii-3a (1.249 g, 1.0 mmol) and compound ii-45b (574 mg, 1.05 mmol) were used to synthesize the target compound in the same way as in step (1) in Example 95.

Yielded amount: 276.2 mg (24%)

$^1$H-NMR (D$_2$O) δ: 7.19 (1H, d, J=8.46 Hz), 7.01 (1H, s), 6.79 (1H, d, J=8.46 Hz), 5.84 (1H, d, J=5.03 Hz), 5.34 (1H, d, J=5.03 Hz), 4.30 (1H, t, J=7.32 Hz), 4.12 (1H, d, J=14.64 Hz), 4.05 (1H, s), 3.92 (6H, d, J=21.66 Hz), 3.50 (1H, d, J=16.47 Hz), 3.11 (3H, br s), 2.85-2.59 (6H, m), 2.47-2.37 (2H, m), 2.15 (2H, d, J=16.47 Hz).

Elem. Anal.: C33H35.1N7O13S2Na1.9(H2O)10.6
Calcd.: C, 38.24; H, 5.47; N, 9.46; S, 6.19; Na, 4.21(%).
Found: C, 38.18; H, 5.35; N, 9.47; S, 6.22; Na, 4.14(%).

Example 112

Synthesis of Compound (II-47)

[Formula 159]

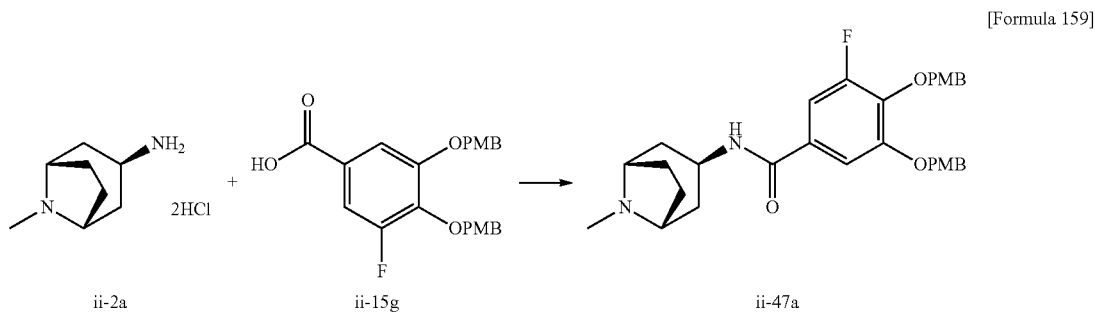

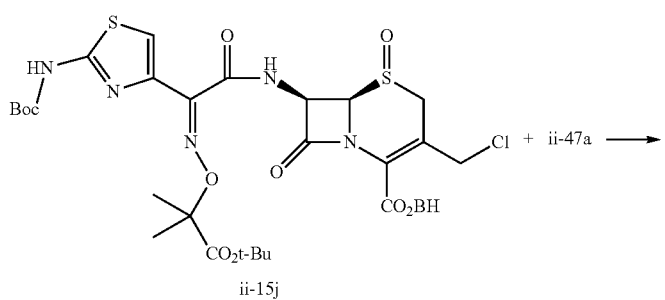

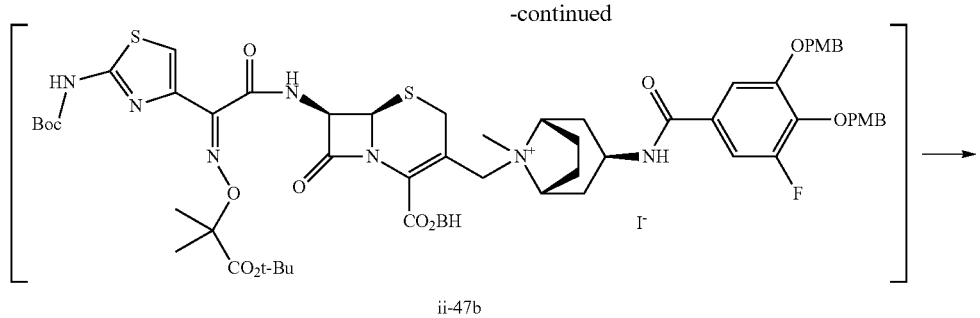

ii-47b

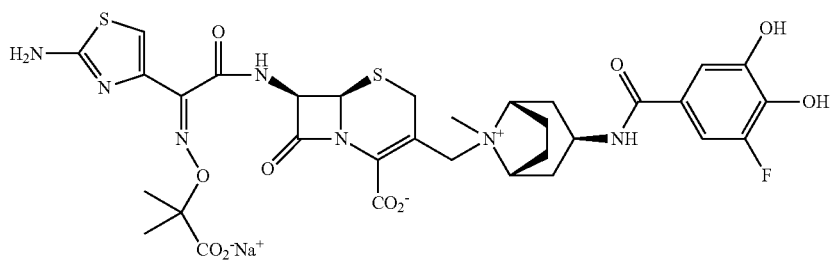

II-47

Step (1): compound ii-2a+compound ii-15g compound ii-47a
Compound ii-15g (1.50 g, 3.64 mmol) was used to synthesize a desired compound in the same way as in step (1) in Example 105. The compound-containing liquid was subjected to amino silica gel column chromatography to elute out the desired compound with chloroform. The desired-compound-containing fraction was concentrated under reduced pressure to yield compound ii-47a (1.46 g, 75%).

$^1$H-NMR (DMSO-d$_6$) δ: 7.84 (1H, d, J=4.42 Hz), 7.40 (2H, d, J=8.54 Hz), 7.33-7.19 (4H, m), 6.96 (2H, d, J=8.54 Hz), 6.85 (2H, d, J=8.54 Hz), 5.15 (2H, s), 5.01 (2H, s), 3.88-3.82 (1H, m), 3.77 (3H, s), 3.73 (3H, s), 3.00 (2H, br s), 2.14 (3H, s), 2.04-1.89 (4H, m), 1.79-1.87 (2H, m), 1.71 (2H, d, J=14.34 Hz).

Step (2): compound ii-15j+compound ii-47a→compound II-47

Compound ii-15j (0.936 g, 1.0 mmol) and compound ii-47a (588 mg, 1.1 mmol) were used to synthesize the target compound in the same way as in step (1) in Example 95.

Yielded amount: 429.6 mg (38%)

$^1$H-NMR (D$_2$O) δ: 7.13-7.08 (2H, m), 6.98 (1H, s), 5.89 (1H, d, J=4.88 Hz), 5.37 (1H, d, J=4.88 Hz), 4.64 (1H, d, J=11.44 Hz), 4.19 (1H, t, J=7.17 Hz), 4.09-3.94 (4H, m), 3.50 (1H, d, J=16.47 Hz), 3.10 (3H, br s), 2.80-2.67 (2H, m), 2.40-2.60 (4H, m), 2.19 (2H, d, J=17.08 Hz), 1.52 (3H, s), 1.50 (3H, s).

Elem. Anal.: C32H35FN7O10S2Na (H2O)9.6(NaHCO3) 0.1

Calcd.: C, 39.95; H, 5.67; F, 1.97; N, 10.16; S, 6.64; Na, 2.62(%).

Found: C, 39.90; H, 5.52; F, 2.04; N, 10.26; S, 6.76; Na, 2.60(%).

Example 113

Synthesis of Compound (II-48)

[Formula 160]

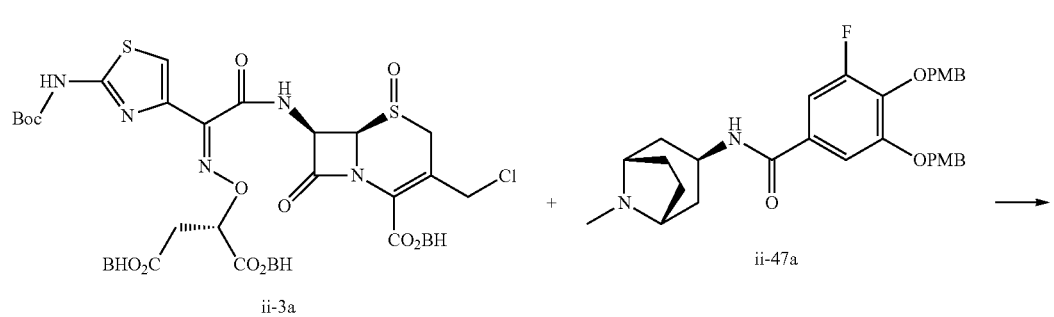

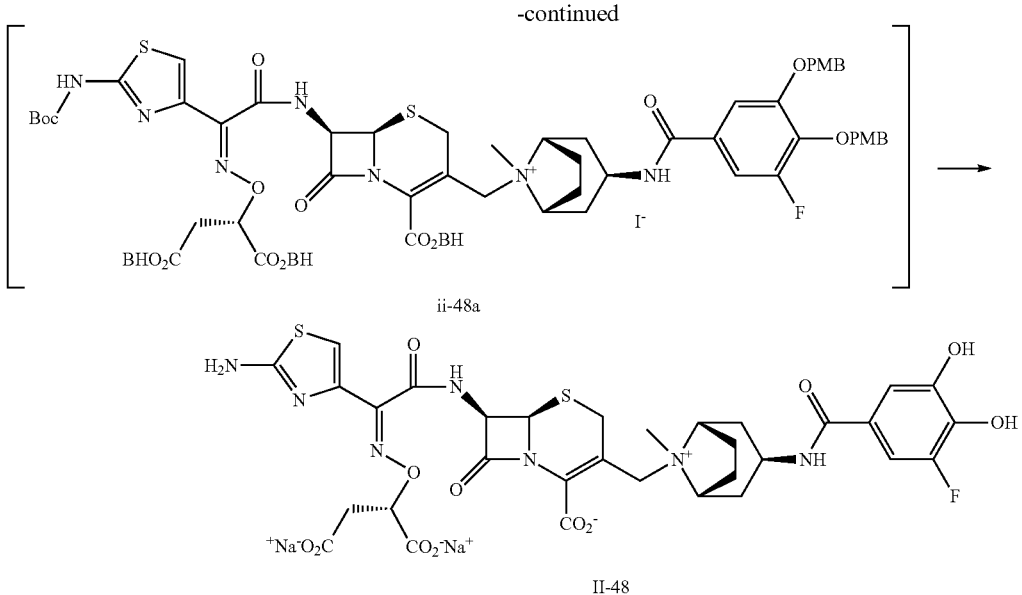
ii-48a
II-48
Step (2): compound ii-3a+compound ii-47a→compound II-48
Compound ii-3a (1.249 g, 1.0 mmol) and compound ii-47a (588 mg, 1.1 mmol) were used to synthesize the target compound in the same way as in step (1) in Example 95.
Yielded amount: 276.2 mg (24%)
$^1$H-NMR (D$_2$O) δ: 7.14-7.06 (2H, m), 7.01 (1H, s), 5.83 (1H, d, J=4.96 Hz), 5.34 (1H, d, J=4.96 Hz), 4.19 (1H, t, J=7.02 Hz), 4.13-3.89 (4H, m), 3.50 (1H, d, J=16.78 Hz), 3.10 (3H, br s), 2.33-2.80 (8H, m), 2.19 (2H, d, J=18.00 Hz).
Elem. Anal.: C32H32FN7O12S2Na2(H2O)11.2
Calcd.: C, 37.04; H, 5.28; F, 1.83; N, 9.45; S, 6.18; Na, 4.43(%).
Found: C, 37.16; H, 5.14; F, 1.90; N, 9.27; S, 5.94; Na, 4.32(%).
Example 114
Synthesis of Compound (II-49)
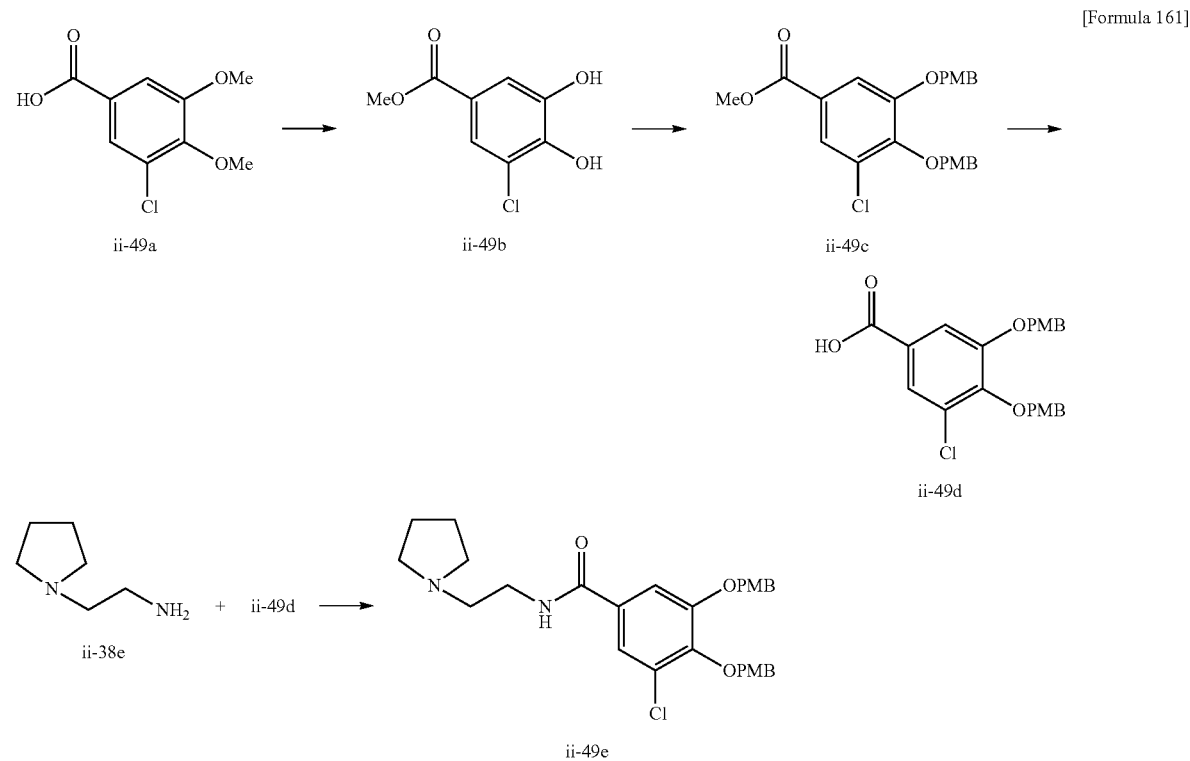

-continued

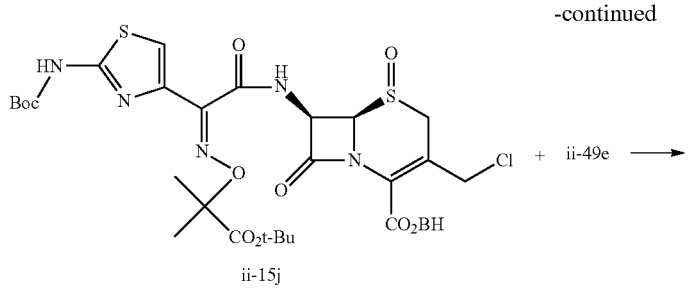

ii-15j + ii-49e →

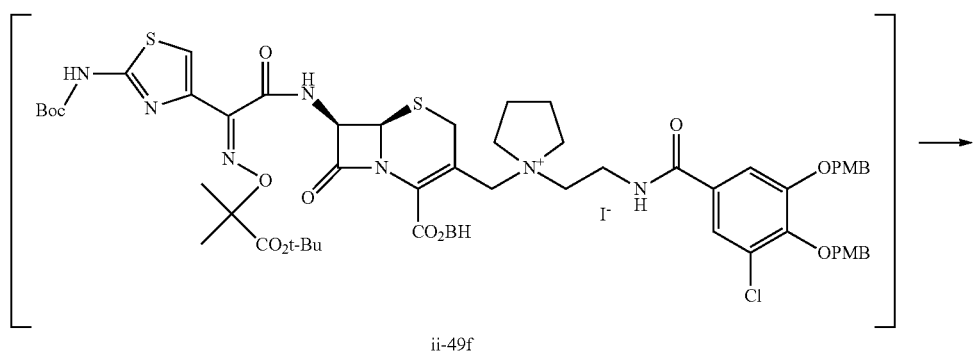

ii-49f

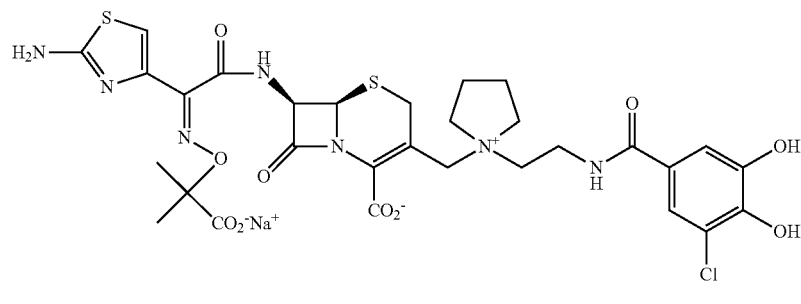

II-49

Step (1): compound ii-49a→compound ii-49b

Compound ii-49a (10.0 g, 46.2 mmol) was used to synthesize the target compound in the same way as in step (1) in Example 103.

Yielded amount: 8.38 g (90%)

¹H-NMR (DMSO-d₆) δ: 10.27 (1H, s), 10.09 (1H, s), 7.38 (1H, d, J=2.01 Hz), 7.34 (1H, d, J=2.01 Hz), 3.79 (3H, s).

Step (2): compound ii-49b compound ii-49c

Compound ii-49b (8.38 g, 41.4 mmol) was used to synthesize the target compound in the same way as in step (2) in Example 103.

Yielded amount: 18.16 g (99%)

¹H-NMR (CDCl₃) δ: 7.68 (1H, d, J=1.53 Hz), 7.58 (1H, d, J=1.98 Hz), 7.37 (2H, d, J=8.54 Hz), 7.30 (2H, d, J=8.54 Hz), 6.92 (2H, d, J=8.54 Hz), 6.81 (2H, d, J=8.54 Hz), 5.08 (2H, s), 5.04 (2H, s), 3.90 (3H, s), 3.83 (3H, s), 3.79 (3H, s).

Step (3): compound ii-49c→compound ii-49d

Compound ii-49c (18.0 g, 40.6 mmol) was used to synthesize the target compound in the same way as in step (3) in Example 103.

Yielded amount: 13.83 g (79%)

¹H-NMR (DMSO-d₆) δ: 7.61 (1H, s), 7.53 (1H, s), 7.44 (2H, d, J=8.16 Hz), 7.27 (2H, d, J=8.16 Hz), 6.98 (2H, d, J=8.16 Hz), 6.85 (2H, d, J=8.16 Hz), 5.17 (2H, s), 5.00 (2H, s), 3.77 (3H, s), 3.73 (3H, s).

Step (4): compound ii-39e→compound ii-49d→compound ii-49e

Compound ii-49d (1.000 g, 2.33 mmol) was used to synthesize the target compound in the same way as in step (4) in Example 103.

Yielded amount: 1.13 g (92%)

¹H-NMR (DMSO-d₆) δ: 8.48 (1H, t, J=5.19 Hz), 7.61 (1H, d, J=1.22 Hz), 7.52 (1H, d, J=1.22 Hz), 7.44 (2H, d, J=8.39 Hz), 7.26 (2H, d, J=8.39 Hz), 6.98 (2H, d, J=8.39 Hz), 6.84 (2H, d, J=8.39 Hz), 5.15 (2H, s), 4.96 (2H, s), 3.78 (3H, s), 3.73 (3H, s), 2.55 (2H, t, J=7.02 Hz), 1.70-1.66 (4H, m)

Step (5): compound ii-15j+compound ii-49e→compound II-49

Compound ii-15j (0.936 g, 1.0 mmol) and compound ii-49e (578 mg, 1.1 mmol) were used to synthesize the target compound in the same way as in step (1) in Example 95.

Yielded amount: 315.9 mg (32%)

¹H-NMR (D₂O) δ: 7.39 (1H, d, J=1.68 Hz), 7.21 (1H, d, J=1.68 Hz), 6.98 (1H, s), 5.86 (1H, d, J=4.73 Hz), 5.36 (1H, d, J=4.73 Hz), 4.12 (1H, d, J=13.42 Hz), 3.97-3.86 (2H, m), 3.77-3.42 (10H, m), 2.22 (4H, br s), 1.51 (3H, s), 1.49 (3H, s).

Elem. Anal.: C30H33ClN7O10S2Na (H2O)8.1 (NaHCO3)0.1

Calcd.: C, 38.94; H, 5.35; Cl, 3.82; N, 10.56; S, 6.91; Na, 2.72(%).

Found: C, 38.90; H, 5.42; Cl, 3.80; N, 10.74; S, 7.02; Na, 2.68(%).

Example 115

Synthesis of Compound (II-50)

Step (1): compound ii-2a+compound ii-49d→compound ii-50a

Compound ii-49d (6.43 g, 15.0 mmol) was used to synthesize a desired compound in the same way as in step (1) in Example 105. The compound-containing liquid was subjected to amino silica gel column chromatography to elute out the desired compound with chloroform. The desired-compound-containing fraction was concentrated under reduced pressure to yield compound ii-50a (8.30 g, 100%).

$^1$H-NMR (DMSO-d$_6$) δ: 7.92 (1H, d, J=4.58 Hz), 7.48-7.42 (4H, m), 7.28 (2H, d, J=8.31 Hz), 6.97 (2H, d, J=8.31 Hz), 6.85 (2H, d, J=8.31 Hz), 5.18 (2H, s), 4.97 (2H, s),

[Formula 162]

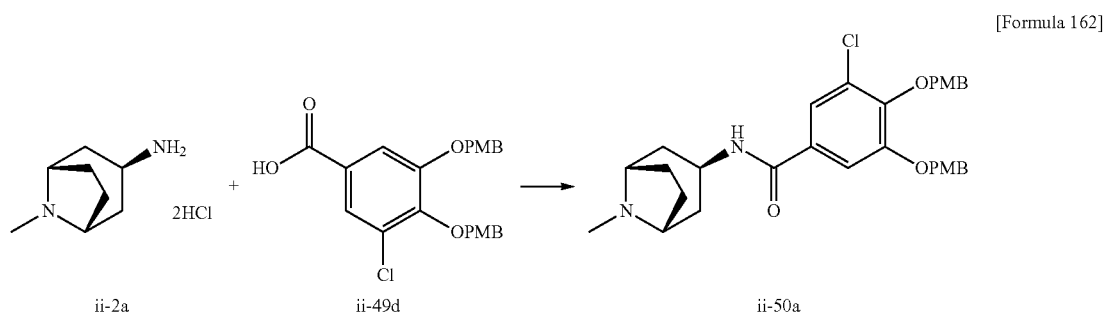

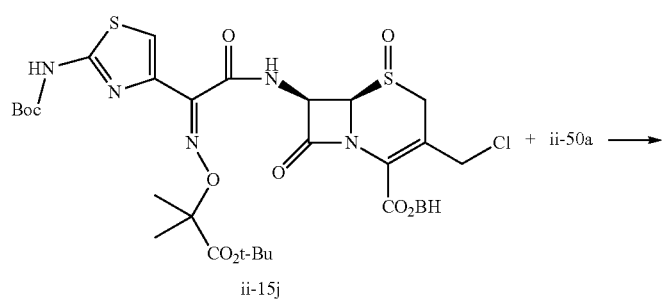

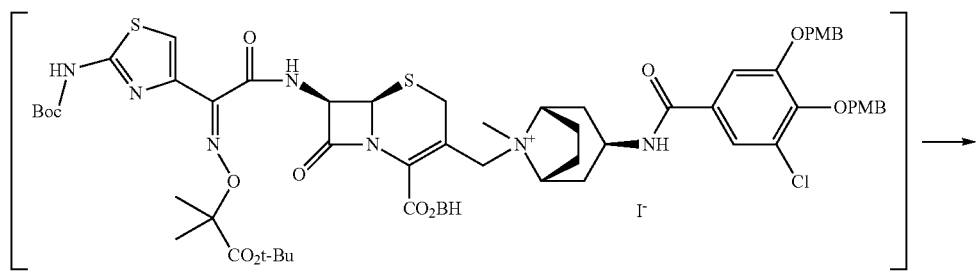

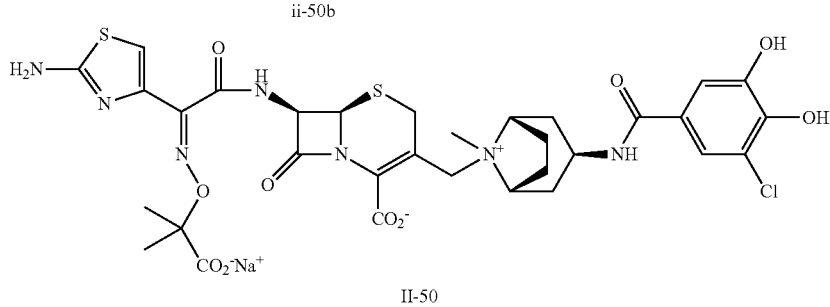

3.89-3.83 (1H, m), 3.77 (3H, s), 3.74 (3H, s), 3.00 (2H, br s), 2.14 (3H, s), 1.80-2.05 (6H, m), 1.73 (2H, d, J=14.03 Hz).

Step (2): compound ii-15j+compound ii-50a→compound II-50

Compound ii-15j (4.68 g, 5.0 mmol) and compound ii-50a (3.03 g, 5.5 mmol) were used to synthesize the target compound in the same way as in step (1) in Example 95.

Yielded amount: 1.75 g (36%)

$^1$H-NMR (D2O) δ; 7.30 (1H, d, J=2.06 Hz), 7.16 (1H, d, J=2.06 Hz), 6.98 (1H, s), 5.89 (1H, d, J=4.88 Hz), 5.37 (1H, d, J=4.88 Hz), 4.18 (1H, t, J=7.32 Hz), 4.09-3.93 (4H, m), 3.50 (1H, d, J=16.62 Hz), 3.10 (3H, hr s), 2.80-2.67 (2H, m), 2.39-2.59 (4H, m), 2.18 (2H, d, J=17.08 Hz), 1.52 (3H, s), 1.50 (3H, s).

Elem. Anal.: C32H35ClN7O10S2Na (H2O)7.3 (NaHCO3)0.1

Calcd.: C, 41.01; H, 5.33; Cl, 3.77; N, 10.43; S, 6.82; Na, 2.69(%).

Found: C, 40.99; H, 5.30; Cl, 3.83; N, 10.48; S, 6.89; Na, 2.62(%).

Example 116

Synthesis of Compound (II-51)

Step (1): compound ii-3a+compound ii-50a→compound II-51

Compound ii-3a (6.31 g, 5.0 mmol) and compound ii-50a (3.03 g, 5.5 mmol) were used to synthesize the target compound in the same way as in step (1) in Example 95.

Yielded amount: 1.10 g (21%)

$^1$H-NMR (D$_2$O) δ: 7.32 (1H, d, J=2.10 Hz), 7.18 (1H, d, J=2.10 Hz), 7.02 (1H, s), 5.84 (1H, d, J=4.87 Hz), 5.34 (1H, d, J=4.87 Hz), 4.97 (1H, t, J=6.63 Hz), 4.62 (1H, d, J=14.10 Hz), 4.19 (1H, t, J=7.13 Hz), 4.13-3.90 (4H, m), 3.50 (1H, d, J=17.12 Hz), 3.10 (3H, hr s), 2.70-2.80 (4H, m), 2.59-2.39 (4H, m), 2.19 (2H, d, J=17.12 Hz).

Elem. Anal.: C32H32ClN7O12S2Na2(H2O)9

Calcd.: C, 37.89; H, 4.97; Cl, 3.50; N, 9.67; S, 6.32; Na, 4.53(%).

Found: C, 37.91; H, 4.95; Cl, 3.53; N, 9.63; S, 6.35; Na, 4.43(%).

[Formula 163]

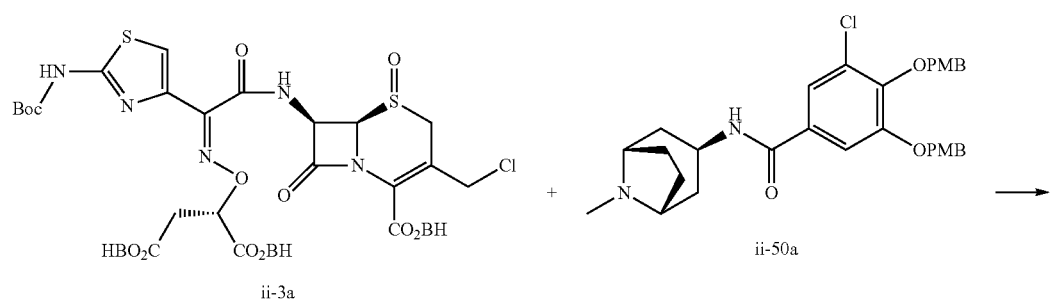

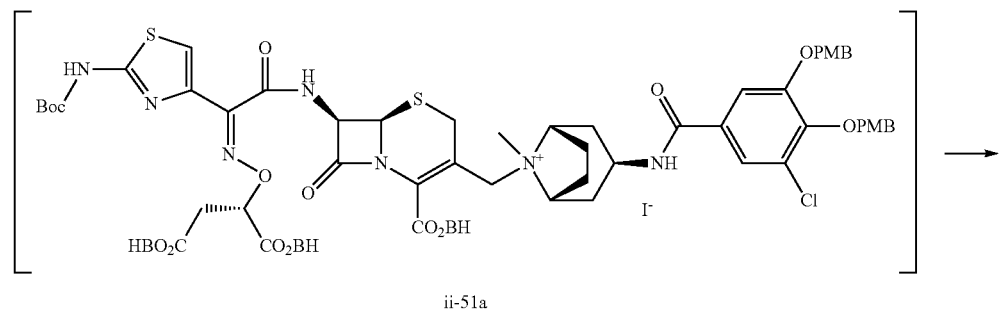

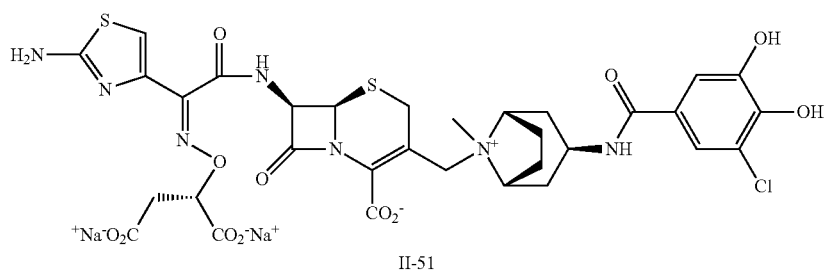

Example 117

Synthesis of Compound (II-52)

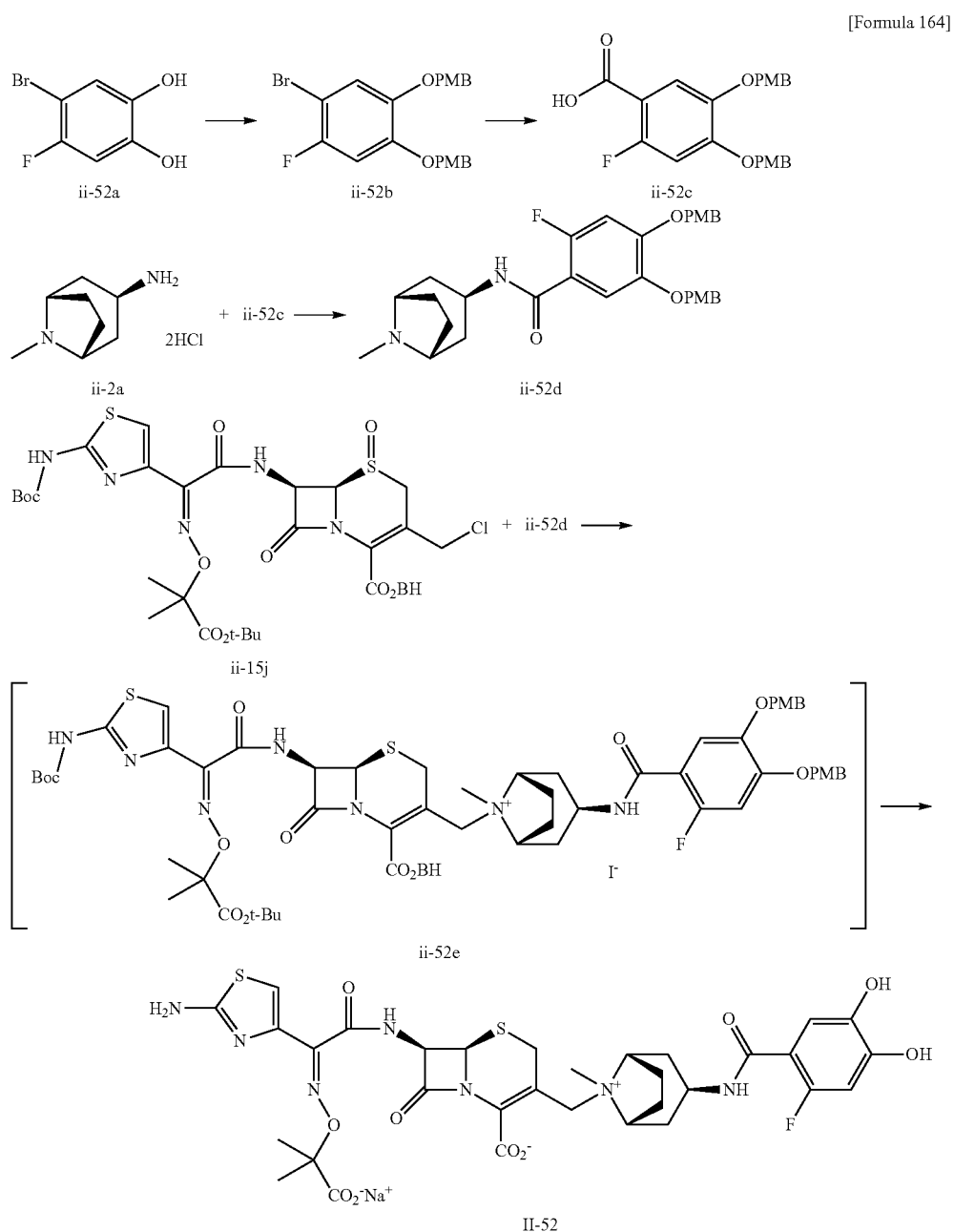

[Formula 164]

Step (1): compound ii-52a→compound ii-52b

Compound ii-52a (4.50 g, 21.74 mmol) synthesized with reference to a method described in US 2009/220194 A1 was suspended into N,N-dimethylformamide (45 mL), and thereto were then added potassium carbonate (9.01 g, 65.2 mmol) p-methoxybenzyl chloride (7.11 mL, 52.2 mmol) and sodium iodide (3.26 g, 21.74 mmol) in turn. The liquid was stirred at 70° C. for 3 hours. The reaction liquid was diluted with ethyl acetate, washed with an aqueous sodium thiosulfate solution, a 2 N aqueous hydrochloric acid solution, a saturated sodium dicarbonate solution and a saturated salt solution, and dried over magnesium sulfate. Magnesium sulfate was filtrated off, and then the liquid was concentrated under reduced pressure. The resultant was subjected to silica gel column chromatography to elute out a desired compound with hexane/ethyl acetate. The desired-compound-containing fraction was concentrated under reduced pressure to yield compound ii-52b (4.62 g, 48%).

$^1$H-NMR (CDCl$_3$) δ: 7.31 (4H, d, J=8.56 Hz), 7.05 (1H, d, J=6.71 Hz), 6.85-6.91 (4H, m), 6.73 (1H, d, J=9.90 Hz), 5.02 (2H, s), 4.99 (2H, s), 3.81 (6H, s).

Step (2): compound ii-52b→compound ii-52c

To a solution of compound ii-52b (4.60 g, 10.28 mmol) in tetrahydrofuran (50 mL) was added a 1.67 M BuLi solution (7.39 mL, 12.34 mmol) in hexane at −78° C., and the resultant solution was stirred at −78° C. for 1 hour. At −78° C., a piece of dry ice was added Co the reaction liquid, and the liquid was stirred at room temperature for 30 minutes. The reaction liquid was diluted with diethyl ether, and thereto was added water to separate the liquid to two phases. The resultant water phase was made into acidity, and then subjected to extraction with ethyl acetate. The organic phase was washed with a saturated salt solution, and dried over magnesium sulfate. Magnesium sulfate was filtrated off, and then the organic phase was concentrated under reduced pressure. Thereto was added diisopropyl ether to precipitate a solid. The solid was collected by filtration, so as to yield compound ii-52c (962 mg, 22%).

$^1$H-NMR (DMSO-$d_6$) δ: 7.40-7.30 (5H, m), 7.06 (1H, d, J=12.20 Hz), 6.94 (2H, d, J=8.62 Hz), 6.90 (2H, d, J=8.62 Hz), 5.11 (2H, s), 5.01 (2H, s), 3.75 (3H, s), 3.74 (3H, s).

Step (3): compound ii-52c→compound ii-52d

Compound ii-2a (586 mg, 2.76 mmol) and compound ii-52c (950 mg, 2.30 mmol) were used to synthesize the target compound in the same way as in step (1) in Example 105.

Yielded amount: 1.07 g (87%)

$^1$H-NMR (DMSO-$d_6$) δ: 7.71 (1H, t, J=5.29 Hz), 7.38 (2H, d, J=8.73 Hz), 7.31 (2H, d, J=8.73 Hz), 7.23 (1H, d, J=7.39 Hz), 7.06 (1H, d, J=12.76 Hz), 6.95 (2H, d, J=8.73 Hz), 6.91 (2H, d, J=8.73 Hz), 5.11 (2H, s), 5.01 (2H, s), 3.93-3.87 (1H, m), 3.75 (3H, s), 3.74 (3H, s), 3.06 (2H, br s), 2.19 (3H, s), 1.84-2.07 (6H, m), 1.71 (2H, d, J=4.27 Hz).

Step (1): compound ii-15a+compound ii-52d→compound II-52

Compound ii-15a (0.842 g, 0.9 mmol) and compound ii-52d (505 mg, 0.945 mmol) were used to synthesize the target compound in the same way as in step (1) in Example 95.

Yielded amount: 396.3 mg (42%)

$^1$H-NMR (D$_2$O) δ: 7.15 (1H, d, J=7.32 Hz), 6.98 (1H, s), 6.73 (1H, d, J=12.35 Hz), 5.89 (1H, d, J=4.96 Hz), 5.37 (1H, d, J=4.96 Hz), 4.23 (1H, t, J=7.09 Hz), 4.10-3.93 (4H, m), 3.50 (1H, d, J=16.47 Hz), 3.10 (3H, br s), 2.80-2.68 (2H, m), 2.37-2.59 (4H, m), 2.17 (2H, d, 17.08 Hz), 1.52 (3H, s), 1.50 (3H, s).

Elem. Anal.: C32H35FN7O10S2Na (H2O)9.8

Calcd.: C, 10.02; H, 5.73; F, 1.98; N, 10.21; S, 6.68; Na, 2.39(%).

Found: C, 40.28; H, 5.62; F, 2.05; N, 9.96; S, 6.63; Na, 2.40(%).

Example 118

Synthesis of Compound (II-53)

[Formula 165]

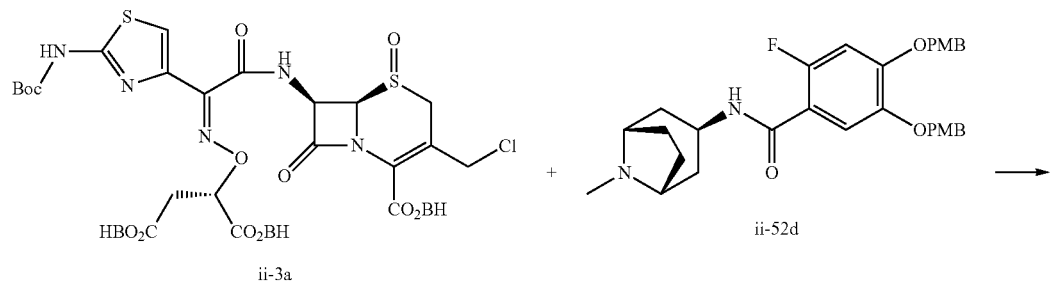

ii-3a ii-52d

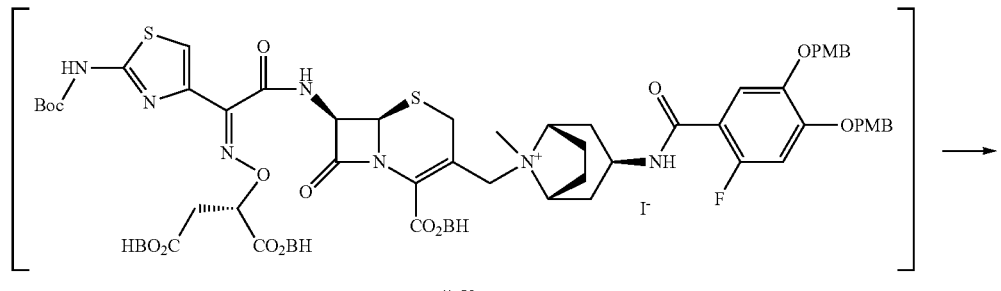

ii-53a

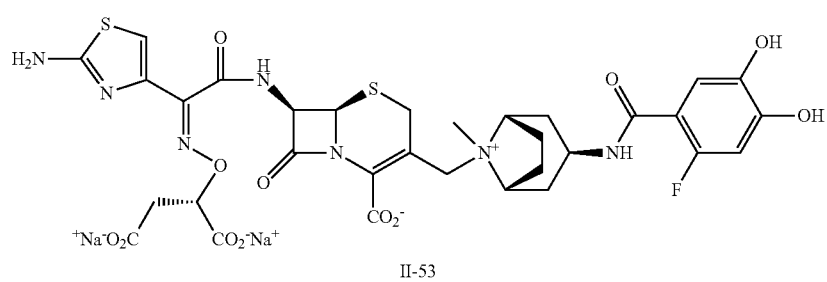

II-53

Step (1): compound ii-3a+compound ii-52d→compound II-53

Compound ii-3a (1.249 g, 1.0 mmol) and compound ii-52d (505 mg, 0.945 mmol) were used to synthesize the target compound in the same way as in step (1) in Example 95.

Yielded amount: 430 mg (45%)

$^1$H-NMR (D$_2$O) δ: 7.12 (1H, d, J=7.32 Hz), 6.99 (1H, s), 6.72 (1H, d, J=12.20 Hz), 5.82 (1H, d, J=4.88 Hz), 3.33 (1H, d, J=4.88 Hz), 5.00-4.96 (1H, m), 4.61 (1H, d, J=13.88 Hz), 4.20 (1H, t, J=6.79 Hz), 4.11-3.88 (1H, m), 3.48 (1H, d, J=16.78 Hz), 3.09 (3H, br s), 2.66-2.79 (4H, m), 2.53-2.09 (6H, m).

Elem. Anal.: C32H32.4FN7O12S2Na1.6(H2O)10

Calcd.: C, 38.16; H, 5.24; F, 1.89; N, 9.74; S, 6.37; Na, 3.65(%).

Found: C, 38.51; H, 5.24; F, 2.05; N, 9.35; S, 6.02; Na, 3.71(%).

Example 119

Synthesis of Compound (II-54)

[Formula 166]

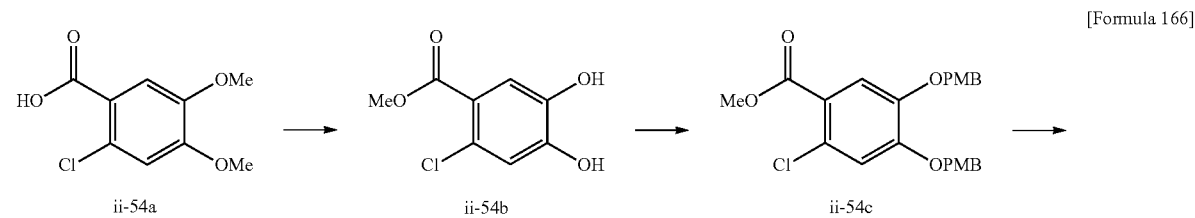

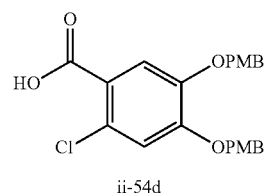

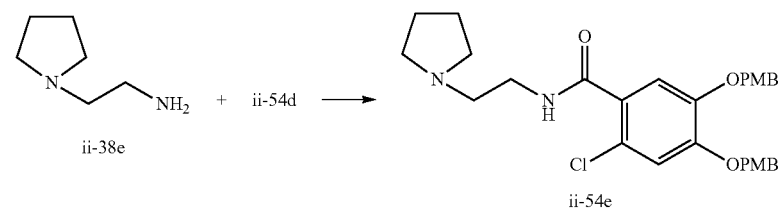

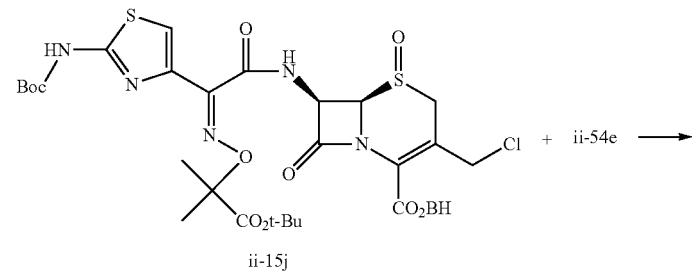

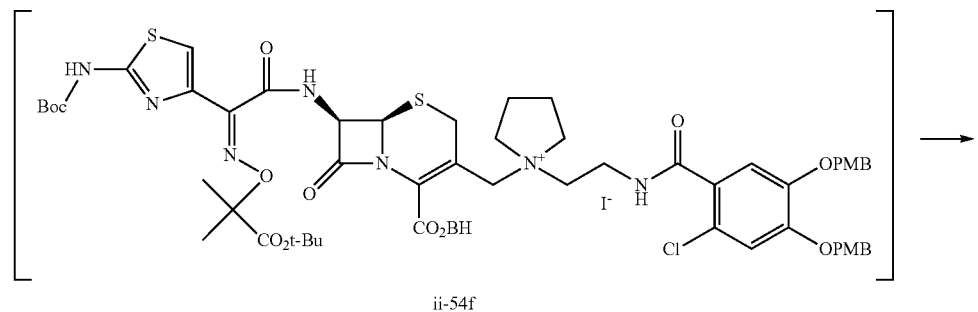

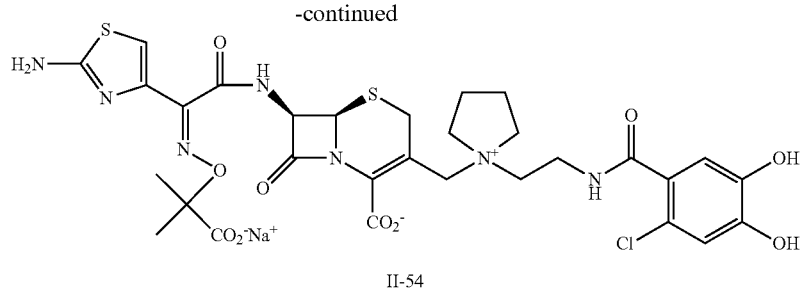

II-54

Step (1): compound ii-54a→compound ii-54b

Compound ii-54a (15.0 g, 69.2 mmol) was used to synthesize the target compound in the same way as in step (1) in Example 103.

Yielded amount: 12.52 g (89%)

$^1$H-NMR (DMSO-$d_6$) δ: 10.16 (1B, br s), 9.74 (1H, br s), 7.29 (1H, s), 6.84 (1H, s), 3.77 (3H, s).

Step (2): compound ii-54b→compound ii-54c

Compound ii-54b (12.0 g, 59.2 mmol) was used to synthesize a desired compound in the same way as in step (2) in Example 103. The reaction liquid was diluted with ethyl acetate, washed with water and a saturated salt solution, and dried over magnesium sulfate. Magnesium sulfate was filtrated off, and the liquid was concentrated under reduced pressure and subjected to silica gel column chromatography to elute out the desired compound with hexane/ethyl acetate. The desired-compound-containing fraction was concentrated under reduced pressure to yield compound ii-54c (15.43 g, 59%).

$^1$H-NMR (CDCl$_3$) δ: 7.50 (1H, s), 7.32 (4H, d, J=8.69 Hz), 6.96 (1H, s), 6.85-6.92 (4H, m), 5.08 (2H, s), 5.05 (2H, s), 3.38 (3H, s), 3.81 (3H, s), 3.80 (3H, s).

Step (3): compound ii-54c→compound ii-54d

Compound ii-54c (15.0 g, 33.9 mmol) was used to synthesize the target compound in the same way as in step (3) in Example 103.

Yielded amount: 13.78 g (95%)

$^1$H-NMR (DMSO-$d_6$) δ: 7.47 (1H, s), 7.38-7.30 (4H, s), 7.19 (1H, s), 6.89-6.97 (4H, m), 5.12 (2H, s), 5.05 (2H, 3.75 (3H, s), 3.74 (3H, s).

Step (4): compound ii-39e+compound ii-54d→compound ii-54e

Compound ii-54d (1.00 g, 2.33 mmol) was used to synthesize the target compound in the same way as in step (4) in Example 103.

Yielded amount: 1.08 g (88%)

$^1$H-NMR (DMSO-$d_6$) δ: 8.16 (1H, t, J=5.64 Hz), 7.35-7.31 (4H, m), 7.12 (1H, s), 7.09 (1H, s), 6.94-6.91 (4H, m), 5.08 (2H, s), 5.02 (2H, s), 3.74 (6H, s), 2.56-2.54 (2H, m), 2.48-2.44 (4H, m), 1.69-1.65 (4H, m).

Step (5): compound ii-15j+compound ii-54e→compound II-54

Compound ii-3a (0.936 g, 1.0 mmol) and compound ii-54e (578 mg, 1.1 mmol) were used to synthesize the target compound in the same way as in step (1) in Example 95.

Yielded amount: 461.8 mg (47%)

$^1$H-NMR (D$_2$O) δ: 6.99 (1H, s), 6.98 (1H, s), 6.95 (1H, s), 5.8 (1H, d, J=4.96 Hz), 5.37 (1H, d, J=4.96 Hz), 4.14 (1H, d, J=14.34 Hz), 3.98-3.46 (11H, m), 2.20-2.27 (4H, m), 1.51 (3H, s), 1.50 (3H, s).

Elem. Anal.: C30H33ClN7O10S2Na (H2O)6.2 (NaHCO3)0.15

Calcd.: C, 40.30; H, 5.11; C$_{1-3.95}$; N, 10.91; S, 7.14; Na, 2.94(%).

Found: C, 40.22; H, 4.99; Cl, 3.84; N, 11.00; S, 7.21; Na, 2.97(%).

Example 120

Synthesis of Compound (II-55)

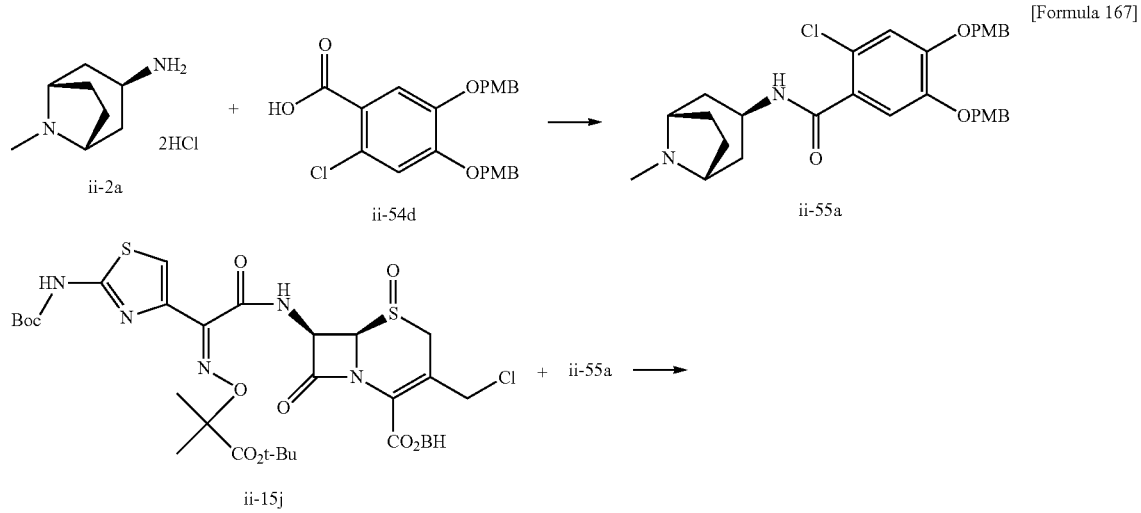

[Formula 167]

-continued

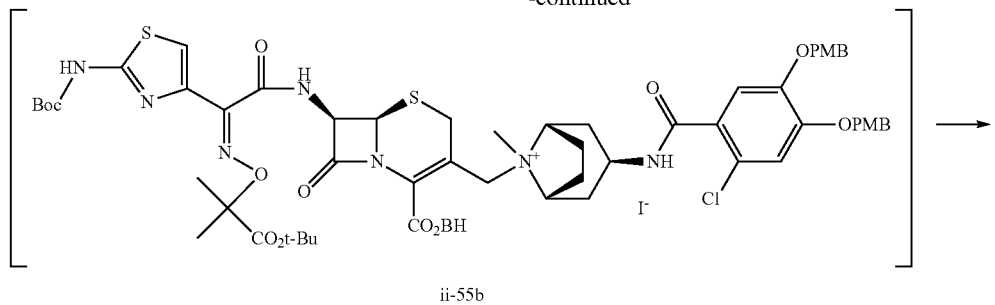

ii-55b

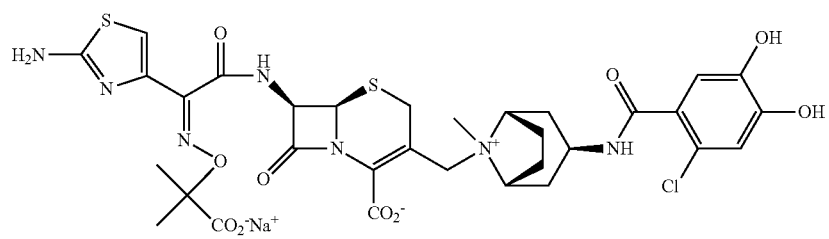

II-55

Step (1): compound ii-2a+compound ii-54d→compound ii-55a Compound ii-54d (214 g, 5.00 mmol) was used to synthesize a desired compound in the same way as in step (4) in Example 104. The resultant was subjected to amino silica gel column chromatography to elute out the desired compound with chloroform. The desired-compound-containing fraction was concentrated under reduced pressure to yield compound ii-55a (2.74 g, 99%).

$^1$H-NMR (DMSO-$d_6$) δ: 7.92 (1H, d, J=5.03 Hz), 7.36-7.31 (4H, m), 7.12 (1H, s), 7.03 (1H, s), 6.95-6.90 (4H, m), 5.09 (2H, s), 5.03 (2H, s), 3.86-3.79 (1H, m), 3.74 (6H, s), 2.96 (2H, br s), 2.13 (3H, s), 1.95-2.04 (2H, m), 1.89 (4H, s), 1.67 (2H, d, J=14.34 Hz).

Step (2): compound ii-15j+compound ii-55a→compound II-55

Compound ii-15j (0.936 g, 1.0 mmol) and compound ii-55a (606 mg, 1.1 mmol) were used to synthesize the target compound in the same way as in step (1) in Example 95.

Yielded amount: 254.5 mg (23%)

$^1$H-NMR (D$_2$O) δ: 6.98-6.96 (3H, m), 5.89 (1H, d, J=5.03 Hz), 5.37 (1H, d, J=5.03 Hz), 4.23 (1H, t, J=6.56 Hz), 4.10-3.91 (4H, m), 3.50 (1H, d, J=17.69 Hz), 3.10 (3H, br s), 2.82-2.71 (2H, m), 2.38-2.56 (4H, m), 2.17 (2H, d, J=18.30 Hz), 1.52 (3H, s), 1.50 (3H, s).

Elem. Anal.: C32H35ClN7O10S2Na (H2O)7.9

Calcd.: C, 40.78; H, 5.43; Cl, 3.76; N, 10.40; S, 6.80; Na, 2.44(%).

Found: C, 40.88; H, 5.41; Cl, 3.94; N, 10.19; S, 6.51; Na, 2.22(%).

Example 121

Synthesis of Compound (II-56)

[Formula 168]

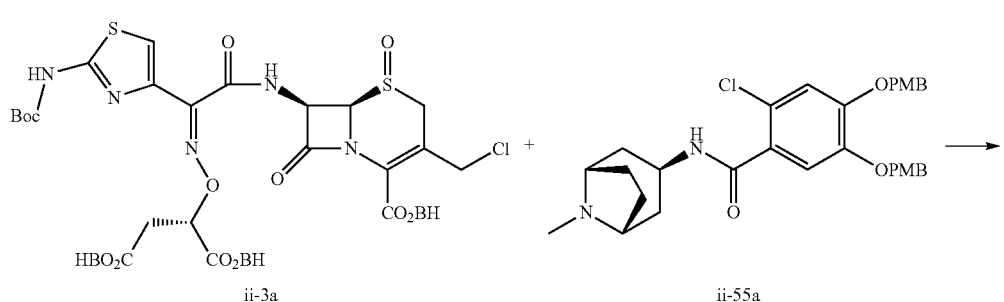

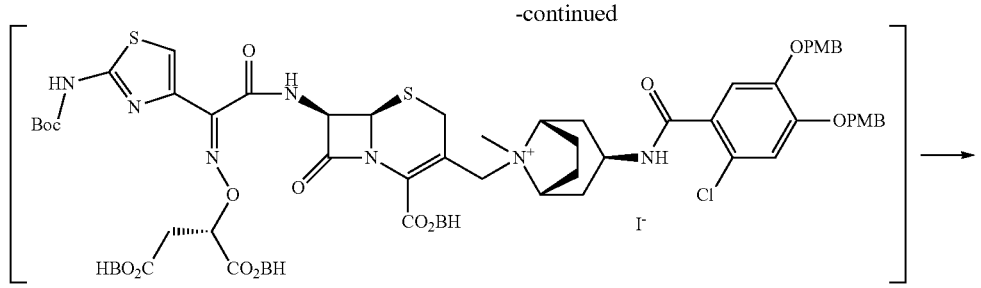

ii-56a

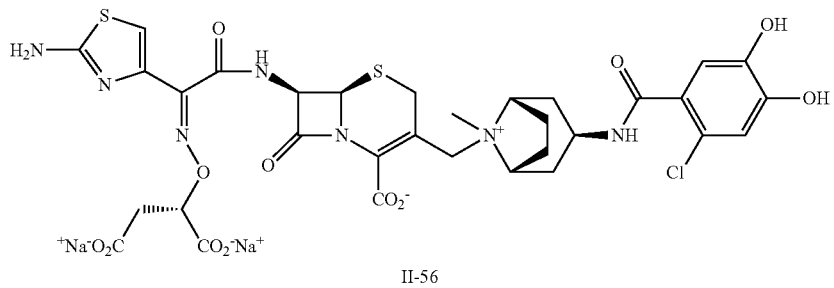

II-56

Step (1): compound ii-3a+compound ii-56a→compound II-56

Compound ii-3a (1.249 g, 1.0 mmol) and compound ii-56a (606 mg, 1.1 mmol) were used to synthesize the target compound in the same way as in step (1) in Example 95.

Yielded amount: 531.4 mg (51%)

$^1$H-NMR (D$_2$O) δ: 7.01-6.95 (3H, m), 5.84 (1H, d, J=4.96 Hz), 5.34 (1H, d, J=4.96 Hz), 4.23 (1H, t, J=7.63 Hz), 4.13-3.89 (4H, m), 3.50 (1H, d, J=17.08 Hz), 3.10 (3H, br s), 2.80-2.69 (4H, m), 2.37-2.58 (4H, m), 2.17 (2H, d, J=16.93 Hz).

Elem. Anal.: C32H32.2ClN7O12S2Na1.8(H2O)8.1

Calcd.: C, 38.68; H, 4.91; Cl, 3.57; N, 9.87; S, 6.45; Na, 4.16(%).

Found: C, 38.83; H, 4.96; Cl, 3.75; N, 9.66; S, 6.16; Na, 4.13(%).

Example 122

Synthesis of Compound (II-57)

[Formula 169]

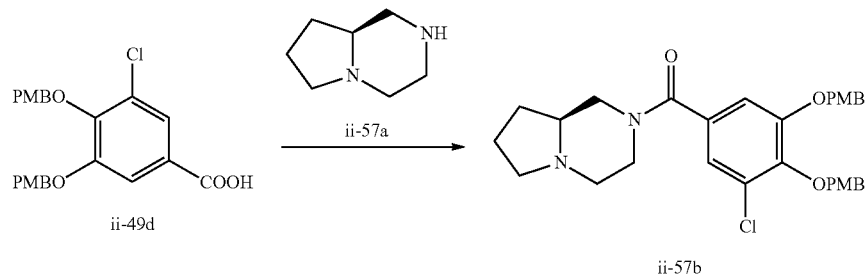

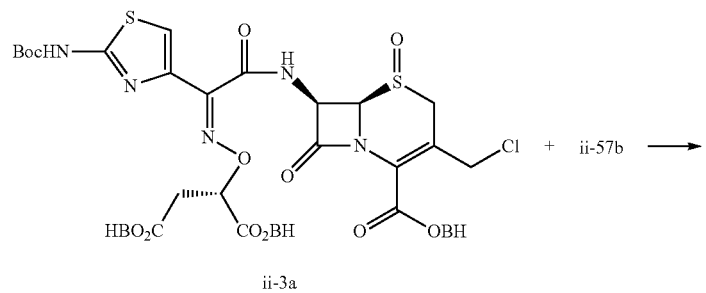

ii-3a

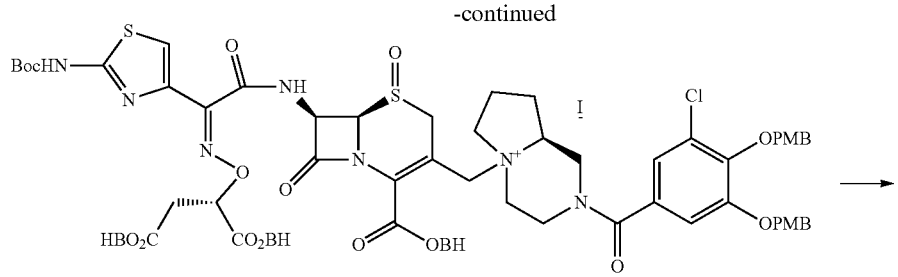

ii-57c

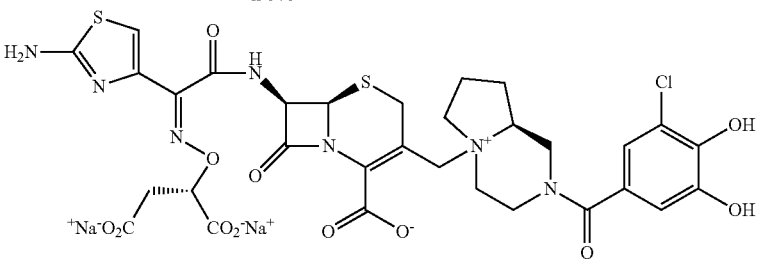

II-57

Step (1): compound ii-49d+compound ii-57a→compound ii-57b

Compound ii-49d (1.29 g, 3.00 mmol) was treated in the same way as in step (6) in Example 80 to yield compound ii-57b (1.61 g, yield: 100%)

$^1$H-NMR (CDCl$_3$) δ: 7.36-7.32 (4H, m), 7.03 (1H, d, J=1.9 Hz), 6.92-6.90 (3H, m), 6.85-6.82 (2H, m), 5.06 (2H, s), 5.00 (2H, s), 3.83 (3H, s), 3.80 (3H, s), 3.17-1.70 (13H, m).

Step (2): compound ii-3a+compound ii-57b→compound II-57

Compound ii-3a (1.29 g, 1.12 mmol) was treated in the same way as in step (2), followed by step (3) in Example 75 to yield compound II-57 (yielded amount: 618 mg, yield: 49%)

MS: 794.47 (M+H)

$^1$H-NMR (D$_2$O) δ: 7.09 (1H, s), 7.00 (1H, s), 6.94 (1H, s), 5.83 (1H, d, J=5.0 Hz), 5.32 (1H, d, J=5.0 Hz), 4.99-4.95 (1H, m), 4.33 (1H, d, J=14.5 Hz), 4.21-3.45 (12H, m), 2.73-2.70 (2H, m), 2.44-2.00 (4H, m).

Elem. Anal. C31H30ClN7Na2O12S2(H2O)6.2 (NaHCO3)0.1

Calcd.: C, 38.98; 8, 4.47; Cl, 3.70; N, 10.23; S, 6.69; Na, 5.04.

Found: C, 38.95; H, 4.50; Cl, 3.88; N, 10.22; S, 6.68; Na, 4.90.

Example 123

Synthesis of Compound (II-58)

[Formula 170]

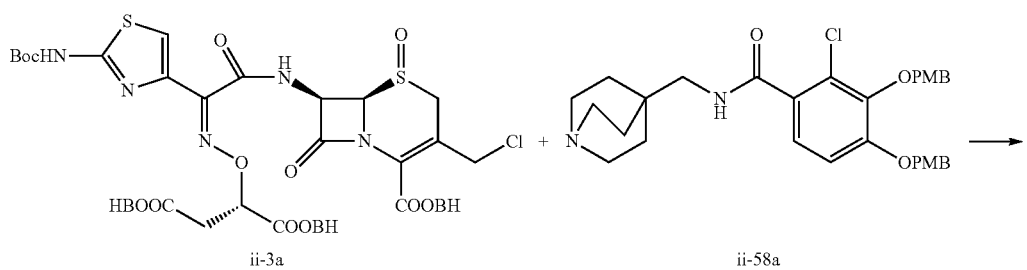

ii-3a     ii-58a

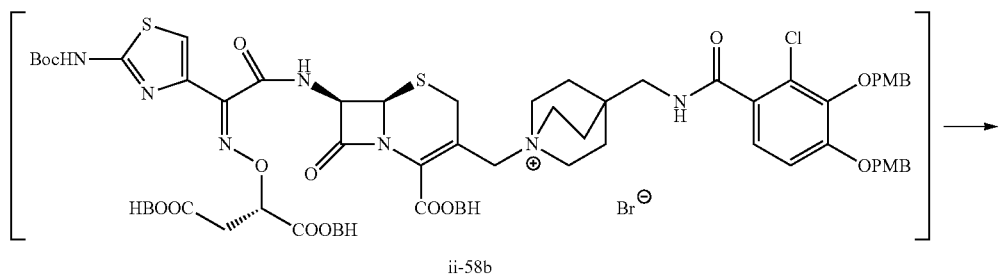

ii-58b

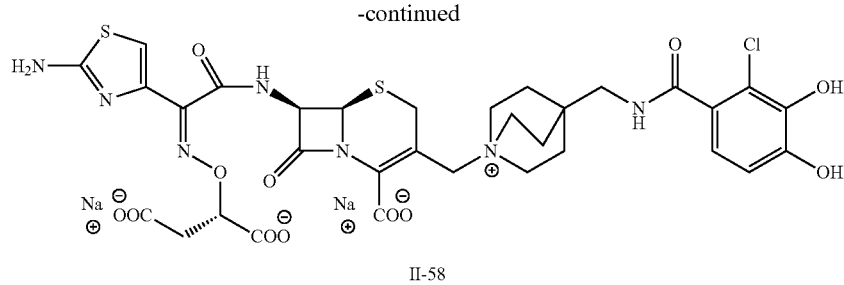

II-58

Step (1): compound ii-3a+compound ii-58a→compound II-58

Sodium bromide (206 mg, 2.0 mmol) was added to a solution of compound ii-3a (1.25 g, 1.0 mmol) in dimethylacetoamide (3 mL), and the resultant was stirred at room temperature for 1 hour. The reaction liquid was cooled to 15° C., and then thereto was added compound ii-59a (551 mg, 1.0 mmol). The resultant was stirred at 15° C. for 6 hours. Thereto was added N,N-dimethylformamide (4.0 mL), and then the solution was cooled to −40° C. Thereto was added phosphorus tribromide (189 μL, 2.0 mmol), and the resultant was stirred at −40° C. for 30 minutes. The reaction mixture was slowly added to a 5% salt solution cooled with ice. The precipitated solid was collected by filtration, washed with water, and suspended into water. The suspension was freeze-dried to yield compound ii-58b as a pink solid. Compound ii-58b yielded was used as it was, without being purified, in the next reaction.

The total amount of compound ii-58b yielded was dissolved in dichloromethane (10 mL), and the solution was cooled to −40° C. Thereto were then added anisole (1.09 mL, 10 mmol) and a 2 mol/L, aluminum chloride solution (5.0 mL, 10 mmol) in nitromethane in turn. The liquid was stirred at −30° C. for 30 minutes. To the reaction liquid were added diisopropyl ether and a small amount of water, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. To the desired-compound-containing fraction was added a 0.2 N aqueous sodium hydroxide solution to adjust the pH to 6.0. Thereafter, a piece of dry ice was added thereto. The resultant was concentrated under reduced pressure, and then freeze-dried to yield compound II-58 as a white powder.

Yielded amount: 570 mg (67%)

$^1$H-NMR (D$_2$O) δ: 7.01 (1H, s), 6.95 (1H, d, J=8.31 Hz), 6.90 (14, d, J=8.31 Hz), 5.82 (1H, d, J=4.87 Hz), 5.33 (1B, d, J=4.87 Hz), 4.97 (1H, dd, J=8.14, 5.12 Hz), 4.59 (1H, d, J=13.93 Hz), 3.94-3.83 (2H, m), 3.60-3.32 (9H, m), 2.73 (1H, s), 2.71 (1H, d, J=3.19 Hz), 1.96 (61-1, t, J=7.39 Hz).

MS (m+1)=808.32

Elem. Anal. C$_{32}$H$_{32}$ClN$_7$O$_{12}$S$_2$Na$_2$·6.6H$_2$O

Calcd.: C, 39.58; H, 4.69; Cl, 365; N, 10.10; S, 6.60; Na, 4.73(%).

Found: C, 39.59; H, 4.69; Cl, 3.85; N, 10.13; S, 6.67; Na, 4.32(%).

Example 124

Synthesis of Compound (II-59)

[Formula 171]

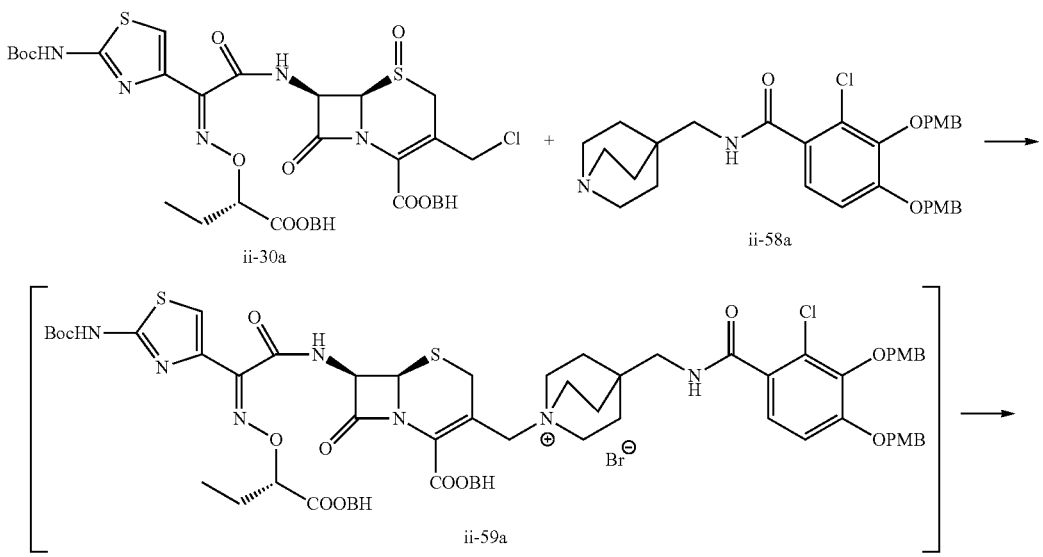

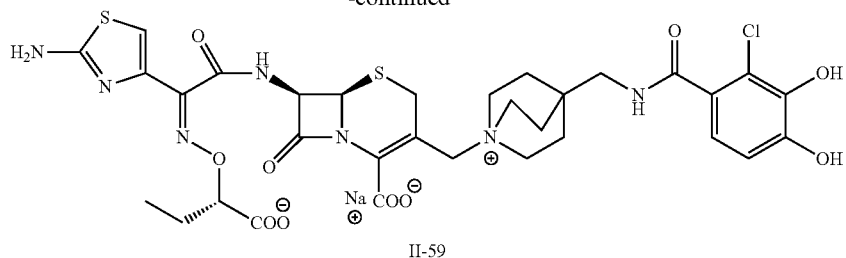

II-59

Step (1): compound ii-30a+compound ii-58a→compound II-59

From compound ii-30a (1.53 g, 1.0 mmol) and compound ii-58a (551 mg, 1.0 mmol), compound II-59 was yielded as a white powder in the same way as in step (1) in Example 123.

Yielded amount: 471 mg (59%)

$^1$H-NMR (D$_2$O) δ: 6.99 (1H, s), 6.93 (1H, d, J=8.39 Hz), 6.88 (1H, d, J=9.39 Hz), 5.87 (1H, d, J=5.03 Hz), 5.35 (1H, d, J=5.03 Hz), 4.59 (1H, d, J=14.03 Hz), 4.53 (1H, t, J=6.10 Hz), 3.92-3.83 (2H, m), 3.59-3.32 (9H, m), 1.95 (6H, t, J=7.63 Hz), 1.92-1.82 (3H, m), 0.97 (3α, t, J=7.40 Hz).

MS (m+1)=778.32

Elem. Anal. C$_{32}$H$_{35}$ClN$_7$O$_{10}$S$_2$Na.6.1H$_2$O

Calcd.: C, 42.23; H, 5.23; Cl, 3.90; N, 10.77; S, 7.05; Na, 2.53(%).

Found: C, 42.14; H, 5.14; Cl, 4.15; N, 10.82; S, 7.13; Na, 2.55(%).

Example 125

Synthesis of Compound (II-60)

[Formula 172]

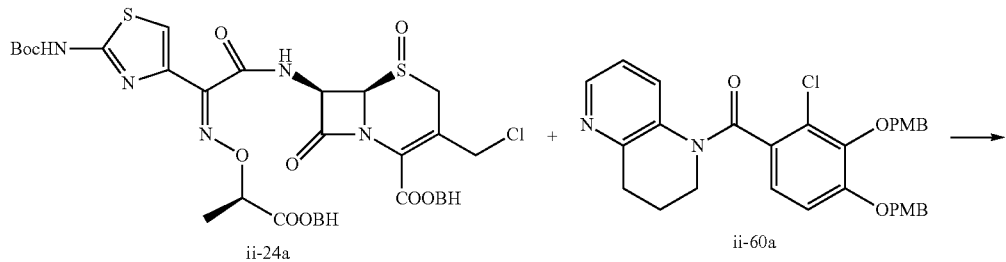

ii-24a + ii-60a →

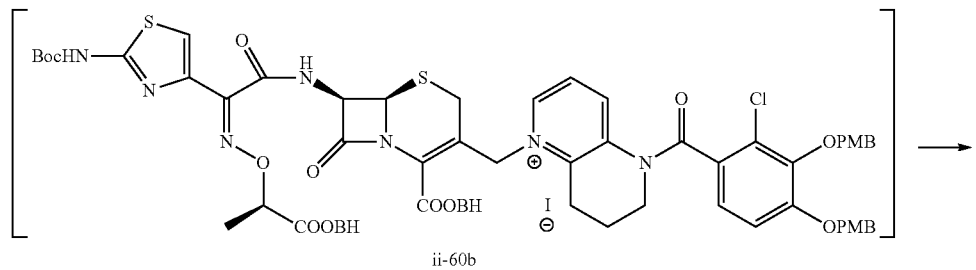

ii-60b →

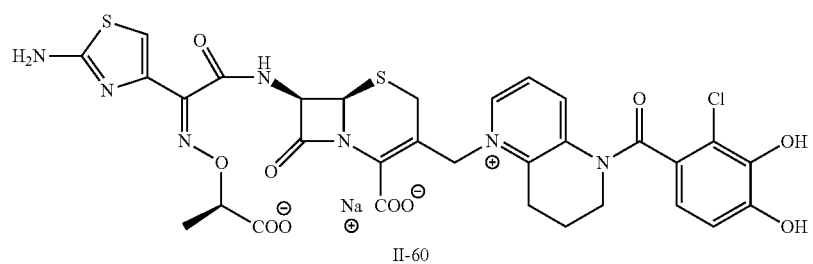

II-60

Step (1): compound ii-24a+compound ii-60a→compound II-60

Compound ii-60a (545 mg, 1.0 mmol) was added to a solution of compound ii-24a (938 mg, 1.0 mmol) in dimethylacetoamide (3 mL). The reaction vessel was degassed under reduced pressure. Thereto was added sodium iodide (300 mg, 2.0 mmol), and the solution was stirred at room temperature for 6 hours. N,N-Dimethylformamide (4.0 mL) was added thereto, and the solution was cooled to −40° C. Thereto was added phosphorus tribromide (189 µL, 2.0 mmol). The solution was stirred at −40° C. for 30 minutes. The reaction mixture was slowly added to a 5% salt solution cooled with ice. The precipitated solid was collected by filtration, washed with water, and suspended into water. The suspension was freeze-dried to yield compound ii-60b as a brown solid. Compound ii-60b yielded was used as it was, without being purified, in the next reaction.

The total amount of compound ii-60b yielded was dissolved in dichloromethane (10 mL), and the solution was cooled to −40° C. Thereto were then added anisole (1.09 mL, 10 mmol) and a 2 mol/L aluminum chloride solution (5.0 mL, 10 mmol) in nitromethane in turn. The liquid was stirred at −30° C. for 30 minutes. To the reaction liquid were added diisopropyl ether and a small amount of water, and the resultant was stirred to generate a precipitate. The supernatant was removed by decantation. To the residue were added a diluted hydrochloric acid solution in water, and acetonitrile. The resultant was stirred to dissolve the residue completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. To the desired-compound-containing fraction was added a 0.2 N aqueous sodium hydroxide solution to adjust the pH to 6.0. Thereafter, a piece of dry ice was added thereto. The resultant was concentrated under reduced pressure, and then freeze-dried to yield compound II-60 as a pale orange powder.

Yielded amount: 313 mg (40%)

$^1$H-NMR (D$_2$O) δ: 8.62 (1H, br s), 8.22 (1H, br s), 7.64 (1H, br s), 7.03 (1H, d, J=8.48 Hz), 7.00 (1B, s), 6.96 (1H, d, J=8.48 Hz), 5.86 (1H, d, J=4.78 Hz), 5.65-5.50 (1H, br m), 5.50-5.33 (1H, br m), 5.28 (1H, d, 34.78 Hz), 4.64 (1H, q, J=7.02 Hz), 4.23-4.00 (1H, br m), 3.76-3.57 (1H, br m), 3.47 (1H, d, J=17.54 Hz), 3.38-3.26 (2H, m), 3.19 (1H, d, J=17.54 Hz), 2.21 (2H, br s), 1.45 (3H, d, J=7.02 Hz).

MS (m+1)=758.39

Elem. Anal.: C$_{31}$H$_{27}$ClN$_7$O$_{10}$S$_2$Na.7.6H$_2$O

Calcd.: C, 40.60; H, 4.64; Cl, 3.87; N, 10.69; S, 6.99; Na, 2.51(%).

Found: C, 40.54; H, 4.51; Cl, 4.05; N, 10.71; S, 7.03; Na, 2.60(%).

Example 126

Synthesis of Compound (II-61)

[Formula 173]

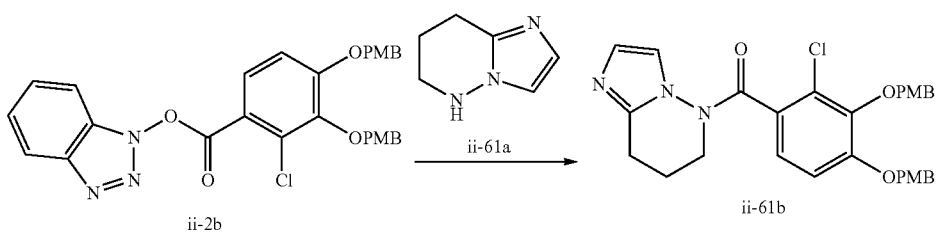

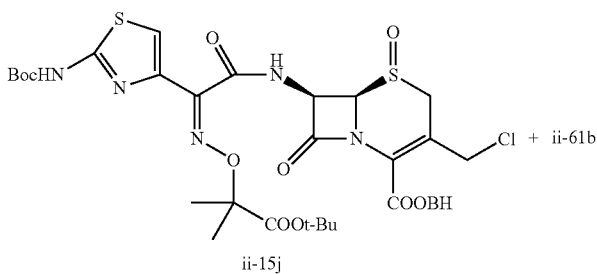

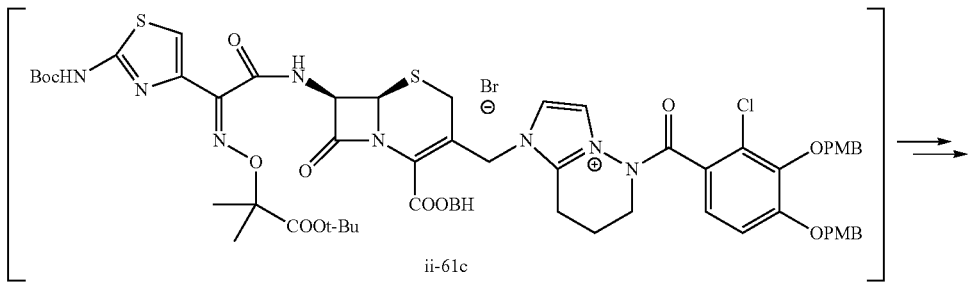

-continued

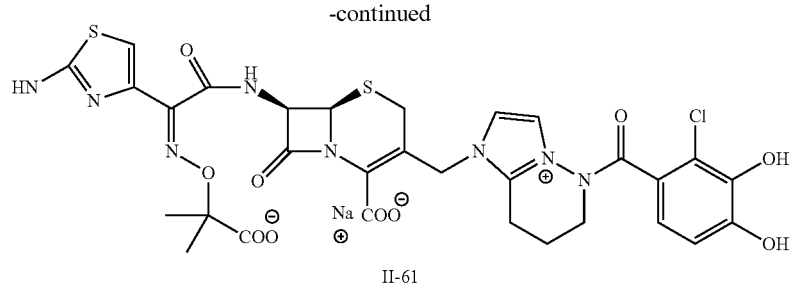

II-61

Step (1): compound ii-2b+compound ii-61a→compound ii-61b

Compound ii-2b (5.46 g, 10 mmol) and triethylamine (1.39 mL, 10 mmol) were added to a solution of compound ii-61a (1.23 g, 10 mmol) synthesized as described in a document (Tetrahedron Letters, 1974, 42, 3715-3718) in dioxane (50 mL). Thereafter, the solution was stirred at 100° C. for 3 hours. To the reaction mixture were added a 5% salt solution, and methanol, and the resultant was subjected to extraction with ethyl acetate. The organic phase was washed with a 1 N aqueous sodium hydroxide solution, and a saturated salt solution in turn, and then dried over magnesium sulfate. The inorganic substance was filtrated off, and the organic phase was concentrated under reduced pressure. The resultant crude product was purified by silica gel column chromatography. The desired-compound-containing fraction was concentrated under reduced pressure. Diisopropyl ether was added to the residue. The precipitated solid was collected by filtration, and dried under reduced pressure to yield compound ii-61b as a white solid.

Yielded amount: 2.27 g (43%)

$^1$H-NMR (CDCl$_3$) δ: 7.35 (2H, d, J=8.56 Hz), 7.30 (2H, d, J=8.56 Hz), 7.04 (1H, br s), 6.95 (1H, br s), 6.93 (2H, d, 8.73 Hz), 6.81 (2H, d, J=8.73 Hz), 5.08 (2H, s), 4.97 (2H, s), 3.84 (3H, s), 3.79 (3H, s), 3.71 (2H, br s), 3.05 (2H, t, J=7.13 Hz), 2.08 (2H, br s).

Step (2): compound ii-15j+compound ii-61b→compound II-61

From compound ii-15j (1.53 g, 1.0 mmol) and compound ii-61b (551 mg, 1.0 mmol), compound II-61 was yielded ds a white powder in the same way as in step (1) in Example 123.

Yielded amount: 540 mg (69%)

$^1$H-NMR (D$_2$O) δ: 7.81 (1H, br s), 7.56 (1H, s), 7.07 (1H, d, J=8.39 Hz), 7.00-6.96 (2H, m), 5.85 (1H, d, J=4.80 Hz), 5.26 (1H, s), 5.26 (1H, d, J=4.80 Hz), 5.14 (1H, d, J=15.17 Hz), 4.98 (1H, d, J=15.17 Hz), 3.98 (2H, br s), 3.57 (1H, d, J=17.69 Hz), 3.32-3.21 (3H, m), 2.21 (2H, br 1.5: (3H, s), 1.50 (3H, s).

MS (m+1)=761.44

Elem. Anal.: C$_{30}$H$_{28}$ClN$_8$O$_{10}$S$_2$Na.6.1H$_2$O

Calcd.: C, 40.35; H, 4.54; Cl, 3.97; N, 12.55; S, 7.18; Na, 2.57(%).

Found: C, 40.32; H, 4.52; Cl, 4.23; N, 12.55; S, 7.21; Na, 2.33(%).

Example 127

Synthesis of Compound (II-62)

[Formula 174]

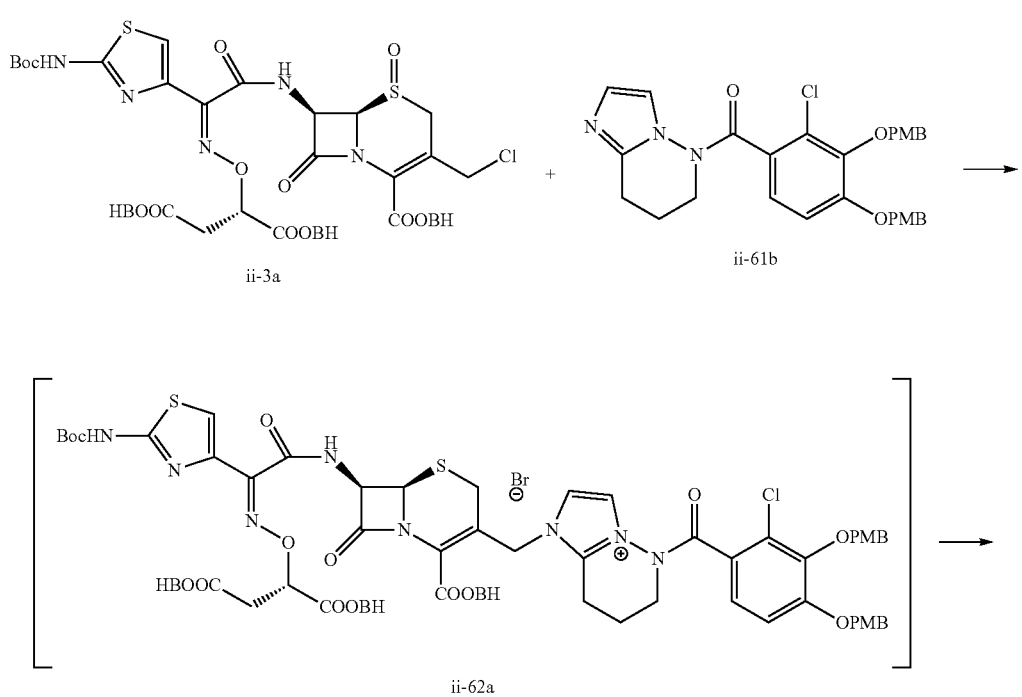

-continued

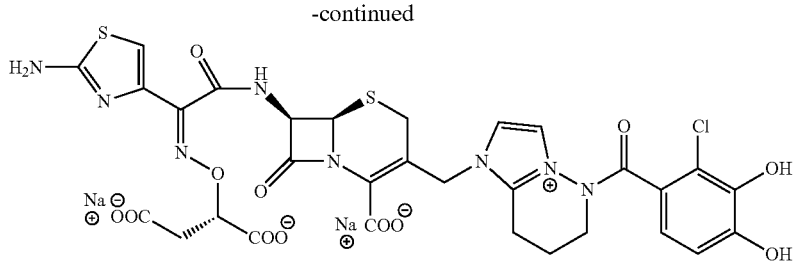

II-62

Step (1): compound ii-3a+compound ii-61b→compound II-62

From compound ii-3a (1.53 g, 1.0 mmol) and compound ii-61b (551 mg, 1.0 mmol), compound II-62 was yielded as a white powder in the same way as in step (1) in Example 123.

Yielded amount: 232 mg (28%)

$^1$H-NMR (D$_2$O) δ: 7.79 (1H, br s), 7.56 (1H, br s), 7.08 (1H, d, J=8.39 Hz), 7.01 (1H, s), 6.98 (1H, d, J=8.39 Hz), 5.82 (1H, d, J=4.73 Hz), 5.23 (1H, d, J=4.73 Hz), 5.16 (1H, d, J=14.95 Hz), 5.01-4.94 (2H, m), 4.00 (2H, br s), 3.54 (1H, d, J=17.84 Hz), 3.31-3.25 (3H, m), 2.73 (1H, s), 2.71 (1H, d, J=4.73 Hz), 2.22 (2H, br s).

MS (m+1)=791.42

Elem. Anal.: C$_{30}$H$_{25}$ClN$_8$O$_{12}$S$_2$Na$_2$·7.0H$_2$O

Calcd.: C, 37.49; H, 4.09; Cl, 3.69; N, 11.66; S, 6.67; Na, 4.78(%).

Found: C, 37.48; H, 4.16; Cl, 3.74; N, 11.66; S, 6.77; Na, 4.62(%).

Example 128

Synthesis of Compound (II-63)

[Formula 175]

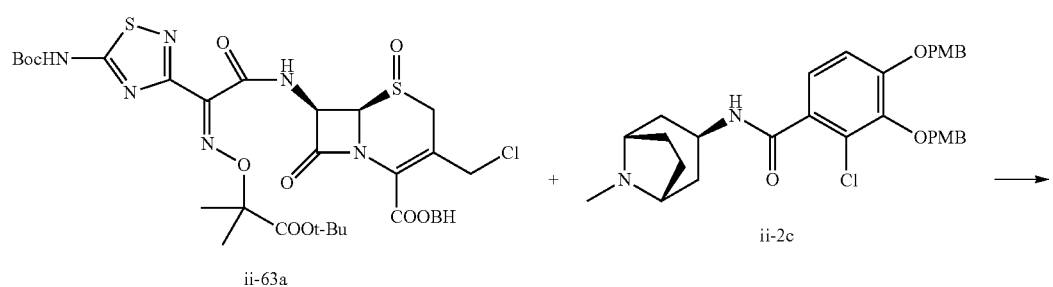

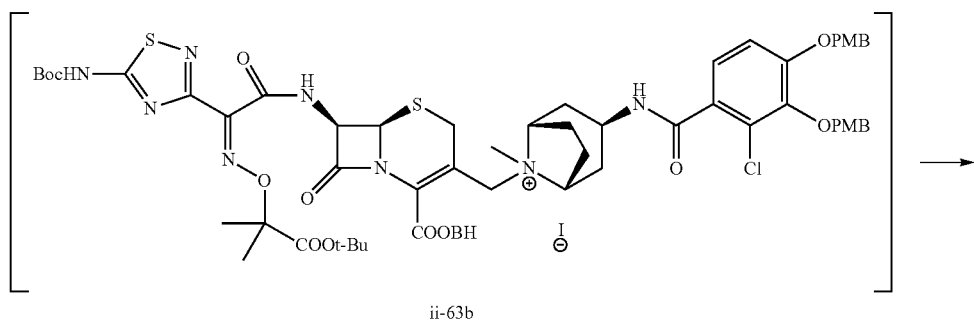

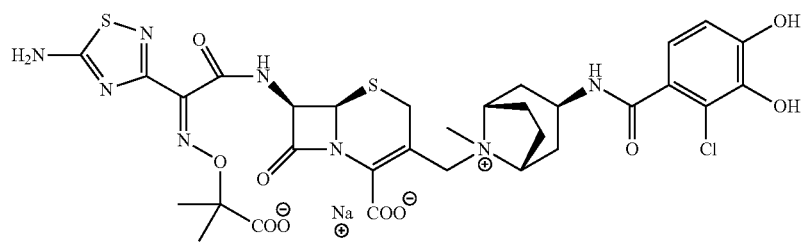

II-63

Step (1): compound ii-63a+compound ii-2c→compound ii-63b→compound II-63

A solution of compound ii-2c (551 mg, 1.0 mmol) in dimethylacetoamide<2 mL) was cooled to −15° C., and thereto was added compound ii-53c (897 mg, 1.0 mmol). The reaction vessel was then degassed under reduced pressure. Thereto was added sodium iodide (300 mg, 2.0 mmol), and the solution was stirred at 15° C. for 6 hours. N,N-Dimethylformamide (4.0 mL) was added thereto, and the solution was cooled to −40° C. Thereto was added phosphorus tribromide (189 μL, 2.0 mmol). The solution was stirred at −40° C. for 30 minutes. The reaction mixture was slowly added to a 5% salt solution cooled with ice. The precipitated solid was collected by filtration, washed with water, and suspended into water. The suspension was freeze-dried to yield compound ii-63b as a brown solid. Compound ii-63b yielded was used as it was, without being purified, in the next reaction.

The total amount of compound ii-63b yielded was dissolved in dichloromethane (10 mL), and the solution was cooled to −40° C. Thereto were then added anisole (1.09 ml, 10 mmol) and a 2 mol/L aluminum chloride solution (5.0 mL, 10 mmol) in nitromethane in turn. The liquid was stirred at −30° C. for 30 minutes. To the reaction liquid were added diisopropyl ether and a small amount of water, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. To the desired-compound-containing fraction was added a 0.2 N aqueous sodium hydroxide solution to adjust the pH to 6.0. Thereafter, a piece of dry ice was added thereto. The resultant was concentrated under reduced pressure, and then freeze-dried to yield compound II-63 as a white powder.

Yielded amount: 256 mg (32%)

$^1$H-NMR (D$_2$O) δ: 6.91 (1H, d, J=8.31 Hz), 6.86 (1H, d, J=8.31 Hz), 5.89 (1H, d, J=4.88 Hz), 5.37 (1H, d, J=4.88 Hz), 4.61 (1H, d, J=13.88 Hz), 4.23 (1H, t, J=7.17 Hz), 4.10-3.92 (4H, m), 3.49 (1H, d, J=16.62 Hz), 3.09 (3H, s), 2.81-2.71 (2H, m), 2.57-2.42 (4H, m), 2.18 (2H, d, J=16.78 Hz), 1.55 (3H, s), 1.54 (3H, s).

MS (m+1)=779.55

Elem. Anal.: $C_{31}H_{34}ClN_8O_{10}S_2Na.8.3H_2O$

Calcd.: C, 39.16; H, 5.36; Cl, 3.73; N, 11.79; S, 6.75; Na, 2.42(%).

Found: C, 39.01; H, 5.31; Cl, 3.86; N, 11.90; S, 6.79; Na, 2.60(%).

Example 129

Synthesis of Compound (II-64)

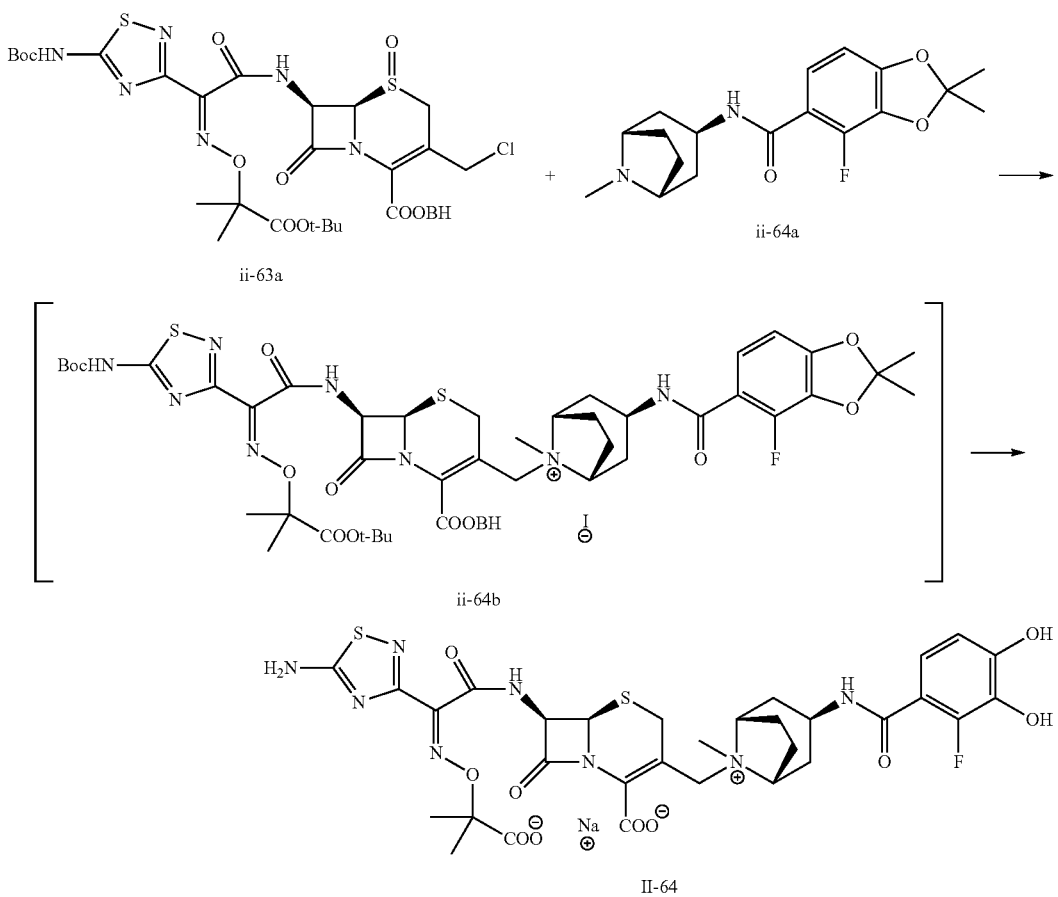

[Formula 176]

Step (1): compound ii-63a+compound ii-64a→compound II-64

From compound ii-63a (1.53 g, 1.0 mmol) and compound ii-64a (551 mg, 1.0 mmol), compound II-64 was yielded as a white powder in the same way as in step (1) in Example 128.

Yielded amount: 186 mg (24%)

$^1$H-NMR (D$_2$O) δ: 7.08 (1H, t, J=8.43 Hz), 6.77 (1H, dd, J=8.43, 1.45 Hz), 5.90 (1H, d, 4.96 Hz), 5.37 (1H, d, 4.96 Hz), 4.63 (1H, d, J=14.18 Hz), 4.23 (1H, t, J=6.79 Hz), 4.10-3.93 (4H, m), 3.50 (1H, d, 16.62 Hz), 3.10 (3H, s), 2.80-2.68 (2H, m), 2.59-2.40 (4H, m), 2.18 (2H, d, J=16.93 Hz), 1.55 (3H, s), 1.54 (3H, s).

MS (m+1)=763.57

Elem. Anal.: $C_{31}H_{34}FN_8O_{10}S_2Na.7.1H_2O$

Calcd.: C, 40.80; H, 5.32; F, 2.08; N, 12.28; S, 7.03; Na, 2.52(%).

Found: C, 40.72; H, 5.40; F, 2.13; N, 12.50; S, 7.06; Na, 2.61(%).

Example 130

Synthesis of Compound (II-65)

[Formula 177]

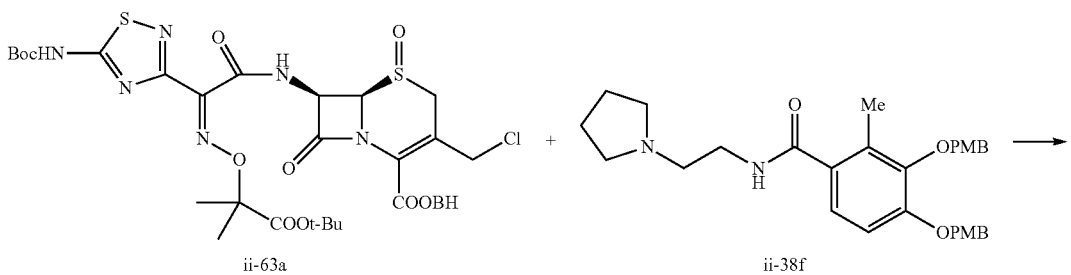

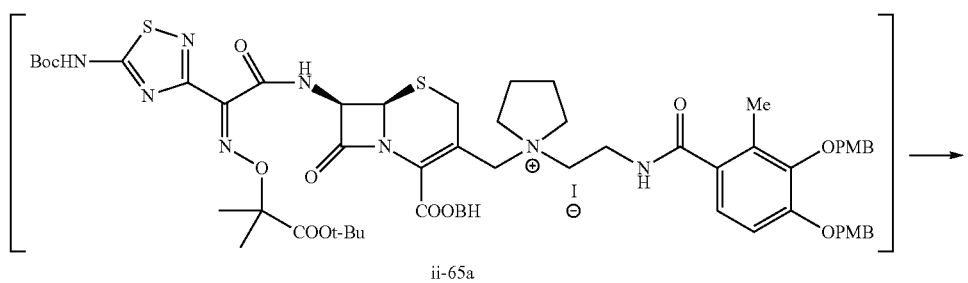

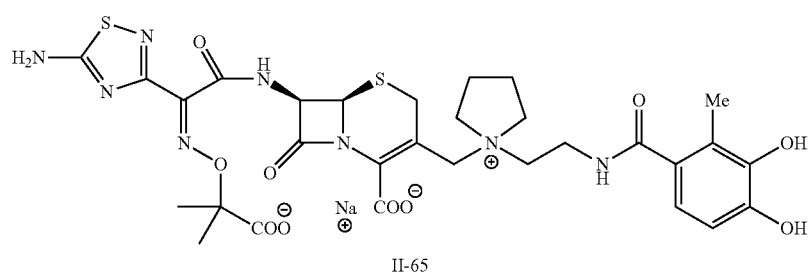

Step (1): compound ii-63a+compound ii-39f→compound II-65

From compound ii-63a (1.53 g, 1.0 mmol) and compound ii-39f (551 mg, 1.0 mmol), compound II-65 was yielded as a white powder in the same way as in step (1) in Example 128.

Yielded amount: 298 mg (40%)

$^1$H-NMR (D$_2$O) δ: 6.90 (1H, d, J=8.31 Hz), 6.80 (1H, d, J=8.31 Hz), 5.89 (1H, d, J=5.04 Hz), 5.37 (1H, d, J=5.04 Hz), 4.12 (1H, d, J=14.27 Hz), 3.97-3.47 (11H, m), 2.23 (7H, s), 1.54 (3M, 1.53 (3H, s).

MS (m+1)=733.57

Elem. Anal.: $C_{30}H_{35}N_9O_{10}S_2Na.7.1H_2O$

Calcd.: C, 40.82; H, 5.62; N, 12.69; S, 7.27; Na, 2.60(%).

Found: C, 40.66; H, 5.44; N, 12.92; S, 7.44; Na, 2.89(%).

Example 131

Synthesis of Compound (II-66)

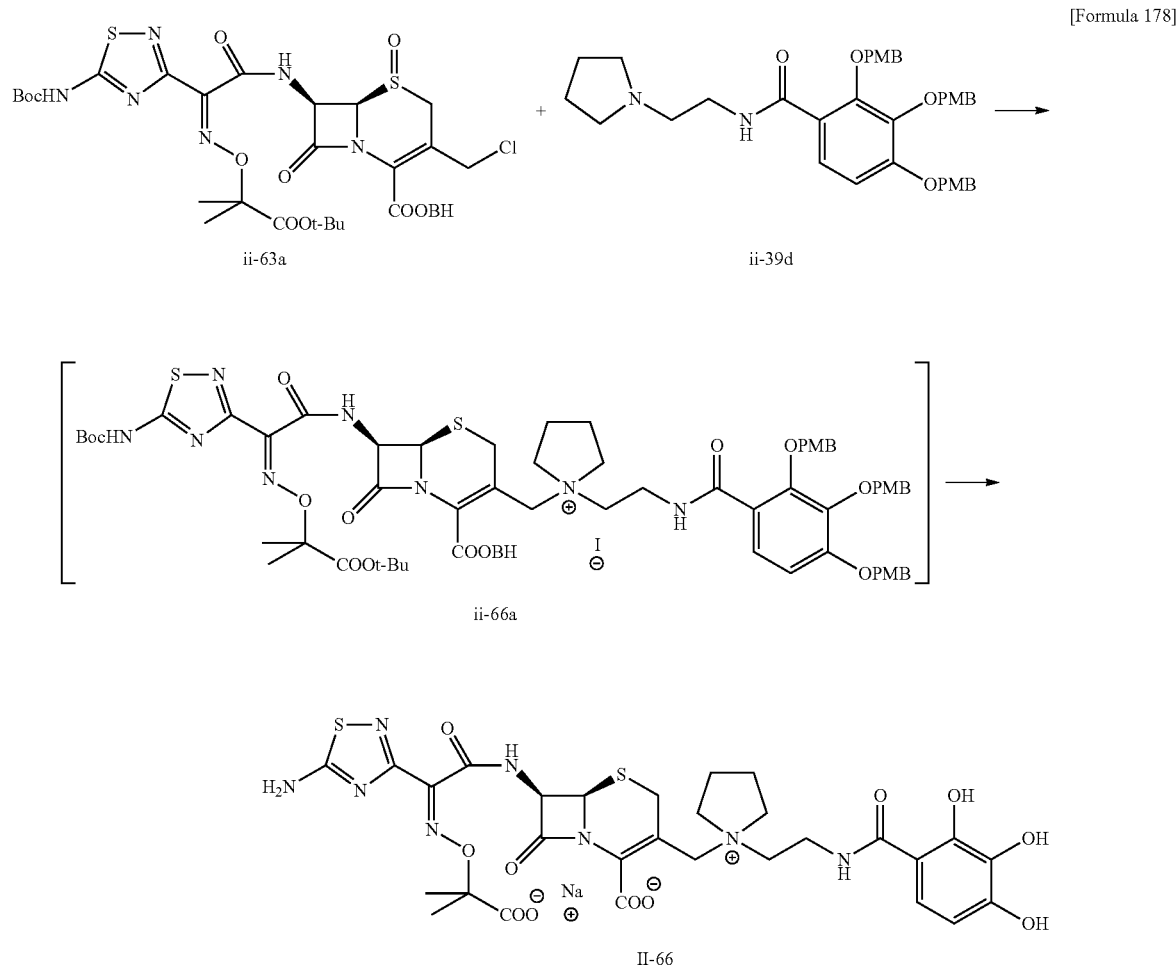

[Formula 178]

Step (1): compound ii-64a+compound ii-39d→compound II-66

From compound ii-63a (1.53 g, 1.0 mmol) and compound ii-39d (551 mg, 1.0 mmol), compound II-66 was yielded as a white powder in the same way as in step (1) in Example 128.
Yielded amount: 254 mg (34%)
$^1$H-NMR (D$_2$O) δ: 7.15 (1H, d, J=8.77 Hz), 6.51 (1H, d, J=8.77 Hz), 5.88 (1H, d, J=5.03 Hz), 5.35 (1H, d, J=5.03 Hz), 4.09 (1H, d, J=14.49 Hz), 3.94-3.43 (11H, m), 2.21 (4H, br s), 1.54 (3H, s), 1.53 (3H, s).

MS (m+1)=735.53
Elem. Anal.: C$_{29}$H$_{33}$N$_7$O$_{11}$S$_2$Na.6.8H$_2$O
Calcd.: C, 39.61; H, 5.34; N, 12.74; S, 7.29; Na, 2.61(%).
Found: C, 39.64; H, 5.25; N, 12.58; S, 7.36; Na, 2.60(%).

Example 132

Synthesis of Compound (II-67)

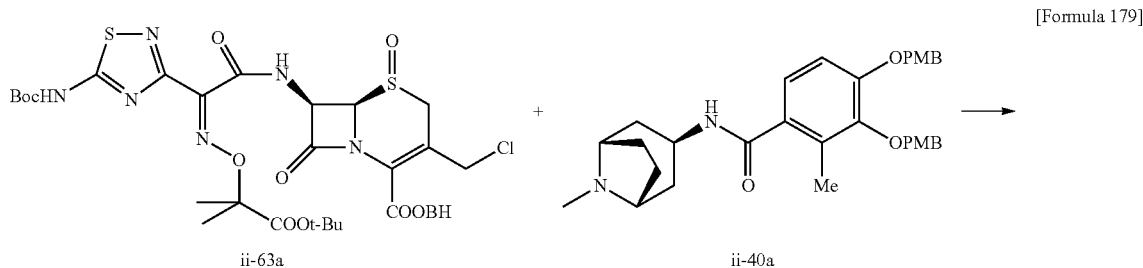

[Formula 179]

-continued

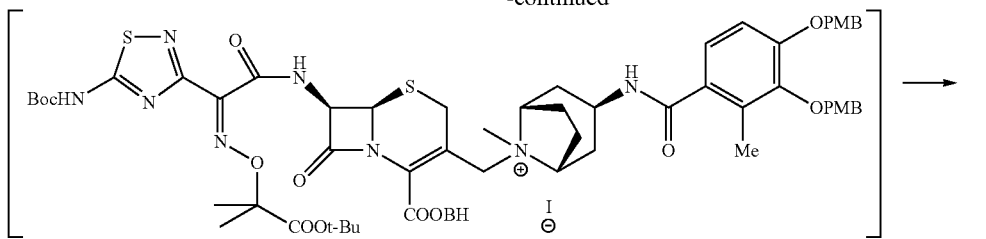

ii-67a

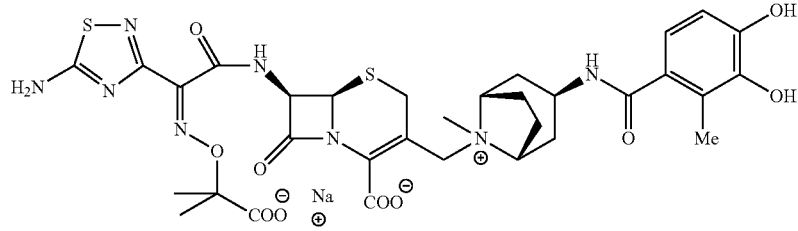

II-67

Step (1): compound ii-63a+compound ii-40a→compound II-67

From compound ii-63a (1.53 g, 1.0 mmol) and compound ii-40a (551 mg, 1.0 mmol), compound II-67 was yielded as a white powder in the same way as in step (1) in Example 128.

Yielded amount: 240 mg (31%)

$^{1}$H-NMR (D$_2$O) δ: 6.84 (1H, d, J=8.24 Hz), 6.77 (1H, d, 8.24 Hz), 5.89 (1H, d, J=4.96 Hz), 5.37 (1H, d, J=4.96 Hz), 4.62 (1H, d, J=13.88 Hz), 4.22 (1H, t, J=7.47 Hz), 4.09-3.92 (4H, m), 3.49 (1H, d, 16.78 Hz), 3.09 (3H, s), 2.81-2.70 (2H, m), 2.56-2.39 (4H, m), 2.22 (3H, s), 2.17 (2H, d, J=17.23 Hz), 1.55 ($^{3}$H, s), 1.54 (3H, s).

MS (m+1)=759.59

Elem. Anal.: C$_{32}$H$_{37}$N$_8$O$_{10}$S$_2$Na.8.8H$_2$O

Calcd.: C, 40.92; H, 5.86; N, 11.93; S, 6.83; Na, 2.45(%).

Found: C, 40.89; H, 5.63; N, 11.79; S, 6.91; Na, 2.68(%).

Example 133

Synthesis of Compound (II-68)

[Formula 180]

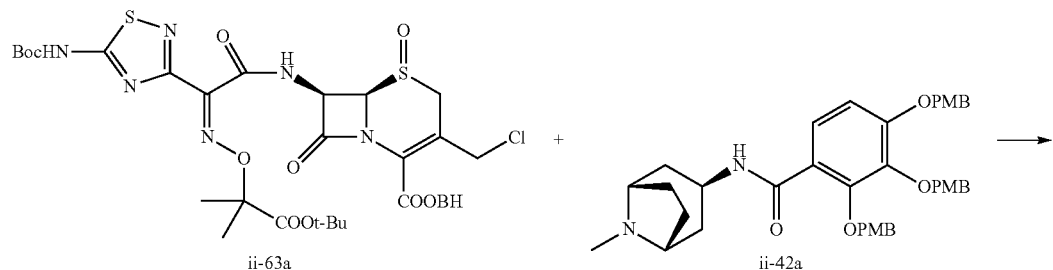

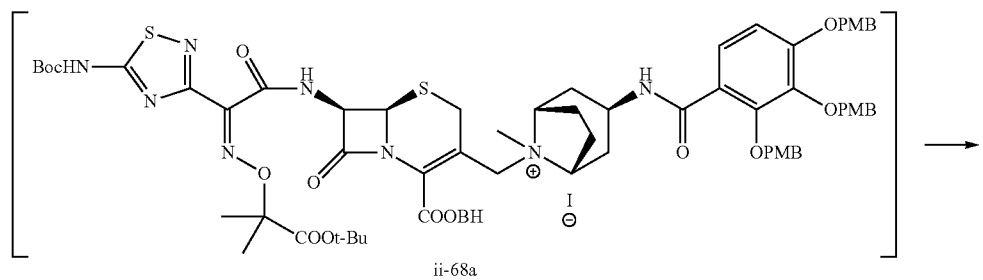

ii-68a

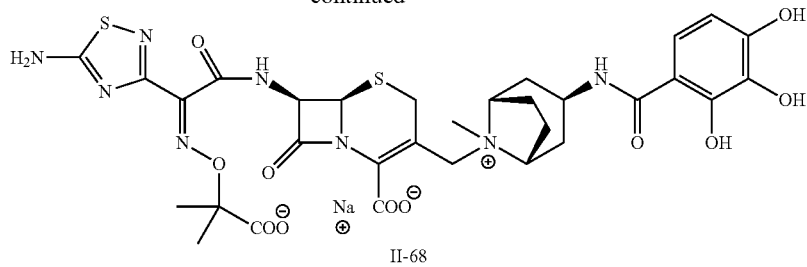

II-68

Step (1): compound ii-63a+compound ii-42a→compound II-68

From compound ii-63a (1.53 g, 1.0 mmol) and compound ii-42a (551 mg, 1.0 mmol), compound II-68 was yielded as a white powder in the same way as in step (1) in Example 128.

Yielded amount: 244 mg (31%)

$^1$H-NMR (D$_2$O) δ: 7.25 (1H, d, J=8.90 Hz), 6.54 (1H, d, J=8.90 Hz), 5.91 (1H, d, J=5.04 Hz), 5.37 (1H, d, J=5.04 Hz), 4.63 (1H, d, J=15.44 Hz), 4.26 (1H, t, J=7.13 Hz), 4.09-3.92 (4H, m), 3.48 (1H, d, J=16.79 Hz), 3.10 (3H, s), 2.80-2.71 (2H, m), 2.57-2.42 (4H, m), 2.12 (2H, d, J=16.95 Hz), 1.56 (3H, s), 1.51 (3H, s).

MS (m+1)=761.55

Elem. Anal.: C$_{31}$H$_{35}$N$_8$O$_{11}$S$_2$Na.6.4H$_2$O

Calcd.: C, 41.46; H, 5.36; N, 12.48; S, 7.14; Na, 2.56(%).

Found: C, 41.41; H, 5.16; N, 12.52; S, 7.23; Na, 2.72(%).

Example 134

Synthesis of Compound (III-1)

[Formula 181]

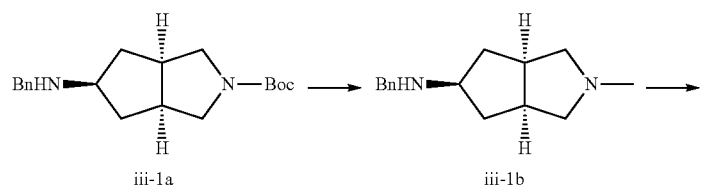

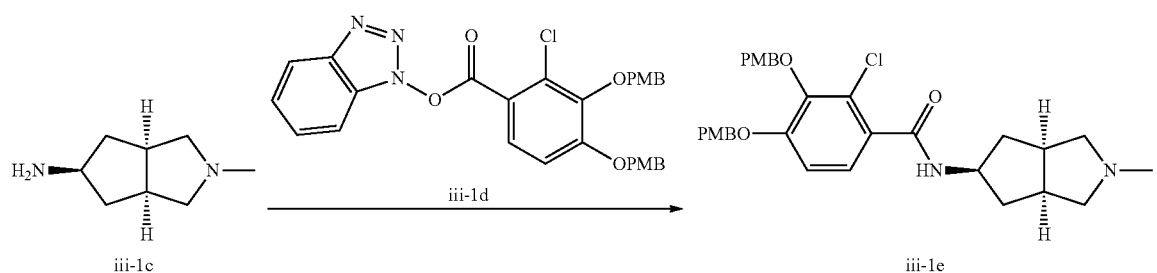

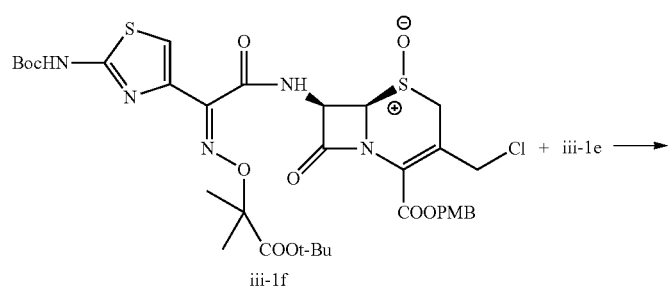

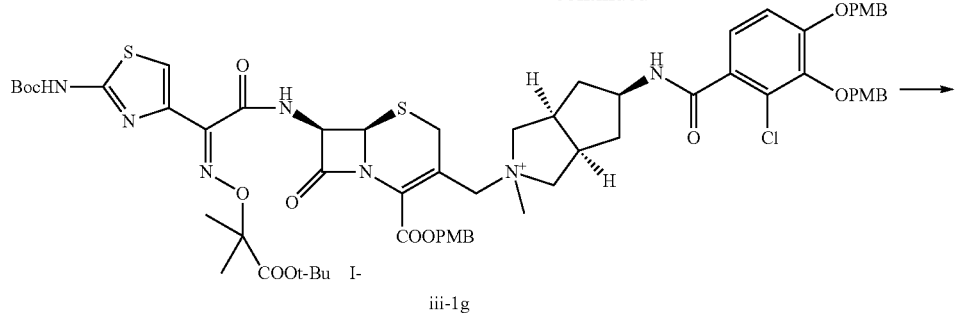

iii-1g

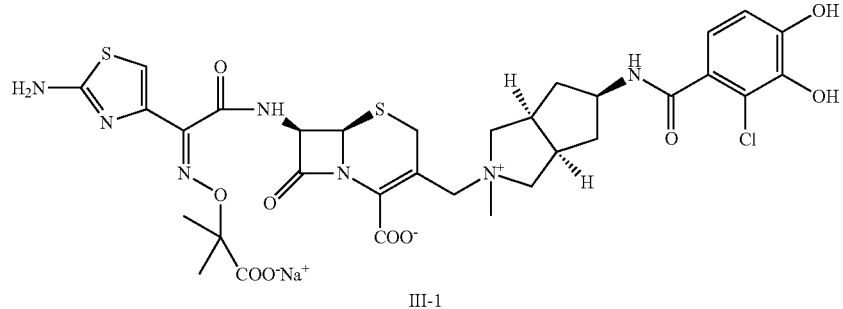

III-1

Step (1): Compound iii-1a→Compound iii-1b→Compound iii-1c→compound iii-1e

To a suspension of lithium aluminum hydride 0.817 g, 47.9 mmol) in tetrahydrofuran (50 ml) was added the known compound iii-1a (5.05 g, 15.96 mmol) (see Bioorganic & Medicinal Chemistry 20 (2010) 16741-676). The reaction mixture was heated at reflux for 6 hr. The reaction mixture was cooled to 0° C., sodium sulfate decahydrate (20g) was added thereto, and stirred at room temperature for 2 hr. The suspension was filtered and the filtrate was concentrated in vacuo to afford compound iii-1b (4.06 g), which was used for the next step without further purification. To a solution of compound iii-1b in methanol (20 mL) and acetic acid (20 mL) was added 20% palladium hydroxide (0.56g), and the mixture was stirred at room temperature under hydrogen atmosphere for 1 day. The resulting mixture was filtered through celite and filtrate was concentrated to afford compound iii-1c (6.16 g).

To a solution of compound iii-1c (1.722 g) in tetrahydrofuran (17 mL) was added triethylamine (4.16 mL, 30 mmol) and compound iii-1d, and the mixture was stirred at room temperature. The aqueous layer was basified by 2 mol/l, sodium hydroxide aqueous solution, extracted with ethyl acetate and the combined extracts were washed with water and brine, dried over magnesium sulfate, filtered, and concentrated in vacuo. The residue was purified by silica gel chromatography to afford compound iii-1e (1.24 g, 2.243 mmol)

$^1$H-NMR (CDCl$_3$) δ: 9.37 (1H, d, J=9.8 Hz), 7.38-7.21 (5H, m), 6.98-6.80 (5H, m), 5.06 (2H, s), 4.92 (2H, s), 4.63-4.55 (1H, m), 3.79 (6H, dd, J=11.1, 8.1 Hz), 2.75-2.67 (4H, m), 2.18-2.02 (6H, m), 1.72-1.57 (2H, m)

Step (2): Compound iii-1e→Compound (III-1)

Compound iii-1e (0.603 g, 1.1 mmol) and compound iii-1f (867 mg, 1.1 mmol) were used to synthesize the target compound in the same way as in step (1) in Example 128.

Yielded amount: 650 mg (75%)

MS (m+1): 778.43

$^1$H-NMR (D$_2$O) δ: 6.99 (1H, s), 6.95-6.84 (2H, m), 5.90 (1H, d, J=4.7 Hz), 5.38 (1H, d, J=5.0 Hz), 4.48-4.40 (1H, m), 4.06-3.85 (5H, m), 3.50-3.09 (10H, m), 3.00 (1H, s), 2.46 (3H, s), 1.63-1.47 (1H, m>.

Elemental Analysis

Calcd.: C, 43.79; H, 5.01; N, 11.17; Cl, 4.04; S, 7.31; Na, 2.62(%).

Found.: C, 43.76; H, 4.93; N, 11.01; Cl, 4.13; S, 7.15; Na, 3.01(%).

Example 135

Synthesis of Compound (III-2)

[Formula 182]

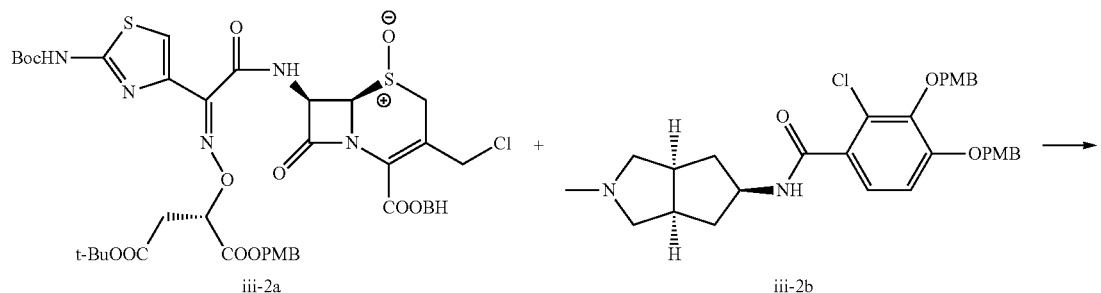

-continued

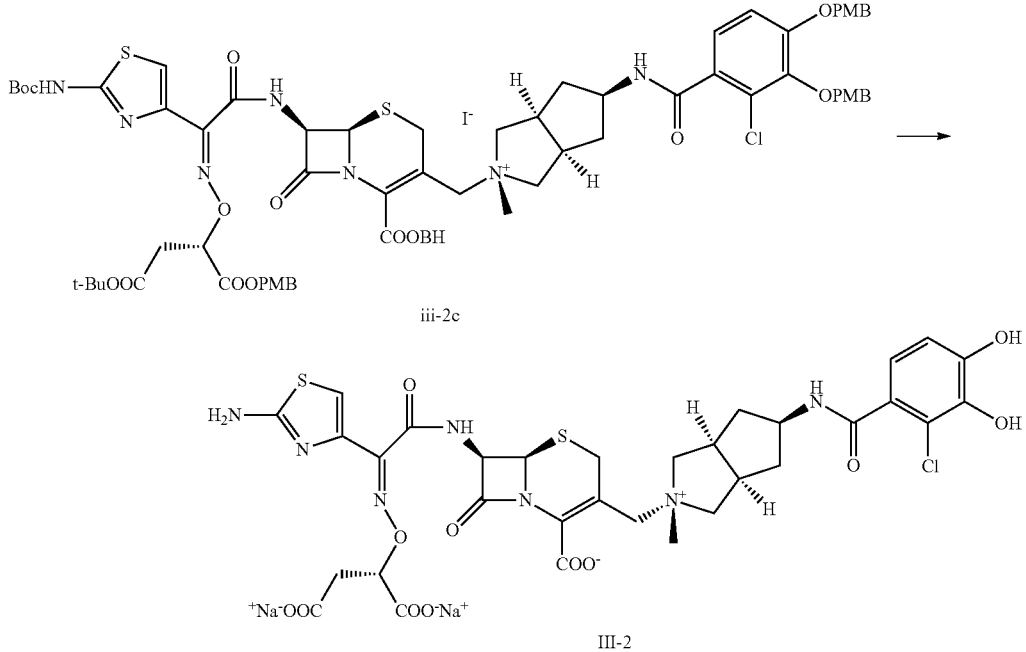

Step: Compound iii-2a→Compound iii-2b→Compound (III-2)

Compound iii-2a (0.460 g, 0.835 mmol) and compound iii-2b (828 mg, 0.835 mmol) were used to synthesize the target compound in the same way as in step (1) in Example 128.

Yielded amount: 247 mg (35%)
MS (m+1)=808.38
$^1$H-NMR (D$_2$O) δ: 7.03 (1H, d, J=7.4 Hz), 6.97-6.88 (2H, m), 5.84 (1H, d, J=5.0 Hz), 5.35 (1H, d, J=5.0 Hz), 4.99-4.88 (2H, m), 4.43 (1H, td, J=11.0, 5.3 Hz), 4.05-3.89 (4H, m), 3.55-3.06 (9H, m), 2.76-2.64 (2H, m), 2.54-2.41 (2H, br m), 1.63-1.52 (2H, m).

Elemental Analysis

Calcd.: C, 40.10; H, 4.61; N, 10.23; Cl, 3.70; S, 6.69; Na, 4.80(%).

Found.: C, 39.90; H, 4.43; N, 10.25; Cl, 3.55; S, 6.83; Na, 5.10(%).

Example 136

Synthesis of Compound (III-3)

[Formula 183]

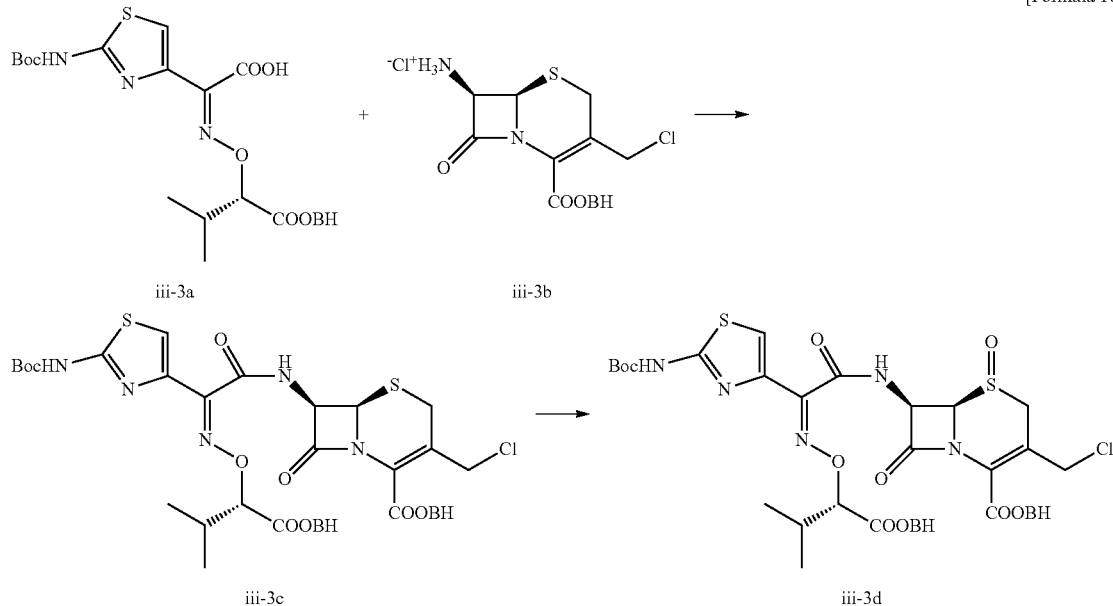

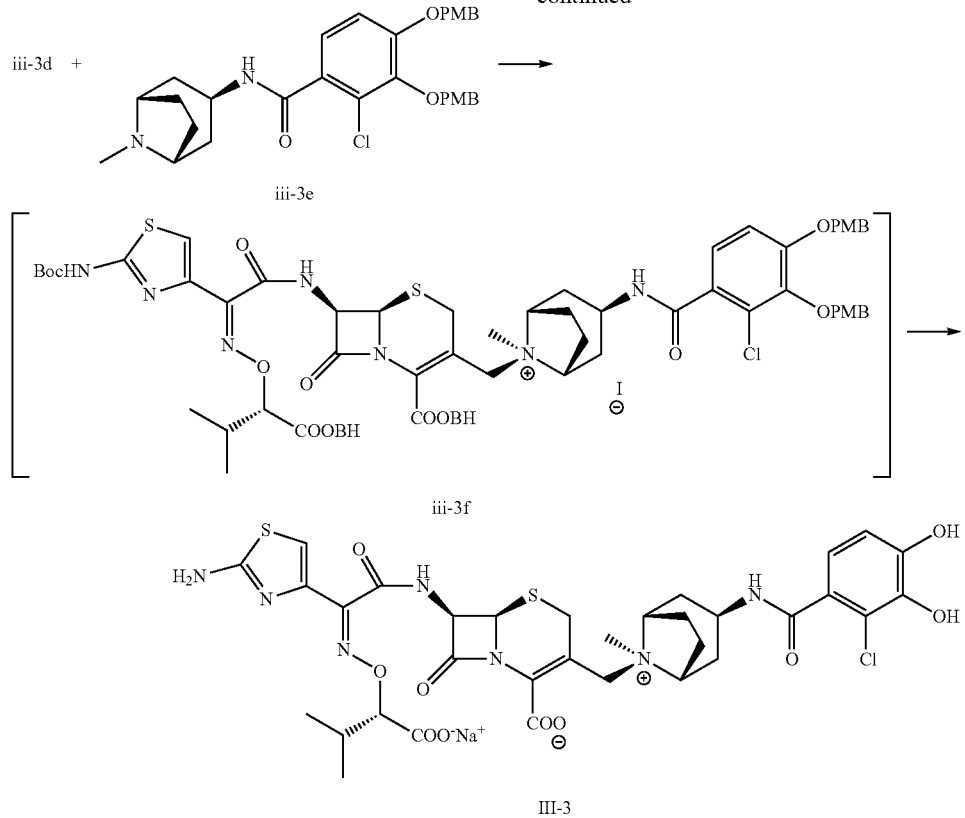

Step (1): Compound iii-3a+Compound iii-3b→Compound iii-3c→Compound iii-3d

To a solution of compound iii-3a (8.19 g, 14.8 mmol) in ethyl acetate (32 mL), compound iii-3b (7.01 g, 15.5 mmol) was added and then cooled to −40° C. Phenyl dichlorophosphate (3.32 ml, 22.2 mmol) was slowly added, and then N-methylmorpholine (6.51 mL, 59.2 mmol) was added dropwise over 25 minutes. After stirring at −40° C. for 1.5 hours, aqueous 0.2 mol/L hydrochloric acid was added Co the reaction mixture, followed by extraction with ethyl acetate. The organic layer was washed with water, aqueous 5% sodium hydrogen carbonate, then saturated brine, and then dried with anhydrous magnesium sulfate. The inorganic substance was removed by filtration, and then concentrated and subsequently drying under reduced pressure to yield compound iii-3c as an yellow foam. The obtained compound iii-3c was used in the next reaction without purification.

A solution of the whole amount of compound iii-3c obtained in methylene chloride (84 ml) was cooled to −40° C. A solution of m-chloroperbenzoic acid (4.32 g, 16.3 mmol) in methylene chloride (56 ml) was added drop-wise thereto over 30 minutes. After stirring at −40° C. for 30 minutes, aqueous 15% sodium thiosulfate solution was added thereto, methylene chloride was evaporated under reduced pressure, followed by extraction with ethyl acetate. The organic layer was washed with aqueous 5% sodium hydrogen carbonate, then saturated brine, and then dried with anhydrous magnesium sulfate. The inorganic substance was removed by filtration, followed by concentration in vacuo. The resulting crude product was purified by silica gel column chromatography to yield compound iii-3d as a white foam.

Yield: 12.9 g, (83%)

$^1$H-NMR (CDCl$_3$) δ: 0.99 (6H, dd, J=11.1, 6.9 Hz), 1.53 (9H, s), 2.40-2.28 (1H, m), 3.35 (1H, d, J=18.5 Hz), 3.76 (1H, d, J=18.5 Hz), 4.17 (1H, d, J=11.6 Hz), 4.58 (1H, dd, J=22.0, 4.7 Hz), 4.77 (1H, d, J=5.3 Hz), 4.96 (1H, d, J=12.4 Hz), 6.21 (1H, dd, J=9.3, 4.8 Hz), 6.96 (1H, s), 6.98 (1H, s), 7.11-7.47 (21H, m), 8.07 (1H, d, J=9.3 Hz), 8.24 (1H,

Step (2) compound iii-3d+compound iii-3e→compound iii-3f→compound (III-3)

A solution of compound iii-3e (5.51 mg, 1.0 mmol) in dimethylacetoamide: (2 mL) was cooled to 15° C., and thereto was added compound iii-3d (1.05 g, 1.0 mmol). The reaction vessel was then degassed under reduced pressure. Thereto was added sodium iodide (300 mg, 2.0 mmol) and the solution was stirred at 15° C. for 6 hours. N,N-Dimethylformamide (4.0 mL) was added thereto, and the solution was cooled to −40° C. Thereto was added phosphorus tribromide (189 µL, 2.0 mmol). The solution was stirred at −40° C. for 30 minutes. The reaction mixture was slowly added to a 5% salt solution cooled with ice. The precipitated solid was collected by filtration, washed with water, and suspended into water. The suspension was freeze-dried to yield compound iii-3f as a brown solid. Compound iii-3f was used in the next reaction without being purified. The total amount of compound iii-3f yielded was dissolved in dichloromethane (10 mL), and the solution was cooled to −40° C. Thereto were then added anisole (1.09 mL, 10 mmol) and 2 mol/L aluminum chloride solution (5.0 mL, 10 mmol) in nitromethane in turn. The liquid was stirred at 0° C. for 30 minutes. To the reaction liquid were added diisopropyl ether and a small amount of water, and the resultant was stirred to generate a precipitate. The supernatant was removed by decantation. To the insoluble matter adhering to the vessel were added a diluted aqueous hydrochloric acid solution, and acetonitrile. The resultant was stirred to dissolve the matter completely. Thereto was then added diisopropyl ether, and the water phase was separated to be collected. The organic phase was again subjected to extraction with water, and then all of the resultant water phases were combined with each other. Thereto was added HP20-SS resin. Acetonitrile was then distilled off therefrom under reduced pressure. The resultant mixed liquid was purified by ODS column chromatography. To the desired-compound-containing fraction was added a 0.2 mol/L aqueous sodium hydroxide solution to adjust the pH to 6.0. Thereafter, a piece of dry ice was added thereto. The resultant was concentrated under reduced pressure, and then freeze-dried to yield compound III-3 as a white powder.

Yielded amount: 369 mg (45%)

$^1$H-NMR (D$_2$O) δ: 6.98 (1H, s), 6.93 (1H, d, J=8.4 Hz), 6.88 (1H, d, J=8.4 Hz), 5.88 (1H, d, J=5.1 Hz), 5.36 (1H, d, J=5.1 Hz), 4.62 (1H, d, J=13.8 Hz), 4.35 (1H, d, J=5.4 Hz), 4.22 (1H, t, J=7.2 Hz), 4.08-3.92 (4H, m), 3.48 (1H, d, J=16.5 Hz), 3.09 (3H, s), 2.79-2.73 (2H, m), 2.50-2.41 (4H, m), 2.19-2.1 (3H, m), 1.00 (6H, d, t=7.2 Hz).

MS (m+1): 792.48

Elem. Anal.: $C_{33}H_{37}ClN_7O_{10}S_2NaH_2O(5.9)$

Calcd.: C, 43.06; H, 5.34; Cl, 3.85; N, 10.65; S, 6.97; Na, 2.50(%).

Found.: C, 42.98; H, 5.21; Cl, 3.90; N, 10.68; S, 7.14; Na, 2.52(%).

Example 138

Synthesis of Compound (III-5)

[Formula 184]

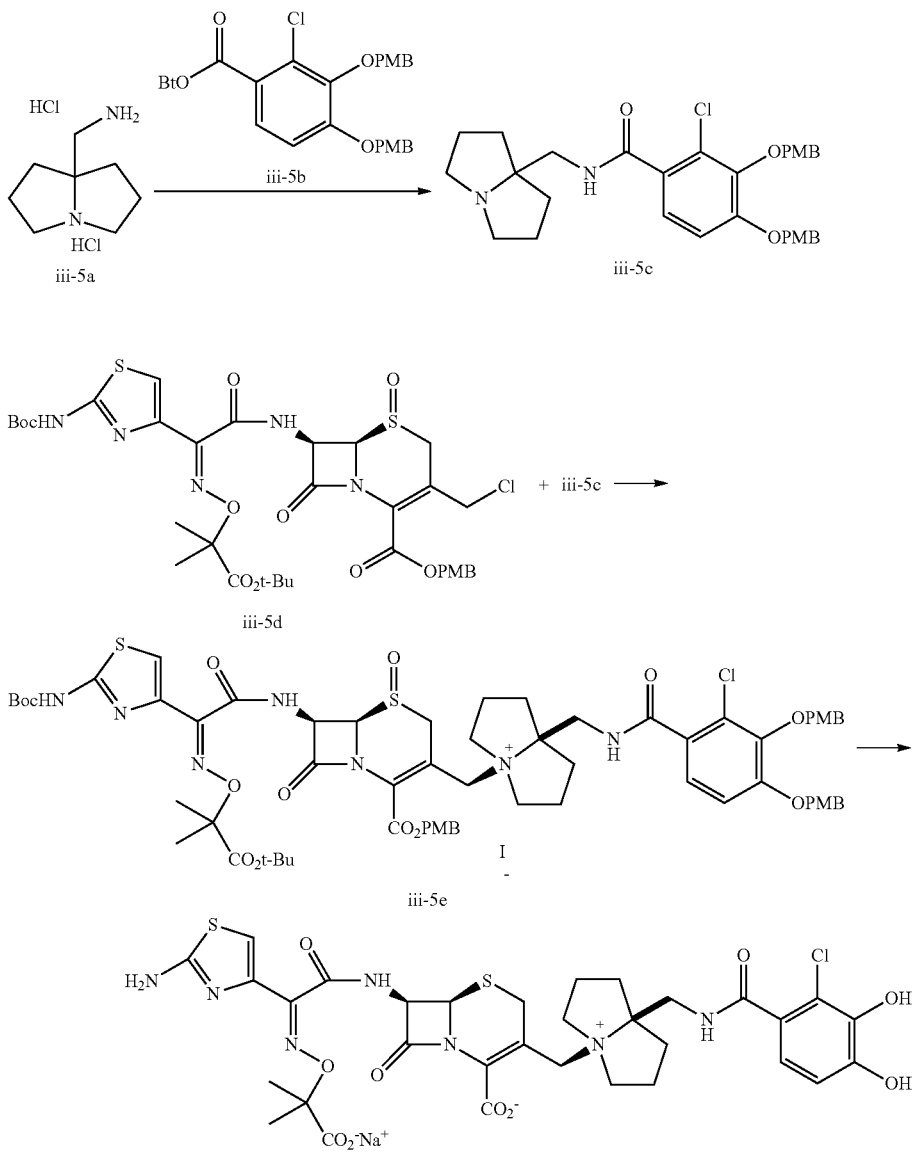

Step (1): Compound iii-5a→Compound iii-5c

The title compound iii-5c was synthesized from compound iii-5a (0.700 g, 3.28 mmol) following a similar procedure described above (0.624 g, 35%).

$^1$H-NMR (CDCl$_3$) δ: 7.38-7.33 (5H, m), 6.99-6.81 (6H, m), 5.07 (2H, s), 4.94 (2H, s), 3.83 (3H, s), 3.80 (3H, s), 3.41 (2H, d, J=5.9 Hz), 3.09-3.02 (2H, m), 2.68-2.60 (2H, m), 1.92-1.62 (8H, m).

Step (2): Compound iii-5d→Compound (III-5)

The title compound III-5 was synthesized from compound iii-5d (0.900 g, 1.13 mmol) following a similar procedure described above.

Yield: 0.045 g (5%)

MS: 778.31 (M+H)

$^1$H-NMR (D$_2$O) δ: 6.98 (1H, s), 6.93-6.84 (2H, m), 5.89 (1H, d, J=4.7 Hz), 5.37 (1H, d, J=4.7 Hz), 4.72 (1H, d, J=13.0 Hz), 4.15 (1H, d, J=13.0 Hz), 4.03-3.69 (6H, m), 3.49-3.44 (2H, m), 2.43-2.04 (8H, m), 1.52 (3H, s), 1.50 (3H, s).

Elemental analysis for C31H30FN7Na2O12S2(H2O)7.1 (NaHCO3)0.1 calcd.: C, 41.24; H, 5.15; Cl, 3.77; N, 10.42; S, 6.82; Na, 3.18.

found.: C, 41.12; H, 5.04; Cl, 3.82; N, 10.50; S, 7.07; Na, 3.35.

Example 139

Synthesis of Compound (III-6)

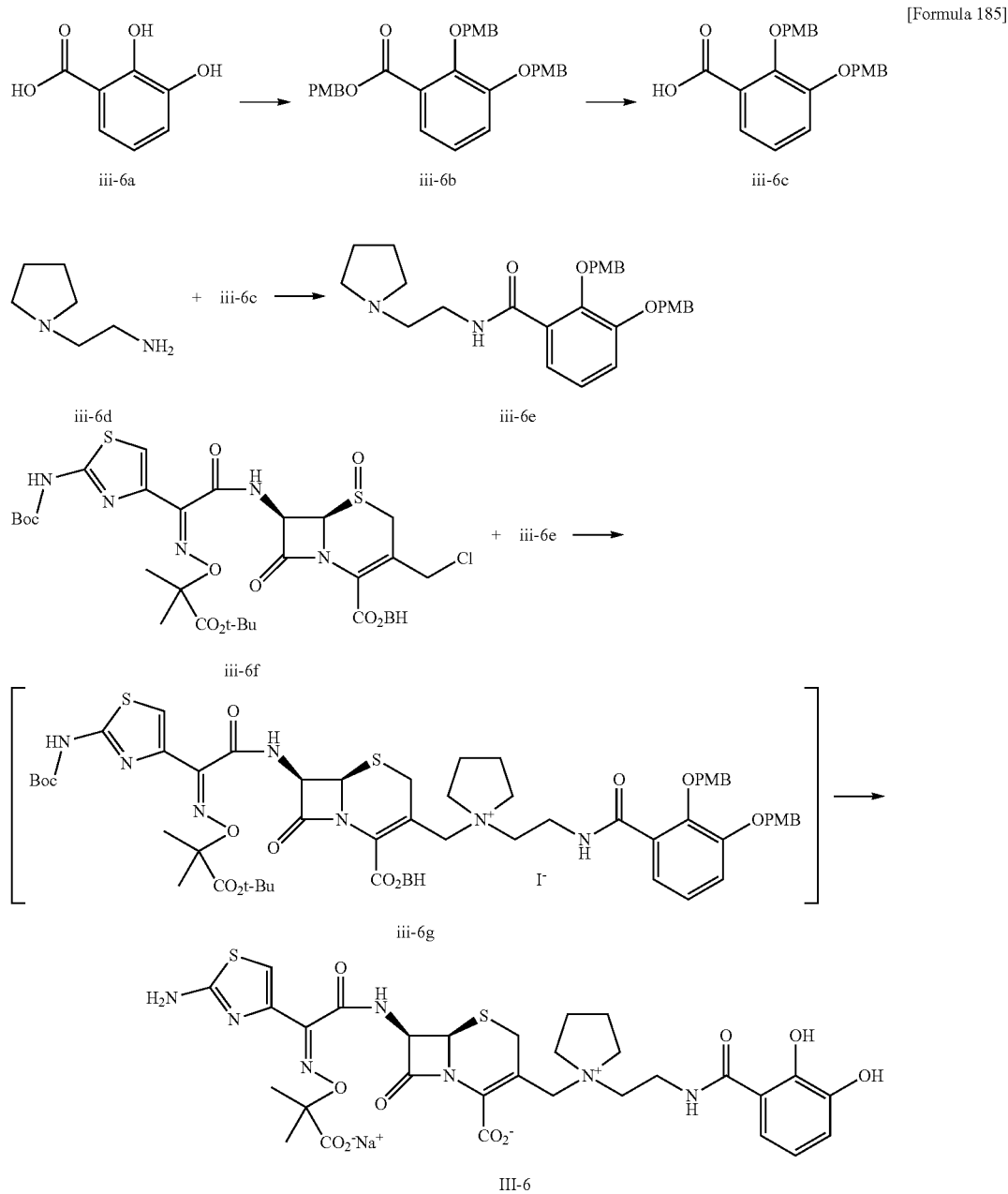

[Formula 185]

Step (1): Compound iii-6a→Compound iii-6b

Compound iii-6a (15.0 g, 97.0 mmol) was dissolved into N,N-dimethylformamide (180 mL), and thereto were then added potassium carbonate (60.5 g, 438 mmol), p-methoxybenzyl chloride (47.7 ml, 0.350 mmol) and sodium iodide (14.6 g, A7.0 mmol) in turn. The liquid was stirred at 70° C. for 2 hours. The reaction liquid was diluted with ethyl acetate, and the organic phase was washed with water and a saturated salt solution, and dried over magnesium sulfate. Magnesium sulfate was filtrated off. The organic phase was then concentrated under reduced pressure. Thereto was added diisopropyl ether/ethyl acetate to precipitate a solid. In this way, compound iii-6b was yielded (26.3 g, 52%).

$^1$H-NMR (CDCl$_3$) δ: 7.32-7.35 (5H, m), 7.17 (2H, d, 8.69 Hz), 7.12-7.01 (2H, m), 6.87 (4H, t, J=9.00 Hz), 6.75 (2H, d, J=8.85 Hz), 5.24 (2H, s), 5.04 (2H, s), 9.94 (2H, s), 3.82 (3H, s>, 3.80 (3H, s), 3.78 (3H, a).

Step (2): Compound iii-6b→Compound iii-6c

An 8 mol/L aqueous sodium hydroxide solution (12.15 ml, 97.0 mmol) was added to a solution of compound iii-6b (25.0 g, 48.6 mmol) in tetrahydrofuran (70 mL) and methanol (60 mL). The resultant solution was stirred at 70° C. for 2 hours. To the reaction liquid was added a 2 mol/L aqueous hydrochloric acid solution (55 mL), and the solution was concentrated under reduced pressure. The precipitated solid was then collected by filtration, and washed with water and diisopropyl ether to yield compound iii-6c (16.9 g, 88%).

$^1$H-NMR (DMSO-d$_6$) δ: 7.42 (2H, d, J=8.73 Hz), 7.32 (1H, dd, J=7.89, 1.85 Hz), 7.27 (2H, d, J=8.73 Hz), 7.20-7.09 (2H, m), 6.96 (2H, d, J=8.73 Hz), 6.84 (2H, d, J=8.73 Hz), 5.10 (2H, s), 4.89 (2H, s) 3.77 (3H, s), 3.74 (3H, s).

Step (3): Compound iii-6d+Compound iii-6c→Compound iii-6e

Compound iii-6c (1.00 g, 2.54 mmol) was suspended into dichloromethane (10 mL). Thereto were then added 1-hydroxybenzotriazole (411 mg, 3.04 mmol) and 1-ethyl-3-(3-dimethylaminopropyl) carbodiimide hydrochloride (535 mg, 2.79 mmol) in turn while cooled with ice. The liquid was stirred at room temperature for 30 minutes. Thereto was added compound iii-6d (353 µl, 2.79 mmol) while cooled with ice. The resultant was stirred at room temperature for 3 hours. The reaction liquid was diluted with dichloromethane, washed with an aqueous sodium hydroxide solution, water and a saturated salt solution, and dried over magnesium sulfate. Magnesium sulfate was filtrated off, and then the liquid was concentrated under reduced pressure. The compound-containing liquid was subjected to amino silica gel column chromatography to elute out the desired compound with chloroform. The desired-compound-containing fraction was concentrated under reduced pressure to yield compound iii-6e (1.23 g, 99%).

$^1$H-NMR (DMSO-d$_6$) (δ: 8.22 (1H, t, J=5.34 Hz), 7.42 (2H, d, J=8.39 Hz), 7.29-7.22 (4H, m), 7.11 (1H, t, J=7.78 Hz), 6.96 (2H, d, J=8.39 Hz), 6.83 (2H, d, J=8.39 Hz), 5.10 (2H, s), 4.93 (2H, s), 3.76 (3H, s), 3.73 (3H, s), 3.30 (2H, q, J=5.80 Hz), 2.44 (2H, t, J=6.71 Hz), 2.38 (411, br s), 1.60 (4H, br s).

Step (4): Compound iii-6f+Compound iii-6e→Compound (III-6)

Sodium iodide (300 mg, 2.0 mmol) was added to a solution of compound iii-6f (936 mg, 1.00 mmol) in dimethylacetoamide (2 mL), and the resultant solution was stirred at room temperature for 5 minutes. The solution was cooled to 0° C., and then thereto was added compound iii-6e (540 mg, 1.10 mmol). Thereafter, the solution was stirred at 0-10° C. for 6 hour. Thereto was added N,N-dimethylformamide (2 mL), and then the solution was cooled to −40° C. Thereto was added phosphorus tribromide (189 µL, 2.0 mmol), and the solution was stirred at −40° C. for 30 minutes. The reaction mixture was slowly added to a 5% salt solution cooled with ice. The precipitated solid was collected by filtration, washed with water, and then suspended into water. The suspension was freeze-dried to yield compound iii-6g as a pale yellow solid. Compound iii-6g was used in the next reaction without being purified.

The total amount of compound iii-6g yielded was dissolved in methylene chloride (10 mL), and the solution was cooled to −40° C. Thereto were then added anisole (1.092 mL, 10.0 mmol) and a 2 ME aluminum chloride solution (5.00 mL, 10.0 mmol) in nitromethane in turn. The resultant was stirred at 0° C. for 1 hour. The reaction liquid was dissolved in water, a 2 mol/L aqueous hydrochloric acid solution, and acetonitrile. The resultant solution was then washed with diisopropyl ether. To the water phase was added HP20-SS resin, and then acetonitrile was distilled off under reduced pressure. The resultant mixed liquid was purified by ODS column chromatography. To the resultant target-compound solution was added a 0.2 mol/L aqueous sodium hydroxide solution until the whole gave a pH of 6.0. Thereafter, a piece of dry ice was added thereto. The resultant solution was concentrated under reduced pressure, and then freeze-dried to yield compound III-6 as a pale yellow powder.

Yielded amount: 397.4 mg, (41%).

$^1$H-NMR (D$_2$O) δ: 7.27 (1H, dd, J=8.01, 1.53 Hz), 7.08 (1H, dd, J=8.01, 1.53 Hz), 6.98 (1H, s), 6.82 (1H, t, 8.01 Hz), 5.88 (1H, d, J=4.96 Hz), 5.36 (1H, d, J=4.96 Hz), 4.13 (1H, d, J=14.18 Hz), 3.98-3.93 (2H, m), 3.87-3.78 (1H, m), 3.69-3.46 (8H, m), 2.23 (4H, br s), 1.51 (3H, s), 1.49 (3H, s).

Elem. Anal.: C30H34N7O10S2Na (H2O)7.3(NaHCO3) 0.21

Calcd.: C, 40.82; H, 5.53; N, 11.03; S, 7.21; Na, 3.13(%).
Found.: C, 40.71; H, 5.43; N, 11.19; S, 7.47; Na, 3.12(%).

Example 140

Synthesis of Compound (III-7)

[Formula 187]

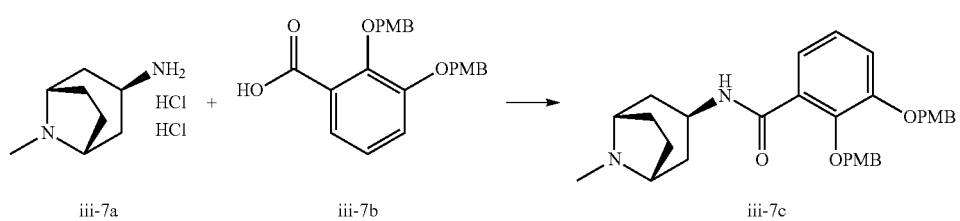

-continued

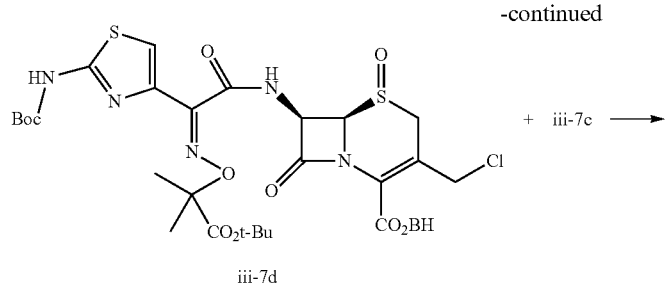
iii-7d

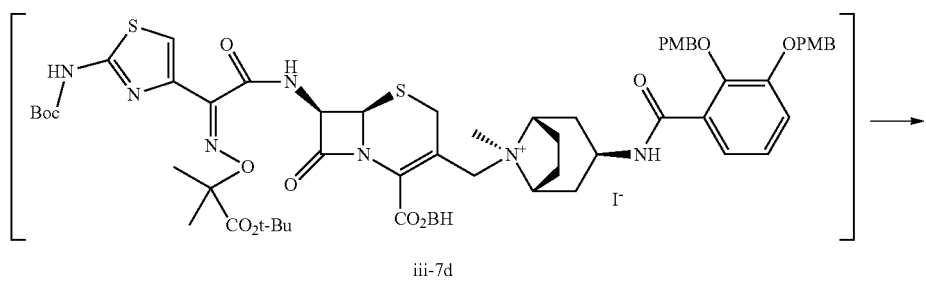
iii-7d

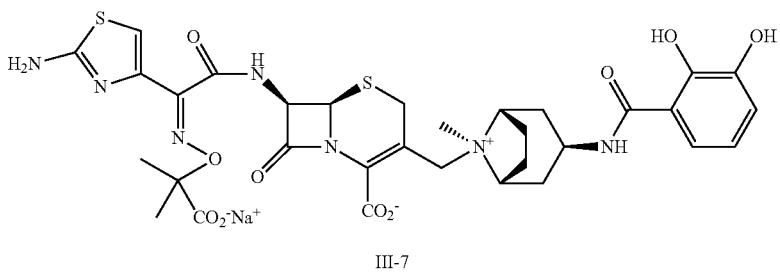
III-7

Step (1): Compound iii-7a+Compound iii-7b→Compound iii-7c

Compound iii-7b (1.97 g, 5.00 mmol) was dissolved in to dichloromethane (20 mL). Thereto were added 1-hydroxybenzotriazole (811 mg, 6.00 mmol) and 1-ethyl-3-(3-dimethylaminopropyl)carbodiimide hydrochloride (1.05 g, 5.50 mmol) in turn while cooled with ice. The liquid was stirred at room temperature for 30 minutes. Thereto were added compound iii-7a (1.28 g, 6.00 mmol) and diisopropylethylamine (2.62 ml, 15.0 mmol) while cooled with ice. The resultant was stirred at room temperature for 3 hours. The reaction liquid was diluted with dichloromethane, and the organic phase was washed with an aqueous sodium hydroxide solution, water and a saturated salt solution, and dried over magnesium sulfate. Magnesium sulfate was filtrated off, and then the organic phase was concentrated under reduced pressure. The compound-containing liquid was subjected to amino silica gel column chromatography toe elute out the desired compound with chloroform. The desired-compound-containing fraction was concentrated under reduced pressure to yield compound iii-7c (2.36 g, 91%).

$^1$H-NMR (DMSO-$d_6$) δ: 8.22 (1H, d, J=6.25 Hz), 7.45 (2H, d, J=8.69 Hz), 7.33-7.22 (4H, m), 7.13 (1H, t, J=7.93 Hz), 6.97 (2H, d, J=8.69 Hz), 6.83 (2H, d, J=8.69 Hz), 5.12 (2H, s), 4.97 (2H, s), 3.90 (1H, q, J=6.66 Hz), 3.77 (3H, s), 3.73 (3H, s), 2.86 (2H, br s), 2.07 (3H, s), 1.99-1.91 (2H, m), 1.76-1.72 (2H, m), 1.50 (2H, d, J=8.08 Hz), 1.42 (2H, d, J=13.88 Hz).

Step (2): Compound iii-7d+Compound iii-7c→Compound (III-7)

Compound iii-7d (936 mg, 1.00 mmol) and compound iii-7c (568 mg, 1.10 mmol) were used to synthesize the target compound III-7 in the same way as described above.

Yielded amount: 556.6 mg, (53%)

$^1$H-NMR (D$_2$O) δ: 7.31 (1H, dd, J=7.78, 1.53 Hz), 7.07 (1H, dd, J=7.78, 1.53 Hz), 6.98 (1H, s), 6.83 (1H, t, J=7.78 Hz), 5.89 (1H, d, J=4.96 Hz), 5.38 (1H, d, J=4.96 Hz), 4.31 (1H, t, J=7.32 Hz), 4.11-3.94 (4H, m), 3.51 (1H, d, J=17.23 Hz), 3.11 (3H, br s), 2.83-2.72 (2H, m), 2.61-2.41 (5H, m), 2.19 (1H, br s), 2.13 (1H, br s), 1.52 (3H, s), 1.50 (3H, s).

Elem. Anal.: C32H36N7O10S2Na (H2O)5.7
Calcd.: C, 44.25; H, 5.50; N, 11.29; S, 7.38; Na, 2.65(%).
Found.: C, 44.28; H, 5.52; N, 11.28; S, 7.18; Na, 2.52(%).

Example 141

Synthesis of Compound (III-8)

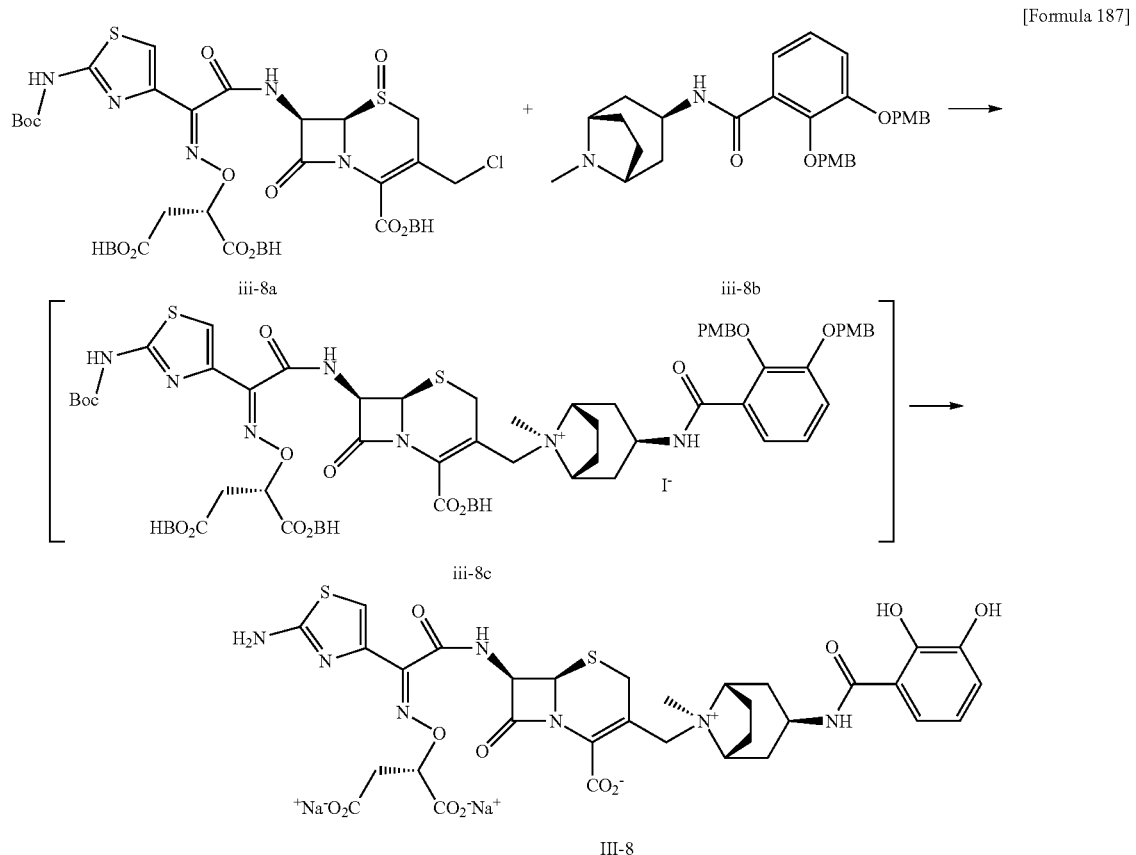

Step (1): Compound iii-8a+Compound iii-8b→Compound (III-8)

Compound iii-8a (1.26 g, 1.00 mmol) and compound iii-8b (568 mg, 1.10 mmol) were used to synthesize the target compound III-8 in the same way as described above.

Yielded amount: 453.7 mg, (42%)

$^1$H-NMR (D$_2$O) δ: 7.30 (1H, d, J=8.06 Hz), 7.09 (1H, d, J=8.06 Hz), 7.01 (1H, s), 6.88 (1H, t, J=8.06 Hz), 5.83 (1H, d, J=4.80 Hz), 5.34 (1H, d, J=4.80 Hz), 4.99-4.95 (1H, m), 4.62 (1H, d, J=15.56 Hz), 4.30 (1H, t, J=7.09 Hz), 4.11 (1H, d, J=14.03 Hz), 4.04 (1H, br s), 3.95-3.90 (2H, m), 3.50 (1H, d, J=16.78 Hz), 3.11 (3H, br s), 2.80-2.72 (4H, m), 2.61-2.39 (4H, m), 2.20 (1H, br s), 2.14 (1H, br s).

Elem. Anal. C32H33.4N7O12S2Na1.6(H2O)6.7
Calcd.: C, 41.34; H, 5.07; N, 10.55; S, 6.90; Na, 3.96(%).
Found.: C, 41.36; H, 5.00; N, 10.41; S, 6.77; Na, 3.95(%).

Example 142

Synthesis of Compound (III-9)

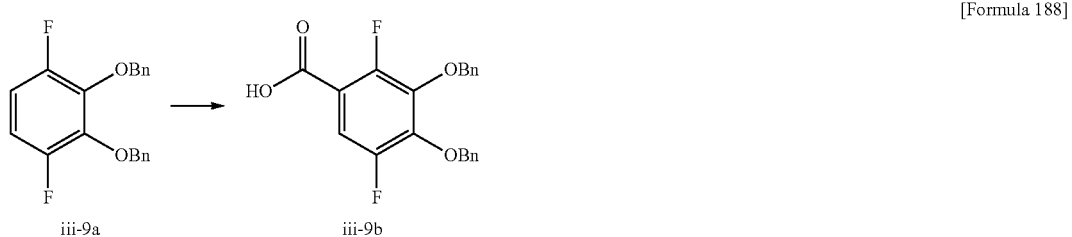

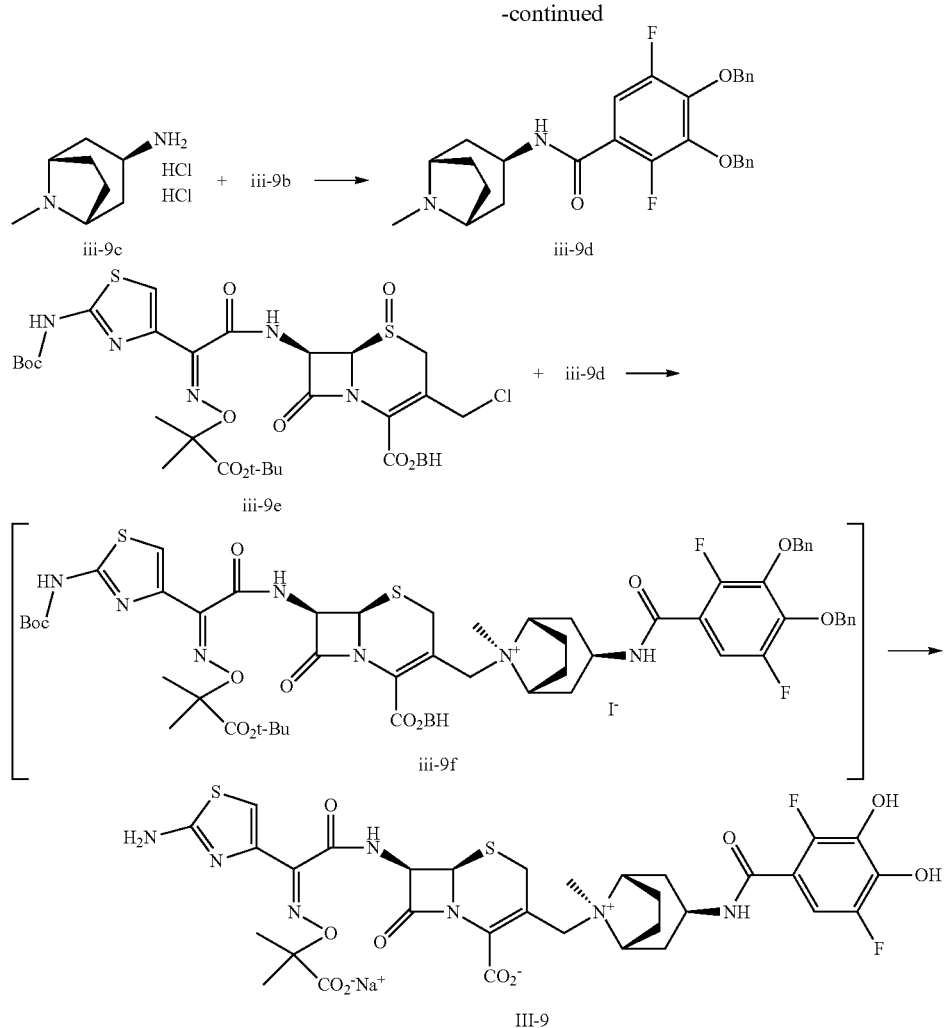

Step (1): Compound iii-9a→Compound iii-9b

Compound iii-9a (1.41 g, 4.32 mmol) synthesized with reference to a method described in J. Med. Chem., 1993, 24, 3947-3955 was dissolved in tetrahydrofuran (50 mL) and thereto were then added a 1.67 M BuLi solution 3.10 ml, 5.18 mmol) in hexane at −78° C., and the resultant solution was stirred at −78° C. for 1 hour. At −78° C., a piece of dry ice was added to the reaction liquid, and the liquid was stirred at room temperature for 30 minutes. The reaction liquid was diluted with diethyl ether, and thereto was added water to separate the liquid to two phases. The resultant water phase was made into acidity, and then subjected to extraction with ethyl acetate. The organic phase was washed with a saturated salt solution, and dried over magnesium sulfate. Magnesium sulfate was filtrated off, and then the organic phase was concentrated under reduced pressure. Thereto was added diisopropyl ether to precipitate a solid. The solid was collected by filtration, so as to yield compound iii-9b (840 mg, 53%). The filtrate was concentrated under reduced pressure to yield compound iii-9b (160 mg, 10%). Compound iii-9b was used in the next reaction without being purified.

Step (2): Compound iii-9c+Compound iii-9b→Compound iii-9d

Compound iii-9c (691 mg, 3.24 mmol) and compound iii-9b (1.00 g, 2.70 mmol) were used to synthesize the target compound iii-9d in the same way as described above.

Yielded amount: 803 mg, (60%)

$^1$H-NMR (DMSO-$d_6$) δ: 8.00 (1H, s), 7.43-7.35 (10H, m), 7.18 (1H, dd, J=10.75, 6.02 Hz), 5.17 (2H, s), 5.11 (2H, s), 3.87 (1H, q, J=5.80 Hz), 2.99 (2H, br s), 2.14 (3H, s), 2.05-1.86 (6H, m), 1.70 (1H, br s), 1.65 (1H, br s).

Step (3): Compound iii-9e+Compound iii-9d→Compound (III-9)

Compound iii-9e (749 mg, 0.800 mmol) and compound iii-9d (402 mg, 0.816 mmol) were used to synthesize the target compound III-9 in the same way as described above.

Yielded amount: 498.8 mg, (52%)

$^1$H-NMR (D$_2$O) δ: 7.02-6.96 (2H, m), 5.89 (1H, d, J=5.04 Hz), 5.38 (1H, d, J=5.04 Hz), 4.29-3.94 (5H, m), 3.51 (1H, d, J=16.79 Hz), 3.10 (3H, br s), 2.81-2.69 (2H, m), 2.60-2.40 (5H, my, 2.21 (1H, br s), 2.15 (1H, br s), 1.52 (3H, s), 1.50 (3H, s).

Elem. Anal.: C32H34F2N7O10S2Na (H2O)8(NaHCO3) 0.09

Calcd.: C, 40.42; H, 5.30; F, 3.99; N, 10.22; S, 6.73; Na, 2.63(%).

Found.: C, 40.36; H, 5.19; F, 3.91; N, 10.41; S, 6.93; Na, 2.63(%).

Example 143

Synthesis of Compound (III-10)

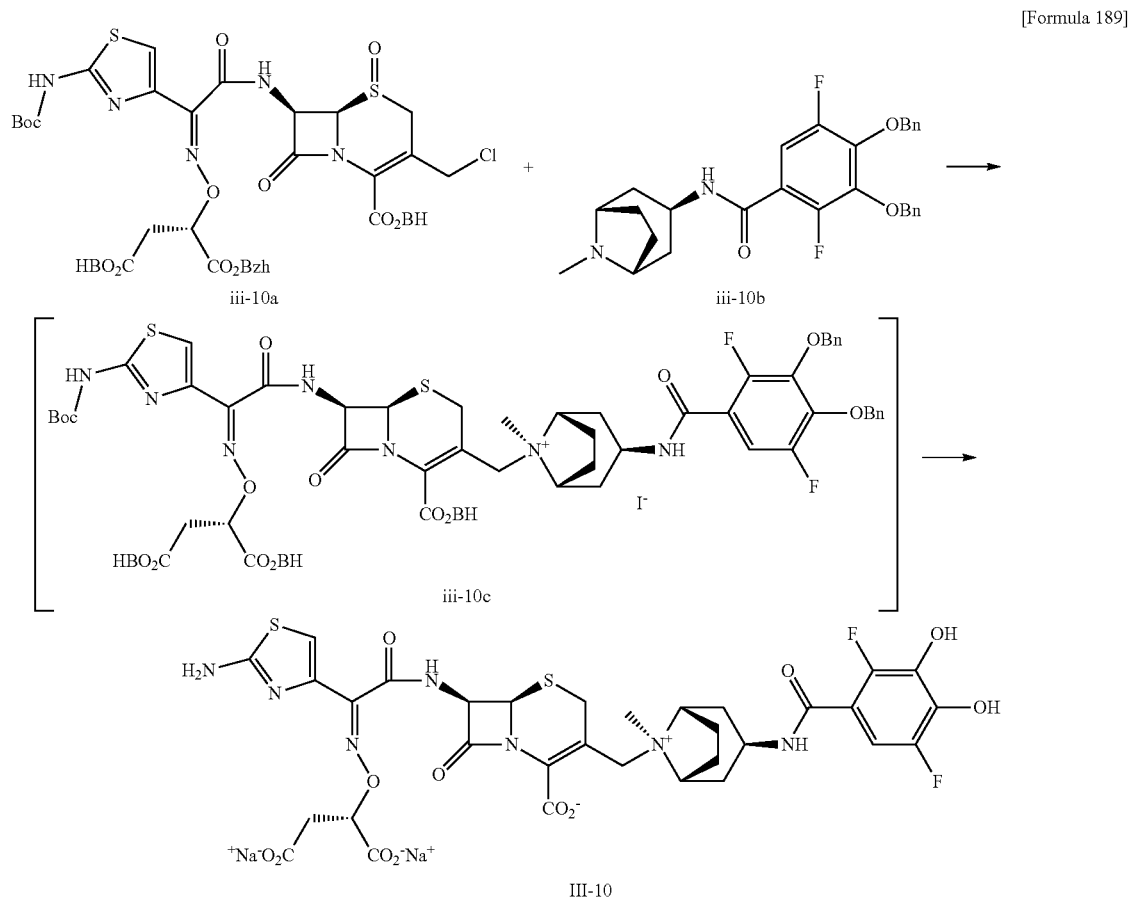

[Formula 189]

Step: Compound iii-10a+Compound iii-10b→Compound (III-10)

Compound iii-10a (1.01 g, 0.800 mmol) and compound iii-10b (402 mg, 0.816 mmol) were used to synthesize the target compound III-10 in the same way as described above.

Yielded amount: 545.2 mg, (62%)

$^1$H-NMR (D$_2$O) δ: 7.04-6.98 (2H, m), 5.84 (1H, d, J=4.87 Hz), 5.35 (1H, d, J=4.87 Hz), 5.01-4.95 (1H, m), 4.62 (1H, d, J=14.94 Hz), 4.26-3.90 (5H, m), 3.50 (1H, d, J=16.62 Hz), 3.10 (3H, br s), 2.80-2.70 (4H, m), 2.61-2.38 (4H, m), 2.21 (1H, br s), 2.15 (1H, br s).

Elem. Anal.: C32H31F2N7O12S2Na2(H2O)10.1 (NaHCO3)0.13

Calcd.: C, 36.87; H, 4.94; F, 3.63; N, 9.37; S, 6.13; Na, 4.68(%).

Found.: C, 36.75; H, 4.73; F, 3.36; N, 9.79; S, 6.56; Na, 4.69(%).

Example 144

Synthesis of Compound (III-11)

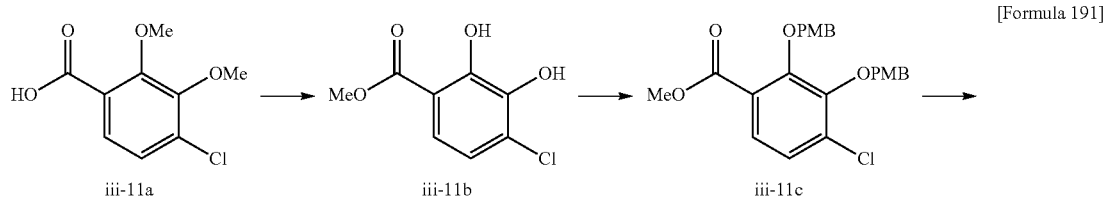

[Formula 191]

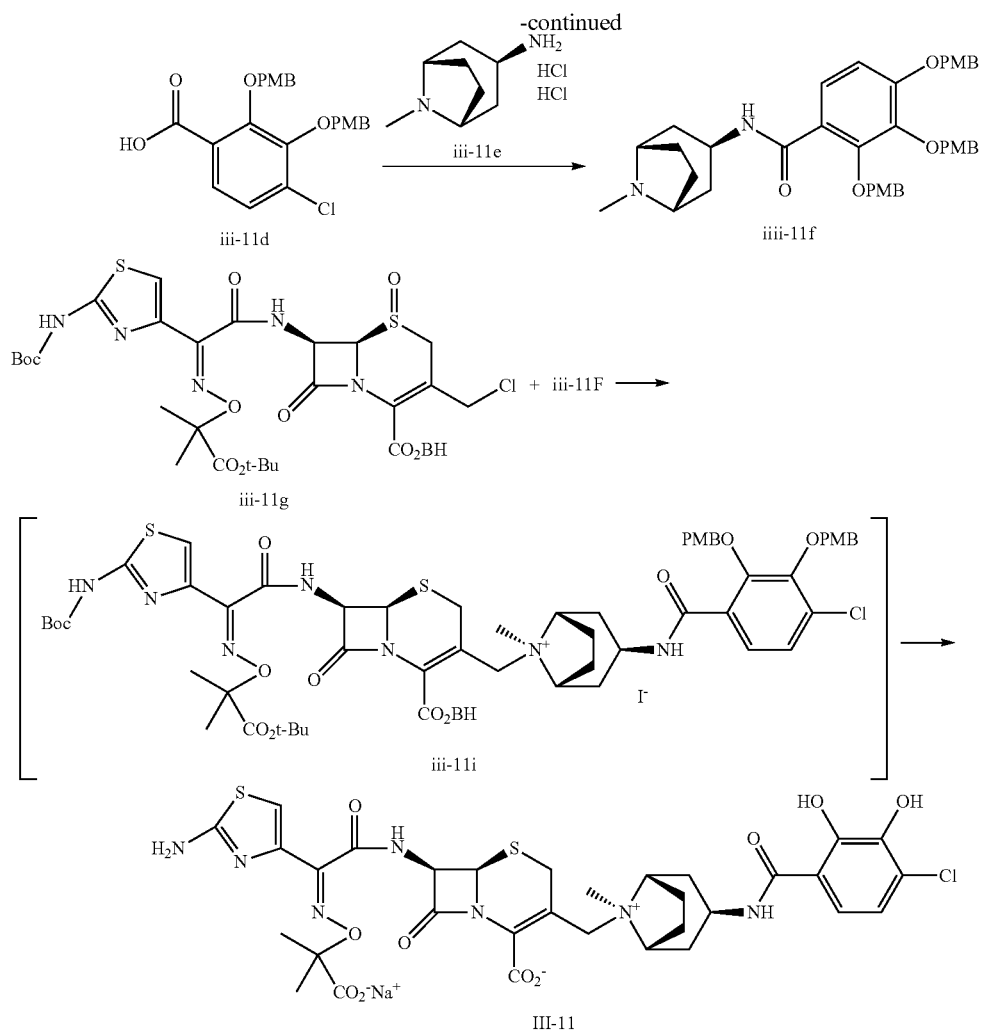

Step (1): Compound iii-11a→Compound iii-11b

Boron tribromide (25.0 g, 100 mmol) was added to a solution of compound iii-11a (3.68 g, 17.0 mmol, synthesized with reference to a method described in *J. Chem. Soc. Perkin trans.* 1, 1995, 1265-1271) in dichloromathane (60 mL) while cooled with ice. The resultant solution was stirred at room temperature for 2 hours. Thereto was added methanol (40 mL) while cooled at −78° C. The resultant was stirred at room temperature for 1 day, and then heated at refluxed for 3 hours. The reaction liquid was diluted with ethyl acetate, washed with a saturated salt solution, and dried over magnesium sulfate. Magnesium sulfate was filtrated off, and then the liquid was concentrated under reduced pressure to yield compound iii-11b (4.07 g, 118%). Compound iii-11b was used in the next reaction without being purified.

Step (2): Compound iii-11b→Compound iii-11c

The total amount of compound iii-11b was dissolved into N,N-dimethylformamide (40 mL), and thereto were then added potassium carbonate (7.04 g, 51.0 mmol), p-methoxybenzyl chloride (5.55 ml, 40.8 mmol) and sodium iodide (2.55 g, 17.0 mmol) in turn. The liquid was stirred at 70° C. for 2 hours. The reaction liquid was diluted with ethyl acetate, and the organic phase was washed with water and a saturated salt solution, and dried over magnesium sulfate. Magnesium sulfate was filtrated off. The organic phase was then concentrated under reduced pressure. The compound-containing liquid was subjected to silica gel column chromatography to elute out the desired compound with hexane/ethyl acetate. The desired-compound-containing fraction was concentrated under reduced pressure to yield compound iii-11c (0.72 g, 9.6%).

$^1$H-NMR (CDCl$_3$) δ: 7.34 (2H, d, J=8.73 Hz), 7.25 (2H, d, J=8.73 Hz), 7.05 (1H, d, J=8.90 Hz), 6.90-6.96 (3H, m), 6.83 (2H, d, J=8.73 Hz), 5.04 (2H, s), 4.99 (2H, s), 3.85 (3H, s), 3.83 (3H, s), 3.80 (3H, s).

Step (3): Compound iii-11c→Compound iii-11d

An 8 mol/l, aqueous sodium hydroxide solution (406 μl, 3.25 mmol) was added to a solution of compound iii-11c (0.72 g, 1.63 mmol) in tetrahydrofuran (3 mL) and methanol (2 mL). The resultant solution was stirred at 70° C. for 5 hours. To the reaction liquid was added a 2 mol/L, aqueous hydrochloric acid solution (4 mL), and the solution was concentrated under reduced pressure. The precipitated solid was then collected by filtration, and washed with water and diisopropyl ether to yield compound iii-11d (442 mg, 63%).

$^1$H-NMR (DMSO-d$_6$) δ: 7.43 (2H, d, J=8.39 Hz), 7.26-7.18 (4H, m), 6.97 (2H, d, J=8.39 Hz), 6.86 (2H, d, J=8.39 Hz), 5.13 (2H, s), 4.90 (2H, s), 3.77 (3H, s), 3.75 (3H, s)

Step (4): Compound iii-11e+Compound iii-11d→Compound iii-11f

Compound iii-11e (262 mg, 1.23 mmol) and compound iii-11d (410 mg, 1.03 mmol) were used to synthesize the target compound in the same way as described above.

Yielded amount: 600 mg, (106%)

$^1$H-NMR (DMSO-$d_6$) δ: 8.14 (1H, d, J=5.04 Hz), 7.42 (2H, d, J=8.73 Hz), 7.22-7.13 (4H, m), 6.97 (2H, d, J=8.56 Hz), 6.85 (2H, d, J=8.73 Hz), 5.11 (2H, s), 4.87 (2H, s), 3.86 (1H, q, J=6.13 Hz), 3.77 (3H, s), 3.74 (3H, s), 2.90 (2H, br s), 2.11 (3H, s), 2.04-1.72 (6H, m), 1.66 (14, br s), 1.61 (14, br s).

Step (5): Compound iii-11g+Compound iii-11f→Compound (III-11)

Compound iii-11g (398 mg, 0.500 mmol) and compound iii-11f (276 mg, 0.500 mmol) were used to synthesize the target compound III-11 in the some way as described above.

Yielded amount: 180.6 mg, (35%)

$^1$H-NMR (D$_2$O) δ: 6.99 (1H, s), 6.92 (1H, d, J=8.56 Hz), 6.86 (1H, d, J=8.56 Hz), 5.89 (1H, d, J=5.04 Hz), 5.38 (1H, d, J=5.04 Hz), 4.63 (1H, d, J=12.59 Hz), 4.29 (14, t, J=7.47 Hz), 4.09-3.94 (4H, m), 3.50 (1H, d, J=16.62 Hz), 3.11 (3H, s), 2.73-2.83 (2H, m), 2.50-2.36 (4H, m), 2.23 (1H, br s), 2.18 (14, br s), 1.52 (3H, s), 1.50 (3H, s).

Elem. Anal.: C32H35ClN7O10S2Na (H2O)8.3

Calcd.: C, 40.47; H, 5.48; Cl, 3.73; N, 10.32; S, 6.75; Na, 2.42(%).

Found.: C, 40.66; H, 5.50; Cl, 4.19; N, 9.97; S, 6.07; Na, 2.09(%).

Example 145

Synthesis of Compound (III-12)

[Formula 192]

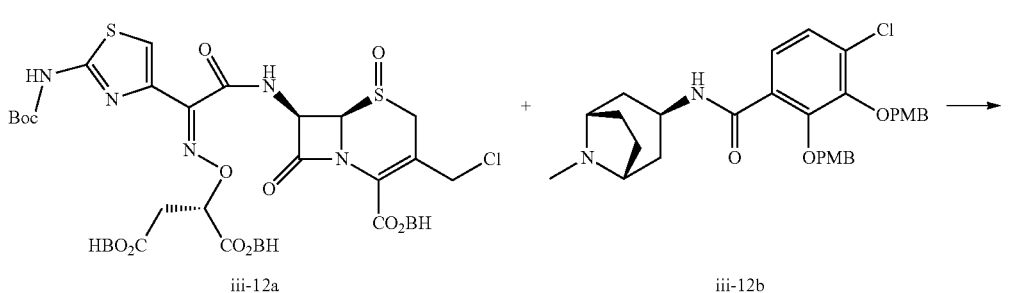

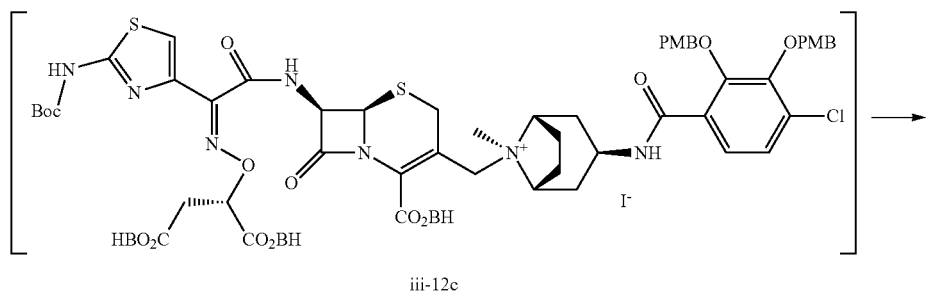

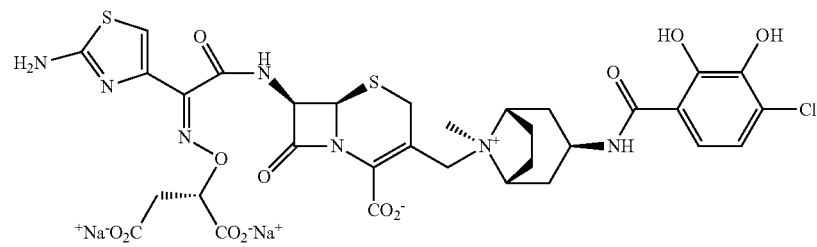

Step (1): Compound iii-12a+Compound iii-12b→Compound (III-12)

Compound iii-12a (631 mg, 0.500 mmol) and compound iii-12b (276 mg, 0.500 mmol) were used to synthesize the target compound III-12 in the same way as described above.

Yielded amount: 302 mg, (55%)

$^1$H-NMR (D$_2$O) δ: 7.02 (1H, s), 6.94 (1H, d, J=8.73 Hz), 6.90 (1H, d, J=8.73 Hz), 5.84 (1H, d, J=4.87 Hz), 5.34 (1H, d, J=4.87 Hz), 4.99-4.91 (1H, m), 4.61 (1H, d, J=14.44 Hz), 4.29 (1H, t, J=7.89 Hz), 4.10 (1H, d, J=14.27 Hz), 4.03 (1H, br s), 3.95-3.89 (2H, m), 3.50 (1H, d, J=16.79 Hz), 3.10 (3H, br s), 2.82-2.69 (4H, m), 2.54-2.35 (4H, m), 2.23 (1H, br s), 2.18 (1H, br s).

Elem. Anal.: C32H32.1ClN7O12S2Na1.9(H2O)10.8

Calcd.: C, 36.79; H, 5.18; Cl, 3.39; N, 9.39; S, 6.14; Na, 4.18(%).

Found.: C, 36.69; H, 4.98; Cl, 3.54; N, 9.42; S, 6.12; Na, 4.11(%)

Example 146

Synthesis of Compound (III-13)

[Formula 192]

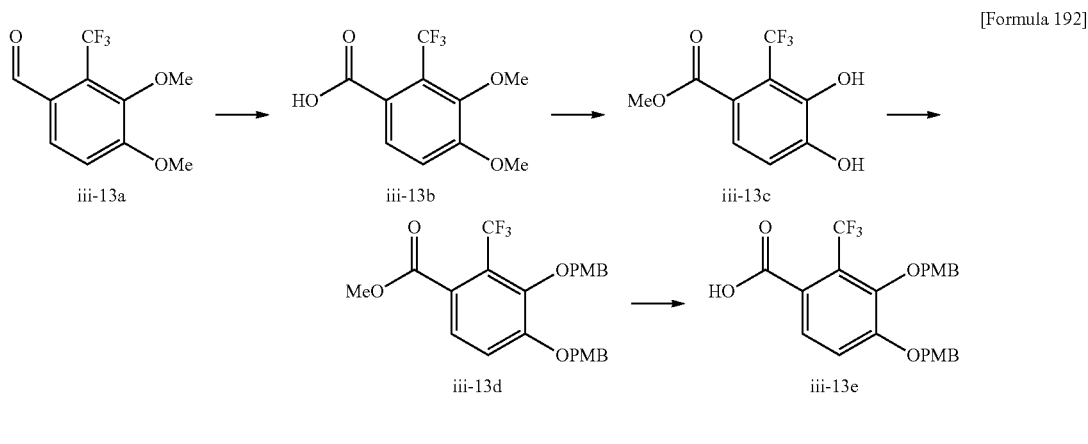

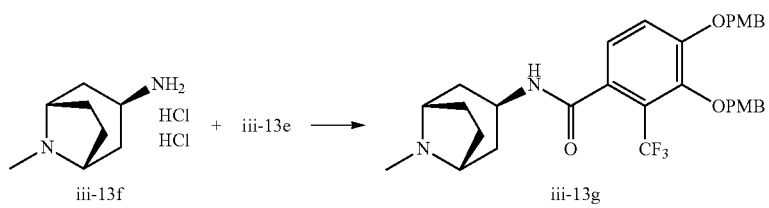

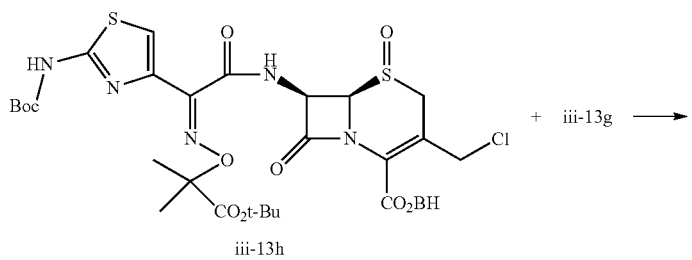

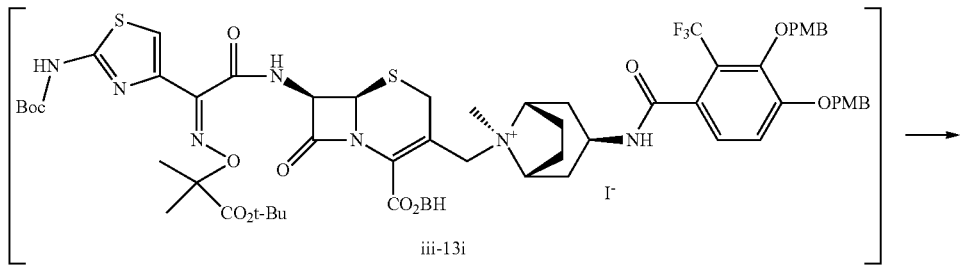

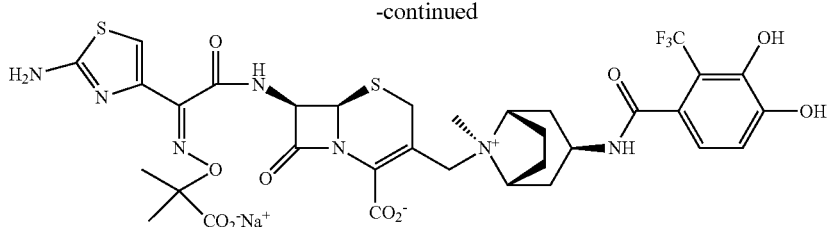

III-13

Step (1): Compound iii-13a→Compound iii-13b

Amide sulfuric acid (8.53 g, 88 mmol) and water (60 mL) were added to a solution of compound iii-13a (5.88 g, 25.1 mmol, synthesized with reference to a method described in *J. Med. Chem.*, 1992, 35, 466-479) in methanol (80 mL). The resultant solution was stirred while cooled with ice. To the solution was added sodium chlorite (7.95 g, 88 mmol). While cooled with ice, the solution was stirred for 2 hour, and then thereto was dropwise added a solution of sodium hydrogensulfite (13.06 g, 126 mural) in water (100 mL). The precipitated solid was then collected by filtration, and washed with water to yield compound iii-13b (5.33 g, 85%).

$^1$H-NMR (DMSO-$d_6$) δ: 7.38 (1H, d, J=8.56 Hz), 7.30 (1H, d; J=8.56 Hz), 3.90 (3H, s), 3.82 (3H, s).

Step (2): Compound iii-13b→Compound iii-13c

Compound iii-13b (5.00 g, 20.0 mmol) was used to synthesize the target compound iii-13c in the same way as described above.

Yielded amount: 5.71 g, (121%)

Step (3): Compound iii-13c→Compound iii-13d

The total amount of compound iii-13c was used to synthesize the target compound iii-13d in the same way as described above.

Yielded amount: 8.03 g, (84%)

$^1$H-NMR (CDCl$_3$) δ: 7.36 (2H, d, J=8.56 Hz), 7.27 (2H, d, J=8.56 Hz), 7.23 (11H, d, J=8.56 Hz), 7.15 (1H, d, J=8.56 Hz), 6.93 (24, d, J=8.56 Hz), 6.82 (2H, d, J=8.56 Hz), 5.10 (2H, s), 4.98 (2H, s), 3.88 (3H, s), 3.84 (3H, s), 3.80 (3H, s).

Step (4): Compound iii-13d→Compound iii-13e

Compound iii-13d (8.00 g, 16.8 mmol) was used to synthesize the target compound iii-13e in the same way as described above.

Yielded amount: 7.35 g, (95%)

$^1$H-NMR (DMSO-$d_6$) δ: 7.53 (1H, d, J=8.56 Hz), 7.47 (2H, d, J=8.39 Hz), 7.31 (1H, d, J=8.56 Hz), 7.21 (2H, d, J=8.39 Hz), 6.99 (24, d, J=8.39 Hz), 6.85 (2H, d, J=8.39 Hz), 5.20 (2H, s), 4.94 (2H, s), 3.78 (3H, s); 3.74 (3H, s).

Step (5): Compound iii-13f+Compound iii-13e→Compound iii-13g

Compound iii-13f (1.28 g, 6.00 mmol) and compound iii-13e (2.31 g, 5.00 mmol) were used to synthesize the target compound in the same way as described above. Thereto was added diisopropyl ether to precipitate a solid. The solid was collected by filtration, so as to yield compound iii-13g (2.73 g, 93%).

$^1$H-NMR (DMSO-$d_6$) δ: 8.15 (1H, d, J=4.58 Hz), 7.50 (1H, d, J=8.46 Hz), 7.45 (2H, d, J=8.69 Hz), 7.24 (2H, d, J=8.69 Hz), 7.05 (1H, d, J=8.46 Hz), 6.98 (2H, d, J=8.69 Hz), 6.87 (2H, d, J=8.69 Hz), 5.20 (2H, s), 4.92 (2H, s), 3.81 (1H, q, J=6.33 Hz), 3.77 (3H, s), 3.75 (3H, s), 3.07 (2H, br s), 2.20 (3H, s), 2.00-2.09 (2H, m), 1.91 (4H, br s), 1.71 (1H, br, 1.66 (1H, br s).

Step (6): Compound iii-13h+Compound iii-13g→Compound (III-13)

Compound iii-13h (796 mg, 1.000 mmol) and compound iii-13g (643 mg, 1.100 mmol) were used to synthesize the target compound III-13 in the same way as described above.

Yielded amount: 243.5 mg, (23%)

$^1$H-NMR (D$_2$O) δ: 7.06 (1H, d, J=8.39 Hz), 6.98 (1H, s), 6.78 (1H, d, J=8.39 Hz), 5.89 (1H, d, J=4.88 Hz), 5.37 (1H, d, J=4.88 Hz), 4.62 (1H, d, J=13.88 Hz), 4.21 (1H, t, J=7.89 Hz), 4.09-3.93 (4H, m), 3.50 (1H, d, J=16.62 Hz), 3.10 (3H, br s), 2.82-2.71 (2H, m), 2.54-2.35 (4H, m), 2.17 (1H, br s), 2.11 (1H, br s), 1.52 (3H, s), 1.50 (3H, s).

Elem. Anal.: C33H35F3N7O10S2Na (H2O)7.6

Calcd.: C, 40.83; H, 5.21; F, 5.87; N, 10.10; S, 6.61; Na, 2.37(%).

Found.: C, 40.92; H, 5.15; F, 5.37; N, 10.08; S, 6.50; Na, 2.41(%).

Example 147

Synthesis of Compound (III-14)

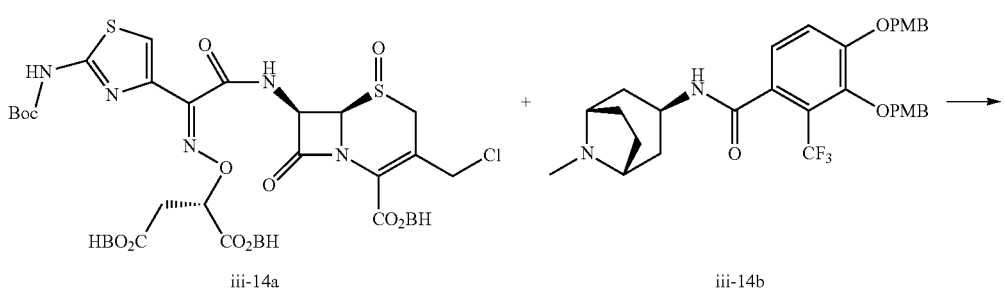

[Formula 193]

iii-14a          iii-14b

-continued

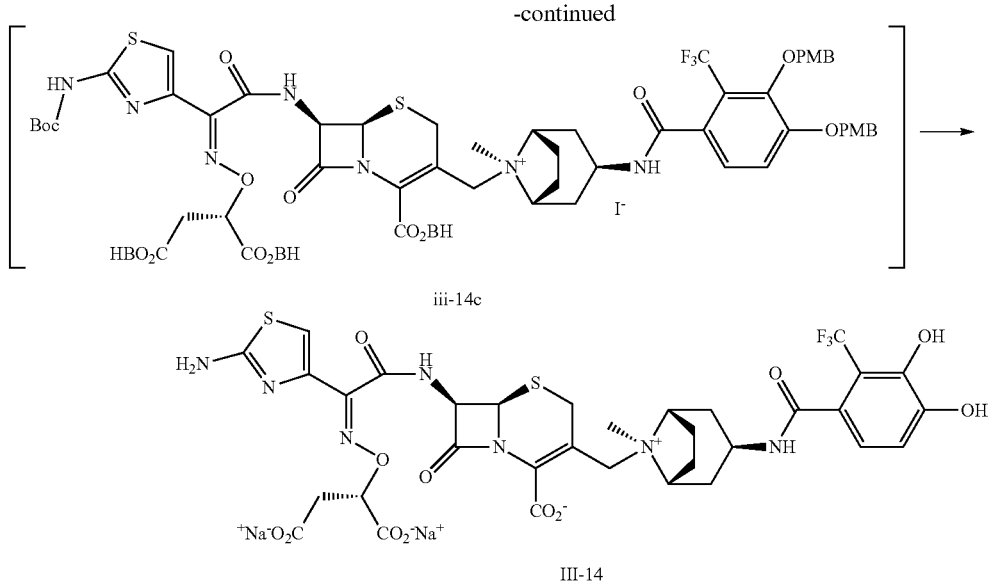

iii-14c

III-14

Step: Compound iii-14a+Compound iii-14b→Compound (III-14)

Compound iii-14a (1.26 g, 1.00 mmol) and compound iii-14b (643 mg, 1.100 mmol) were used to synthesize the target compound III-14 in the same way as described above.

Yielded amount: 312 mg, (27%)

$^1$H-NMR (D$_2$O) δ: 7.09 (1H, d, J=7.85 Hz), 7.01 (1H, s), 6.84 (1H, d, J=7.85 Hz), 5.84 (1H, d, J=4.42 Hz), 5.34 (1H, d, J=4.42 Hz), 4.99-4.93 (1H, m), 4.61 (1H, d, J=15.56 Hz), 4.22 (1H, t, J=8.31 Hz), 4.10 (1H, d, J=13.27 Hz), 4.03 (1H, br s), 3.96-3.89 (2H, m), 3.49 (1H, d, J=18.30 Hz), 3.10 (3H, br s), 2.81-2.70 (4H, m), 2.56-2.23 (4H, m), 2.17 (1H, br s), 2.11 (1H, br s).

Elem. Anal.: C33H32.4F3N7O12S2Na1.6(H2O)7.9

Calcd.: C, 38.89; H, 4.77; F, 5.59; N, 9.62; S, 6.29; Na, 3.61(%).

Found.: C, 38.92; H, 4.68; F, 5.61; N, 9.52; S, 6.16; Na, 3.62(%).

Example 148

Synthesis of Compound (III-15)

[Formula 194]

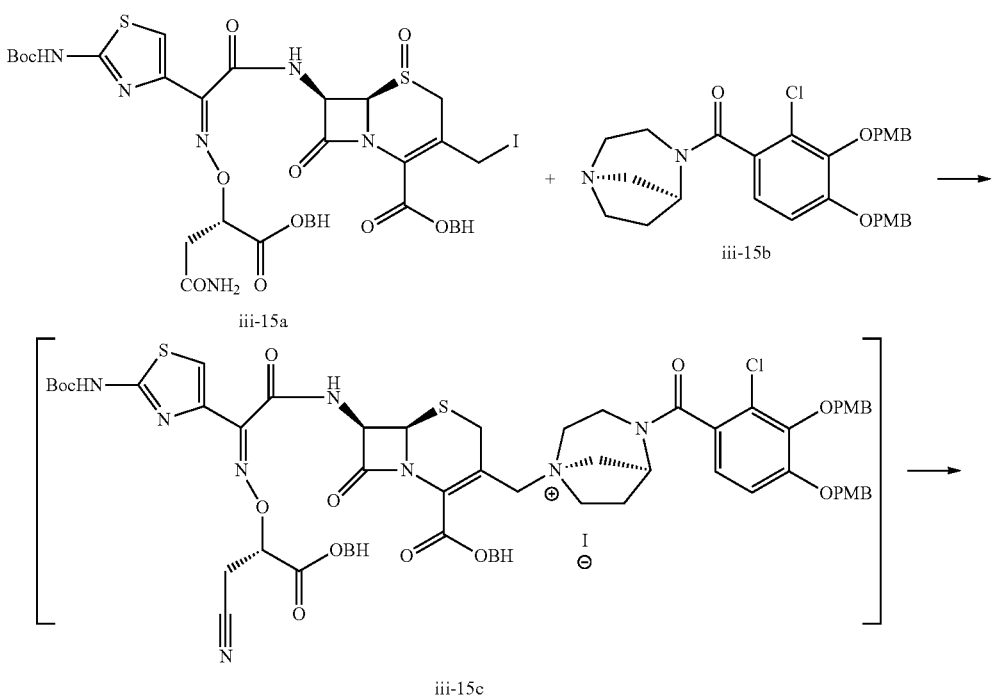

iii-15a iii-15b iii-15c

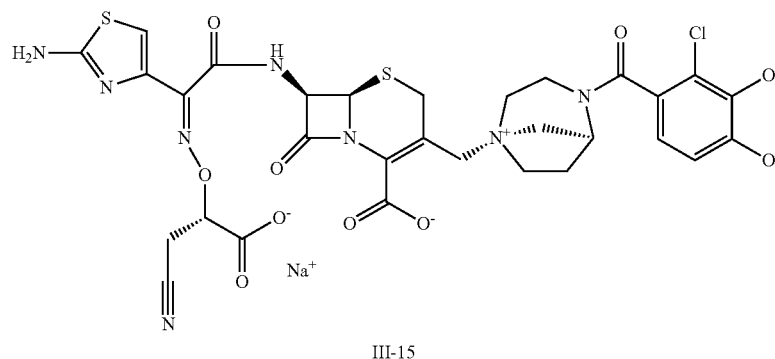

III-15

Step (1): Compound iii-15a→Compound iii-15c

To a solution of Compound iii-15a (32.99 g, 30.3 mmol) in N,N-dimethylacetoamide (99mL) was added sodium iodide (9.07 g, 60.7 mmol), and the reaction mixture was stirred for at room temperature 5 minutes. The reaction solution was cooled at 0° C., and then compound iii-15b (15.8 g, 30.3 mmol) was added dropwise thereto for an hour, and sodium hydrogen carbonate (10.2 g, 121 mmol) was added thereto and the reaction mixture was stirred for an hour at 15° C. After the reaction was completed, to the reaction mixture was added N,N-dimethylformamide (200 mL) and the mixture was cooled at −40° C., and added phosphorus tribromide (5.71 ml, 60.5 mmol) and stirred for an hour. The reaction solution was added pre-cooled 5% sodium hydrogen sulfite aqueous solution (3 L) and then filtered, washed with water, and air-dried.

Step (2): Compound iii-15c→Compound (III-15)

To a solution of compound iii-15c (1.95 g, 1 mmol) in methylene chloride (10 mL) was added anisole (1.0 mL, 10 mmol) and the mixture was cooled at −40'C. To the reaction mixture was added 2 mol/L aluminum chloride in nitromethane (5 mL) and stirred for 50 minutes at 0° C. To the reaction solution was added 2 mol/L hydrochloride acid solution (60mL), acetonitrile (50mL), and diethyl ether (100 mL). The aqueous layer was washed with diethyl ether, and concentrated under reduced pressure, and then the residue was purified by HP20SS column chromatography and eluted with acetonitrile-water. The intended fractions were collected, and 0.2 mol/L solution of sodium hydroxide was added thereto to adjust them to pH=6, and thereby a sodium salt thereof was formed. Concentrating in vacuo and subsequent lyophilization yielded Compound III-15 as a white amorphous powder.

Yield: 57.8 mg, (7.4%)

$^1$H-NMR (D$_2$O) δ: 2.20-4.80 (15.5H, m), 5.33-5.37 (1H, m), 5.45-5.60 (0.5H, m), 5.85-5.88 (1H, m), 6.75-6.76 (1H, m), 6.90-6.93 (1H, m), 7.07 (1H, s)

Elemental analysis: C30H29N8ClN8O10S2Na (H2O)5.8 (NaHCO3)0.2

Calculated value: C, 40.06; H, 4.54; Cl, 3.92; N, 12.38; S, 7.08; Na, 3.05(%).

Experimental value: C, 39.95; H, 4.27; Cl, 4.20; N, 12.41; S, 7.00; Na, 3.28(%).

Example 149

Synthesis of Compound (III-16)

[Formula 195]

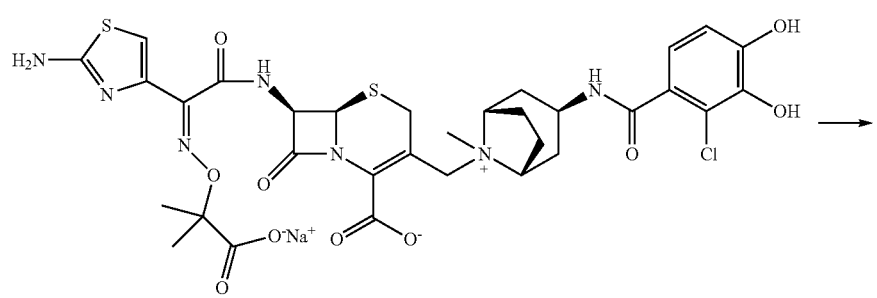

III-16 crude

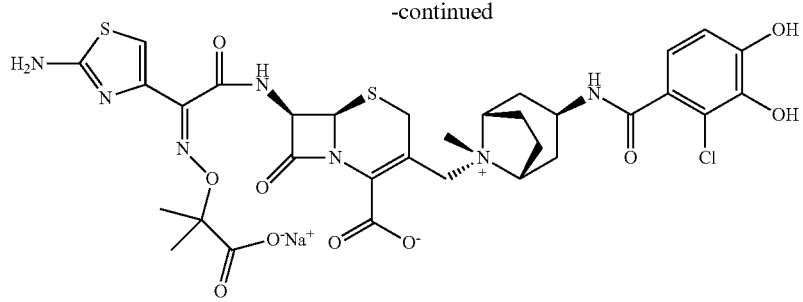

III-16

A mixture at the ratio of nine to one, containing Compound III-16 as a minor component, was purified by reversed-phase HPLC and lyophilized to obtain Compound III-16 (9 mg).

$^1$H-NMR (D$_2$O) δ: 1.51 (3H, s), 1.53 (3H, s), 2.18-2.48 (8H, m), 2.96 (1H, s), 3.51 (1H, d, J=16.5 Hz), 3.86-4.02 (3H, m), 4.25 (1H, m), 4.47 (1H, d, J=14.1 Hz), 4.57 (1H, d, J=14.1 Hz), 5.35 (1H, d, J=4.5 Hz), 5.89 (1H, d, J=4.5 Hz), 6.69 (1H, d, J=8.4 Hz), 6.73 (1H, d, J=8.4 Hz), 6.99 (1H, s).

The present invention include the compounds of the formula (I-A), (I-B), and (I-C) having the combination of K, -E-D- and Cy selected from K1 to K29, ED1 to ED92, and Cy1 to Cy3 as shoo in the following Table 1 to Table 9.

[Formula 196]

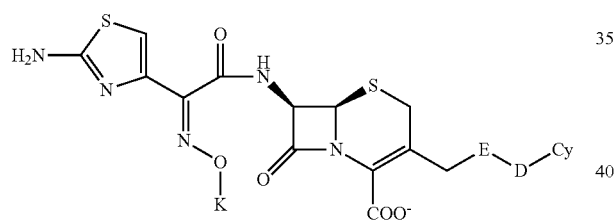

(I-A)

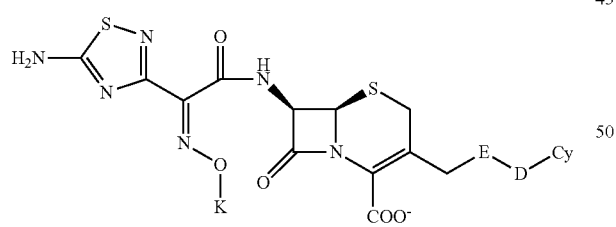

(I-B)

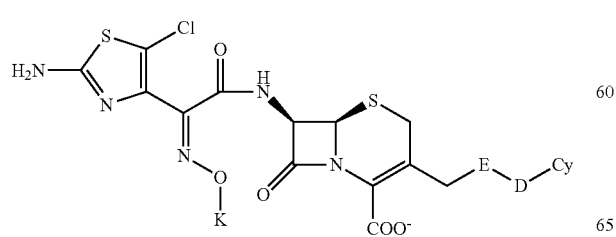

(I-C)

TABLE 1

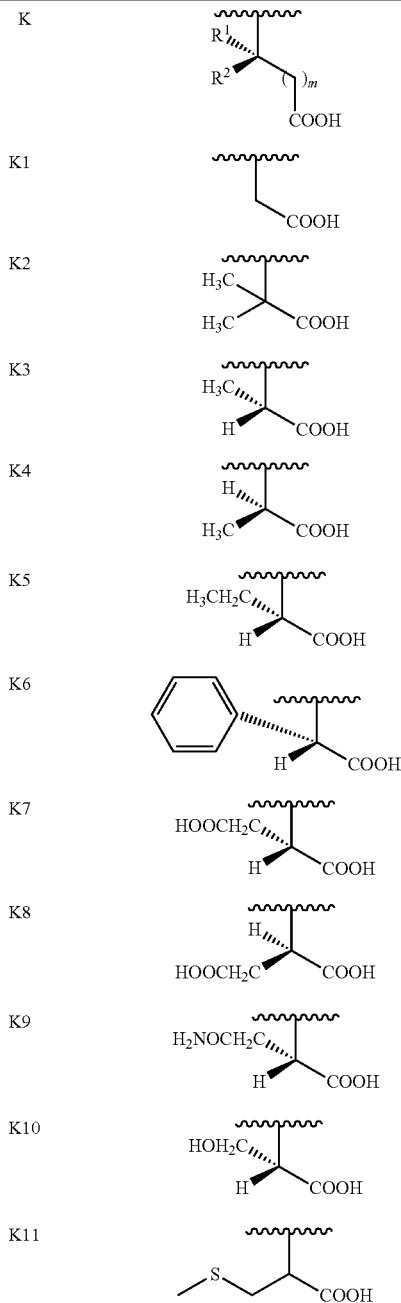

TABLE 1-continued

| | |
|---|---|
| K12 | cyclopropyl-COOH |
| K13 | cyclobutyl-COOH |
| K14 | cyclopentyl-COOH |
| K15 | cyclohexyl-COOH |
| K16 | cyclopentenyl-COOH |
| K17 | (CH$_3$)$_2$CH-CH$_2$-COOH (neopentyl type with COOH) |
| K18 | -(CH$_2$)$_3$-COOH |
| K19 | H$_3$C-CH(-)-CH$_2$-COOH |
| K20 | -CH(CH$_2$COOH)(CH$_2$COOH) |
| K21 | HOOC-CH$_2$-CH$_2$-CH(-)-COOH |
| K22 | CH$_3$O-CH$_2$-CH(-)-COOH |

TABLE 2

| | |
|---|---|
| K23 | H$_2$NOC-CH$_2$-CH$_2$-CH(-)-COOH |
| K24 | HOOC-CH(-)-COOH |
| K25 | HO-CH(CH$_3$)-CH(-)-COOH |
| K26 | FH$_2$C-CH(-)-COOH |
| K27 | F$_3$C-CH(-)-COOH |
| K28 | benzyl-CH(-)-COOH |
| K29 | (4-hydroxybenzyl)-CH(-)-COOH |

TABLE 3

—E—D—

| | |
|---|---|
| ED1 | bicyclic diazabicyclooctane with N-methyl quaternary |
| ED2 | bicyclic diazabicycloheptane quaternary N |
| ED3 | bicyclic diazabicyclo quaternary N |

TABLE 3-continued

—E—D—

| | |
|---|---|
| ED4 | (structure) |
| ED5 | (structure) |
| ED6 | (structure) |
| ED7 | (structure) |
| ED8 | (structure) |
| ED9 | (structure) |
| ED10 | (structure) |
| ED11 | (structure) |

TABLE 3-continued

—E—D—

| | |
|---|---|
| ED12 | (structure) |
| ED13 | (structure) |
| ED14 | (structure) |
| ED15 | (structure) |
| ED16 | (structure) |
| ED17 | (structure) |
| ED18 | (structure) |

| | | | |
|---|---|---|---|
| ED19 | 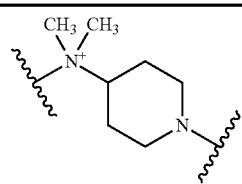 | ED28 | 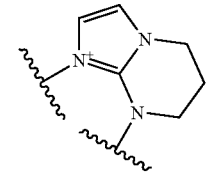 [SMILES: *N1CCCn2cc[n+](*)c21] |
| ED20 | 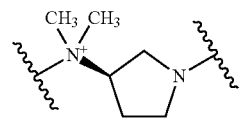 | ED29 | 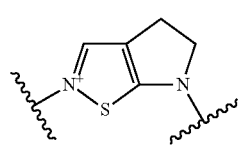 [SMILES: *N1CCc2c[n+](*)sc21] |
| ED21 | 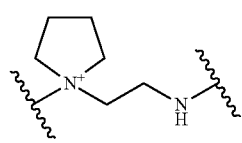 | ED30 | 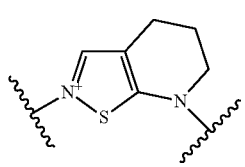 [SMILES: *N1CCCc2c[n+](*)sc21] |
| ED22 | 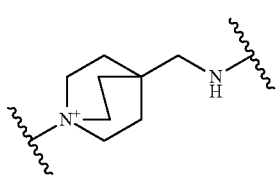 | ED31 | 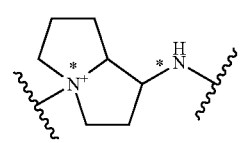 [SMILES: *NC1CC[N+]2(*)CCCC12] |
| ED23 | 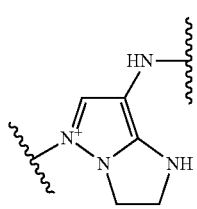 | ED32 | 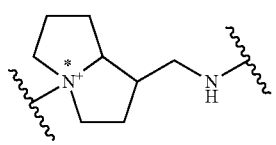 [SMILES: *NCC1CC[N+]2(*)CCCC12] |
| ED24 | 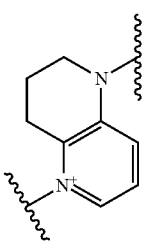 | ED33 | 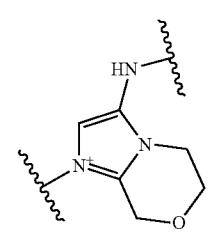 [SMILES: *Nc1c[n+](*)c2n1CCOC2] |
| ED25 | 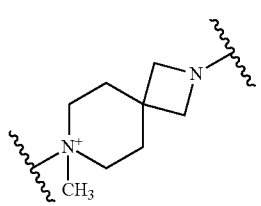 | ED34 | 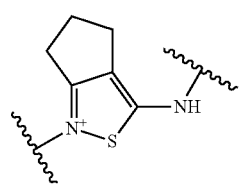 [SMILES: *Nc1s[n+](*)c2c1CCC2] |
| ED26 | 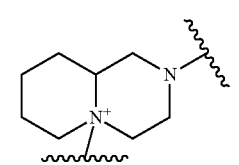 | ED35 | 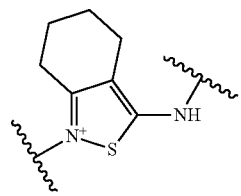 [SMILES: *Nc1s[n+](*)c2c1CCCC2] |
| ED27 | 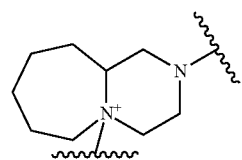 | | |

TABLE 4-continued
| | |
|---|---|
| ED36 | 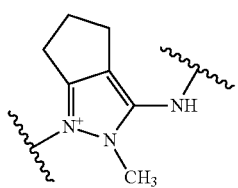 [SMILES: *Nc1c2c([n+](*)n1C)CCC2] |
TABLE 5
| | |
|---|---|
| ED37 | 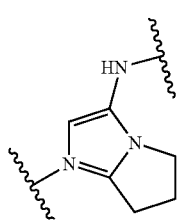 |
| ED38 | 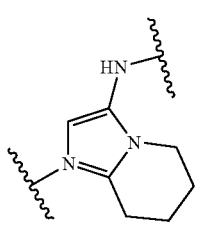 |
| ED39 | 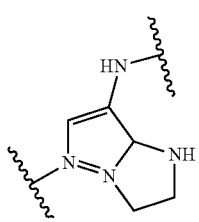 |
| ED40 | 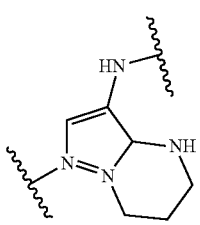 |
| ED41 | 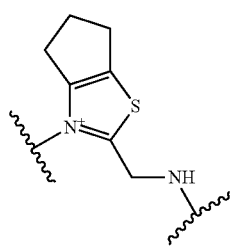 [SMILES: *NCc1sc2c([n+]1*)CCC2] |
TABLE 5-continued
| | |
|---|---|
| ED42 | 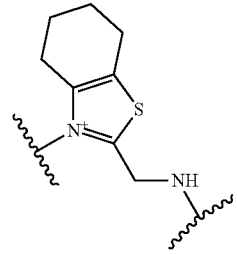 [SMILES: *NCc1sc2c([n+]1*)CCCC2] |
| ED43 | 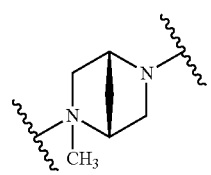 |
| ED44 | 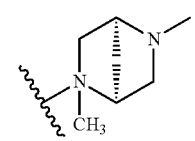 |
| ED45 | 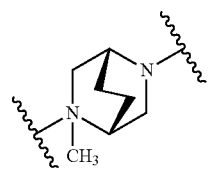 |
| ED46 | 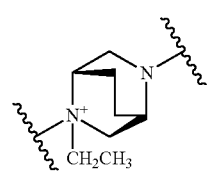 |
| ED47 | 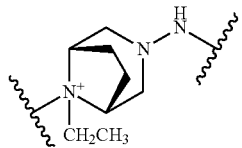 [SMILES: *NN1C[C@H]2CC[C@@H](C1)[N+]2(*)CC] |
| ED48 | 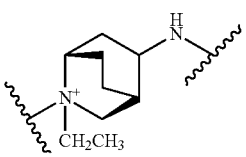 |
| ED49 | 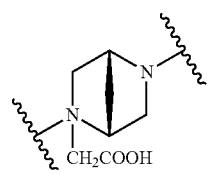 |

| | | | |
|---|---|---|---|
| ED50 | 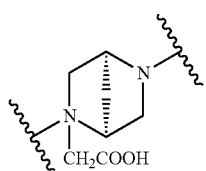 | ED58 | 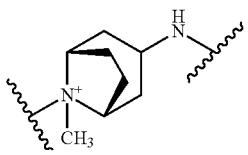 |
| ED51 | 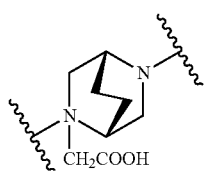 | ED59 | 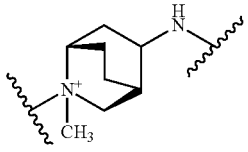 |
| ED52 | 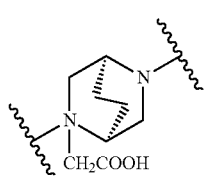 | ED60 | 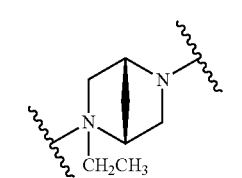 |
| ED53 | 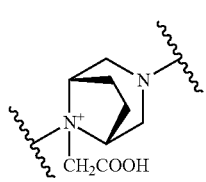 | ED61 | 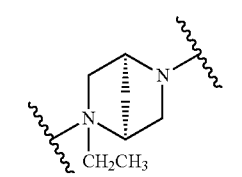 |
| ED54 | 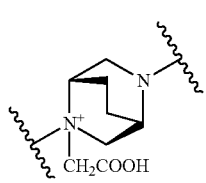 | ED62 | 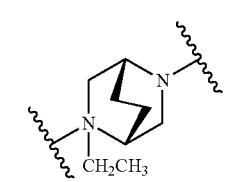 |
| | | ED63 | 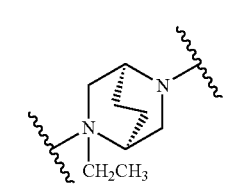 |
TABLE 5-continued
TABLE 6
TABLE 6-continued
| | | | |
|---|---|---|---|
| ED55 | 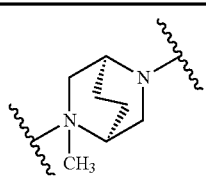 | ED64 | 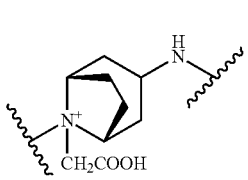 |
| ED56 | 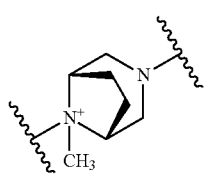 | ED65 | 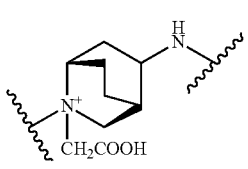 |
| ED57 | 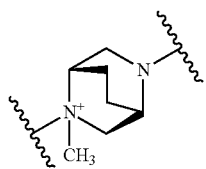 | ED66 | 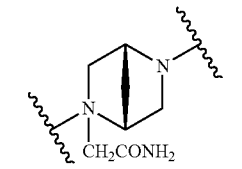 |

TABLE 6-continued

| ED67 | structure with CH₂CONH₂ |
| ED68 | structure with CH₂CONH₂ |
| ED69 | structure with CH₂CONH₂ |
| ED70 | structure with N⁺ and CH₂CONH₂ |
| ED71 | structure with N⁺ and CH₂CONH₂ |
| ED72 | structure with N⁺ and CH₂CONH₂ |

TABLE 7

| ED73 | structure with CH₂CH₂OH |
| ED74 | structure with CH₂CH₂OH |
| ED75 | structure with CH₂CH₂OH |
| ED76 | structure with CH₂CH₂OH |
| ED77 | structure with N⁺ and CH₂CH₂OH |
| ED78 | structure with N⁺ and CH₂CH₂OH |
| ED79 | structure with N⁺ and CH₂CH₂OH |
| ED80 | structure with N⁺ and CH₂CH₂OH |
| ED81 | imidazo-piperazine structure |
| ED82 | tetrahydroindazole structure with CH₃ |
| ED83 | structure with N⁺ and CH₂CH₃ |

TABLE 7-continued

ED84 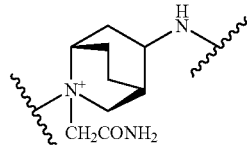

ED85 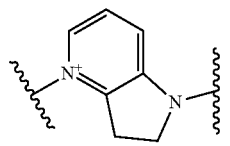 [SMILES: *N1CCc2c1ccc[n+]2*]

ED86 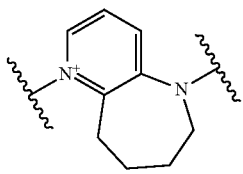 [SMILES: *N1CCCCc2c1ccc[n+]2*]

ED87 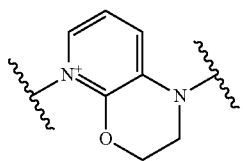 [SMILES: *N1CCOc2c1ccc[n+]2*]

ED88 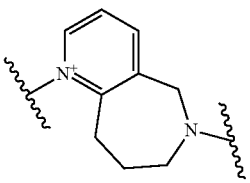 [SMILES: *N1CCCc2c(ccc[n+]2*)C1]

ED89 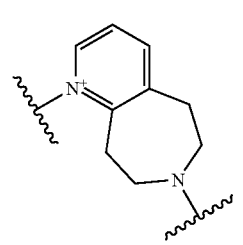 [SMILES: *N1CCc2ccc[n+](*)c2CC1]

ED90 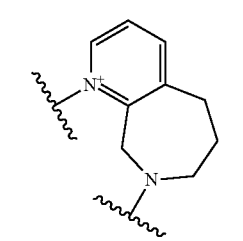 [SMILES: *N1CCCc2ccc[n+](*)c2C1]

TABLE 8

ED91 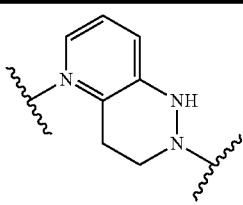

TABLE 8-continued

ED92 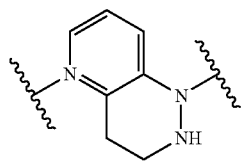

TABLE 9

Cy 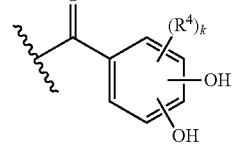

Cy1 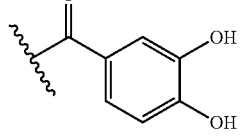

Cy2 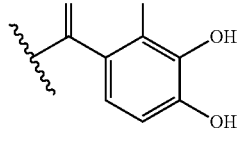

Cy3 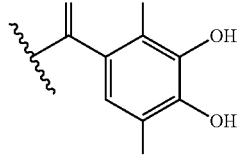

(K, ED, Cy)=(K1, ED1, Cy1), (K1, ED1, Cy2), (K1, ED1, Cy3), (K1, ED2, Cy1), (K1, ED2, Cy2), (K1, ED2, Cy3), (K1, ED3, Cy1), (K1, ED3, Cy2), (K1, ED3, Cy3), (K1, ED4, Cy1), (K1, ED4, Cy2), (K1, ED4, Cy3), (K1, ED5, Cy1), (K1, ED5, Cy2), (K1, ED5, Cy3), (K1, ED6, Cy1), (K1, ED6, Cy2), (K1, ED6, Cy3), (K1, ED7, Cy1), (K1, ED7, Cy2), (K1, ED7, Cy3), (K1, ED8, Cy1), (K1, ED8, Cy2), (K1, ED8, Cy3), (K1, ED9, Cy1), (K1, ED9, Cy2), (K1, ED9, Cy3), (K1, ED10, Cy1), (K1, ED10, Cy2), (K1, ED10, Cy3), (K1, ED11, Cy1), (K1, ED11, Cy2), (K1, ED11, Cy3), (K1, ED12, Cy1), (K1, ED12, Cy2), (K1, ED12, Cy3), (K1, ED13, Cy1), (K1, ED13, Cy2), (K1, ED13, Cy3), (K1, ED14, Cy1), (K1, ED14, Cy2), (K1, ED14, Cy3), (K1, ED15, Cy1), (K1, ED15, Cy2), (K1, ED15, Cy3), (K1, ED16, Cy1), (K1, ED16, Cy2), (K1, ED16, Cy3), (K1, ED17, Cy1), (K1, ED17, Cy2), (K1, ED17, Cy3), (K1, ED18, Cy1), (K1, ED18, Cy2), (K1, ED18, Cy3), (K1, ED19, Cy1), (K1, ED19, Cy2), (K1, ED19, Cy3), (K1, ED20, Cy1), (K1, ED20, Cy2), (K1, ED20, Cy3), (K1, ED21, Cy1), (K1, ED21, Cy2), (K1, ED21, Cy3), (K1, ED22, Cy1), (K1, ED22, Cy2), (K1, ED22, Cy3), (K1, ED23, Cy1), (K1, ED23, Cy2), (K1, ED23, Cy3), (K1, ED24, Cy1), (K1, ED24, Cy2), (K1, ED24, Cy3), (K1, ED25, Cy1), (K1, ED25, Cy2), (K1, ED25, Cy3), (K1, ED26, Cy1), (K1, ED24, Cy2), (K1, ED26, Cy3), (K1, ED27, Cy1), (K1, ED27, Cy2), (K1, ED27, Cy3), (K1, ED28, Cy1), (K1, ED28, Cy2), (K1, ED28, Cy3), (K1, ED29, Cy1), (K1, ED29, Cy2), (K1, ED29, Cy3), (K1,

ED30, Cy1), (K1, ED30, Cy2), (K1, ED30, Cy3), (K1, ED31, Cy1), (K1, ED31, Cy2), (K1, ED31, Cy3), (K1, ED32, Cy1), (K1, ED32, Cy2), (K1, ED32, Cy3), (K1, ED33, Cy1), (K1, ED33, Cy2), (K1, ED33, Cy3), (K1, ED34, Cy1), (K1, ED34, Cy2), (K1, ED34, Cy3), (K1, ED35, Cy1), (K1, ED35, Cy2), (K1, ED35, Cy3), (K1, ED36, Cy1), (K1, ED36, Cy2), (K1, ED36, Cy3), (K1, ED37, Cy1), (K1, ED37, Cy2), (K1, ED37, Cy3), (K1, ED38, Cy1), (K1, ED38, Cy2), (K1, ED38, Cy3), (K1, ED39, Cy1), (K1, ED39, Cy2), (K1, ED39, Cy3), (K1, ED40, Cy1), (K1, ED40, Cy2), (K1, ED40, Cy3), (K1, ED41, Cy1), (K1, ED41, Cy2), (K1, ED41, Cy3), (K1, ED42, Cy1), (K1, ED42, Cy2), (K1, ED42, Cy3), (K1, ED43, Cy1), (K1, ED43, Cy2), (K1, ED43, Cy3), (K1, ED44, Cy1), (K1, ED44, Cy2), (K1, ED44, Cy3), (K1, ED45, Cy1), (K1, ED45, Cy2), (K1, ED45, Cy3), (K1, ED46, Cy1), (K1, ED46, Cy2), (K1, ED46, Cy3), (K1, ED47, Cy1), (K1, ED47, Cy2), (K1, ED47, Cy3), (K1, ED48, Cy1), (K1, ED48, Cy2), (K1, ED48, Cy3), (K1, ED49, Cy1), (K1, ED49, Cy2), (K1, ED49, Cy3), (K1, ED50, Cy1), (K1, ED50, Cy2), (K1, ED50, Cy3), (K1, ED51, Cy1), (K1, ED51, Cy2), (K1, ED51, Cy3), (K1, ED52, Cy1), (K1, ED52, Cy2), (K1, ED52, Cy3), (K1, ED53, Cy1), (K1, ED53, Cy2), (K1, ED53, Cy3), (K1, ED54, Cy1), (K1, ED54, Cy2), (K1, ED54, Cy3), (K1, ED55, Cy1), (K1, ED55, Cy2), (K1, ED55, Cy3), (K1, ED56, Cy1), (K1, ED56, Cy2), (K1, ED56, Cy3), (K1, ED57, Cy1), (K1, ED57, Cy2), (K1, ED57, Cy3), (K1, ED58, Cy1), (K1, ED58, Cy2), (K1, ED58, Cy3), (K1, ED59, Cy1), (K1, ED59, Cy2), (K1, ED59, Cy3), (K1, ED60, Cy1), (K1, ED60, Cy2), (K1, ED60, Cy3), (K1, ED61, Cy1), (K1, ED61, Cy2), (K1, ED61, Cy3), (K1, ED62, Cy1), (K1, ED62, Cy2), (K1, ED62, Cy3), (K1, ED63, Cy1), (K1, ED63, Cy2), (K1, ED63, Cy3), (K1, ED64, Cy1), (K1, ED64, Cy2), (K1, ED64, Cy3), (K1, ED65, Cy1), (K1, ED65, Cy2), (K1, ED65, Cy3), (K1, ED66, Cy1), (K1, ED66, Cy2), (K1, ED66, Cy3), (K1, ED67, Cy1), (K1, ED67, Cy2), (K1, ED67, Cy3), (K1, ED68, Cy1), (K1, ED68, Cy2), (K1, ED68, Cy3), (K1, ED69, Cy1), (K1, ED69, Cy2), (K1, ED69, Cy3), (K1, ED70, Cy1), (K1, ED70, Cy2), (K1, ED70, Cy3), (K1, ED71, Cy1), (K1, ED71, Cy2), (K1, ED71, Cy3), (K1, ED72, Cy1), (K1, ED72, Cy2), (K1, ED72, Cy3), (K1, ED73, Cy1), (K1, ED73, Cy2), (K1, ED73, Cy3), (K1, ED74, Cy1), (K1, ED74, Cy2), (K1, ED74, Cy3), (K1, ED75, Cy1), (K1, ED75, Cy2), (K1, ED75, Cy3), (K1, ED76, Cy1), (K1, ED76, Cy2), (K1, ED76, Cy3), (K1, ED77, Cy1), (K1, ED77, Cy2), (K1, ED77, Cy3), (K1, ED78, Cy1), (K1, ED78, Cy2), (K1, ED78, Cy3), (K1, ED79, Cy1), (K1, ED79, Cy2), (K1, ED79, Cy3), (K1, ED80, Cy1), (K1, ED80, Cy2), (K1, ED80, Cy3), (K1, ED81, Cy1), (K1, ED81, Cy2), (K1, ED81, Cy3), (K1, ED82, Cy1), (K1, ED82, Cy2), (K1, ED82, Cy3), (K1, ED83, Cy1), (K1, ED83, Cy2), (K1, ED83, Cy3), (K1, ED84, Cy1), (K1, ED84, Cy2), (K1, ED84, Cy3), (K1, ED85, Cy1), (K1, ED85, Cy2), (K1, ED85, Cy3), (K1, ED86, Cy1), (K1, ED86, Cy2), (K1, ED86, Cy3), (K1, ED87, Cy1), (K1, ED87, Cy2), (K1, ED87, Cy3), (K1, ED88, Cy1), (K1, ED88, Cy2), (K1, ED88, Cy3), (K1, ED89, Cy1), (K1, ED89, Cy2), (K1, ED89, Cy3), (K1, ED90, Cy1), (K1, ED90, Cy2), (K1, ED90, Cy3), (K1, ED91, Cy1), (K1, ED91, Cy2), (K1, ED91, Cy3), (K1, ED92, Cy1), (K1, ED92, Cy2), (K1, ED92, Cy3), (K2, ED1, Cy1), (K2, ED1, Cy2), (K2, ED1, Cy3), (K2, ED2, Cy1), (K2, ED2, Cy2), (K2, ED2, Cy3), (K2, ED3, Cy1), (K2, ED3, Cy2), (K2, ED3, Cy3), (K2, ED4, Cy1), (K2, ED4, Cy2), (K2, ED4, Cy3), (K2, ED5, Cy1), (K2, ED5, Cy2), (K2, ED5, Cy3), (K2, ED6, Cy1), (K2, ED6, Cy2), (K2, ED6, Cy3), (K2, ED7, Cy1), (K2, ED7, Cy2), (K2, ED7, Cy3), (K2, ED8, Cy1), (K2, ED8, Cy2), (K2, ED8, Cy3), (K2, ED9, Cy1), (K2, ED9, Cy2), (K2, ED9, Cy3), (K2, ED10, Cy1), (K2, ED10, Cy2), (K2, ED10, Cy3), (K2, ED11, Cy1), (K2, ED11, Cy2), (K2, ED11, Cy3), (K2, ED12, Cy1), (K2, ED12, Cy2), (K2, ED12, Cy3), (K2, ED13, Cy1), (K2, ED13, Cy2), (K2, ED13, Cy3), (K2, ED14, Cy1), (K2, ED14, Cy2), (K2, ED14, Cy3), (K2, ED15, Cy1), (K2, ED1S, Cy2), (K2, ED15, Cy3), (K2, ED16, Cy1), (K2, ED16, Cy2), (K2, ED16, Cy3), (K2, ED17, Cy1), (K2, ED17, Cy2), (K2, ED17, Cy3), (K2, ED18, Cy1), (K2, ED18, Cy2), (K2, ED18, Cy3), (K2, ED19, Cy1), (K2, ED19, Cy2), (K2, ED19, Cy3), (K2, ED20, Cy1), (K2, ED20, Cy2), (K2, ED20, Cy3), (K2, ED21, Cy1), (K2, ED21, Cy2), (K2, ED21, Cy3), (K2, ED22, Cy1), (K2, ED22, Cy2), (K2, ED22, Cy3), (K2, ED23, Cy1), (K2, ED23, Cy2), (K2, ED23, Cy3), (K2, ED24, Cy1), (K2, ED24, Cy2), (K2, ED24, Cy3), (K2, ED25, Cy1), (K2, ED25, Cy2), (K2, ED25, Cy3), (K2, ED26, Cy1), (K2, ED25, Cy2), (K2, ED26, Cy3), (K2, ED27, Cy1), (K2, ED27, Cy2), (K2, ED27, Cy3), (K2, ED28, Cy1), (K2, ED28, Cy2), (K2, ED28, Cy3), (K2, ED29, Cy1), (K2, ED29, Cy2), (K2, ED29, Cy3), (K2, ED30, Cy1), (K2, ED30, Cy2), (K2, ED30, Cy3), (K2, ED31, Cy1), (K2, ED31, Cy2), (K2, ED31, Cy3), (K2, ED32, Cy1), (K2, ED32, Cy2), (K2, ED32, Cy3), (K2, ED33, Cy1), (K2, ED33, Cy2), (K2, ED33, Cy3), (K2, ED34, Cy1), (K2, ED34, Cy2), (K2, ED34, Cy3), (K2, ED35, Cy1), (K2, ED35, Cy2), (K2, ED35, Cy3), (K2, ED36, Cy1), (K2, ED36, Cy2), (K2, ED36, Cy3), (K2, ED37, Cy1), (K2, ED37, Cy2), (K2, ED37, Cy3), (K2, ED38, Cy1), (K2, ED38, Cy2), (K2, ED38, Cy3), (K2, ED39, Cy1), (K2, ED39, Cy2), (K2, ED39, Cy3), (K2, ED40, Cy1), (K2, ED40, Cy2), (K2, ED40, Cy3), (K2, ED41, Cy1), (K2, ED41, Cy2), (K2, ED41, Cy3), (K2, ED42, Cy1), (K2, ED42, Cy2), (K2, ED42, Cy3), (K2, ED43, Cy1), (K2, ED43, Cy2), (K2, ED43, Cy3), (K2, ED44, Cy1), (K2, ED44, Cy2), (K2, ED44, Cy3), (K2, ED45, Cy1), (K2, ED45, Cy2), (K2, ED45, Cy3), (K2, ED46, Cy1), (K2, ED46, Cy2), (K2, ED46, Cy3), (K2, ED47, Cy1), (K2, ED47, Cy2), (K2, ED47, Cy3), (K2, ED48, Cy1), (K2, ED48, Cy2), (K2, ED48, Cy3), (K2, ED49, Cy1), (K2, ED49, Cy2), (K2, ED49, Cy3), (K2, ED50, Cy1), (K2, ED50, Cy2), (K2, ED50, Cy3), (K2, ED51, Cy1), (K2, ED51, Cy2), (K2, ED51, Cy3), (K2, ED52, Cy1), (K2, ED52, Cy2), (K2, ED52, Cy3), (K2, ED53, Cy1), (K2, ED53, Cy2), (K2, ED53, Cy3), (K2, ED54, Cy1), (K2, ED54, Cy2), (K2, ED54, Cy3), (K2, ED55, Cy1), (K2, ED55, Cy2), (K2, ED55, Cy3), (K2, ED56, Cy1), (K2, ED56, Cy2), (K2, ED56, Cy3), (K2, ED57, Cy1), (K2, ED57, Cy2), (K2, ED57, Cy3), (K2, ED58, Cy1), (K2, ED58, Cy2), (K2, ED58, Cy3), (K2, ED59, Cy1), (K2, ED59, Cy2), (K2, ED59, Cy3), (K2, ED60, Cy1), (K2, ED60, Cy2), (K2, ED60, Cy3), (K2, ED61, Cy1), (K2, ED61, Cy2), (K2, ED61, Cy3), (K2, ED62, Cy1), (K2, ED62, Cy2), (K2, ED62, Cy3), (K2, ED63, Cy1), (K2, ED63, Cy2), (K2, ED63, Cy3), (K2, ED64, Cy1), (K2, ED64, Cy2), (K2, ED64, Cy3), (K2, ED65, Cy1), (K2, ED65, Cy2), (K2, ED65, Cy3), (K2, ED66, Cy1), (K2, ED66, Cy2), (K2, ED66, Cy3), (K2, ED67, Cy1), (K2, ED67, Cy2), (K2, ED67, Cy3), (K2, ED68, Cy1), (K2, ED68, Cy2), (K2, ED68, Cy3), (K2, ED69, Cy1), (K2, ED69, Cy2), (K2, ED69, Cy3), (K2, ED70, Cy1), (K2, ED70, Cy2), (K2, ED70, Cy3), (K2, ED71, Cy1), (K2, ED71, Cy2), (K2, ED71, Cy3), (K2, ED72, Cy1), (K2, ED72, Cy2), (K2, ED72, Cy3), (K2, ED73, Cy1), (K2, ED73, Cy2), (K2, ED73, Cy3), (K2, ED74, Cy1), (K2, ED74, Cy2), (K2, ED74, Cy3), (K2, ED75, Cy1), (K2, ED75, Cy2), (K2, ED75, Cy1), (K2, ED76, Cy1), (K2, ED76, Cy2), (K2, ED76, Cy3), (K2, ED77, Cy1), (K2, ED77, Cy2), (K2, ED77, Cy3), (K2, ED78, Cy1), (K2, ED78, Cy2), (K2, ED78, Cy3), (K2, ED79, Cy1), (K2, ED79, Cy2), (K2, ED79, Cy3), (K2, ED80, Cy1), (K2, ED80, Cy2), (K2, ED80, Cy3), (K2, ED81, Cy1), (K2, ED81, Cy2), (K2, ED81, Cy3), (K2, ED82, Cy1), (K2, ED82, Cy2), (K2, ED82, Cy3), (K2, ED83, Cy1), (K2, ED83, Cy2), (K2, ED83, Cy3), (K2, ED84, Cy1), (K2, ED84, Cy2), (K2, ED84, Cy3), (K2, ED85, Cy1), (K2, ED85, Cy2), (K2, ED85, Cy3), (K2, ED86, Cy1), (K2, ED86, Cy2), (K2, ED86,

Cy3), (K2, ED87, Cy1), (K2, ED87, Cy2), (K2, ED87, Cy3), (K2, ED88, Cy1), (K2, ED88, Cy2), (K2, ED88, Cy3), (K2, ED89, Cy1), (K2, ED89, Cy2), (K2, ED89, Cy3), (K2, ED90, Cy1), (K2, ED90, Cy2), (K2, ED90, Cy3), (K2, ED91, Cy1), (K2, ED91, Cy2), (K2, ED91, Cy3), (K2, ED92, Cy1), (K2, ED92, Cy2), (K2, ED92, Cy3), (K3, ED1, Cy1), (K3, ED1, Cy2), (K3, ED1, Cy3), (K3, ED2, Cy1), (K3, ED2, Cy2), (K3, ED2, Cy3), (K3, ED3, Cy1), (K3, ED3, Cy2), (K3, ED3, Cy3), (K3, ED4, Cy1), (K3, ED4, Cy2), (K3, ED4, Cy3), (K3, ED5, Cy1), (K3, ED5, Cy2), (K3, ED5, Cy3), (K3, ED6, Cy1), (K3, ED6, Cy2), (K3, ED6, Cy3), (K3, ED7, Cy1), (K3, ED7, Cy2), (K3, ED7, Cy3), (K3, ED8, Cy1), (K3, ED8, Cy2), (K3, ED8, Cy3), (K3, ED9, Cy1), (K3, ED9, Cy2), (K3, ED9, Cy3), (K3, ED10, Cy1), (K3, ED10, Cy2), (K3, ED10, Cy3), (K3, ED11, Cy1), (K3, ED11, Cy2), (K3, ED11, Cy3), (K3, ED12, Cy1), (K3, ED12, Cy2), (K3, ED12, Cy3), (K3, ED13, Cy1), (K3, ED13, Cy2), (K3, ED13, Cy3), (K3, ED14, Cy1), (K3, ED14, Cy2), (K3, ED14, Cy3), (K3, ED15, Cy1), (K3, ED15, Cy2), (K3, ED15, Cy3), (K3, ED16, Cy1), (K3, ED16, Cy2), (K3, ED16, Cy3), (K3, ED17, Cy1), (K3, ED17, Cy2), (K3, ED17, Cy3), (K3, ED18, Cy1), (K3, ED18, Cy2), (K3, ED18, Cy3), (K3, ED19, Cy1), (K3, ED19, Cy2), (K3, ED19, Cy3), (K3, ED20, Cy1), (K3, ED20, Cy2), (K3, ED20, Cy3), (K3, ED21, Cy1), (K3, ED21, Cy2), (K3, ED21, Cy3), (K3, ED22, Cy1), (K3, ED22, Cy2), (K3, ED22, Cy3), (K3, ED23, Cy1), (K3, ED23, Cy2), (K3, ED23, Cy3), (K3, ED24, Cy1), (K3, ED24, Cy2), (K3, ED24, Cy3), (K3, ED25, Cy1), (K3, ED25, Cy2), (K3, ED25, Cy3), (K3, ED26, Cy1), (K3, ED25, Cy2), (K3, ED26, Cy3), (K3, ED27, Cy1), (K3, ED27, Cy2), (K3, ED27, Cy3), (K3, ED28, Cy1), (K3, ED28, Cy2), (K3, ED28, Cy3), (K3, ED29, Cy1), (K3, ED29, Cy2), (K3, ED29, Cy3), (K3, ED30, Cy1), (K3, ED30, Cy2), (K3, ED30, Cy3), (K3, ED31, Cy1), (K3, ED31, Cy2), (K3, ED31, Cy3), (K3, ED32, Cy1), (K3, ED32, Cy2), (K3, ED32, Cy3), (K3, ED33, Cy1), (K3, ED33, Cy2), (K3, ED33, Cy3), (K3, ED34, Cy1), (K3, ED34, Cy2), (K3, ED34, Cy3), (K3, ED35, Cy1), (K3, ED35, Cy2), (K3, ED35, Cy3), (K3, ED36, Cy1), (K3, ED36, Cy2), (K3, ED36, Cy3), (K3, ED37, Cy1), (K3, ED37, Cy2), (K3, ED37, Cy3), (K3, ED38, Cy1), (K3, ED38, Cy2), (K3, ED38, Cy3), (K3, ED39, Cy1), (K3, ED39, Cy2), (K3, ED39, Cy3), (K3, ED40, Cy1), (K3, ED40, Cy2), (K3, ED40, Cy3), (K3, ED41, Cy1), (K3, ED41, Cy2), (K3, ED41, Cy3), (K3, ED42, Cy1), (K3, ED42, Cy2), (K3, ED42, Cy3), (K3, ED43, Cy1), (K3, ED43, Cy2), (K3, ED43, Cy3), (K3, ED44, Cy1), (K3, ED44, Cy2), (K3, ED44, Cy3), (K3, ED45, Cy1), (K3, ED45, Cy2), (K3, ED45, Cy3), (K3, ED46, Cy1), (K3, ED46, Cy2), (K3, ED46, Cy3), (K3, ED47, Cy1), (K3, ED47, Cy2), (K3, ED47, Cy3), (K3, ED48, Cy1), (K3, ED48, Cy2), (K3, ED48, Cy3), (K3, ED49, Cy1), (K3, ED49, Cy2), (K3, ED49, Cy3), (K3, ED50, Cy1), (K3, ED50, Cy2), (K3, ED50, Cy3), (K3, ED51, Cy1), (K3, ED51, Cy2), (K3, ED51, Cy3), (K3, ED52, Cy1), (K3, ED52, Cy2), (K3, ED52, Cy3), (K3, ED53, Cy1), (K3, ED53, Cy2), (K3, ED53, Cy3), (K3, ED54, Cy1), (K3, ED54, Cy2), (K3, ED54, Cy3), (K3, ED55, Cy1), (K3, ED55, Cy2), (K3, ED55, Cy3), (K3, ED56, Cy1), (K3, ED56, Cy2), (K3, ED56, Cy3), (K3, ED57, Cy1), (K3, ED57, Cy2), (K3, ED57, Cy3), (K3, ED58, Cy1), (K3, ED58, Cy2), (K3, ED58, Cy3), (K3, ED59, Cy1), (K3, ED59, Cy2), (K3, ED59, Cy3), (K3, ED60, Cy1), (K3, ED60, Cy2), (K3, ED60, Cy3), (K3, ED61, Cy1), (K3, ED61, Cy2), (K3, ED61, Cy3), (K3, ED62, Cy1), (K3, ED62, Cy2), (K3, ED62, Cy3), (K3, ED63, Cy1), (K3, ED63, Cy2), (K3, ED63, Cy3), (K3, ED64, Cy1), (K3, ED64, Cy2), (K3, ED64, Cy3), (K3, ED65, Cy1), (K3, ED65, Cy2), (K3, ED65, Cy3), (K3, ED66, Cy1), (K3, ED64, Cy2), (K3, ED66, Cy3), (K3, ED67, Cy1), (K3, ED67, Cy2), (K3, ED67, Cy3), (K3, ED68, Cy1), (K3, ED68, Cy2), (K3, ED68, Cy3), (K3, ED69, Cy1), (K3, ED69, Cy2), (K3, ED69, Cy3), (K3, ED70, Cy1), (K3, ED70, Cy2), (K3, ED70, Cy3), (K3, ED71, Cy1), (K3, ED71, Cy2), (K3, ED71, Cy3), (K3, ED72, Cy1), (K3, ED72, Cy2), (K3, ED72, Cy3), (K3, ED73, Cy1), (K3, ED73, Cy2), (K3, ED73, Cy3), (K3, ED74, Cy1), (K3, ED74, Cy2), (K3, ED74, Cy3), (K3, ED75, Cy1), (K3, ED75, Cy2), (K3, ED75, Cy3), (K3, ED76, Cy1), (K3, ED76, Cy2), (K3, ED76, Cy3), (K3, ED77, Cy1), (K3, ED77, Cy2), (K3, ED77, Cy3), (K3, ED78, Cy1), (K3, ED78, Cy2), (K3, ED78, Cy3), (K3, ED79, Cy1), (K3, ED79, Cy2), (K3, ED79, Cy3), (K3, ED80, Cy1), (K3, ED80, Cy2), (K3, ED80, Cy3), (K3, ED81, Cy1), (K3, ED81, Cy2), (K3, ED81, Cy3), (K3, ED82, Cy1), (K3, ED82, Cy2), (K3, ED82, Cy3), (K3, ED83, Cy1), (K3, ED83, Cy2), (K3, ED83, Cy3), (K3, ED84, Cy1), (K3, ED84, Cy2), (K3, ED84, Cy3), (K3, ED85, Cy1), (K3, ED85, Cy2), (K3, ED85, Cy3), (K3, ED86, Cy1), (K3, ED86, Cy2), (K3, ED86, Cy3), (K3, ED87, Cy1), (K3, ED87, Cy2), (K3, ED87, Cy3), (K3, ED88, Cy1), (K3, ED88, Cy2), (K3, ED88, Cy3), (K3, ED89, Cy1), (K3, ED89, Cy2), (K3, ED89, Cy3), (K3, ED90, Cy1), (K3, ED90, Cy2), (K3, ED90, Cy0), (K3, ED91, Cy1), (K3, ED91, Cy2), (K3, ED91, Cy3), (K3, ED92, Cy1), (K3, ED92, Cy2), (K3, ED92, Cy3), (K4, ED1, Cy1), (K4, ED1, Cy2), (K4, ED1, Cy3), (K4, ED2, Cy1), (K4, ED2, Cy2), (K4, ED2, Cy3), (K4, ED3, Cy1), (K4, ED3, Cy2), (K4, ED3, Cy3), (K4, ED4, Cy1), (K4, ED4, Cy2), (K4, ED4, Cy3), (K4, ED5, Cy1), (K4, ED5, Cy2), (K4, ED5, Cy3), (K4, ED6, Cy1), (K4, ED6, Cy2), (K4, ED6, Cy3), (K4, ED7, Cy1), (K4, ED7, Cy2), (K4, ED7, Cy3), (K4, ED8, Cy1), (K4, ED8, Cy2), (K1, ED8, Cy3), (K4, ED9, Cy1), (K4, ED9, Cy2), (K4, ED9, Cy3), (K4, ED10, Cy1), (K4, ED10, Cy2), (K4, ED10, Cy3), (K4, ED11, Cy1), (K4, ED11, Cy2), (K4, ED11, Cy3), (K4, ED12, Cy1), (K4, ED12, Cy2), (K4, ED12, Cy3), (K4, ED13, Cy1), (K4, ED13, Cy2), (K4, ED13, Cy3), (K4, ED14, Cy1), (K4, ED14, Cy2), (K4, ED14, Cy3), (K4, ED15, Cy1), (K4, ED15, Cy2), (K4, ED15, Cy3), (K4, ED16, Cy1), (K4, ED16, Cy2), (K4, ED16, Cy3), (K4, ED17, Cy1), (K4, ED17, Cy2), (K4, ED17, Cy3), (K4, ED18, Cy1), (K4, ED18, Cy2), (K4, ED18, Cy3), (K4, ED19, Cy1), (K4, ED19, Cy2), (K4, ED19, Cy3), (K4, ED20, Cy1), (K4, ED20, Cy2), (K4, ED20, Cy3), (K4, ED21, Cy1), (K4, ED21, Cy2), (K4, ED21, Cy3), (K4, ED22, Cy1), (K4, ED22, Cy2), (K4, ED22, Cy3), (K4, ED23, Cy1), (K4, ED23, Cy2), (K4, ED23, Cy3), (K4, ED24, Cy1), (K4, ED24, Cy2), (K4, ED24, Cy3), (K4, ED25, Cy1), (K4, ED25, Cy2), (K4, ED25, Cy3), (K4, ED26, Cy1), (K4, ED26, Cy2), (K4, ED26, Cy3), (K4, ED27, Cy1), (K4, ED27, Cy2), (K4, ED27, Cy3), (K4, ED28, Cy1), (K4, ED28, Cy2), (K4, ED28, Cy3), (K4, ED29, Cy1), (K4, ED29, Cy2), (K4, ED29, Cy3), (K4, ED30, Cy1), (K4, ED30, Cy2), (K4, ED30, Cy3), (K4, ED31, Cy1), (K4, ED31, Cy2), (K4, ED31, Cy3), (K4, ED32, Cy1), (K4, ED32, Cy2), (K4, ED32, Cy3), (K4, ED33, Cy1), (K4, ED33, Cy2), (K4, ED33, Cy3), (K4, ED34, Cy1), (K4, ED34, Cy2), (K4, ED34, Cy3), (K4, ED35, Cy1), (K4, ED35, Cy2), (K4, ED35, Cy3), (K4, ED36, Cy1), (K4, ED36, Cy2), (K4, ED36, Cy3), (K4, ED37, Cy1), (K4, ED37, Cy2), (K4, ED37, Cy3), (K4, ED38, Cy1), (K4, ED38, Cy2), (K4, ED38, Cy3), (K4, ED39, Cy1), (K4, ED39, Cy2), (K4, ED39, Cy3), (K4, ED40, Cy1), (K4, ED40, Cy2), (K4, ED40, Cy3), (K4, ED41, Cy1), (K4, ED41, Cy2), (K4, ED41, Cy3), (K4, ED42, Cy1), (K4, ED42, Cy2), (K4, ED42, Cy3), (K4, ED43, Cy1), (K4, ED43, Cy2), (K4, ED43, Cy3), (K4, ED44, Cy1), (K4, ED44, Cy2), (K4, ED44, Cy3), (K4, ED45, Cy1), (K4, ED45, Cy2), (K4, ED45, Cy3), (K4, ED46, Cy1), (K4, ED46, Cy2), (K4, ED46, Cy3), (K4, ED47, Cy1), (K4, ED47, Cy2), (K4, ED47, Cy3), (K4, ED48, Cy1), (K4, ED48, Cy2), (K4, ED48, Cy3), (K4, ED49, Cy1), (K4, ED49, Cy2), (K4, ED49, Cy3), (K4, ED50, Cy1), (K4, ED50, Cy2), (K4, ED50, Cy3), (K4, ED51, Cy1), (K4, ED51, Cy2), (K4, ED51, Cy3), (K4, ED52, Cy1), (K4, ED52, Cy2), (K4, ED52, Cy3), (K4, ED53, Cy1), (K4, ED53, Cy2), (K4, ED53, Cy3), (K4, ED54, Cy1), (K4, ED54, Cy2), (K4, ED54, Cy3), (K4, ED55, Cy1), (K4, ED55, Cy2), (K4, ED55, Cy3), (K4, ED56, Cy1), (K4, ED56, Cy2), (K4, ED56, Cy3), (K4, ED57, Cy1), (K4, ED57, Cy2), (K4, ED57, Cy3), (K4, ED58, Cy1), (K4, ED58, Cy2), (K4, ED58, Cy3), (K4, ED59, Cy1), (K4, ED59, Cy2), (K4, ED59, Cy3), (K4, ED60, Cy1), (K4, ED60, Cy2), (K4, ED60, Cy3), (K4, ED61, Cy1), (K4, ED61, Cy2), (K4, ED61, Cy3), (K4, ED62, Cy1), (K4, ED62, Cy2), (K4, ED62, Cy3), (K4, ED63, Cy1), (K4, ED63, Cy2), (K4, ED63, Cy3), (K4, ED64, Cy1), (K4, ED64, Cy2), (K4, ED64, Cy3), (K4, ED65, Cy1), (K4, ED65, Cy2), (K4, ED65, Cy3), (K4, ED66, Cy1), (K4, ED66, Cy2), (K4, ED66, Cy3), (K4, ED67, Cy1), (K4, ED67, Cy2), (K4, ED67, Cy3), (K4, ED68, Cy1), (K4, ED68, Cy2), (K4, ED68, Cy3), (K4, ED69, Cy1), (K4, ED69, Cy2), (K4, ED69, Cy3), (K4, ED70, Cy1), (K4, ED70, Cy2), (K4, ED70, Cy3), (K4, ED71, Cy1), (K4, ED71, Cy2), (K4, ED71, Cy3), (K4, ED72, Cy1), (K4, ED72, Cy2), (K4, ED72, Cy3), (K4, ED73, Cy1), (K4, ED73, Cy2), (K4, ED73, Cy3), (K4, ED74, Cy1), (K4, ED74, Cy2), (K4, ED74, Cy3), (K4, ED75, Cy1), (K4, ED75, Cy2), (K4, ED75, Cy3), (K4, ED76, Cy1), (K4, ED76, Cy2), (K4, ED76, Cy3), (K4, ED77, Cy1), (K4, ED77, Cy2), (K4, ED77, Cy3), (K4, ED78, Cy1), (K4, ED78, Cy2), (K4, ED78, Cy3), (K4, ED79, Cy1), (K4, ED79, Cy2), (K4, ED79, Cy3), (K4, ED80, Cy1), (K4, ED80, Cy2), (K4, ED80, Cy3), (K4, ED81, Cy1), (K4, ED81, Cy2), (K4, ED81, Cy3), (K4, ED82, Cy1), (K4, ED82, Cy2), (K4, ED82, Cy3), (K4, ED83, Cy1), (K4, ED83, Cy2), (K1, ED83, Cy3), (K4, ED84, Cy1), (K4, ED84, Cy2), (K4, ED84, Cy3), (K4, ED85, Cy1), (K4, ED85, Cy2), (K4, ED85, Cy3), (K4, ED86, Cy1), (K4, ED86, Cy2), (K4, ED86, Cy3), (K4, ED87, Cy1), (K4, ED87, Cy2), (K4, ED87, Cy3), (K4, ED88, Cy1), (K4, ED88, Cy2), (K4, ED88, Cy3), (K4, ED89, Cy1), (K4, ED89, Cy2), (K4, ED89, Cy3), (K4, ED90, Cy1), (K4, ED90, Cy2), (K4, ED90, Cy3), (K4, ED91, Cy1), (K4, ED91, Cy2), (K4, ED91, Cy3), (K4, ED92, Cy1), (K4, ED92, Cy2), (K4, ED92, Cy3)

(K5, ED1, Cy1), (K5, ED1, Cy2), (K5, ED1, Cy3), (K5, ED2, Cy1), (K5, ED2, Cy2), (K5, ED2, Cy3), (K5, ED3, Cy1), (K5, ED3, Cy2), (K5, ED3, Cy3), (K5, ED4, Cy1), (K5, ED4, Cy2), (K5, ED4, Cy3), (K5, ED5, Cy1), (K5, ED5, Cy2), (K5, ED5, Cy3), (K5, ED6, Cy1), (K5, ED6, Cy2), (K5, ED6, Cy3), (K5, ED7, Cy1), (K5, ED7, Cy2), (K5, ED7, Cy3), (K5, ED5, Cy1), (K5, ED8, Cy2), (K5, ED8, Cy3), (K5, ED9, Cy1), (K5, ED9, Cy2), (K5, ED9, Cy3), (K5, ED10, Cy1), (K5, ED10, Cy2), (K5, ED10, Cy3), (K5, ED11, Cy1), (K5, ED11, Cy2), (K5, ED11, Cy3), (K5, ED12, Cy1), (K5, ED12, Cy2), (K5, ED12, Cy3), (K5, ED13, Cy1), (K5, ED13, Cy2), (K5, ED13, Cy3), (K5, ED14, Cy1), (K5, ED14, Cy2), (K5, ED14, Cy3), (K5, ED15, Cy1), (K5, ED15, Cy2), (K5, ED15, Cy3), (K5, ED16, Cy1), (K5, ED16, Cy2), (K5, ED16, Cy3), (K5, ED17, Cy1), (K5, ED17, Cy2), (K5, ED17, Cy3), (K5, ED18, Cy1), (K5, ED18, Cy2), (K5, ED18, Cy3), (K5, ED19, Cy1), (K5, ED19, Cy2), (K5, ED19, Cy3), (K5, ED20, Cy1), (K5, ED20, Cy2), (K5, ED20, Cy3), (K5, ED21, Cy1), (K5, ED21, Cy2), (K5, ED21, Cy3), (K5, ED22, Cy1), (K5, ED22, Cy2), (K5, ED22, Cy3), (K5, ED23, Cy1), (K5, ED23, Cy2), (K5, ED23, Cy3), (K5, ED24, Cy1), (K5, ED24, Cy2), (K5, ED24, Cy3), (K5, ED25, Cy1), (K5, ED25, Cy2), (K5, ED25, Cy3), (K5, ED26, Cy1), (K5, ED26, Cy2), (K5, ED26, Cy3), (K5, ED27, Cy1), (K5, ED27, Cy2), (K5, ED27, Cy3), (K5, ED28, Cy1), (K5, ED28, Cy2), (K5, ED28, Cy3), (K5, ED29, Cy1), (K5, ED29, Cy2), (K5, ED29, Cy3), (K5, ED30, Cy1), (K5, ED30, Cy2), (K5, ED30, Cy3), (K5, ED31, Cy1), (K5, ED31, Cy2), (K5, ED31, Cy3), (K5, ED32, Cy1), (K5, ED32, Cy2), (K5, ED32, Cy3), (K5, ED33, Cy1), (K5, ED33, Cy2), (K5, ED33, Cy3), (K5, ED34, Cy1), (K5, ED34, Cy2), (K5, ED34, Cy3), (K5, ED35, Cy1), (K5, ED35, Cy2), (K5, ED35, Cy3), (K5, ED36, Cy1), (K5, ED36, Cy2), (K5, ED36, Cy3), (K5, ED37, Cy1), (K5, ED37, Cy2), (K5, ED37, Cy3), (K5, ED38, Cy1), (K5, ED38, Cy2), (K5, ED38, Cy3), (K5, ED39, Cy1), (K5, ED39, Cy2), (K5, ED39, Cy3), (K5, ED40, Cy1), (K5, ED40, Cy2), (K5, ED40, Cy3), (K5, ED41, Cy1), (K5, ED41, Cy2), (K5, ED41, Cy3), (K5, ED42, Cy1), (K5, ED42, Cy2), (K5, ED42, Cy3), (K5, ED43, Cy1), (K5, ED43, Cy2), (K5, ED43, Cy3), (K5, ED14, Cy1), (K5, ED44, Cy2), (K5, ED44, Cy3), (K5, ED45, Cy1), (K5, ED45, Cy2), (K5, ED45, Cy3), (K5, ED46, Cy1), (K5, ED46, Cy2), (K5, ED46, Cy3), (K5, ED47, Cy1), (K5, ED47, Cy2), (K5, ED47, Cy3), (K5, ED48, Cy1), (K5, ED48, Cy2), (K5, ED48, Cy3), (K5, ED49, Cy1), (K5, ED49, Cy2), (K5, ED49, Cy3), (K5, ED50, Cy1), (K5, ED50, Cy2), (K5, ED50, Cy3), (K5, ED51, Cy1), (K5, ED51, Cy2), (K5, ED51, Cy3), (K5, ED52, Cy1), (K5, ED52, Cy2), (K5, ED52, Cy3), (K5, ED53, Cy1), (K5, ED53, Cy2), (K5, ED53, Cy3), (K5, ED54, Cy1), (K5, ED54, Cy2), (K5, ED54, Cy3), (K5, ED55, Cy1), (K5, ED55, Cy2), (K5, ED55, Cy3), (K5, ED56, Cy1), (K5, ED56, Cy2), (K5, ED56, Cy3), (K5, ED57, Cy1), (K5, ED57, Cy2), (K5, ED57, Cy3), (K5, ED58, Cy1), (K5, ED58, Cy2), (K5, ED58, Cy3), (K5, ED59, Cy1), (K5, ED59, Cy2), (K5, ED59, Cy3), (K5, ED60, Cy1), (K5, ED60, Cy2), (K5, ED60, Cy3), (K5, ED61, Cy1), (K5, ED61, Cy2), (K5, ED61, Cy3), (K5, ED62, Cy1), (K5, ED62, Cy2), (K5, ED62, Cy3), (K5, ED63, Cy1), (K5, ED63, Cy2), (K5, ED63, Cy3), (K5, ED64, Cy1), (K5, ED64, Cy2), (K5, ED64, Cy3), (K5, ED65, Cy1), (K5, ED65, Cy2), (K5, ED65, Cy3), (K5, ED66, Cy1), (K5, ED66, Cy2), (K5, ED66, Cy3), (K5, ED67, Cy1), (K5, ED67, Cy2), (K5, ED67, Cy3), (K5, ED68, Cy1), (K5, ED68, Cy2), (K5, ED68, Cy3), (K5, ED69, Cy1), (K5, ED69, Cy2), (K5, ED69, Cy3), (K5, ED70, Cy1), (K5, ED70, Cy2), (K5, ED70, Cy3), (K5, ED71, Cy1), (K5, ED71, Cy2), (K5, ED71, Cy3), (K5, ED72, Cy1), (K5, ED72, Cy2), (K5, ED72, Cy3), (K5, ED73, Cy1), (K5, ED73, Cy2), (K5, ED73, Cy3), (K5, ED74, Cy1), (K5, ED74, Cy2), (K5, ED74, Cy3), (K5, ED75, Cy1), (K5, ED75, Cy2), (K5, ED75, Cy3), (K5, ED76, Cy1), (K5, ED76, Cy2), (K5, ED76, Cy3), (K5, ED77, Cy1), (K5, ED77, Cy2), (K5, ED77, Cy3), (K5, ED78, Cy1), (K5, ED78, Cy2), (K5, ED78, Cy3), (K5, ED79, Cy1), (K5, ED79, Cy2), (K5, ED79, Cy3), (K5, ED80, Cy1), (K5, ED80, Cy2), (K5, ED80, Cy3), (K5, ED81, Cy1), (K5, ED81, Cy2), (K5, ED81, Cy3), (K5, ED82, Cy1), (K5, ED82, Cy2), (K5, ED82, Cy3), (K5, ED83, Cy1), (K5, ED83, Cy2), (K5, ED83, Cy3), (K5, ED84, Cy1), (K5, ED84, Cy2), (K5, ED84, Cy3), (K5, ED85, Cy1), (K5, ED85, Cy2), (K5, ED85, Cy3), (K5, ED86, Cy1), (K5, ED86, Cy2), (K5, ED86, Cy3), (K5, ED87, Cy1), (K5, ED87, Cy2), (K5, ED87, Cy3), (K5, ED88, Cy1), (K5, ED88, Cy2), (K5, ED88, Cy3), (K5, ED89, Cy1), (K5, ED89, Cy2), (K5, ED89, Cy3), (K5, ED90, Cy1), (K5, ED90, Cy2), (K5, ED90, Cy3), (DS, ED91, Cy1), (K5, ED91, Cy2), (K5, ED91, Cy3), (K5, ED92, Cy1), (K5, ED92, Cy2), (K5, ED92, Cy3), (K6, ED1, Cy1), (K6, ED1, Cy2), (K6, ED1, Cy3), (K6, ED2, Cy1), (K6, ED2, Cy2), (K6, ED2, Cy3), (K6, ED3, Cy1), (K6, ED3, Cy2), (K6, ED3, Cy3), (K6, ED4, Cy1), (K6, ED4, Cy2), (K6, ED4, Cy3), (K6, ED5, Cy1), (K6, ED5, Cy2), (K6, ED5, Cy3), (K6, ED6, Cy1), (K6, ED6, Cy2), (K6, ED6, Cy3), (K6, ED7, Cy1), (K6, ED7, Cy2), (K6, ED7, Cy3), (K6, ED8, Cy1), (K6, ED5, Cy2), (K6, ED5, Cy3), (K6, ED9, Cy1), (K6, ED9, Cy2), (K6, ED9, Cy3), (K6, ED10, Cy1), (K6, ED10, Cy2), (K6, ED10, Cy3), (K6, ED11, Cy1), (K6, ED11, Cy2), (K6, ED11, Cy3), (K6, ED12, Cy1), (K6, ED12, Cy2), (K6, ED12, Cy3), (K6, ED13, Cy1), (K6, ED13, Cy2), (K6, ED13, Cy3), (K6, ED14, Cy1), (K6, ED14, Cy2), (K6, ED14, Cy3), (K6, ED15, Cy1), (K6, ED15, Cy2), (K6,

ED15, Cy3), (K6, ED16, Cy1), (K6, ED16, Cy2), (K6, ED16, Cy3), (K6, ED17, Cy1), (K6, ED17, Cy2), (K6, ED17, Cy3), (K6, ED18, Cy1), (K6, ED18, Cy2), (K6, ED18, Cy3), (K6, ED19, Cy1), (K6, ED19, Cy2), (K6, ED19, Cy3), (K6, ED20, Cy1), (K6, ED20, Cy2), (K6, ED20, Cy3), (K6, ED21, Cy1), (K6, ED21, Cy2), (K6, ED21, Cy3), (K6, ED22, Cy1), (K6, ED22, Cy2), (K6, ED22, Cy3), (K6, ED23, Cy1), (K6, ED23, Cy2), (K6, ED23, Cy3), (K6, ED24, Cy1), (K6, ED24, Cy2), (K6, ED24, Cy3), (K6, ED25, Cy1), (K6, ED25, Cy2), (K6, ED25, Cy3), (K6, ED26, Cy1), (K6, ED26, Cy2), (K6, ED26, Cy3), (K6, ED27, Cy1), (K6, ED27, Cy2), (K6, ED27, Cy3), (K6, ED28, Cy1), (K6, ED28, Cy2), (K6, ED28, Cy3), (K6, ED29, Cy1), (K6, ED29, Cy2), (K6, ED29, Cy3), (K6, ED30, Cy1), (K6, ED30, Cy2), (K6, ED30, Cy3), (K6, ED31, Cy1), (K6, ED31, Cy2), (K6, ED31, Cy3), (K6, ED32, Cy1), (K6, ED32, Cy2), (K6, ED32, Cy3), (K6, ED33, Cy1), (K6, ED33, Cy2), (K6, ED33, Cy3), (K6, ED34, Cy1), (K6, ED34, Cy2), (K6, ED34, Cy3), (K6, ED35, Cy1), (K6, ED35, Cy2), (K6, ED35, Cy3), (K6, ED36, Cy1), (K6, ED36, Cy2), (K6, ED36, Cy3), (K6, ED37, Cy1), (K6, ED37, Cy2), (K6, ED37, Cy3), (K6, ED38, Cy1), (K6, ED38, Cy2), (K6, ED38, Cy3), (K6, ED39, Cy1), (K6, ED39, Cy2), (K6, ED39, Cy3), (K6, ED40, Cy1) ED40, Cy2), (K6, ED40, Cy3), (K6, ED41, Cy1), (K6, ED41, Cy2), (K6, ED41, Cy3), (K6, ED42, Cy1), (K6, ED42, Cy2), (K6, ED42, Cy3), (K6, ED43, Cy1), (K6, ED43, Cy2), (K6, ED43, Cy3), (K6, ED44, Cy1), (K6, ED44, Cy2), (K6, ED44, Cy3), (K6, ED45, Cy1), (K6, ED45, Cy2), (K6, ED45, Cy3), (K6, ED46, Cy1), (K6, ED46, Cy2), (K6, ED46, Cy3), (K6, ED47, Cy1), (K6, ED47, Cy2), (K6, ED47, Cy3), (K6, ED48, Cy1), (K6, ED48, Cy2), (K6, ED48, Cy3), (K6, ED49, Cy1), (K6, ED49, Cy2), (K6, ED49, Cy3), (K6, ED50, Cy1), (K6, ED50, Cy2), (K6, ED50, Cy3), (K6, ED51, Cy1), (K6, ED51, Cy2), (K6, ED51, Cy3), (K6, ED52, Cy1), (K6, ED52, Cy2), (K6, ED52, Cy3), (K6, ED53, Cy1), (K6, ED53, Cy2), (K6, ED53, Cy3), (K6, ED54, Cy1), (K6, ED54, Cy2), (K6, ED54, Cy3), (K6, ED55, Cy1), (K6, ED55, Cy2), (K6, ED55, Cy3), (K6, ED56, Cy1), (K6, ED56, Cy2), (K6, ED56, Cy3), (K6, ED57, Cy1), (K6, ED57, Cy2), (K6, ED57, Cy3), (K6, ED58, Cy1), (K6, ED58, Cy2), (K6, ED58, Cy3), (K6, ED59, Cy1), (K6, ED59, Cy2), (K6, ED59, Cy3), (K6, ED60, Cy1), (K6, ED60, Cy2), (K6, ED60, Cy3), (K6, ED61, Cy1), (K6, ED61, Cy2), (K6, ED61, Cy3), (K6, ED62, Cy1), (K6, ED62, Cy2), (K6, ED62, Cy3), (K6, ED63, Cy1), (K6, ED63, Cy2), (K6, ED63, Cy3), (K6, ED64, Cy1), (K6, ED69, Cy2), (K6, ED65, Cy1), (K6, ED65, Cy2), (K6, ED65, Cy3), (K6, ED66, Cy1), (K6, ED66, Cy2), (K6, ED66, Cy3), (K6, ED67, Cy1), (K6, ED67, Cy2), (K6, ED67, Cy3), (K6, ED68, Cy1), (K6, ED68, Cy2), (K6, ED68, Cy3), (K6, ED69, Cy1), (K6, ED69, Cy2), (K6, ED69, Cy3), (K6, ED70, Cy1), (K6, ED70, Cy2), (K6, ED70, Cy3), (K6, ED71, Cy1), (K6, ED71, Cy2), (K6, ED71, Cy3), (K6, ED72, Cy1), (K6, ED72, Cy2), (K6, ED72, Cy3), (K6, ED73, Cy1), (K6, ED73, Cy2), (K6, ED73, Cy3), (K6, ED79, Cy1), (K6, ED74, Cy2), (K6, ED74, Cy3), (K6, ED75, Cy1), (K6, ED75, Cy2), (K6, ED75, Cy3), (K6, ED76, Cy1), (K6, ED76, Cy2), (K6, ED76, Cy3), (K6, ED77, Cy1), (K6, ED77, Cy2), (K6, ED77, Cy3), (K6, ED78, Cy1), (K6, ED78, Cy2), (K6, ED78, Cy3), (K6, ED79, Cy1), (K6, ED79, Cy2), (K6, ED79, Cy3), (K6, ED80, Cy1), (K6, ED80, Cy2), (K6, ED80, Cy3), (K6, ED81, Cy1), (K6, ED81, Cy2), (K6, ED81, Cy3), (K6, ED82, Cy1), (K6, ED82, Cy2), (K6, ED82, Cy3), (K6, ED83, Cy1), (K6, ED83, Cy2), (K0, ED83, Cy3), (K6, ED84, Cy1), (K6, ED84, Cy2), (K6, ED84, Cy3), (K6, ED85, Cy1), (K6, ED85, Cy2), (K6, ED85, Cy3), (K6, ED86, Cy1), (K0, ED86, Cy2), (K6, ED86, Cy3), (K6, ED87, Cy1), (K6, ED87, Cy2), (K6, ED87, Cy3), (K6, ED88, Cy1), (K6, ED88, Cy2), (K6, ED88, Cy3), (K6, ED89, Cy1), (K6, ED89, Cy2), (K6, ED89, Cy3), (K6, ED90, Cy1), (K6, ED90, Cy2), (K6, ED90, Cy3), (K6, ED91, Cy1), (K6, ED91, Cy2), (K6, ED91, Cy3), (K6, ED92, Cy1), (K6, ED92, Cy2), (K6, ED92, Cy3), (K7, ED1, Cy1), (K7, ED1, Cy2), (K7, ED1, Cy3), (K7, ED2, Cy1), (K7, ED2, Cy2), (K7, ED2, Cy3), (K7, ED3, Cy1), (K7, ED3, Cy2), (K7, ED3, Cy3), (K7, ED4, Cy1), (K7, ED4, Cy2), (K7, ED4, Cy3), (K7, ED5, Cy1), (K7, ED5, Cy2), (K7, ED5, Cy3), (K7, ED5, Cy1), (K7, ED5, Cy2), (K7, ED6, Cy3), (K7, ED7, Cy1), (K7, ED7, Cy2), (K7, ED7, Cy3), (K7, ED5, Cy1), (K7, ED5, Cy2), (K7, ED5, Cy3), (K7, ED9, Cy1), (K7, ED9, Cy2), (K7, ED9, Cy3), (K7, ED10, Cy1), (K7, ED10, Cy2), (K7, ED10, Cy3), (K7, ED11, Cy1), (K7, ED11, Cy2), (K7, ED11, Cy3), (K7, ED12, Cy1), (K7, ED12, Cy2), (K7, ED12, Cy3), (K7, ED13, Cy1), (K7, ED13, Cy2), (K7, ED13, Cy3), (K7, ED14, Cy1), (K7, ED14, Cy2), (K7, ED14, Cy3), (K7, ED15, Cy1), (K7, ED15, Cy2), (K7, ED15, Cy3), (K7, ED16, Cy1), (K7, ED16, Cy2), (K7, ED16, Cy3), (K7, ED17, Cy1), (K7, ED17, Cy2), (K7, ED17, Cy3), (K7, ED18, Cy1), (K7, ED18, Cy2), (K7, ED18, Cy3), (K7, ED19, Cy1), (K7, ED19, Cy2), (K7, ED19, Cy3), (K7, ED20, Cy1), (K7, ED20, Cy2), (K7, ED20, Cy3), (K7, ED21, Cy1), (K7, ED21, Cy2), (K7, ED21, Cy3), (K7, ED22, Cy1), (K7, ED22, Cy2), (K7, ED22, Cy3), (K7, ED23, Cy1), (K7, ED23, Cy2), (K7, ED23, Cy3), (K7, ED24, Cy1), (K7, ED29, Cy2), (K7, ED24, Cy3), (K7, ED25, Cy1), (K7, ED25, Cy2), (K7, ED25, Cy3), (K7, ED26, Cy1), (K7, ED25, Cy2), (K7, ED26, Cy3), (K7, ED27, Cy1), (K7, ED27, Cy2), (K7, ED27, Cy3), (K7, ED28, Cy1), (K7, ED28, Cy2), (K7, ED28, Cy3), (K7, ED29, Cy1), (K7, ED29, Cy2), (K7, ED29, Cy3), (K7, ED30, Cy1), (K7, ED30, Cy2), (K7, ED30, Cy3), (K7, ED31, Cy1), (K7, ED31, Cy2), (K7, ED31, Cy3), (K7, ED32, Cy1), (K7, ED32, Cy2), (K7, ED32, Cy3), (K7, ED33, Cy1), (K7, ED33, Cy2), (K7, ED33, Cy3), (K7, ED34, Cy1), (K7, ED34, Cy2), (K7, ED34, Cy3), (K7, ED35, Cy1), (K7, ED35, Cy2), (K7, ED35, Cy3), (K7, ED36, Cy1), (K7, ED36, Cy2), (K7, ED36, Cy3), (K7, ED37, Cy1), (K7, ED37, Cy2), (K7, ED37, Cy3), (K7, ED38, Cy1), (K7, ED38, Cy2), (K7, ED38, Cy3), (K7, ED39, Cy1), (K7, ED39, Cy2), (K7, ED39, Cy3), (K7, ED40, Cy1), (K7, ED40, Cy2), (K7, ED40, Cy3), (K7, ED41, Cy1), (K7, ED41, Cy2), (K7, ED41, Cy3), (K7, ED42, Cy1), (K7, ED92, Cy2), (K7, ED42, Cy3), (K7, ED43, Cy1), (K7, ED43, Cy2), (K7, ED43, Cy3), (K7, ED44, Cy1), (K7, ED44, Cy2), (K7, ED44, Cy3), (K7, ED45, Cy1), (K7, ED45, Cy2), (K7, ED45, Cy3), (K7, ED46, Cy1), (K7, ED46, Cy2), (K7, ED46, Cy3), (K7, ED47, Cy1), (K7, ED47, Cy2), (K7, ED97, Cy3), (K7, ED48, Cy1), (K7, ED48, Cy2), (K7, ED48, Cy3), (K7, ED49, Cy1), (K7, ED49, Cy2), (K7, ED49, Cy3), (K7, ED50, Cy1), (K7, ED50, Cy2), (K7, ED50, Cy3), (K7, ED51, Cy1), (K7, ED51, Cy2), (K7, ED51, Cy3), (K7, ED52, Cy1), (K7, ED52, Cy2), (K7, ED52, Cy3), (K7, ED53, Cy1), (K7, ED53, Cy2), (K7, ED53, Cy3), (K7, ED54, Cy1), (K7, ED54, Cy2), (K7, ED54, Cy3), (K7, ED55, Cy1), (K7, ED55, Cy2), (K7, ED55, Cy3), (K7, ED56, Cy1), (K7, ED56, Cy2), (K7, ED56, Cy3), (K7, ED57, Cy1), (K7, ED57, Cy2), (K7, ED57, Cy3), (K7, ED58, Cy1), (K7, ED58, Cy2), (K7, ED58, Cy3), (K7, ED59, Cy1), (K7, ED59, Cy2), (K7, ED59, Cy3), (K7, ED60, Cy1), (K7, ED60, Cy2), (K7, ED60, Cy3), (K7, ED61, Cy1), (K7, ED61, Cy2), (K7, ED61, Cy3), (K7, ED62, Cy1), (K7, ED62, Cy2), (K7, ED62, Cy3) (K7, ED63, Cy1), (K7, ED63, Cy2), (K7, ED63, Cy3), (K7, ED64, Cy1), (K6, ED64, Cy2), (K7, ED64, Cy3), (K7, ED65, Cy1), (K7, ED65, Cy2), (K7, ED65, Cy3), (K7, ED66, Cy1), (K7, ED66, Cy2), (K7, ED66, Cy3), (K7, ED67, Cy1), (K7, ED67, Cy2), (K7, ED67, Cy3), (K7, ED68, Cy1), (K7, ED68, Cy2), (K7, ED68, Cy3), (K7, ED69, Cy1), (K7, ED69, Cy2), (K7, ED69, Cy3), (K7, ED70, Cy1), (K7, ED70, Cy2), (K7, ED70, Cy3), (K7, ED71, Cy1), (K7, ED71, Cy2), (K7, ED71, Cy3), (K7, ED72, Cy1), (K7,

ED72, Cy2), (K7, ED72, Cy3), (K7, ED73, Cy1), (K7, ED73, Cy2), (K7, ED73, Cy3), (K7, ED74, Cy1), (K7, ED74, Cy2), (K7, ED74, Cy3), (K7, ED75, Cy1), (K7, ED75, Cy2), (K7, ED75, Cy3), (K7, ED76, Cy1), (K7, ED76, Cy2), (K7, ED76, Cy3), (K7, ED77, Cy1), (K7, ED77, Cy2), (K7, ED77, Cy3), (K7, ED78, Cy1), (K7, ED78, Cy2), (K7, ED78, Cy3), (K7, ED79, Cy1), (K7, ED79, Cy2), (K7, ED79, Cy3), (K7, ED80, Cy1), (K7, ED80, Cy2), (K7, ED80, Cy3), (K7, ED81, Cy1), (K7, ED81, Cy2), (K7, ED81, Cy3), (K7, ED82, Cy1), (K7, ED82, Cy2), (K7, ED82, Cy3), (K7, ED83, Cy1), (K7, ED88, Cy2), (K7, ED83, Cy1), (K7, ED84, Cy1), (K7, ED84, Cy2), (K7, ED84, Cy3), (K7, ED85, Cy1), (K7, ED85, Cy2), (K7, ED85, Cy3), (K7, ED86, Cy1), (K7, ED86, Cy2), (K7, ED86, Cy3), (K7, ED87, Cy1), (K7, ED87, Cy2), (K7, ED87, Cy3), (K7, ED88, Cy1), (K7, ED88, Cy2), (K7, ED88, Cy3), (K7, ED89, Cy1), (K7, ED89, Cy2), (K7, ED89, Cy3), (K7, ED90, Cy1), (K7, ED90, Cy2), (K7, ED90, Cy3), (K7, ED91, Cy1), (K7, ED91, Cy2), (K7, ED91, Cy3), (K7, ED92, Cy1), (K7, ED92, Cy2), (K7, ED92, Cy3)

(K8, ED1, Cy1), (K8, ED1, Cy2), (K8, ED1, Cy3), (K8, ED2, Cy1), (K8, ED2, Cy2), (K8, ED2, Cy3), (K8, Cy1), (K8, ED3, Cy2), (K8, ED3, Cy3), (K8, Ed4, Cy1), (K8, ED4, Cy2), (K8, ED4, Cy3), (K8, ED5, Cy1), (K8, ED5, Cy2), (K8, ED5, Cy3), (K8, ED6, Cy1), (K8, ED6, Cy2), (K8, ED6, Cy3), (K5, ED7, Cy1), (K8, ED7, Cy2), (K8, ED7, Cy3), (K8, ED5, Cy1), (K8, ED8, Cy2), (K8, ED8, Cy3), (K8, ED9, Cy1), (K8, ED9, Cy2), (K8, ED9, Cy3), (K8, ED10, Cy1), (K8, ED10, Cy2), (K8, ED10, Cy3), (K8, ED11, Cy1), (K8, ED11, Cy2), (K8, ED11, Cy3), (K8, ED12, Cy1), (K8, ED12, Cy2), (K8, ED12, Cy3), (K8, ED13, Cy1), (K8, ED13, Cy2), (K8, ED13, Cy3), (K8, ED14, Cy1), (K8, ED14, Cy2), (K8, ED14, Cy3), (K8, ED15, Cy1), (K8, ED15, Cy2), (K8, ED15, Cy3), (K8, ED16, Cy1), (K8, ED16, Cy2), (K8, ED16, Cy3), (K8, ED17, Cy1), (K8, ED17, Cy2), (K8, ED17, Cy3), (K8, ED18, Cy1), (K8, ED18, Cy2), (K8, ED18, Cy3), (K8, ED19, Cy1), (K8, ED19, Cy2), (K8, ED19, Cy3), (K8, ED20, Cy1), (K8, ED20, Cy2), (K8, ED20, Cy3), (K8, ED21, Cy1), (K8, ED21, Cy2), (K8, ED21, Cy3), (K8, ED22, Cy1), (K8, ED22, Cy2), (K8, ED22, Cy3), (K8, ED23, Cy1), (K8, ED23, Cy2), (K8, ED23, Cy3), (K8, ED24, Cy1), (K8, ED24, Cy2), (K8, ED24, Cy3), (K8, ED25, Cy1), (K8, ED25, Cy2), (K8, ED25, Cy3), (K8, ED26, Cy1), (K8, ED26, Cy2), (K8, ED26, Cy3), (K8, ED27, Cy1), (K8, ED27, Cy2), (K8, ED27, Cy3), (K8, ED28, Cy1), (K8, ED28, Cy2), (K8, ED28, Cy3), (K8, ED29, Cy1), (K8, ED29, Cy2), (K8, ED29, Cy3), (K8, ED30, Cy1), (K8, ED30, Cy2), (K8, ED30, Cy3), (K8, ED31, Cy1), (K8, ED31, Cy2), (K8, ED31, Cy3), (K8, ED32, Cy1), (K8, ED32, Cy2), (K8, ED32, Cy3), (K8, ED33, Cy1), (K8, ED33, Cy2), (K8, ED33, Cy3), (K8, ED34, Cy1), (K8, ED34, Cy2), (K8, ED34, Cy3), (K8, ED35, Cy1), (K8, ED35, Cy2), (K8, ED35, Cy3), (K8, ED36, Cy1), (K8, ED36, Cy2), (K8, ED36, Cy3), (K8, ED37, Cy1), (K8, ED37, Cy2), (K8, ED37, Cy3), (K8, ED38, Cy1), (K8, ED38, Cy2), (K8, ED38, Cy3), (K8, ED39, Cy1), (K8, ED39, Cy2), (K8, ED39, Cy3), (K8, ED40, Cy1), (K8, ED40, Cy2), (K8, ED40, Cy3), (K8, ED41, Cy1), (K8, ED41, Cy2), (K8, ED11, Cy3), (K8, ED42, Cy1), (K8, ED42, Cy2), (K8, ED42, Cy3), (K8, ED43, Cy1), (K8, ED43, Cy2), (K8, ED43, Cy3), (K8, ED44, Cy1), (K8, ED44, Cy2), (K8, ED44, Cy3), (K8, ED45, Cy1), (K8, ED45, Cy2), (K8, ED45, Cy3), (K8, ED46, Cy1), (K8, ED46, Cy2), (K8, ED46, Cy3), (K8, ED47, Cy1), (K8, ED47, Cy2), (K8, ED47, Cy3), (K8, ED48, Cy1), (K8, ED5, Cy2), (K8, ED48, Cy3), (K8, ED49, Cy1), (K8, ED49, Cy2), (K8, ED49, Cy3), (K8, ED50, Cy1), (K8, ED50, Cy2), (K8, ED50, Cy3), (K8, ED51, Cy1), (K8, ED51, Cy2), (K8, ED52, Cy1), (K8, ED52, Cy2), (K8, ED52, Cy3), (K8, ED53, Cy1), (K8, ED53, Cy2), (K8, ED53, Cy3), (K8, ED54, Cy1), (K8, ED54, Cy2), (K8, ED54, Cy3), (K8, ED55, Cy1), (K8, ED55, Cy2), (K8, ED55, Cy3), (K8, ED56, Cy1), (K8, ED56, Cy2), (K8, ED56, Cy3), (K8, ED57, Cy1), (K8, ED57, Cy2), (K8, ED57, Cy3), (K8, ED58, Cy1), (K8, ED58, Cy2), (K8, ED55, Cy3), (K8, ED59, Cy1), (K8, ED59, Cy2), (K8, ED59, Cy3), (K8, ED60, Cy1), (K8, ED60, Cy2), (K8, ED60, Cy3), (K8, ED61, Cy1), (K8, ED61, Cy2), (K8, ED61, Cy3), (K8, ED62, Cy1), (K8, ED62, Cy2), (K8, ED62, Cy3), (K8, ED63, Cy1), (K8, ED63, Cy2), (K8, ED63, Cy3), (K8, ED64, Cy1), (K8, ED64, Cy2), (K8, ED64, Cy3), (K8, ED65, Cy1), (K8, ED65, Cy2), (K8, ED65, Cy3), (K8, ED66, Cy1), (K8, ED65, Cy2), (K8, ED66, Cy3), (K8, ED67, Cy1), (K8, ED67, Cy2), (K8, ED67, Cy3), (K8, ED68, Cy1), (K8, ED68, Cy2), (K8, ED68, Cy3), (K8, ED69, Cy1), (K8, ED69, Cy2), (K2, ED69, Cy3), (K8, ED70, Cy1), (K8, ED70, Cy2), (K8, ED70, Cy3), (K8, ED71, Cy1), (K8, ED71, Cy2), (K8, ED71, Cy3), (K8, ED72, Cy1), (K8, ED72, Cy2), (K8, ED72, Cy3), (K8, ED73, Cy1), (K8, ED73, Cy2), (K8, ED73, Cy3), (K8, ED74, Cy1), (K8, ED74, Cy2), (K8, ED74, Cy3), (K8, ED75, Cy1), (K8, ED75, Cy2), (K8, ED75, Cy3), (K8, ED76, Cy1), (K8, ED76, Cy2), (K8, ED76, Cy3), (K8, ED77, Cy1), (K8, ED77, Cy2), (K8, ED77, Cy3), (K8, ED7S, Cy1), (K8, ED78, Cy2), (K8, ED78, Cy3), (K8, ED79, Cy1), (K8, ED79, Cy2), (K8, ED79, Cy3), (K8, ED80, Cy1), (K8, ED80, Cy2), (K8, ED80, Cy3), (K8, ED81, Cy1), (K8, ED81, Cy2), (K8, ED81, Cy3), (K8, ED82, Cy1), (K8, ED82, Cy2), (K8, ED82, Cy3), (K8, ED83, Cy1), (K8, ED83, Cy2), (K8, ED83, Cy3), (K8, ED84, Cy1), (K8, ED84, Cy2), (K8, ED84, Cy3), (K8, ED85, Cy1), (K8, ED85, Cy2), (K8, ED85, Cy3), (K8, ED86, Cy1), (K8, ED86, Cy2), (K8, ED86, Cy3), (K8, ED87, Cy1), (K8, ED87, Cy2), (K8, ED87, Cy3), (K8, ED88, Cy1), (K8, ED88, Cy2), (K8, ED88, Cy3), (K8, ED89, Cy1), (K8, ED89, Cy2), (K8, ED89, Cy3), (K8, ED90, Cy1), (K8, ED90, Cy2), (K8, ED90, Cy3), (K8, ED91, Cy1), (K8, ED91, Cy2), (K8, ED91, Cy3), (K8, ED92, Cy1), (K8, ED92, Cy2), (K8, ED92, Cy3), (K9, ED1, Cy1), (K9, ED1, Cy2), (K9, ED1, Cy3), (K9, ED2, Cy1), (K9, ED2, Cy2), (K9, ED2, Cy3), (K9, ED3, Cy1), (K9, ED3, Cy2), (K9, ED3, Cy3), (K9, ED4, Cy1), (K9, ED4, Cy2), (K9, ED4, Cy3), (K9, ED5, Cy1), (K9, ED5, Cy2), (K9, ED5, Cy3), (K9, ED6, Cy1), (K9, ED6, Cy2), (K9, ED6, Cy3), (K9, ED7, Cy1), (K9, ED7, Cy2), (K9, ED7, Cy3), (K9, ED8, Cy1), (K9, ED8, Cy2), (K9, ED5, Cy3), (K9, ED9, Cy1), (K9, ED9, Cy2), (K9, ED9, Cy3), (K9, ED10, Cy1), (K9, ED10, Cy2), (K9, ED10, Cy3), (K9, ED11, Cy1), (K9, ED11, Cy2), (K9, ED11, Cy3), (K9, ED12, Cy1), (K9, ED12, Cy2), (K9, ED12, Cy3), (K9, ED13, Cy1), (K9, ED13, Cy2), (K9, ED13, Cy3), (K9, ED14, Cy1), (K9, ED14, Cy2), (K9, ED14, Cy3), (K9, ED15, Cy1), (K9, ED15, Cy2), (K9, ED15, Cy3), (K9, ED16, Cy1), (K9, ED16, Cy2), (K9, ED16, Cy3), (K9, ED17, Cy1), (K9, ED17, Cy2), (K9, ED17, Cy3), (K9, ED18, Cy1), (K9, ED18, Cy2), (K9, ED18, Cy3), (K9, ED19, Cy1), (K9, ED19, Cy2), (K9, ED19, Cy3), (K9, ED20, Cy1), (K9, ED20, Cy2), (K9, ED20, Cy3), (K9, ED21, Cy1), (K9, ED21, Cy2), (K9, ED21, Cy3), (K9, ED22, Cy1), (K9, ED22, Cy2), (K9, ED22, Cy3), (K9, ED23, Cy1), (K9, ED23, Cy2), (K9, ED23, Cy3), (K9, ED24, Cy1), (K9, ED24, Cy2), (K9, ED24, Cy3), (K9, ED25, Cy1), (K9, ED25, Cy2), (K9, ED25, Cy3), (K9, ED26, Cy1), (K9, ED26, Cy2), (K9, ED26, Cy3), (Kg, ED27, Cy1), (K9, ED27, Cy2), (K9, ED27, Cy3), (K9, ED28, Cy1), (K9, ED28, Cy2), (K9, ED28, Cy3), (K9, ED29, Cy1), (K9, ED29, Cy2), (K9, ED29, Cy3), (K9, ED30, Cy1), (K9, ED30, Cy2), (K9, ED30, Cy3), (K9, ED31, Cy1), (K9, ED31, Cy2), (K9, ED31, Cy3), (K9, ED32, Cy1), (K9, ED32, Cy2), (K9, ED32, Cy3), (K9, ED33, Cy1), (K9, ED33, Cy2), (K9, ED33, Cy3), (K9, ED34, Cy1), (K9, ED34, Cy2), (K9, ED34, Cy3), (K9, ED35, Cy1), (K9, ED35, Cy2), (K9, ED35, Cy3), (K9, ED36, Cy1), (K9, ED36, Cy2), (K9, ED36,

Cy3), (K9, ED37, Cy1), (K9, ED37, Cy2), (K9, ED37, Cy3), (K9, ED38, Cy1), (K9, ED38, Cy2), (K9, ED38, Cy3), (K9, ED39, Cy1), (K9, ED39, Cy2), (K9, ED39, Cy3), (K9, ED40, Cy1), (K9, ED40, Cy2), (K9, ED40, Cy3), (K9, ED41, Cy1), (K9, ED41, Cy2), (K9, ED41, Cy3), (K9, ED42, Cy1), (K9, ED42, Cy2), (K9, ED42, Cy3), (K9, ED43, Cy1), (K9, ED43, Cy2), (K9, ED43, Cy3), (K9, ED44, Cy1), (K9, ED44, Cy2), (K9, ED44, Cy3), (K9, ED45, Cy1), (K9, ED45, Cy2), (K9, ED45, Cy3), (K9, ED46, Cy1), (K9, ED46, Cy2), (K9, ED46, Cy3), (K9, ED47, Cy1), (K9, ED47, Cy2), (K9, ED47, Cy3), (K9, ED48, Cy1), (K9, ED48, Cy2), (K9, ED48, Cy3), (K9, ED49, Cy1), (K9, ED19, Cy2), (K9, ED49, Cy3), (K9, ED50, Cy1), (K9, ED50, Cy2), (K9, ED50, Cy3), (K9, ED51, Cy1), (K9, ED51, Cy2), (K9, ED51, Cy3), (K9, ED52, Cy1), (K9, ED52, Cy2), (K9, ED52, Cy3), (K9, ED53, Cy1), (K9, ED53, Cy2), (K9, ED53, Cy3), (K9, ED54, Cy1), (K9, ED54, Cy2), (K9, ED54, Cy3), (K9, ED55, Cy1), (K9, ED55, Cy2), (K9, ED55, Cy3), (K9, ED56, Cy1), (K9, ED56, Cy2), (K9, ED56, Cy3), (K9, ED57, Cy1), (K9, ED57, Cy2), (K9, ED57, Cy3), (K9, ED58, Cy1), (K9, ED58, Cy2), (K9, ED58, Cy3), (K9, ED59, Cy1), (K9, ED5S, Cy2), (K9, ED59, Cy3), (K9, ED60, Cy1), (K9, ED60, Cy2), (K9, ED60, Cy3), (K9, ED61, Cy1), (K9, ED61, Cy2), (K9, ED61, Cy3), (K9, ED62, Cy1), (K9, ED62, Cy2), (K9, ED62, Cy3), (K9, ED63, Cy1), (K9, ED63, Cy2), (K9, ED63, Cy3), (K9, ED64, Cy1), (K9, ED64, Cy2), (K9, ED64, Cy3), (K9, ED65, Cy1), (K9, ED65, Cy2), (K9, ED65, Cy3), (K9, ED66, Cy1), (K9, ED66, Cy2), (K9, ED66, Cy3), (K9, ED67, Cy1), (K9, ED67, Cy2), (K9, ED67, Cy3), (K9, ED68, Cy1), (K9, ED68, Cy2), (K9, ED68, Cy3), (K9, ED69, Cy1), (K9, ED69, Cy2), (K9, ED69, Cy3), (K9, ED70, Cy1), (K9, ED70, Cy2), (K9, ED70, Cy3), (K9, ED71, Cy1), (K9, ED71, Cy2), (K9, ED71, Cy3), (K9, ED72, Cy1), (K9, ED72, Cy2), (K9, ED72, Cy3), (K9, ED73, Cy1), (K9, ED73, Cy2), (K9, ED73, Cy3), (K9, ED74, Cy1), (K9, ED74, Cy2), (K9, ED74, Cy3), (By, ED75, Cy1), (K9, ED75, Cy2), (K9, ED75, Cy3), (K9, ED76, Cy1), (K9, ED76, Cy2), (K9, ED76, Cy3), (K9, ED77, Cy1), (K9, ED77, Cy2), (K9, ED77, Cy3), (K9, ED78, Cy1), (K9, ED78, Cy2), (K9, ED78, Cy3), (K9, ED79, Cy1), (K9, ED79, Cy2), (K9, ED79, Cy3), (K9, ED80, Cy1), (K9, ED80, Cy2), (K9, ED80, Cy3), (K9, ED81, Cy1), (K9, ED81, Cy2), (K9, ED81, Cy3), (K9, ED82, Cy1), (K9, ED82, Cy2), (K9, ED82, Cy3), (K9, ED83, Cy1), (K9, ED83, Cy2), (K9, ED83, Cy3), (K9, ED84, Cy1), (K9, ED84, Cy2), (K9, ED84, Cy3), (K9, ED85, Cy1), (K9, ED85, Cy2), (K9, ED85, Cy3), (K9, ED86, Cy1), (K9, ED86, Cy2), (K9, ED86, Cy3), (K9, ED87, Cy1), (K9, ED87, Cy2), (K9, ED87, Cy3), (K9, ED88, Cy1), (K9, ED88, Cy2), (K9, ED88, Cy3), (K9, ED89, Cy1), (K9, ED89, Cy2), (K9, ED89, Cy3), (K9, ED90, Cy1), (K9, ED90, Cy2), (K9, ED90, Cy3), (K9, ED91, Cy1), (K9, ED91, Cy2), (K9, ED91, Cy3), (K9, ED92, Cy1), (K9, ED92, Cy2), (K9, ED92, Cy3), (K10, ED1, Cy1), (K10, ED1, Cy2), (K10, ED1, Cy3), (K10, ED2, Cy1), (K10, ED2, Cy2), (K10, ED2, Cy3), (K10, ED3, Cy1), (K10, ED3, Cy2), (K10, ED3, Cy3), (K10, ED4, Cy1), (K10, ED4, Cy2), (K10, ED4, Cy3), (K10, ED5, Cy1), (K10, ED5, Cy2), (K10, ED5, Cy3), (K10, ED6, Cy1), (K10, ED6, Cy2), (K10, ED6, Cy3), (K10, ED7, Cy1), (K10, ED7, Cy2), (K10, ED7, Cy3), (K10, ED8, Cy1), (K10, ED8, Cy2), (K10, ED8, Cy3), (K10, ED9, Cy1), (K10, ED9, Cy2), (K10, ED9, Cy3), (K10, ED10, Cy1), (K10, ED10, Cy2), (K10, ED10, Cy3), (K10, ED11, Cy1), (K10, ED11, Cy2), (K10, ED11, Cy3), (K10, ED12, Cy1), (K10, ED12, Cy2), (K10, ED1.2, Cy3), (K10, ED13, Cy1), (K10, ED13, Cy2), (K10, ED13, Cy3), (K10, ED14, Cy1), (K10, ED14, Cy2), (K10, ED14, Cy3), (K10, ED15, Cy1), (K10, ED15, Cy2), (K10, ED15, Cy3), (K10, ED16, Cy1), (K10, ED16, Cy2), (K10, ED16, Cy3), (K10, ED17, Cy1), (K10, ED17, Cy2), (K10, ED17, Cy3), (K10, ED18, Cy1), (K10, ED18, Cy2), (K10, ED18, Cy3), (K10, ED19, Cy1), (K10, ED19, Cy2), (K10, ED19, Cy3), (K10, ED20, Cy1), (K10, ED20, Cy2), (K10, ED20, Cy3), (K10, ED21, Cy1), (K10, ED21, Cy2), (K10, ED21, Cy3), (K10, ED22, Cy1), (K10, ED22, Cy2), (K10, ED22, Cy3), (K10, ED23, Cy1), (K10, ED23, Cy2), (K10, ED23, Cy3), (K10, ED24, Cy1), (K10, ED24, Cy2), (K10, ED24, Cy3), (K10, ED25, Cy1), (K10, ED25, Cy2), (K10, ED25, Cy3), (K10, ED26, Cy1), (K10, ED26, Cy2), (K10, ED26, Cy3), (K10, ED27, Cy1), (K10, ED27, Cy2), (K10, ED27, Cy3), (K10, ED28, Cy1), (K10, ED28, Cy2), (K10, ED28, Cy3), (K10, ED29, Cy1), (K10, ED29, Cy2), (K10, ED29, Cy3), (K10, ED30, Cy1), (K10, ED30, Cy2), (K10, ED30, Cy3), (K10, ED31, Cy1), (K10, ED31, Cy2), (K10, ED31, Cy3), (K10, ED32, Cy1), (K10, ED32, Cy2), (K10, ED32, Cy3), (K10, ED33, Cy1), (K10, ED33, Cy2), (K10, ED33, Cy3), (K10, ED34, Cy1), (K10, ED34, Cy2), (K10, ED34, Cy3), (K10, ED35, Cy1), (K10, ED35, Cy2), (K10, ED35, Cy3), (K10, ED36, Cy1), (K10, ED36, Cy2), (K10, ED36, Cy3), (K10, ED37, Cy1), (K10, ED37, Cy2), (K10, ED37, Cy3), (K10, ED38, Cy1), (K10, ED38, Cy2), (K10, ED38, Cy3), (K10, ED39, Cy1), (K10, ED39, Cy2), (K10, ED39, Cy3), (K10, ED40, Cy1), (K10, ED40, Cy2), (K10, ED40, Cy3), (K10, ED41, Cy1), (K10, ED41, Cy2), (K10, ED41, Cy3), (K10, ED42, Cy1), (K10, ED42, Cy2), (K10, ED42, Cy3), (K10, ED43, Cy1), (K10, ED43, Cy2), (K10, ED43, Cy3), (K10, ED44, Cy1), (K10, ED44, Cy2), (K10, ED44, Cy3), (K10, ED45, Cy1), (K10, ED45, Cy2), (K10, ED45, Cy3), (K10, ED46, Cy1), (K10, ED46, Cy2), (K10, ED46, Cy3), (K10, ED47, Cy1), (K10, ED47, Cy2), (K10, ED47, Cy3), (K10, ED48, Cy1), (K10, ED48, Cy2), (K10, ED48, Cy3), (K10, ED49, Cy1), (K10, ED49, Cy2), (K10, ED49, Cy3), (K10, ED50, Cy1), (K10, ED50, Cy2), (K10, ED50, Cy3), (K10, ED51, Cy1), (K10, ED51, Cy2), (K10, ED51, Cy3), (K10, ED52, Cy1), (K10, ED52, Cy2), (K10, ED52, Cy3), (K10, ED53, Cy1), (K10, ED53, Cy2), (K10, ED53, Cy3), (K10, ED54, Cy1), (K10, ED54, Cy2), (K10, ED54, Cy3), (K10, ED55, Cy1), (K10, ED55, Cy2), (K10, ED55, Cy3), (K10, ED56, Cy1), (K10, ED56, Cy2), (K10, ED56, Cy3), (K10, ED57, Cy1), (K10, ED57, Cy2), (K10, ED57, Cy3), (K10, ED58, Cy1), (K10, ED58, Cy2), (K10, ED58, Cy3), (K10, ED59, Cy1), (K10, ED59, Cy2), (K10, ED59, Cy3), (K10, ED60, Cy1), (K10, ED60, Cy2), (K10, ED60, Cy3), (K10, ED61, Cy1), (K10, ED61, Cy2), (K10, ED61, Cy3), (K10, ED62, Cy1), (K10, ED62, Cy2), (K10, ED62, Cy3), (K10, ED63, Cy1), (K10, ED63, Cy2), (K10, ED63, Cy3), (K10, ED64, Cy1), (K10, ED64, Cy2), (K10, ED64, Cy3), (K10, ED65, Cy1), (K10, ED65, Cy2), (K10, ED65, Cy3), (K10, ED66, Cy1), (K10, ED66, Cy2), (K10, ED66, Cy3), (K10, ED67, Cy1), (K10, ED67, Cy2), (K10, ED67, Cy3), (K10, ED68, Cy1), (K10, ED68, Cy2), (K10, ED68, Cy3), (K10, ED69, Cy1), (K10, ED69, Cy2), (K10, ED69, Cy3), (K10, ED70, Cy1), (K10, ED70, Cy2), (K10, ED70, Cy3), (K10, ED71, Cy1), (K10, ED71, Cy2), (K10, ED71, Cy3), (K10, ED72, Cy1), (K10, ED72, Cy2), (K10, ED72, Cy3), (K10, ED73, Cy1), (K10, ED73, Cy2), (K10, ED73, Cy3), (K10, ED74, Cy1), (K10, ED74, Cy2), (K10, ED74, Cy3), (K10, ED75, Cy1), (K10, ED75, Cy2), (K10, ED75, Cy3), (K10, ED76, Cy1), (K10, ED76, Cy2), (K10, ED76, Cy3), (K10, ED77, Cy1), (K10, ED77, Cy2), (K10, ED77, Cy3), (K10, ED78, Cy1), (K10, ED78, Cy2), (K10, ED78, Cy3), (K10, ED79, Cy1), (K10, ED79, Cy2), (K10, ED79, Cy3), (K10, ED80, Cy1), (K10, ED80, Cy2), (K10, ED80, Cy3), (K10, ED81, Cy1), (K10, ED81, Cy2), (K10, ED81, Cy3), (K10, ED82, Cy1), (K10, ED82, Cy2), (K10, ED82, Cy3), (K10, ED83, Cy1), (K10, ED83, Cy2), (K10, ED83, Cy3), (K10, ED84, Cy1), (K10, ED84, Cy2), (K10,

ED84, Cy3), (K10, ED85, Cy1), (K10, ED85, Cy2), (K10, ED85, Cy3), (K10, ED86, Cy1), (K10, ED86, Cy2), (K10, ED86, Cy3), (K10, ED87, Cy1), (K10, ED87, Cy2), (K10, ED87, Cy3), (K10, ED88, Cy1), (K10, ED88, Cy2), (K10, ED88, Cy3), (K10, ED89, Cy1), (K10, ED89, Cy2), (K10, ED89, Cy3), (K10, ED90, Cy1), (K10, ED90, Cy2), (K10, ED90, Cy3), (K10, ED91, Cy1), (K10, ED91, Cy2), (K10, ED91, Cy3), (K10, ED92, Cy1), (K10, ED92, Cy2), (K10, ED92, Cy3), (K11, ED1, Cy1), (K11, ED1, Cy2), (K11, ED1, Cy3), (K11, ED2, Cy1), (K11, ED2, Cy2), (K11, ED2, Cy3), (K11, ED3, Cy1), (K11, ED3, Cy2), (K11, ED3, Cy3), (K11, ED4, Cy1), (K11, ED4, Cy2), (K11, ED4, Cy3), (K11, ED5, Cy1), (K11, ED5, Cy2), (K11, ED5, Cy3), (K11, ED6, Cy1), (K11, ED6, Cy2), ED6, Cy3), (K11, ED7, Cy1), (K11, ED7, Cy2), (K11, ED7, Cy3), (K11, ED8, Cy1), (K11, ED8, Cy2), (K11, ED8, Cy3), (K11, ED9, Cy1), (K11, ED9, Cy2), (K11, ED9, Cy3), (K11, ED10, Cy1), (K11, ED10, Cy2), (K11, ED10, Cy3), (K11, ED11, Cy1), (K11, ED11, Cy2), ED11, Cy3), (K11, ED12, Cy1), (K11, ED12, Cy2), (K11, ED12, Cy3), (K11, ED13, Cy1), (K11, ED13, Cy2), (K11, ED13, Cy3), (K11, ED14, Cy1), (K11, ED14, Cy2), (K11, ED14, Cy3), (K11, ED15, Cy1), (K11, ED15, Cy2), (K11, ED15, Cy3), (K11, ED16, Cy1), (K11, ED16, Cy2), (K11, ED16, Cy3), ED17, Cy1), (K11, ED17, Cy2), (K11, ED17, Cy3), (K11, ED18, Cy1), (K11, ED18, Cy2), (K11, ED18, Cy3), (K11, ED19, Cy1), (K11, ED19, Cy2), (K11, ED19, Cy3), (K11, ED20, Cy1), (K11, ED20, Cy2), (K11, ED20, Cy3), (K11, ED21, Cy1), (K11, ED21, Cy2), (K11, ED21, Cy3), (K11, ED22, Cy1), (K11, ED22, Cy2), (K11, ED22, Cy3), (K11, ED23, Cy1), (K11, ED23, Cy2), (K11, ED23, Cy3), (K11, ED24, Cy1), (K11, ED24, Cy2), (K11, ED24, Cy3), (K11, ED25, Cy1), (K11, ED25, Cy2), (K11, ED25, Cy3), (K11, ED26, Cy1), (K11, ED26, Cy2), (K11, ED26, Cy3), (K11, ED27, Cy1), (K11, ED27, Cy2), (K11, ED27, Cy3), (K11, ED28, Cy1), (K11, ED28, Cy2), (K11, ED28, Cy3), (K11, ED29, Cy1), (K11, ED29, Cy2), (K11, ED29, Cy3), (K11, ED30, Cy1), (K11, ED30, Cy2), (K11, ED30, Cy3), (K11, ED31, Cy1), (K11, ED31, Cy2), (K11, ED31, Cy3), (K11, ED32, Cy1), (K11, ED32, Cy2), (K11, ED32, Cy3), (K11, ED33, Cy1), (K11, ED33, Cy2), (K11, ED33, Cy3), (K11, ED34, Cy1), (K11, ED34, Cy2), (K11, ED34, Cy3), (K11, ED35, Cy1), (K11, ED35, Cy2), (K11, ED35, Cy3), (K11, ED36, Cy1), (K11, ED36, Cy2), (K11, ED36, Cy3), (K11, ED37, Cy1), (K11, ED37, Cy2), (K11, ED37, Cy3), (K11, ED38, Cy1), (K11, ED38, Cy2), (K11, ED38, Cy3), (K11, ED39, Cy1), (K11, ED39, Cy2), (K11, ED39, Cy3), (K11, ED40, Cy1), (K11, ED40, Cy2), (K11, ED40, Cy3), (K11, ED41, Cy1), (K11, ED41, Cy2), (K11, ED41, Cy3), (K11, ED42, Cy1), (K11, ED42, Cy2), (K11, ED42, Cy3), (K11, ED43, Cy1), (K11, ED43, Cy2), (K11, ED43, Cy3), (K11, ED44, Cy1), (K11, ED44, Cy2), (K11, ED44, Cy3), (N11, ED45, Cy1), (K11, ED45, Cy2), (K11, ED45, Cy3), (K11, ED46, Cy1), (K11, ED46, Cy2), (K11, ED46, Cy3), (K11, ED47, Cy1), (K11, ED47, Cy2), (K11, ED47, Cy3), (K11, ED48, Cy1), (K11, ED48, Cy2), (K11, ED48, Cy3), (K11, ED49, Cy1), (K11, ED49, Cy2), (K11, ED49, Cy3), (K11, ED50, Cy1), (K11, ED50, Cy2), (K11, ED50, Cy3), (K11, ED51, Cy1), (K11, ED51, Cy2), (K11, ED51, Cy3), (K11, ED52, Cy1), (K11, ED52, Cy2), (K11, ED52, Cy3), (K11, ED53, Cy1), (K11, ED53, Cy2), (K11, ED53, Cy3), (K11, ED51, Cy1), (K11, ED54, Cy2), (K11, ED54, Cy3), (K11, ED55, Cy1), (K11, ED55, Cy2), (K11, ED55, Cy3), (K11, ED56, Cy1), (K11, ED56, Cy2), (K11, ED56, Cy3), (K11, ED57, Cy1), (K11, ED57, Cy2), (K11, ED57, Cy3), (K11, ED58, Cy1), (K11, ED58, Cy2), (K11, ED58, Cy3), (K11, ED59, Cy1), (K11, ED59, Cy2), (K11, ED59, Cy3), (K11, ED60, Cy1), (K11, ED60, Cy2), (K11, ED60, Cy3), (K11, ED61, Cy1), (K11, ED61, Cy2), (K11, ED61, Cy3), (K11, ED62, Cy1), (K11, ED62, Cy2), (K11, ED62, Cy3), (K11, ED63, Cy1), (K11, ED63, Cy2), (K11, ED63, Cy3), (K11, ED64, Cy1), (K11, ED64, Cy2), (K11, ED64, Cy3), (K1, ED65, Cy1), (K11, ED65, Cy2), (K11, ED65, Cy3), (K11, ED66, Cy1), (K11, ED66, Cy2), (K11, ED66, Cy3), (K11, ED67, Cy1), (K11, ED67, Cy2), (K11, ED67, Cy3), (K11, ED68, Cy1), (K11, ED68, Cy2), (K11, ED68, Cy3), (K11, ED69, Cy1), (K11, ED69, Cy2), (K11, ED69, Cy3), (K11, ED70, Cy1), (K11, ED70, Cy2), (K11, ED70, Cy3), (K11, ED71, Cy1), (K11, ED71, Cy2), (K11, ED71, Cy3), (K11, ED72, Cy1), (K11, ED72, Cy2), (K11, ED72, Cy3), (K11, ED73, Cy1), (K11, ED73, Cy2), (K11, ED73, Cy3), (K11, ED74, Cy1), (K11, ED74, Cy2), (K11, ED74, Cy3), (K11, ED75, Cy1), (K11, ED75, Cy2), (K11, ED75, Cy3), (K11, ED76, Cy1), (K11, ED76, Cy2), (K11, ED76, Cy3), (K11, ED77, Cy1), (K11, ED77, Cy2), (K11, ED77, Cy3), (K11, ED78, Cy1), (K11, ED78, Cy2), (K11, ED78, Cy3), (K11, ED79, Cy1), (K11, ED79, Cy2), (K11, ED79, Cy3), (K11, ED80, Cy1), (K11, ED80, Cy2), (K11, ED80, Cy3), (K11, ED81, Cy1), (K11, ED81, Cy2), (K11, ED81, Cy3), (K11, ED82, Cy1), (K11, ED82, Cy2), (K11, ED82, Cy3), (K11, ED83, Cy1), (K11, ED83, Cy2), (K11, ED83, Cy3), (K11, ED84, Cy1) (K11, ED84, Cy2), (K11, ED84, Cy3), (K11, ED85, Cy1), (K11, ED85, Cy2), (K11, ED85, Cy3), (K11, ED86, Cy1), (K11, ED86, Cy2), (K11, ED86, Cy3), (K11, ED87, Cy1), (K11, ED87, Cy2), (K11, ED87, Cy3), (K11, ED88, Cy1), (K11, ED88, Cy2), (K11, ED88, Cy3), (K11, ED89, Cy1), (K11, ED89, Cy2), (K11, ED89, Cy3), (K11, ED90, Cy1), (K11, ED90, Cy2), (K11, ED90, Cy3), (K11, ED91, Cy1), (K11, ED91, Cy2), (K11, ED91, Cy3), (K11, ED92, Cy1), (K11, ED92, Cy2), (K11, ED92, Cy3)
(K12, ED1, Cy1), (K12, ED1, Cy2), (K12, ED1, Cy3), (K12, ED2, Cy1), (K12, ED2, Cy2), (K12, ED2, Cy3), (K12, ED3, Cy1), (K12, ED3, Cy2), (K12, ED3, Cy3), (K12, ED4, Cy1), (K12, ED4, Cy2), (K12, ED4, Cy3), (K12, ED5, Cy1), (K12, ED5, Cy2), (K12, ED5, Cy3), (K12, ED6, Cy1), (K12, ED6, Cy2), (K12, ED6, Cy3), (K12, ED7, Cy1), (K12, ED7, Cy2), (K12, ED7, Cy3), (K12, ED5, Cy1), (K12, ED5, Cy2), (K12, ED5, Cy3), (K12, ED9, Cy1), (K12, ED9, Cy2), (K12, ED9, Cy3), (K12, ED10, Cy1), (K12, ED10, Cy2), (K12, ED10, Cy3), (K12, ED11, Cy1), (K12, ED11, Cy2), (K12, ED11, Cy3), (K12, ED12, Cy1), (K12, ED12, Cy2), (K12, ED12, Cy3), (K12, ED13, Cy1), (K12, ED13, Cy2), (K12, ED13, Cy3), (K12, ED14, Cy1), (K12, ED14, Cy2), (K12, ED14, Cy3), (K12, ED15, Cy1), (K12, ED15, Cy2), (K12, ED15, Cy3), (K12, ED16, Cy1), (K12, ED16, Cy2), (K12, ED16, Cy3), (K12, ED17, Cy1) (K12, ED17, Cy2), (K12, ED17, Cy3), (K12, ED18, Cy1), (K12, ED18, Cy2), (K12, ED18, Cy3), (K12, ED19, Cy1), (K12, ED19, Cy2), (K12, ED19, Cy3) (K12, ED20, Cy1), (K12, ED20, Cy2), (K12, ED20, Cy3), (K12, ED21, Cy1), (K12, ED21, Cy2), (K12, ED21, Cy3), (K12, ED22, Cy1), (K12, ED22, Cy2), (K12, ED22, Cy3), (K12, ED23, Cy1), (K12, ED23, Cy2), (K12, ED23, Cy3), (K12, ED24, Cy1), (K12, ED24, Cy2), (K12, ED24, Cy3), (K12, ED25, Cy1), (K12, ED25, Cy2), (K12, ED25, Cy3), (K12, ED26, Cy1), (K12, ED26, Cy2), (K12, ED26, Cy3), (K12, ED27, Cy1), (K12, ED27, Cy2), (K12, ED27, Cy3), (K12, ED28, Cy1), (K12, ED28, Cy2), (K12, ED28, Cy3), (K12, ED29, Cy1), (K12, ED29, Cy2), (K12, ED29, Cy3), (K12, ED30, Cy1), (K12, ED30, Cy2), (K12, ED30, Cy3), (K12, ED31, Cy1), (K12, ED31, Cy2), (K12, ED31, Cy3), (K12, ED32, Cy1), (K12, ED32, Cy2), (K12, ED32, Cy3), (K12, ED33, Cy1), (K12, ED33, Cy2), (K12, ED33, Cy3), (K12, ED34, Cy1), (K12, ED34, Cy2), (K12, ED34, Cy3), (K12, ED35, Cy1), (K12, ED35, Cy2), (K12, ED35, Cy3), (K12, ED36, Cy1), (K12, ED36, Cy2), (K12,

ED36, Cy3), (K12, ED37, Cy1), (K12, ED37, Cy2), (K12, ED37, Cy3), (K12, ED38, Cy1), (K12, ED38, Cy2), (K12, ED38, Cy3), (K12, ED39, Cy1), (K12, ED39, Cy2), (K12, ED39, Cy3), (K12, ED40, Cy1), (K12, ED40, Cy2), (K12, ED40, Cy3), (K12, ED41, Cy1), (K12, ED41, Cy2), (K12, ED41, Cy3), (K12, ED42, Cy1), (K12, ED42, Cy2), (K12, ED42, Cy3), (K12, ED43, Cy1), (K12, ED43, Cy2), (K12, ED43, Cy3), (K12, ED44, Cy1), (K12, ED44, Cy2), (K12, ED44, Cy3), (K12, ED45, Cy1), (K12, ED45, Cy2), (K12, ED45, Cy3), (K12, ED46, Cy1), (K12, ED46, Cy2), (K12, ED46, Cy3), (K12, ED47, Cy1), (K12, ED47, Cy2), (K12, ED47, Cy3), (K12, ED48, Cy1), (K12, ED48, Cy2), (K12, ED48, Cy3), (K12, ED49, Cy1), (K12, ED49, Cy2), (K12, ED49, Cy3), (K12, ED50, Cy1), (K12, ED50, Cy2), (K12, ED50, Cy3), (K12, ED51, Cy1), (K12, ED51, Cy2), (K12, ED51, Cy3), (K12, ED52, Cy1), (K12, ED52, Cy2), (K12, ED52, Cy3), (K12, ED53, Cy1), (K12, ED53, Cy2), (K12, ED53, Cy3), (K12, ED54, Cy1), (K12, ED54, Cy2), (K12, ED54, Cy3), (K12, ED55, Cy1), (K12, ED55, Cy2), (K12, ED55, Cy3), (K12, ED56, Cy1), (K12, ED56, Cy2), (K12, ED56, Cy3), (K12, ED57, Cy1), (K12, ED57, Cy2), (K12, ED57, Cy3), (K12, ED58, Cy1), (K12, ED58, Cy2), (K12, ED58, Cy3), (K12, ED59, Cy1), (K12, ED59, Cy2), (K12, ED59, Cy3), (K12, ED60, Cy1), (K12, ED60, Cy2), (K12, ED60, Cy3), (K12, ED61, Cy1), (K12, ED61, Cy2), (K12, ED61, Cy3), (K12, ED62, Cy1), (K12, ED62, Cy2), (K12, ED62, Cy3), (K12, ED63, Cy1), (K12, ED63, Cy2), (K12, ED63, Cy3), (K12, ED64, Cy1), (K12, ED64, Cy2), (K12, ED64, Cy3), (K12, ED65, Cy1), (K12, ED65, Cy2), (K12, ED65, Cy3), (K12, ED66, Cy1), (K12, ED66, Cy2), (K12, ED66, Cy3), (K12, ED67, Cy1), (K12, ED67, Cy2), (K12, ED67, Cy3), (K12, ED68, Cy1), (K12, ED68, Cy2), (K12, ED68, Cy3), (K12, ED69, Cy1), (K12, ED69, Cy2), (K12, ED69, Cy3), (K12, ED70, Cy1), (K12, ED70, Cy2), (K12, ED70, Cy3), (K12, ED71, Cy1), (K12, ED71, Cy2), (K12, ED71, Cy3), (K12, ED72, Cy1), (K12, ED72, Cy2), (K12, ED72, Cy3), (K12, ED73, Cy1), (K12, ED73, Cy2), (K12, ED73, Cy3), (K12, ED74, Cy1), (K12, ED74, Cy2), (K12, ED74, Cy3), (K12, ED75, Cy1), (K12, ED75, Cy2), (K12, ED75, Cy3), (K12, ED76, Cy1), (K12, ED76, Cy2), (K12, ED76, Cy3), (K12, ED77, Cy1), (K12, ED77, Cy2), (K12, ED77, Cy3), (K12, ED78, Cy1), (K12, ED78, Cy2), (K12, ED78, Cy3), (K12, ED79, Cy1), (K12, ED79, Cy2), (K12, ED79, Cy3), (K12, ED80, Cy1), (K12, ED80, Cy2), (K12, ED80, Cy3), (K12, ED81, Cy1), (K12, ED81, Cy2), (K12, ED81, Cy3), (K12, ED82, Cy1), (K12, ED82, Cy2), (K12, ED82, Cy3), (K12, ED83, Cy1), (K12, ED83, Cy2), (K12, ED83, Cy3), (K12, ED84, Cy1), (K12, ED84, Cy2), (K12, ED84, Cy3), (K12, ED85, Cy1), (K12, ED85, Cy2), (K12, ED85, Cy3), (K12, ED86, Cy1), (K12, ED86, Cy2), (K12, ED86, Cy3), (K12, ED87, Cy1), (K12, ED87, Cy2), (K12, ED87, Cy3), (K12, ED88, Cy1), (K12, ED88, Cy2), (K12, ED88, Cy3), (K12, ED89, Cy1), (K12, ED89, Cy2), (K12, ED89, Cy3), (K12, ED90, Cy1), (K12, ED90, Cy2), (K12, ED90, Cy3), (K12, ED91, Cy1), (K12, ED91, Cy2), (K12, ED91, Cy3), (K12, ED92, Cy1), (K12, ED92, Cy2), (K12, ED92, Cy3), (K13, ED1, Cy1), (K13, ED1, Cy2), (K13, ED1, Cy3), (K13, ED2, Cy1), (K13, ED2, Cy2), (K13, ED2, Cy3), (K13, ED3, Cy1), (K13, ED3, Cy2), (K13, ED3, Cy3), (K13, ED4, Cy1), (K13, ED4, Cy2), (K13, ED4, Cy3), (K13, ED5, Cy1), (K13, ED5, Cy2), (K13, ED5, Cy3), (K13, ED6, Cy1), (K13, ED6, Cy2), (K13, ED6, Cy3), (K13, ED7, Cy1), (K13, ED7, Cy2), (K13, ED7, Cy3), (K13, ED5, Cy1), (K13, ED8, Cy2), (K13, ED8, Cy3), (K13, ED9, Cy1), (K13, ED9, Cy2), (K13, ED9, Cy3), (K13, ED10, Cy1), (K13, ED10, Cy2), (K13, ED10, Cy3), (K13, ED11, Cy1), (K13, ED11, Cy2), (K13, ED11, Cy3), (K13, ED12, Cy1), (K13, ED12, Cy2), (K13, ED12, Cy3), (K13, ED13, Cy1), (K13, ED13, Cy2), (K13, ED13, Cy3), (K13, ED14, Cy1), (K13, ED14, Cy2), (K13, ED14, Cy3), (K13, ED15, Cy1), (K13, ED15, Cy2), (K13, ED15, Cy3), (K13, ED16, Cy1), (K13, ED16, Cy2), (K13, ED16, Cy3), (K13, ED17, Cy1), (K13, ED17, Cy2), (K13, ED17, Cy3), (K13, ED18, Cy1), (K13, ED18, Cy2), (K13, ED18, Cy3), (K13, ED19, Cy1), (K13, ED19, Cy2), (K13, ED19, Cy3), (K13, ED20, Cy1), (K13, ED20, Cy2), (K13, ED20, Cy3), (K13, ED21, Cy1), (K13, ED21, Cy2), (K13, ED21, Cy3), (K13, ED22, Cy1), (K13, ED22, Cy2), (K13, ED22, Cy3), (K13, ED23, Cy1), (K13, ED23, Cy2), (K13, ED23, Cy3), (K13, ED24, Cy1), (K13, ED24, Cy2), (K13, ED24, Cy3), (K13, ED25, Cy1), (K13, ED25, Cy2), (K13, ED25, Cy3), (K13, ED26, Cy1), (K13, ED26, Cy2), (K13, ED26, Cy3), (K13, ED27, Cy1), (K13, ED27, Cy2), (K13, ED27, Cy3), (K13, ED28, Cy1), (K13, ED28, Cy2), (K13, ED28, Cy3), (K13, ED29, Cy1), (K13, ED29, Cy2), (K13, ED29, Cy3), (K13, ED30, Cy1), (K13, ED30, Cy2), (K13, ED30, Cy3), (K13, ED31, Cy1), (K13, ED31, Cy2), (K13, ED31, Cy3), (K13, ED32, Cy1), (K13, ED32, Cy2), (K13, ED32, Cy3), (K13, ED33, Cy1), (K13, ED33, Cy2), (K13, ED33, Cy3), (K13, ED34, Cy1), (K13, ED34, Cy2), (K13, ED34, Cy3), (K13, ED35, Cy1), (K13, ED35, Cy2), (K13, ED35, Cy3), (K13, ED36, Cy1), (K13, ED36, Cy2), (K13, ED36, Cy3), (K13, ED37, Cy1), (K13, ED37, Cy2), (K13, ED37, Cy3), (K13, ED38, Cy1), (K13, ED38, Cy2), (K13, ED38, Cy3), (K13, ED39, Cy1), (K13, ED39, Cy2), (K13, ED39, Cy3), (K13, ED40, Cy1), (K13, ED40, Cy2), (K13, ED40, Cy3), (K13, ED41, Cy1), (K13, ED41, Cy2), (K13, ED91, Cy3), (K13, ED42, Cy1), (K13, ED42, Cy2), (K13, ED42, Cy3), (K13, ED93, Cy1), (K13, ED43, Cy2), (K13, ED43, Cy3), (K13, ED44, Cy1), (K13, ED44, Cy2), (K13, ED44, Cy3), (K13, ED45, Cy1), (K13, ED45, Cy2), (K13, ED45, Cy3), (K13, ED46, Cy1), (K13, ED46, Cy2), (K13, ED46, Cy3), (K13, ED47, Cy1), (K13, ED47, Cy2), (K13, ED47, Cy3), (K13, ED48, Cy1), (K13, ED48, Cy2), (K13, ED48, Cy3), (K13, ED49, Cy1), (K13, ED49, Cy2), (K13, ED49, Cy3), (K13, ED50, Cy1), (K13, ED50, Cy2), (K13, ED50, Cy3), (K13, ED51, Cy1), (K13, ED51, Cy2), (K13, ED51, Cy3), (K13, ED52, Cy1), (K13, ED52, Cy2), (K13, ED52, Cy3), (K13, ED53, Cy1), (K13, ED53, Cy2), (K13, ED53, Cy3), (K13, ED59, Cy1), (K13, ED59, Cy2), (K13, ED54, Cy3), (K13, ED55, Cy1), (K13, ED55, Cy2), (K13, ED55, Cy3), (K13, ED56, Cy1), (K13, ED56, Cy2), (K13, ED56, Cy3), (K13, ED67, Cy1), (K13, ED57, Cy2), (K13, ED57, Cy3), (K13, ED58, Cy1), (K13, ED58, Cy2), (K13, ED58, Cy3), (K13, ED59, Cy1), (K13, ED59, Cy2), (K13, ED59, Cy3), (K13, ED60, Cy1), (K13, ED60, Cy2), (K13, ED60, Cy3), (K13, ED61, Cy1), (K13, ED61, Cy2), (K13, ED61, Cy3), (K13, ED62, Cy1), (K13, ED62, Cy2), (K13, ED62, Cy3), (K13, ED63, Cy1), (K13, ED63, Cy2), (K13, ED63, Cy3), (K13, ED64, Cy1), (K13, ED64, Cy2), (K13, ED64, Cy3), (K13, ED65, Cy1), (K13, ED65, Cy2), (K13, ED65, Cy3), (K13, ED66, Cy1), (K13, ED66, Cy2), (K13, ED66, Cy3), (K13, ED67, Cy1), (K13, ED67, Cy2), (K13, ED67, Cy3), (K13, ED68, Cy1), (K13, ED68, Cy2), (K13, ED68, Cy3), (K13, ED69, Cy1), (K13, ED69, Cy2), (K13, ED69, Cy3), (K13, ED70, Cy1), (K13, ED70, Cy2), (K13, ED70, Cy3), (K13, ED71, Cy1), (K13, ED71, Cy2), (K13, ED71, Cy3), (K13, ED72, Cy1), (K13, ED72, Cy2), (K13, ED72, Cy3), (K13, ED73, Cy1), (K13, ED73, Cy2), (K13, ED73, Cy3), (K13, ED74, Cy1), (K13, ED74, Cy2), (K13, ED74, Cy3), (K13, ED75, Cy1), (K13, ED75, Cy2), (K13, ED75, Cy3), (K13, ED76, Cy1), (K13, ED76, Cy2), (K13, ED76, Cy3), (K13, ED77, Cy1), (K13, ED77, Cy2), (K13, ED77, Cy3), (K13, ED78, Cy1), (K13, ED78, Cy2), (K13,

ED78, Cy3), (K13, ED79, Cy1), (K13, ED79, Cy2), (K13, ED79, Cy3), (K13, ED80, Cy1), (K13, ED80, Cy2), (K13, ED80, Cy3), (K13, ED81, Cy1), (K13, ED81, Cy2), (K13, ED81, Cy3), (K13, ED82, Cy1), (K13, ED82, Cy2), (K13, ED82, Cy3), (K13, ED83, Cy1), (K13, ED83, Cy2), (K13, ED83, Cy3), (K13, ED84, Cy1), (K13, ED84, Cy2), (K13, ED84, Cy3), (K13, ED85, Cy1), (K13, ED85, Cy2), (K13, ED85, Cy3), (K13, ED86, Cy1), (K13, ED86, Cy2), (K13, ED86, Cy3), (K13, ED87, Cy1), (K13, ED87, Cy2), (K13, ED87, Cy3), (K13, ED88, Cy1), (K13, ED88, Cy2), (K13, ED88, Cy3), (K13, ED89, Cy1), (K13, ED89, Cy2), (K13, ED89, Cy3), (K13, ED90, Cy1), (K13, ED90, Cy2), (K13, ED90, Cy3), (K13, ED91, Cy1), (K13, ED91, Cy2), (K13, ED91, Cy3), (K13, ED92, Cy1), (K13, ED92, Cy2), (K13, ED92, Cy3), (K14, ED1, Cy1), (K14, ED1, Cy2), (K14, ED1, Cy3), (K14, ED2, Cy1), (K14, ED2, Cy2), (K14, ED2, Cy1), (K14, ED3, Cy1), (K14, ED3, Cy2), (K14, ED3, Cy3), (K14, ED4, Cy1), (K14, ED4, Cy2), (K14, ED4, Cy3), (K14, ED5, Cy1), (K14, ED5, Cy2), (K14, ED5, Cy3), (K14, ED6, Cy1), (K14, ED6, Cy2), (K14, ED6, Cy3), (K14, ED7, Cy1), (K14, ED7, Cy2), (K14, ED7, Cy3), (K14, ED5, Cy1), (K14, ED5, Cy2), (K14, ED8, Cy3), (K14, ED9, Cy1), (K14, ED9, Cy2), (K14, Cy3), (K14, ED10, Cy1), (K14, ED10, Cy2), (K14, ED10, Cy3), (K14, ED11, Cy1), (K14, ED11, Cy2), (K14, ED11, Cy3), (K14, ED12, Cy1), (K14, ED12, Cy2), (K14, ED12, Cy3), (K14, ED13, Cy1), (K14, ED13, Cy2), (K14, ED13, Cy3), (K14, ED14, Cy1), (K14, ED14, Cy2), (K14, ED14, Cy3), (K14, ED15, Cy1), (K14, ED15, Cy2), (K14, ED15, Cy3), (K14, ED16, Cy1), (K14, ED16, Cy2), (K14, ED16, Cy3), (K14, ED17, Cy1), (K14, ED17, Cy2), (K14, ED17, Cy3), (K14, ED18, Cy1), (K14, ED18, Cy2), (K14, ED18, Cy3), (K14, ED19, Cy1), (K14, ED19, Cy2), (K14, ED19, Cy3), (K14, ED20, Cy1), (K14, ED20, Cy2), (K14, ED20, Cy3), (K14, ED21, Cy1), (K14, ED21, Cy2), (K14, ED21, Cy3), (K14, ED22, Cy1), (K14, ED22, Cy2), (K14, ED22, Cy3), (K14, ED23, Cy1), (K14, ED23, Cy2), (K14, ED23, Cy3), (K14, ED24, Cy1), (K14, ED24, Cy2), (K14, ED24, Cy3), (K14, ED25, Cy1), (K14, ED25, Cy2), (K14, ED25, Cy3), (K14, ED26, Cy1), (K14, ED26, Cy2), (K14, ED26, Cy3), (K14, ED27, Cy1), (K14, ED27, Cy2), (K14, ED27, Cy3), (K14, ED28, Cy1), (K14, ED28, Cy2), (K14, ED28, Cy3), (K14, ED29, Cy1), (K14, ED29, Cy2), (K14, ED29, Cy3), (K14, ED30, Cy1), (K14, ED30, Cy2), (K14, ED30, Cy3), (K14, ED31, Cy1), (K14, ED31, Cy2), (K14, ED31, Cy3), (K14, ED32, Cy1), (K14, ED32, Cy2), (K14, ED32, Cy3), (K14, ED33, Cy1), (K14, ED33, Cy2), (K14, ED33, Cy3), (K14, ED34, Cy1), (K14, ED34, Cy2), (K14, ED34, Cy3), (K14, ED35, Cy1), (K14, ED35, Cy2), (K14, ED35, Cy3), (K14, ED36, Cy1), (K14, ED36, Cy2), (K14, ED36, Cy3), (K14, ED37, Cy1), (K14, ED37, Cy2), (K14, ED37, Cy3), (K14, ED38, Cy1), (K14, ED38, Cy2), (K14, ED38, Cy3), (K14, ED39, Cy1), (K14, ED39, Cy2), (K14, ED39, Cy3), (K14, ED40, Cy1), (K14, ED40, Cy2), (K14, ED40, Cy3), (K14, ED41, Cy1), (K14, ED41, Cy2), (K14, ED41, Cy3), (K14, ED42, Cy1), (K14, ED42, Cy2), (K14, ED42, Cy3), (K14, ED43, Cy1), (K14, ED43, Cy2), (K14, ED43, Cy1), (K14, ED44, Cy1), (K14, ED44, Cy2), (K14, ED44, Cy3), (K14, ED45, Cy1), (K14, ED45, Cy2), (K14, ED45, Cy3), (K14, ED46, Cy1), (K14, ED46, Cy2), (K14, ED46, Cy3), (K14, ED47, Cy1), (K14, ED47, Cy2), (K14, ED47, Cy3), (K14, ED48, Cy1), (K14, ED48, Cy2), (K14, ED48, Cy3), (K14, ED49, Cy1), (K14, ED49, Cy2), (K14, ED49, Cy3), (K14, ED50, Cy1), (K14, ED50, Cy2), (K14, ED50, Cy3), (K14, ED51, Cy1), (K14, ED51, Cy2), (K14, ED51, Cy3), (K14, ED52, Cy1), (K14, ED52, Cy2), (K14, ED52, Cy3), (K14, ED53, Cy1), (K14, ED53, Cy2), (K14, ED53, Cy3), (K14, ED54, Cy1), (K14, ED54, Cy2), (K14, ED54, Cy3), (K14, ED55, Cy1), (K14, ED55, Cy2), (K14, ED55, Cy3), (K14, ED56, Cy1), (K14, ED56, Cy2), (K14, ED56, Cy3), (K14, ED57, Cy1), (K14, ED57, Cy2), (K14, ED57, Cy3), (K14, ED58, Cy1), (K14, ED58, Cy2), (K14, ED58, Cy3), (K14, ED59, Cy1), (K14, ED59, Cy2), (K14, ED59, Cy3), (K14, ED60, Cy1), (K14, ED60, Cy2), (K14, ED60, Cy3), (K14, ED61, Cy1), (K14, ED61, Cy2), (K14, ED61, Cy3), (K14, ED62, Cy1), (K14, ED62, Cy2), (K14, ED62, Cy3), (K14, ED63, Cy1), (K14, ED63, Cy2), (K14, ED63, Cy3), (K14, ED64, Cy1), (K14, ED64, Cy2), (K14, ED64, Cy3), (K14, ED65, Cy1), (K14, ED65, Cy2), (K14, ED65, Cy3), (K14, ED66, Cy1), (K14, ED66, Cy2), (K14, ED66, Cy3), (K14, ED67, Cy1), (K14, ED67, Cy2), (K14, ED67, Cy3), (K14, ED68, Cy1), (K14, ED68, Cy2), (K14, ED68, Cy3), (K14, ED69, Cy1), (K14, ED69, Cy2), (K14, ED69, Cy3), (K14, ED70, Cy1), (K14, ED70, Cy2), (K14, ED70, Cy3), (K14, ED71, Cy1), (K14, ED71, Cy2), (K14, ED71, Cy3), (K14, ED72, Cy1), (K14, ED72, Cy2), (K14, ED72, Cy3), (K14, ED73, Cy1), (K14, ED73, Cy2), (K14, ED73, Cy3), (K14, ED74, Cy1), (K14, ED74, Cy2), (K14, ED74, Cy3), (K14, ED75, Cy1), (K14, ED75, Cy2), (K14, ED75, Cy3), (K14, ED76, Cy1), (K14, ED76, Cy2), (K14, ED76, Cy3), (K14, ED77, Cy1), (K14, ED77, Cy2), (K14, ED77, Cy3), (K14, ED78, Cy1), (K14, ED78, Cy2), (K14, ED78, Cy3), (K14, ED79, Cy1), (K14, ED79, Cy2), (K14, ED79, Cy3), (K14, ED80, Cy1), (K14, ED80, Cy2), (K14, ED80, Cy3), (K14, ED81, Cy1), (K14, ED81, Cy2), (K14, ED81, Cy3), (K14, ED82, Cy1), (K14, ED82, Cy2), (K14, ED82, Cy3), (K14, ED83, Cy1), (K14, ED83, Cy2), (K14, ED84, Cy3), (K14, ED84, Cy1), (K14, ED84, Cy2), (K14, ED84, Cy3), (K14, ED85, Cy1), (K14, ED85, Cy2), (K14, ED85, Cy3), (K14, ED86, Cy1), (K14, ED86, Cy2), (K14, ED86, Cy3), (K14, ED87, Cy1), (K14, ED87, Cy2), (K14, ED87, Cy3), (K14, ED88, Cy1), (K14, ED88, Cy2), (K14, ED88, Cy3), (K14, ED89, Cy1), (K14, ED89, Cy2), (K14, ED89, Cy3), (K14, ED90, Cy1), (K14, ED90, Cy2), (K14, ED90, Cy3), (K14, ED91, Cy1), (K14, ED91, Cy2), (K14, ED91, Cy3), (K14, ED92, Cy1), (K14, ED92, Cy2), (K14, ED92, Cy3)

(K15, ED1, Cy1), (K15, ED1, Cy2), (K15, ED1, Cy3), (K15, ED2, Cy1), (K15, ED2, Cy2), (K15, ED2, Cy3), (K15, ED3, Cy1), (K15, ED3, Cy2), (K15, ED3, Cy3), (K15, ED4, Cy1), (K15, ED4, Cy2), (K15, ED4, Cy3), (K15, ED5, Cy1), (K15, ED5, Cy2), (K15, ED5, Cy3), (K15, ED6, Cy1), (K15, ED6, Cy2), (K15, ED6, Cy3), (K15, ED7, Cy1), (K15, ED7, Cy2), (K15, ED7, Cy3), (K15, ED5, Cy1), (K15, ED8, Cy2), (K15, ED8, Cy3), (K15, ED9, Cy1), (K15, ED9, Cy2), (K15, ED9, Cy3), (K15, ED10, Cy1), (K15, ED10, Cy2), (K15, ED10, Cy3), (K15, ED11, Cy1), (K15, ED11, Cy2), (K15, ED11, Cy3), (K15, ED12, Cy1), (K15, ED12, Cy2), (K15, ED12, Cy3), (K15, ED13, Cy1), (K15, ED13, Cy2), (K15, ED13, Cy3), (K15, ED14, Cy1), (K15, ED14, Cy2), (K15, ED14, Cy3), (K15, ED15, Cy1), (K15, ED15, Cy2), (K15, ED15, Cy3), (K15, ED16, Cy1), (K15, ED16, Cy2), (K15, ED16, Cy3), (K15, ED17, Cy1), (K15, ED17, Cy2), (K15, ED17, Cy3), (K15, ED18, Cy1), (K15, ED18, Cy2), (K15, ED18, Cy3), (K15, ED19, Cy1), (K15, ED19, Cy2), (K15, ED19, Cy3), (K15, ED20, Cy1), (K15, ED20, Cy2), (K15, ED20, Cy3), (K15, ED21, Cy1), (K15, ED21, Cy2), (K15, ED21, Cy3), (K15, ED22, Cy1), (K15, ED22, Cy2), (K15, ED22, Cy3), (K15, ED23, Cy1), (K15, ED23, Cy2), (K15, ED23, Cy3), (K15, ED24, Cy1), (K15, ED24, Cy2), (K15, ED24, Cy3), (K15, ED25, Cy1), (K15, ED25, Cy2), (K15, ED25, Cy3), (K15, ED26, Cy1), (K15, ED26, Cy2), (K15, ED26, Cy3), (K15, ED27, Cy1), (K15, ED27, Cy2), (K15, ED27, Cy3), (K15, ED28, Cy1), (K15, ED28, Cy2), (K15,

ED28, Cy3), (K15, ED29, Cy1), (K15, ED29, Cy2), (K15, ED29, Cy3), (K15, ED30, Cy1), (K15, ED30, Cy2), (K15, ED30, Cy3), (K15, ED31, Cy0, (K15, ED31, Cy2), (K15, ED31, Cy3), (K15, ED32, Cy1), (K15, ED32, Cy2), (K15, ED32, Cy3), (K15, ED33, Cy1), (K15, ED33, Cy2), (K15, ED33, Cy3), (K15, ED39, Cy1), (K15, ED34, Cy2), (K15, ED34, Cy3), (K15, ED35, Cy1), (K15, ED35, Cy2), (K15, ED35, Cy3), (K15, ED36, Cy1), (K15, ED36, Cy2), (K15, ED36, Cy3), (K15, ED37, Cy1), (K15, ED37, Cy2), (K15, ED37, Cy3), (K15, ED38, Cy1), (K15, ED38, Cy2), (K15, ED38, Cy3), (K15, ED39, Cy1), (K15, ED39, Cy2), (K15, ED39, Cy3), (K15, ED40, Cy1), (K15, ED40, Cy2), (K15, ED40, Cy3), (K15, ED41, Cy1), (K15, ED41, Cy2), (K15, ED41, Cy3), (K15, ED42, Cy1), (K15, ED42, Cy2), (K15, ED93, Cy3), (K15, ED44, Cy1), (K15, ED44, Cy2), (K15, ED44, Cy3), (K15, ED45, Cy1), (K15, ED45, Cy2), (K15, ED45, Cy3), (K15, ED46, Cy1), (K15, ED96, Cy2), (K15, ED46, Cy3), (K15, ED47, Cy1), (K15, ED47, Cy2), (K15, ED47, Cy3), (K15, ED48, Cy1), (K15, ED48, Cy2), (K15, ED48, Cy3), (K15, ED49, Cy1), (K15, ED49, Cy2), (K15, ED49, Cy3), (K15, ED50, Cy1), (K15, ED50, Cy2), (K15, ED50, Cy3), (K15, ED51, Cy1), (K15, ED51, Cy2), (K15, ED51, Cy3), (K15, ED52, Cy1), (K15, ED52, Cy2), (K15, ED52, Cy3), (K15, ED53, Cy1), (K15, ED53, Cy2), (K15, ED53, Cy3), (K15, ED54, Cy1), (K15, ED54, Cy2), (K15, ED54, Cy3), (K15, ED55, Cy1), (K15, ED55, Cy2), (K15, ED55, Cy3), (K15, ED56, Cy1), (K15, ED56, Cy2), (K15, ED56, Cy3), (K15, ED57, Cy1), (K15, ED57, Cy2), (K15, ED57, Cy3), (K15, ED58, Cy1), (K15, ED58, Cy2), (K15, ED58, Cy3), (K15, ED59, Cy1), (K15, ED59, Cy2), (K15, ED59, Cy3), (K15, ED60, Cy1), (K15, ED60, Cy2), (K15, ED60, Cy3), (K15, ED61, Cy1), (K15, ED61, Cy2), (K15, ED61, Cy3), (K15, ED62, Cy1), (K15, ED62, Cy2), (K15, ED62, Cy3), (K15, ED63, Cy1), (K15, ED63, Cy2), (K15, ED63, Cy3), (K15, ED64, Cy1), (K15, ED64, Cy2), (K15, ED64, Cy3), (K15, ED65, Cy1), (K15, ED65, Cy2), (K15, ED65, Cy3), (K15, ED66, Cy1), (K15, ED66, Cy2), (K15, ED66, Cy3), (K15, ED67, Cy1), (K15, ED67, Cy2), (K15, ED67, Cy3), (K15, ED67, Cy1), (K15, ED68, Cy2), (K15, ED68, Cy3), (K15, ED69, Cy1), (K15, ED69, Cy2), (K15, ED69, Cy3), (K15, ED70, Cy1), (K15, ED70, Cy2), (K15, ED70, Cy3), (K15, ED71, Cy1), (K15, ED71, Cy2), (K15, ED71, Cy3), (K15, ED72, Cy1), (K15, ED72, Cy2), (K15, ED72, Cy3), (K15, ED73, Cy1), (K15, ED73, Cy2), (K15, ED73, Cy3), (K15, ED74, Cy1), (K15, ED79, Cy2), (K15, ED74, Cy3), (K15, ED75, Cy1), (K15, ED75, Cy2), (K15, ED75, Cy3), (K15, ED76, Cy1), (K15, ED76, Cy2), (K15, ED76, Cy3), (K15, ED77, Cy1), (K15, ED77, Cy2), (K15, ED77, Cy3), (K15, ED78, Cy1), (K15, ED78, Cy2), (K15, ED78, Cy3), (K15, ED79, Cy1), (K15, ED79, Cy2), (K15, ED79, Cy3), (K15, ED80, Cy1), (K15, ED80, Cy2), (K15, ED80, Cy3), (K15, ED81, Cy1), (K15, ED81, Cy2), (K15, ED81, Cy3), (K15, ED82, Cy1), (K15, ED82, Cy2), (K15, ED82, Cy3), (K15, ED83, Cy1), (K15, ED83, Cy2), (K15, ED83, Cy3), (K15, ED84, Cy1), (K15, ED84, Cy2), (K15, ED84, Cy3), (K15, ED85, Cy1), (K15, ED85, Cy2), (K15, ED85, Cy3), (K15, ED86, Cy1), (K15, ED86, Cy2), (K15, ED86, Cy3), (K15, ED87, Cy1), (K15, ED87, Cy2), (K15, ED87, Cy3), (K15, ED88, Cy1), (K15, ED88, Cy2), (K15, ED88, Cy3), (K15, ED89, Cy1), (K15, ED89, Cy2), (K15, ED89, Cy3), (K15, ED90, Cy1), (K15, ED90, Cy2), (K15, ED90, Cy3), (K15, ED91, Cy1), (K15, ED91, Cy2), (K15, ED91, Cy3), (K15, ED92, Cy1), (K15, ED92, Cy2), (K15, ED92, Cy3)

(K16, ED1, Cy1), (K16, ED1, Cy2), (K16, ED1, Cy3), (K16, ED2, Cy1), (K16, ED2, Cy2), (K16, ED2, Cy3), (K16, ED3, Cy1), (K16, ED3, Cy2), (K16, ED3, Cy3), (K16, ED4, Cy1), (K16, ED4, Cy2), (K16, ED4, Cy3), (K16, ED5, Cy1), (K16, ED5, Cy2), (K16, ED5, Cy3), (K16, ED6, Cy1), (K16, ED6, Cy2), (K16, ED6, Cy3), (K16, ED7, Cy1), (K16, ED7, Cy2), (K16, ED7, Cy3), (K16, ED8, Cy2), (K16, ED8, Cy3), (K16, ED9, Cy1), (K16, ED9, Cy2), (K16, ED9, Cy3), (K16, ED10, Cy1), (K16, ED10, Cy2), (K16, ED10, Cy3), (K16, ED11, Cy1), (K16, ED11, Cy2), (K16, ED11, Cy3), (K16, ED12, Cy1), (K16, ED12, Cy2), (K16, ED12, Cy3), (K16, ED13, Cy1), (K16, ED13, Cy2), (K16, ED13, Cy3), (K16, ED14, Cy1), (K16, ED14, Cy2), (K16, ED14, Cy3), (K16, ED15, Cy1), (K16, ED15, Cy2), (K16, ED15, Cy3), (K16, ED16, Cy1), (K16, ED16, Cy2), (K16, ED16, Cy3), (K16, ED17, Cy1), (K16, ED17, Cy2), (K16, ED17, Cy3), (K16, ED18, Cy1), (K16, ED18, Cy2), (K16, ED18, Cy3), (K16, ED19, Cy1), (K16, ED19, Cy2), (K16, ED19, Cy3), (K16, ED20, Cy1), (K16, ED20, Cy2), (K16, ED20, Cy3), (K16, ED21, Cy1), (K16, ED21, Cy2), (K16, ED21, Cy3), (K16, ED22, Cy1), (K16, ED22, Cy2), (K16, ED22, Cy3), (K16, ED23, Cy1), (K16, ED23, Cy2), (K16, ED23, Cy3), (K16, ED24, Cy1), (K16, ED24, Cy2), (K16, ED24, Cy3), (K16, ED25, Cy1), (K16, ED25, Cy2), (K16, ED25, Cy3), (K16, ED26, Cy1), (K16, ED26, Cy2), (K16, ED26, Cy3), (K16, ED27, Cy1), (K16, ED27, Cy2), (K16, ED27, Cy3), (K16, ED28, Cy1), (K16, ED28, Cy2), (K16, ED28, Cy3), (K16, ED29, Cy1), (K16, ED29, Cy2), (K16, ED29, Cy3), (K16, ED30, Cy1), (K16, ED30, Cy2), (K16, ED30, Cy3), (K16, ED31, Cy1), (K16, ED31, Cy2), (K16, ED31, Cy3), (K16, ED32, Cy1), (K16, ED32, Cy2), (K16, ED32, Cy3), (K16, ED33, Cy1), (K16, ED33, Cy2), (K16, ED33, Cy3), (K16, ED34, Cy1), (K16, ED34, Cy2), (K16, ED34, Cy3), (K16, ED35, Cy1), (K16, ED35, Cy2), (K16, ED35, Cy3), (K16, ED36, Cy1), (K16, ED36, Cy2), (K16, ED36, Cy3), (K16, ED37, Cy1), (K16, ED37, Cy2), (K16, ED37, Cy3), (K16, ED38, Cy1), (K16, ED38, Cy2), (K16, ED38, Cy3), (K16, ED39, Cy1), (K16, ED39, Cy2), (K16, ED39, Cy3), (K16, ED40, Cy1), (K16, ED40, Cy2), (K16, ED40, Cy3), (K16, ED41, Cy1), (K16, ED41, Cy2), (K16, ED41, Cy3), (K16, ED42, Cy1), (K16, ED42, Cy2), (K16, ED42, Cy3), (K16, ED43, Cy1), (K16, ED43, Cy2), (K16, ED43, Cy3), (K16, ED44, Cy1), (K16, ED94, Cy2), (K16, ED44, Cy3), (K16, ED45, Cy1), (K16, ED45, Cy2), (K16, ED45, Cy3), (K16, ED46, Cy1), (K16, ED46, Cy2), (K16, ED46, Cy3), (K16, ED47, Cy1), (K16, ED47, Cy2), (K16, ED47, Cy3), (K16, ED48, Cy1), (K16, ED48, Cy2), (K16, ED48, Cy3), (K16, ED49, Cy1), (K16, ED49, Cy2), (K16, ED49, Cy3), (K16, ED50, Cy1), (K16, ED50, Cy2), (K16, ED50, Cy3), (K16, ED51, Cy1), (K16, ED51, Cy2), (K16, ED51, Cy3), (K16, ED52, Cy1), (K16, ED52, Cy2), (K16, ED52, Cy3), (K16, ED53, Cy1), (K16, ED53, Cy2), (K16, ED53, Cy3), (K16, ED54, Cy1), (K16, ED54, Cy2), (K16, ED54, Cy3), (K16, ED55, Cy1), (K16, ED55, Cy2), (K16, ED55, Cy3), (K16, ED56, Cy1), (K16, ED56, Cy2), (K16, ED56, Cy3), (K16, ED57, Cy1), (K16, ED57, Cy2), (K16, ED57, Cy3), (K16, ED58, Cy1), (K16, ED58, Cy2), (K16, ED58, Cy3), (K16, ED59, Cy1), (K16, ED59, Cy2), (K16, ED59, Cy3), (K16, ED60, Cy1), (K16, ED60, Cy2), (K16, ED60, Cy3), (K16, ED61, Cy1), (K16, ED61, Cy2), (K16, ED61, Cy3), (K16, ED62, Cy1), (K16, ED62, Cy2), (K16, ED62, Cy3), (K16, ED63, Cy1), (K16, ED63, Cy2), (K16, ED63, Cy3), (K16, ED64, Cy1), (K16, ED64, Cy2), (K16, ED64, Cy3), (K16, ED65, Cy1), (K16, ED65, Cy2), (K16, ED65, Cy3), (K16, ED66, Cy1), (K16, ED66, Cy2), (K16, ED66, Cy3), (K16, ED67, Cy1), (K16, ED67, Cy2), (K16, ED67, Cy3), (K16, ED68, Cy1), (K16, ED68, Cy2), (K16, ED68, Cy3), (K16, ED69, Cy1), (K16, ED69, Cy2), (K16, ED69, Cy3), (K16, ED70, Cy1), (K16, ED70, Cy2), (K16,

ED70, Cy3), (K16, ED71, Cy1), (K16, ED71, Cy2), (K16, ED71, Cy3), (K16, ED72, Cy1), (K16, ED72, Cy2), (K16, ED72, Cy3), (K16, ED73, Cy1), (K16, ED73, Cy2), (K16, ED73, Cy3), (K16, ED74, Cy1), (K16, ED74, Cy2), (K16, ED74, Cy3), (K16, ED75, Cy1), (K16, ED75, Cy2), (K16, ED75, Cy3), (K16, ED76, Cy1), (K16, ED76, Cy2), (K16, ED76, Cy3), (K16, ED77, Cy1), (K16, ED77, Cy2), (K16, ED77, Cy3), (K16, ED78, Cy1), (K16, ED78, Cy2), (K16, ED78, Cy3), (K16, ED79, Cy1), (K16, ED79, Cy2), (K16, ED79, Cy3), (K16, ED80, Cy1), (K16, ED80, Cy2), (K16, ED80, Cy3), (K16, ED81, Cy1), (K16, ED81, Cy2), (K16, ED81, Cy3), (K16, ED82, Cy1), (K16, ED82, Cy2), (K16, ED82, Cy3), (K16, ED83, Cy1), (K16, ED83, Cy2), (K16, ED83, Cy3), (K16, ED84, Cy1), (K16, ED84, Cy2), (K16, ED84, Cy3), (K16, ED85, Cy1), (K16, ED85, Cy2), (K16, ED85, Cy3), (K16, ED86, Cy1), (K16, ED86, Cy2), (K16, ED86, Cy3), (K16, ED87, Cy1), (K16, ED87, Cy2), (K16, ED87, Cy3), (K16, ED88, Cy1), (K16, ED88, Cy2), (K16, ED88, Cy3), (K16, ED89, Cy1), (K16, ED89, Cy2), (K16, ED89, Cy3), (K16, ED90, Cy1), (K16, ED90, Cy2), (K16, ED90, Cy3), (K16, ED91, Cy1), (K16, ED91, Cy2), (K16, ED91, Cy3), (K16, ED92, Cy1), (K16, ED92, Cy2), (K16, ED92, Cy3), (K17, ED1, Cy1), (K17, ED1, Cy2), (K17, ED1, Cy3), (K17, ED2, Cy1), (K17, ED2, Cy2), (K17, ED2, Cy3), (K17, ED3, Cy1), (K17, ED3, Cy2), (K17, ED3, Cy3), (K17, ED4, Cy1), (K17, ED4, Cy2), (K17, ED4, Cy3), (K17, ED5, Cy1), (K17, ED5, Cy2), (K17, ED5, Cy3), (K17, ED6, Cy1), (K17, ED6, Cy2), (K17, ED6, Cy3), (K17, ED7, Cy1), (K17, ED7, Cy2), (K17, ED7, Cy3), (K17, ED8, Cy1), (K17, ED5, Cy2), (K17, ED8, Cy3), (K17, ED9, Cy1), (K17, ED9, Cy2), (K17, ED9, Cy3), (K17, ED10, Cy1), (K17, ED10, Cy2), (K17, ED10, Cy3), (K17, ED11, Cy1), (K17, ED11, Cy2), (K17, ED11, Cy3), (K17, ED12, Cy1), (K17, ED12, Cy2), (K17, ED12, Cy3), (K17, ED13, Cy1), (K17, ED13, Cy2), (K17, ED13, Cy3), (K17, ED14, Cy1), (K17, ED14, Cy2), (K17, ED14, Cy3), (K17, ED15, Cy1), (K17, ED15, Cy2), (K17, ED15, Cy3), (K17, ED16, Cy1), (K17, ED16, Cy2), (K17, ED16, Cy3), (K17, ED17, Cy1), (K17, ED17, Cy2), (K17, ED17, Cy3), (K17, ED1.8, Cy1), (K17, ED18, Cy2), (K17, ED18, Cy3), (K17, ED19, Cy1), (K17, ED19, Cy2), (K17, ED19, Cy3), (K17, ED20, Cy1), (K17, ED28, Cy2), (K17, ED28, Cy3), (K17, ED21, Cy1), (K17, ED21, Cy2), (K17, ED21, Cy3), (K17, ED22, Cy1), (K17, ED22, Cy2), (K17, ED22, Cy3), (K17, ED23, Cy1), (K17, ED23, Cy2), (K17, ED23, Cy3), (K17, ED24, Cy1), (K17, ED24, Cy2), (K17, ED24, Cy3), (K17, ED25, Cy1), (K17, ED25, Cy2), (K17, ED25, Cy3), (K17, ED26, Cy1), (K17, ED26, Cy2), (K17, ED26, Cy3), (K17, ED27, Cy1), (K17, ED27, Cy2), (K17, ED27, Cy3), (K17, ED28, Cy1), (K17, ED28, Cy2), (K17, ED28, Cy3), (K17, ED29, Cy1), (K17, ED29, Cy2), (K17, ED29, Cy3), (K17, ED30, Cy1), (K17, ED30, Cy2), (K17, ED30, Cy3), (K17, ED31, Cy1), (K17, ED31, Cy2), (K17, ED31, Cy3), (K17, ED32, Cy1), (K17, ED32, Cy2), (K17, ED32, Cy3), (K17, ED33, Cy1), (K17, ED33, Cy2), (K17, ED33, Cy3), (K17, ED34, Cy1), (K17, ED34, Cy2), (K17, ED34, Cy3), (K17, ED35, Cy1), (K17, ED35, Cy2), (K17, ED35, Cy3), (K17, ED36, Cy1), (K17, ED36, Cy2), (K17, ED36, Cy3), (K17, ED37, Cy1), (K17, ED37, Cy2), (K17, ED37, Cy3), (K17, ED38, Cy1), (K17, ED38, Cy2), (K17, ED38, Cy3), (K17, ED39, Cy1), (K17, ED39, Cy2), (K17, ED39, Cy3), (K17, ED40, Cy1), (K17, ED40, Cy2), (K17, ED40, Cy3), (K17, ED41, Cy1), (K17, ED41, Cy2), (K17, ED41, Cy3), (K17, ED42, Cy1), (K17, ED42, Cy2), (K17, ED42, Cy3), (K17, ED43, Cy1), (K17, ED43, Cy2), (K17, ED43, Cy3), (K17, ED44, Cy1), (K17, ED44, Cy2), (K17, ED44, Cy3), (K17, ED45, Cy1), (K17, ED45, Cy2), (K17, ED45, Cy3), (K17, ED46, Cy1), (K17, ED46, Cy2), (K17, ED46, Cy3), (K17, ED47, Cy1), (K17, ED47, Cy2), (K17, ED47, Cy3), (K17, ED48, Cy1), (K17, ED48, Cy2), (K17, ED48, Cy3), (K17, ED49, Cy1), (K17, ED49, Cy2), (K17, ED49, Cy3), (K17, ED50, Cy1), (K17, ED50, Cy2), (K17, ED50, Cy3), (K17, ED51, Cy1), (K17, ED51, Cy2), (K17, ED51, Cy3), (K17, ED52, Cy1), (K17, ED52, Cy2), (K17, ED52, Cy3), (K17, ED53, Cy1), (K17, ED53, Cy2), (K17, ED53, Cy3), (K17, ED54, Cy1), (K17, ED54, Cy2), (K17, ED54, Cy3), (K17, ED55, Cy1), (K17, ED55, Cy2), (K17, ED55, Cy3), (K17, ED56, Cy1), (K17, ED56, Cy2), (K17, ED56, Cy3), (K17, ED57, Cy1), (K17, ED57, Cy2), (K17, ED57, Cy3), (K17, ED58, Cy1), (K17, ED58, Cy2), (K17, ED58, Cy3), (K17, ED59, Cy1), (K17, ED59, Cy2), (K17, ED59, Cy3), (K17, ED60, Cy1), (K17, ED60, Cy2), (K17, ED60, Cy3), (K17, ED61, Cy1), (K17, ED61, Cy2), (K17, ED61, Cy3), (K17, ED62, Cy1), (K17, ED62, Cy2), (K17, ED62, Cy3), (K17, ED63, Cy1), (K17, ED63, Cy2), (K17, ED63, Cy3), (K17, ED64, Cy1), (K17, ED64, Cy2), (K17, ED64, Cy3), (K17, ED65, Cy1), (K17, ED65, Cy2), (K17, ED65, Cy3), (K17, ED66, Cy1), (K17, ED66, Cy2), (K17, ED66, Cy3), (K17, ED67, Cy1), (K17, ED67, Cy2), (K17, ED67, Cy3), (K17, ED68, Cy1), (K17, ED68, Cy2), (K17, ED68, Cy3), (K17, ED69, Cy1), (K17, ED69, Cy2), (K17, ED69, Cy3), (K17, ED70, Cy1), (K17, ED70, Cy2), (K17, ED70, Cy3), (K17, ED71, Cy1), (K17, ED71, Cy2), (K17, ED71, Cy3), (K17, ED72, Cy1), (K17, ED72, Cy2), (K17, ED72, Cy3), (K17, ED73, Cy1), (K17, ED73, Cy2), (K17, ED73, Cy3), (K17, ED74, Cy1), (K17, ED74, Cy2), (K17, ED74, Cy3), (K17, ED75, Cy1), (K17, ED75, Cy2), (K17, ED75, Cy3), (K17, ED76, Cy1), (K17, ED76, Cy2), (K17, ED76, Cy3), (K17, ED77, Cy1), (K17, ED77, Cy2), (K17, ED77, Cy3), (K17, ED78, Cy1), (K17, ED78, Cy2), (K17, ED78, Cy3), (K17, ED79, Cy1), (K17, ED79, Cy2), (K17, ED79, Cy3), (K17, ED80, Cy1), (K17, ED80, Cy2), (K17, ED80, Cy3), (K17, ED81, Cy1), (K17, ED81, Cy2), (K17, ED81, Cy3), (K17, ED82, Cy1), (K17, ED82, Cy2), (K17, ED82, Cy3), (K17, ED83, Cy1), (K17, ED83, Cy2), (K17, ED83, Cy3), (K17, ED84, Cy1), (K17, ED84, Cy2), (K17, ED84, Cy3), (K17, ED85, Cy1), (K17, ED85, Cy2), (K17, ED85, Cy3), (K17, ED86, Cy1), (K17, ED86, Cy2), (K17, ED86, Cy3), (K17, ED87, Cy1), (K17, ED87, Cy2), (K17, ED87, Cy3), (K17, ED88, Cy1), (K17, ED88, Cy2), (K17, ED88, Cy3), (K17, ED89, Cy1), (K17, ED89, Cy2), (K17, ED89, Cy3), (K17, ED90, Cy1), (K17, ED90, Cy2), (K17, ED90, Cy3), (K17, ED91, Cy1), (K17, ED91, Cy2), (K17, ED91, Cy3), (K17, ED92, Cy1), (K17, ED92, Cy2), (K17, ED92, Cy3)'(K18, ED1, Cy1), (K18, ED1, Cy2), (K18, ED1, Cy3), (K18, ED2, Cy1), (K18, ED2, Cy2), (K18, ED2, Cy3), (K18, ED3, Cy1), (K18, ED3, Cy2), (K18, ED3, Cy3), (K18, ED4, Cy1), (K18, ED4, Cy2), (K18, ED4, Cy3), (K18, ED5, Cy1), (K18, ED5, Cy2), (K18, ED5, Cy3), (K18, ED6, Cy1), (K18, ED6, Cy2), (K18, ED6, Cy3), (K18, ED6, Cy1), (K18, ED7, Cy2), (K18, ED7, Cy3), (K18, ED8, Cy1), (K18, ED5, Cy2), (K18, ED5, Cy3), (K18, ED9, Cy1), (K18, ED9, Cy2), (K18, ED9, Cy3), (K18, ED10, Cy1), (K18, ED10, Cy2), (K18, ED10, Cy3), (K18, ED11, Cy1), (K18, ED11, Cy2), (K18, ED11, Cy3), (K18, ED12, Cy1), (K18, ED12, Cy2), (K18, ED12, Cy3), (K18, ED13, Cy1), (K18, ED13, Cy2), (K18, ED13, Cy3), (K18, ED14, Cy1), (K18, ED14, Cy2), (K18, ED14, Cy3), (K18, ED15, Cy1), (K18, ED15, Cy2), (K18, ED15, Cy3), (K18, ED16, Cy1), (K18, ED16, Cy2), (K18, ED16, Cy3), (K18, ED17, Cy1), (K18, ED17, Cy2), (K18, ED17, Cy3), (K18, ED18, Cy1), (K18, ED18, Cy2), (K18, ED18, Cy3), (K18, ED19, Cy1), (K18, ED19, Cy2), (K18, ED19, Cy3), (K18, ED20, Cy1), (K18, ED20, Cy2), (K18, ED20, Cy3), (K18, ED21, Cy1), (K18, ED21, Cy2), (K18, ED21,

Cy3), (K18, ED22, Cy1), (K18, ED22, Cy2), (K18, ED22, Cy3), (K18, ED23, Cy1), (K18, ED23, Cy2), (K18, ED23, Cy3), (K18, ED24, Cy1), (K18, ED24, Cy2), (K18, ED24, Cy3), (K18, ED25, Cy1), (K18, ED25, Cy2), (K18, ED25, Cy3), (K18, ED26, Cy1), (K18, ED26, Cy2), (K18, ED26, Cy3), (K18, ED27, Cy1), (K18, ED27, Cy2), (K18, ED27, Cy3), (K18, ED28, Cy1), (K18, ED28, Cy2), (K18, ED28, Cy3), (K18, ED29, Cy1), (K18, ED29, Cy2), (K18, ED29, Cy3), (K18, ED30, Cy1), (K18, ED30, Cy2), (K18, ED30, Cy3), (K18, ED31, Cy1), (K18, ED31, Cy2), (K18, ED31, Cy3), (K18, ED32, Cy1), (K18, ED32, Cy2), (K18, ED32, Cy3), (K18, ED33, Cy1), (K18, ED33, Cy2), (K18, ED33, Cy3), (K18, ED34, Cy1), (K18, ED34, Cy2), (K18, ED34, Cy3), (K18, ED35, Cy1), (K18, ED35, Cy2), (K18, ED35, Cy3), (K18, ED36, Cy1), (K18, ED36, Cy2), (K18, ED36, Cy3), (K18, ED37, Cy1), (K18, ED37, Cy2), (K18, ED37, Cy3), (K18, ED38, Cy1), (K18, ED38, Cy2), (K18, ED38, Cy3), (K18, ED39, Cy1), (K18, ED39, Cy2), (K18, ED39, Cy3), (K18, ED40, Cy1), (K18, ED40, Cy2), (K18, ED40, Cy3), (K18, ED41, Cy1), (K18, ED41, Cy2), (K18, ED41, Cy3), (K18, ED42, Cy1), (K18, ED42, Cy2), (K18, ED42, Cy3), (K18, ED43, Cy1), (K18, ED43, Cy2), (K18, ED43, Cy3), (K18, ED44, Cy1), (K18, ED44, Cy2), (K18, ED44, Cy3), (K18, ED45, Cy1), (K18, ED45, Cy2), (K18, ED45, Cy3), (K18, ED46, Cy1), (K18, ED46, Cy2), (K18, ED46, Cy3), (K19, ED47, Cy1), (K18, ED47, Cy2), (K18, ED47, Cy3), (K18, ED48, Cy1), (K18, ED48, Cy2), (K18, ED48, Cy3), (K18, ED49, Cy1), (K18, ED49, Cy2), (K18, ED49, Cy3), (K18, ED50, Cy1), (K18, ED50, Cy2), (K18, ED50, Cy3), (K18, ED51, Cy1), (K18, ED51, Cy2), (K18, ED51, Cy3), (K18, ED52, Cy1), (K18, ED52, Cy2), (K18, ED52, Cy3), (K18, ED53, Cy1), (K18, ED53, Cy2), (K18, ED53, Cy3), (K18, ED54, Cy1), (K18, ED54, Cy2), (K18, ED54, Cy3), (K18, ED55, Cy1), (K18, ED55, Cy2), (K18, ED55, Cy3), (K18, ED56, Cy1), (K18, ED56, Cy2), (K18, ED56, Cy3), (K18, ED57, Cy1), (K18, ED57, Cy2), (K18, ED57, Cy3), (K18, ED58, Cy1), (K18, ED58, Cy2), (K18, ED58, Cy3), (K18, ED59, Cy1), (K18, ED59, Cy2), (K18, ED59, Cy3), (K18, ED60, Cy1), (K18, ED60, Cy2), (K18, ED60, Cy3), (K18, ED61, Cy1), (K18, ED61, Cy2), (K18, ED61, Cy3), (K18, ED62, Cy1), (K18, ED62, Cy2), (K18, ED62, Cy3), (K18, ED63, Cy1), (K18, ED63, Cy2), (K18, ED63, Cy3), (K18, ED64, Cy1), (K18, ED64, Cy2), (K18, ED64, Cy3), (K18, ED65, Cy1), (K18, ED65, Cy2), (K18, ED65, Cy3), (K18, ED66, Cy1), (K18, ED66, Cy2), (K18, ED66, Cy3), (K18, ED67, Cy1), (K18, ED67, Cy2), (K18, ED67, Cy3), (K18, ED68, Cy1), (K18, ED68, Cy2), (K18, ED68, Cy3), (K18, ED69, Cy1), (K18, ED69, Cy2), (K18, ED69, Cy3), (K18, ED70, Cy1), (K18, ED70, Cy2), (K18, ED70, Cy3), (K18, ED71, Cy1), (K18, ED71, Cy2), (K18, ED71, Cy3), (K18, ED72, Cy1), (K18, ED72, Cy2), (K18, ED72, Cy3), (K18, ED73, Cy1), (K18, ED73, Cy2), (K18, ED73, Cy3), (K18, ED74, Cy1), (K18, ED74, Cy2), (K18, ED74, Cy3), (K18, ED75, Cy1), (K18, ED75, Cy2), (K18, ED75, Cy3), (K18, ED76, Cy1), (K18, ED76, Cy2), (K18, ED76, Cy3), (K18, ED77, Cy1), (K18, ED77, Cy2), (K18, ED77, Cy3), (K18, ED78, Cy1), (K18, ED78, Cy2), (K18, ED78, Cy3), (K18, ED79, Cy1), (K18, ED79, Cy2), (K18, ED79, Cy3), (K18, ED80, Cy1), (K18, ED80, Cy2), (K18, ED80, Cy3), (K18, ED81, Cy1), (K18, ED81, Cy2), (K18, ED81, Cy3), (K18, ED82, Cy1), (K18, ED82, Cy2), (K18, ED82, Cy3), (K13, ED33, Cy1), (K18, ED83, Cy2), (K18, ED83, Cy3), (K18, ED84, Cy1), (K18, ED84, Cy2), (K18, ED84, Cy3), (K18, ED85, Cy1), (K18, ED85, Cy2), (K18, ED85, Cy3), (K18, ED86, Cy1), (K18, ED86, Cy2), (K18, ED86, Cy3), (K18, ED87, Cy1), (K18, ED87, Cy2), (K18, ED87, Cy3), (K18, ED88, Cy1), (K18, ED88, Cy2), (K18, ED88, Cy3), (K18, ED89, Cy1), (K18, ED89, Cy2), (K18, ED89, Cy3), (K18, ED90, Cy1), (K18, ED90, Cy2), (K18, ED90, Cy3), (K18, ED91, Cy1), (K18, ED91, Cy2), (K18, ED91, Cy3), (K18, ED92, Cy1), (K18, ED92, Cy2), (K18, ED92, Cy3), (K19, ED1, Cy1), (K19, ED1, Cy2), (K19, ED1, Cy3), (K19, ED2, Cy1), (K19, ED2, Cy2), (K19, ED2, Cy3), (K19, ED3, Cy1), (K19, ED3, Cy2), (K19, ED3, Cy3), (K19, ED4, Cy1), (K19, ED4, Cy2), (K19, ED4, Cy3), (K19, ED5, Cy1), (K19, ED5, Cy2), (K19, ED5, Cy3), (K19, ED6, Cy1), (K19, ED6, Cy2), (K19, ED6, Cy3), (K19, ED7, Cy1), (K19, ED7, Cy2), (K19, ED7, Cy3), (K19, ED8, Cy1), (K19, ED8, Cy2), (K19, ED8, Cy3), (K19, ED9, Cy1), (K19, ED9, Cy2), (K19, ED9, Cy3), (K19, ED10, Cy1), (K19, ED10, Cy2), (K19, ED10, Cy3), (K19, ED11, Cy1), (K19, ED11, Cy2), (K19, ED11, Cy3), (K19, ED12, Cy1), (K19, ED12, Cy2), (K19, ED12, Cy3), (K19, ED13, Cy1), (K19, ED13, Cy2), (K19, ED13, Cy3), (K19, ED14, Cy1), (K19, ED14, Cy2), (K19, ED14, Cy3), (K19, ED15, Cy1), (K19, ED15, Cy2), (K19, ED15, Cy3), (K19, ED16, Cy1), (K19, ED16, Cy2), (K19, ED16, Cy3), (K19, ED17, Cy1), (K19, ED17, Cy2), (K19, ED17, Cy3), (K19, ED18, Cy1), (K19, ED18, Cy2), (K19, ED18, Cy3), (K19, ED19, Cy1), (K19, ED19, Cy2), (K19, ED19, Cy3), (K19, ED20, Cy1), (K19, ED20, Cy2), (K19, ED20, Cy3), (K19, ED21, Cy1), (K19, ED21, Cy2), (K19, ED21, Cy3), (K19, ED22, Cy1), (K19, ED22, Cy2), (K19, ED22, Cy3), (K19, ED23, Cy1), (K19, ED23, Cy2), (K19, ED23, Cy3), (K19, ED24, Cy1), (K19, ED24, Cy2), (K19, ED24, Cy3), (K19, ED25, Cy1), (K19, ED25, Cy2), (K19, ED25, Cy3), (K19, ED26, Cy1), (K19, ED26, Cy2), (K19, ED26, Cy3), (K19, ED27, Cy1), (K19, ED27, Cy2), (K19, ED27, Cy3), (K19, ED28, Cy1), (K19, ED28, Cy2), (K19, ED28, Cy3), (K19, ED29, Cy1), (K19, ED29, Cy2), (K19, ED29, Cy3), (K19, ED30, Cy1), (K19, ED30, Cy2), (K19, ED30, Cy3), (K19, ED31, Cy1), (K19, ED31, Cy2), (K19, ED31, Cy3), (K19, ED32, Cy1), (K19, ED32, Cy2), (K19, ED32, Cy3), (K19, ED33, Cy1), (K19, ED33, Cy2), (K19, ED33, Cy3), (K19, ED34, Cy1), (K19, ED34, Cy2), (K19, ED34, Cy3), (K19, ED35, Cy1), (K19, ED35, Cy2), (K19, ED35, Cy3), (K19, ED36, Cy1), (K19, ED36, Cy2), (K19, ED36, Cy3), (K19, ED37, Cy1), (K19, ED37, Cy2), (K19, ED37, Cy3), (K19, ED38, Cy1), (K19, ED38, Cy2), (K19, ED38, Cy3), (K19, ED39, Cy1), (K19, ED39, Cy2), (K19, ED39, Cy3), (K19, ED40, Cy1), (K19, ED40, Cy2), (K19, ED40, Cy3), (K19, ED41, Cy1), (K19, ED41, Cy2), (K19, ED91, Cy3), (K19, ED42, Cy1), (K19, ED42, Cy2), (K19, ED42, Cy3), (K19, ED93, Cy1), (K19, ED43, Cy2), (K19, ED43, Cy3), (K19, ED44, Cy1), (K19, ED44, Cy2), (K19, ED44, Cy3), (K19, ED45, Cy1), (K19, ED45, Cy2), (K19, ED45, Cy3), (K19, ED46, Cy1), (K19, ED46, Cy2), (K19, ED46, Cy3), (K19, ED47, Cy1), (K19, ED47, Cy2), (K19, ED47, Cy3), (K19, ED48, Cy1), (K19, ED48, Cy2), (K19, ED48, Cy3), (K19, ED99, Cy1), (K19, ED49, Cy2), (K19, ED49, Cy3), (K19, ED50, Cy1), (K19, ED50, Cy2), (K19, ED50, Cy3), (K19, ED51, Cy1), (K19, ED51, Cy2), (K19, ED51, Cy3), (K19, ED52, Cy1), (K19, ED52, Cy2), (K19, ED52, Cy3), (K19, ED53, Cy1), (K19, ED53, Cy2), (K19, ED53, Cy3), (K19, ED59, Cy1), (K19, ED54, Cy2), (K19, ED54, Cy3), (K19, ED55, Cy1), (K19, ED55, Cy2), (K19, ED55, Cy3), (K19, ED56, Cy1), (K19, ED56, Cy2), (K19, ED56, Cy3), (K19, ED57, Cy1), (K19, ED57, Cy2), (K19, ED57, Cy3), (K19, ED58, Cy1), (K19, ED58, Cy2), (K19, ED58, Cy3), (K19, ED59, Cy1), (K19, ED59, Cy2), (K19, ED59, Cy3), (K19, ED60, Cy1), (K19, ED60, Cy2), (K19, ED60, Cy3), (K19, ED61, Cy1), (K19, ED61, Cy2), (K19, ED61, Cy3), (K19, ED62, Cy1), (K19, ED62, Cy2), (K19, ED62, Cy3), (K19, ED63, Cy1), (K19, ED63, Cy2), (K19,

ED63, Cy3), (K19, ED64, Cy1), (K19, ED64, Cy2), (K19, ED64, Cy3), (K19, ED65, Cy1), (K19, ED65, Cy2), (K19, ED65, Cy3), (K19, ED66, Cy1), (K19, ED66, Cy2), (K19, ED66, Cy3), (K19, ED67, Cy1), (K19, ED67, Cy2), (K19, ED67, Cy3), (K19, ED68, Cy1), (K19, ED68, Cy2), (K19, ED68, Cy3), (K19, ED69, Cy1), (K19, ED69, Cy2), (K19, ED69, Cy3), (K19, ED70, Cy1), (K19, ED70, Cy2), (K19, ED70, Cy3), (K19, ED71, Cy1), (K19, ED71, Cy2), (K19, ED71, Cy3), (K19, ED72, Cy1), (K19, ED72, Cy2), (K19, ED72, Cy3), (K19, ED73, Cy1), (K19, ED73, Cy2), (K19, ED73, Cy3), (K19, ED74, Cy1), (K19, ED74, Cy2), (K19, ED74, Cy3), (K19, ED75, Cy1), (K19, ED75, Cy2), (K19, ED75, Cy3), (K19, ED76, Cy1), (K19, ED76, Cy2), (K19, ED76, Cy3), (K19, ED77, Cy1), (K19, ED77, Cy2), (K19, ED77, Cy3), (K19, ED78, Cy1), (K19, ED78, Cy2), (K19, ED78, Cy3), (K19, ED79, Cy1), (K19, ED79, Cy2), (K19, ED79, Cy3), (K19, ED80, Cy1), (K19, ED80, Cy2), (K19, ED80, Cy3), (K19, ED81, Cy1), (K19, ED81, Cy2), (K19, ED81, Cy3), (K19, ED82, Cy1), (K19, ED82, Cy2), (K19, ED82, Cy3), (K19, ED83, Cy1), (K19, ED83, Cy2), (K19, ED83, Cy3), (K19, ED84, Cy1), (K19, ED84, Cy2), (K19, ED84, Cy3), (K19, ED85, Cy1), (K19, ED85, Cy2), (K19, ED85, Cy3), (K19, ED86, Cy1), (K19, ED86, Cy2), (K19, ED86, Cy3), (K19, ED87, Cy1), (K19, ED87, Cy2), (K19, ED87, Cy3), (K19, ED88, Cy1), (K19, ED88, Cy2), (K19, ED88, Cy3), (K19, ED89, Cy1), (K19, ED89, Cy2), (K19, ED89, Cy3), (K19, ED90, Cy1), (K19, ED90, Cy2), (K19, ED90, Cy3), (K19, ED91, Cy1), (K19, ED91, Cy2), (K19, ED91, Cy3), (K19, ED92, Cy1), (K19, ED92, Cy2), (K19, ED92, Cy3), (K20, ED1, Cy1), (K20, ED1, Cy2), (K20, ED1, Cy3), (K20, ED2, Cy1), (K20, ED2, Cy2), (K20, ED2, Cy3), (K28, ED3, Cy1), (K20, ED3, Cy2), (K20, ED3, Cy3), (K20, ED4, Cy1), (K20, ED4, Cy2), (K20, ED4, Cy3), (K20, ED5, Cy1), (K20, ED5, Cy2), (K20, ED5, Cy3), (K20, ED6, Cy1), (K20, ED6, Cy2), (K20, ED6, Cy3), (K20, ED7, Cy1), (K20, ED7, Cy2), (K20, ED7, Cy3), (K20, ED8, Cy1), (K20, ED5, Cy2), (K20, ED8, Cy3), (K20, ED9, Cy1), (K20, ED9, Cy2), (K20, ED9, Cy3), (K20, ED10, Cy1), (K20, ED10, Cy2), (K20, ED10, Cy3), (K20, ED11, Cy1), (K20, ED11, Cy2), (K20, ED11, Cy3), (K20, ED12, Cy1), (K20, ED12, Cy2), (K20, ED12, Cy3), (K20, ED13, Cy1), (K20, ED13, Cy2), (K20, ED13, Cy3), (K20, ED14, Cy1), (K20, ED14, Cy2), (K20, ED14, Cy3), (K20, ED15, Cy1), (K20, ED15, Cy2), (K20, ED15, Cy3), (K20, ED16, Cy1), (K20, ED16, Cy2), (K20, ED16, Cy3), (K20, ED17, Cy1), (K20, ED17, Cy2), (K20, ED17, Cy3), (K20, ED18, Cy1), (K20, ED18, Cy2), (K20, ED18, Cy3), (K20, ED19, Cy1), (K20, ED19, Cy2), (K20, ED19, Cy3), (K20, ED20, Cy1), (K20, ED20, Cy2), (K20, ED20, Cy3), (K20, ED21, Cy1), (K20, ED21, Cy2), (K20, ED21, Cy3), (K20, ED22, Cy1), (K20, ED22, Cy2), (K20, ED22, Cy3), (K20, ED23, Cy1), (K20, ED23, Cy2), (K20, ED23, Cy3), (K20, ED24, Cy1), (K20, ED24, Cy2), (K20, ED24, Cy3), (K20, ED25, Cy1), (K20, ED25, Cy2), (K20, ED25, Cy3), (K20, ED26, Cy1), (K20, ED26, Cy2), (K20, ED26, Cy3), (K20, ED27, Cy1), (K20, ED27, Cy2), (K20, ED27, Cy3), (K20, ED2S, Cy1), (K20, ED28, Cy2), (K20, ED28, Cy3), (K20, ED29, Cy1), (K20, ED29, Cy2), (K20, ED29, Cy3), (K20, ED30, Cy1), (K20, ED30, Cy2), (K20, ED30, Cy3), (K20, ED31, Cy1), (K20, ED31, Cy2), (K20, ED31, Cy3), (K20, ED32, Cy1), (K20, ED32, Cy2), (K20, ED32, Cy3), (K20, ED33, Cy1), (K20, ED33, Cy2), (K20, ED33, Cy3), (K20, ED34, Cy1), (K20, ED34, Cy2), (K20, ED34, Cy3), (K20, ED35, Cy1), (K20, ED35, Cy2), (K20, ED35, Cy3), (K20, ED36, Cy1), (K20, ED36, Cy2), (K20, ED36, Cy3), (K20, ED37, Cy1), (K20, ED37, Cy2), (K20, ED37, Cy3), (K20, ED38, Cy1), (K20, ED38, Cy2), (K20, ED38, Cy3), (K20, ED39, Cy1), (K20, ED39, Cy2), (K20, ED39, Cy3), (K20, ED40, Cy1), (K20, ED40, Cy2), (K20, ED40, Cy3), (K20, ED41, Cy1), (K20, ED41, Cy2), (K20, ED41, Cy3), (K20, ED42, Cy1), (K20, ED42, Cy2), (K20, ED42, Cy3), (K20, ED43, Cy1), (K20, ED43, Cy2), (K20, ED43, Cy3), (K20, ED44, Cy1), (K20, ED44, Cy2), (K20, ED44, Cy3), (K20, ED45, Cy1), (K20, ED45, Cy2), (K20, ED45, Cy3), (K20, ED46, Cy1), (K20, ED46, Cy2), (K20, ED46, Cy3), (K20, ED47, Cy1), (K20, ED47, Cy2), (K20, ED47, Cy3), (K20, ED48, Cy1), (K20, ED48, Cy2), (K20, ED48, Cy3), (K20, ED49, Cy1), (K20, ED49, Cy2), (K20, ED49, Cy3), (K20, ED50, Cy1), (K20, ED50, Cy2), (K20, ED50, Cy3), (K20, ED51, Cy1), (K20, ED51, Cy2), (K20, ED51, Cy3), (K20, ED52, Cy1), (K20, ED52, Cy2), (K20, ED52, Cy3), (K20, ED53, Cy1), (K20, ED53, Cy2), (K20, ED53, Cy3), (K20, ED54, Cy1), (K20, ED54, Cy2), (K20, ED54, Cy3), (K20, ED55, Cy1), (K20, ED55, Cy2), (K20, ED55, Cy3), (K20, ED56, Cy1), (K20, ED56, Cy2), (K20, ED56, Cy3), (K20, ED57, Cy1), (K20, ED57, Cy2), (K20, ED57, Cy3), (K20, ED58, Cy1), (K20, ED58, Cy2), (K20, ED58, Cy3), (K20, ED59, Cy1), (K20, ED59, Cy2), (K20, ED59, Cy3), (K20, ED60, Cy1), (K20, ED60, Cy2), (K20, ED60, Cy3), (K20, ED61, Cy1), (K20, ED61, Cy2), (K20, ED61, Cy3), (K20, ED62, Cy1), (K20, ED62, Cy2), (K20, ED62, Cy3), (K20, ED63, Cy1), (K20, ED63, Cy2), (K20, ED63, Cy3), (K20, ED64, Cy1), (K20, ED64, Cy2), (K20, ED64, Cy3), (K20, ED65, Cy1), (K20, ED65, Cy2), (K20, ED65, Cy3), (K20, ED66, Cy1), (K20, ED66, Cy2), (K20, ED66, Cy3), (K20, ED67, Cy1), (K20, ED67, Cy2), (K20, ED67, Cy3), (K20, ED68, Cy1), (K20, ED68, Cy2), (K20, ED68, Cy3), (K20, ED69, Cy1), (K20, ED69, Cy2), (K20, ED69, Cy3), (K20, ED70, Cy1), (K20, ED70, Cy2), (K20, ED70, Cy3), (K20, ED71, Cy1), (K20, ED71, Cy2), (K20, ED71, Cy3), (K20, ED72, Cy1), (K20, ED72, Cy2), (K20, ED72, Cy3), (K20, ED73, Cy1), (K20, ED73, Cy2), (K20, ED73, Cy3), (K20, ED74, Cy1), (K20, ED74, Cy2), (K20, ED74, Cy3), (K20, ED75, Cy1), (K20, ED75, Cy2), (K20, ED75, Cy3), (K20, ED76, Cy1), (K20, ED76, Cy2), (K20, ED76, Cy3), (K20, ED77, Cy1), (K20, ED77, Cy2), (K20, ED77, Cy3), (K20, ED78, Cy1), (K20, ED78, Cy2), (K20, ED78, Cy3), (K20, ED79, Cy1), (K20, ED79, Cy2), (K20, ED79, Cy3), (K20, ED80, Cy1), (K20, ED80, Cy2), (K20, ED80, Cy3), (K20, ED81, Cy1), (K20, ED81, Cy2), (K20, ED81, Cy3), (K20, ED82, Cy1), (K20, ED82, Cy2), (K20, ED82, Cy3), (K20, ED83, Cy1), (K20, ED83, Cy2), (K20, ED83, Cy3), (K20, ED84, Cy1), (K20, ED84, Cy2), (K20, ED84, Cy3), (K20, ED85, Cy1), (K20, ED85, Cy2), (K20, ED85, Cy3), (K20, ED86, Cy1), (K20, ED86, Cy2), (K20, ED86, Cy3), (K20, ED87, Cy1), (K20, ED87, Cy2), (K20, ED87, Cy3), (K20, ED88, Cy1), (K20, ED88, Cy2), (K20, ED88, Cy3), (K20, ED89, Cy1), (K20, ED89, Cy2), (K20, ED89, Cy3), (K20, ED90, Cy1), (K20, ED90, Cy2), (K20, ED90, Cy3), (K20, ED91, Cy1), (K20, ED91, Cy2), (K20, ED91, Cy3), (K20, ED92, Cy1), (K20, ED92, Cy2), (K20, ED92, Cy3), (K21, ED1, Cy1), (K21, ED1, Cy2), (K21, ED1, Cy3), (K21, ED2, Cy1), (K21, ED2, Cy2), (K21, ED2, Cy3), (K21, ED3, Cy1), (K21, ED3, Cy2), (K21, ED3, Cy3), (K21, ED4, Cy1), (K21, ED4, Cy2), (K21, ED4, Cy3), (K21, ED5, Cy1), (K21, ED5, Cy2), (K21, ED5, Cy3), (K21, ED6, Cy1), (K21, ED6, Cy2), (K21, ED6, Cy3), (K21, ED6, Cy1), (K21, ED7, Cy2), (K21, ED7, Cy3), (K21, ED8, Cy1), (K21, ED8, Cy2), (K21, ED8, Cy3), (K21, ED9, Cy1), (K21, ED9, Cy2), (K21, ED9, Cy3), (K21, ED10, Cy1), (K21, ED10, Cy2), (K21, ED10, Cy3), (K21, ED11, Cy1), (K21, ED11, Cy2), (K21, ED11, Cy3), (K21, ED12, Cy1), (K21, ED12, Cy2), (K21, ED12, Cy3), (K21, ED13, Cy1), (K21, ED13, Cy2), (K21,

ED13, Cy3), (K21, ED14, Cy1), (K21, ED14, Cy2), (K21, ED14, Cy3), (K21, ED15, Cy1), (K21, ED15, Cy2), (K21, ED15, Cy3), (K21, ED16, Cy1), (K21, ED16, Cy2), (K21, ED16, Cy3), (K21, ED17, Cy1), (K21, ED17, Cy2), (K21, ED17, Cy3), (K21, ED18, Cy1), (K21, ED18, Cy2), (K21, ED18, Cy3), (K21, ED19, Cy1), (K21, ED19, Cy2), (K21, ED19, Cy3), (K21, ED20, Cy1), (K21, ED20, Cy2), (K21, ED20, Cy3), (K21, ED21, Cy1), (K21, ED21, Cy2), (K21, ED21, Cy3), (K21, ED22, Cy1), (K21, ED22, Cy2), (K21, ED22, Cy3), (K21, ED23, Cy1), (K21, ED23, Cy2), (K21, ED23, Cy3), (K21, ED24, Cy1), (K21, ED24, Cy2), (K21, ED24, Cy3), (K21, ED25, Cy1), (K21, ED25, Cy2), (K21, ED25, Cy3), (K21, ED26, Cy1), (K21, ED26, Cy2), (K21, ED26, Cy3), (K21, ED27, Cy1), (K21, ED27, Cy2), (K21, ED27, Cy3), (K21, ED28, Cy1), (K21, ED28, Cy2), (K21, ED28, Cy3), (K21, ED29, Cy1), (K21, ED29, Cy2), (K21, ED29, Cy3), (K21, ED30, Cy1), (K21, ED30, Cy2), (K21, ED30, Cy3), (K21, ED31, Cy1), (K21, ED31, Cy2), (K21, ED31, Cy3), (K21, ED32, Cy1), (K21, ED32, Cy2), (K21, ED32, Cy3), (K21, ED33, Cy1), (K21, ED33, Cy2), (K21, ED33, Cy3), (K21, ED34, Cy1), (K21, ED34, Cy2), (K21, ED34, Cy3), (K21, ED35, Cy1), (K21, ED35, Cy2), (K21, ED35, Cy3), (K21, ED36, Cy1), (K21, ED36, Cy2), (K21, ED36, Cy3), (K21, ED37, Cy1), (K21, ED37, Cy2), (K21, ED37, Cy3), (K21, ED38, Cy1), (K21, ED38, Cy2), (K21, ED38, Cy3), (K21, ED39, Cy1), (K21, ED39, Cy2), (K21, ED39, Cy3), (K21, ED40, Cy1), (K21, ED40, Cy2), (K21, ED40, Cy3), (K21, ED41, Cy1), (K21, ED41, Cy2), (K21, ED41, Cy3), (K21, ED42, Cy1), (K21, ED42, Cy2), (K21, ED42, Cy3), (K21, ED43, Cy1), (K21, ED43, Cy2), (K21, ED43, Cy3), (K21, ED44, Cy1), (K21, ED44, Cy2), (K21, ED44, Cy3), (K21, ED45, Cy1), (K21, ED45, Cy2), (K21, ED45, Cy3), (K21, ED46, Cy1), (K21, ED46, Cy2), (K21, ED46, Cy3), (K21, ED47, Cy1), (K21, ED47, Cy2), (K21, ED47, Cy3), (K21, ED48, Cy1), (K21, ED48, Cy2), (K21, ED48, Cy3), (K21, ED49, Cy1), (K21, ED49, Cy2), (K21, ED49, Cy3), (K21, ED50, Cy1), (K21, ED50, Cy2), (K21, ED50, Cy3), (K21, ED51, Cy1), (K21, ED51, Cy2), (K21, ED51, Cy3), (K21, ED52, Cy1), (K21, ED52, Cy2), (K21, ED52, Cy3), (K21, ED53, Cy1), (K21, ED53, Cy2), (K21, ED53, Cy3), (K21, ED54, Cy1), (K21, ED54, Cy2), (K21, ED54, Cy3), (K21, ED55, Cy1), (K21, ED55, Cy2), (K21, ED55, Cy3), (K21, ED56, Cy1), (K21, ED56, Cy2), (K21, ED56, Cy3), (K21, ED57, Cy1), (K21, ED57, Cy2), (K21, ED57, Cy3), (K21, ED58, Cy1), (K21, ED58, Cy2), (K21, ED58, Cy3), (K21, ED59, Cy1), (K21, ED59, Cy2), (K21, ED59, Cy3), (K21, ED60, Cy1), (K21, ED60, Cy2), (K21, ED60, Cy3), (K21, ED61, Cy1), (K21, ED61, Cy2), (K21, ED61, Cy3), (K21, ED62, Cy1), (K21, ED62, Cy2), (K21, ED62, Cy3), (K21, ED63, Cy1), (K21, ED63, Cy2), (K21, ED63, Cy3), (K21, ED64, Cy1), (K21, ED64, Cy2), (K21, ED64, Cy3), (K21, ED65, Cy1), (K21, ED65, Cy2), (K21, ED65, Cy3), (K21, ED66, Cy1), (K21, ED66, Cy2), (K21, ED66, Cy3), (K21, ED67, Cy1), (K21, ED67, Cy2), (K21, ED67, Cy3), (K21, ED68, Cy1), (K21, ED68, Cy2), (K21, ED68, Cy3), (K21, ED69, Cy1), (K21, ED69, Cy2), (K21, ED69, Cy3), (K21, ED70, Cy1), (K21, ED70, Cy2), (K21, ED70, Cy3), (K21, ED71, Cy1), (K21, ED71, Cy2), (K21, ED71, Cy3), (K21, ED72, Cy1), (K21, ED72, Cy2), (K21, ED72, Cy3), (K21, ED73, Cy1), (K21, ED73, Cy2), (K21, ED73, Cy3), (K21, ED74, Cy1), (K21, ED74, Cy2), (K21, ED74, Cy3), (K21, ED75, Cy1), (K21, ED75, Cy2), (K21, ED75, Cy3), (K21, ED76, Cy1), (K21, ED76, Cy2), (K21, ED76, Cy3), (K21, ED77, Cy1), (K21, ED77, Cy2), (K21, ED77, Cy3), (K21, ED78, Cy1), (K21, ED78, Cy2), (K21, ED78, Cy3), (K21, ED79, Cy1), (K21, ED79, Cy2), (K21, ED79, Cy3), (K21, ED80, Cy1), (K21, ED80, Cy2), (K21, ED80, Cy3), (K21, ED81, Cy1), (K21, ED81, Cy2), (K21, ED81, Cy3), (K21, ED82, Cy1), (K21, ED82, Cy2), (K21, ED82, Cy3), (K21, ED83, Cy1), (K21, ED83, Cy2), (K21, ED83, Cy3), (K21, ED84, Cy1), (K21, ED84, Cy2), (K21, ED84, Cy3), (K21, ED85, Cy1), (K21, ED85, Cy2), (K21, ED85, Cy3), (K21, ED86, Cy1), (K21, ED86, Cy2), (K21, ED86, Cy3), (K21, ED87, Cy1), (K21, ED87, Cy2), (K21, ED87, Cy3), (K21, ED88, Cy1), (K21, ED88, Cy2), (K21, ED88, Cy3), (K21, ED89, Cy1), (K21, ED89, Cy2), (K21, ED89, Cy3), (K21, ED90, Cy1), (K21, ED90, Cy2), (K21, ED90, Cy3), (K21, ED91, Cy1), (K21, ED91, Cy2), (K21, ED91, Cy3), (K21, ED92, Cy1), (K21, ED92, Cy2), (K21, ED92, Cy3), (K22, ED1, Cy1), (K22, ED1, Cy2), (K22, ED1, Cy1), (K22, ED2, Cy1), (K22, ED2, Cy2), (K22, ED2, Cy3), (K22, ED3, Cy1), (K22, ED3, Cy2), (K22, ED3, Cy3), (K22, ED4, Cy1), (K22, ED4, Cy2), (K22, ED4, Cy3), (K22, ED5, Cy1), (K22, ED5, Cy2), (K22, ED5, Cy3), (K22, ED6, Cy1), (K22, ED6, Cy2), (K22, ED6, Cy3), (K22, ED7, Cy3), (K22, ED7, Cy2), (K22, ED7, Cy3), (K22, ED5, Cy1), (K22, ED8, Cy2), (K22, ED8, Cy3), (K22, ED9, Cy1), (K22, ED9, Cy2), (K22, ED9, Cy3), (K22, ED10, Cy1), (K22, ED10, Cy2), (K22, ED10, Cy3), (K22, ED11, Cy1), (K22, ED11, Cy2), (K22, ED11, Cy3), (K22, ED12, Cy1), (K22, ED12, Cy2), (K22, ED12, Cy3), (K22, ED13, Cy1), (K22, ED13, Cy2), (K22, ED13, Cy3), (K22, ED14, Cy1), (K22, ED14, Cy2), (K22, ED14, Cy3), (K22, ED15, Cy1), (K22, ED15, Cy2), (K22, ED15, Cy3), (K22, ED16, Cy1), (K22, ED16, Cy2), (K22, ED16, Cy3), (K22, ED17, Cy1), (K22, ED17, Cy2), (K22, ED17, Cy3), (K22, ED18, Cy1), (K22, ED18, Cy2), (K22, ED18, Cy3), (K22, ED19, Cy1), (K22, ED19, Cy2), (K22, ED19, Cy3), (K22, ED20, Cy1), (K22, ED20, Cy2), (K22, ED20, Cy3), (K22, ED21, Cy1), (K22, ED21, Cy2), (K22, ED21, Cy3), (K22, ED22, Cy1), (K22, ED22, Cy2), (K22, ED22, Cy3), (K22, ED23, Cy1), (K22, ED23, Cy2), (K22, ED23, Cy3), (K22, ED24, Cy1), (K22, ED24, Cy2), (K22, ED24, Cy3), (K22, ED25, Cy1), (K22, ED25, Cy2), (K22, ED25, Cy3), (K22, ED26, Cy1), (K22, ED26, Cy2), (K22, ED26, Cy3), (K22, ED27, Cy1), (K22, ED27, Cy2), (K22, ED27, Cy3), (K22, ED28, Cy1), (K22, ED28, Cy2), (K22, ED28, Cy3), (K22, ED29, Cy1), (K22, ED29, Cy2), (K22, ED29, Cy3), (K22, ED30, Cy1), (K22, ED30, Cy2), (K22, ED30, Cy3), (K22, ED31, Cy1), (K22, ED31, Cy2), (K22, ED31, Cy3), (K22, ED32, Cy1), (K22, ED32, Cy2), (K22, ED32, Cy3), (K22, ED33, Cy1), (K22, ED33, Cy2), (K22, ED33, Cy3), (K22, ED34, Cy1), (K22, ED34, Cy2), (K22, ED34, Cy3), (K22, ED35, Cy1), (K22, ED35, Cy2), (K22, ED35, Cy3), (K22, ED36, Cy1), (K22, ED36, Cy2), (K22, ED36, Cy3), (K22, ED37, Cy1), (K22, ED37, Cy2), (K22, ED37, Cy3), (K22, ED38, Cy1), (K22, ED38, Cy2), (K22, ED38, Cy3), (K22, ED39, Cy1), (K22, ED39, Cy2), (K22, ED39, Cy3), (K22, ED48, Cy1), (K22, ED40, Cy2), (K22, ED40, Cy3), (K22, ED41, Cy1), (K22, ED41, Cy2), (K22, ED41, Cy3), (K22, ED42, Cy1), (K22, ED42, Cy2), (K22, ED42, Cy3), (K22, ED43, Cy1), (K22, ED43, Cy2), (K22, ED43, Cy3), (K22, ED44, Cy1), (K22, ED44, Cy2), (K22, ED44, Cy3), (K22, ED45, Cy1), (K22, ED46, Cy2), (K22, ED46, Cy3), (K22, ED46, Cy1), (K22, ED46, Cy2), (K22, ED46, Cy3), (K22, ED47, Cy1), (K22, ED47, Cy2), (K22, ED47, Cy3), (K22, ED48, Cy1), (K22, ED48, Cy2), (K22, ED48, Cy3), (K22, ED49, Cy1), (K22, ED49, Cy2), (K22, ED49, Cy3), (K22, ED50, Cy1), (K22, ED50, Cy2), (K22, ED50, Cy3), (K22, ED51, Cy1), (K22, ED51, Cy2), (K22, ED51, Cy3), (K22, ED52, Cy1), (K22, ED52, Cy2), (K22, ED52, Cy3), (K22, ED53, Cy1), (K22, ED53, Cy2), (K22, ED53, Cy3), (K22, ED54, Cy1), (K22, ED54, Cy2), (K22, ED54, Cy3), (K22, ED55, Cy1), (K22, ED55, Cy2), (K22,

ED55, Cy3), (K22, ED56, Cy1), (K22, ED56, Cy2), (K22, ED56, Cy3), (K22, ED57, Cy1), (K22, ED57, Cy2), (K22, ED57, Cy3), (K22, ED58, Cy1), (K22, ED58, Cy2), (K22, ED58, Cy3), (K22, ED59, Cy1), (K22, ED59, Cy2), (K22, ED59, Cy3), (K22, ED68, Cy1), (K22, ED60, Cy2), (K22, ED60, Cy3), (K22, ED61, Cy1), (K22, ED61, Cy2), (K22, ED61, Cy3), (K22, ED62, Cy1), (K22, ED62, Cy2), (K22, ED62, Cy3), (K22, ED63, Cy1), (K22, ED63, Cy2), (K22, ED63, Cy3), (K22, ED64, Cy1), (K22, ED64, Cy2), (K22, ED64, Cy3), (K22, ED65, Cy1), (K22, ED65, Cy2), (K22, ED65, Cy3), (K22, ED66, Cy1), (K22, ED66, Cy2), (K22, ED66, Cy3), (K22, ED67, Cy1), (K22, ED67, Cy2), (K22, ED67, Cy3), (K22, ED68, Cy1), (K22, ED68, Cy2), (K22, ED68, Cy3), (K22, ED69, Cy1), (K22, ED69, Cy2), (K22, ED69, Cy3), (K22, ED70, Cy1), (K22, ED70, Cy2), (K22, ED70, Cy3), (K22, ED71, Cy1), (K22, ED71, Cy2), (K22, ED71, Cy3), (K22, ED72, Cy1), (K22, ED72, Cy2), (K22, ED72, Cy3), (K22, ED73, Cy1), (K22, ED73, Cy2), (K22, ED73, Cy3), (K22, ED74, Cy1), (K22, ED74, Cy2), (K22, ED74, Cy3), (K22, ED75, Cy1), (K22, ED75, Cy2), (K22, ED75, Cy3), (K22, ED76, Cy1), (K22, ED76, Cy2), (K22, ED76, Cy3), (K22, ED77, Cy1), (K22, ED77, Cy2), (K22, ED77, Cy3), (K22, ED78, Cy1), (K22, ED78, Cy2), (K22, ED78, Cy3), (K22, ED79, Cy1), (K22, ED79, Cy2), (K22, ED79, Cy3), (K22, ED80, Cy1), (K22, ED80, Cy2), (K22, ED80, Cy3), (K22, ED81, Cy1), (K22, ED81, Cy2), (K22, ED81, Cy3), (K22, ED82, Cy1), (K22, ED82, Cy2), (K22, ED82, Cy3), (K22, ED83, Cy1), (K22, ED83, Cy2), (K22, ED83, Cy3), (K22, ED84, Cy1), (K22, ED89, Cy2), (K22, ED84, Cy3), (K22, ED85, Cy1), (K22, ED85, Cy2), (K22, ED85, Cy3), (K22, ED86, Cy1), (K22, ED86, Cy2), (K22, ED86, Cy3), (K22, ED87, Cy1), (K22, ED87, Cy2), (K22, ED87, Cy3), (K22, ED88, Cy1), (K22, ED88, Cy2), (K22, ED88, Cy3), (K22, ED89, Cy1), (K22, ED89, Cy2), (K22, ED89, Cy3), (K22, ED90, Cy1), (K22, ED90, Cy2), (K22, ED90, Cy3), (K22, ED91, Cy1), (K22, ED91, Cy2), (K22, ED91, Cy3), (K22, ED92, Cy1), (K22, ED92, Cy2), (K22, ED92, Cy3), (K23, ED1, Cy1), (K23, ED1, Cy2), (K23, ED1, Cy3), (K23, ED2, Cy1), (K23, ED2, Cy2), (K23, ED2, Cy3), (K23, ED3, Cy1), (K23, ED3, Cy2), (K23, ED3, Cy3), (K23, ED4, Cy1), (K23, ED9, Cy2), (K23, ED4, Cy3), (K23, ED5, Cy1), (K23, ED5, Cy2), (K23, ED5, Cy3), (K23, ED6, Cy1), (K23, ED6, Cy2), (K23, ED6, Cy3), (K23, ED7, Cy1), (K23, ED7, Cy2), (K23, ED7, Cy3), (K23, ED8, Cy1), (K23, ED8, Cy2), (K23, ED8, Cy3), (K23, ED9, Cy1), (K23, ED9, Cy2), (K23, ED9, Cy3), (K23, ED10, Cy1), (K23, ED10, Cy2), (K23, ED10, Cy3), (K23, ED11, Cy1), (K23, ED11, Cy2), (K23, ED11, Cy3), (K23, ED12, Cy1), (K23, ED12, Cy2), (K23, ED12, Cy3), (K23, ED13, Cy1), (K23, ED13, Cy2), (K23, ED13, Cy3), (K23, ED14, Cy1), (K23, ED14, Cy2), (K23, ED14, Cy3), (K23, ED15, Cy1), (K23, ED15, Cy2), (K23, ED15, Cy3), (K23, ED16, Cy1), (K23, ED16, Cy2), (K23, ED16, Cy3), (K23, ED17, Cy1), (K23, ED17, Cy2), (K23, ED17, Cy3), (K23, ED18, Cy1), (K23, ED18, Cy2), (K23, ED18, Cy3), (K23, ED19, Cy1), (K23, ED19, Cy2), (K23, ED19, Cy3), (K23, ED20, Cy1), (K23, ED20, Cy2), (K23, ED20, Cy3), (K23, ED21, Cy1), (K23, ED21, Cy2), (K23, ED21, Cy3), (K23, ED22, Cy1), (K23, ED22, Cy2), (K23, ED22, Cy3), (K23, ED23, Cy1), (K23, ED23, Cy2), (K23, ED23, Cy3), (K23, ED24, Cy1), (K23, ED24, Cy2), (K23, ED24, Cy3), (K23, ED25, Cy1), (K23, ED25, Cy2), (K23, ED25, Cy3), (K23, ED26, Cy1), (K23, ED26, Cy2), (K23, ED26, Cy3), (K23, ED27, Cy1), (K23, ED27, Cy2), (K23, ED27, Cy3), (K23, ED28, Cy1), (K23, ED28, Cy2), (K23, ED28, Cy3), (K23, ED29, Cy1), (K23, ED29, Cy2), (K23, ED29, Cy3), (K23, ED38, Cy1), (K23, ED30, Cy2), (K23, ED30, Cy3), (K23, ED31, Cy1), (K23, ED31, Cy2), (K23, ED31, Cy3), (K23, ED32, Cy1), (K23, ED32, Cy2), (K23, ED32, Cy3), (K23, ED33, Cy1), (K23, ED33, Cy2), (K23, ED33, Cy3), (K23, ED34, Cy1), (K23, ED34, Cy2), (K23, ED34, Cy3), (K23, ED35, Cy1), (K23, ED35, Cy2), (K23, ED35, Cy3), (K23, ED36, Cy1), (K23, ED36, Cy2), (K23, ED36, Cy3), (K23, ED37, Cy1), (K23, ED37, Cy2), (K23, ED37, Cy3), (K23, ED38, Cy1), (K23, ED38, Cy2), (K23, ED38, Cy3), (K23, ED39, Cy1), (K23, ED39, Cy2), (K23, ED39, Cy3), (K23, ED40, Cy1), (K23, ED90, Cy2), (K23, ED40, Cy3), (K23, ED41, Cy1), (K23, ED41, Cy2), (K23, ED41, Cy3), (K23, ED42, Cy1), (K23, ED42, Cy2), (K23, ED42, Cy3), (K23, ED43, Cy1), (K23, ED43, Cy2), (K23, ED43, Cy3), (K23, ED44, Cy1), (K23, ED44, Cy2), (K23, ED44, Cy3), (K23, ED45, Cy1), (K23, ED45, Cy2), (K23, ED45, Cy3), (K23, ED46, Cy1), (K23, ED46, Cy2), (K23, ED46, Cy3), (K23, ED47, Cy1), (K23, ED47, Cy2), (K23, ED47, Cy3), (K23, ED48, Cy1), (K23, ED49, Cy2), (K23, ED48, Cy3), (K23, ED49, Cy1), (K23, ED49, Cy2), (K23, ED49, Cy3), (K23, ED50, Cy1), (K23, ED50, Cy2), (K23, ED50, Cy3), (K23, ED51, Cy1), (K23, ED51, Cy2), (K23, ED51, Cy3), (K23, ED52, Cy1), (K23, ED52, Cy2), (K23, ED52, Cy3), (K23, ED53, Cy1), (K23, ED53, Cy2), (K23, ED53, Cy3), (K23, ED54, Cy1), (K23, ED54, Cy2), (K23, ED54, Cy3), (K23, ED55, Cy1), (K23, ED55, Cy2), (K23, ED55, Cy3), (K23, ED56, Cy1), (K23, ED56, Cy2), (K23, ED56, Cy3), (K23, ED57, Cy1), (K23, ED57, Cy2), (K23, ED57, Cy3), (K23, ED58, Cy1), (K23, ED58, Cy2), (K23, ED58, Cy3), (K23, ED59, Cy1), (K23, ED59, Cy2), (K23, ED59, Cy3), (K23, ED60, Cy1), (K23, ED60, Cy2), (K23, ED60, Cy3), (K23, ED61, Cy1), (K23, ED61, Cy2), (K23, ED61, Cy3), (K23, ED62, Cy1), (K23, ED62, Cy2), (K23, ED62, Cy3), (K23, ED63, Cy1), (K23, ED63, Cy2), (K23, ED63, Cy3), (K23, ED64, Cy1), (K23, ED64, Cy2), (K23, ED64, Cy3), (K23, ED65, Cy1), (K23, ED65, Cy2), (K23, ED65, Cy3), (K23, ED66, Cy1), (K23, ED66, Cy2), (K23, ED66, Cy3), (K23, ED67, Cy1), (K23, ED67, Cy2), (K23, ED67, Cy3), (K23, ED68, Cy1), (K23, ED68, Cy2), (K23, ED68, Cy3), (K23, ED69, Cy1), (K23, ED69, Cy2), (K23, ED69, Cy3), (K23, ED70, Cy1), (K23, ED70, Cy2), (K23, ED70, Cy3), (K23, ED71, Cy1), (K23, ED71, Cy2), (K23, ED71, Cy3), (K23, ED72, Cy1), (K23, ED72, Cy2), (K23, ED72, Cy3), (K23, ED73, Cy1), (K23, ED73, Cy2), (K23, ED73, Cy3), (K23, ED74, Cy1), (K23, ED74, Cy2), (K23, ED74, Cy3), (K23, ED75, Cy1), (K23, ED75, Cy2), (K23, ED75, Cy3), (K23, ED76, Cy1), (K23, ED76, Cy2), (K23, ED76, Cy3), (K23, ED77, Cy1), (K23, ED77, Cy2), (K23, ED77, Cy3), (K23, ED78, Cy1), (K23, ED78, Cy2), (K23, ED78, Cy3), (K23, ED79, Cy1), (K23, ED79, Cy2), (K23, ED79, Cy3), (K23, ED80, Cy1), (K23, ED80, Cy2), (K23, ED80, Cy3), (K23, ED81, Cy1), (K23, ED81, Cy2), (K23, ED81, Cy3), (K23, ED82, Cy1), (K23, ED82, Cy2), (K23, ED82, Cy3), (K23, ED83, Cy1), (K23, ED83, Cy2), (K23, ED83, Cy3), (K23, ED84, Cy1), (K23, ED84, Cy2), (K23, ED84, Cy3), (K23, ED85, Cy1), (K23, ED85, Cy2), (K23, ED85, Cy3), (K23, ED86, Cy1), (K23, ED86, Cy2), (K23, ED86, Cy3), (K23, ED87, Cy1), (K23, ED87, Cy2), (K23, ED87, Cy3), (K23, ED88, Cy1), (K23, ED88, Cy2), (K23, ED88, Cy3), (K23, ED89, Cy1), (K23, ED89, Cy2), (K23, ED89, Cy3), (K23, ED90, Cy1), (K23, ED90, Cy2), (K23, ED90, Cy3), (K23, ED91, Cy1), (K23, ED91, Cy2), (K23, ED91, Cy3), (K23, ED92, Cy1), (K23, ED92, Cy2), (K23, ED92, Cy3), (K24, ED1, Cy1), (K24, ED1, Cy2), (K24, ED1, Cy3), (K24, ED2, Cy1), (K24, ED2, Cy2), (K24, ED2, Cy3), (K24, ED3, Cy1), (K24, ED3, Cy2), (K24, ED3, Cy3), (K24, ED4, Cy1), (K24, ED4, Cy2), (K24, ED4, Cy3), (K24, ED5, Cy1), (K24, ED5, Cy2), (K24, ED5, Cy3), (K24, ED6, Cy1), (K24, ED6, Cy2), (K24, ED6, Cy3), (K24, ED6, Cy1), (K24, ED7, Cy2), (K24, ED7, Cy3), (K24, ED8, Cy1), (K24, ED8, Cy2), (K24, ED8, Cy3), (K24, En, Cy1), (K24, ED9, Cy2), (K24, ED9, Cy3), (K24, ED10, Cy1), (K24, ED10, Cy2), (K24, ED10, Cy3), (K24, ED11, Cy1), (K24, ED11, Cy2), (K24, ED11, Cy3), (K24, ED12, Cy1), (K24, ED12, Cy2), (K24, ED12, Cy3), (K24, ED13, Cy1), (K24, ED13, Cy2), (K24, ED13, Cy3), (K24, ED14, Cy1), (K24, ED14, Cy2), (K24, ED14, Cy3), (K24, ED15, Cy1), (K24, ED15, Cy2), (K24, ED15, Cy3), (K24, ED16, Cy1), (K24, ED16, Cy2), (K21, ED16, Cy3), (K24, ED17, Cy1), (K24, ED17, Cy2), (K24, ED17, Cy3), (K24, ED18, Cy1), (K24, ED18, Cy2), (K24, ED18, Cy3), (K24, ED19, Cy1), (K24, ED19, Cy2), (K24, ED19, Cy3), (K24, ED20, Cy1), (K24, ED20, Cy2), (K24, ED20, Cy3), (K24, ED21, Cy1), (K24, ED21, Cy2), (K24, ED21, Cy3), (K24, ED22, Cy1), (K24, ED22, Cy2), (K24, ED22, Cy3), (K24, ED23, Cy1), (K24, ED23, Cy2), (K24, ED23, Cy3), (K24, ED24, Cy1), (K24, ED24, Cy2), (K24, ED24, Cy3), (K24, ED25, Cy1), (K24, ED25, Cy2), (K24, ED25, Cy3), (K24, ED26, Cy1), (K24, ED26, Cy2), (K24, ED26, Cy3), (K24, ED27, Cy1), (K24, ED27, Cy2), (K24, ED27, Cy3), (K24, ED28, Cy1), (K24, ED28, Cy2), (K24, ED28, Cy3), (K24, ED29, Cy1), (K24, ED29, Cy2), (K24, ED29, Cy3), (K24, ED30, Cy1), (K24, ED30, Cy2), (K24, ED30, Cy3), (K24, ED31, Cy1), (K24, ED31, Cy2), (K24, ED31, Cy3), (K24, ED32, Cy1), (K24, ED32, Cy2), (K24, ED32, Cy3), (K24, ED33, Cy1), (K24, ED33, Cy2), (K24, ED33, Cy3), (K24, ED34, Cy1), (K24, ED34, Cy2), (K24, ED34, Cy3), (K24, ED35, Cy1), (K24, ED35, Cy2), (K24, ED35, Cy3), (K24, ED36, Cy1), (K24, ED36, Cy2), (K24, ED36, Cy3), (K24, ED37, Cy1), (K24, ED37, Cy2), (K24, ED37, Cy3), (K24, ED38, Cy1), (K24, ED38, Cy2), (K24, ED38, Cy3), (K24, ED39, Cy1), (K24, ED39, Cy2), (K24, ED39, Cy3), (K24, ED40, Cy1), (K24, ED40, Cy2), (K24, ED40, Cy3), (K24, ED41, Cy1), (K24, ED41, Cy2), (K24, ED41, Cy3), (K24, ED42, Cy1), (K24, ED42, Cy2), (K24, ED42, Cy3), (K24, ED43, Cy1), (K24, ED43, Cy2), (K24, ED43, (K24, ED44, Cy3), (K24, ED44, Cy2), (K24, ED44, Cy3), (K24, ED45, Cy1), (K24, ED45, Cy2), (K24, ED45, Cy3), (K24, ED46, Cy1), (K24, ED46, Cy2), (K24, ED46, Cy3), (K24, ED47, Cy1), (K24, ED47, Cy2), (K24, ED47, Cy3), (K24, ED48, Cy1), (K24, ED48, Cy2), (K24, ED48, Cy3), (K24, ED49, Cy1), (K24, ED49, Cy2), (K24, ED49, Cy3), (K24, ED50, Cy1), (K24, ED50, Cy2), (K24, ED50, Cy3), (K24, ED51, Cy1), (K24, ED51, Cy2), (K24, ED51, Cy3), (K24, ED52, Cy1), (K24, ED52, Cy2), (K24, ED52, Cy3), (K24, ED53, Cy1), (K24, ED53, Cy2), (K24, ED53, Cy3), (K24, ED54, Cy1), (K24, ED54, Cy2), (K24, ED54, Cy3), (K24, ED55, Cy1), (K24, ED55, Cy2), (K24, ED55, Cy3), (K24, ED56, Cy1), (K24, ED56, Cy2), (K24, ED56, Cy3), (K24, ED57, Cy1), (K24, ED57, Cy2), (K24, ED57, Cy3), (K24, ED58, Cy1), (K24, ED58, Cy2), (K24, ED58, Cy3), (K24, ED59, Cy1), (K24, ED59, Cy2), (K24, ED59, Cy3), (K24, ED60, Cy1), (K24, ED60, Cy2), (K24, ED60, Cy3), (K24, ED61, Cy1), (K24, ED61, Cy2), (K24, ED61, Cy3), (K24, ED62, Cy1), (K24, ED62, Cy2), (K24, ED62, Cy3), (K24, ED63, Cy1), (K24, ED63, Cy2), (K24, ED63, Cy3), (K24, ED64, Cy1), (K24, ED64, Cy2), (K24, ED64, Cy3), (K24, ED65, Cy1), (K24, ED65, Cy2), (K24, ED65, Cy3), (K24, ED66, Cy1), (K24, ED66, Cy2), (K24, ED66, Cy3), (K24, ED67, Cy1), (K24, ED67, Cy2), (K24, ED67, Cy3), (K24, ED68, Cy1), (K24, ED68, Cy2), (K24, ED68, Cy3), (K24, ED69, Cy1), (K24, ED69, Cy2), (K24, ED69, Cy3), (K24, ED70, Cy1), (K24, ED70, Cy2), (K24, ED70, Cy3), (K24, ED71, Cy1), (K24, ED71, Cy2), (K24, ED71, Cy3), (K24, ED72, Cy1), (K24, ED72, Cy2), (K24, ED72, Cy3), (K24, ED73, Cy1), (K24, ED73, Cy2), (K24, ED73, Cy3), (K24, ED74, Cy1), (K24, ED74, Cy2), (K24, ED74, Cy3), (K24, ED75, Cy1), (K24, ED75, Cy2), (K24, ED75, Cy3), (K24, ED76, Cy1), (K24, ED76, Cy2), (K24, ED76, Cy3), (K24, ED77, Cy1), (K24, ED77, Cy2), (K24, ED77, Cy3), (K24, ED78, Cy1), (K24, ED78, Cy2), (K24, ED78, Cy3), (K24, ED79, Cy1), (K24, ED79, Cy2), (K24, ED79, Cy3), (K24, ED80, Cy1), (K24, ED80, Cy2), (K24, ED80, Cy3), (K24, ED81, Cy1), (K24, ED81, Cy2), (K24, ED81, Cy3), (K24, ED82, Cy1), (K24, ED82, Cy2), (K24, ED82, Cy3), (K24, ED83, Cy1), (K24, ED83, Cy2), (K24, ED83, Cy3), (K24, ED84, Cy1), (K24, ED84, Cy2), (K24, ED84, Cy3), (K24, ED85, Cy1), (K24, ED85, Cy2), (K24, ED85, Cy3), (K29, ED86, Cy1), (K24, ED86, Cy2), (K24, ED86, Cy3), (K24, ED87, Cy1), (K24, ED87, Cy2), (K24, ED87, Cy3), (K24, ED88, Cy1), (K24, ED88, Cy2), (K24, ED88, Cy3), (K24, ED89, Cy1), (K29, ED89, Cy2), (K24, ED89, Cy3), (K24, ED90, Cy1), (K24, ED90, Cy2), (K29, ED90, Cy3), (K24, ED91, Cy1), (K24, ED91, Cy2), (K24, ED91, Cy3), (K24, ED92, Cy1), (K24, ED92, Cy2), (K29, ED92, Cy3), (K25, ED1, Cy1), (K25, ED1, Cy2), (K25, ED1, Cy3), (K25, ED2, Cy1), (K25, ED2, Cy2), (K25, ED2, Cy3), (K25, ED3, Cy1), (K25, ED3, Cy2), (K25, ED3, Cy3), (K25, ED4, Cy1), (K25, EN, Cy2), (K25, ED4, Cy3), (K25, ED5, Cy1), (K25, ED5, Cy2), (K25, ED5, Cy3), (K25, ED6, Cy1), (K25, ED6, Cy2), (K25, ED6, Cy3), (K25, ED7, Cy1), (K25, ED7, Cy2), (K25, ED7, Cy3), (K25, ED5, Cy1), (K25, ED5, Cy2), (K25, ED5, Cy3), (K25, ED9, Cy1), (K25, ED9, Cy2), (K25, ED9, Cy3), (K25, ED10, Cy1), (K25, ED10, Cy2), (K25, ED10, Cy3), (K25, ED11, Cy1), (K25, ED11, Cy2), (K25, ED11, Cy3), (K25, ED12, Cy1), (K25, ED12, Cy2), (K25, ED12, Cy3), (K25, ED13, Cy1), (K25, ED13, Cy2), (K25, ED13, Cy3), (K25, ED14, Cy1), (K25, ED14, Cy2), (K25, ED14, Cy3), (K25, ED15, Cy1), (K25, ED15, Cy2), (K25, ED15, Cy3), (K25, ED16, Cy1), (K25, ED16, Cy2), (K25, ED16, Cy3), (K25, ED17, Cy1), (K25, ED17, Cy2), (K25, ED17, Cy3), (K25, ED18, Cy1), (K25, ED25, Cy2), (K25, ED18, Cy3), (K25, ED19, Cy1), (K25, ED19, Cy2), (K25, ED19, Cy3), (K25, ED20, Cy1), (K25, ED20, Cy2), (K25, ED20, Cy3), (K25, ED21, Cy1), (K25, ED21, Cy2), (K25, ED21, Cy3), (K25, ED22, Cy1), (K25, ED22, Cy2), (K25, ED22, Cy3), (K25, ED23, Cy1), (K25, ED23, Cy2), (K25, ED23, Cy3), (K25, ED24, Cy1), (K25, ED24, Cy2), (K25, ED24, Cy3), (K25, ED25, Cy1), (K25, ED25, Cy2), (K25, ED25, Cy3), (K25, ED26, Cy1), (K25, ED26, Cy2), (K25, ED26, Cy3), (K25, ED27, Cy1), (K25, ED27, Cy2), (K25, ED27, Cy3), (K25, ED28, Cy1), (K25, ED28, Cy2), (K25, ED28, Cy3), (K25, ED29, Cy1), (K25, ED29, Cy2), (K25, ED29, Cy3), (K25, ED30, Cy1), (K25, ED30, Cy2), (K25, ED30, Cy3), (K25, ED31, Cy1), (K25, ED31, Cy2), (K25, ED31, Cy3), (K25, ED32, Cy1), (K25, ED32, Cy2), (K25, ED32, Cy3), (K25, ED33, Cy1), (K25, ED33, Cy2), (K25, ED33, Cy3), (K25, ED34, Cy1), (K25, ED34, Cy2), (K25, ED34, Cy3), (K25, ED35, Cy1), (K25, ED35, Cy2), (K25, ED35, Cy3), (K25, ED36, Cy1), (K25, ED36, Cy2), (K25, ED36, Cy3), (K25, ED37, Cy1), (K25, ED37, Cy2), (K25, ED37, Cy3), (K25, ED38, Cy1), (K25, ED38, Cy2), (K25, ED38, Cy3), (K25, ED39, Cy1), (K25, ED39, Cy2), (K25, ED39, Cy3), (K25, ED40, Cy1), (K25, ED40, Cy2), (K25, ED40, Cy3), (K25, ED41, Cy1), (K25, ED41, Cy2), (K25, ED41, Cy3), (K25, ED42, Cy1), (K25, ED42, Cy2), (K25, ED42, Cy3), (K25, ED43, Cy1), (K25, ED43, Cy2), (K25, ED43, Cy3), (K25, ED44, Cy1), (K25, ED44, Cy2), (K25, ED44, Cy3), (K25, ED45, Cy1), (K25, ED45, Cy2), (K25, ED45, Cy3), (K25, ED46, Cy1), (K25, ED46, Cy2), (K25, ED46, Cy3), (K25, ED47, Cy1), (K25, ED47, Cy2), (K25,

ED47, Cy3), (K25, ED48, Cy1), (K25, ED48, Cy2), (K25, ED48, Cy3), (K25, ED49, Cy1), (K25, ED49, Cy2), (K25, ED49, Cy3), (K25, ED50, Cy1), (K25, ED50, Cy2), (K25, ED50, Cy3), (K25, ED51, Cy1), (K25, ED51, Cy2), (K25, ED51, Cy3), (K25, ED52, Cy1), (K25, ED52, Cy2), (K25, ED52, Cy3), (K25, ED53, Cy1), (K25, ED53, Cy2), (K25, ED53, Cy3), (K25, ED54, Cy1), (K25, ED54, Cy2), (K25, ED54, Cy3), (K25, ED55, Cy1), (K25, ED55, Cy2), (K25, ED55, Cy3), (K25, ED56, Cy1), (K25, ED56, Cy2), (K25, ED56, Cy3), (K25, ED57, Cy1), (K25, ED57, Cy2), (K25, ED57, Cy3), (K25, ED58, Cy1), (K25, ED58, Cy2), (K25, ED58, Cy3), (K25, ED59, Cy1), (K25, ED59, Cy2), (K25, ED59, Cy3), (K25, ED60, Cy1), (K25, ED60, Cy2), (K25, ED60, Cy3), (K25, ED61, Cy1), (K25, ED61, Cy2), (K25, ED61, Cy3), (K25, ED62, Cy1), (K25, ED62, Cy2), (K25, ED62, Cy3), (K25, ED63, Cy1), (K25, ED63, Cy2), (K25, ED63, Cy3), (K25, ED64, Cy1), (K25, ED64, Cy2), (K25, ED64, Cy3), (K25, ED65, Cy1), (K25, ED65, Cy2), (K25, ED65, Cy3), (K25, ED66, Cy1), (K25, ED66, Cy2), (K25, ED66, Cy3), (K25, ED67, Cy1), (K25, ED67, Cy2), (K25, ED67, Cy3), (K25, ED68, Cy1), (K23, ED68, Cy2), (K25, ED68, Cy3), (K25, ED69, Cy1), (K25, ED69, Cy2), (K25, ED69, Cy3), (K25, ED70, Cy1), (K25, ED70, Cy2), (K25, ED70, Cy3), (K25, ED71, Cy1), (K25, ED71, Cy2), (K25, ED71, Cy3), (K25, ED72, Cy1), (K25, ED72, Cy2), (K25, ED72, Cy3), (K25, ED73, Cy1), (K25, ED73, Cy2), (K25, ED73, Cy3), (K25, ED74, Cy1), (K25, ED74, Cy2), (K25, ED74, Cy3), (K25, ED75, Cy1), (K25, ED75, Cy2), (K25, ED75, Cy3), (K25, ED76, Cy1), (K25, ED76, Cy2), (K25, ED76, Cy3), (K25, ED77, Cy1), (K25, ED77, Cy2), (K25, ED77, Cy3), (K25, ED78, Cy1), (K25, ED78, Cy2), (K25, ED78, Cy3), (K25, ED79, Cy1), (K25, ED79, Cy2), (K25, ED79, Cy3), (K25, ED80, Cy1), (K25, ED80, Cy2), (K25, ED80, Cy3), (K25, ED81, Cy1), (K25, ED81, Cy2), (K25, ED81, Cy3), (K25, ED82, Cy1), (K25, ED82, Cy2), (K25, ED82, Cy3), (K25, ED83, Cy1), (K25, ED83, Cy2), (K25, ED83, Cy3), (K25, ED84, Cy1), (K25, ED84, Cy2), (K25, ED84, Cy3), (K25, ED85, Cy1), (K25, ED85, Cy2), (K25, ED85, Cy3), (K25, ED86, Cy1), (K25, ED86, Cy2), (K25, ED86, Cy3), (K23, ED87, Cy1), (K25, ED87, Cy2), (K25, ED87, Cy3), (K25, ED88, Cy1), (K25, ED88, Cy2), (K25, ED88, Cy3), (K25, ED89, Cy1), (K25, ED89, Cy2), (K25, ED89, Cy3), (K25, ED90, Cy1), (K25, ED90, Cy2), (K25, ED90, Cy3), (K25, ED91, Cy1), (K25, ED91, Cy2), (K25, ED91, Cy3), (K25, ED92, Cy1), (K25, ED92, Cy2), (K25, ED92, Cy3), (K26, ED1, Cy1), (K26, ED1, Cy2), (K26, ED1, Cy3), (K26, ED2, Cy1), (K26, ED2, Cy2), (K26, ED2, Cy3), (K26, ED3, Cy1), (K26, ED3, Cy2), (K26, ED3, Cy3), (K26, ED4, Cy1), (K26, ED4, Cy2), (K26, ED4, Cy3), (K26, ED5, Cy1), (K26, ED5, Cy2), (K26, ED5, Cy3), (K26, ED6, Cy1), (K26, ED6, Cy2), (K26, ED6, Cy3), (K26, ED7, Cy1), (K26, ED7, Cy2), (K26, ED7, Cy3), (K26, ED5, Cy1), (K26, ED8, Cy2), (K26, ED8, Cy3), (K26, ED9, Cy1), (K26, ED9, Cy2), (K26, ED9, Cy3), (K26, ED10, Cy1), (K26, ED10, Cy2), (K26, ED10, Cy3), (K26, ED11, Cy1), (K26, ED11, Cy2), (K26, ED11, Cy3), (K26, ED12, Cy1), (K26, ED12, Cy2), (K26, ED12, Cy3), (K26, ED13, Cy1), (K26, ED13, Cy2), (K26, ED13, Cy3), (K26, ED14, Cy1), (K26, ED14, Cy2), (K26, ED14, Cy3), (K26, ED15, Cy1), (K26, ED15, Cy2), (K26, ED15, Cy3), (K26, ED16, Cy1), (K26, ED16, Cy2), (K26, ED16, Cy3), (K26, ED17, Cy1), (K26, ED17, Cy2), (K26, ED17, Cy3), (K26, ED18, Cy1), (K26, ED18, Cy2), (K26, ED18, Cy3), (K26, ED19, Cy1), (K26, ED19, Cy2), (K26, ED19, Cy3), (K26, ED20, Cy1), (K26, ED20, Cy2), (K26, ED20, Cy3), (K26, ED21, Cy1), (K26, ED21, Cy2), (K26, ED21, Cy3), (K26, ED22, Cy1), (K26, ED22, Cy2), (K26, ED22, Cy3), (K26, ED23, Cy1), (K26, ED23, Cy2), (K26, ED23, Cy3), (K26, ED24, Cy1), (K26, ED24, Cy2), (K26, ED24, Cy3), (K26, ED25, Cy1), (K26, ED25, Cy2), (K26, ED25, Cy3), (K26, ED26, Cy1), (K26, ED26, Cy2), (K26, ED26, Cy3), (K26, ED27, Cy1), (K26, ED27, Cy2), (K26, ED27, Cy3), (K26, ED28, Cy1), (K26, ED28, Cy2), (K26, ED28, Cy3), (K26, ED29, Cy1), (K26, ED29, Cy2), (K26, ED29, Cy3), (K26, ED30, Cy1), (K26, ED30, Cy2), (K26, ED30, Cy3), (K26, ED31, Cy1), (K26, ED31, Cy2), (K26, ED31, Cy3), (K26, ED32, Cy1), (K26, ED32, Cy2), (K26, ED32, Cy3), (K26, ED33, Cy1), (K26, ED33, Cy2), (K26, ED33, Cy3), (K26, ED34, Cy1), (K26, ED34, Cy2), (K26, ED34, Cy3), (K26, ED35, Cy1), (K26, ED35, Cy2), (K26, ED35, Cy3), (K26, ED36, Cy1), (K26, ED36, Cy2), (K26, ED36, Cy3), (K26, ED37, Cy1), (K26, ED37, Cy2), (K26, ED37, Cy3), (K26, ED38, Cy1), (K26, ED38, Cy2), (K26, ED38, Cy3), (K26, ED39, Cy1), (K26, ED39, Cy2), (K26, ED39, Cy3), (K26, ED40, Cy1), (K26, ED40, Cy2), (K26, ED40, Cy3), (K26, ED41, Cy1), (K26, ED41, Cy2), (K26, ED41, Cy3), (K26, ED42, Cy1), (K26, ED42, Cy2), (K26, ED42, Cy3), (K26, ED43, Cy1), (K26, ED43, Cy2), (K26, ED43, Cy3), (K26, ED44, Cy1), (K26, ED44, Cy2), (K26, ED44, Cy3), (K26, ED45, Cy1), (K26, ED45, Cy2), (K26, ED45, Cy3), (K26, ED46, Cy1), (K26, ED46, Cy2), (K26, ED46, Cy3), (K26, ED47, Cy1), (K26, ED47, Cy2), (K26, ED47, Cy3), (K26, ED48, Cy1), (K26, ED48, Cy2), (K26, ED48, Cy3), (K26, ED49, Cy1), (K26, ED49, Cy2), (K26, ED49, Cy3), (K26, ED50, Cy1), (K26, ED50, Cy2), (K26, ED50, Cy3), (K26, ED51, Cy1), (K26, ED51, Cy2), (K26, ED51, Cy3), (K26, ED52, Cy1), (K26, ED52, Cy2), (K26, ED52, Cy3), (K26, ED53, Cy1), (K26, ED53, Cy2), (K26, ED53, Cy3), (K26, ED54, Cy1), (K26, ED54, Cy2), (K26, ED54, Cy3), (K26, ED55, Cy1), (K26, ED55, Cy2), (K26, ED55, Cy3), (K26, ED56, Cy1), (K26, ED56, Cy2), (K26, ED56, Cy3), (K26, ED57, Cy1), (K26, ED57, Cy2), (K26, ED57, Cy3), (K26, ED58, Cy1), (K26, ED58, Cy2), (K26, ED58, Cy3), (K26, ED59, Cy1), (K26, ED59, Cy2), (K26, ED59, Cy3), (K26, ED60, Cy1), (K26, ED60, Cy2), (K26, ED60, Cy3), (K26, ED61, Cy1), (K26, ED61, Cy2), (K26, ED61, Cy3), (K26, ED62, Cy1), (K26, ED62, Cy2), (K26, ED62, Cy3), (K26, ED63, Cy1), (K26, ED63, Cy2), (K26, ED63, Cy3), (K26, ED64, Cy1), (K26, ED64, Cy2), (K26, ED64, Cy3), (K26, ED65, Cy1), (K26, ED65, Cy2), (K26, ED65, Cy3), (K26, ED66, Cy1), (K26, ED66, Cy2), (K26, ED66, Cy3), (K26, ED67, Cy1), (K26, ED67, Cy2), (K26, ED67, Cy3), (K26, ED68, Cy1), (K26, ED68, Cy2), (K26, ED68, Cy3), (K26, ED69, Cy1), (K26, ED69, Cy2), (K26, ED69, Cy3), (K26, ED70, Cy1), (K26, ED70, Cy2), (K26, ED70, Cy3), (K26, ED71, Cy1), (K26, ED71, Cy2), (K26, ED71, Cy3), (K26, ED72, Cy1), (K26, ED72, Cy2), (K26, ED72, Cy3), (K26, ED73, Cy1), (K26, ED73, Cy2), (K26, ED73, Cy3), (K26, ED74, Cy1), (K26, ED74, Cy2), (K26, ED74, Cy3), (K26, ED75, Cy1), (K26, ED75, Cy2), (K26, ED75, Cy3), (K26, ED76, Cy1), (K26, ED76, Cy2), (K26, ED76, Cy3), (K26, ED77, Cy1), (K26, ED77, Cy2), (K26, ED77, Cy3), (K26, ED78, Cy1), (K26, ED78, Cy2), (K26, ED78, Cy3), (K26, ED79, Cy1), (K26, ED79, Cy2), (K26, ED79, Cy3), (K26, ED80, Cy1), (K26, ED80, Cy2), (K26, ED80, Cy3), (K26, ED81, Cy1), (K26, ED81, Cy2), (K26, ED81, Cy3), (K26, ED82, Cy1), (K26, ED82, Cy2), (K26, ED82, Cy3), (K26, ED83, Cy1), (K26, ED83, Cy2), (K26, ED83, Cy3), (K26, ED84, Cy1), (K26, ED84, Cy2), (K26, ED84, Cy3), (K26, ED85, Cy1), (K26, ED85, Cy2), (K26, ED85, Cy3), (K26, ED86, Cy1), (K26, ED86, Cy2), (K26, ED86, Cy3), (K26, ED87, Cy1), (K26, ED87, Cy2), (K26, ED87, Cy3), (K26, ED88, Cy1), (K26, ED88, Cy2), (K26, ED88, Cy3), (K26, ED89, Cy1), (K26, ED89, Cy2), (K26,

ED89, Cy3), (K26, ED90, Cy1), (K26, ED90, Cy2), (K26, ED90, Cy3), (K26, ED91, Cy1), (K26, ED91, Cy2), (K26, ED91, Cy1), (K26, ED92, Cy1), (K26, ED92, Cy2), (K26, ED92, Cy3), (K27, ED1, Cy1), (K27, ED1, Cy2), (K27, ED1, Cy3), (K27, ED2, Cy1), (K27, ED2, Cy2), (K27, ED2, Cy3), (K27, ED3, Cy1), (K27, ED3, Cy2), (K27, ED3, Cy1), (K27, ED4, Cy1), (K27, ED4, Cy2), (K27, ED4, Cy3), (K27, ED5, Cy1), (K27, ED5, Cy2), (K27, ED5, Cy3), (K27, ED6, Cy1), (K27, ED6, Cy2), (K27, ED6, Cy3), (K27, ED7, Cy1), (K27, ED7, Cy2), (K27, ED7, Cy1), (K27, ED5, Cy1), (K27, ED8, Cy2), (K27, ED8, Cy3), (K27, ED9, Cy1), (K27, ED9, Cy2), (K27, ED9, Cy3), (K27, ED10, Cy1), (K27, ED10, Cy2), (K27, ED10, Cy3), (K27, ED11, Cy1), (K27, ED11, Cy2), (K27, ED11, Cy3), (K27, ED12, Cy1), (K27, ED12, Cy2), (K27, ED12, Cy3), (K27, ED13, Cy1), (K27, ED13, Cy2), (K27, ED13, Cy3), (K27, ED14, Cy1), (K28, ED14, Cy2), (K27, ED14, Cy3), (K27, ED15, Cy1), (K27, ED15, Cy2), (K27, ED15, Cy3), (K27, ED16, Cy1), (K28, ED16, Cy2), (K27, ED16, Cy3), (K28, ED17, Cy1), (K28, ED17, Cy2), (K27, ED17, Cy3), (K27, ED18, Cy1), (K28, ED18, Cy2), (K27, ED18, Cy3), (K27, ED19, Cy1), (K27, ED19, Cy2), (K27, ED19, Cy3), (K27, ED20, Cy1), (K27, ED20, Cy2), (K27, ED20, Cy3), (K27, ED21, Cy1), (K27, ED21, Cy2), (K27, ED21, Cy3), (K27, ED22, Cy1), (K27, ED22, Cy2), (K27, ED22, Cy3), (K27, ED23, Cy1), (K27, ED23, Cy2), (K27, ED23, Cy3), (K27, ED24, Cy1), (K27, ED24, Cy2), (K27, ED24, Cy3), (K27, ED25, Cy1), (K27, ED25, Cy2), (K27, ED25, Cy3), (K27, ED26, Cy1), (K27, ED26, Cy2), (K27, ED26, Cy3), (K27, ED27, Cy1), (K27, ED27, Cy2), (K27, ED27, Cy3), (K27, ED28, Cy1), (K27, ED28, Cy2), (K27, ED28, Cy3), (K27, ED29, Cy1), (K27, ED29, Cy2), (K27, ED29, Cy3), (K27, ED30, Cy1), (K27, ED30, Cy2), (K27, ED30, Cy3), (K27, ED31, Cy1), (K27, ED31, Cy2), (K27, ED31, Cy3), (K27, ED32, Cy1), (K27, ED32, Cy2), (K27, ED32, Cy3), (K27, ED33, Cy1), (K27, ED33, Cy2), (K27, ED33, Cy3), (K27, ED34, Cy1), (K27, ED34, Cy2), (K27, ED34, Cy3), (K27, ED35, Cy1), (K27, ED35, Cy2), (K27, ED35, Cy3), (K27, ED36, Cy1), (K27, ED36, Cy2), (K27, ED36, Cy3), (K27, ED37, Cy1), (K27, ED37, Cy2), (K27, ED37, Cy3), (K27, ED38, Cy1), (K27, ED38, Cy2), (K27, ED38, Cy3), (K27, ED39, Cy1), (K27, ED39, Cy2), (K27, ED39, Cy3), (K27, ED40, Cy1), (K27, ED40, Cy2), (K27, ED40, Cy3), (K27, ED41, Cy1), (K27, ED41, Cy2), (K27, ED41, Cy3), (K27, ED42, Cy1), (K27, ED42, Cy2), (K27, ED42, Cy3), (K27, ED43, Cy1), (K27, ED43, Cy2), (K27, ED43, Cy3), (K27, ED44, Cy1), (K27, ED44, Cy2), (K27, ED44, Cy3), (K27, ED45, Cy1), (K27, ED45, Cy2), (K27, ED45, Cy3), (K27, ED46, Cy1), (K27, ED46, Cy2), (K27, ED46, Cy3), (K27, ED47, Cy1), (K27, ED47, Cy2), (K27, ED47, Cy3), (K27, ED48, Cy1), (K27, ED48, Cy2), (K27, ED48, Cy3), (K27, ED49, Cy1), (K27, ED49, Cy2), (K27, ED49, Cy3), (K27, ED50, Cy1), (K27, ED50, Cy2), (K27, ED50, Cy3), (K27, ED51, Cy1), (K27, ED51, Cy2), (K27, ED51, Cy3), (K27, ED52, Cy1), (K27, ED52, Cy2), (K27, ED52, Cy3), (K27, ED53, Cy1), (K27, ED53, Cy2), (K27, ED53, Cy3), (K27, ED54, Cy1), (K27, ED54, Cy2), (K27, ED54, Cy3), (K27, ED55, Cy1), (K27, ED55, Cy2), (K27, ED55, Cy3), (K27, ED56, Cy1), (K27, ED56, Cy2), (K27, ED56, Cy3), (K27, ED57, Cy1), (K27, ED57, Cy2), (K27, ED57, Cy3), (K27, ED58, Cy1), (K27, ED58, Cy2), (K27, ED58, Cy3), (K27, ED59, Cy1), (K27, ED59, Cy2), (K27, ED59, Cy3), (K27, ED60, Cy1), (K27, ED60, Cy2), (K27, ED60, Cy3), (K27, ED61, Cy1), (K27, ED61, Cy2), (K27, ED61, Cy3), (K27, ED62, Cy1), (K27, ED62, Cy2), (K27, ED62, Cy3), (K27, ED63, Cy1), (K27, ED63, Cy2), (K27, ED63, Cy3), (K27, ED64, Cy1), (K27, ED64, Cy2), (K27, ED64, Cy3), (K27, ED65, Cy1), (K27, ED65, Cy2), (K27, ED65, Cy3), (K27, ED66, Cy1), (K27, ED66, Cy2), (K27, ED66, Cy3), (K27, ED67, Cy1), (K27, ED67, Cy2), (K27, ED67, Cy3), (K27, ED68, Cy1), (K27, ED68, Cy2), (K27, ED68, Cy3), (K27, ED69, Cy1), (K27, ED69, Cy2), (K27, ED69, Cy3), (K27, ED70, Cy1), (K27, ED70, Cy2), (K27, ED70, Cy3), (K27, ED71, Cy1), (K27, ED71, Cy2), (K27, ED71, Cy3), (K27, ED72, Cy1), (K27, ED72, Cy2), (K27, ED72, Cy3), (K27, ED73, Cy1), (K27, ED73, Cy2), (K27, ED73, Cy3), (K27, ED74, Cy1), (K27, ED74, Cy2), (K27, ED74, Cy3), (K27, ED75, Cy1), (K27, ED75, Cy2), (K27, ED75, Cy3), (K27, ED76, Cy1), (K27, ED76, Cy2), (K27, ED76, Cy3), (K27, ED77, Cy1), (K27, ED77, Cy2), (K27, ED77, Cy3), (K27, ED78, Cy1), (K27, ED78, Cy2), (K27, ED78, Cy3), (K27, ED79, Cy1), (K27, ED79, Cy2), (K27, ED79, Cy3), (K27, ED80, Cy1), (K27, ED80, Cy2), (K27, ED80, Cy3), (K27, ED81, Cy1), (K27, ED81, Cy2), (K27, ED81, Cy3), (K27, ED82, Cy1), (K27, ED82, Cy2), (K27, ED82, Cy3), (K27, ED83, Cy1), (K27, ED83, Cy2), (K27, ED83, Cy3), (K27, ED84, Cy1), (K27, ED84, Cy2), (K27, ED84, Cy3), (K27, ED85, Cy1), (K27, ED85, Cy2), (K27, ED85, Cy3), (K27, ED86, Cy1), (K27, ED86, Cy2), (K27, ED86, Cy3), (K27, ED87, Cy1), (K27, ED87, Cy2), (K27, ED87, Cy3), (K27, ED88, Cy1), (K27, ED88, Cy2), (K27, ED88, Cy3), (K27, ED89, Cy1), (K27, ED89, Cy2), (K27, ED89, Cy3), (K27, ED90, Cy1), (K27, ED90, Cy2), (K27, ED90, Cy3), (K27, ED91, Cy1), (K27, ED91, Cy2), (K27, ED91, Cy3), (K27, ED92, Cy1), (K27, ED92, Cy2), (K27, ED92, Cy3), (K28, ED1, Cy1), (K28, ED1, Cy2), (K28, ED1, Cy3), (K28, ED2, Cy1), (K28, ED2, Cy2), (K28, ED2, Cy3), (K28, ED3, Cy1), (K28, ED3, Cy2), (K28, ED3, Cy3), (K28, ED4, Cy1), (K28, ED4, Cy2), (K28, ED4, Cy3), (K28, ED5, Cy1), (K28, ED5, Cy2), (K28, ED5, Cy3), (K28, ED6, Cy1), (K28, ED6, Cy2), (K28, ED6, Cy3), (K28, ED7, Cy1), (K28, ED7, Cy2), (K28, ED7, Cy3), (K28, ED8, Cy1), (K28, ED8, Cy2), (K28, ED8, Cy3), (K28, ED9, Cy1), (K28, ED9, Cy2), (K28, ED9, Cy3), (K28, ED10, Cy1), (K28, ED10, Cy2), (K28, ED10, Cy3), (K28, ED11, Cy1), (K28, ED11, Cy2), (K28, ED11, Cy3), (K28, ED12, Cy1), (K28, ED12, Cy2), (K28, ED12, Cy3), (K28, ED13, Cy1), (K28, ED13, Cy2), (K28, ED13, Cy3), (K28, ED14, Cy1), (K28, ED14, Cy2), (K28, ED14, Cy3), (K28, ED15, Cy1), (K28, ED15, Cy2), (K28, ED15, Cy3), (K28, ED16, Cy1), (K28, ED16, Cy2), (K28, ED16, Cy3), (K28, ED17, Cy1), (K28, ED17, Cy2), (K28, ED17, Cy3), (K28, ED18, Cy1), (K28, ED18, Cy2), (K28, ED18, Cy3), (K28, ED19, Cy1), (K28, ED19, Cy2), (K28, ED19, Cy3), (K28, ED20, Cy1), (K28, ED20, Cy2), (K28, ED20, Cy3), (K28, ED21, Cy1), (K28, ED21, Cy2), (K28, ED21, Cy3), (K28, ED22, Cy1), (K28, ED22, Cy2), (K28, ED22, Cy3), (K28, ED23, Cy1), (K28, ED23, Cy2), (K28, ED23, Cy3), (K28, ED24, Cy1), (K28, ED24, Cy2), (K28, ED24, Cy3), (K28, ED25, Cy1), (K29, ED25, Cy2), (K28, ED25, Cy3), (K28, ED26, Cy1), (K28, ED26, Cy2), (K28, ED26, Cy3), (K28, ED27, Cy1), (K28, ED27, Cy2), (K28, ED27, Cy3), (K28, ED28, Cy1), (K28, ED28, Cy2), (K28, ED28, Cy3), (K28, ED29, Cy1), (K23, ED29, Cy2), (K23, ED29, Cy1), (K28, ED30, Cy1), (K28, ED30, Cy2), (K28, ED30, Cy3), (K28, ED31, Cy1), (K28, ED31, Cy2), (K28, ED31, Cy3), (K28, ED32, Cy1), (K28, ED32, Cy2), (K28, ED32, Cy3), (K28, ED33, Cy1), (K28, ED33, Cy2), (K28, ED33, Cy3), (K28, ED34, Cy1), (K28, ED34, Cy2), (K28, ED34, Cy3), (K28, ED35, Cy1), (K28, ED35, Cy2), (K28, ED35, Cy3), (K28, ED36, Cy1), (K28, ED36, Cy2), (K28, ED36, Cy3), (K28, ED37, Cy1), (K28, ED37, Cy2), (K28, ED37, Cy3), (K28, ED38, Cy1), (K28, ED38, Cy2), (K28, ED38, Cy3), (K28, ED39, Cy1), (K28, ED39, Cy2), (K28,

ED39, Cy3), (K28, ED40, Cy1), (K28, ED40, Cy2), (K28, ED40, Cy3), (K28, ED41, Cy1), (K28, ED41, Cy2), (K28, ED41, Cy3), (K28, ED42, Cy1), (K28, ED42, Cy2), (K28, ED42, Cy3), (K28, ED43, Cy1), (K28, ED43, Cy2), (K28, ED43, Cy3), (K28, ED44, Cy1), (K28, ED44, Cy2), (K28, ED44, Cy3), (K28, ED45, Cy1), (K28, ED45, Cy2), (K28, ED45, Cy3), (K28, ED46, Cy1), (K28, ED46, Cy2), (K28, ED46, Cy3), (K28, ED47, Cy1), (K28, ED47, Cy2), (K28, ED47, Cy3), (K28, ED48, Cy1), (K28, ED48, Cy2), (K28, ED48, Cy3), (K28, ED49, Cy1), (K28, ED49, Cy2), (K28, ED49, Cy3), (K28, ED50, Cy1), (K28, ED50, Cy2), (K28, ED50, Cy3), (K28, ED51, Cy1), (K28, ED51, Cy2), (K28, ED51, Cy3), (K28, ED52, Cy1), (K28, ED52, Cy2), (K28, ED52, Cy3), (K28, ED53, Cy1), (K28, ED53, Cy2), (K28, ED53, Cy3), (K28, ED54, Cy1), (K28, ED54, Cy2), (K28, ED54, Cy3), (K28, ED55, Cy1), (K28, ED55, Cy2), (K28, ED55, Cy3), (K28, ED56, Cy1), (K28, ED56, Cy2), (K28, ED56, Cy3), (K28, ED57, Cy1), (K28, ED57, Cy2), (K28, ED57, Cy3), (K28, ED58, Cy1), (K28, ED58, Cy2), (K28, ED58, Cy3), (K28, ED59, Cy1), (K28, ED59, Cy2), (K28, ED59, Cy3), (K28, ED60, Cy1), (K28, ED60, Cy2), (K28, ED60, Cy3), (K28, ED61, Cy1), (K28, ED61, Cy2), (K28, ED61, Cy3), (K28, ED62, Cy1), (K28, ED62, Cy2), (K28, ED62, Cy3), (K28, ED63, Cy1), (K28, ED63, Cy2), (K28, ED63, Cy3), (K28, ED64, Cy1), (K28, ED64, Cy2), (K28, ED64, Cy3), (K28, ED65, Cy1), (K28, ED65, Cy2), (K28, ED65, Cy3), (K28, ED66, Cy1), (K28, ED66, Cy2), (K28, ED66, Cy3), (K28, ED67, Cy1), (K28, ED67, Cy2), (K28, ED67, Cy3), (K28, ED68, Cy1), (K28, ED68, Cy2), (K28, ED68, Cy3), (K28, ED69, Cy1), (K28, ED69, Cy2), (K28, ED69, Cy3), (K28, ED70, Cy1), (K28, ED70, Cy2), (K28, ED70, Cy3), (K28, ED71, Cy1), (K28, ED71, Cy2), (K28, ED71, Cy3), (K28, ED72, Cy1), (K28, ED72, Cy2), (K28, ED72, Cy3), (K28, ED73, Cy1), (K28, ED73, Cy2), (K28, ED73, Cy3), (K28, ED74, Cy1), (K28, ED74, Cy2), (K28, ED74, Cy3), (K28, ED75, Cy1), (K28, ED75, Cy2), (K28, ED75, Cy3), (K28, ED76, Cy1), (K28, ED76, Cy2), (K28, ED76, Cy3), (K28, ED77, Cy1), (K28, ED77, Cy2), (K28, ED77, Cy3), (K28, ED78, Cy1), (K28, ED78, Cy2), (K28, ED78, Cy3), (K28, ED79, Cy1), (K28, ED79, Cy2), (K28, ED79, Cy3), (K28, ED80, Cy1), (K28, ED80, Cy2), (K28, ED80, Cy3), (K28, ED81, Cy1), (K28, ED81, Cy2), (K28, ED81, Cy3), (K28, ED82, Cy1), (K28, ED82, Cy2), (K28, ED82, Cy3), (K28, ED83, Cy1), (K28, ED83, Cy2), (K28, ED83, Cy3), (K28, ED84, Cy1), (K28, ED84, Cy2), (K28, ED84, Cy3), (K28, ED85, Cy1), (K28, ED85, Cy2), (K28, ED85, Cy3), (K28, ED86, Cy1), (K28, ED86, Cy2), (K28, ED86, Cy3), (K28, ED87, Cy1), (K28, ED87, Cy2), (K28, ED87, Cy3), (K28, ED88, Cy1), (K28, EBBS, Cy2), (K28, ED88, Cy3), (K28, ED89, Cy1), (K28, ED89, Cy2), (K28, ED89, Cy3), (K28, ED90, Cy1), (K28, ED90, Cy2), (K28, ED90, Cy3), (K28, ED91, Cy1), (K28, ED91, Cy2), (K28, ED91, Cy3), (K28, ED92, Cy1), (K28, ED92, Cy2), (K28, ED92, Cy3), (K29, ED1, Cy1), (K29, ED1, Cy2), (K29, ED1, Cy3), (K29, ED2, Cy1), (K29, ED2, Cy2), (K29, ED2, Cy3), (K29, ED3, Cy1), (K29, ED3, Cy2), (K29, ED3, Cy3), (K29, ED4, Cy1), (K29, ED4, Cy2), (K29, ED4, Cy3), (K29, ED5, Cy1), (K29, ED5, Cy2), (K29, ED5, Cy3), (K29, ED6, Cy1), ED6, Cy2), (K29, ED6, Cy3), (K29, ED7, Cy1), (K29, ED7, Cy2), (K29, ED7, Cy3), (K29, ED8, Cy1), (K29, ED8, Cy2), (K29, ED8, Cy3), (K29, ED9, Cy1), (K29, ED9, Cy2), (K29, ED9, Cy3), (K29, ED10, Cy1), (K29, ED10, Cy2), (K29, ED10, Cy3), (K29, ED11, Cy1), (K29, ED11, Cy2), (K29, ED11, Cy3), (K29, ED12, Cy1), (K29, ED12, Cy2), (K29, ED12, Cy3), (K29, ED13, Cy1), (K29, ED13, Cy2), (K29, ED13, Cy3), (K29, ED14, Cy1), (K29, ED14, Cy2), (K29, ED14, Cy3), (K29, ED15, Cy1), (K29, ED15, Cy2), (K29, ED15, Cy3), (K29, ED16, Cy1), (K29, ED16, Cy2), (K29, ED16, Cy3), (K29, ED17, Cy1), (K29, ED17, Cy2), (K29, ED17, Cy3), (K29, ED18, Cy1), (K29, ED18, Cy2), (K29, ED18, Cy3), (K29, ED19, Cy1), (K29, ED19, Cy2), (K29, ED19, Cy3), (K29, ED20, Cy1), (K29, ED20, Cy2), (K29, ED20, Cy3), (K29, ED21, Cy1), (K29, ED21, Cy2), (K29, ED21, Cy3), (K29, ED22, Cy1), (K29, ED22, Cy2), (K29, ED22, Cy3), (K29, ED23, Cy1), (K29, ED23, Cy2), (K29, ED23, Cy3), (K29, ED24, Cy1), (K29, ED24, Cy2), (K29, ED24, Cy3), (K29, ED25, Cy1), (K29, ED25, Cy2), (K29, ED25, Cy3), (K29, ED26, Cy1), (K29, ED26, Cy2), (K29, ED26, Cy3), (K29, ED27, Cy1), (K29, ED27, Cy2), (K29, ED27, Cy3), (K29, ED28, Cy1), (K29, ED28, Cy2), (K29, ED28, Cy3), (K29, ED29, Cy1), (K29, ED29, Cy2), (K29, ED29, Cy3), (K29, ED38, Cy1), (K29, ED30, Cy2), (K29, ED30, Cy3), (K29, ED31, Cy1), (K29, ED31, Cy2), (K29, ED31, Cy3), (K29, ED32, Cy1), (K29, ED32, Cy2), (K29, ED32, Cy3), (K29, ED33, Cy1), (K29, ED33, Cy2), (K29, ED33, Cy3), (K29, ED34, Cy1), (K29, ED34, Cy2), (K29, ED34, Cy3), (K29, ED35, Cy1), (K29, ED35, Cy2), (K29, ED35, Cy3), (K29, ED36, Cy1), (K29, ED36, Cy2), (K29, ED36, Cy3), (K29, ED37, Cy1), (K29, ED37, Cy2), (K29, ED37, Cy3), (K29, ED38, Cy1), (K29, ED38, Cy2), (K29, ED38, Cy3), (K29, ED39, Cy1), (K29, ED39, Cy2), (K29, ED39, Cy3), (K29, ED40, Cy1), (K29, ED40, Cy2), (K29, ED40, Cy3), (K29, ED41, Cy1), (K29, ED41, Cy2), (K29, ED41, Cy3), (K29, ED42, Cy1), (K29, ED42, Cy2), (K29, ED42, Cy3), (K29, ED43, Cy1), (K29, ED43, Cy2), (K29, ED43, Cy3), (K29, ED44, Cy1), (K29, ED44, Cy2), (K29, ED44, Cy3), (K29, ED45, Cy1), (K29, ED45, Cy2), (K29, ED45, Cy3), (K29, ED46, Cy1), (K29, ED46, Cy2), (K29, ED46, Cy3), (K29, ED47, Cy1), (K29, ED47, Cy2), (K29, ED47, Cy3), (K29, ED48, Cy1), (K29, ED48, Cy2), (K29, ED48, Cy3), (K29, ED49, Cy1), (K29, ED49, Cy2), (K29, ED49, Cy3), (K29, ED50, Cy1), (K29, ED50, Cy2), (K29, ED50, Cy3), (K29, ED51, Cy1), (K29, ED51, Cy2), (K29, ED51, Cy3), (K29, ED52, Cy1), (K29, ED52, Cy2), (K29, ED52, Cy3), (K29, ED53, Cy1), (K29, ED53, Cy2), (K29, ED53, Cy3), (K29, ED54, Cy1), (K29, ED54, Cy2), (K29, ED54, Cy3), (K29, ED55, Cy1), (K29, ED55, Cy2), (K29, ED55, Cy3), (K29, ED56, Cy1), (K29, ED56, Cy2), (K29, ED56, Cy3), (K29, ED57, Cy1), (K29, ED57, Cy2), (K29, ED57, Cy3), (K29, ED58, Cy1), (K29, ED58, Cy2), (K29, ED58, Cy3), (K29, ED59, Cy1), (K29, ED59, Cy2), (K29, ED59, Cy3), (K29, ED60, Cy1), (K29, ED60, Cy2), (K29, ED60, Cy3), (K29, ED61, Cy1), (K29, ED61, Cy2), (K29, ED61, Cy3), (K29, ED62, Cy1), (K29, ED62, Cy2), (K29, ED62, Cy3), (K29, ED63, Cy1), (K29, ED63, Cy2), (K29, ED63, Cy3), (K29, ED64, Cy1), (K29, ED64, Cy2), (K29, ED64, Cy3), (K29, ED65, Cy1), (K29, ED65, Cy2), (K29, ED65, Cy3), (K29, ED66, Cy1), (K29, ED66, Cy2), (K29, ED66, Cy3), (K29, ED67, Cy1), (K29, ED67, Cy2), (K29, ED67, Cy3), (K29, ED68, Cy1), (K29, ED68, Cy2), (K29, ED68, Cy3), (K29, ED69, Cy1), (K29, ED69, Cy2), (K29, ED69, Cy3), (K29, ED70, Cy1), (K29, ED70, Cy2), (K29, ED70, Cy3), (K29, ED71, Cy1), (K29, ED71, Cy2), (K29, ED71, Cy3), (K29, ED72, Cy1), (K29, ED72, Cy2), (K29, ED72, Cy3), (K29, ED73, Cy1), (K29, ED73, Cy2), (K29, ED73, Cy3), (K29, ED74, Cy1), (K29, ED74, Cy2), (K29, ED74, Cy3), (K29, ED75, Cy1), (K29, ED75, Cy2), (K29, ED75, Cy3), (K29, ED76, Cy1), (K29, ED76, Cy2), (K29, ED76, Cy3), (K29, ED77, Cy1), (K29, ED77, Cy2), (K29, ED77, Cy3), (K29, ED78, Cy1), (K29, ED78, Cy2), (K29, ED78, Cy3), (K29, ED79, Cy1), (K29, ED79, Cy2), (K29, ED79, Cy3), (K29, ED80, Cy1), (K29, ED80, Cy2), (K29, ED80, Cy3), (K29, ED81, Cy1), (K29, ED81, Cy2), (K29, ED81,

Cy3), (K29, ED82, Cy1), (K29, ED82, Cy2), (K29, ED82, Cy3), (K29, ED83, Cy1), (K29, ED83, Cy2), (K29, ED83, Cy3), (K29, ED84, Cy1), (K29, ED84, Cy2), (K29, ED84, Cy3), (K29, ED85, Cy1), (K29, ED85, Cy2), (K29, ED85, Cy3), (K29, ED86, Cy1), (K29, ED86, Cy2), (K29, ED86, Cy3), (K29, ED87, Cy1), (K29, ED87, Cy2), (K29, ED87, Cy3), (K29, ED88, Cy1), (K29, ED88, Cy2), (K29, ED88, Cy3), (K29, ED89, Cy1), (K29, ED89, Cy2), (K29, ED89, Cy3), (K29, ED90, Cy1), (K29, ED90, Cy2), (K29, ED90, Cy3), (K29, ED91, Cy1), (K29, ED91, Cy2), (K29, ED91, Cy3), (K29, ED92, Cy1), (K29, ED92, Cy2), (K29, ED92, Cy3), provided that the compounds described in PCT/JP2009/068400 (WO2010/050468) are excluded.

Experimental Example 1

The antimicrobial activity in vitro of the present compound (I) was determined.

(Test Methods)
(Microbe/Strain Species Nos. 1-4):

Measurement of Minimum Inhibitory Concentration (MIC, μg/ml) was conducted according to the standard method of the Japan Society for Chemotherapy and the amount of bacteria for inoculation was 1000 cfu/spot, and sensitive disc medium was used as the test medium, and conducted using agar plate incubation.

(Microbe/Strain Species No. 5):

Measurement of Minimum Inhibitory Concentration (MIC, μg/ml) was conducted according to the CLSI (Clinical and Laboratory Standards Institute) and the amount of bacteria for inoculation was 10000 cfu/spot, and Mueller-Hinton agar medium was used as the test medium, and conducted using agar plate incubation.

Test results are shown in Tables 10-20. In the tables, the unit of the values of inhibitory activity is μg/ml.

TABLE 10

| Bacteria Strain No. | Bacteria Species | Strain Name | Compound (I-1) | Compound (I-5) | Compound (I-6) | Compound (I-9) | Compound (I-14) |
|---|---|---|---|---|---|---|---|
| 1 | Klebsiella pneumoniae | ATCC 700603 | 0.25 | 0.25 | 1 | 0.125 | 0.5 |
| 2 | Pseudomonas aeruginosa | SR24 | 0.063 | 0.063 | 0.063 | 0.063 | 0.125 |
| 3 | Pseudomonas aeruginosa | SR27060 | 0.25 | 0.5 | 0.5 | 0.25 | 0.25 |
| 4 | Acinetobacter baumannii | SR24396 | 0.25 | 0.125 | 0.125 | 0.125 | 0.125 |
| 5 | Stenotrohomonas maltophilia | SR21970 | 1 | 0.5 | 1 | 0.5 | 1 |

TABLE 11

| Bacteria Strain No. | Bacteria Species | Strain Name | Compound (I-15) | Compound (I-18) | Compound (I-19) | Compound (I-21) | Compound (I-23) |
|---|---|---|---|---|---|---|---|
| 1 | Klebsiella pneumoniae | ATCC 700603 | 0.25 | 0.5 | 0.5 | 0.5 | 0.5 |
| 2 | Pseudomonas aeruginosa | SR24 | 0.063 | 0.063 | 0.125 | 0.125 | 0.063 |
| 3 | Pseudomonas aeruginosa | SR27060 | 0.5 | 1 | 0.125 | 1 | 0.5 |
| 4 | Acinetobacter baumannii | SR24396 | 0.25 | 0.125 | 0.125 | 0.125 | 0.125 |
| 5 | Stenotrohomonas maltophilia | SR21970 | 1 | 2 | 0.5 | 1 | 1 |

TABLE 12

| Bacteria Strain No. | Bacteria Species | Strain Name | Compound (I-25) | Compound (I-28) | Compound (I-31) | Compound (I-34) | Compound (I-35) |
|---|---|---|---|---|---|---|---|
| 1 | Klebsiella pneumoniae | ATCC 700603 | 0.25 | 0.25 | 1 | 0.5 | 1 |
| 2 | Pseudomonas aeruginosa | SR24 | 0.125 | 0.125 | 0.063 | 0.063 | 0.063 |
| 3 | Pseudomonas aeruginosa | SR27060 | 0.5 | 0.25 | 0.5 | 0.5 | 0.25 |
| 4 | Acinetobacter baumannii | SR24396 | 0.125 | 0.125 | 0.25 | 0.125 | 0.5 |
| 5 | Stenotrohomonas maltophilia | SR21970 | 1 | 2 | 1 | 0.5 | 1 |

TABLE 13

| Bacteria Strain No. | Bacteria Species | Strain Name | Compound (I-36) | Compound (I-37) | Compound (I-38) | Compound (I-41) | Compound (I-42) |
|---|---|---|---|---|---|---|---|
| 1 | Klebsiella pneumoniae | ATCC 700603 | 0.5 | 0.5 | 1 | 0.5 | 0.25 |
| 2 | Pseudomonas aeruginosa | SR24 | 0.125 | 0.125 | 0.125 | 0.125 | 0.063 |
| 3 | Pseudomonas aeruginosa | SR27060 | 0.25 | 1 | 2 | 0.5 | 1 |
| 4 | Acinetobacter baumannii | SR24396 | 0.5 | 0.125 | 0.25 | 0.125 | 0.25 |
| 5 | Stenotrohomonas maltophilia | SR21970 | 1 | 1 | 1 | 1 | 1 |

TABLE 14

| Bacteria Strain No. | Bacteria Species | Strain Name | Compound (I-51) | Compound (I-52) | Compound (I-59) | Compound (I-63) |
|---|---|---|---|---|---|---|
| 1 | Klebsiella pneumoniae | ATCC 700603 | 0.25 | 0.5 | 0.25 | 1 |
| 2 | Pseudomonas aeruginosa | SR24 | 0.063 | 0.125 | 0.063 | 0.063 |
| 3 | Pseudomonas aeruginosa | SR27060 | 0.5 | 2 | 0.25 | 0.5 |
| 4 | Acinetobacter baumannii | SR24396 | 0.125 | 0.125 | 0.125 | 0.25 |
| 5 | Stenotrohomonas maltophilia | SR21970 | 1 | 1 | 0.5 | 0.5 |

TABLE 15

| Bacteria Strain No. | Bacteria Species | Strain Name | Compound (II-1) | Compound (II-2) | Compound (II-3) | Compound (II-5) | Compound (II-7) |
|---|---|---|---|---|---|---|---|
| 1 | Klebsiella pneumoniae | ATCC 7000603 | 0.25 | 0.5 | 0.5 | 0.5 | 0.5 |
| 2 | Pseudomonas aeruginosa | SR24 | 0.125 | 0.125 | 0.125 | 0.125 | 0.25 |
| 3 | Pseudomonas aeruginosa | SR27060 | 0.5 | 1 | 0.5 | 0.25 | 0.5 |
| 4 | Acinetobacter baumannii | SR24396 | 0.063 | 0.25 | 0.125 | 0.125 | 0.125 |
| 5 | Stenotrophomonas maltophilia | SR21970 | 2 | 2 | 0.5 | 4 | 0.5 |

TABLE 16

| Bacteria Strain No. | Bacteria Species | Strain Name | Compound (II-9) | Compound (II-15) | Compound (II-16) | Compound (II-25) | Compound (II-28) |
|---|---|---|---|---|---|---|---|
| 1 | Klebsiella pneumoniae | ATCC 7000603 | 1 | 0.125 | 0.25 | 0.5 | 0.25 |
| 2 | Pseudomonas aeruginosa | SR24 | 0.25 | 0.063 | 0.125 | 0.125 | 0.125 |
| 3 | Pseudomonas aeruginosa | SR27060 | 0.5 | 0.25 | 0.5 | 1 | 1 |
| 4 | Acinetobacter baumannii | SR24396 | 0.063 | 0.125 | 0.125 | 0.063 | 0.125 |
| 5 | Stenotrophomonas maltophilia | SR21970 | 0.25 | 0.5 | 0.5 | 1 | 0.5 |

TABLE 17

| Bacteria Strain No. | Bacteria Species | Strain Name | Compound (II-29) | Compound (II-36) | Compound (II-37) | Compound (II-47) | Compound (II-48) |
|---|---|---|---|---|---|---|---|
| 1 | Klebsiella pneumoniae | ATCC 7000603 | 0.125 | 0.5 | 0.5 | 0.25 | 0.25 |
| 2 | Pseudomonas aeruginosa | SR24 | 0.125 | 0.25 | 0.25 | 0.063 | 0.063 |
| 3 | Pseudomonas aeruginosa | SR27060 | 0.5 | 0.5 | 0.25 | 0.25 | 0.25 |
| 4 | Acinetobacter baumannii | SR24396 | 0.25 | 0.25 | 0.25 | 0.25 | 0.125 |
| 5 | Stenotrophomonas maltophilia | SR21970 | 0.5 | 1 | 0.5 | 0.5 | 0.5 |

TABLE 18

| Bacteria Strain No. | Bacteria Species | Strain Name | Compound (II-49) | Compound (II-50) | Compound (II-51) | Compound (II-55) | Compound (II-56) |
|---|---|---|---|---|---|---|---|
| 1 | Klebsiella pneumoniae | ATCC 7000603 | 0.125 | 0.25 | 0.25 | 0.25 | 0.25 |
| 2 | Pseudomonas aeruginosa | SR24 | 0.125 | 0.125 | 0.125 | — | — |
| 3 | Pseudomonas aeruginosa | SR27060 | 0.5 | 0.5 | 0.25 | 0.5 | 0.5 |
| 4 | Acinetobacter baumannii | SR24396 | 0.125 | 0.25 | 0.125 | 0.25 | 0.25 |
| 5 | Stenotrophomonas maltophilia | SR21970 | 0.5 | 0.5 | 0.25 | 0.5 | 0.5 |

TABLE 19

| Bacteria Strain No. | Bacteria Species | Strain Name | Compound (II-57) | Compound (II-58) | Compound (II-59) | Compound (II-63) |
|---|---|---|---|---|---|---|
| 1 | Klebsiella pneumoniae | ATCC 7000603 | 0.25 | 0.5 | 0.5 | 1 |
| 2 | Pseudomonas aeruginosa | SR24 | 0.063 | 0.25 | 0.25 | 0.063 |
| 3 | Pseudomonas aeruginosa | SR27060 | 0.5 | 0.5 | 0.5 | 0.5 |

TABLE 19-continued

| Bacteria Strain No. | Bacteria Species | Strain Name | Compound (II-57) | Compound (II-58) | Compound (II-59) | Compound (II-63) |
|---|---|---|---|---|---|---|
| 4 | Acinetobacter baumannii | SR24396 | 0.063 | 0.125 | 0.125 | 0.125 |
| 5 | Stenotrophomonas maltophilia | SR21970 | 0.5 | 0.5 | 1 | 0.5 |

TABLE 20

| Bacteria Strain No. | Bacteria Species | Strain Name | Compound (III-3) | Compound (III-5) | Compound (III-9) | Compound (III-10) | Compound (III-14) |
|---|---|---|---|---|---|---|---|
| 1 | Klebsiella pneumoniae | ATCC 700603 | 0.25 | 0.125 | 0.125 | 0.125 | 0.5 |
| 2 | Pseudomonas aeruginosa | SR24 | 0.125 | 0.125 | | | 0.25 |
| 3 | Pseudomonas aeruginosa | SR27060 | 0.5 | 0.5 | 0.25 | 0.25 | 0.5 |
| 4 | Acinetobacter baumannii | SR24396 | 0.125 | 0.25 | 0.125 | 0.125 | 0.125 |
| 5 | Stenotrohomonas maltophilia | SR21970 | 0.5 | 0.25 | 0.5 | 0.5 | 0.25 |

Description of the bacterial strain in the above tables and enzyme (beta-lactamase) produced thereby are shown in Table 21.

TABLE 21

| Bacteria Species | Strain Name | Enzyme Produced | Strain Type |
|---|---|---|---|
| K. pneumoniae | ATCC700603 | SHV-18 | ESBL producer strain |
| P. aeruginosa | SR24 | None | Ceftazidime sensitive strain |
| P. aeruginosa | SR27060 | IMP-1 | MBL producer strain (carbapenem resistant strain) |
| A. baumannii | SR24396 | None | |
| S. maltophilia | SR21970 | L-1 | MBL producer strain (carbapenem resistant strain) |

Experimental Example 2

The antimicrobial activity in vivo of the present compound (I) was determined.

(Test Methods)

Mice (ICR type, male, 5 weeks) were inoculated intraperitoneally with P. aeruginosa SR27001 (multi-resistant Pseudomonas aeruginosa; IMP-1 producing strain) to raise infection. One and half hours after, mice were treated with intravenious administration in twice, and then the ED50 value was calculated based on the survival rate after 7 days.

The antimicrobial activity in vitro (MIC) of the test compounds was determined according to the method of Experimental Example 1. The results are shown in Table 22

TABLE 22

| | P. aerugonosa SR27001 | |
|---|---|---|
| | ED50 (mg/kg) | MIC (µg/mL)* |
| Compound (I-25) | 3.34 | 1 |
| Compound (I-13) | 4.22 | 1 |
| Compound (I-20) | 5.48 | 2 |
| CFPM | >100 | >64 |

*Addition of Tf

The structure of the comparative compound is shown below.

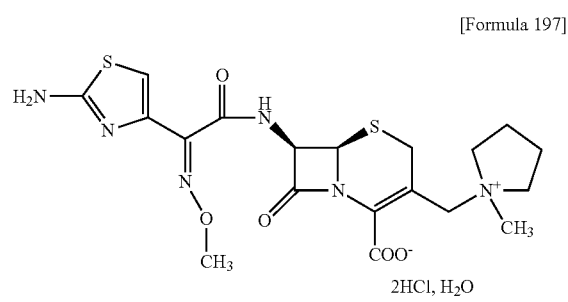

[Formula 197]

CFPM

As shown in the above results, the compounds of the present invention have a wide antimicrobial spectrum, in particular, potent antimicrobial spectrum against Gram negative bacteria, and/or effectiveness against multi-drug resistant bacteria, and exhibited high stability against beta-lactamase producing Gram negative bacteria. In comparison to cefepime hydrochloride hydrate (CFPM), a launched beta-lactamase resident cefarospolin antibiotics having a similar structure, the compound of the present invention showed a higher antimicrobial activity, thus being useful as medicines.

Formulation Example 1

Powder of a compound of the present invention is loaded to prepare a formulation for injection.

Industrial Applicability

The compounds of the present invention have a wide antimicrobial spectrum, and are effective as an antimicrobial drug having high stability against beta-lactamase producing Gram negative bacteria. Moreover, the compounds have good bioavailability, and high water solubility, and thus particularly useful for injectable formulation.

The invention claimed is:
1. A compound of the formula:

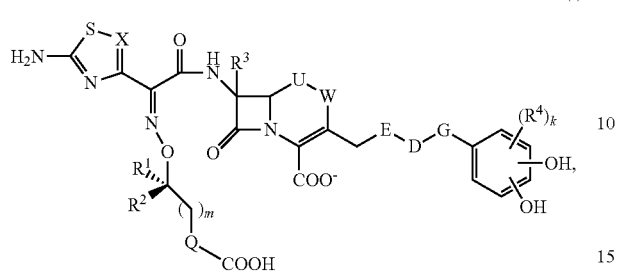
(I)

wherein,
X is —N=, —CH=, —C(—R⁵)=, —C(—Br)=, or —C(—Cl)=;
R⁵ is $C_{1-8}$ alkyl or halo$C_{1-8}$alkyl;
W is —CH₂—, —S— or —O—;
U is —CH₂—, —S— or —O— when W is —CH₂—, or U is —CH₂— when W is —S— or —O—;
R¹ and R² are independently hydrogen, halogen, hydroxyl, carboxy, an optionally substituted $C_{1-8}$ alkyl, an optionally substituted carbocyclic group, or an optionally substituted heterocyclic group; or
R¹ and R² are taken together with an adjacent atom to form optionally substituted carbocyclic group or an optionally substituted heterocyclic group;
R³ is hydrogen, —OCH₃ or —NH—CH(=O);
each R⁴ is independently hydrogen, halogen, hydroxyl, —CN, —C(=O)—R⁶, —C(=O)—OH, $C_{1-8}$ alkyl, halo$C_{1-8}$alkyl, or —OR⁶;
k is an integer from 0 to 2;
R⁶ is $C_{1-8}$ alkyl or halo$C_{1-8}$alkyl;
m is an integer from 0 to 2;
Q is a single bond, optionally substituted carbocyclic group, or an optionally substituted heterocyclic group;
G is i) —C(=O)— or ii) a 5-membered heterocyclic group;
wherein
i) when G is —C(=O)—, then
a) D is a single bond, —NH— or —R⁷—NH— wherein R⁷ is $C_{1-8}$ alkylene; and E is optionally substituted cyclic group selected from the group consisting of formulae (1)-(3), (5)-(8), (10)-(11), (26)-(27) and (30)-(31) below, where the substituent group in the optionally substituted cyclic group for E is at least one group selected independently from the group consisting of optionally subsituted $C_{1-8}$ alkyl or Substituent Group Alpha; or
b) D is a group of following formula:

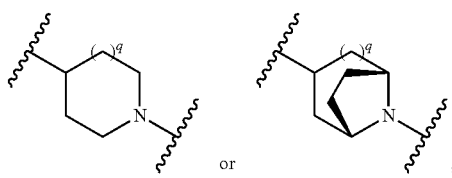

wherein q is 0 or 1, and E is a group of following formula (46); and ii) when G is the 5-membered heterocyclic group; then
D is —CH₂— or —CH₂—CH₂—, and E is a group of following formula (10) in following cyclic groups of the moiety E:

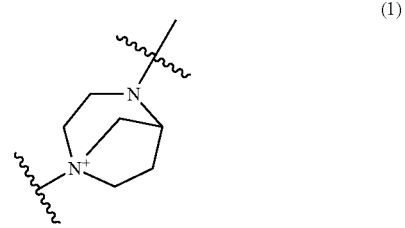
(1)

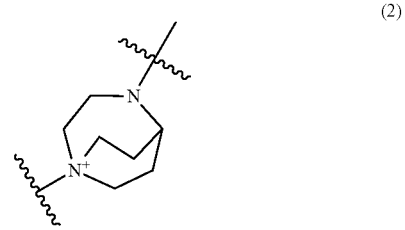
(2)

(3)
(5)
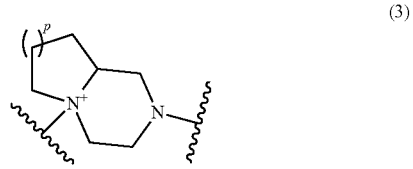

(6)
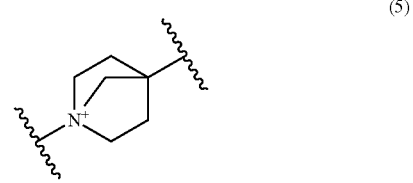

(7)
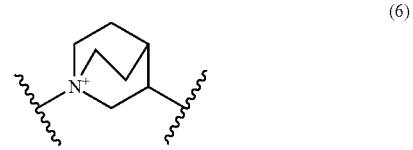

(8)
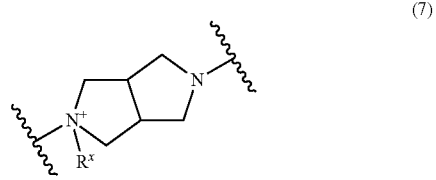

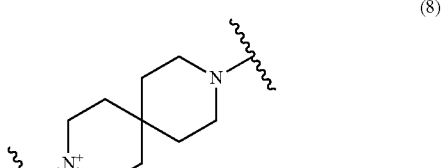

(10)
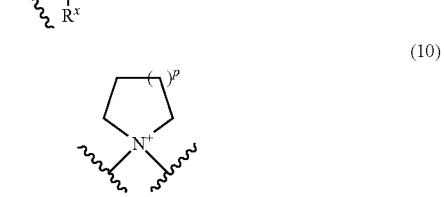

-continued
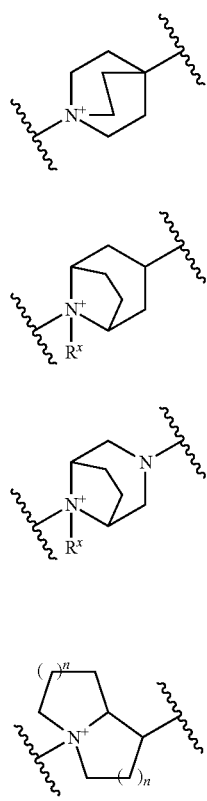
wherein, p is an integer from 1 to 3, n is 1 or 2, and $R^x$ is optionally substitued $C_{1-8}$ alkyl; provided that following compounds from (A-1) to (A-38) are excluded,
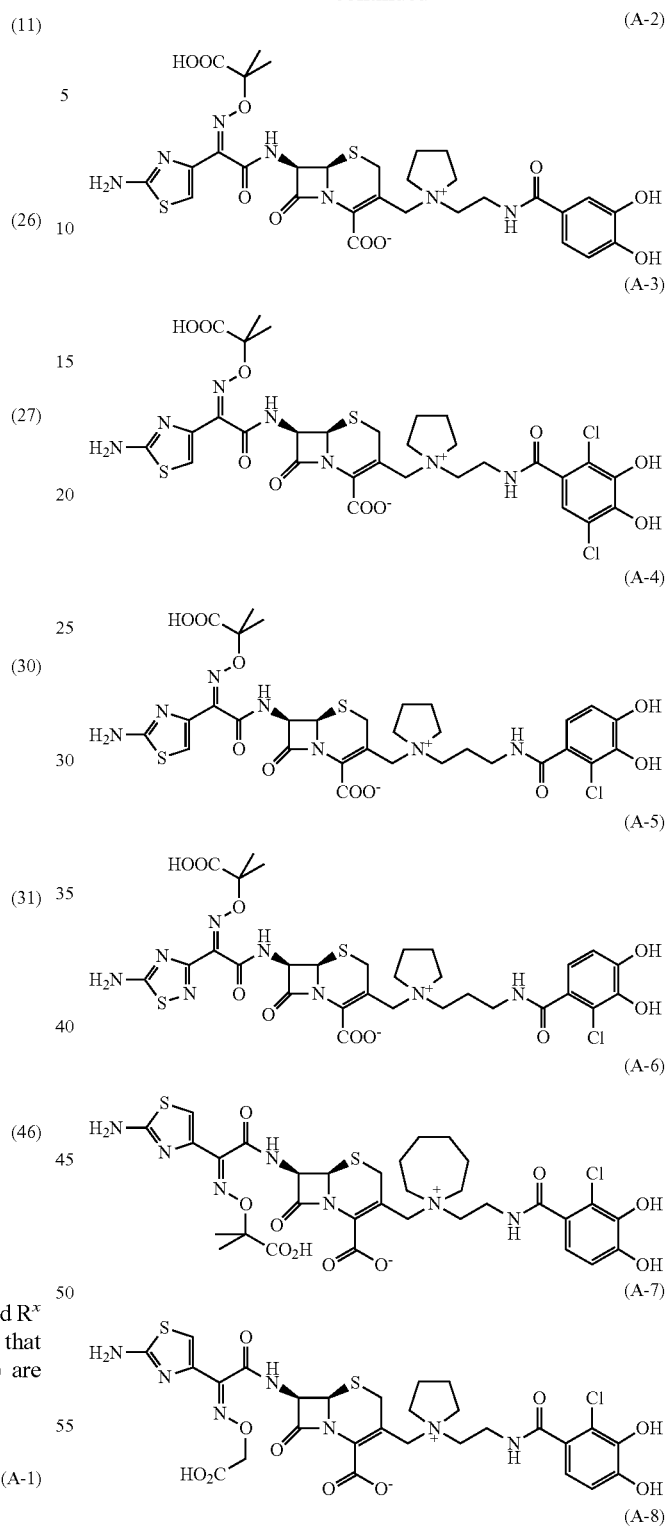

(A-9) 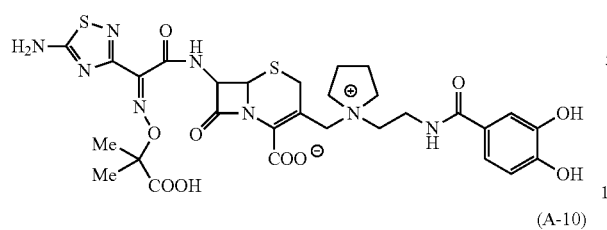
(A-10) 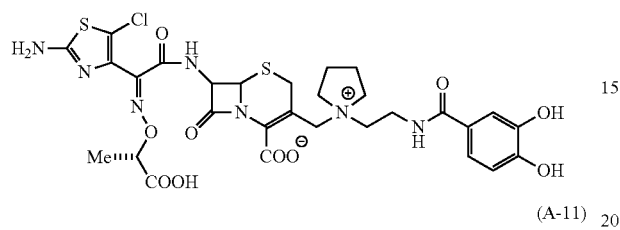
(A-11) 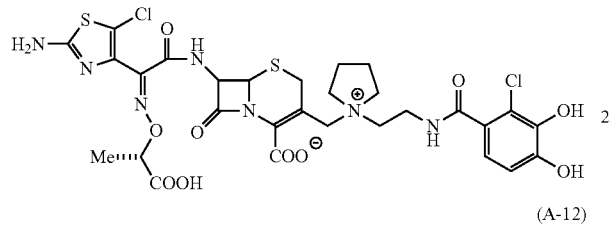
(A-12) 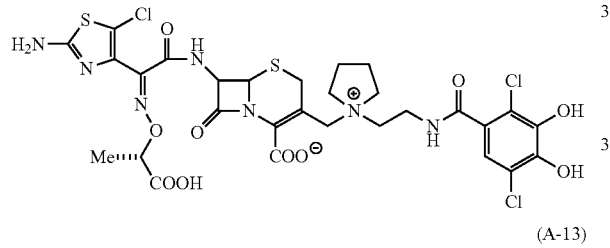
(A-13) 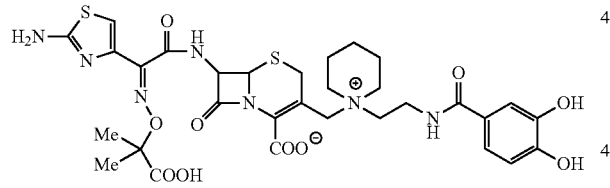
(A-14) 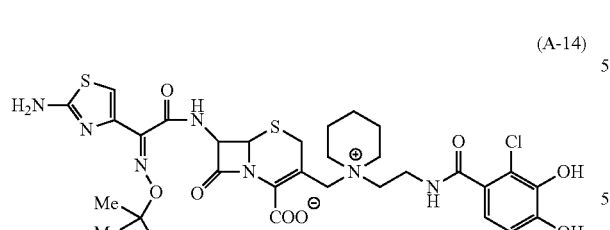
(A-15) 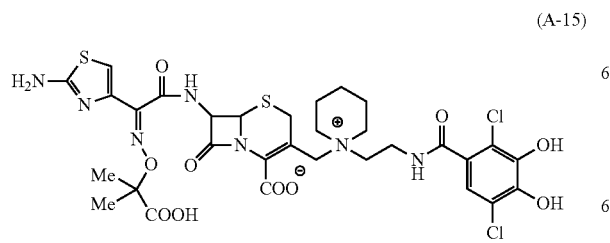
(A-16) 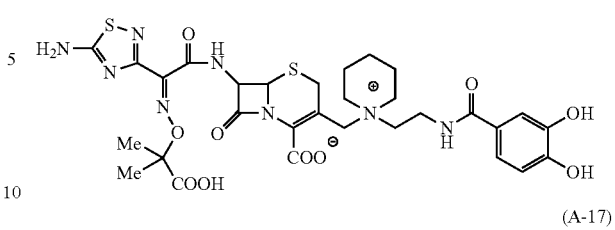
(A-17) 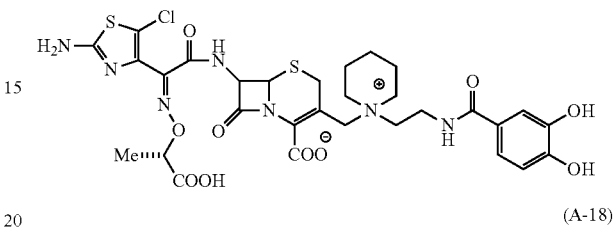
(A-18) 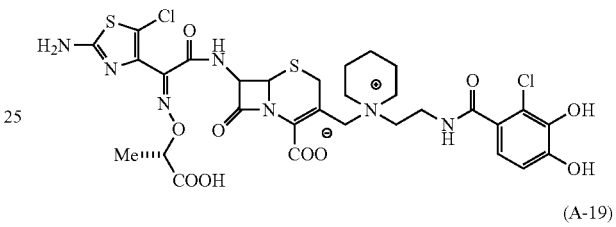
(A-19) 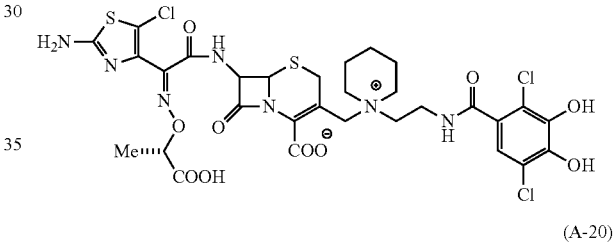
(A-20) 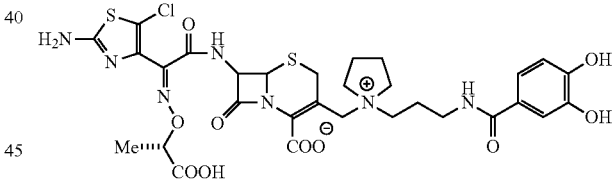
(A-21) 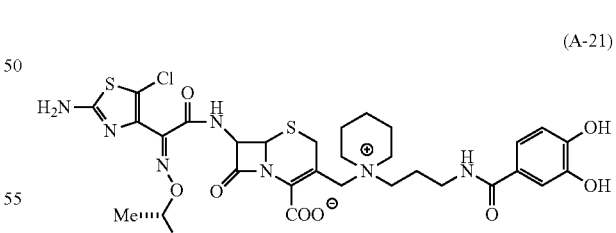
(A-22) 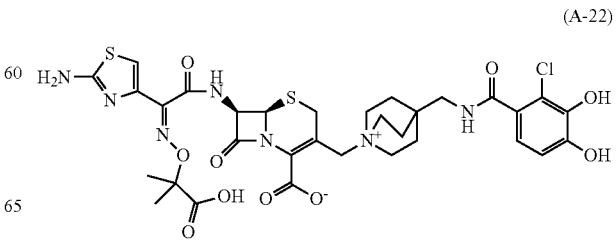

(A-23) 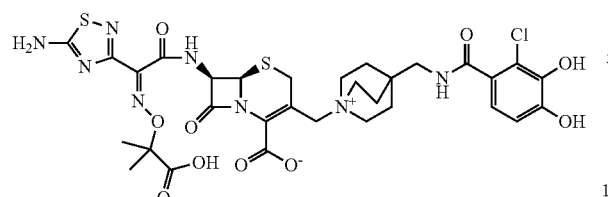
(A-24) 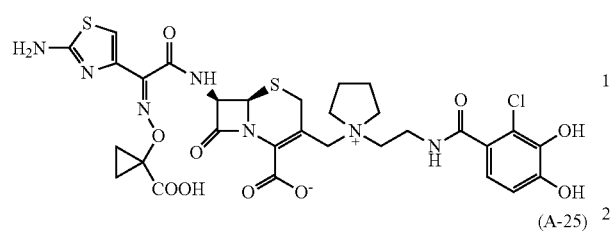
(A-25) 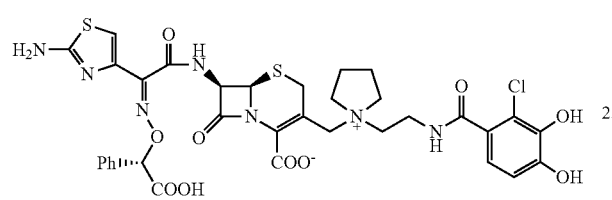
(A-26) 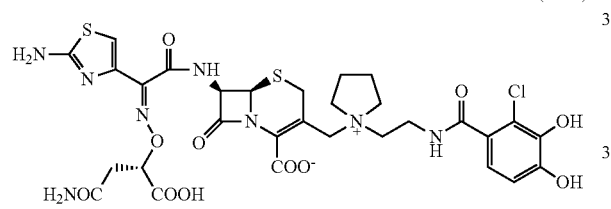
(A-27) 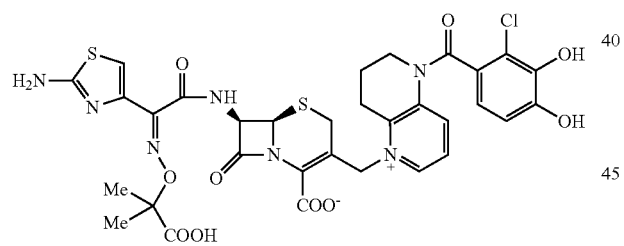
(A-28) 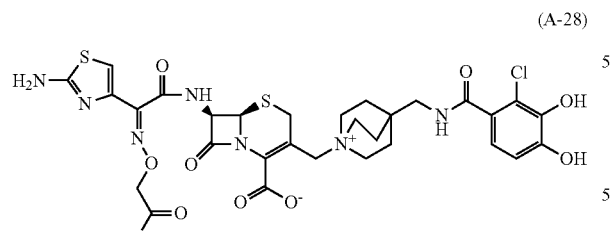
(A-29) 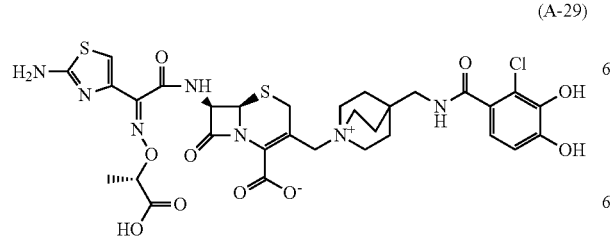
(A-30) 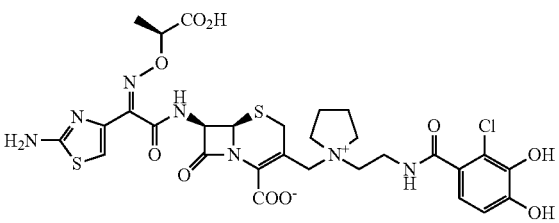
(A-31) 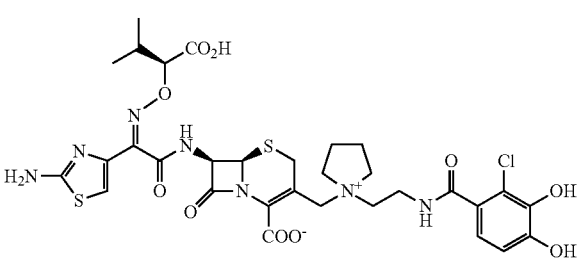
(A-32) 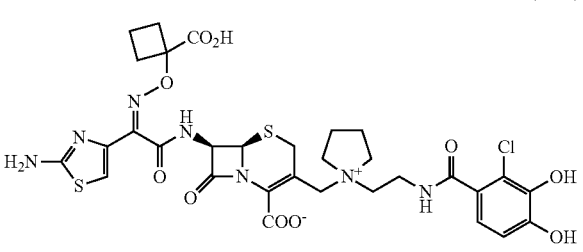
(A-33) 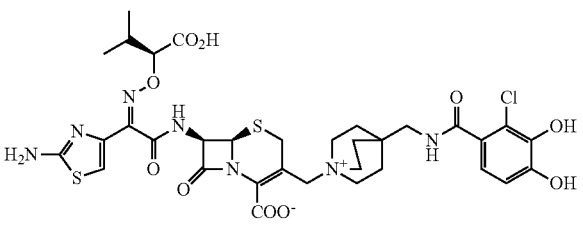
(A-34) 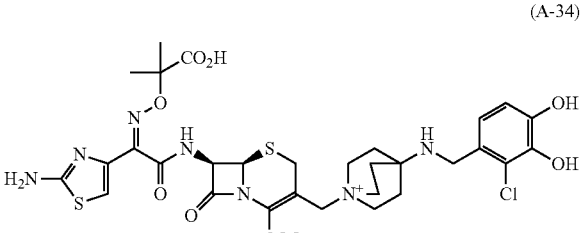
(A-35) 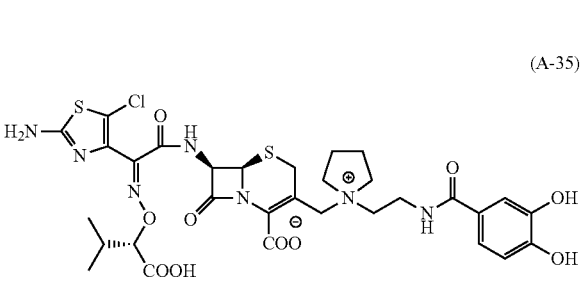

-continued

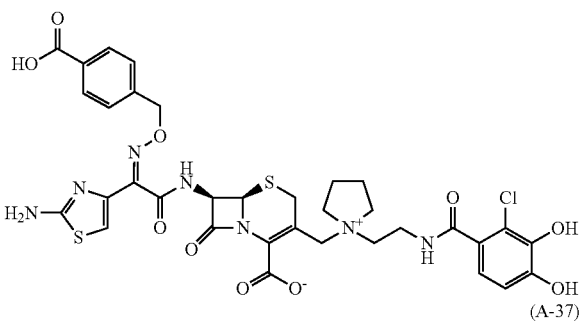
(A-36)

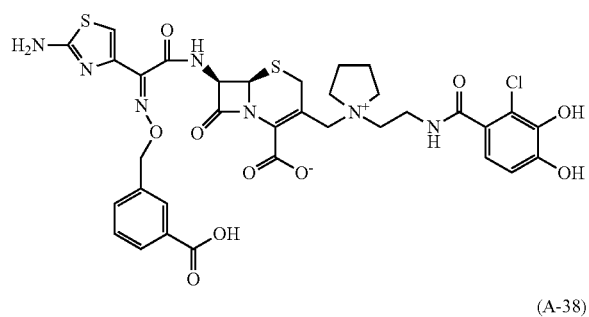
(A-37)

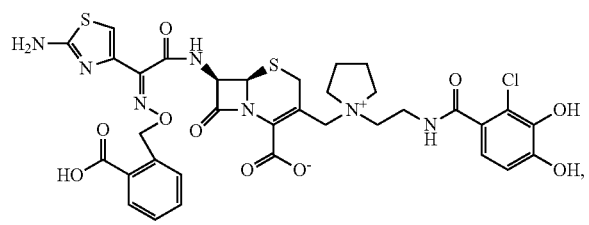
(A-38)

and
wherein the substituent group in each of the optionally substituted $C_{1-8}$ alkyl, the optionally substituted carbocyclic group, and the optionally substituted heterocyclic group is at least one group selected independently from the Substituent Group Alpha,
wherein the Substituent Group Alpha consists of halogen, hydroxy, $C_{1-8}$ alkoxy, hydroxy$C_{1-8}$alkoxy, $C_{1-8}$ alkoxy $C_{1-8}$ alkoxy, carboxy, amino, acylamino, $C_{1-8}$ alkylamino, imino, hydroxyimino, $C_{1-8}$ alkoxyimino, $C_{1-8}$ alkylthio, carbamoyl, $C_{1-8}$ alkylcarbamoyl, hydroxy$C_{1-8}$alkylcarbamoyl, sulfamoyl, $C_{1-8}$ alkylsulfamoyl, $C_{1-8}$ alkylsulfinyl, cyano, nitro, a carbocyclic group, and a heterocyclic group,
or an ester, which is formed at at least one site selected from the group consisting of a 4-position of a cephem skeleton and a 7-position thereof, a protected compound at the amino on the ring in the 7-side chain, a pharmaceutically acceptable salt, or a solvate thereof.

2. The compound, or an ester, the protected compound at the amino on the ring in the 7-side chain, the pharmaceutically acceptable salt, or a solvate thereof according to claim 1, wherein G is —C(═O)—; D is the single bond, —NH— or —R$^7$—NH— wherein R$^7$ is $C_{1-8}$ alkylene; and E is selected from the group consisting of the formulae (1)-(3), (5)-(8), (10)-(11), (26)-(27) and (30)-(31).

3. The compound, or the ester, the protected compound at the amino on the ring in the 7-side chain, the pharmaceutically acceptable salt, or the solvate thereof according to claim 2, wherein D is —NH—, —CH$_2$—NH— or —CH$_2$—CH$_2$—NH—.

4. The compound, or the ester, the protected compound at the amino on the ring in the 7-side chain, the pharmaceutically acceptable salt, or the solvate thereof according to claim 3, wherein E is a group selected from the group consisting of the formulae (5), (6), (10), (11), (26), and (30)-(31).

5. The compound, or the ester, the protected compound at the amino on the ring in the 7-side chain, the pharmaceutically acceptable salt, or the solvate thereof according to claim 3, wherein E is of the formula (26) or (31).

6. The compound, or the ester, the protected compound at the amino on the ring in the 7-side chain, the pharmaceutically acceptable salt, or the solvate thereof according to claim 2, wherein D is the single bond.

7. The compound, or the ester, the protected compound at the amino on the ring in the 7-side chain, the pharmaceutically acceptable salt, or the solvate thereof according to claim 6, wherein E is a group selected from the group consisting of the formulae from (1) to (3), (7), (8), and (27).

8. The compound, or the ester, the protected compound at the amino on the ring in the 7-side chain, the pharmaceutically acceptable salt, or the solvate thereof according to claim 6, wherein E is a group selected from the group consisting of the formulae from (1) to (3), and (7).

9. The compound, or the ester, the protected compound at the amino on the ring in the 7-side chain, the pharmaceutically acceptable salt, or the solvate thereof according to claim 1, wherein G is —C(═O)—; and D is the group of the formula:

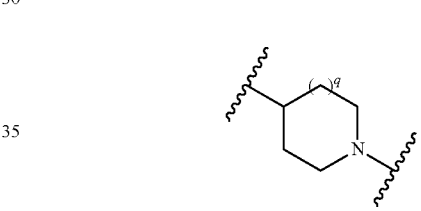

wherein, q is as defined in claim 1.

10. The compound, or the ester, the protected compound at the amino on the ring in the 7-side chain, the pharmaceutically acceptable salt, or the solvate thereof according to claim 1, wherein G is the 5-membered heterocyclic group; and D is —CH$_2$— or —CH$_2$—CH$_2$—.

11. The compound, or the ester, the protected compound at the amino on the ring in the 7-side chain, the pharmaceutically acceptable salt, or the solvate thereof according to claim 1, wherein U is —S—.

12. The compound, or the ester, the protected compound at the amino on the ring in the 7-side chain, the pharmaceutically acceptable salt, or the solvate thereof according to claim 1, wherein W is —CH$_2$—.

13. The compound, or the ester, the protected compound at the amino on the ring in the 7-side chain, the pharmaceutically acceptable salt, or the solvate thereof according to claim 1, wherein R$^3$ is hydrogen or —OCH$_3$.

14. The compound, or the ester, the protected compound at the amino on the ring in the 7-side chain, the pharmaceutically acceptable salt, or the solvate thereof according to claim 1, wherein X is —N═, —CH═, or —C(—Cl)═.

15. The compound, or the ester, the protected compound at the amino on the ring in the 7-side chain, the pharmaceutically acceptable salt, or the solvate thereof according to claim 1, wherein a group represented by a formula:

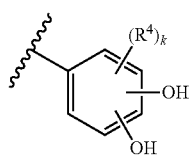

in the formula (I),
is a group represented by a formula:

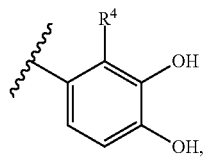

wherein, $R^4$ is as defined in claim 1.

16. The compound, or the ester, the protected compound at the amino on the ring in the 7-side chain, the pharmaceutically acceptable salt, or the solvate thereof according to claim 1, wherein $R^4$ is each independently hydrogen or halogen.

17. The compound, or the ester, the protected compound at the amino on the ring in the 7-side chain, the pharmaceutically acceptable salt, or the solvate thereof according to claim 1, wherein $R^1$ is the optionally substituted $C_{1-8}$ alkyl,
wherein one or more optional substituents for the optionally substituted $C_{1-8}$ alkyl are at least one group selected from the group consisting of fluorine, chlorine, bromine, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, $C_{1-8}$ alkylsulfamoyl, cyano, nitro, phenyl, cyclopropyl, cyclobutyl, cyclohexyl, pyridyl, and morpholinyl; and $R^2$ is hydrogen.

18. The compound, or the ester, the protected compound at the amino on the ring in the 7-side chain, the pharmaceutically acceptable salt, or the solvate thereof according to claim 1, wherein $R^1$ is hydrogen; and $R^2$ is the optionally substituted $C_{1-8}$ alkyl,
wherein one or more optional substituents for the optionally substituted $C_{1-8}$ alkyl are at least one group selected from fluorine, chlorine, bromine, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, $C_{1-8}$ alkylsulfamoyl, cyano, nitro, phenyl, cyclopropyl, cyclobutyl, cyclohexyl, pyridyl, and morpholinyl.

19. The compound, or the ester, the protected compound at the amino on the ring in the 7-side chain, the pharmaceutically acceptable salt, or the solvate thereof according to claim 1, wherein $R^1$ and $R^2$ are each $C_{1-8}$ alkyl.

20. The compound, or the ester, the protected compound at the amino on the ring in the 7-side chain, the pharmaceutically acceptable salt, or the solvate thereof according to claim 1, wherein m is 0.

21. A pharmaceutical composition, which comprising the compound, or the ester, the protected compound at the amino on the ring in the 7-side chain, the pharmaceutically acceptable salt, or the solvate thereof according to claim 1.

22. The pharmaceutical composition according to claim 21, which possesses an antimicrobial activity.

23. A method for treating a bacterial infectious disease, characterized in a step of administering the compound, or the ester, the protected compound at the amino on the ring in the 7-side chain, the pharmaceutically acceptable salt, or the solvate thereof according to claim 1.

\* \* \* \* \*